US011649459B2

(12) United States Patent
Castoreno et al.

(10) Patent No.: US 11,649,459 B2
(45) Date of Patent: May 16, 2023

(54) SUPEROXIDE DISMUTASE 1 (SOD1) IRNA COMPOSITIONS AND METHODS OF USE THEREOF FOR TREATING OR PREVENTING SUPEROXIDE DISMUTASE 1-(SOD1-) ASSOCIATED NEURODEGENERATIVE DISEASES

(71) Applicant: Alnylam Pharmaceuticals, Inc., Cambridge, MA (US)

(72) Inventors: Adam Castoreno, Framingham, MA (US); Jason Gilbert, Hingham, MA (US); Charalambos Kaittanis, Cambridge, MA (US); James D. McIninch, Burlington, MA (US); Stuart Milstein, Arlington, MA (US); Mark K. Schlegel, Boston, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 17/852,554

(22) Filed: Jun. 29, 2022

(65) Prior Publication Data
US 2022/0356478 A1  Nov. 10, 2022

Related U.S. Application Data

(63) Continuation of application No. PCT/US2022/016046, filed on Feb. 11, 2022.

(60) Provisional application No. 63/270,176, filed on Oct. 21, 2021, provisional application No. 63/148,991, filed on Feb. 12, 2021.

(51) Int. Cl.
*C12N 15/113* (2010.01)
*A61P 25/00* (2006.01)
*C12N 9/02* (2006.01)

(52) U.S. Cl.
CPC .......... *C12N 15/1137* (2013.01); *A61P 25/00* (2018.01); *C12N 9/0089* (2013.01); *C12N 2310/111* (2013.01); *C12N 2310/14* (2013.01); *C12N 2310/53* (2013.01); *C12N 2320/31* (2013.01); *C12Y 115/01001* (2013.01)

(58) Field of Classification Search
CPC .......... C12N 15/1137; C12N 2310/111; C12N 2310/14; C12N 2310/53; C12N 2320/31; A61P 25/00
See application file for complete search history.

(56) References Cited

U.S. PATENT DOCUMENTS

| 7,498,316 | B2 | 3/2009 | Xu et al. |
| 7,632,938 | B2 | 12/2009 | Khvorova et al. |
| 7,645,576 | B2 | 1/2010 | Lo et al. |
| 7,951,784 | B2 | 5/2011 | Rana et al. |
| 8,039,610 | B2 | 10/2011 | Khvorova et al. |
| 9,879,253 | B2 | 1/2018 | Zamore et al. |
| 10,131,904 | B2 | 11/2018 | Pavco et al. |
| 10,280,418 | B2 | 5/2019 | Mueller et al. |
| 10,385,341 | B2 | 8/2019 | Swayze |
| 10,513,710 | B2 | 12/2019 | Khvorova et al. |
| 10,570,395 | B2 | 2/2020 | Hou et al. |
| 10,590,420 | B2 | 3/2020 | Barkats et al. |
| 10,597,660 | B2 | 3/2020 | Sah et al. |
| 10,633,654 | B2 | 4/2020 | Pavco et al. |
| 10,669,546 | B2 | 6/2020 | Swayze |
| 10,731,217 | B2 | 8/2020 | Lo et al. |
| 10,835,621 | B2 | 11/2020 | Aebischer et al. |
| 10,920,227 | B2 | 2/2021 | Sah et al. |
| 10,968,453 | B2 | 4/2021 | Swayze |
| 11,332,733 | B2 | 5/2022 | Seth et al. |
| 2004/0192629 | A1 | 9/2004 | Xu et al. |
| 2005/0202414 | A1 | 9/2005 | Jia et al. |
| 2005/0244851 | A1 | 11/2005 | Blume et al. |
| 2006/0229268 | A1 | 10/2006 | Benjamin et al. |
| 2007/0259827 | A1 | 11/2007 | Aronin et al. |
| 2010/0087334 | A1 | 4/2010 | Khvorova et al. |
| 2012/0015850 | A1 | 1/2012 | Khvorova et al. |
| 2017/0009304 | A1 | 1/2017 | Zhuo |
| 2020/0157547 | A1 | 5/2020 | Sah et al. |
| 2020/0354723 | A1 | 11/2020 | Swayze |
| 2021/0009987 | A1 | 1/2021 | Nelles et al. |
| 2021/0052744 | A1 | 2/2021 | Aebischer et al. |
| 2021/0139915 | A1 | 5/2021 | Sah et al. |
| 2021/0207167 | A1 | 7/2021 | Hou et al. |
| 2021/0214749 | A1 | 7/2021 | Hou et al. |

(Continued)

FOREIGN PATENT DOCUMENTS

| WO | WO-2004/042027 A2 | 5/2004 |
| WO | WO-2004/080406 A2 | 9/2004 |

(Continued)

OTHER PUBLICATIONS

A. McCampbell, et al., Antisense oligonucleotides extend survival and reverse decrement in muscle response in ALS models, J Clin Invest. 2018;128(8):3558-3567.

(Continued)

*Primary Examiner* — J. E. Angell
(74) *Attorney, Agent, or Firm* — McCarter & English, LLP; Maria Laccotripe Zacharakis; Deborah L. Nagle

(57) ABSTRACT

The disclosure relates to double stranded ribonucleic acid (dsRNAi) agents and compositions targeting a SOD1 gene, as well as methods of inhibiting expression of a SOD1 gene and methods of treating subjects having a SOD1-associated neurodegenerative disease or disorder, e.g., Amyotrophic Lateral Sclerosis (ALS), Alzheimer's disease (AD), Parkinson's disease (PD), and Down's syndrome (DS), using such dsRNAi agents and compositions.

30 Claims, 20 Drawing Sheets
Specification includes a Sequence Listing.

(56) References Cited

U.S. PATENT DOCUMENTS

| | | |
|---|---|---|
| 2021/0230632 A1 | 7/2021 | Sah et al. |
| 2021/0254103 A1 | 8/2021 | Sah et al. |
| 2021/0277418 A1 | 9/2021 | Sah et al. |
| 2021/0355454 A1 | 11/2021 | Cardinal et al. |
| 2021/0361318 A1 | 11/2021 | Patzke et al. |
| 2021/0371470 A1 | 12/2021 | Murlidharan et al. |
| 2021/0380969 A1 | 12/2021 | Nonnenmacher et al. |
| 2022/0042044 A1 | 2/2022 | Nonnenmacher et al. |
| 2022/0162609 A1 | 5/2022 | Sah et al. |
| 2022/0168449 A1 | 6/2022 | Belle et al. |
| 2022/0168450 A1 | 6/2022 | Sah et al. |

FOREIGN PATENT DOCUMENTS

| | | |
|---|---|---|
| WO | WO-2005/014782 A2 | 2/2005 |
| WO | WO-2005/096781 A2 | 10/2005 |
| WO | WO-2006/066203 A2 | 6/2006 |
| WO | WO-2007/092182 A2 | 8/2007 |
| WO | WO-2009/102427 A2 | 8/2009 |
| WO | WO-2013/074974 A2 | 5/2013 |
| WO | WO-2013/165816 A2 | 11/2013 |
| WO | WO-2015/051283 A1 | 4/2015 |
| WO | WO-2016/016449 A1 | 2/2016 |
| WO | WO-2016/028649 A1 | 2/2016 |
| WO | WO-2016/049512 A1 | 3/2016 |
| WO | WO-2016/107877 A1 | 7/2016 |
| WO | WO-2017/153936 A1 | 9/2017 |
| WO | WO-2017/223194 A1 | 12/2017 |
| WO | WO-2018/098328 A1 | 5/2018 |
| WO | WO-2019/060686 A1 | 3/2019 |
| WO | WO-2019/217459 A1 | 11/2019 |
| WO | WO-2019/222479 A1 | 11/2019 |
| WO | WO-2020/010042 A1 | 1/2020 |
| WO | WO-2020/097044 A1 | 5/2020 |
| WO | WO-2020/222182 A1 | 11/2020 |
| WO | WO-2021/092371 A2 | 5/2021 |
| WO | WO-2021/202651 A1 | 10/2021 |
| WO | WO-2021/226167 A1 | 11/2021 |
| WO | WO-2021/230987 A1 | 11/2021 |

OTHER PUBLICATIONS

T. Miller et al., Phase 1-2 Trial of Antisense Oligonucleotide Tofersen for SOD1 ALS, N Engl J Med 2020;383:109-19.

| siRNA | Rat PK[a] | | | | | Met-ID |
|---|---|---|---|---|---|---|
| | Tissue exposure (AUC$_{last}$ (day*µg/g)) | | | | | Antisense |
| | Cerebral Cortex | Brain-stem | Spine (cervical) | Spine (thoracic) | Spine (lumbar) | (4-1344 hr pool)[b] |
| AD-1395731 | 255 | 197 | 225 | 528 | 1300 | 3' N-1 (37%) |
| AD-1395756 | 438 | 406 | 431 | 1020 | 1830 | 3' N-1 (17%) |
| AD-1395762 | 276 | 299 | 392 | 771 | 1640 | 3' N-1 (30%) |

[a] Parents and active metabolites are combined
[b] mean of cerebral cortex and lumbar spinal cord

FIG. 6

| Group No | Test Material | Dose Level (mg/dose) | Dose Volume (mL/dose) | Dose Concentration (mg/mL) | Number of Main Study Males | | |
|---|---|---|---|---|---|---|---|
| | | | | | Necropsy Day 31 | Necropsy Day 85 | Necropsy Day 169 |
| 1 | aCSF | 0 | 2 | 0 | 2 | 2 | - |
| 2 | AD-1395731 | 70 | 2 | 35 | 4 | 4 | 1 |
| 3 | AD-1395756 | 70 | 2 | 35 | 4 | 4 | 1 |
| 4 | AD-1395762 | 70 | 2 | 35 | 4 | 4 | 1 |
| 5 | aCSF | 0 | 2 | 0 | 2 | 2 | - |
| 6 | AD-1395731 | 120 | 2 | 60 | 4 | 4 | - |

FIG. 7

SUPEROXIDE DISMUTASE 1 (SOD1) IRNA COMPOSITIONS AND METHODS OF USE THEREOF FOR TREATING OR PREVENTING SUPEROXIDE DISMUTASE 1-(SOD1-) ASSOCIATED NEURODEGENERATIVE DISEASES

RELATED APPLICATIONS

This application is a 35 § U.S.C. 111(a) continuation application which claims the benefit of priority to PCT/US2022/016046, filed on Feb. 11, 2022, which claims the benefit of priority to U.S. Provisional Application No. 63/148,991, filed on Feb. 12, 2021, and U.S. Provisional Application No. 63/270,176, filed on Oct. 21, 2021. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Jun. 9, 2022, is named 121301_12703_SL.txt and is 365,258 bytes in size.

BACKGROUND OF THE INVENTION

Superoxide dismutase 1 (SOD1), also known as Cu/Zn superoxide dismutase (Cu/ZnSOD), is a ubiquitously expressed antioxidant enzyme that metabolizes superoxide radicals produced during cellular metabolism to molecular oxygen and hydrogen peroxide, and plays an important role in protecting cells from oxidative damage (McCord J M and Fridovich I. (1969) *J Bio Chem.* 244:6049-6055; Rosen D R (1993) *Nature.* 364:362; Trist B, et al. (2020) *Angew Chem Int Ed Engl.* Accepted Author Manuscript). The human SOD1 gene is located on chromosome 21q22.11 and it produces a 16 kDa protein that normally forms a 32 kDa homodimer. In mammalian cells, SOD1 is widely distributed in the cytosol, nucleus, lysosomes, peroxisomes, and intermembrane space (IMS) of mitochondria (Fukai T and Ushio-Fukai M. (2011) *Antioxid Redox Signal.* 15(6):1583-1606; Zhang S, et al. (2015) *Free Radic Biol Med.* 85:33-44; Huai J and Zhang Z. (2019) *Front. Neurol.* 10:527). The high cytosolic abundance of SOD1 distinguishes it from two other mammalian superoxide dismutases also involved in metabolizing superoxide radicals: the mitochondrial tetrameric manganese superoxide dismutase (SOD2) and the extracellular tetrameric Cu/Zn superoxide dismutase (SOD3). However, the activity of SOD1 accounts for approximately 50-80% of the total SOD activity in mammalian cells (Mindola P, et al. (2016) *Front. Physiol.* 7:594).

The structure of each SOD1 subunit consists of a β-barrel core and seven loops at the edge which are held together by an intramolecular disulfide bond, a binuclear metal binding site holding a copper and a zinc ions responsible for the catalyzing activity of SOD1, and a global hydrogen bond network (Huai J and Zhang Z. (2019) *Front. Neurol.* 10:527). Previous studies have shown that the stability, structure, and function of SOD1 is controlled by its post-translational modification, metal ion binding, and disulfide bond status. Loss of the metal cofactors and/or disruption of the disulfide bonds, often associated with mutations in the SOD1 gene, can result in pathogenic misfolding, aggregation, and/or dysfunction of SOD1 protein (Huai J and Zhang Z. (2019) *Front. Neurol.* 10:527).

Approximately 200 mutations have been documented throughout coding and non-coding regions of the SOD1 gene. Mutant SOD1 proteins are susceptible to misfolding which can compromise protective antioxidant function and result in the formation of abnormal molecular interactions (e.g., between multiple misfolded SOD1 units (aggregation) and between misfolded SOD1 and other cellular constituents), thereby contributing to pathology through both loss-of-function actions (e.g., diminished antioxidant activity, impaired nuclear translocation and promoter binding, and disrupted SOD1 redox signaling) and gain-of-function actions (e.g., neurotoxicity) (Trist B, et al. (2020) *Angew Chem Int Ed Engl.* Accepted Author Manuscript). SOD1 has been implicated in contributing to the pathology of many different diseases, including, for example, heart failure, cancer (e.g., lung adenocarcinoma, non-small-cell lung cancer, and breast cancer), diabetes, Amyotrophic Lateral Sclerosis (ALS), Alzheimer's disease (AD), Parkinson's disease, and Down's syndrome (DS) (Banks C J and Anderson J L. (2019) *Redox Biol.* 26:101270; Trist B, et al. (2020) *Angew Chem Int Ed Engl.* Accepted Author Manuscript). In the context of neurodegenerative disease, SOD1 has been implicated in the initiation and/or acceleration of damaging pathways in both neurons and surrounding glia, including: disruption of proteasome function, degradation of microtubules and microfilaments, endoplasmic reticulum stress, and redox dyshomeostasis. More specifically, mutant SOD1 has been implicated in a familial form of amyotrophic lateral sclerosis (fALS) where various SOD1 mutations can increase the propensity of SOD1 to aggregate, which is understood to induce motor neuron death. Additionally, wild-type SOD1 misfolding and dysfunction has been implicated in the death of spinal cord motor neurons in sporadic ALS (aALS), in the death of substantia nigra pars compacta (SNc) dopamine neurons in Parkinson's disease, and the death of neurons within the frontal cortex and hippocampus in Alzheimer's disease (Trist B, et al. (2020) *Angew Chem Int Ed Engl.* Accepted Author Manuscript). In addition, SOD1 has been implicated in neuron death by exacerbating other detrimental cellular pathologies, including Aβ plaque formation in Alzheimer's disease and α-synuclein deposition in Parkinson's disease.

Effective treatments for superoxide dismutase 1-associated neurodegenerative diseases are currently not available and any treatments that are available are palliative. Thus, there remains a need for an agent that can selectively and efficiently silence the SOD1 gene using the cell's own RNAi machinery that has both high biological activity and in vivo stability, and that can effectively inhibit expression of a target SOD1 gene.

BRIEF SUMMARY OF THE INVENTION

The present disclosure provides RNAi agent compositions which effect the RNA-induced silencing complex (RISC)-mediated cleavage of RNA transcripts of a superoxide dismutase 1 (SOD1) gene. The SOD1 gene may be within a cell, e.g., a cell within a subject, such as a human. The present disclosure also provides methods of using the RNAi agent compositions of the disclosure for inhibiting the expression of a SOD1 gene and/or for treating a subject who would benefit from inhibiting or reducing the expression of a SOD1 gene, e.g., a subject suffering or prone to suffering from a SOD1-associated neurodegenerative disease, e.g., Amyotrophic Lateral Sclerosis (ALS), Alzheimer's disease (AD), Parkinson's disease (PD), and Down's syndrome (DS).

Accordingly, in one aspect, the present invention provides a double stranded ribonucleic acid (dsRNA) agent, or a pharmaceutically acceptable salt thereof, comprising a sense strand and an antisense strand forming a double stranded region, wherein a) the nucleotide sequence of the sense strand differs by no more than 4 bases from the nucleotide sequence 5'-csascuu(Uhd)aaUfCfCfucuauccasgsa-3' (SEQ ID NO: 11) and the nucleotide sequence of the antisense strand differs by no more than 4 bases from the nucleotide sequence 5'-VPusdCsugdGadTagagdGaUfuaaagugsasg-3' (SEQ ID NO: 12), wherein VP is a 5'-vinyl phosphonate; (Uhd) is 2'-O-hexadecyl-uridine-3'-phosphate; s is a phosphorothioate linkage; a, g, c and u are 2'-O-methyl (2'-OMe) A, G, C, and U; dC, dG, and dT are 2'-deoxy C, G, and T; and Cf and Uf are 2'-deoxy-2'-fluoro (2'-F) C and U;

b) the nucleotide sequence of the sense strand differs by no more than 4 bases from the nucleotide sequence 5'-csasggu(Chd)cuCfAfCfuuuaauccsusa-3' (SEQ ID NO: 13) and the nucleotide sequence of the antisense strand differs by no more than 4 bases from the nucleotide sequence 5'-VPusdAsggdAudTaaagdTgAfggaccugscsg-3' (SEQ ID NO: 14), wherein VP is a 5'-vinyl phosphonate; (Chd) is 2'-O-hexadecyl-cytidine-3'-phosphate; s is a phosphorothioate linkage; a, g, c and u are 2'-O-methyl (2'-OMe) A, G, C, and U; dA and dT are 2'-deoxy A and T; and Af and Cf are 2'-deoxy-2'-fluoro (2'-F) A and C;

c) the nucleotide sequence of the sense strand differs by no more than 4 bases from the nucleotide sequence 5'-ususcgag(Chd)aGfAfAfggaaaguasasa-3' (SEQ ID NO: 15) and the nucleotide sequence of the antisense strand differs by no more than 4 bases from the nucleotide sequence 5'-VPusUfsuadCu(Tgn)uccuucUfgCfucgaasasu-3' (SEQ ID NO: 16), wherein VP is a 5'-vinyl phosphonate; (Chd) is 2'-O-hexadecyl-cytidine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dC is 2'-deoxy C; and Af, Cf, Gf, and Uf are 2'-deoxy-2'-fluoro (2'-F) A, C, G, and U;

d) the nucleotide sequence of the sense strand differs by no more than 4 bases from the nucleotide sequence 5'-gsasaag(Uhd)aaUfGfGfaccagugasasa-3' (SEQ ID NO: 17) and the nucleotide sequence of the antisense strand differs by no more than 4 bases from the nucleotide sequence 5'-VPusUfsucdAc(Tgn)gguccaUfuAfcuuucscsu-3' (SEQ ID NO: 18), wherein VP is a 5'-vinyl phosphonate; (Uhd) is 2'-O-hexadecyl-uridine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA is 2'-deoxy A; and Af, Gf, and Uf are 2'-deoxy-2'-fluoro (2'-F) A, G, and U;

e) the nucleotide sequence of the sense strand differs by no more than 4 bases from the nucleotide sequence 5'-asgsga(Uhd)gaaGfAfGfaggcaugususa-3' (SEQ ID NO: 19) and the nucleotide sequence of the antisense strand differs by no more than 4 bases from the nucleotide sequence 5'-VPusAfsacdAu(G2p)ccucucUfuCfauccususu-3' (SEQ ID NO: 20), wherein VP is a 5'-vinyl phosphonate; (Uhd) is 2'-O-hexadecyl-uridine-3'-phosphate; (G2p) is guanosine-2'-phosphate; s is a phosphorothioate linkage; a, g, c and u are 2'-O-methyl (2'-OMe) A, G, C, and U; dA is 2'-deoxy A; and Af, Cf, Gf, and Uf are 2'-deoxy-2'-fluoro (2'-F) A, C, G, and U;

f) the nucleotide sequence of the sense strand differs by no more than 4 bases from the nucleotide sequence 5'-asasgga(Ahd)agUfAfAfuggaccagsusa-3' (SEQ ID NO: 21) and the nucleotide sequence of the antisense strand differs by no more than 4 bases from the nucleotide sequence 5'-VPusdAscudGg(Tgn)ccaudTaCfuuuccuuscsu-3' (SEQ ID NO: 22), wherein VP is a 5'-vinyl phosphonate; (Ahd) is 2'-O-hexadecyl-adenosine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA, dG, and dT are 2'-deoxy A, G, and T; and Af, Cf, and Uf are 2'-deoxy-2'-fluoro (2'-F) A, C, and U;

g) the nucleotide sequence of the sense strand differs by no more than 4 bases from the nucleotide sequence 5'-asuscaa(Uhd)uuCfGfAfgcagaaggsasa-3' (SEQ ID NO: 23) and the nucleotide sequence of the antisense strand differs by no more than 4 bases from the nucleotide sequence 5'-VPusUfsccdTu(C2p)ugcucgAfaAfuugausgsg-3' (SEQ ID NO: 24), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U;

h) the nucleotide sequence of the sense strand differs by no more than 4 bases from the nucleotide sequence 5'-cscsuca(Chd)uuUfAfAfuccucuauscsa-3' (SEQ ID NO: 25) and the nucleotide sequence of the antisense strand differs by no more than 4 bases from the nucleotide sequence 5'-VPusdGsaudAg(Agn)ggaudTaAfagugaggsasc-3' (SEQ ID NO: 26), wherein VP is a 5'-vinyl phosphonate; (Chd) is 2'-O-hexadecyl-cytidine-3'-phosphate; (Agn) is adenosine-glycol nucleic acid (GNA), S-isomer; s is a phosphorothioate linkage; a, g, c and u are 2'-O-methyl (2'-OMe) A, G, C, and U; dA, dG, and dT are 2'-deoxy A, G, and T; and Af and Uf are 2'-deoxy-2'-fluoro (2'-F) A and U;

i) the nucleotide sequence of the sense strand differs by no more than 4 bases from the nucleotide sequence 5'-asasgga(Uhd)gaAfGfAfgaggcaugsusa-3' (SEQ ID NO: 27) and the nucleotide sequence of the antisense strand differs by no more than 4 bases from the nucleotide sequence 5'-VPusAfscadTg(C2p)cucucuUfcAfuccuususg-3' (SEQ ID NO: 28), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Gf, and Uf are 2'-deoxy-2'-fluoro (2'-F) A, G, and U; or j) the nucleotide sequence of the sense strand differs by no more than 4 bases from the nucleotide sequence 5'-asasuuu(Chd)gaGfCfAfgaaggaaasgsa-3' (SEQ ID NO: 29) and the nucleotide sequence of the antisense strand differs by no more than 4 bases from the nucleotide sequence 5'-VPusCfsuudTc(C2p)uucugcUfcGfaaauusgsg-3' (SEQ ID NO: 30), wherein VP is a 5'-vinyl phosphonate; (Chd) is 2'-O-hexadecyl-cytidine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U.

In one embodiment, a) the nucleotide sequence of the sense strand differs by no more than 3 bases from the nucleotide sequence 5'-cscuu(Uhd)aaUfCfCfucuauccasgsa-3' (SEQ ID NO: 11) and the nucleotide sequence of the antisense strand differs by no more than 3 bases from the nucleotide sequence 5'-VPusdCsugdGadTagagdGaUfuaaagugsasg-3' (SEQ ID NO: 12), wherein VP is a 5'-vinyl phosphonate; (Uhd) is 2'-O-hexadecyl-uridine-3'-phosphate; s is a phosphorothioate linkage; a, g, c and u are 2'-O-methyl (2'-OMe) A, G, C, and U; dC, dG, and dT are 2'-deoxy C, G, and T; and Cf and Uf are 2'-deoxy-2'-fluoro (2'-F) C and U;

b) the nucleotide sequence of the sense strand differs by no more than 3 bases from the nucleotide sequence 5'-csasggu(Chd)cuCfAfCfuuuaauccsusa-3' (SEQ ID NO: 13) and the nucleotide sequence of the antisense strand differs by no more than 3 bases from the nucleotide sequence 5'-VPusdAsggdAudTaaagdTgAfggaccugscsg-3' (SEQ ID NO: 14), wherein VP is a 5'-vinyl phosphonate; (Chd) is 2'-O-hexadecyl-cytidine-3'-phosphate; s is a phosphorothioate linkage; a, g, c and u are 2'-O-methyl (2'-OMe) A, G, C, and U; dA and dT are 2'-deoxy A and T; and Af and Cf are 2'-deoxy-2'-fluoro (2'-F) A and C;

c) the nucleotide sequence of the sense strand differs by no more than 3 bases from the nucleotide sequence 5'-ususcgag(Chd)aGfAfAfggaaaguasasa-3' (SEQ ID NO: 15) and the nucleotide sequence of the antisense strand differs by no more than 3 bases from the nucleotide sequence 5'-VPusUfsuadCu(Tgn)uccuucUfgCfucgaasasu-3' (SEQ ID NO: 16), wherein VP is a 5'-vinyl phosphonate; (Chd) is 2'-O-hexadecyl-cytidine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dC is 2'-deoxy C; and Af, Cf, Gf, and Uf are 2'-deoxy-2'-fluoro (2'-F) A, C, G, and U;

d) the nucleotide sequence of the sense strand differs by no more than 3 bases from the nucleotide sequence 5'-gsasaag(Uhd)aaUfGfGfaccagugasasa-3' (SEQ ID NO: 17) and the nucleotide sequence of the antisense strand differs by no more than 3 bases from the nucleotide sequence 5'-VPusUfsucdAc(Tgn)gguccaUfuAfcuuucscsu-3' (SEQ ID NO: 18), wherein VP is a 5'-vinyl phosphonate; (Uhd) is 2'-O-hexadecyl-uridine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA is 2'-deoxy A; and Af, Gf, and Uf are 2'-deoxy-2'-fluoro (2'-F) A, G, and U;

e) the nucleotide sequence of the sense strand differs by no more than 3 bases from the nucleotide sequence 5'-asgsga(Uhd)gaaGfAfGfaggcaugususa-3' (SEQ ID NO: 19) and the nucleotide sequence of the antisense strand differs by no more than 3 bases from the nucleotide sequence 5'-VPusAfsacdAu(G2p)ccucucUfuCfauccususu-3' (SEQ ID NO: 20), wherein VP is a 5'-vinyl phosphonate; (Uhd) is 2'-O-hexadecyl-uridine-3'-phosphate; (G2p) is guanosine-2'-phosphate; s is a phosphorothioate linkage; a, g, c and u are 2'-O-methyl (2'-OMe) A, G, C, and U; dA is 2'-deoxy A; and Af, Cf, Gf, and Uf are 2'-deoxy-2'-fluoro (2'-F) A, C, G, and U; f) the nucleotide sequence of the sense strand differs by no more than 3 bases from the nucleotide sequence 5'-asasgga(Ahd)agUfAfAfuggaccagsusa-3' (SEQ ID NO: 21) and the nucleotide sequence of the antisense strand differs by no more than 3 bases from the nucleotide sequence 5'-VPusdAscudGg(Tgn)ccaudTaCfuuuccuuscsu-3' (SEQ ID NO: 22), wherein VP is a 5'-vinyl phosphonate; (Ahd) is 2'-O-hexadecyl-adenosine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA, dG, and dT are 2'-deoxy A, G, and T; and Af, Cf, and Uf are 2'-deoxy-2'-fluoro (2'-F) A, C, and U;

g) the nucleotide sequence of the sense strand differs by no more than 3 bases from the nucleotide sequence 5'-asuscaa(Uhd)uuCfGfAfgcagaaggsasa-3' (SEQ ID NO: 23) and the nucleotide sequence of the antisense strand differs by no more than 3 bases from the nucleotide sequence 5'-VPusUfsccdTu(C2p)ugcucgAfaAfuugausgsg-3' (SEQ ID NO: 24), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U;

h) the nucleotide sequence of the sense strand differs by no more than 3 bases from the nucleotide sequence 5'-cscsuca(Chd)uuUfAfAfuccucuauscsa-3' (SEQ ID NO: 25) and the nucleotide sequence of the antisense strand differs by no more than 3 bases from the nucleotide sequence 5'-VPusdGsaudAg(Agn)ggaudTaAfagugaggsasc-3' (SEQ ID NO: 26), wherein VP is a 5'-vinyl phosphonate; (Chd) is 2'-O-hexadecyl-cytidine-3'-phosphate; (Agn) is adenosine-glycol nucleic acid (GNA), S-isomer; s is a phosphorothioate linkage; a, g, c and u are 2'-O-methyl (2'-OMe) A, G, C, and U; dA, dG, and dT are 2'-deoxy A, G, and T; and Af and Uf are 2'-deoxy-2'-fluoro (2'-F) A and U;

i) the nucleotide sequence of the sense strand differs by no more than 3 bases from the nucleotide sequence 5'-asasgga(Uhd)gaAfGfAfgaggcaugsusa-3' (SEQ ID NO: 27) and the nucleotide sequence of the antisense strand differs by no more than 3 bases from the nucleotide sequence 5'-VPusAfscadTg(C2p)cucucuUfcAfuccuususg-3' (SEQ ID NO: 28), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Gf, and Uf are 2'-deoxy-2'-fluoro (2'-F) A, G, and U; or j) the nucleotide sequence of the sense strand differs by no more than 3 bases from the nucleotide sequence 5'-asasuuu(Chd)gaGfCfAfgaaggaaasgsa-3' (SEQ ID NO: 29) and the nucleotide sequence of the antisense strand differs by no more than 3 bases from the nucleotide sequence 5'-VPusCfsuudTc(C2p)uucugcUfcGfaaauusgsg-3' (SEQ ID NO: 30), wherein VP is a 5'-vinyl phosphonate; (Chd) is 2'-O-hexadecyl-cytidine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U.

In one embodiment, a) the nucleotide sequence of the sense strand differs by no more than 2 bases from the nucleotide sequence 5'-cscscuu(Uhd)aaUfCfCfucuauccasgsa-3' (SEQ ID NO: 11) and the nucleotide sequence of the antisense strand differs by no more than 2 bases from the nucleotide sequence 5'-VPusdCsugdGadTagagdGaUfuaaagugsasg-3' (SEQ ID NO: 12), wherein VP is a 5'-vinyl phosphonate; (Uhd) is 2'-O-hexadecyl-uridine-3'-phosphate; s is a phosphorothioate linkage; a, g, c and u are 2'-O-methyl (2'-OMe) A, G, C, and U; dC, dG, and dT are 2'-deoxy C, G, and T; and Cf and Uf are 2'-deoxy-2'-fluoro (2'-F) C and U;

b) the nucleotide sequence of the sense strand differs by no more than 2 bases from the nucleotide sequence 5'-csasggu(Chd)cuCfAfCfuuuaauccsusa-3' (SEQ ID NO: 13) and the nucleotide sequence of the antisense strand differs by no more than 2 bases from the nucleotide sequence 5'-VPusdAsggdAudTaaagdTgAfggaccugscsg-3' (SEQ ID NO: 14), wherein VP is a 5'-vinyl phosphonate; (Chd) is 2'-O-hexadecyl-cytidine-3'-phosphate; s is a phosphorothioate linkage; a, g, c and u are 2'-O-methyl (2'-OMe) A, G, C, and U; dA and dT are 2'-deoxy A and T; and Af and Cf are 2'-deoxy-2'-fluoro (2'-F) A and C;

c) the nucleotide sequence of the sense strand differs by no more than 2 bases from the nucleotide sequence 5'-ususcgag(Chd)aGfAfAfggaaaguasasa-3' (SEQ ID NO: 15) and the nucleotide sequence of the antisense strand differs by no more than 2 bases from the nucleotide sequence 5'-VPusUfsuadCu(Tgn)uccuucUfgCfucgaasasu-3' (SEQ ID NO: 16), wherein VP is a 5'-vinyl phosphonate; (Chd) is 2'-O-hexadecyl-cytidine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dC is 2'-deoxy C; and Af, Cf, Gf, and Uf are 2'-deoxy-2'-fluoro (2'-F) A, C, G, and U;

d) the nucleotide sequence of the sense strand differs by no more than 2 bases from the nucleotide sequence 5'-gsasaag(Uhd)aaUfGfGfaccagugasasa-3' (SEQ ID NO: 17) and the nucleotide sequence of the antisense strand differs by no more than 2 bases from the nucleotide sequence 5'-VPusUfsucdAc(Tgn)gguccaUfuAfcuuucscsu-3' (SEQ ID NO: 18), wherein VP is a 5'-vinyl phosphonate; (Uhd) is 2'-O-hexadecyl-uridine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA is 2'-deoxy A; and Af, Gf, and Uf are 2'-deoxy-2'-fluoro (2'-F) A, G, and U;

e) the nucleotide sequence of the sense strand differs by no more than 2 bases from the nucleotide sequence 5'-asgsga(Uhd)gaaGfAfGfaggcaugususa-3' (SEQ ID NO: 19) and the nucleotide sequence of the antisense strand differs by no more than 2 bases from the nucleotide sequence 5'-VPusAfsacdAu(G2p)ccucucUfuCfauccususu-3' (SEQ ID NO: 20), wherein VP is a 5'-vinyl phosphonate; (Uhd) is 2'-O-hexadecyl-uridine-3'-phosphate; (G2p) is guanosine-2'-phosphate; s is a phosphorothioate linkage; a, g, c and u are 2'-O-methyl (2'-OMe) A, G, C, and U; dA is 2'-deoxy A; and Af, Cf, Gf, and Uf are 2'-deoxy-2'-fluoro (2'-F) A, C, G, and U;

f) the nucleotide sequence of the sense strand differs by no more than 2 bases from the nucleotide sequence 5'-asasgga(Ahd)agUfAfAfuggaccagsusa-3' (SEQ ID NO: 21) and the nucleotide sequence of the antisense strand differs by no more than 2 bases from the nucleotide sequence 5'-VPusdAscudGg(Tgn)ccaudTaCfuuuccuuscsu-3' (SEQ ID NO: 22), wherein VP is a 5'-vinyl phosphonate; (Ahd) is 2'-O-hexadecyl-adenosine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA, dG, and dT are 2'-deoxy A, G, and T; and Af, Cf, and Uf are 2'-deoxy-2'-fluoro (2'-F) A, C, and U;

g) the nucleotide sequence of the sense strand differs by no more than 2 bases from the nucleotide sequence 5'-asus-caa(Uhd)uuCfGfAfgcagaaggsasa-3' (SEQ ID NO: 23) and the nucleotide sequence of the antisense strand differs by no more than 2 bases from the nucleotide sequence 5'-VPusUfsccdTu(C2p)ugcucgAfaAfuugausgsg-3' (SEQ ID NO: 24), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U;

h) the nucleotide sequence of the sense strand differs by no more than 2 bases from the nucleotide sequence 5'-cscsuca(Chd)uuUfAfAfuccucuauscsa-3' (SEQ ID NO: 25) and the nucleotide sequence of the antisense strand differs by no more than 2 bases from the nucleotide sequence 5'-VPusdGsaudAg(Agn)ggaudTaAfagugaggsasc-3' (SEQ ID NO: 26), wherein VP is a 5'-vinyl phosphonate; (Chd) is 2'-O-hexadecyl-cytidine-3'-phosphate; (Agn) is adenosine-glycol nucleic acid (GNA), S-isomer; s is a phosphorothioate linkage; a, g, c and u are 2'-O-methyl (2'-OMe) A, G, C, and U; dA, dG, and dT are 2'-deoxy A, G, and T; and Af and Uf are 2'-deoxy-2'-fluoro (2'-F) A and U;

i) the nucleotide sequence of the sense strand differs by no more than 2 bases from the nucleotide sequence 5'-asasgga(Uhd)gaAfGfAfgaggcaugsusa-3' (SEQ ID NO: 27) and the nucleotide sequence of the antisense strand differs by no more than 2 bases from the nucleotide sequence 5'-VPusAfscadTg(C2p)cucucuUfcAfuccuususg-3' (SEQ ID NO: 28), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Gf, and Uf are 2'-deoxy-2'-fluoro (2'-F) A, G, and U; or j) the nucleotide sequence of the sense strand differs by no more than 2 bases from the nucleotide sequence 5'-asasuuu(Chd)gaGfCfAfgaaggaaasgsa-3' (SEQ ID NO: 29) and the nucleotide sequence of the antisense strand differs by no more than 2 bases from the nucleotide sequence 5'-VPusCfsuudTc(C2p)uucugcUfcGfaaauusgsg-3' (SEQ ID NO: 30), wherein VP is a 5'-vinyl phosphonate; (Chd) is 2'-O-hexadecyl-cytidine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U.

In one embodiment, a) the nucleotide sequence of the sense strand differs by no more than 1 base from the nucleotide sequence 5'-csascuu(Uhd)aaUfCfCfucuauccasgsa-3' (SEQ ID NO: 11) and the nucleotide sequence of the antisense strand differs by no more than 1 base from the nucleotide sequence 5'-VPusdCsugdGadTagagdGaUfuaaagugsasg-3' (SEQ ID NO: 12), wherein VP is a 5'-vinyl phosphonate; (Uhd) is 2'-O-hexadecyl-uridine-3'-phosphate; s is a phosphorothioate linkage; a, g, c and u are 2'-O-methyl (2'-OMe) A, G, C, and U; dC, dG, and dT are 2'-deoxy C, G, and T; and Cf and Uf are 2'-deoxy-2'-fluoro (2'-F) C and U;

b) the nucleotide sequence of the sense strand differs by no more than 1 base from the nucleotide sequence 5'-csasggu(Chd)cuCfAfCfuuuaauccsusa-3' (SEQ ID NO: 13) and the nucleotide sequence of the antisense strand differs by no more than 1 base from the nucleotide sequence 5'-VPusdAsggdAudTaaagdTgAfggaccugscsg-3' (SEQ ID NO: 14), wherein VP is a 5'-vinyl phosphonate; (Chd) is 2'-O-hexadecyl-cytidine-3'-phosphate; s is a phosphorothioate linkage; a, g, c and u are 2'-methyl (2'-OMe) A, G, C, and U; dA and dT are 2'-deoxy A and T; and Af and Cf are 2'-deoxy-2'-fluoro (2'-F) A and C;

c) the nucleotide sequence of the sense strand differs by no more than 1 base from the nucleotide sequence 5'-ususcgag(Chd)aGfAfAfggaaaguasasa-3' (SEQ ID NO: 15) and the nucleotide sequence of the antisense strand differs by no more than 1 base from the nucleotide sequence 5'-VPusUfsuadCu(Tgn)uccuucUfgCfucgaasasu-3' (SEQ ID NO: 16), wherein VP is a 5'-vinyl phosphonate; (Chd) is 2'-O-hexadecyl-cytidine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dC is 2'-deoxy C; and Af, Cf, Gf, and Uf are 2'-deoxy-2'-fluoro (2'-F) A, C, G, and U;

d) the nucleotide sequence of the sense strand differs by no more than 1 base from the nucleotide sequence 5'-gsasaag(Uhd)aaUfGfGfaccagugasasa-3' (SEQ ID NO: 17) and the nucleotide sequence of the antisense strand differs by no more than 1 base from the nucleotide sequence 5'-VPusUfsucdAc(Tgn)gguccaUfuAfcuuucscsu-3' (SEQ ID NO: 18), wherein VP is a 5'-vinyl phosphonate; (Uhd) is 2'-O-hexadecyl-uridine-3'-phosphate; (Tgn) is thymidine-glycol nucleic acid (GNA), S-Isomer;

s is a phosphorothioate linkage; a, g, c and u are 2'-O-methyl (2'-OMe) A, G, C, and U; dA is 2'-deoxy A; and Af, Gf, and Uf are 2'-deoxy-2'-fluoro (2'-F) A, G, and U;

e) the nucleotide sequence of the sense strand differs by no more than 1 base from the nucleotide sequence 5'-asgsga(Uhd)gaaGfAfGfaggcaugususa-3' (SEQ ID NO: 19) and the nucleotide sequence of the antisense strand differs by no more than 1 base from the nucleotide sequence 5'-VPusAfsacdAu(G2p)ccucucUfuCfauccususu-3' (SEQ ID NO: 20), wherein VP is a 5'-vinyl phosphonate; (Uhd) is 2'-O-hexadecyl-uridine-3'-phosphate; (G2p) is guanosine-2'-phosphate; s is a phosphorothioate linkage; a, g, c and u are 2'-O-methyl (2'-OMe) A, G, C, and U; dA is 2'-deoxy A; and Af, Cf, Gf, and Uf are 2'-deoxy-2'-fluoro (2'-F) A, C, G, and U;

f) the nucleotide sequence of the sense strand differs by no more than 1 base from the nucleotide sequence 5'-asasgga(Ahd)agUfAfAfuggaccagsusa-3' (SEQ ID NO: 21) and the nucleotide sequence of the antisense strand differs by no more than 1 base from the nucleotide sequence 5'-VPusdAscudGg(Tgn)ccaudTaCfuuuccuuscsu-3' (SEQ ID NO: 22), wherein VP is a 5'-vinyl phosphonate; (Ahd) is 2'-O-hexadecyl-adenosine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA, dG, and dT are 2'-deoxy A, G, and T; and Af, Cf, and Uf are 2'-deoxy-2'-fluoro (2'-F) A, C, and U;

g) the nucleotide sequence of the sense strand differs by no more than 1 base from the nucleotide sequence 5'-asuscaa(Uhd)uuCfGfAfgcagaaggsasa-3' (SEQ ID NO: 23) and the nucleotide sequence of the antisense strand differs by no more than 1 base from the nucleotide sequence 5'-VPusUfsccdTu(C2p)ugcucgAfaAfuugausgsg-3' (SEQ ID NO: 24), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U;

h) the nucleotide sequence of the sense strand differs by no more than 1 base from the nucleotide sequence 5'-cscsuca(Chd)uuUfAfAfuccucuauscsa-3' (SEQ ID NO: 25) and the nucleotide sequence of the antisense strand differs by no more than 1 base from the nucleotide sequence 5'-VPusdGsaudAg(Agn)ggaudTaAfagugaggsasc-3' (SEQ ID NO: 26), wherein VP is a 5'-vinyl phosphonate; (Chd) is 2'-O-hexadecyl-cytidine-3'-phosphate; (Agn) is adenosine-glycol nucleic acid (GNA), S-isomer; s is a phosphorothioate linkage; a, g, c and u are 2'-O-methyl (2'-OMe) A, G, C, and U; dA, dG, and dT are 2'-deoxy A, G, and T; and Af and Uf are 2'-deoxy-2'-fluoro (2'-F) A and U;

i) the nucleotide sequence of the sense strand differs by no more than 1 base from the nucleotide sequence 5'-asasgga(Uhd)gaAfGfAfgaggcaugsusa-3' (SEQ ID NO: 27) and the nucleotide sequence of the antisense strand differs by no more than 1 base from the nucleotide sequence 5'-VPusAfscadTg(C2p)cucucuUfcAfuccuususg-3' (SEQ ID NO: 28), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Gf, and Uf are 2'-deoxy-2'-fluoro (2'-F) A, G, and U; or j) the nucleotide sequence of the sense strand differs by no more than 1 base from the nucleotide sequence 5'-asasuuu(Chd)gaGfCfAfgaaggaaasgsa-3' (SEQ ID NO: 29) and the nucleotide sequence of the antisense strand differs by no more than 1 base from the nucleotide sequence 5'-VPusCfsuudTc(C2p)uucugcUfcGfaaauusgsg-3' (SEQ ID NO: 30), wherein VP is a 5'-vinyl phosphonate; (Chd) is 2'-O-hexadecyl-cytidine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U.

In one embodiment, a) the nucleotide sequence of the sense strand comprises the nucleotide sequence 5'-csascuu(Uhd)aaUfCfCfucuauccasgsa-3' (SEQ ID NO: 11) and the nucleotide sequence of the antisense strand comprises the nucleotide sequence 5'-VPusdCsugdGadTagagdGaUfuaaagugsasg-3' (SEQ ID NO: 12), wherein VP is a 5'-vinyl phosphonate; (Uhd) is 2'-O-hexadecyl-uridine-3'-phosphate; s is a phosphorothioate linkage; a, g, c and u are 2'-O-methyl (2'-OMe) A, G, C, and U; dC, dG, and dT are 2'-deoxy C, G, and T; and Cf and Uf are 2'-deoxy-2'-fluoro (2'-F) C and U;

b) the nucleotide sequence of the sense strand comprises the nucleotide sequence 5'-csasggu(Chd)cuCfAfCfuuuaauccsusa-3' (SEQ ID NO: 13) and the nucleotide sequence of the antisense strand comprises the nucleotide sequence 5'-VPusdAsggdAudTaaagdTgAfggaccugscsg-3' (SEQ ID NO: 14), wherein VP is a 5'-vinyl phosphonate; (Chd) is 2'-O-hexadecyl-cytidine-3'-phosphate; s is a phosphorothioate linkage; a, g, c and u are 2'-O-methyl (2'-OMe) A, G, C, and U; dA and dT are 2'-deoxy A and T; and Af and Cf are 2'-deoxy-2'-fluoro (2'-F) A and C;

c) the nucleotide sequence of the sense strand comprises the nucleotide sequence 5'-ususcgag(Chd)aGfAfAfggaaaguasasa-3' (SEQ ID NO: 15) and the nucleotide sequence of the antisense strand comprises the nucleotide sequence 5'-VPusUfsuadCu(Tgn)uccuucUfgCfucgaasasu-3' (SEQ ID NO: 16), wherein VP is a 5'-vinyl phosphonate; (Chd) is 2'-O-hexadecyl-cytidine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dC is 2'-deoxy C; and Af, Cf, Gf, and Uf are 2'-deoxy-2'-fluoro (2'-F) A, C, G, and U;

d) the nucleotide sequence of the sense strand comprises the nucleotide sequence 5'-gsasaag(Uhd)aaUfGfGfaccagugasasa-3' (SEQ ID NO: 17) and the nucleotide sequence of the antisense strand comprises the nucleotide sequence 5'-VPusUfsucdAc(Tgn)gguccaUfuAfcuuucscsu-3' (SEQ ID NO: 18), wherein VP is a 5'-vinyl phosphonate; (Uhd) is 2'-O-hexadecyl-uridine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA is 2'-deoxy A; and Af, Gf, and Uf are 2'-deoxy-2'-fluoro (2'-F) A, G, and U;

e) the nucleotide sequence of the sense strand comprises the nucleotide sequence 5'-asgsga(Uhd)gaaGfAfGfaggcaugususa-3' (SEQ ID NO: 19) and the nucleotide sequence of the antisense strand comprises the nucleotide sequence 5'-VPusAfsacdAu(G2p)ccucucUfuCfauccususu-3' (SEQ ID NO: 20), wherein VP is a 5'-vinyl phosphonate; (Uhd) is 2'-O-hexadecyl-uridine-3'-phosphate; (G2p) is guanosine-2'-phosphate; s is a phosphorothioate linkage; a, g, c and u are 2'-O-methyl (2'-OMe) A, G, C, and U; dA is 2'-deoxy A; and Af, Cf, Gf, and Uf are 2'-deoxy-2'-fluoro (2'-F) A, C, G, and U;

f) the nucleotide sequence of the sense strand comprises the nucleotide sequence 5'-asasgga(Ahd)agUfAfAfuggaccagsusa-3' (SEQ ID NO: 21) and the nucleotide sequence of the antisense strand comprises the nucleotide sequence 5'-VPusdAscudGg(Tgn)ccaudTaCfuuuccuuscsu- 3' (SEQ ID NO: 22), wherein VP is a 5'-vinyl phosphonate; (Ahd) is 2'-O-hexadecyl-adenosine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA, dG, and dT are 2'-deoxy A, G, and T; and Af, Cf, and Uf are 2'-deoxy-2'-fluoro (2'-F) A, C, and U;

g) the nucleotide sequence of the sense strand comprises the nucleotide sequence 5'-asuscaa(Uhd)uuCfGfAfgcagaaggsasa-3' (SEQ ID NO: 23) and the nucleotide sequence of the antisense strand comprises from the nucleotide sequence 5'-VPusUfsccdTu(C2p)ugcucgAfaAfuugausgsg-3' (SEQ ID NO: 24), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U;

h) the nucleotide sequence of the sense strand comprises the nucleotide sequence 5'-cscsuca(Chd)uuUfAfAfuccucuauscsa-3' (SEQ ID NO: 25) and the nucleotide sequence of the antisense strand comprises the nucleotide sequence 5'-VPusdGsaudAg(Agn)ggaudTaAfagugaggsasc-3' (SEQ ID NO: 26), wherein VP is a 5'-vinyl phosphonate; (Chd) is 2'-O-hexadecyl-cytidine-3'-phosphate; (Agn) is adenosine-glycol nucleic acid (GNA), S-isomer; s is a phosphorothioate linkage; a, g, c and u are 2'-O-methyl (2'-OMe) A, G, C, and U; dA, dG, and dT are 2'-deoxy A, G, and T; and Af and Uf are 2'-deoxy-2'-fluoro (2'-F) A and U;

i) the nucleotide sequence of the sense strand comprises the nucleotide sequence 5'-asasgga(Uhd)gaAfGfAfgaggcaugsusa-3' (SEQ ID NO: 27) and the nucleotide sequence of the antisense strand comprises the nucleotide sequence 5'-VPusAfscadTg(C2p)cucucuUfcAfuccuususg-3' (SEQ ID NO: 28), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Gf, and Uf are 2'-deoxy-2'-fluoro (2'-F) A, G, and U; or j) the nucleotide sequence of the sense strand comprises the nucleotide sequence 5'-asasuuu(Chd)gaGfCfAfgaaggaaasgsa-3' (SEQ ID NO: 29) and the nucleotide sequence of the antisense strand comprises the nucleotide sequence 5'-VPusCfsuudTc(C2p)uucugcUfcGfaaauusgsg-3' (SEQ ID NO: 30), wherein VP is a 5'-vinyl phosphonate; (Chd) is 2'-O-hexadecyl-cytidine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U.

In one embodiment, a) the nucleotide sequence of the sense strand consists of the nucleotide sequence 5'-csascuu(Uhd)aaUfCfCfucuauccasgsa-3' (SEQ ID NO: 11) and the nucleotide sequence of the antisense strand consists of the nucleotide sequence 5'-VPusdCsugdGadTagagdGaUfuaaagugsasg-3' (SEQ ID NO: 12), wherein VP is a 5'-vinyl phosphonate; (Uhd) is 2'-O-hexadecyl-uridine-3'-phosphate; s is a phosphorothioate linkage; a, g, c and u are 2'-O-methyl (2'-OMe) A, G, C, and U; dC, dG, and dT are 2'-deoxy C, G, and T; and Cf and Uf are 2'-deoxy-2'-fluoro (2'-F) C and U;

b) the nucleotide sequence of the sense strand consists of the nucleotide sequence 5'-csasggu(Chd)cuCfAfCfuuuaauccsusa-3' (SEQ ID NO: 13) and the nucleotide sequence of the antisense strand consists of the nucleotide sequence 5'-VPusdAsggdAudTaaagdTgAfggaccugscsg-3' (SEQ ID NO: 14), wherein VP is a 5'-vinyl phosphonate; (Chd) is 2'-O-hexadecyl-cytidine-3'-phosphate; s is a phosphorothioate linkage; a, g, c and u are 2'-O-methyl (2'-OMe) A, G, C, and U; dA and dT are 2'-deoxy A and T; and Af and Cf are 2'-deoxy-2'-fluoro (2'-F) A and C;

c) the nucleotide sequence of the sense strand consists of the nucleotide sequence 5'-ususcgag(Chd)aGfAfAfggaaaguasasa-3' (SEQ ID NO: 15) and the nucleotide sequence of the antisense strand consists of the nucleotide sequence 5'-VPusUfsuadCu(Tgn)uccuucUfgCfucgaasasu-3' (SEQ ID NO: 16), wherein VP is a 5'-vinyl phosphonate; (Chd) is 2'-O-hexadecyl-cytidine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dC is 2'-deoxy C; and Af, Cf, Gf, and Uf are 2'-deoxy-2'-fluoro (2'-F) A, C, G, and U;

d) the nucleotide sequence of the sense strand consists of the nucleotide sequence 5'-gsasaag(Uhd)aaUfGfGfaccagugasasa-3' (SEQ ID NO: 17) and the nucleotide sequence of the antisense strand consists of the nucleotide sequence 5'-VPusUfsucdAc(Tgn)gguccaUfuAfcuuucscsu-3' (SEQ ID NO: 18), wherein VP is a 5'-vinyl phosphonate; (Uhd) is 2'-O-hexadecyl-uridine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA is 2'-deoxy A; and Af, Gf, and Uf are 2'-deoxy-2'-fluoro (2'-F) A, G, and U;

e) the nucleotide sequence of the sense strand consists of the nucleotide sequence 5'-asgsga(Uhd)gaaGfAfGfaggcaugususa-3' (SEQ ID NO: 19) and the nucleotide sequence of the antisense strand consists of the nucleotide sequence 5'-VPusAfsacdAu(G2p)ccucucUfuCfauccususu-3' (SEQ ID NO: 20), wherein VP is a 5'-vinyl phosphonate; (Uhd) is 2'-O-hexadecyl-uridine-3'-phosphate; (G2p) is guanosine-2'-phosphate; s is a phosphorothioate linkage; a, g, c and u are 2'-O-methyl (2'-OMe) A, G, C, and U; dA is 2'-deoxy A; and Af, Cf, Gf, and Uf are 2'-deoxy-2'-fluoro (2'-F) A, C, G, and U;

f) the nucleotide sequence of the sense strand consists of the nucleotide sequence 5'-asasgga(Ahd)agUfAfAfuggaccagsusa-3' (SEQ ID NO: 21) and the nucleotide sequence of the antisense strand consists of the nucleotide sequence 5'-VPusdAscudGg(Tgn)ccaudTaCfuuuccuuscsu-3' (SEQ ID NO: 22), wherein VP is a 5'-vinyl phosphonate; (Ahd) is 2'-O-hexadecyl-adenosine-3'-phosphate; (Tgn) is thymidine-glycol nucleic acid (GNA), S-Isomer; s is a phosphorothioate linkage; a, g, c and u are 2'-O-methyl (2'-OMe) A, G, C, and U; dA, dG, and dT are 2'-deoxy A, G, and T; and Af, Cf, and Uf are 2'-deoxy-2'-fluoro (2'-F) A, C, and U;

g) the nucleotide sequence of the sense strand consists of the nucleotide sequence 5'-asuscaa(Uhd)uuCfGfAfgcagaaggsasa-3' (SEQ ID NO: 23) and the nucleotide sequence of the antisense strand consists of from the nucleotide sequence 5'-VPusUfsccdTu(C2p)ugcucgAfaAfuugausgsg-3' (SEQ ID NO: 24), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U;

h) the nucleotide sequence of the sense strand consists of the nucleotide sequence 5'-cscsuca(Chd)uuUfAfAfuccucuauscsa-3' (SEQ ID NO: 25) and the nucleotide sequence of the antisense strand consists of the nucleotide sequence 5'-VPusdGsaudAg(Agn)ggaudTaAfagugaggsasc-3' (SEQ ID NO: 26), wherein VP is a 5'-vinyl phosphonate; (Chd) is 2'-O-hexadecyl-cytidine-3'-phosphate; (Agn) is adenosine-glycol nucleic acid (GNA), S-isomer; s is a phosphorothioate linkage; a, g, c and u are 2'-O-methyl (2'-OMe) A, G, C, and U; dA, dG, and dT are 2'-deoxy A, G, and T; and Af and Uf are 2'-deoxy-2'-fluoro (2'-F) A and U;

i) the nucleotide sequence of the sense strand consists of the nucleotide sequence 5'-asasgga(Uhd)gaAfGfAfgagg-caugsusa-3' (SEQ ID NO: 27) and the nucleotide sequence of the antisense strand consists of the nucleotide sequence 5'-VPusAfscadTg(C2p)cucucuUfcAfuccuususg-3' (SEQ ID NO: 28), wherein VP is a 5'-vinyl phosphonate; (Uhd) is 2'-O-hexadecyl-uridine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Gf, and Uf are 2'-deoxy-2'-fluoro (2'-F) A, G, and U; or j) the nucleotide sequence of the sense strand consists of the nucleotide sequence 5'-asasuuu(Chd)gaGfCfAfgaaggaaasgsa-3' (SEQ ID NO: 29) and the nucleotide sequence of the antisense strand consists of the nucleotide sequence 5'-VPusCfsuudTc(C2p)uucugcUfcGfaaauusgsg-3' (SEQ ID NO: 30), wherein VP is a 5'-vinyl phosphonate; (Chd) is 2'-O-hexadecyl-cytidine-3'-phosphate; (C2p) is cytidine-2'-phosphate; s is a phosphorothioate linkage; a, g, c and u are 2'-O-methyl (2'-OMe) A, G, C, and U; dT is 2'-deoxy T; and Af, Cf, Gf, and Uf are 2'-deoxy-2'-fluoro (2'-F) A, C, G, and U.

In one embodiment, the dsRNA agent is in the form of a sodium salt.

In one aspect, the present invention provides a double stranded ribonucleic acid (dsRNA) agent for inhibiting expression of superoxide dismutase 1 (SOD1), wherein the dsRNA agent comprises a sense strand and an antisense strand forming a double stranded region, wherein the sense strand comprises at least 15, e.g., 15, 16, 17, 18, 19, 20, or 21, contiguous nucleotides from any one of the nucleotide sequences of nucleotides 201-223, 204-226, 207-229, 216-238, 219-241, 328-350, 333-355, 336-358, 372-394, or 373-395 of SEQ ID NO: 1, and the antisense strand comprises at least 15, e.g., 15, 16, 17, 18, 19, 20, 21, 22, or 23, contiguous nucleotides from the corresponding nucleotide sequence of SEQ ID NO: 2, wherein (i) the dsRNA agent comprises at least one modified nucleotide, (ii) the double stranded region is 15-30 nucleotide pairs in length, and (iii) the sense strand or the antisense strand is conjugated to one or more lipophilic moieties.

In one embodiment, the sense strand comprises at least 15, e.g., 15, 16, 17, 18, 19, 20, or 21, contiguous nucleotides from any one of the nucleotide sequences of nucleotides 207-229, 219-241, 328-350, or 336-358 of SEQ ID NO: 1, and the antisense strand comprises at least 15, e.g., 15, 16, 17, 18, 19, 20, 21, 22, or 23, contiguous nucleotides from the corresponding nucleotide sequence of SEQ ID NO: 2.

In another embodiment, the sense strand comprises at least 15, e.g., 15, 16, 17, 18, 19, 20, or 21 contiguous nucleotides from any one of the nucleotide sequences of nucleotides 207-229, 328-350, or 336-358 of SEQ ID NO: 1, and the antisense strand comprises at least 15, e.g., 15, 16, 17, 18, 19, 20, 21, 22, or 23, contiguous nucleotides from the corresponding nucleotide sequence of SEQ ID NO: 2.

In one embodiment, the sense strand comprises at least 15, e.g., 15, 16, 17, 18, 19, 20, or 21, contiguous nucleotides from nucleotides 336-358 of SEQ ID NO: 1, and the antisense strand comprises at least 15, e.g., 15, 16, 17, 18, 19, 20, 21, 22, or 23, contiguous nucleotides from the corresponding nucleotide sequence of SEQ ID NO: 2.

In another embodiment, the antisense strand comprises at least 15, e.g., 15, 16, 17, 18, 19, 20, 21, 22, or 23, contiguous nucleotides from any one of the antisense strand nucleotide sequences of a duplex selected from the group consisting of AD-1395762, AD-1395756, AD-1395731, AD-1395743, AD-1395771, AD-1395738, AD-1395718, AD-1395760, AD-1395764, or AD-1395724.

In one embodiment, the antisense strand comprises at least 15, e.g., 15, 16, 17, 18, 19, 20, 21, 22, or 23, contiguous nucleotides from any one of the antisense strand nucleotide sequences of a duplex selected from the group consisting of AD-1395762, AD-1395756, AD-1395731, and AD-1395743.

In one embodiment, the antisense strand comprises at least 15, e.g., 15, 16, 17, 18, 19, 20, 21, 22, or 23, contiguous nucleotides from any one of the antisense strand nucleotide sequences of a duplex selected from the group consisting of AD-1395762, AD-1395756, and AD-1395731.

In another embodiment, the antisense strand comprises at least 15, e.g., 15, 16, 17, 18, 19, 20, 21, 22, or 23, contiguous nucleotides from the antisense strand nucleotide sequence of duplex AD-1395762.

In one embodiment, all of the nucleotides of the sense strand and all of the nucleotides of the antisense strand comprise a modification.

In one embodiment, at least one of the modified nucleotides is selected from the group a deoxy-nucleotide, a 3'-terminal deoxythimidine (dT) nucleotide, a 2'-O-methyl modified nucleotide, a 2'-fluoro modified nucleotide, a 2'-deoxy-modified nucleotide, a 2'-5'-linked ribonucleotide (3'-RNA), a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a 5'-phosphorothioate group, a nucleotide comprising a 5'-methylphosphonate group, a nucleotide comprising a 5' phosphate or 5' phosphate mimic, a nucleotide comprising vinyl phosphonate, a glycol nucleic acid (GNA), a glycol nucleic acid S-Isomer (S-GNA), a nucleotide comprising 2-hydroxymethyl-tetrahydrofuran-5-phosphate, a nucleotide comprising 2'-deoxy-thymidine-3'phosphate, a nucleotide comprising 2'-deoxy-guanosine-3'-phosphate, and a terminal nucleotide linked to a cholesteryl derivative and a dodecanoic acid bisdecylamide group; and combinations thereof.

In one embodiment, the modified nucleotide is selected from the group consisting of a 2'-deoxy-2'-fluoro modified nucleotide, a 2'-deoxy-modified nucleotide, 3'-terminal deoxythimidine nucleotides (dT), a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

In another embodiment, the modifications on the nucleotides are independently selected from the group consisting of 2'-deoxy, 2'-O-methyl, 3'-RNA, GNA, S-GNA, and 2'-deoxy-2'-fluoro modifications.

In one embodiment, the dsRNA agent further comprises at least one phosphorothioate internucleotide linkage.

In one embodiment, the dsRNA agent comprises 6-8 phosphorothioate internucleotide linkages.

In one embodiment, at least one strand comprises a 3' overhang of at least 1 nucleotide.

In another embodiment, at least one strand comprises a 3' overhang of 2 nucleotides.

In one embodiment, the double stranded region is 17-23 nucleotide pairs in length.

In another embodiment, the double stranded region is 19-21 nucleotide pairs in length.

In one embodiment, the double stranded region is 21-23 nucleotide pairs in length.

In one embodiment, each strand has 19-30 nucleotides.

In one embodiment, the one or more lipophilic moieties are conjugated to one or more internal positions on at least one strand.

In one embodiment, one lipophilic moiety is conjugated an internal position selected from the group consisting of positions 4-8 and 13-18 on the sense strand, and positions 6-10 and 15-18 on the antisense strand, counting from the 5' end of each strand.

In one embodiment, the internal position is selected from the group consisting of positions 5, 6, 7, 15, and 17 on the sense strand, counting from the 5'-end of the strand.

In another embodiment, the internal position is selected from the group consisting of positions 15 and 17 on the antisense strand, counting from the 5'-end of the strand.

In one embodiment, the internal position is selected from the group consisting of positions 6 and 7 of the sense strand.

In one embodiment, the lipophilic moiety is an aliphatic, alicyclic, or polyalicyclic compound.

In one embodiment, the lipophilic moiety contains a saturated or unsaturated C4-C30 hydrocarbon chain, and an optional functional group selected from the group consisting of hydroxyl, amine, carboxylic acid, sulfonate, phosphate, thiol, azide, and alkyne.

In one embodiment, the lipophilic moiety contains a saturated or unsaturated C6-C18 hydrocarbon chain.

In one embodiment, the lipophilic moiety contains a saturated or unsaturated C16 hydrocarbon chain.

In one embodiment, the saturated or unsaturated C16 hydrocarbon chain is conjugated to position 6 or 7 of the sense strand, counting from the 5'-end of the sense strand.

In one embodiment, the dsRNA agent further comprises a phosphate or phosphate mimic at the 5'-end of the antisense strand.

In one embodiment, the phosphate mimic is a 5'-vinyl phosphonate (VP).

In another embodiment, the phosphate mimic is a 5'-E-vinyl phosphonate (VP).

In one embodiment, the base pair at the 1 position of the 5'-end of the antisense strand of the duplex is an AU base pair.

In one embodiment, the sense strand has a total of 21 nucleotides and the antisense strand has a total of 23 nucleotides.

The present invention also provides cells and pharmaceutical compositions comprising a pharmaceutically acceptable diluent comprising the dsRNA agents disclosed herein.

In one aspect the present invention provides a method of inhibiting expression of a SOD1 gene in a cell. The method includes contacting the cell with a dsRNA agent or a pharmaceutical composition of the invention; and maintaining the cell produced in step (a) for a time sufficient to obtain degradation of the mRNA transcript of the SOD1 gene, thereby inhibiting expression of the SOD1 gene in the cell.

In one embodiment, the cell is within a human subject.

In one embodiment, the subject meets at least one diagnostic criterion for a SOD1-associated neurodegenerative disease or has been diagnosed with a SOD1-associated neurodegenerative disease.

In one embodiment, the SOD1-associated neurodegenerative disease is selected from the group consisting of Amyotrophic Lateral Sclerosis (ALS), Alzheimer's disease (AD), Parkinson's disease (PD), and Down's syndrome (DS).

In one aspect, the present invention provides a method of treating a subject diagnosed with a SOD1-associated neurodegenerative disease, the method comprising administering to the subject a therapeutically effective amount of a dsRNA agent or a pharmaceutical composition of the invention, thereby treating the subject.

In one embodiment, treating comprises amelioration of at least one sign or symptom of the disease.

In another embodiment, treating comprises prevention of progression of the disease.

In one embodiment, the SOD1-associated neurodegenerative disease is selected from the group consisting of Amyotrophic Lateral Sclerosis (ALS), Alzheimer's disease (AD), Parkinson's disease (PD), and Down's syndrome (DS).

In another aspect, the present invention provides a method of preventing development of a SOD1-associated neurodegenerative disease in a subject meeting at least one diagnostic criterion for a SOD1-associated neurodegenerative disease, the method comprising administering to the subject a therapeutically effective amount of a dsRNA agent or a pharmaceutical composition of the invention, thereby preventing the development of a SOD1-associated neurodegenerative disease in the subject meeting at least one diagnostic criterion for a SOD1-associated neurodegenerative disease.

In one embodiment, the subject is human.

In one embodiment, the subject has been diagnosed with a SOD1-associated neurodegenerative disease.

In one embodiment, the SOD1-associated neurodegenerative disease is selected from the group consisting of Amyotrophic Lateral Sclerosis (ALS), Alzheimer's disease (AD), Parkinson's disease (PD), and Down's syndrome (DS).

In one embodiment, the dsRNA agent is administered to the subject intrathecally or intracerebroventricularly.

In one aspect, the instant disclosure provides a double stranded ribonucleic acid (RNAi) agent for inhibiting expression of a superoxide dismutase 1 (SOD1) gene, wherein the RNAi agent includes a sense strand and an antisense strand, and wherein the antisense strand includes a region of complementarity which includes at least 15, e.g., 15, 16, 17, 18, 19, 20, 21, 22, or 23, contiguous nucleotides differing by no more than 3 nucleotides (i.e., differing by 3, 2, 1, or 0 nucleotides) from any one of the antisense sequences listed in any one of Tables 2-7, 12, 13, and 18-20. In certain embodiments, the antisense strand includes a region of complementarity which includes at least 15, e.g., 15, 16, 17, 18, 19, 20, 21, 22, or 23, contiguous nucleotides of any one of the antisense sequences listed in any one of Tables 2-7, 12, 13, and 18-20. In certain embodiments, the antisense strand includes a region of complementarity which includes at least 19, e.g., 19, 20, 21, 22, or 23, contiguous nucleotides differing by no more than 3 nucleotides (i.e., differing by 3, 2, 1, or 0 nucleotides) from any one of the antisense sequences listed in any one of Tables 2-7, 12, 13, and 18-20. In certain embodiments, the antisense strand includes a region of complementarity which includes at least 19 e.g., 19, 20, 21, 22, or 23, contiguous nucleotides of any one of the antisense sequences listed in any one of Tables 2-7, 12, 13, and 18-20. In certain embodiments, thymine-to-uracil or uracil-to-thymine differences between aligned (compared) sequences are not counted as nucleotides that differ between the aligned (compared) sequences.

In some embodiments, the sense strand or the antisense strand is conjugated to one or more lipophilic moieties.

In some embodiments, the agents include one or more lipophilic moieties conjugated to one or more internal nucleotide positions, optionally via a linker or carrier.

In other embodiments, the agent further comprises a targeting ligand that targets a liver tissue, e.g., one or more GalNAc derivatives, optionally conjugated to the double stranded RNAi agent via a linker or carrier.

In yet other embodiments, the agents further comprise one or more lipophilic moieties conjugated to one or more internal nucleotide positions, optionally via a linker or carrier and a targeting ligand that targets a liver tissue, e.g., one or more GalNAc derivatives, optionally conjugated to the double stranded RNAi agent via a linker or carrier.

Another aspect of the instant disclosure provides a double stranded RNAi agent for inhibiting expression of a superoxide dismutase 1 (SOD1) gene, wherein the dsRNA agent includes a sense strand and an antisense strand, wherein the sense strand includes at least 15, e.g., 15, 16, 17, 18, 19, 20, or 21, contiguous nucleotides differing by no more than 3 nucleotides (i.e., differing by 3, 2, 1, or 0 nucleotides) from any one of the sense strand sequences presented in Tables 2-7, 12, 13, and 18-20; and wherein the antisense strand includes at least 15, e.g., 15, 16, 17, 18, 19, 20, 21, 22, or 23, contiguous nucleotides differing by no more than 3, e.g., 3, 2, 1, or 1, nucleotides from any one of antisense strand nucleotide sequences presented in Tables 2-7, 12, 13, and 18-20. In certain embodiments, the sense strand includes at least 15 e.g., 15, 16, 17, 18, 19, 20, or 21, contiguous nucleotides of any one of the sense strand sequences presented in Tables 2-7, 12, 13, and 18-20; and the antisense strand includes at least 15, e.g., 15, 16, 17, 18, 19, 20, 21, 22, or 23, contiguous nucleotides of any one of the antisense strand nucleotide sequences presented in Tables 2-7, 12, 13, and 18-20. In certain embodiments, the sense strand includes at least 19 e.g., 19, 20, or 21, contiguous nucleotides of any one of the sense strand sequences presented in Tables 2-7, 12, 13, and 18-20; and the antisense strand includes at least 19 e.g., 19, 20, 21, 22, or 23, contiguous nucleotides of any one of the antisense strand nucleotide sequences presented in Tables 2-7, 12, 13, and 18-20.

In some embodiments, the agents include one or more lipophilic moieties conjugated to one or more internal nucleotide positions, optionally via a linker or carrier.

In other embodiments, the agent further comprises a targeting ligand that targets a liver tissue, e.g., one or more GalNAc derivatives, optionally conjugated to the double stranded RNAi agent via a linker or carrier.

In yet other embodiments, the agents further comprise one or more lipophilic moieties conjugated to one or more internal nucleotide positions, optionally via a linker or carrier and a targeting ligand that targets a liver tissue, e.g., one or more GalNAc derivatives, optionally conjugated to the double stranded RNAi agent via a linker or carrier.

An additional aspect of the disclosure provides a double stranded RNAi agent for inhibiting expression of an superoxide dismutase 1 (SOD1) gene, wherein the dsRNA agent includes a sense strand and an antisense strand, wherein the sense strand includes at least 15 contiguous nucleotides differing by no more than 3 nucleotides (i.e., differing by 3, 2, 1, or 0 nucleotides) from any one of the nucleotide sequences of SEQ ID NOs: 1, 3, 5, 7, or 9, or a nucleotide sequence having at least 90% nucleotide sequence identity, e.g. 90, 91, 92, 93, 94, 95, 96, 97, 98, 99, or 100% identity, to the entire nucleotide sequence of any one of SEQ ID NOs: 1, 3, 5, 7, or 9, wherein a substitution of a uracil for any thymine of SEQ ID NOs: 1, 3, 5, 7, and 9 (when comparing aligned sequences) does not count as a difference that contributes to the differing by no more than 3 nucleotides (i.e., differing by 3, 2, 1, or 0 nucleotides) from any one of the nucleotide sequences of SEQ ID NOs: 1, 3, 5, 7, or 9, or the nucleotide sequence having at least 90% nucleotide sequence identity, e.g. 90, 91, 92, 93, 94, 95, 96, 97, 98, 99, or 100% identity, to the entire nucleotide sequence of any one of SEQ ID NOs: 1, 3, 5, 7, or 9; and wherein the antisense strand includes at least 15 contiguous nucleotides differing by no more than 3 nucleotides from any one of the nucleotide sequences of SEQ ID NOs: 2, 4, 6, 8, or 10, or a nucleotide sequence having at least 90% nucleotide sequence identity, e.g. 90, 91, 92, 93, 94, 95, 96, 97, 98, 99, or 100% identity, to the entire nucleotide sequence of any one of SEQ ID NOs: 2, 4, 6, 8, or 10, wherein a substitution of a uracil for any thymine of SEQ ID NOs: 2, 4, 6, 8, or 10 (when comparing aligned sequences) does not count as a difference that contributes to the differing by no more than 3 nucleotides from any one of the nucleotide sequences of SEQ ID NOs: 2, 4, 6, 8, or 10, or the nucleotide sequence having at least 90% nucleotide sequence identity, e.g. 90, 91, 92, 93, 94, 95, 96, 97, 98, 99, or 100% identity, to the entire nucleotide sequence of any one of SEQ ID NOs: 2, 4, 6, 8, or 10, wherein at least one of the sense strand and the antisense strand includes one or more lipophilic moieties conjugated to one or more internal nucleotide positions, optionally via a linker or carrier.

In one embodiment, the double stranded RNAi agent targeted to SOD1 comprises a sense strand which includes at least 15 e.g., 15, 16, 17, 18, 19, 20, or 21, contiguous nucleotides differing by no more than 3 nucleotides (i.e., differing by 3, 2, 1, or 0 nucleotides) from the nucleotide sequence of the sense strand nucleotide sequence of a duplex in Tables 2-7, 12, 13, and 18-20.

In one embodiment, the double stranded RNAi agent targeted to SOD1 comprises an antisense strand which includes at least 15 e.g., 15, 16, 17, 18, 19, 20, 21, 22, or 23, contiguous nucleotides differing by no more than 3 nucleotides (i.e., differing by 3, 2, 1, or 0 nucleotides) from the antisense nucleotide sequence of a duplex in one of Tables 2-7, 12, 13, and 18-20.

In some embodiments, the agent further comprises a targeting ligand that targets a liver tissue, e.g., one or more GalNAc derivatives, optionally conjugated to the double stranded RNAi agent via a linker or carrier.

Optionally, the double stranded RNAi agent includes at least one modified nucleotide.

In certain embodiments, the lipophilicity of the lipophilic moiety, measured by log $K_{ow}$, exceeds 0.

In some embodiments, the hydrophobicity of the double-stranded RNAi agent, measured by the unbound fraction in a plasma protein binding assay of the double-stranded RNAi agent, exceeds 0.2. In a related embodiment, the plasma protein binding assay is an electrophoretic mobility shift assay using human serum albumin protein.

In certain embodiments, substantially all of the nucleotides of the sense strand are modified nucleotides. Optionally, all of the nucleotides of the sense strand are modified nucleotides.

In some embodiments, substantially all of the nucleotides of the antisense strand are modified nucleotides. Optionally, all of the nucleotides of the antisense strand are modified nucleotides.

Optionally, all of the nucleotides of the sense strand and all of the nucleotides of the antisense strand are modified nucleotides.

In one embodiment, at least one of the modified nucleotides is a deoxy-nucleotide, a 3'-terminal deoxythimidine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a 5'-phosphorothioate group, a nucleotide comprising a 5'-methylphosphonate group, a nucleotide comprising a 5' phosphate or 5' phosphate mimic, a nucleotide comprising vinyl phosphonate, a nucleotide comprising adenosine-glycol nucleic acid (GNA), a nucleotide comprising thymidine-glycol nucleic acid (GNA)S-Isomer, a nucleotide comprising 2-hydroxymethyl-tetrahydrofurane-5-phosphate, a nucleotide comprising 2'-deoxythymidine-3'phosphate, a nucleotide comprising 2'-deoxyguanosine-3'-phosphate, or a terminal nucleotide linked to a cholesteryl derivative or a dodecanoic acid bisdecylamide group.

In a related embodiment, the modified nucleotide is a 2'-deoxy-2'-fluoro modified nucleotide, a 2'-deoxy-modified nucleotide, 3'-terminal deoxythimidine nucleotides (dT), a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

In one embodiment, the modified nucleotide includes a short sequence of 3'-terminal deoxythimidine nucleotides (dT).

In another embodiment, the modifications on the nucleotides are 2'-O-methyl, 2'fluoro, and GNA modifications.

In an additional embodiment, the double stranded RNAi agent includes at least one phosphorothioate internucleotide linkage. Optionally, the double stranded RNAi agent includes 6-8 (e.g., 6, 7, or 8) phosphorothioate internucleotide linkages.

In certain embodiments, the region of complementarity is at least 17 nucleotides in length. Optionally, the region of complementarity is 19-23 nucleotides in length. Optionally, the region of complementarity is 19 nucleotides in length.

In one embodiment, each strand is no more than 30 nucleotides in length.

In another embodiment, at least one strand includes a 3' overhang of at least 1 nucleotide. Optionally, at least one strand includes a 3' overhang of at least 2 nucleotides.

In certain embodiments, the double stranded RNAi agent further includes a lipophilic ligand, e.g., a C16 ligand, conjugated to the 3' end of the sense strand through a monovalent or branched bivalent or trivalent linker. In certain embodiments, the double stranded RNAi agent further includes a lipophilic ligand, e.g., a C16 ligand, conjugated to an internal nucleotide positon, e.g., through a monovalent or branched bivalent or trivalent linker.

In certain embodiments, the ligand is a C16 ligand. In one embodiment, the ligand is conjugated at the 2'-position of a nucleotide or modified nucleotide within the sense or antisense strand. For example, a C16 ligand may be conjugated as shown in the following structure:

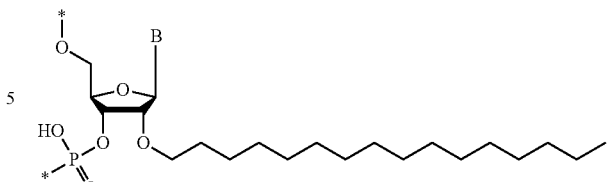

where * denotes a bond to an adjacent nucleotide, and B is a nucleobase or a nucleobase analog, optionally where B is adenine, guanine, cytosine, thymine or uracil.

In other embodiments, the agent further comprises a targeting ligand that targets a liver tissue, e.g., one or more GalNAc derivatives, optionally conjugated to the double stranded RNAi agent via a linker or carrier. In certain embodiments, one of the modified strands in Tables 3, 5, 7, 13, 18, and 20 are conjugated to a targeting ligand that targets a liver tissue. In certain embodiments, the targeting ligand is an L96 ligand, e.g., one or more GalNAc derivatives, optionally conjugated to the double stranded RNAi agent via a linker or carrier. In certain embodiments, the L96 ligand is conjugated to the end of one of the strands. In certain embodiments the L96 ligand is conjugated to the 3' end of the sense strand.

In yet other embodiments, the agents further comprise a lipophilic ligand, e.g., a C16 ligand, conjugated to an internal nucleotide position, e.g., through a monovalent or branched bivalent or trivalent linker, and a targeting ligand that targets a liver tissue, e.g., one or more GalNAc derivatives conjugated to the 3' end of the sense strand through a monovalent or branched bivalent or trivalent linker.

In yet other embodiments, the agents further comprise a lipophilic ligand, e.g., a C16 ligand, conjugated to the 3' end of the sense strand through a monovalent or branched bivalent or trivalent linker and a targeting ligand that targets a liver tissue, e.g., one or more GalNAc derivatives conjugated to the 3' end of the sense strand through a monovalent or branched bivalent or trivalent linker.

In another embodiment, the region of complementarity to SOD1 includes any one of the antisense sequences in any one of Tables 2-7, 12, 13, and 18-20.

In an additional embodiment, the region of complementarity to SOD1 is that of any one of the antisense sequences in any one of Tables 2-7, 12, 13, and 18-20. In some embodiments, the internal nucleotide positions include all positions except the terminal two positions from each end of the strand.

In a related embodiment, the internal positions include all positions except terminal three positions from each end of the strand. Optionally, the internal positions exclude the cleavage site region of the sense strand.

In some embodiments, the internal positions exclude positions 9-12, counting from the 5'-end of the sense strand. In certain embodiments, the sense strand is 21 nucleotides in length.

In other embodiments, the internal positions exclude positions 11-13, counting from the 3'-end of the sense strand. Optionally, the internal positions exclude the cleavage site region of the antisense strand. In certain embodiments, the sense strand is 21 nucleotides in length.

In some embodiments, the internal positions exclude positions 12-14, counting from the 5'-end of the antisense strand. In certain embodiments, the antisense strand is 23 nucleotides in length.

In another embodiment, the internal positions exclude positions 11-13 on the sense strand, counting from the 3'-end, and positions 12-14 on the antisense strand, counting from the 5'-end. In certain embodiments, the sense strand is 21 nucleotides in length and the antisense strand is 23 nucleotides in length.

In an additional embodiment, one or more lipophilic moieties are conjugated to one or more of the following internal positions: positions 4-8 and 13-18 on the sense strand, and positions 6-10 and 15-18 on the antisense strand, counting from the 5' end of each strand. Optionally, one or more lipophilic moieties are conjugated to one or more of the following internal positions: positions 5, 6, 7, 15, and 17 on the sense strand, and positions 15 and 17 on the antisense strand, counting from the 5'-end of each strand. In certain embodiments, the sense strand is 21 nucleotides in length and the antisense strand is 23 nucleotides in length.

In certain embodiments, the lipophilic moiety is an aliphatic, alicyclic, or polyalicyclic compound. Optionally, the lipophilic moiety is lipid, cholesterol, retinoic acid, cholic acid, adamantane acetic acid, 1-pyrene butyric acid, dihydrotestosterone, 1,3-bis-O(hexadecyl)glycerol, geranyloxyhexyanol, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

In some embodiments, the lipophilic moiety contains a saturated or unsaturated C4-C30 hydrocarbon chain, and an optional functional group selected that is hydroxyl, amine, carboxylic acid, sulfonate, phosphate, thiol, azide, or alkyne.

In certain embodiments, the lipophilic moiety contains a saturated or unsaturated C6-C18 hydrocarbon chain. Optionally, the lipophilic moiety contains a saturated or unsaturated C16 hydrocarbon chain. In a related embodiment, the lipophilic moiety is conjugated via a carrier that replaces one or more nucleotide(s) in the internal position(s). In certain embodiments, the carrier is a cyclic group that is pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, or decalinyl; or is an acyclic moiety based on a serinol backbone or a diethanolamine backbone.

In some embodiments, the lipophilic moiety is conjugated to the double-stranded RNAi agent via a linker containing an ether, thioether, urea, carbonate, amine, amide, maleimide-thioether, disulfide, phosphodiester, sulfonamide linkage, a product of a click reaction, or carbamate.

In one embodiment, the lipophilic moiety is conjugated to a nucleobase, sugar moiety, or internucleosidic linkage.

In another embodiment, the double-stranded RNAi agent further includes a phosphate or phosphate mimic at the 5'-end of the antisense strand. Optionally, the phosphate mimic is a 5'-vinyl phosphonate (VP). When the phosphate mimic is a 5'-vinyl phosphonate (VP), the 5'-terminal nucleotide may have the following structure,

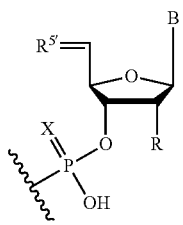

wherein X is O or S;

R is hydrogen, hydroxy, fluoro, or $C_{1-20}$alkoxy (e.g., methoxy or n-hexadecyloxy);

$R^{5'}$ is =C(H)—P(O)(OH)$_2$ and the double bond between the C5' carbon and R5' is in the E or Z orientation (e.g., E orientation); and B is a nucleobase or a modified nucleobase, optionally where B is adenine, guanine, cytosine, thymine, or uracil.

In certain embodiments, the double-stranded RNAi agent further includes a targeting ligand that targets a receptor which mediates delivery to a CNS tissue, e.g., a hydrophilic ligand. In certain embodiments, the targeting ligand is a C16 ligand.

In some embodiments, the double-stranded RNAi agent further includes a targeting ligand that targets a brain tissue, e.g., striatum.

In some embodiments, the double-stranded RNAi agent further includes a targeting ligand that targets a liver tissue or cell type, e.g., hepatocytes.

In one embodiment, the lipophilic moiety or targeting ligand is conjugated via a bio-cleavable linker that is DNA, RNA, disulfide, amide, functionalized monosaccharides or oligosaccharides of galactosamine, glucosamine, glucose, galactose, mannose, or a combination thereof.

In a related embodiment, the 3' end of the sense strand is protected via an end cap which is a cyclic group having an amine, the cyclic group being pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, or decalinyl.

In one embodiment, the RNAi agent includes at least one modified nucleotide that is a 2'-O-methyl modified nucleotide, a 2'-fluoro modified nucleotide, a nucleotide that includes a glycol nucleic acid (GNA) or a nucleotide that includes a vinyl phosphonate. Optionally, the RNAi agent includes at least one of each of the following modifications: 2'-O-methyl modified nucleotide, a 2'-fluoro modified nucleotide, a nucleotide comprising a glycol nucleic acid (GNA) and a nucleotide comprising vinyl phosphonate.

In another embodiment, the RNAi agent includes a pattern of modified nucleotides as provided below in Tables 2-7, 12, 13, and 18-20 where locations of 2'-C16, 2'-O-methyl, GNA, phosphorothioate, and 2'-fluoro modifications, irrespective of the individual nucleotide base sequences of the displayed RNAi agents.

Another aspect of the instant disclosure provides a double stranded RNAi agent for inhibiting expression of a SOD1 gene, wherein the double stranded RNAi agent includes a sense strand complementary to an antisense strand, wherein the antisense strand includes a region complementary to part of an mRNA encoding SOD1, wherein each strand is about 14 to about 30 nucleotides in length, wherein the double stranded RNAi agent is represented by formula (III):

sense:
5' $n_p$-$N_a$-(X X X)$_i$-$N_b$-Y Y Y -$N_b$-(Z Z Z)$_j$-$N_a$- $n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' (III)

wherein:

j, k, and l are each independently 0 or 1;

p, p', q, and q' are each independently 0-6;

each $N_a$ and $N_a'$ independently represents an oligonucleotide sequence including 0-25 nucleotides which are either modified or unmodified or combinations thereof, each sequence including at least two differently modified nucleotides;

each $N_b$ and $N_b'$ independently represents an oligonucleotide sequence including 0-10 nucleotides which are either modified or unmodified or combinations thereof;

each $n_p$, $n_p'$, $n_q$, and $n_q'$, each of which may or may not be present, independently represents an overhang nucleotide;

XXX, YYY, ZZZ, X'X'X', Y'Y'Y', and Z'Z'Z' each independently represent one motif of three identical modifications on three consecutive nucleotides;

modifications on $N_b$ differ from the modification on Y and modifications on $N_b'$ differ from the modification on Y'; and wherein the sense strand is conjugated to at least one ligand.

In one embodiment, i is 0; j is 0; i is 1; j is 1; both i and j are 0; or both i and j are 1.

In another embodiment, k is 0; l is 0; k is 1; l is 1; both k and l are 0; or both k and l are 1.

In certain embodiments, XXX is complementary to X'X'X', YYY is complementary to Y'Y'Y', and ZZZ is complementary to Z'Z'Z'.

In another embodiment, the YYY motif occurs at or near the cleavage site of the sense strand.

In an additional embodiment, the Y'Y'Y' motif occurs at the 11, 12 and 13 positions of the antisense strand from the 5'-end. Optionally, the Y' is 2'-O-methyl.

In some embodiments, formula (III) is represented by formula (IIIa):

```
sense:
5' n_p -N_a -Y Y Y -N_a - n_q 3' antisense:
3' n_p'-N_a'- Y'Y'Y'- N_a'- n_q' 5'   (IIIa).
```

In another embodiment, formula (III) is represented by formula (IIIb):

```
sense:
5' n_p -N_a -Y Y Y -N_b -Z Z Z -N_a - n_q 3' antisense:
3' n_p'-N_a'- Y'Y'Y'-N_b'-Z'Z'Z'- N_a'- n_q' 5'   (IIIb)
``` wherein each $N_b$ and $N_b'$ independently represents an oligonucleotide sequence including 1-5 modified nucleotides.

In an additional embodiment, formula (III) is represented by formula (IIIc):

```
sense:
5' n_p -N_a -X X X -N_b -Y Y Y -N_a - n_q 3' antisense:
3' n_p'-N_a'- X'X'X'-N_b'- Y'Y'Y'- N_a'- n_q' 5'   (IIIc)
``` wherein each $N_b$ and $N_b'$ independently represents an oligonucleotide sequence including 1-5 modified nucleotides.

In certain embodiments, formula (III) is represented by formula (IIId):

```
                                                    (IIId)
sense:
5' n_p-N_a-X X X-N_b-Y Y Y-N_b-Z Z Z-N_a-n_q 3' antisense:
3' n_p'-N_a'-X'X'X'-N_b'-Y'Y'Y'-N_b'-Z'Z'Z'-N_a'-n_q' 5'
``` wherein each $N_b$ and $N_b'$ independently represents an oligonucleotide sequence including 1-5 modified nucleotides and each $N_a$ and $N_a'$ independently represents an oligonucleotide sequence including 2-10 modified nucleotides.

In another embodiment, the double stranded region is 15-30 nucleotide pairs in length. Optionally, the double stranded region is 17-23 nucleotide pairs in length.

In certain embodiments, the double stranded region is 17-25 nucleotide pairs in length. Optionally, the double stranded region is 23-27 nucleotide pairs in length.

In some embodiments, the double stranded region is 19-21 nucleotide pairs in length. Optionally, the double stranded region is 21-23 nucleotide pairs in length.

In certain embodiments, each strand independently has 15-30 nucleotides. Optionally, each strand independently has 19-30 nucleotides. Optionally, each strand independently has 19-23 nucleotides.

In certain embodiments, the double stranded region is 19-21 nucleotide pairs in length and each strand has 19-23 nucleotides.

In another embodiment, the modifications on the nucleotides of the RNAi agent are LNA, glycol nucleic acid (GNA), hexitol nucleic acid (HNA), a cyclohexene nucleic acid (CeNA), 2'-methoxyethyl, 2'-O-alkyl, 2'-O-allyl, 2'-C-allyl, 2'-fluoro, 2'-deoxy or 2'-hydroxyl, and combinations thereof. Optionally, the modifications on nucleotides include 2'-O-methyl, 2'-fluoro, or GNA, and combinations thereof. In a related embodiment, the modifications on the nucleotides are 2'-O-methyl or 2'-fluoro modifications.

In one embodiment the RNAi agent includes a ligand that is or includes one or more lipophilic, e.g., C16, moieties attached through a bivalent or trivalent branched linker.

In other embodiments, the agent further comprises a targeting ligand that targets a liver tissue, e.g., one or more GalNAc derivatives.

In yet other embodiments, the agents further comprise a lipophilic ligand, e.g., a C16 ligand, conjugated to the 3' end of the sense strand through a monovalent or branched bivalent or trivalent linker and a targeting ligand that targets a liver tissue, e.g., one or more GalNAc derivatives conjugated to the 3' end of the sense strand through a monovalent or branched bivalent or trivalent linker.

In certain embodiments, the ligand is attached to the 3' end of the sense strand.

In some embodiments, the RNAi agent further includes at least one phosphorothioate or methylphosphonate internucleotide linkage. In a related embodiment, the phosphorothioate or methylphosphonate internucleotide linkage is at the 3'-terminus of one strand. Optionally, the strand is the antisense strand. In another embodiment, the strand is the sense strand. In a related embodiment, the phosphorothioate or methylphosphonate internucleotide linkage is at the 5'-terminus of one strand. Optionally, the strand is the antisense strand. In another embodiment, the strand is the sense strand.

In another embodiment, the phosphorothioate or methylphosphonate internucleotide linkage is at the both the 5'- and 3'-terminus of one strand. Optionally, the strand is the antisense strand. In another embodiment, the strand is the sense strand.

In an additional embodiment, the base pair at the 1 position of the 5'-end of the antisense strand of the RNAi agent duplex is an A:U base pair.

In certain embodiments, the Y nucleotides contain a 2'-fluoro modification.

In some embodiments, the Y' nucleotides contain a 2'-O-methyl modification.

In certain embodiments, p'>0. Optionally, p'=2.

In some embodiments, q'=0, p=0, q=0, and p' overhang nucleotides are complementary to the target mRNA.

In certain embodiments, q'=0, p=0, q=0, and p' overhang nucleotides are non-complementary to the target mRNA.

In one embodiment, the sense strand of the RNAi agent has a total of 21 nucleotides and the antisense strand has a total of 23 nucleotides.

In another embodiment, at least one $n_p'$ is linked to a neighboring nucleotide via a phosphorothioate linkage. Optionally, all $n_p'$ are linked to neighboring nucleotides via phosphorothioate linkages.

In certain embodiments, the SOD1 RNAi agent of the instant disclosure is one of those listed in Tables 2-7, 12, 13, and 18-20. In some embodiments, all of the nucleotides of the sense strand and all of the nucleotides of the antisense strand include a modification.

Another aspect of the instant disclosure provides a double stranded RNAi agent for inhibiting expression of a SOD1 gene in a cell, wherein the double stranded RNAi agent includes a sense strand complementary to an antisense strand, wherein the antisense strand includes a region complementary to part of an mRNA encoding a SOD1 gene, wherein each strand is about 14 to about 30 nucleotides in length, wherein the double stranded RNAi agent is represented by formula (III):

$$\text{sense:} \quad 5' \ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3' \quad \text{(III)}$$

$$\text{antisense:} \quad 3' \ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$$

wherein:

j, k, and l are each independently 0 or 1;

p, p', q, and q' are each independently 0-6;

each $N_a$ and $N_a'$ independently represents an oligonucleotide sequence including 0-25 nucleotides which are either modified or unmodified or combinations thereof, each sequence including at least two differently modified nucleotides;

each $N_b$ and $N_b'$ independently represents an oligonucleotide sequence including 0-10 nucleotides which are either modified or unmodified or combinations thereof;

each $n_p$, $n_p'$, $n_q$, and $n_q'$, each of which may or may not be present independently represents an overhang nucleotide;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand, optionally wherein the ligand is one or more lipophilic, e.g., C16, ligands, or one or more GalNAc derivatives.

An additional aspect of the instant disclosure provides a double stranded RNAi agent for inhibiting expression of a SOD1 gene in a cell, wherein the double stranded RNAi agent includes a sense strand complementary to an antisense strand, wherein the antisense strand includes a region complementary to part of an mRNA encoding SOD1, wherein each strand is about 14 to about 30 nucleotides in length, wherein the double stranded RNAi agent is represented by formula (III):

$$\text{sense:} \quad 5' \ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3' \quad \text{(III)}$$

$$\text{antisense:} \quad 3' \ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$$

wherein:

j, k, and l are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence including 0-25 nucleotides which are either modified or unmodified or combinations thereof, each sequence including at least two differently modified nucleotides;

each $N_b$ and $N_b'$ independently represents an oligonucleotide sequence including 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl, glycol nucleic acid (GNA) or 2'-fluoro modifications;

modifications on $N_b$ differ from the modification on Y and modifications on $N_b'$ differ from the modification on Y'; and wherein the sense strand is conjugated to at least one ligand, optionally where the ligand is one or more lipophilic, e.g., C16, ligands, or one or more GalNAc derivatives.

Another aspect of the instant disclosure provides a double stranded RNAi agent for inhibiting expression of a SOD1 gene in a cell, wherein the double stranded RNAi agent includes a sense strand complementary to an antisense strand, wherein the antisense strand includes a region complementary to part of an mRNA encoding SOD1 (SEQ ID NO: 1, or a nucleotide sequence having at least 90% nucleotide sequence identity, e.g. 90, 91, 92, 93, 94, 95, 96, 97, 98, 99 or 100% identity, to the entire nucleotide sequence of SEQ ID NO:1), wherein each strand is about 14 to about 30 nucleotides in length, wherein the double stranded RNAi agent is represented by formula (III):

$$\text{sense:} \quad 5' \ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3' \quad \text{(III)}$$

$$\text{antisense:} \quad 3' \ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$$

wherein:

j, k, and l are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence including 0-25 nucleotides which are either modified or unmodified or combinations thereof, each sequence including at least two differently modified nucleotides;

each $N_b$ and $N_b'$ independently represents an oligonucleotide sequence including 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand, optionally wherein the ligand is one or more lipophilic, e.g., C16, ligands, or one or more GalNAc derivatives.

An additional aspect of the instant disclosure provides a double stranded RNAi agent for inhibiting expression of a SOD1 gene in a cell, wherein the double stranded RNAi agent includes a sense strand complementary to an antisense strand, wherein the antisense strand includes a region complementary to part of an mRNA encoding SOD1 (SEQ ID NO: 1, or a nucleotide sequence having at least 90% nucleotide sequence identity, e.g. 90, 91, 92, 93, 94, 95, 96, 97, 98, 99, or 100% identity, to the entire nucleotide sequence of SEQ ID NO: 1), wherein each strand is about 14 to about 30 nucleotides in length, wherein the double stranded RNAi agent is represented by formula (III):

```
                                                    (III)
sense:
5' n_p-N_a-(X X X)_i-N_b -Y Y Y-N_b-(Z Z Z)_j-N_a-n_q 3' antisense:
3' n_p'-N_a'-(X'X'X')_k-N_b'-Y'Y'Y'-N_b'-(Z'Z'Z')_l

N_a'-n_q' 5'
``` wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence including 0-25 nucleotides which are either modified or unmodified or combinations thereof, each sequence including at least two differently modified nucleotides;

each $N_b$ and $N_b'$ independently represents an oligonucleotide sequence including 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y';

wherein the sense strand includes at least one phosphorothioate linkage; and wherein the sense strand is conjugated to at least one ligand, optionally wherein the ligand is one or more lipophilic, e.g., C16, ligands or one or more GalNAc derivatives.

Another aspect of the instant disclosure provides a double stranded RNAi agent for inhibiting expression of a SOD1 gene in a cell, wherein the double stranded RNAi agent includes a sense strand complementary to an antisense strand, wherein the antisense strand includes a region complementary to part of an mRNA encoding SOD1 (SEQ ID NO: 1, or a nucleotide sequence having at least 90% nucleotide sequence identity, e.g. 90, 91, 92, 93, 94, 95, 96, 97, 98, 99, or 100% identity, to the entire nucleotide sequence of SEQ ID NO: 1), wherein each strand is about 14 to about 30 nucleotides in length, wherein the double stranded RNAi agent is represented by formula (III):

```
                                                  (IIIa)
sense:    5' n_p-N_a-Y Y Y-N_a-n_q 3' antisense: 3' n_p'-N_a'-Y'Y'Y'-N_a'-n_q' 5'
``` wherein:

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence including 0-25 nucleotides which are either modified or unmodified or combinations thereof, each sequence including at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand includes at least one phosphorothioate linkage; and wherein the sense strand is conjugated to at least one ligand, optionally wherein the ligand is one or more lipophilic, e.g., C16 ligands, or one or more GalNAc derivatives.

An additional aspect of the instant disclosure provides a double stranded RNAi agent for inhibiting expression of a SOD1 gene, wherein the double stranded RNAi agent targeted to SOD1 includes a sense strand and an antisense strand forming a double stranded region, wherein the sense strand includes at least 15 e.g., 15, 16, 17, 18, 19, 20, or 21, contiguous nucleotides differing by no more than 3 nucleotides (i.e., differing by 3, 2, 1, or 0 nucleotides) from any one of the nucleotide sequences of SEQ ID NOs: 1, 3, 5, 7, and 9, or a nucleotide sequence having at least 90% nucleotide sequence identity, e.g. 90, 91, 92, 93, 94, 95, 96, 97, 98, 99, or 100% identity, to the entire nucleotide sequence of any one of SEQ ID NOs: 1, 3, 5, 7, or 9, and the antisense strand includes at least 15 e.g., 15, 16, 17, 18, 19, 20, 21, 22, or 23, contiguous nucleotides differing by no more than 3 nucleotides (i.e., differing by 3, 2, 1, or 0 nucleotides) from any one of the nucleotide sequences of SEQ ID NOs: 2, 4, 6, 8, and 10, or a nucleotide sequence having at least 90% nucleotide sequence identity, e.g. 90, 91, 92, 93, 94, 95, 96, 97, 98, 99, or 100% identity, to the entire nucleotide sequence of any one of SEQ ID NOs: 2, 4, 6, 8, and 10; wherein a substitution of a uracil for any thymine in the sequences provided in the SEQ ID NOs: 1-6 (when comparing aligned sequences) does not count as a difference that contributes to the differing by no more than 3 nucleotides from any one of the nucleotide sequences provided in SEQ ID NOs: 1-6, wherein substantially all of the nucleotides of the sense strand include a modification that is a 2'-O-methyl modification, a GNA, or a 2'-fluoro modification, wherein the sense strand includes two phosphorothioate internucleotide linkages at the 5'-terminus, wherein substantially all of the nucleotides of the antisense strand include a modification selected from the group consisting of a 2'-O-methyl modification and a 2'-fluoro modification, wherein the antisense strand includes two phosphorothioate internucleotide linkages at the 5'-terminus and two phosphorothioate internucleotide linkages at the 3'-terminus, and wherein the sense strand is conjugated to one or more lipophilic, e.g., C16, ligands, optionally, further comprising a liver targeting ligand, e.g., a ligand comprising one or more GalNAc derivatives.

Another aspect of the instant disclosure provides a double stranded RNAi agent for inhibiting expression of a SOD1 gene, wherein the double stranded RNAi agent targeted to SOD1 includes a sense strand and an antisense strand forming a double stranded region, wherein the sense strand includes at least 15 e.g., 15, 16, 17, 18, 19, 20, or 21, contiguous nucleotides differing by no more than 3 nucleotides (i.e., differing by 3, 2, 1, or 0 nucleotides) from any one of the nucleotide sequences of SEQ ID NOs: 1, 3, 5, 7, and 9, or a nucleotide sequence having at least 90% nucleotide sequence identity, e.g. 90, 91, 92, 93, 94, 95, 96, 97, 98, 99, or 100% identity, to the entire nucleotide sequence of any one of SEQ ID NOs: 1, 3, 5, 7, or 9, and the antisense strand includes at least 15 e.g., 15, 16, 17, 18, 19, 20, 21, 22, or 23, contiguous nucleotides differing by no more than 3 nucleotides (i.e., differing by 3, 2, 1, or 0 nucleotides) from any one of the nucleotide sequences of SEQ ID NOs: 2, 4, 6, 8, and 10, or a nucleotide sequence having at least 90% nucleotide sequence identity, e.g. 90, 91, 92, 93, 94, 95, 96, 97, 98, 99, or 100% identity, to the entire nucleotide sequence of any one of SEQ ID NOs: 2, 4, 6, 8, and 10, wherein a substitution of a uracil for any thymine in the sequences provided in the SEQ ID NOs: 1-10 (when comparing aligned sequences) does not count as a difference that contributes to the differing by no more than 3 nucleotides from any one of the nucleotide sequences provided in SEQ ID NOs:1-10; wherein the sense strand includes at least one 3'-terminal deoxythimidine nucleotide (dT), and wherein the antisense strand includes at least one 3'-terminal deoxythimidine nucleotide (dT).

In one embodiment, all of the nucleotides of the sense strand and all of the nucleotides of the antisense strand are modified nucleotides.

In another embodiment, each strand has 19-30 nucleotides.

In certain embodiments, the antisense strand of the RNAi agent includes at least one thermally destabilizing modification of the duplex within the first 9 nucleotide positions of the 5' region or a precursor thereof. Optionally, the thermally destabilizing modification of the duplex is one or more of

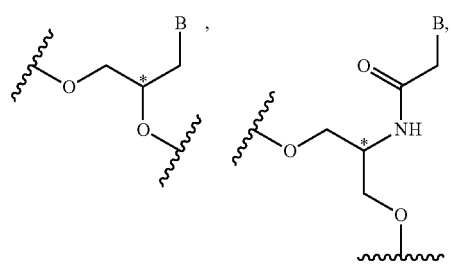

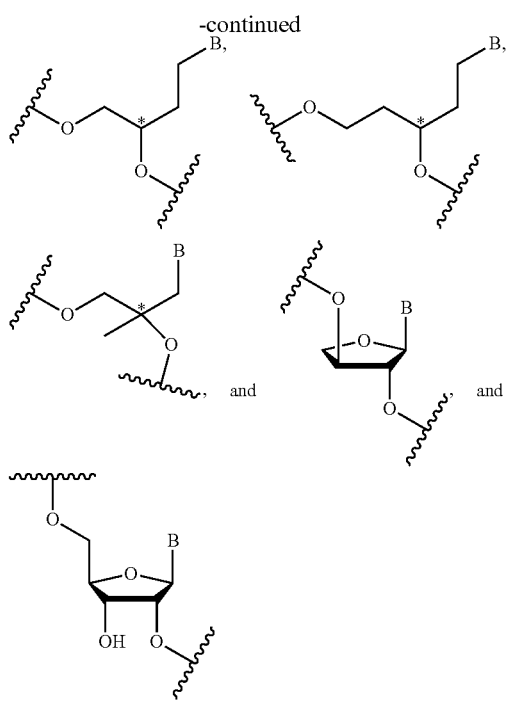

wherein B is nucleobase.

Another aspect of the instant disclosure provides a cell containing a double stranded RNAi agent of the instant disclosure.

An additional aspect of the instant disclosure provides a pharmaceutical composition for inhibiting expression of a SOD1 gene that includes a double stranded RNAi agent of the instant disclosure.

In one embodiment, the double stranded RNAi agent is administered in an unbuffered solution. Optionally, the unbuffered solution is saline or water.

In another embodiment, the double stranded RNAi agent is administered with a buffer solution. Optionally, the buffer solution includes acetate, citrate, prolamine, carbonate, or phosphate or any combination thereof. In another embodiment, the buffer solution is phosphate buffered saline (PBS).

Another aspect of the disclosure provides a pharmaceutical composition that includes a double stranded RNAi agent of the instant disclosure and a lipid formulation.

In one embodiment, the lipid formulation includes a lipid nanoparticle (LNP).

An additional aspect of the disclosure provides a method of inhibiting expression of a SOD1 gene in a cell, the method involving: (a) contacting the cell with a double stranded RNAi agent of the instant disclosure or a pharmaceutical composition of the instant disclosure; and (b) maintaining the cell produced in step (a) for a time sufficient to obtain degradation of the mRNA transcript of a SOD1 gene, thereby inhibiting expression of the SOD1 gene in the cell.

In one embodiment, the cell is within a subject. Optionally, the subject is a human.

In certain embodiments, the subject is a rhesus monkey, a cynomolgous monkey (also known as a crab-eating macaque), a mouse, dog, or a rat.

In certain embodiments, the human subject suffers from a SOD1-associated neurodegenerative disease, e.g., Amyotrophic Lateral Sclerosis (ALS), Alzheimer's disease (AD), Parkinson's disease (PD), and Down's syndrome (DS).

In certain embodiments, the method further involves administering an additional therapeutic agent or therapy to the subject. Exemplary additional therapeutics and treatments include, for example, sedatives, antidepressants, clonazepam, sodium valproate, opiates, antiepileptic drugs, cholinesterase inhibitors, memantine, benzodiazepines, levodopa, COMT inhibitors (e.g., tolcapone and entacapone), dopamine agonists (e.g., bromocriptine, pergolide, pramipexole, ropinirole, piribedil, cabergoline, apomorphine and lisuride), MAO-B inhibitors (e.g., safinamide, selegiline and rasagiline), amantadine, an anticholinergic, modafinil, pimavanserin, doxepin, rasagline, an antipsychotic, an atypical antipsychotic (e.g., amisulpride, olanzapine, risperidone, and clozapine), riluzole, edaravone, deep brain stimulation, non-invasive ventilation (NIV), invasive ventilation physical therapy, occupational therapy, speech therapy, dietary changes and swallowing technique a feeding tube, a PEG tube, probiotics, and psychological therapy.

In certain embodiments, the double stranded RNAi agent is administered at a dose of about 0.01 mg/kg to about 50 mg/kg.

In some embodiments, the double stranded RNAi agent is administered to the subject intrathecally.

In one embodiment, the method reduces the expression of a SOD1 gene in a brain (e.g., striatum) or spine tissue. Optionally, the brain or spine tissue is striatum, frontal cortex, temporal cortex, cerebellum, hippocampus, cervical spine, lumbar spine, or thoracic spine.

In one embodiment, the method reduces the expression of a SOD1 gene in an eye (with or without lens), heart, kidney, liver, lung and/or muscle tissue or cell.

In some embodiments, the double stranded RNAi agent is administered to the subject subcutaneously.

In some embodiments, the double stranded RNAi agent is administered to the subject intracerebroventricularly.

In some embodiments, the double stranded RNAi agent is administered to the subject intrathecally.

In one embodiment, the method reduces the expression of a SOD1 gene in the liver.

In other embodiments, the method reduces the expression of a SOD1 gene in the liver and the brain.

Another aspect of the instant disclosure provides a method of inhibiting the expression of SOD1 in a subject, the method involving: administering to the subject a therapeutically effective amount of a double stranded RNAi agent of the disclosure or a pharmaceutical composition of the disclosure, thereby inhibiting the expression of SOD1 in the subject.

An additional aspect of the disclosure provides a method for treating or preventing a disorder or SOD1-associated neurodegenerative disease or disorder in a subject, the method involving administering to the subject a therapeutically effective amount of a double stranded RNAi agent of the disclosure or a pharmaceutical composition of the disclosure, thereby treating or preventing a SOD1-associated neurodegenerative disease or disorder in the subject.

In certain embodiments, the SOD1-associated neurodegenerative disease or disorder is selected from the group consisting of Amyotrophic Lateral Sclerosis (ALS), Alzheimer's disease (AD), Parkinson's disease (PD), and Down's syndrome (DS).

Another aspect of the instant disclosure provides a kit for performing a method of the instant disclosure, the kit including: a) a double stranded RNAi agent of the instant disclosure, and b) instructions for use, and c) optionally, a device for administering the double stranded RNAi agent to the subject.

An additional aspect of the instant disclosure provides a double stranded ribonucleic acid (RNAi) agent for inhibiting expression of a SOD1 gene, wherein the RNAi agent possesses a sense strand and an antisense strand, and wherein the antisense strand includes a region of complementarity which includes at least 15 e.g., 15, 16, 17, 18, 19, 20, 21, 22, or 23, contiguous nucleotides differing by no more than 3 nucleotides (i.e., differing by 3, 2, 1, or 0 nucleotides), e.g., at least 15 e.g., 15, 16, 17, 18, 19, 20, 21, 22, or 23, nucleotides (i.e., differing by 3, 2, 1, or 0 nucleotides), at least 19, e.g., 19, 20, 21, 22, or 23, nucleotides (i.e., differing by 3, 2, 1, or 0 nucleotides), from any one of the antisense strand nucleobase sequences of Tables 2-7, 12, 13, and 18-20. In one embodiment, the RNAi agent includes one or more of the following modifications: a 2'-O-methyl modified nucleotide, a 2'-fluoro modified nucleotide, a 2'-C-alkyl-modified nucleotide, a nucleotide comprising a glycol nucleic acid (GNA), a phosphorothioate (PS) and a vinyl phosphonate (VP). Optionally, the RNAi agent includes at least one of each of the following modifications: a 2'-O-methyl modified nucleotide, a 2'-fluoro modified nucleotide, a 2'-C-alkyl-modified nucleotide, a nucleotide comprising a glycol nucleic acid (GNA), a phosphorothioate and a vinyl phosphonate (VP).

In another embodiment, the RNAi agent includes four or more PS modifications, optionally six to ten PS modifications, optionally eight PS modifications.

In an additional embodiment, each of the sense strand and the antisense strand of the RNAi agent possesses a 5'-terminus and a 3'-terminus, and the RNAi agent includes eight PS modifications positioned at each of the penultimate and ultimate internucleotide linkages from the respective 3'- and 5'-termini of each of the sense and antisense strands of the RNAi agent.

In another embodiment, each of the sense strand and the antisense strand of the RNAi agent includes a 5'-terminus and a 3'-terminus, and the RNAi agent includes only one nucleotide including a GNA. Optionally, the nucleotide including a GNA is positioned on the antisense strand at the seventh nucleobase residue from the 5'-terminus of the antisense strand.

In an additional embodiment, each of the sense strand and the antisense strand of the RNAi agent includes a 5'-terminus and a 3'-terminus, and the RNAi agent includes one to four 2'-C-alkyl-modified nucleotides. Optionally, the 2'-C-alkyl-modified nucleotide is a 2'-C16-modified nucleotide. Optionally, the RNAi agent includes a single 2'-C-alkyl, e.g., C16-modified nucleotide. Optionally, the single 2'-C-alkyl, e.g., C16-modified nucleotide is located on the sense strand at the sixth nucleobase position from the 5'-terminus of the sense strand.

In another embodiment, each of the sense strand and the antisense strand of the RNAi agent includes a 5'-terminus and a 3'-terminus, and the RNAi agent includes two or more 2'-fluoro modified nucleotides. Optionally, each of the sense strand and the antisense strand of the RNAi agent includes two or more 2'-fluoro modified nucleotides. Optionally, the 2'-fluoro modified nucleotides are located on the sense strand at nucleobase positions 7, 9, 10, and 11 from the 5'-terminus of the sense strand and on the antisense strand at nucleobase positions 2, 14, and 16 from the 5'-terminus of the antisense strand.

In an additional embodiment, each of the sense strand and the antisense strand of the RNAi agent includes a 5'-terminus and a 3'-terminus, and the RNAi agent includes one or more VP modifications. Optionally, the RNAi agent includes a single VP modification at the 5'-terminus of the antisense strand.

In another embodiment, each of the sense strand and the antisense strand of the RNAi agent includes a 5'-terminus and a 3'-terminus, and the RNAi agent includes two or more 2'-O-methyl modified nucleotides. Optionally, the RNAi agent includes 2'-O-methyl modified nucleotides at all nucleobase locations not modified by a 2'-fluoro, a 2'-C-alkyl or a glycol nucleic acid (GNA). Optionally, the two or more 2'-O-methyl modified nucleotides are located on the sense strand at positions 1, 2, 3, 4, 5, 8, 12, 13, 14, 15, 16, 17, 18, 19, 20, and 21 from the 5'-terminus of the sense strand and on the antisense strand at positions 1, 3, 4, 5, 6, 8, 9, 10, 11, 12, 13, 15, 17, 18, 19, 20, 21, 22 and 23 from the 5'-terminus of the antisense strand.

In another embodiment, the RNAi agent is a pharmaceutically acceptable salt thereof. "Pharmaceutically acceptable salts" of each of RNAi agents herein include, but are not limited to, a sodium salt, a calcium salt, a lithium salt, a potassium salt, an ammonium salt, a magnesium salt, an mixtures thereof. One skilled in the art will appreciate that the RNAi agent, when provided as a polycationic salt having one cation per free acid group of the optionally modified phosophodiester backbone and/or any other acidic modifications (e.g., 5'-terminal phosphonate groups). For example, an oligonucleotide of "n" nucleotides in length contains n-1 optionally modified phosophodiesters, so that an oligonucleotide of 21 nt in length may be provided as a salt having up to 20 cations (e.g, 20 sodium cations). Similarly, an RNAi agents having a sense strand of 21 nt in length and an antisense strand of 23 nt in length may be provided as a salt having up to 42 cations (e.g, 42 sodium cations). In the preceding example, where the RNAi agent also includes a 5'-terminal phosphate or a 5'-terminal vinylphosphonate group, the RNAi agent may be provided as a salt having up to 44 cations (e.g, 44 sodium cations).

In another embodiment, an antisense oligonucleotide is provided having a nucleotide sequence that is any one of the antisense nucleotide sequences listed in any one of Tables 3, 5, 7, 13, 18, and 20 but lacking the 3'-terminal nucleotide (3'N-1 AS), or a pharmaceutically acceptable salt thereof (see, for example, FIG. 5). In another embodiment, a dsRNA duplex is provided comprising an antisense strand having a nucleotide sequence that is any one of the antisense nucleotide sequences listed in any one of Tables 3, 5, 7, 13, 18, and 20 but lacking the 3'-terminal nucleotide (3'N-1 AS), and a sense strand that is substantially complementary to the antisense oligonucleotide, or a pharmaceutically acceptable salt thereof. In another embodiment, a dsRNA duplex is provided comprising any one of the duplexes in any one of Tables 3, 5, 7, 13, 18, or 20, where the antisense nucleotide sequence is replaced with an antisense oligonucleotide sequence lacking the 3'-terminal nucleotide (3'N-1 AS), or a pharmaceutically acceptable salt thereof.

In one embodiment, an antisense oligonucleotide is provided having the nucleotide sequence of any one of SEQ ID NO. 1369-1378 (see Table 23), or a pharmaceutically acceptable salt thereof. In one embodiment, an antisense oligonucleotide is provided having the nucleotide sequence of SEQ ID NO. 1369, or a pharmaceutically acceptable salt thereof. In one embodiment, an antisense oligonucleotide is provided having the nucleotide sequence of SEQ ID NO. 1370, or a pharmaceutically acceptable salt thereof. In one embodiment, an antisense oligonucleotide is provided having the nucleotide sequence of SEQ ID NO. 1371, or a pharmaceutically acceptable salt thereof.

In another embodiment, a dsRNA duplex is provided comprising an antisense strand having a nucleotide sequence of SEQ ID NO. 1369, and a sense strand that is substantially complementary to the antisense oligonucleotide, or a pharmaceutically acceptable salt thereof. In another embodiment, a dsRNA duplex is provided comprising an antisense strand having a nucleotide sequence of SEQ ID NO. 1370, and a sense strand that is substantially complementary to the antisense oligonucleotide, or a pharmaceutically acceptable salt thereof. In another embodiment, a dsRNA duplex is provided comprising an antisense strand having a nucleotide sequence of SEQ ID NO. 1371, and a sense strand that is substantially complementary to the antisense oligonucleotide, or a pharmaceutically acceptable salt thereof.

In another embodiment, a dsRNA duplex is provided comprising an antisense strand having a nucleotide sequence of SEQ ID NO. 1369, and a sense strand having a sequence of SEQ ID NO. 11, or a pharmaceutically acceptable salt thereof. In another embodiment, a dsRNA duplex is provided comprising an antisense strand having a nucleotide sequence of SEQ ID NO. 1370, and a sense strand having a nucleotide sequence of SEQ ID NO. 1371, or a pharmaceutically acceptable salt thereof. In another embodiment, a dsRNA duplex is provided comprising an antisense strand having a nucleotide sequence of SEQ ID NO. 1371, and a sense strand having a nucleotide sequence of SEQ ID NO. 15, or a pharmaceutically acceptable salt thereof.

The present invention is further illustrated by the following detailed description and drawings.

BRIEF DESCRIPTION OF THE DRAWINGS

FIG. 5 discloses SEQ ID NOS 1366, 1366, 1366, 1366-1367, 1367, 1367-1368 and 1368, respectively, in order of appearance.

FIG. 6 is a Table summarizing the tissue exposure and metabolite profiling of duplexes AD-1395762, AD-1395756, and AD-1395731.

FIG. 7 is a Table depicting the study protocol assessing the effect of the indicated uplexes on SOD1 mRNA and protein expression in non-human primates.

FIG. 8C discloses SEQ ID NOS 1281, 1284, 71 and 1366-1368, respectively, in order of appearance.

FIG. 12B, Be(2)C); positions 319-337 (FIG. 12C, PCH; FIG. 12D, Be(2)C); positions 364-382 (FIG. 12E, PCH; FIG. 12F, Be(2)C); and positions 516-540 (FIG. 12G, PCH; FIG. 12H, Be(2)C).

DETAILED DESCRIPTION OF THE INVENTION

Figure 1:
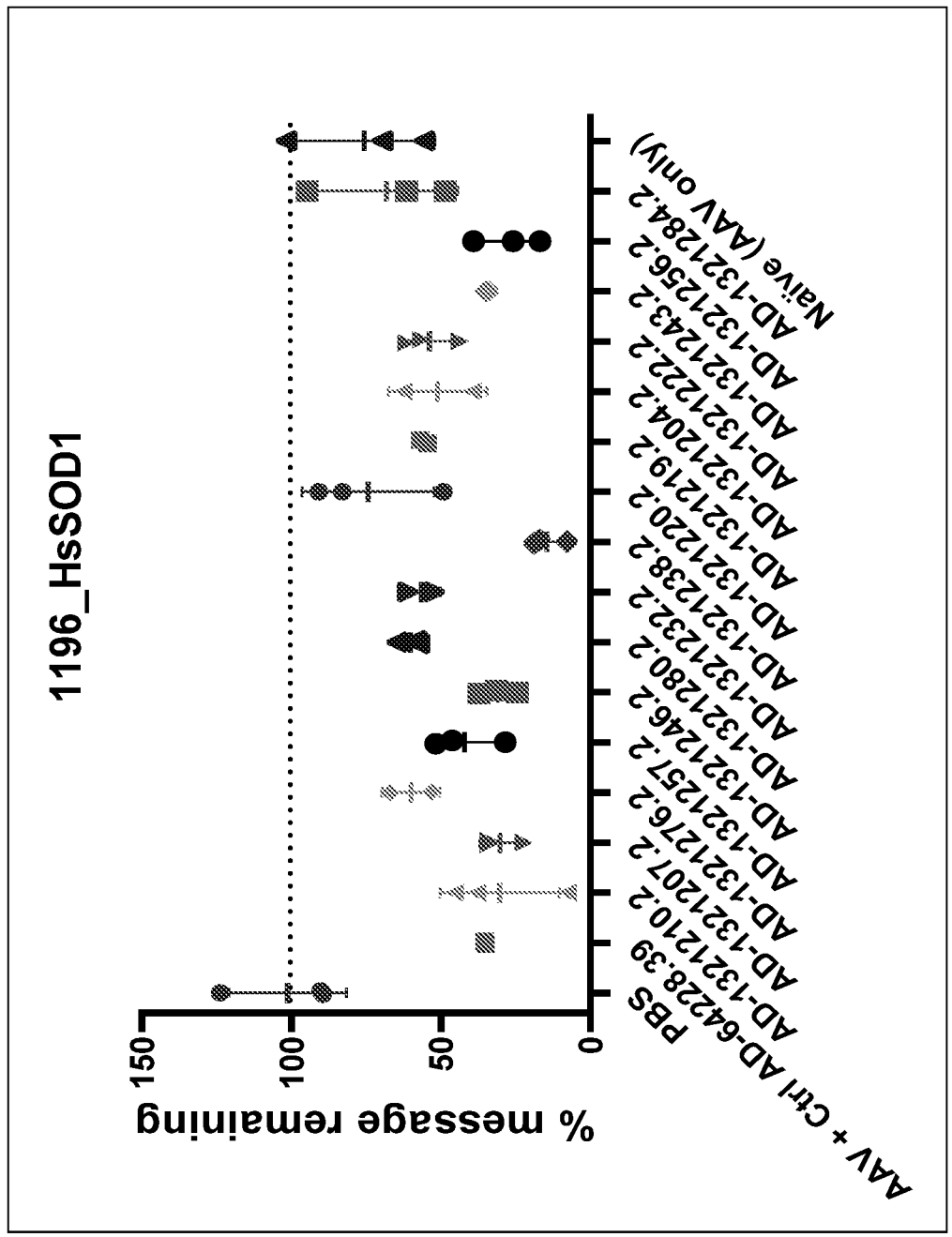
FIG. 1 is a graph depicting human SOD1 mRNA levels in mice subcutaneously administered a single 3 mg/kg dose of the indicated dsRNA duplexes. Human SOD1 mRNA levels are shown relative to control levels detected with PBS treatment.

The present disclosure provides RNAi compositions, which effect the RNA-induced silencing complex (RISC)-mediated cleavage of RNA transcripts of a SOD1 gene. The SOD1 gene may be within a cell, e.g., a cell within a subject, such as a human. The present disclosure also provides methods of using the RNAi compositions of the disclosure for inhibiting the expression of a SOD1 gene or for treating a subject having a disorder that would benefit from inhibiting or reducing the expression of a SOD1 gene, e.g., a SOD1-associated neurodegenerative disease, e.g., Amyotrophic Lateral Sclerosis (ALS), Alzheimer's disease (AD), Parkinson's disease (PD), and Down's syndrome (DS).

The RNAi agents of the disclosure include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of a SOD1 gene. In certain embodiments, the RNAi agents of the disclosure include an RNA strand (the antisense strand) having a region which is about 21-23 nucleotides in length, which region is substantially complementary to at least part of an mRNA transcript of a SOD1 gene.

In certain embodiments, the RNAi agents of the disclosure include an RNA strand (the antisense strand) which can include longer lengths, for example up to 66 nucleotides, e.g., 36-66, 26-36, 25-36, 31-60, 22-43, 27-53 nucleotides in length with a region of at least 19 contiguous nucleotides that is substantially complementary to at least a part of an mRNA transcript of a SOD1 gene. These RNAi agents with the longer length antisense strands preferably include a second RNA strand (the sense strand) of 20-60 nucleotides in length wherein the sense and antisense strands form a duplex of 18-30 contiguous nucleotides.

The use of these RNAi agents enables the targeted degradation of mRNAs of a SOD1 gene in mammals. Thus, methods and compositions including these RNAi agents are useful for treating a subject who would benefit by a reduction in the levels or activity of a SOD1 protein, such as a subject having a SOD1-associated neurodegenerative disease, e.g., Amyotrophic Lateral Sclerosis (ALS), Alzheimer's disease (AD), Parkinson's disease (PD), and Down's syndrome (DS).

The following detailed description discloses how to make and use compositions containing RNAi agents to inhibit the expression of a SOD1 gene, as well as compositions and methods for treating subjects having diseases and disorders that would benefit from inhibition or reduction of the expression of the genes.

I. Definitions

In order that the present disclosure may be more readily understood, certain terms are first defined. In addition, it should be noted that whenever a value or range of values of a parameter are recited, it is intended that values and ranges intermediate to the recited values are also intended to be part of this disclosure.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

The term "at least", "no less than", or "or more" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "or less" is understood as the value adjacent to the phrase and logical lower values or intergers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range. As used herein, ranges include both the upper and lower limit.

As used herein, methods of detection can include determination that the amount of analyte present is below the level of detection of the method.

In the event of a conflict between an indicated target site and the nucleotide sequence for a sense or antisense strand, the indicated sequence takes precedence.

In the event of a conflict between a chemical structure and a chemical name, the chemical structure takes precedence.

As used herein, the term "Superoxide dismutase 1," used interchangeably with the term "SOD1," refers to the well-known gene and polypeptide, also known in the art as Superoxide Dismutase [Cu—Zn], Cu/Zn Superoxide Dismutase, Epididymis Secretory Protein Li 44, EC 1.15.1.1, and Indophenoloxidase A. The term "SOD1" includes human SOD1, the amino acid and nucleotide sequence of which may be found in, for example, GenBank Accession No. NM_000454.4 (GI:48762945; SEQ ID NO:1); mouse SOD1, the amino acid and nucleotide sequence of which may be found in, for example, GenBank Accession No. NM_011434.1 (GI:45597446; SEQ ID NO:3); *Macaca fascicularis* (crab-eating macaque, also known as cynomolgus monkey) SOD1, the amino acid and nucleotide sequence of which may be found in, for example, GenBank Accession No. NM_001285406.1 (GI:549432988; SEQ ID NO:5); dog SOD1, the amino acid and nucleotide sequence of which may be found in, for example, GenBank Accession No. NM_001003035.1 (GI:50978673; SEQ ID NO:7); and rat SOD1, the amino acid and nucleotide sequence of which may be found in, for example, GenBank Accession No. NM_017050.1 (GI:8394327; SEQ ID NO:9).

Additional examples of SOD1 mRNA sequences are readily available using, e.g., GenBank, UniProt, OMIM, and the *Macaca* genome project web site.

Exemplary SOD1 nucleotide sequences may also be found in SEQ ID NOs:1-10. SEQ ID NOs: 2, 4, 6, 8, and 10 are the reverse complement sequences of SEQ ID NOs: 1, 3, 5, 7, and 9, respectively.

Further information on SOD1 is provided, for example in the NCBI Gene database at www.ncbi.nlm.nih.gov/gene/6647.

The entire contents of each of the foregoing GenBank Accession numbers and the Gene database numbers are incorporated herein by reference as of the date of filing this application.

The terms "Superoxide dismutase 1" and "SOD1," as used herein, also refers to naturally occurring DNA sequence variations of the SOD1 gene. Numerous sequence variations within the SOD1 gene have been identified and may be found at, for example, NCBI dbSNP and UniProt (see, e.g., www.ncbi.nlm.nih.gov/snp?LinkName=gene_snp&from_uid=6647, the entire contents of which is incorporated herein by reference as of the date of filing this application.

As used herein, "target sequence" refers to a contiguous portion of the nucleotide sequence of an mRNA molecule formed during the transcription of a SOD1 gene, including mRNA that is a product of RNA processing of a primary transcription product. In one embodiment, the target portion of the sequence will be at least long enough to serve as a substrate for RNAi-directed cleavage at or near that portion of the nucleotide sequence of an mRNA molecule formed during the transcription of a SOD1 gene. In one embodiment, the target sequence is within the protein coding region of the SOD1 gene. In another embodiment, the target sequence is within the 3' UTR of the SOD1 gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. In some embodiments, the target sequence is about 19 to about 30 nucleotides in length. In other embodiments, the target sequence is about 19 to about 25 nucleotides in length. In still other embodiments, the target sequence is about 19 to about 23 nucleotides in length. In some embodiments, the target sequence is about 21 to about 23 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T", and "U" each generally stand for a nucleotide that contains guanine, cytosine, adenine, thymidine, and uracil as a base, respectively in the context of a modified or unmodified nucleotide. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, thymidine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the disclosure.

The terms "iRNA", "RNAi agent," "iRNA agent," "RNA interference agent" as used interchangeably herein, refer to an agent that contains RNA as that term is defined herein, and which mediates the targeted cleavage of an RNA transcript via an RNA-induced silencing complex (RISC) pathway. RNA interference (RNAi) is a process that directs the sequence-specific degradation of mRNA. RNAi modulates, e.g., inhibits, the expression of SOD1 in a cell, e.g., a cell within a subject, such as a mammalian subject.

In one embodiment, an RNAi agent of the disclosure includes a single stranded RNAi that interacts with a target RNA sequence, e.g., a SOD1 target mRNA sequence, to direct the cleavage of the target RNA. Without wishing to be bound by theory it is believed that long double stranded RNA introduced into cells is broken down into double-stranded short interfering RNAs (siRNAs) comprising a sense strand and an antisense strand by a Type III endonuclease known as Dicer (Sharp et al. (2001) Genes Dev. 15:485). Dicer, a ribonuclease-III-like enzyme, processes these dsRNA into 19-23 base pair short interfering RNAs with characteristic two base 3' overhangs (Bernstein, et al., (2001) Nature 409:363). These siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188). Thus, in one aspect the disclosure relates to a single stranded RNA (ssRNA) (the antisense strand of a siRNA duplex) generated within a cell and which promotes the formation of a RISC complex to effect silencing of the target gene, i.e., a SOD1 gene. Accordingly, the term "siRNA" is also used herein to refer to an RNAi as described above.

In another embodiment, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) Cell 150:883-894, the entire contents of each of which are hereby incorporated herein by reference. Any of the antisense nucleotide sequences described herein may be used as a single-stranded siRNA as described herein or as chemically modified by the methods described in Lima et al., (2012) Cell 150:883-894.

In another embodiment, a "RNAi agent" for use in the compositions and methods of the disclosure is a double stranded RNA and is referred to herein as a "double stranded RNAi agent," "double stranded RNA (dsRNA) molecule," "dsRNA agent," or "dsRNA". The term "dsRNA" refers to a complex of ribonucleic acid molecules, having a duplex structure comprising two anti-parallel and substantially complementary nucleic acid strands, referred to as having "sense" and "antisense" orientations with respect to a target RNA, i.e., a SOD1 gene. In some embodiments of the disclosure, a double stranded RNA (dsRNA) triggers the degradation of a target RNA, e.g., an mRNA, through a post-transcriptional gene-silencing mechanism referred to herein as RNA interference or RNAi.

In general, a dsRNA molecule can include ribonucleotides, but as described in detail herein, each or both strands can also include one or more non-ribonucleotides, e.g., a deoxyribonucleotide, a modified nucleotide. In addition, as used in this specification, an "RNAi agent" may include ribonucleotides with chemical modifications; an RNAi agent may include substantial modifications at multiple nucleotides.

As used herein, the term "modified nucleotide" refers to a nucleotide having, independently, a modified sugar moiety, a modified internucleotide linkage, or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the disclosure include all types of modifications disclosed herein or known in the art. Any such modifications, as used in a siRNA type molecule, are encompassed by "RNAi agent" for the purposes of this specification and claims.

In certain embodiments of the instant disclosure, inclusion of a deoxy-nucleotide—which is acknowledged as a naturally occurring form of nucleotide—if present within a RNAi agent can be considered to constitute a modified nucleotide.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at at least 4, at least 5, at least 6, at least 7, at least 8, at least 9, at least 10, at least 20, at least 23 or more unpaired nucleotides or nucleotides not directed to the target site of the dsRNA. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

In certain embodiment, the two strands of double-stranded oligomeric compound can be linked together. The two strands can be linked to each other at both ends, or at one end only. By linking at one end is meant that 5'-end of first strand is linked to the 3'-end of the second strand or 3'-end of first strand is linked to 5'-end of the second strand. When the two strands are linked to each other at both ends, 5'-end of first strand is linked to 3'-end of second strand and 3'-end of first strand is linked to 5'-end of second strand. The two strands can be linked together by an oligonucleotide linker including, but not limited to, (N)n; wherein N is independently a modified or unmodified nucleotide and n is 3-23. In some embodiments, n is 3-10, e.g., 3, 4, 5, 6, 7, 8, 9, or 10. In some embodiments, the oligonucleotide linker is selected from the group consisting of GNRA, (G)4, (U)4, and (dT)4, wherein N is a modified or unmodified nucleotide and R is a modified or unmodified purine nucleotide. Some of the nucleotides in the linker can be involved in base-pair interactions with other nucleotides in the linker. The two strands can also be linked together by a non-nucleoside linker, e.g. a linker described herein. It will be appreciated by one of skill in the art that any oligonucleotide chemical modifications or variations describe herein can be used in the oligonucleotide linker.

Hairpin and dumbbell type oligomeric compounds will have a duplex region equal to or at least 14, 15, 15, 16, 17, 18, 19, 29, 21, 22, 23, 24, or 25 nucleotide pairs. The duplex region can be equal to or less than 200, 100, or 50, in length. In some embodiments, ranges for the duplex region are 15-30, 17 to 23, 19 to 23, and 19 to 21 nucleotides pairs in length.

The hairpin oligomeric compounds can have a single strand overhang or terminal unpaired region, in some embodiments at the 3', and in some embodiments on the antisense side of the hairpin. In some embodiments, the overhangs are 1-4, more generally 2-3 nucleotides in length. The hairpin oligomeric compounds that can induce RNA interference are also referred to as "shRNA" herein.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one embodiment, an RNAi agent of the invention is a dsRNA, each strand of which is 24-30 nucleotides in length, that interacts with a target RNA sequence, e.g., a SOD1 target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

In one embodiment, an RNAi agent of the invention is a dsRNA agent, each strand of which comprises 19-23 nucleotides that interacts with a SOD1 RNA sequence to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). In one embodiment, an RNAi agent of the invention is a dsRNA of 24-30 nucleotides that interacts with a SOD1 RNA sequence to direct the cleavage of the target RNA.

As used herein, the term "nucleotide overhang" refers to at least one unpaired nucleotide that protrudes from the duplex structure of a RNAi agent, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively, the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the antisense strand of a dsRNA has a 1-10 nucleotide, e.g., 0-3, 1-3, 2-4, 2-5, 4-10, 5-10, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the overhang on the sense strand or the antisense strand, can include extended lengths longer than 10 nucleotides, e.g., 1-30 nucleotides, 2-30 nucleotides, 10-30 nucleotides, or 10-15 nucleotides in length. In certain embodiments, an extended overhang is on the sense strand of the duplex. In certain embodiments, an extended overhang is present on the 3' end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3' end of the antisense strand of the duplex. In certain embodiments, an extended overhang is present on the 5'end of the antisense strand of the duplex. In certain embodiments, one or more of the nucleotides in the overhang is replaced with a nucleoside thiophosphate. In certain embodiments, the overhang includes a self-complementary portion such that the overhang is capable of forming a hairpin structure that is stable under physiological conditions.

In certain embodiments, at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, the entire contents of each of which are incorporated by reference herein). Such structures may include single-stranded extensions (on one or both sides of the molecule) as well as double-stranded extensions.

In certain embodiments, the 3' end of the sense strand and the 5' end of the antisense strand are joined by a polynucleotide sequence comprising ribonucleotides, deoxyribonucleotides or both, optionally wherein the polynucleotide sequence comprises a tetraloop sequence. In certain embodiments, the sense strand is 25-35 nucleotides in length.

A tetraloop may contain ribonucleotides, deoxyribonucleotides, modified nucleotides, and combinations thereof. Typically, a tetraloop has 4 to 5 nucleotides. In some embodiments, the loop comprises a sequence set forth as GAAA. In some embodiments, at least one of the nucleotide of the loop (GAAA) comprises a nucleotide modification. In some embodiments, the modified nucleotide comprises a 2'-modification. In some embodiments, the 2'-modification is a modification selected from the group consisting of 2'-aminoethyl, 2'-fluoro, 2'-O-methyl, 2'-O-methoxyethyl, 2'-aminodiethoxymethanol, 2'-adem, and 2'-deoxy-2'-fhioro-d-arabinonucleic acid. In some embodiments, all of the nucleotides of the loop are modified. In some embodiments, the G in the GAAA sequence comprises a 2'-OH. In some embodiments, each of the nucleotides in the GAAA sequence comprises a 2'-O-methyl modification. In some embodiments, each of the A in the GAAA sequence comprises a 2'-OH and the G in the GAAA sequence comprises a 2'-O-methyl modification. In preferred embodiments, In some embodiments, each of the A in the GAAA sequence comprises a 2'-O-methoxyethyl (MOE) modification and the G in the GAAA sequence comprises a 2'-O-methyl modification; or each of the A in the GAAA sequence comprises a 2'-adem modification and the G in the GAAA sequence comprises a 2'-O-methyl modification. See, e.g., PCT Publication No. WO 2020/206350, the entire contents of which are incorporated herein by reference.

An exemplary 2' adem modified nucleotide is shown below:

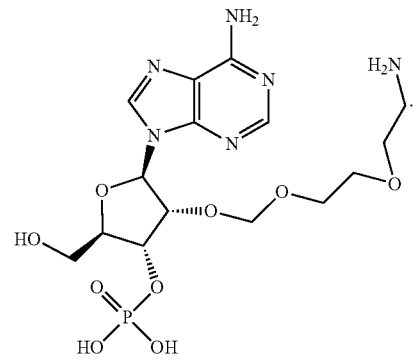 [SMILES: NCCOCCOCO[C@@H]1[C@H](OP(=O)(O)O)[C@@H](CO)O[C@H]1n1cnc2c(N)ncnc21]

In one embodiment of the dsRNA, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In one embodiment, the antisense strand of a dsRNA has a 1-10 nucleotide, e.g., 0-3, 1-3, 2-4, 2-5, 4-10, 5-10, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the overhang on the sense strand or the antisense strand, or both, can include extended lengths longer than 10 nucleotides, e.g., 1-30 nucleotides, 2-30 nucleotides, 10-30 nucleotides, or 10-15 nucleotides in length. In certain embodiments, an extended overhang is on the sense strand of the duplex. In certain embodiments, an extended overhang is present on the 3'end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the overhang is replaced with a nucleoside thiophosphate. In certain embodiments, the overhang includes a self-complementary portion such that the overhang is capable of forming a hairpin structure that is stable under physiological conditions.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double stranded over its entire length.

The term "antisense strand" or "guide strand" refers to the strand of a RNAi agent, e.g., a dsRNA, which includes a region that is substantially complementary to a target sequence, e.g., a SOD1 mRNA.

As used herein, the term "region of complementarity" refers to the region on the antisense strand that is substantially complementary to a sequence, for example a target sequence, e.g., a SOD1 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- or 3'-terminus of the RNAi agent.

In some embodiments, a double stranded RNA agent of the invention includes a nucleotide mismatch in the antisense strand. In some embodiments, the antisense strand of the double stranded RNA agent of the invention includes no more than 4 mismatches with the target mRNA, e.g., the antisense strand includes 4, 3, 2, 1, or 0 mismatches with the target mRNA. In some embodiments, the antisense strand double stranded RNA agent of the invention includes no more than 4 mismatches with the sense strand, e.g., the antisense strand includes 4, 3, 2, 1, or 0 mismatches with the sense strand. In some embodiments, a double stranded RNA agent of the invention includes a nucleotide mismatch in the sense strand. In some embodiments, the sense strand of the double stranded RNA agent of the invention includes no more than 4 mismatches with the antisense strand, e.g., the sense strand includes 4, 3, 2, 1, or 0 mismatches with the antisense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA agent. In some embodiments, the mismatch(s) is not in the seed region.

Thus, an RNAi agent as described herein can contain one or more mismatches to the target sequence. In one embodiment, a RNAi agent as described herein contains no more than 3 mismatches (i.e., 3, 2, 1, or 0 mismatches). In one embodiment, an RNAi agent as described herein contains no more than 2 mismatches. In one embodiment, an RNAi agent as described herein contains no more than 1 mismatch. In one embodiment, an RNAi agent as described herein contains 0 mismatches. In certain embodiments, if the antisense strand of the RNAi agent contains mismatches to the target sequence, the mismatch can optionally be restricted to be within the last 5 nucleotides from either the 5'- or 3'-end of the region of complementarity. For example, in such embodiments, for a 23 nucleotide RNAi agent, the strand which is complementary to a region of a SOD1 gene, generally does not contain any mismatch within the central 13 nucleotides. The methods described herein or methods known in the art can be used to determine whether an RNAi agent containing a mismatch to a target sequence is effective in inhibiting the expression of a SOD1 gene. Consideration of the efficacy of RNAi agents with mismatches in inhibiting expression of a SOD1 gene is important, especially if the particular region of complementarity in a SOD1 gene is known to have polymorphic sequence variation within the population.

The term "sense strand" or "passenger strand" as used herein, refers to the strand of a RNAi agent that includes a region that is substantially complementary to a region of the antisense strand as that term is defined herein.

As used herein, "substantially all of the nucleotides are modified" are largely but not wholly modified and can include not more than 5, 4, 3, 2, or 1 unmodified nucleotides.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can be, for example, "stringent conditions", where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within a RNAi agent, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression, in vitro or in vivo. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogsteen base pairing.

The terms "complementary," "fully complementary" and "substantially complementary" herein can be used with respect to the base matching between the sense strand and the antisense strand of a dsRNA, or between two oligonucleotides or polynucleotides, such as the antisense strand of a RNAi agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding SOD1). For example, a polynucleotide is complementary to at least a part of a SOD1 mRNA if the sequence is substantially complementary to a non-interrupted portion of an mRNA encoding SOD1.

Accordingly, in some embodiments, the antisense strand polynucleotides disclosed herein are fully complementary to the target SOD1 sequence.

In other embodiments, the antisense strand polynucleotides disclosed herein are substantially complementary to the target SOD1 sequence and comprise a contiguous nucleotide sequence which is at least about 80% complementary over its entire length to the equivalent region of the nucleotide sequence of SEQ ID NOs: 1, 3, 5, 7, or 9 for SOD1, or a fragment of SEQ ID NOs: 1, 3, 5, 7, or 9, such as about 85%, about 90%, or about 95% complementary.

In other embodiments, the antisense polynucleotides disclosed herein are substantially complementary to the target SOD1 sequence and comprise a contiguous nucleotide sequence which is at least about 80% complementary over its entire length to any one of the sense strand nucleotide sequences in any one of Tables 2-7, 12, 13, and 18-20, or a fragment of any one of the sense strand nucleotide sequences in any one of Tables 2-7, 12, 13, and 18-20, such as about 85%, about 90%, or about 95% complementary.

In one embodiment, an RNAi agent of the disclosure includes a sense strand that is substantially complementary to an antisense polynucleotide which, in turn, is the same as a target SOD1 sequence, and wherein the sense strand polynucleotide comprises a contiguous nucleotide sequence which is at least about 80% complementary over its entire length to the equivalent region of the nucleotide sequence of SEQ ID NOs: 2, 4, 6, 8, or 10, or a fragment of any one of SEQ ID NOs: 2, 4, 6, 8, or 10, such as about 85%, about 90%, or about 95% complementary.

In some embodiments, an iRNA of the invention includes a sense strand that is substantially complementary to an antisense polynucleotide which, in turn, is complementary to a target SOD1 sequence, and wherein the sense strand polynucleotide comprises a contiguous nucleotide sequence which is at least about 80% complementary over its entire length to any one of the antisense strand nucleotide sequences in any one of any one of Tables 2-7, 12, 13, and 18-20, or a fragment of any one of the antisense strand nucleotide sequences in any one of Tables 2-7, 12, 13, and 18-20, such as about 85%, about 90%, or about 95% complementary.

In some embodiments, the double-stranded region of a double-stranded iRNA agent is equal to or at least, 10, 11, 12, 13, 14, 15, 16, 17, 18, 19, 20, 21, 22, 23, 23, 24, 25, 26, 27, 28, 29, 30 or more nucleotide pairs in length.

In some embodiments, the antisense strand of a double-stranded iRNA agent is equal to or at least 14, 15, 16, 17, 18, 19, 20, 21, 22, 23, 23, 24, 25, 26, 27, 28, 29, or 30 nucleotides in length.

In some embodiments, the sense strand of a double-stranded iRNA agent is equal to or at least 10, 11, 12, 13, 14, 15, 16, 17, 18, 19, 20, 21, 22, 23, 23, 24, 25, 26, 27, 28, 29, or 30 nucleotides in length.

In one embodiment, the sense and antisense strands of the double-stranded iRNA agent are each independently 15 to 30 nucleotides in length.

In one embodiment, the sense and antisense strands of the double-stranded iRNA agent are each independently 19 to 25 or 19 to 30 nucleotides in length.

In one embodiment, the sense and antisense strands of the double-stranded iRNA agent are each independently 21 to 23 nucleotides in length.

In one embodiment, the sense strand of the iRNA agent is 21-nucleotides in length, and the antisense strand is 23-nucleotides in length, wherein the strands form a double-stranded region of 21 consecutive base pairs having a 2-nucleotide long single stranded overhangs at the 3'-end.

In one aspect of the invention, an agent for use in the methods and compositions of the invention is a single-stranded antisense nucleic acid molecule that inhibits a target mRNA via an antisense inhibition mechanism. The single-stranded antisense RNA molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences described herein.

In one embodiment, at least partial suppression of the expression of a SOD1 gene, is assessed by a reduction of the amount of SOD1 mRNA which can be isolated from or detected in a first cell or group of cells in which a SOD1 gene is transcribed and which has or have been treated such that the expression of a SOD1 gene is inhibited, as compared to a second cell or group of cells substantially identical to the first cell or group of cells but which has or have not been so treated (control cells). The degree of inhibition may be expressed in terms of:

$$\frac{(mRNA \text{ in control cells}) - (mRNA \text{ in treated cells})}{(mRNA \text{ in control cells})} \cdot 100\%$$

In one embodiment, inhibition of expression is determined by the dual luciferase method in Example 1 wherein the RNAi agent is present at 10 nM.

The phrase "contacting a cell with an RNAi agent," such as a dsRNA, as used herein, includes contacting a cell by any possible means. Contacting a cell with an RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the central nervous system (CNS), optionally via intrathecal, intracerebroventricular or other injection, or to the bloodstream or the subcutaneous space, such that the agent will subsequently reach the tissue where the cell to be contacted is located. For example, the RNAi agent may contain or be coupled to a ligand, e.g., a lipophilic moiety or moieties as described below and further detailed, e.g., in PCT Publication No. WO 2019/217459, which is incorporated herein by reference, that directs or otherwise stabilizes the RNAi agent at a site of interest, e.g., the CNS. In some embodiments, the RNAi agent may contain or be coupled to a ligand, e.g., one or more GalNAc derivatives as described below, that directs or otherwise stabilizes the RNAi agent at a site of interest, e.g., the liver. In other embodiments, the RNAi agent may contain or be coupled to a lipophilic moiety or moieties and one or more GalNAc derivatives. Combinations of in vitro and in vivo methods of contacting are also possible. For example, a cell may also be contacted in vitro with an RNAi agent and subsequently transplanted into a subject.

In one embodiment, contacting a cell with an RNAi agent includes "introducing" or "delivering the RNAi agent into the cell" by facilitating or effecting uptake or absorption into the cell. Absorption or uptake of a RNAi agent can occur through unaided diffusive or active cellular processes, or by auxiliary agents or devices. Introducing a RNAi agent into a cell may be in vitro or in vivo. For example, for in vivo introduction, a RNAi agent can be injected into a tissue site or administered systemically. In vitro introduction into a cell includes methods known in the art such as electroporation and lipofection. Further approaches are described herein below or are known in the art.

The term "lipophile" or "lipophilic moiety" broadly refers to any compound or chemical moiety having an affinity for lipids. One way to characterize the lipophilicity of the lipophilic moiety is by the octanol-water partition coefficient, log $K_{ow}$, where $K_{ow}$, is the ratio of a chemical's concentration in the octanol-phase to its concentration in the aqueous phase of a two-phase system at equilibrium. The octanol-water partition coefficient is a laboratory-measured property of a substance. However, it may also be predicted by using coefficients attributed to the structural components of a chemical which are calculated using first-principle or empirical methods (see, for example, Tetko et al., *J. Chem. Inf. Comput. Sci.* 41:1407-21 (2001), which is incorporated herein by reference in its entirety). It provides a thermodynamic measure of the tendency of the substance to prefer a non-aqueous or oily milieu rather than water (i.e. its hydrophilic/lipophilic balance). In principle, a chemical substance is lipophilic in character when its log $K_{ow}$ exceeds 0. Typically, the lipophilic moiety possesses a log $K_{ow}$ exceeding 1, exceeding 1.5, exceeding 2, exceeding 3, exceeding 4, exceeding 5, or exceeding 10. For instance, the log $K_{ow}$ of 6-amino hexanol, for instance, is predicted to be approximately 0.7. Using the same method, the log $K_{ow}$ of cholesteryl N-(hexan-6-ol) carbamate is predicted to be 10.7.

The lipophilicity of a molecule can change with respect to the functional group it carries. For instance, adding a hydroxyl group or amine group to the end of a lipophilic moiety can increase or decrease the partition coefficient (e.g., log $K_{ow}$) value of the lipophilic moiety.

Alternatively, the hydrophobicity of the double-stranded RNAi agent, conjugated to one or more lipophilic moieties, can be measured by its protein binding characteristics. For instance, in certain embodiments, the unbound fraction in the plasma protein binding assay of the double-stranded RNAi agent could be determined to positively correlate to the relative hydrophobicity of the double-stranded RNAi agent, which could then positively correlate to the silencing activity of the double-stranded RNAi agent.

In one embodiment, the plasma protein binding assay determined is an electrophoretic mobility shift assay (EMSA) using human serum albumin protein. An exemplary protocol of this binding assay is illustrated in detail in, e.g., PCT Publication No. WO 2019/217459. The hydrophobicity of the double-stranded RNAi agent, measured by fraction of unbound siRNA in the binding assay, exceeds 0.15, exceeds 0.2, exceeds 0.25, exceeds 0.3, exceeds 0.35, exceeds 0.4, exceeds 0.45, or exceeds 0.5 for an enhanced in vivo delivery of siRNA.

Accordingly, conjugating the lipophilic moieties to the internal position(s) of the double-stranded RNAi agent provides optimal hydrophobicity for the enhanced in vivo delivery of siRNA.

The term "lipid nanoparticle" or "LNP" is a vesicle comprising a lipid layer encapsulating a pharmaceutically active molecule, such as a nucleic acid molecule, e.g., a RNAi agent or a plasmid from which a RNAi agent is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), or a non-primate (such as a rat, or a mouse). In a preferred embodiment, the subject is a human, such as a human being treated or assessed for a disease, disorder, or condition that would benefit from reduction in SOD1 expression; a human at risk for a disease, disorder, or condition that would benefit from reduction in SOD1 expression; a human having a disease, disorder, or condition that would benefit from reduction in SOD1 expression; or human being treated for a disease, disorder, or condition that would benefit from reduction in SOD1 expression as described herein.

As used herein, the terms "treating" or "treatment" refer to a beneficial or desired result including, but not limited to, alleviation or amelioration of one or more signs or symptoms associated with SOD1 gene expression or SOD1 protein production, e.g., SOD1-associated neurodegenerative disease, e.g., Amyotrophic Lateral Sclerosis (ALS), Alzheimer's disease (AD), Parkinson's disease (PD), and Down's syndrome (DS), decreased expression, deposition, and/or activity of SOD1 in regions of increased neuronal death in subjects having such neurodegenerative diseases. "Treatment" can also mean prolonging survival as compared to expected survival in the absence of treatment.

The term "lower" in the context of the level of SOD1 in a subject or a disease marker or symptom refers to a statistically significant decrease in such level. The decrease can be, for example, at least 10%, 15%, 20%, 25%, 30%, %, 40%, 45%, 50%, 55%, 60%, 65%, 70%, 75%, 80%, 85%, 90%, 95%, or more. In certain embodiments, a decrease is at least 20%. In certain embodiments, the decrease is at least 50% in a disease marker, e.g., protein or gene expression level. "Lower" in the context of the level of SOD1 in a subject is preferably down to a level accepted as within the range of normal for an individual without such disorder. In certain embodiments, "lower" is the decrease in the difference between the level of a marker or symptom for a subject suffering from a disease and a level accepted within the range of normal for an individual, e.g., the level of decrease in bodyweight between an obese individual and an individual having a weight accepted within the range of normal.

As used herein, "prevention" or "preventing," when used in reference to a disease, disorder, or condition thereof, that would benefit from a reduction in expression of a SOD1 gene or production of a SOD1 protein, refers to a reduction in the likelihood that a subject will develop a symptom associated with such a disease, disorder, or condition, e.g., a symptom of a SOD1-associated neurodegenerative disease. The failure to develop a disease, disorder, or condition, or the reduction in the development of a symptom associated with such a disease, disorder, or condition, e.g., neuroinflammation (e.g., by at least about 10% on a clinically accepted scale for that disease or disorder), or the exhibition of delayed symptoms delayed (e.g., by days, weeks, months or years) is considered effective prevention.

As used herein, the term "SOD1-associated neurodegenerative disease" or "SOD1-associated neurodegenerative disorder" is understood as any disease or disorder that would benefit from reduction in the expression or activity of SOD1. Such SOD1-neurodegenerative diseases are characterized by SOD1 protein misfolding, e.g., increased SOD1 deposition in areas of the brain associated with neuronal cell death in such diseases (see, e.g., Trist B, et al. (2020) *Angew Chem Int Ed Engl*. Accepted Author Manuscript), e.g., Amyotrophic Lateral Sclerosis (ALS), Alzheimer's disease (AD), Parkinson's disease (PD), and Down's syndrome (DS).

In one embodiment, a SOD1-associated neurodegenerative disease is "Amyotrophic Lateral Sclerosis" ("ALS"), also known as Lou Gehrig's disease.

Amyotrophic lateral sclerosis (ALS) is a progressive disease that affects motor neurons in the spinal cord and the brain. In ALS, motor neurons die (atrophy) over time, leading to muscle weakness, a loss of muscle mass, and an inability to control movement.

Mutations in the SOD1 gene cause approximately 20% of inherited familial amyotrophic lateral sclerosis (fALS) cases and up to approximately 5% of sporadic ALS (sALS) cases. The resulting mutations, including, e.g., amino-acid substitutions, insertions, deletions, and/or genetic polymorphisms, destabilize SOD 1's protein structure, leading to its misfolding and self-assembly into neurotoxic oligomers and aggregates, a process that contributes to the characteristic motor neuron degeneration in affected individuals.

People with sporadic ALS usually first develop features of the condition in their late fifties or early sixties. Sporadic and familial ALS present similar pathological and clinical profiles.

The earliest symptoms of ALS include muscle twitching, cramping, stiffness, or weakness. Affected individuals may develop slurred speech (dysarthria) and, later, difficulty chewing or swallowing (dysphagia). Many people with ALS experience malnutrition because of reduced food intake due to dysphagia and an increase in their body's energy demands (metabolism) due to prolonged illness. Muscles become weaker as the disease progresses, and arms and legs begin to look thinner as muscle tissue atrophies. Individuals with ALS eventually lose muscle strength and the ability to walk. Affected individuals eventually become wheelchair-dependent and increasingly require help with personal care and other activities of daily living. Over time, muscle weakness causes affected individuals to lose the use of their hands and arms. Breathing becomes difficult because the muscles of the respiratory system weaken. Most people with ALS die from respiratory failure within 2 to 10 years after the signs and symptoms of ALS first appear; however, disease progression varies widely among affected individuals.

SOD1 accumulation has been found in the motor neurons, spinal cord, and associated cells of postmortem mutant SOD1 transgenic mice and human ALS patient tissues. Furthermore, SOD1 transgenic mice, an art-recognized model of ALS, which express mutated SOD1 forms in similar or elevated levels as to the endogenous mouse protein have been shown to recapitulate the ALS-phenotype. These mice develop severe degeneration of motor neurons which leads to progressive paralysis of the hindlimbs and forelimbs and death, as seen in ALS human patients. These mice also present pathology found in postmortem tissues from human patients, such as SOD1 cytoplasmic inclusions, gliosis, glutamate excitotoxicity, vacuolization of mitochondria, and disrupted axonal transport (Mina M, et al. (2018) *J Transl Neurosci*. 3:9).

In one embodiment, a SOD1-associated neurodegenerative disease is "Alzheimer's disease" ("AD"). AD is a chronic neurodegenerative disease that usually starts slowly and gradually worsens over time. The most common early symptom is difficulty in remembering recent events. As the disease advances, symptoms can include problems with language, disorientation (including easily getting lost), mood swings, loss of motivation, not managing self-care, and behavioral issues. As a person's condition declines, they often withdraw from family and society. Gradually, bodily functions are lost, ultimately leading to death.

Neuropathologically, AD is characterised by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Degeneration is also present in brainstem nuclei like the locus coeruleus. Studies using MRI and PET have documented reductions in the size of specific brain regions in people with AD as they progressed from mild cognitive impairment to Alzheimer's disease, and in comparison with similar images from healthy older adults.

Both amyloid plaques and neurofibrillary tangles are clearly visible by microscopy in brains of those afflicted by AD. Plaques are dense, mostly insoluble deposits of beta-amyloid peptide and cellular material outside and around neurons. Tangles (neurofibrillary tangles) are aggregates of the microtubule-associated protein tau which has become hyperphosphorylated and accumulate inside the cells themselves. Although many older individuals develop some plaques and tangles as a consequence of ageing, the brains of people with AD have a greater number of them in specific brain regions such as the temporal lobe. Lewy bodies are not rare in the brains of people with AD.

The post-mortem and in vivo examinations of individuals with AD have also showed an accumulation of products of free radicals damage in the central nervous system and in the peripheral tissues. Additionally, SOD1 aggregates have been identified in AD brains and we shown to be associated with amyloid senile plaques and neurofibrillary tangles (Choi J, et al. (2005) *JBC*. 280:11648-11655).

In one embodiment, SOD1-associated neurodegenerative disease is "Parkinson's disease" ("PD"). Parkinson disease is a progressive disorder of the nervous system. The disorder affects several regions of the brain, especially an area called the substantia nigra that controls balance and movement. PD leads to loss of dopaminergic neurons within the basal ganglia.

Often the first symptom of Parkinson disease is trembling or shaking (tremor) of a limb, especially when the body is at rest. Typically, the tremor begins on one side of the body, usually in one hand. Tremors can also affect the arms, legs, feet, and face. Other characteristic symptoms of Parkinson disease include rigidity or stiffness of the limbs and torso, slow movement (bradykinesia) or an inability to move (akinesia), and impaired balance and coordination (postural instability). These symptoms worsen slowly over time.

Parkinson disease can also affect emotions and thinking ability (cognition). Some affected individuals develop psychiatric conditions such as depression and visual hallucinations. People with Parkinson disease also have an increased risk of developing dementia, which is a decline in intellectual functions including judgment and memory.

Previous studies have demonstrated that the total level of SOD1 protein is significantly increased the brains of PD patients (Choi J, et al. (2005) *JBC.* 280:11648-11655). Additionally, deposition of SOD1 in Lewy bodies in the brains of PD patients has beed detected (Nishiyama L, et al. (1995) *Acta Neuropathologica,* 89:471-474).

In one embodiment, a SOD1-associated neurodegenerative disease is "Down's syndrome (DS)". Down syndrome ("DS") is caused by trisomy of human chromosome 21 (Hsa21) and the increased expression, due to dosage, of some subset of the encoded genes. DS patients present different morphological characteristics, for example, short height, obesity and bilateral epicanthic eyefolds. Additionally, muscular hypotonia and neurodegeneration with age may be noted during life. The syndrome is associated with mental retardation, congenital heart disease, immune system disorders, digestive problems, endocrine system deficits, and different biochemical disorders. Evidence from in vivo, in vitro, and animal models studies have shown that oxidative stress is involved in DS. Thus, it has been proposed that the increased oxidative stress observed in these subjects is mainly caused to an excessive activity of SOD1, an enzyme coded on HSA21 (21q22.1). Patients with DS have also shown elevated levels of SOD1 and appear to have increased lipid peroxidation and oxidative damage to DNA as well as elevated glutathione peroxidase activity (Campos C and Casado A. (2015) *Indian J Med Res.* 142(2):113-119).

"Therapeutically effective amount," as used herein, is intended to include the amount of an RNAi agent that, when administered to a subject having a SOD1-associated neurodegenerative disease, is sufficient to effect treatment of the disease (e.g., by diminishing, ameliorating, or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of a RNAi agent that, when administered to a subject having a SOD1-associated neurodegenerative disorder, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of a RNAi agent that produces some desired local or systemic effect at a reasonable benefit/risk ratio applicable to any treatment. A RNAi agent employed in the methods of the present disclosure may be administered in a sufficient amount to produce a reasonable benefit/risk ratio applicable to such treatment.

The phrase "pharmaceutically acceptable" is employed herein to refer to those compounds (including salts), materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the brain (e.g., whole brain or certain segments of brain, e.g., striatum, or certain types of cells in the brain, such as, e.g., neurons and glial cells (astrocytes, oligodendrocytes, microglial cells)). In other embodiments, a "sample derived from a subject" refers to liver tissue (or subcomponents thereof) derived from the subject. In some embodiments, a "sample derived from a subject" refers to blood drawn from the subject or plasma or serum derived therefrom. In further embodiments, a "sample derived from a subject" refers to brain tissue (or subcomponents thereof) or retinal tissue (or subcomponents thereof) derived from the subject.

II. RNAi Agents of the Disclosure

Described herein are RNAi agents which inhibit the expression of a SOD1 gene. In one embodiment, the RNAi agent includes double stranded ribonucleic acid (dsRNA) molecules for inhibiting the expression of a SOD1 gene in a cell, such as a cell within a subject, e.g., a mammal, such as a human having a SOD1-associated neurodegenerative disease, e.g., Amyotrophic Lateral Sclerosis (ALS), Alzheimer's disease (AD), Parkinson's disease (PD), and Down's syndrome (DS). The dsRNA includes an antisense strand having a region of complementarity which is complementary to at least a part of an mRNA formed in the expression of a SOD1 gene. The region of complementarity is about 15-30 nucleotides or less in length. Upon contact with a cell expressing the SOD1 gene, the RNAi agent inhibits the expression of the SOD1 gene (e.g., a human gene, a primate gene, a non-primate gene) by at least 50% as assayed by, for example, a PCR or branched DNA (bDNA)-based method, or by a protein-based method, such as by immunofluorescence analysis, using, for example, western blotting or flowcytometric techniques. In preferred embodiments, inhibition of expression is by at least 50% as assayed by the Dual-Glo luciferase assay in Example 1 where the siRNA is at a 10 nM concentration.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a SOD1 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 15 to 30 base pairs in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. In certain preferred embodiments, the duplex structure is 18 to 25 base pairs in length, e.g., 18-25, 18-24, 18-23, 18-22, 18-21, 18-20, 19-25, 19-24, 19-23, 19-22, 19-21, 19-20, 20-25, 20-24, 20-23, 20-22, 20-21, 21-25, 21-24, 21-23, 21-22, 22-25, 22-24, 22-23, 23-25, 23-24 or 24-25 base pairs in length, for example, 19-21 basepairs in length. Ranges and lengths intermediate to the above recited ranges and lengths are also contemplated to be part of the disclosure.

Similarly, the region of complementarity to the target sequence is 15 to 30 nucleotides in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, for example 19-23 nucleotides in length or 21-23 nucleotides in length. Ranges and lengths intermediate to the above recited ranges and lengths are also contemplated to be part of the disclosure.

In some embodiments, the dsRNA is 15 to 23 nucleotides in length, 25 to 30 nucleotides in length, 20 to 30 nucleotides in length or 19 to 30 nucleotides in length. In general, the dsRNA is long enough to serve as a substrate for the Dicer enzyme. For example, it is well known in the art that dsRNAs longer than about 21-23 nucleotides can serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 15 to 36 base pairs, e.g., 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs, for example, 19-21 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, a RNAi agent useful to target SOD1 expression is not generated in the target cell by cleavage of a larger dsRNA.

A dsRNA as described herein can further include one or more single-stranded nucleotide overhangs e.g., 1, 2, 3, or 4 nucleotides. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA. In certain embodiments, longer, extended overhangs are possible.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

An siRNA can be produced, e.g., in bulk, by a variety of methods. Exemplary methods include: organic synthesis and RNA cleavage, e.g., in vitro cleavage.

An siRNA can be made by separately synthesizing a single stranded RNA molecule, or each respective strand of a double-stranded RNA molecule, after which the component strands can then be annealed.

A large bioreactor, e.g., the OligoPilot II from Pharmacia Biotec AB (Uppsala Sweden), can be used to produce a large amount of a particular RNA strand for a given siRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the 21 to 23 nucleotide strand for the siRNA. Typically, the two complementary strands are produced separately and then annealed, e.g., after release from the solid support and deprotection.

Organic synthesis can be used to produce a discrete siRNA species. The complementary of the species to a SOD1 gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

In one embodiment, RNA generated is carefully purified to remove endsiRNA is cleaved in vitro into siRNAs, for example, using a Dicer or comparable RNAse III-based activity. For example, the dsiRNA can be incubated in an in vitro extract from *Drosophila* or using purified components, e.g., a purified RNAse or RISC complex (RNA-induced silencing complex). See, e.g., Ketting et al. *Genes Dev* 2001 Oct. 15; 15(20):2654-9 and Hammond Science 2001 Aug. 10; 293(5532):1146-50.

dsiRNA cleavage generally produces a plurality of siRNA species, each being a particular 21 to 23 nt fragment of a source dsiRNA molecule. For example, siRNAs that include sequences complementary to overlapping regions and adjacent regions of a source dsiRNA molecule may be present.

Regardless of the method of synthesis, the siRNA preparation can be prepared in a solution (e.g., an aqueous or organic solution) that is appropriate for formulation. For example, the siRNA preparation can be precipitated and redissolved in pure double-distilled water, and lyophilized. The dried siRNA can then be resuspended in a solution appropriate for the intended formulation process.

In one aspect, a dsRNA of the disclosure includes at least two nucleotide sequences, a sense sequence and an antisense sequence. The sense strand sequence for SOD1 may be selected from the group of sequences provided in any one of Tables 2-7, 12, 13, and 18-20, and the corresponding nucleotide sequence of the antisense strand of the sense strand may be selected from the group of sequences of any one of Tables 2-7, 12, 13, and 18-20. In this aspect, one of the two sequences is complementary to the other of the two sequences, with one of the sequences being substantially complementary to a sequence of an mRNA generated in the expression of a SOD1 gene. As such, in this aspect, a dsRNA will include two oligonucleotides, where one oligonucleotide is described as the sense strand (passenger strand) in any one of Tables 2-7, 12, 13 and 18-20, and the second oligonucleotide is described as the corresponding antisense strand (guide strand) of the sense strand in any one of Tables 2-7, 12, 13, and 18-20 for SOD1.

In one embodiment, the substantially complementary sequences of the dsRNA are contained on separate oligonucleotides. In another embodiment, the substantially complementary sequences of the dsRNA are contained on a single oligonucleotide.

It will be understood that, although the sequences provided herein are described as modified or conjugated sequences, the RNA of the RNAi agent of the disclosure e.g., a dsRNA of the disclosure, may comprise any one of the sequences set forth in any one of Tables 2-7, 12, 13, and 18-20 that is un-modified, un-conjugated, or modified or conjugated differently than described therein. One or more lipophilic ligands or one or more GalNAc ligands can be included in any of the positions of the RNAi agents provided in the instant application.

The skilled person is well aware that dsRNAs having a duplex structure of about 20 to 23 base pairs, e.g., 21, base pairs have been hailed as particularly effective in inducing RNA interference (Elbashir et al., (2001) *EMBO J.*, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided herein, dsRNAs described herein can include at least one strand of a length of minimally 21 nucleotides. It can be reasonably expected that shorter duplexes minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences provided herein, and differing in their ability to inhibit the expression of a SOD1 gene by not more than 10, 15, 20, 25, or 30% inhibition from a dsRNA comprising the full sequence using the in vitro assay with Cos7 and a 10 nM concentration of the RNA agent and the PCR assay as provided in the examples herein, are contemplated to be within the scope of the present disclosure.

In addition, the RNAs described herein identify a site(s) in a SOD1 transcript that is susceptible to RISC-mediated cleavage. As such, the present disclosure further features RNAi agents that target within this site(s). As used herein, a RNAi agent is said to target within a particular site of an RNA transcript if the RNAi agent promotes cleavage of the transcript anywhere within that particular site. Such a RNAi agent will generally include at least about 15 contiguous nucleotides, preferably at least 19 nucleotides, from one of the sequences provided herein coupled to additional nucleotide sequences taken from the region contiguous to the selected sequence in a SOD1 gene.

An RNAi agent as described herein can contain one or more mismatches to the target sequence. In one embodiment, an RNAi agent as described herein contains no more than 3 mismatches (i.e., 3, 2, 1, or 0 mismatches). In one embodiment, an RNAi agent as described herein contains no more than 2 mismatches. In one embodiment, an RNAi agent as described herein contains no more than 1 mismatch. In one embodiment, an RNAi agent as described herein contains 0 mismatches. In certain embodiments, if the antisense strand of the RNAi agent contains mismatches to the target sequence, the mismatch can optionally be restricted to be within the last 5 nucleotides from either the 5'- or 3'-end of the region of complementarity. For example, in such embodiments, for a 23 nucleotide RNAi agent, the strand which is complementary to a region of a SOD1 gene generally does not contain any mismatch within the central 13 nucleotides. The methods described herein or methods known in the art can be used to determine whether an RNAi agent containing a mismatch to a target sequence is effective in inhibiting the expression of a SOD1 gene. Consideration of the efficacy of RNAi agents with mismatches in inhibiting expression of a SOD1 gene is important, especially if the particular region of complementarity in a SOD1 gene is known to have polymorphic sequence variation within the population.

III. Modified RNAi Agents of the Disclosure

In one embodiment, the RNA of the RNAi agent of the disclosure e.g., a dsRNA, is un-modified, and does not comprise, e.g., chemical modifications or conjugations known in the art and described herein. In preferred embodiments, the RNA of an RNAi agent of the disclosure, e.g., a dsRNA, is chemically modified to enhance stability or other beneficial characteristics. In certain embodiments of the disclosure, substantially all of the nucleotides of an RNAi agent of the disclosure are modified. In other embodiments of the disclosure, all of the nucleotides of an RNAi agent of the disclosure are modified. RNAi agents of the disclosure in which "substantially all of the nucleotides are modified" are largely but not wholly modified and can include not more than 5, 4, 3, 2, or 1 unmodified nucleotides. In still other embodiments of the disclosure, RNAi agents of the disclosure can include not more than 5, 4, 3, 2 or 1 modified nucleotides.

The nucleic acids featured in the disclosure can be synthesized or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of RNAi agents useful in the embodiments described herein include, but are not limited to, RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified RNAi agent will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, e.g., sodium salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in RNAi agents, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the RNAi agents of the disclosure are described in, for example, in Nielsen et al., Science, 1991, 254, 1497-1500.

Some embodiments featured in the disclosure include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— of the above-referenced U.S.

Pat. No. 5,489,677, and the amide backbones of the above-referenced U.S. Pat. No. 5,602,240. In some embodiments, the RNAs featured herein have morpholino backbone structures of the above-referenced U55,034,506. The native phosphodiester backbone can be represented as O—P(O)(OH)—OCH2-.

Modified RNAs can also contain one or more substituted sugar moieties. The RNAi agents, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[CH_2)_{11}CH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a RNAi agent, or a group for improving the pharmacodynamic properties of a RNAi agent, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$), 2'-O-hexadecyl, and 2'-fluoro (2'-F). Similar modifications can also be made at other positions on the RNA of a RNAi agent, particularly the 3' position of the sugar on the 3' terminal nucleotide or in 2'-5' linked dsRNAs and the 5' position of 5' terminal nucleotide. RNAi agents can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An RNAi agent of the disclosure can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) *Angewandte Chemie, International Edition,* 30:613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

An RNAi agent of the disclosure can also be modified to include one or more bicyclic sugar moities. A "bicyclic sugar" is a furanosyl ring modified by a ring formed by the bridging of two carbons, whether adjacent or non-adjacent. A "bicyclic nucleoside" ("BNA") is a nucleoside having a sugar moiety comprising a ring formed by bridging two carbons, whether adjacent or non-adjacent, of the sugar ring, thereby forming a bicyclic ring system. In certain embodiments, the bridge connects the 4'-carbon and the 2'-carbon of the sugar ring, optionally, via the 2'-acyclic oxygen atom. Thus, in some embodiments an agent of the disclosure may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-$CH_2$—O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the disclosure include without limitation nucleosides comprising a bridge between the 4' and the 2' ribosyl ring atoms. In certain embodiments, the antisense polynucleotide agents of the disclosure include one or more bicyclic nucleosides comprising a 4' to 2' bridge.

A locked nucleoside can be represented by the structure (omitting stereochemistry),

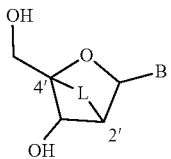

wherein B is a nucleobase or modified nucleobase and L is the linking group that joins the 2'-carbon to the 4'-carbon of the ribose ring. Examples of such 4' to 2' bridged bicyclic nucleosides, include but are not limited to 4'-($CH_2$)—O-2' (LNA); 4'-($CH_2$)—S-2'; 4'-($CH_2$)$_2$—O-2' (ENA); 4'-CH($CH_3$)—O-2' (also referred to as "constrained ethyl" or "cEt") and 4'-CH($CH_2OCH_3$)—O-2' (and analogs thereof; see, e.g., U.S. Pat. No. 7,399,845); 4'-C($CH_3$)($CH_3$)—O-2' (and analogs thereof; see e.g., U.S. Pat. No. 8,278,283); 4'-$CH_2$—N($OCH_3$)-2' (and analogs thereof; see e.g., U.S. Pat. No. 8,278,425); 4'-$CH_2$—O—N($CH_3$)-2' (see, e.g., U.S. Patent Publication No. 2004/0171570); 4'-$CH_2$—N(R)—O-2', wherein R is H, C1-C12 alkyl, or a nitrogen protecting group (see, e.g., U.S. Pat. No. 7,427,672; *Greene's Protective Groups in Organic Synthesis, Fourth Edition*, 2006, eds. John Wiley & Sons, Inc.); 4'-$CH_2$—C(H)($CH_3$)-2' (see, e.g., Chattopadhyaya et al., *J. Org. Chem.*, 2009, 74, 118-134); and 4'-$CH_2$—C(=$H_2$)-2' (and analogs thereof; see, e.g., U.S. Pat. No. 8,278,426). The entire contents of each of the foregoing are hereby incorporated herein by reference.

Additional representative US Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

An RNAi agent of the disclosure can also be modified to include one or more constrained ethyl nucleotides. As used herein, a "constrained ethyl nucleotide" or "cEt" is a locked nucleic acid comprising a bicyclic sugar moiety comprising a 4'-CH($CH_3$)—O-2' bridge (i.e., L in the preceding structure). In one embodiment, a constrained ethyl nucleotide is in the S conformation referred to herein as "S-cEt."

An RNAi agent of the disclosure may also include one or more "conformationally restricted nucleotides" ("CRN"). CRN are nucleotide analogs with a linker connecting the C2' and C4' carbons of ribose or the C3 and –C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US 2013/0190383; and WO 2013/036868, the entire contents of each of which are hereby incorporated herein by reference.

In some embodiments, a RNAi agent of the disclosure comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series*, 52, 133-134 (2008) and Fluiter et al., *Mol. Biosyst.*, 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3'-phosphate, inverted 2'-deoxy-modified ribonucleotide, such as inverted dT(idT), inverted dA (idA), and inverted abasic 2'-deoxyribonucleotide (iAb) and others. Disclosure of this modification can be found in WO 2011/005861.

In one example, the 3' or 5' terminal end of a oligonucleotide is linked to an inverted 2'-deoxy-modified ribonucleotide, such as inverted dT(idT), inverted dA (idA), or a inverted abasic 2'-deoxyribonucleotide (iAb). In one particular example, the inverted 2'-deoxy-modified ribonucleotide is linked to the 3'end of an oligonucleotide, such as the 3'-end of a sense strand described herein, where the linking is via a 3'-3' phosphodiester linkage or a 3'-3'-phosphorothioate linkage.

In another example, the 3'-end of a sense strand is linked via a 3'-3'-phosphorothioate linkage to an inverted abasic ribonucleotide (iAb). In another example, the 3'-end of a sense strand is linked via a 3'-3'-phosphorothioate linkage to an inverted dA (idA).

In one particular example, the inverted 2'-deoxy-modified ribonucleotide is linked to the 3'end of an oligonucleotide, such as the 3'-end of a sense strand described herein, where the linking is via a 3'-3' phosphodiester linkage or a 3'-3'-phosphorothioate linkage.

In another example, the 3'-terminal nucleotides of a sense strand is an inverted dA (idA) and is linked to the preceding nucleotide via a 3'-3'-linkage (e.g., 3'-3'-phosphorothioate linkage).

Other modifications of a RNAi agent of the disclosure include a 5' phosphate or 5' phosphate mimic, e.g., a 5'-terminal phosphate or phosphate mimic on the antisense strand of a RNAi agent. Suitable phosphate mimics are disclosed in, for example US 2012/0157511, the entire contents of which are incorporated herein by reference.

A. Modified RNAi Agents Comprising Motifs of the Disclosure

In certain aspects of the disclosure, the double-stranded RNAi agents of the disclosure include agents with chemical modifications as disclosed, for example, in WO 2013/

075035, the entire contents of which are incorporated herein by reference. As shown herein and in WO 2013/075035, a superior result may be obtained by introducing one or more motifs of three identical modifications on three consecutive nucleotides into a sense strand or antisense strand of an RNAi agent, particularly at or near the cleavage site. In some embodiments, the sense strand and antisense strand of the RNAi agent may otherwise be completely modified. The introduction of these motifs interrupts the modification pattern, if present, of the sense or antisense strand. The RNAi agent may be optionally conjugated with a lipophilic ligand, e.g., a C16 ligand, for instance on the sense strand. The RNAi agent may be optionally modified with a (S)-glycol nucleic acid (GNA) modification, for instance on one or more residues of the antisense strand.

Accordingly, the disclosure provides double stranded RNAi agents capable of inhibiting the expression of a target gene (i.e., a SOD1 gene) in vivo. The RNAi agent comprises a sense strand and an antisense strand. Each strand of the RNAi agent may be 15-30 nucleotides in length. For example, each strand may be 16-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. In certain embodiments, each strand is 19-23 nucleotides in length.

The sense strand and antisense strand typically form a duplex double stranded RNA ("dsRNA"), also referred to herein as an "RNAi agent." The duplex region of an RNAi agent may be 15-30 nucleotide pairs in length. For example, the duplex region can be 16-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length. In preferred embodiments, the duplex region is 19-21 nucleotide pairs in length.

In one embodiment, the RNAi agent may contain one or more overhang regions or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. In preferred embodiments, the nucleotide overhang region is 2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-O-methyl, thymidine (T), and any combinations thereof.

For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double blunt-ended of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In another embodiment, the RNAi agent is a double blunt-ended of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet another embodiment, the RNAi agent is a double blunt-ended of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 2'-fluoro, e.g., in an alternating motif. Optionally, the RNAi agent further comprises a ligand (e.g., a lipophilic ligand, optionally a C16 ligand).

In one embodiment, the RNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3 ' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1~4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand.

For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adajacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motif of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two, or three nucleotides in the duplex region.

In one embodiment, the RNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxythimidine (dT). In another embodiment, the nucleotide at the 3'-end of the antisense strand is deoxythimidine (dT). In one embodiment, there is a short sequence of deoxythimidine nucleotides, for example, two dT nucleotides on the 3'-end of the sense or antisense strand.

In one embodiment, the sense strand sequence may be represented by formula (I):

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;
each $N_b$ independently represents an oligonucleotide sequence comprising 0-10 modified nucleotides;
each $n_p$ and $n_q$ independently represent an overhang nucleotide;
wherein Nb and Y do not have the same modification; and
XXX, YYY and ZZZ each independently represent one motif of three identical modifications on three consecutive nucleotides. Preferably YYY is all 2'-F modified nucleotides.

In one embodiment, the $N_a$ or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of – the sense strand, the count starting from the 1$^{st}$ nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas:

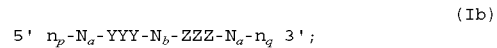

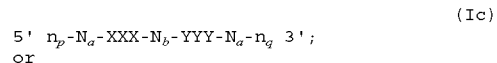

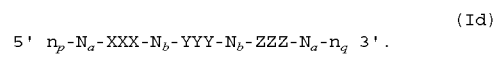

When the sense strand is represented by formula (Ib), $N_b$ represents an oligonucleotide sequence comprising 0-10, 0-7, 0-5, 0-4, 0-2 or 0 modified nucleotides.

Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6. Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

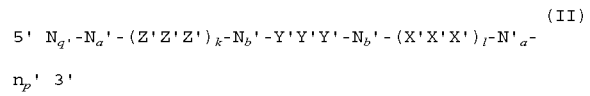

wherein:
k and l are each independently 0 or 1;
p' and q' are each independently 0-6;
each $N_a'$ independently represents an oligonucleotide sequence comprising 0-25 modified nucleotides, each sequence comprising at least two differently modified nucleotides;
each $N_b'$ independently represents an oligonucleotide sequence comprising 0-10 modified nucleotides;

each $n_p'$ and $n_q'$ independently represent an overhang nucleotide;
wherein $N_b'$ and Y' do not have the same modification; and X'X'X', Y'Y'Y' and Z'Z'Z' each independently represent one motif of three identical modifications on three consecutive nucleotides.

In one embodiment, the $N_a'$ or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1" nucleotide, from the 5'-end; or optionally, the count starting at the $1^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and 1 is 0, or k is 0 and l is 1, or both k and 1 are 1.

The antisense strand can therefore be represented by the following formulas:

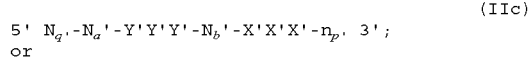
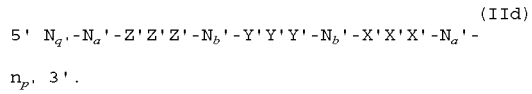

When the antisense strand is represented by formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and 1 is 0 and the antisense strand may be represented by the formula:

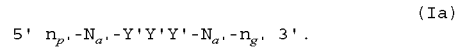

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1" nucleotide from the 5'-end, or optionally, the count starting at the $1^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the $1^{st}$ nucleotide from the 5'-end, or optionally, the count starting at the $1^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the disclosure may comprise a sense strand and an antisense strand, each strand having 14 to 30 nucleotides, the RNAi duplex represented by formula (III):

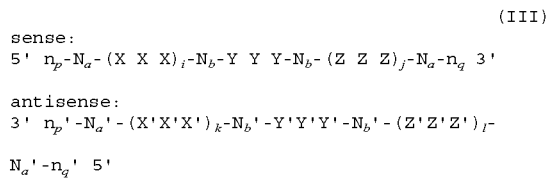

wherein:

j, k, and l are each independently 0 or 1;

p, p', q, and q' are each independently 0-6;

each $N_a$ and $N_a'$ independently represents an oligonucleotide sequence comprising 0-25 modified nucleotides, each sequence comprising at least two differently modified nucleotides;

each $N_b$ and $N_b'$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

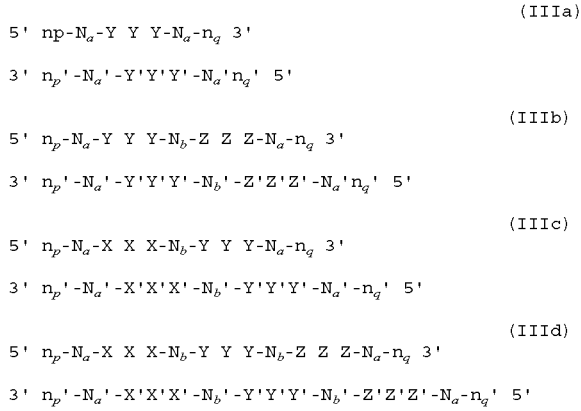

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more C16 (or related) moieties attached through a bivalent or trivalent branched linker (described below). In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more lipophilic, e.g., C16 (or related) moieties, optionally attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more lipophilic, e.g., C16 (or related) moieties attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the disclosure. Such publications include WO2007/091269, WO2010/141511, WO2007/117686, WO2009/014887, and WO2011/031520; and U.S. Pat. No. 7,858,769, the entire contents of each of which are hereby incorporated herein by reference.

In certain embodiments, the compositions and methods of the disclosure include a vinyl phosphonate (VP) modification of an RNAi agent as described herein. In exemplary embodiments, a 5'-vinyl phosphonate modified nucleotide of the disclosure has the structure:

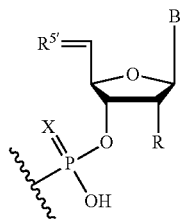

wherein X is O or S;

R is hydrogen, hydroxy, fluoro, or $C_{1-20}$alkoxy (e.g., methoxy or n-hexadecyloxy);

$R^{5'}$ is =C(H)—P(O)(OH)$_2$ and the double bond between the C5' carbon and R5' is in the E or Z orientation (e.g., E orientation); and B is a nucleobase or a modified nucleobase, optionally where B is adenine, guanine, cytosine, thymine, or uracil.

In one embodiment, $R^{5'}$ is =C(H)—P(O)(OH)$_2$ and the double bond between the C5' carbon and R5' is in the E orientation. In another embodiment, R is methoxy and $R^{5'}$ is =C(H)—P(O)(OH)$_2$ and the double bond between the C5' carbon and R5' is in the E orientation. In another embodiment, X is S, R is methoxy, and $R^{5'}$ is =C(H)—P(O)(OH)$_2$ and the double bond between the C5' carbon and R5' is in the E orientation.

A vinyl phosphonate of the instant disclosure may be attached to either the antisense or the sense strand of a dsRNA of the disclosure. In certain preferred embodiments, a vinyl phosphonate of the instant disclosure is attached to the antisense strand of a dsRNA, optionally at the 5' end of the antisense strand of the dsRNA.

Vinyl phosphate modifications are also contemplated for the compositions and methods of the instant disclosure. An exemplary vinyl phosphate structure includes the preceding structure, where $R^{5'}$ is =C(H)—OP(O)(OH)$_2$ and the double bond between the C5' carbon and $R^{5'}$ is in the E or Z orientation (e.g., E orientation).

E. Thermally Destabilizing Modifications

In certain embodiments, a dsRNA molecule can be optimized for RNA interference by incorporating thermally destabilizing modifications in the seed region of the antisense strand. As used herein "seed region" means at positions 2-9 of the 5'-end of the referenced strand. For example, thermally destabilizing modifications can be incorporated in the seed region of the antisense strand to reduce or inhibit off-target gene silencing.

The term "thermally destabilizing modification(s)" includes modification(s) that would result with a dsRNA with a lower overall melting temperature (Tm) than the Tm of the dsRNA without having such modification(s). For example, the thermally destabilizing modification(s) can decrease the Tm of the dsRNA by 1-4° C., such as one, two, three or four degrees Celcius. And, the term "thermally destabilizing nucleotide" refers to a nucleotide containing one or more thermally destabilizing modifications.

It has been discovered that dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, one or more thermally destabilizing modification(s) of the duplex is/are located in positions 2-9, or preferably positions 4-8, from the 5'-end of the antisense strand. In some further embodiments, the thermally destabilizing modification(s) of the duplex is/are located at position 6, 7 or 8 from the 5'-end of the antisense strand. In still some further embodiments, the thermally destabilizing modification of the duplex is located at position 7 from the 5'-end of the antisense strand. In some embodiments, the thermally destabilizing modification of the duplex is located at position 2, 3, 4, 5 or 9 from the 5'-end of the antisense strand.

The thermally destabilizing modifications can include, but are not limited to, abasic modification; mismatch with the opposing nucleotide in the opposing strand; and sugar modification such as 2'-deoxy modification, acyclic nucleotide, e.g., unlocked nucleic acids (UNA) or glycol nucleic acid (GNA); and 2'-5'-linked ribonucleotides ("3'-RNA").

Exemplified abasic modifications include, but are not limited to the following:

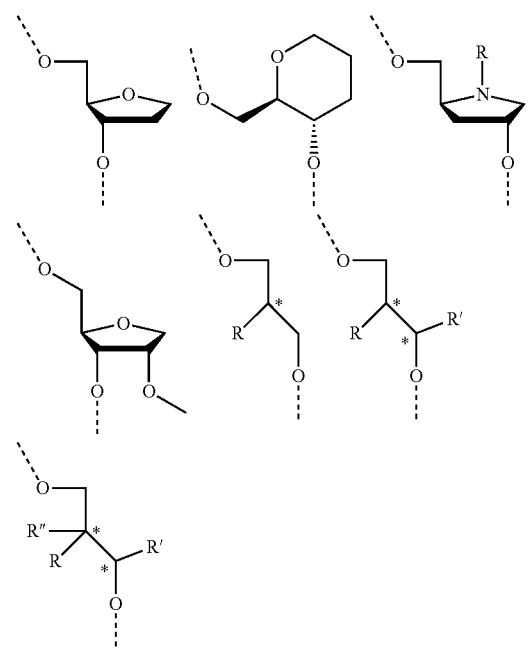

Wherein R=H, Me, Et or OMe; R'=H, Me, Et or OMe; R"=H, Me, Et or OMe

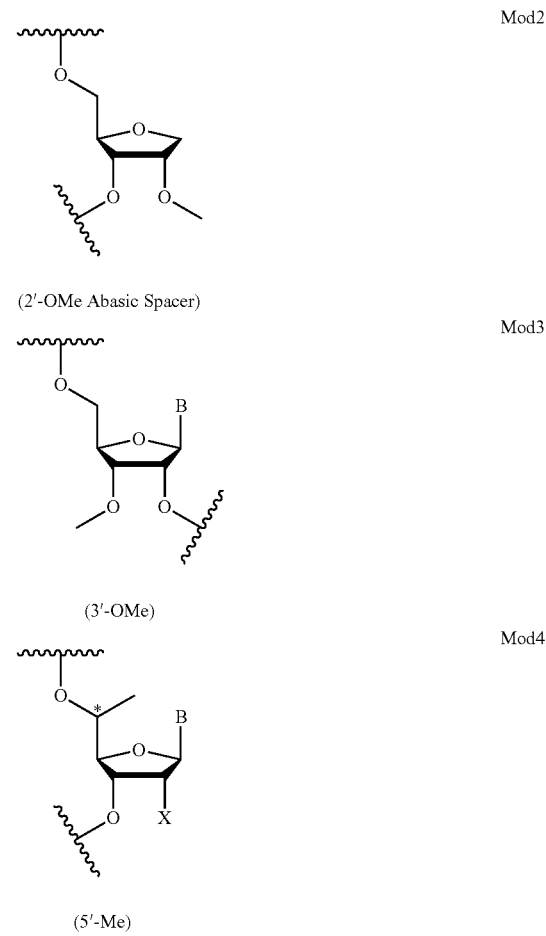

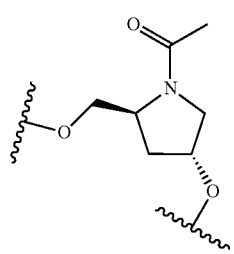

(Hyp-spacer)

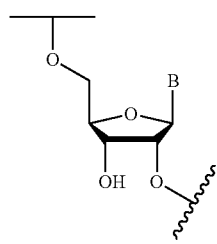

(3'-RNA)

X = OMe, F wherein B is a modified or unmodified nucleobase.

Exemplified sugar modifications include, but are not limited to the following:

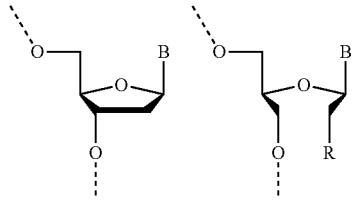

2'-deoxy unlocked nucleic acid
R= H, OH, O-alkyl

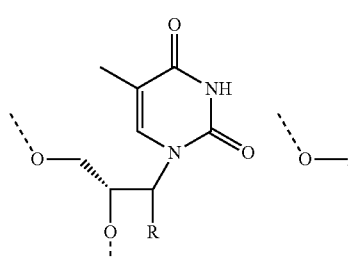 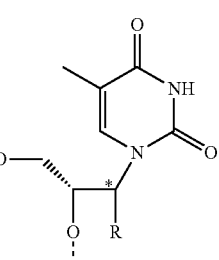

glycol nucleic acid
R= H, OH, O-alkyl glycol nucleic acid
R= H, OH, O-alkyl

Mod5

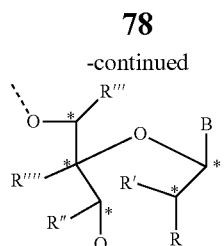

unlocked nucleic acid
R= H, OH, $CH_3$, $CH_2CH_3$, O-alkyl, $NH_2$, NHMe, $NMe_2$
R'= H, OH, $CH_3$, $CH_2CH_3$, O-alkyl, $NH_2$, NHMe, $NMe_2$
R''= H, OH, $CH_3$, $CH_2CH_3$, O-alkyl, $NH_2$, NHMe, $NMe_2$
R'''= H, OH, $CH_3$, $CH_2CH_3$, O-alkyl, $NH_2$, NHMe, $NMe_2$
R''''= H, OH, $CH_3$, $CH_2CH_3$, O-alkyl, $NH_2$, NHMe, $NMe_2$ R = H, methyl, ethyl wherein B is a modified or unmodified nucleobase.

In some embodiments the thermally destabilizing modification of the duplex is selected from the group consisting of:

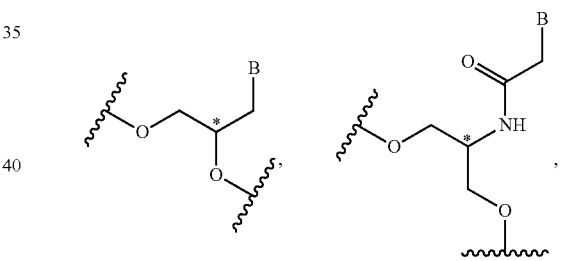

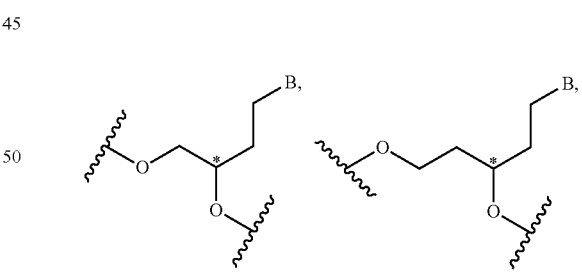

, and           and

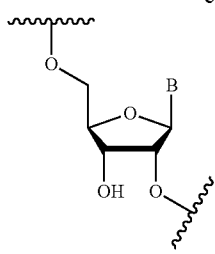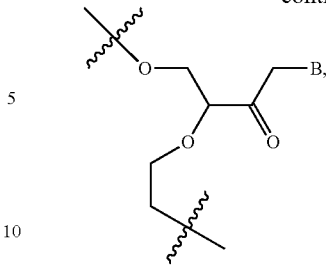

wherein B is a modified or unmodified nucleobase and the asterisk on each structure represents either R, S or racemic.

In some embodiments the thermally destabilizing modification of the duplex is selected from the group consisting of:

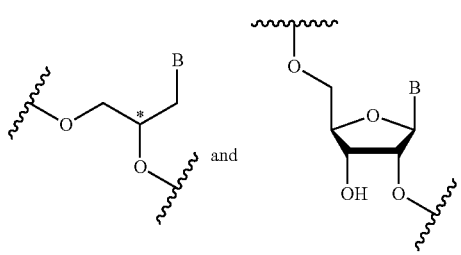

wherein B is a modified or unmodified nucleobase and the asterisk represents either R, S or racemic (e.g. S).

The term "acyclic nucleotide" refers to any nucleotide having an acyclic ribose sugar, for example, where any of bonds between the ribose carbons (e.g., C1'-C2', C2'-C3', C3'-C4', C4'-O4', or C1'-O4') is absent or at least one of ribose carbons or oxygen (e.g., C1', C2', C3', C4', or O4') are independently or in combination absent from the nucleotide. In some embodiments, acyclic nucleotide is

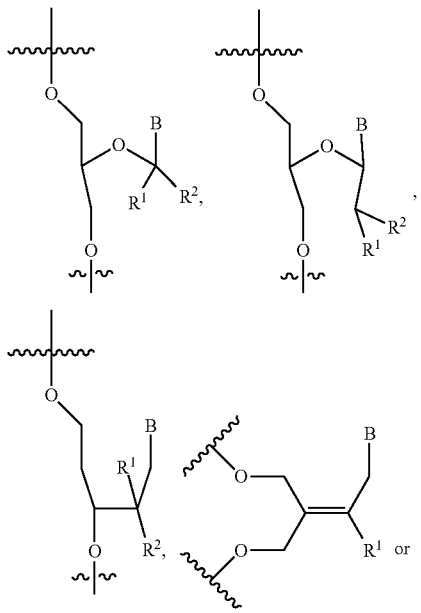

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

(R)-GNA

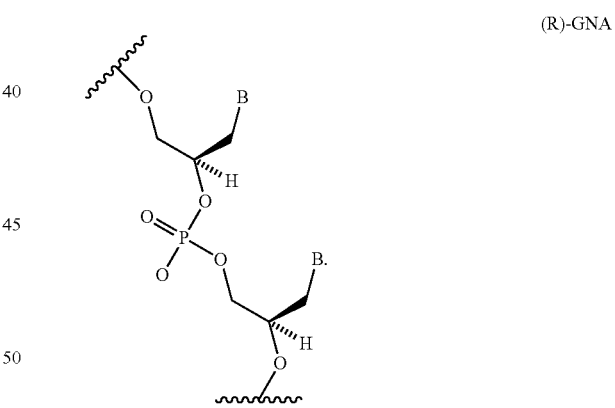

The thermally destabilizing modification of the duplex can be mismatches (i.e., noncomplementary base pairs) between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA molecule contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired Watson-Crick hydrogen-bonding to the complementary base on the target mRNA, such as modified nucleobases:

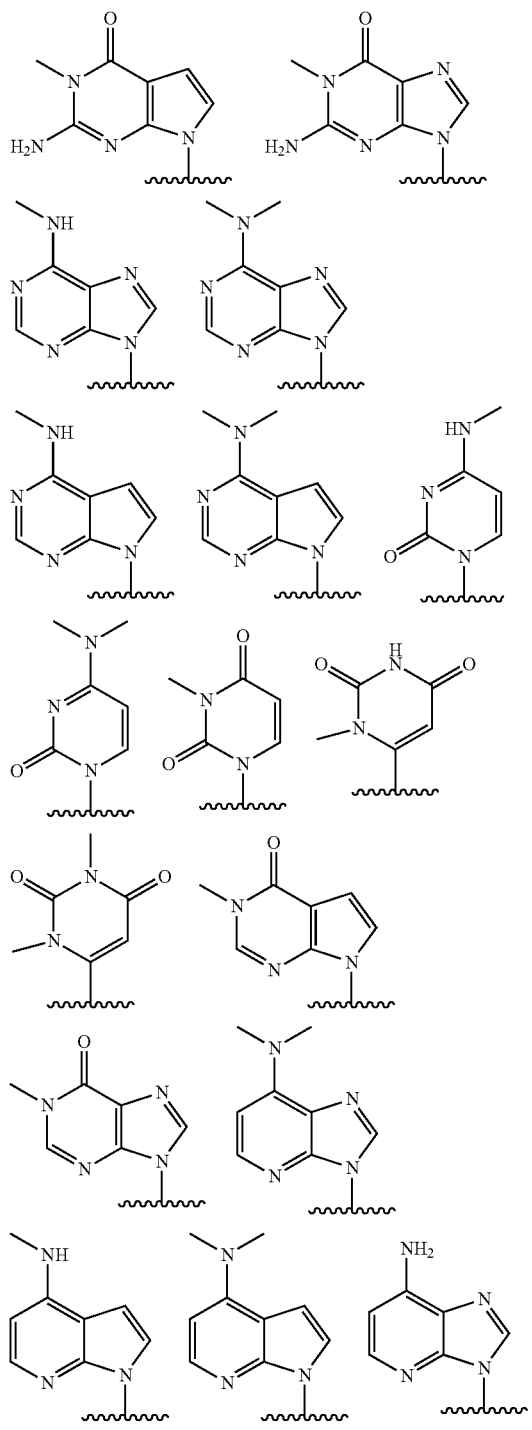

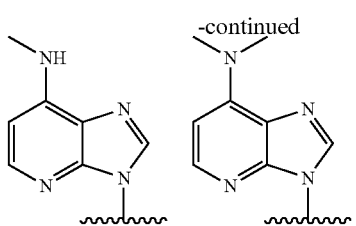

-continued

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

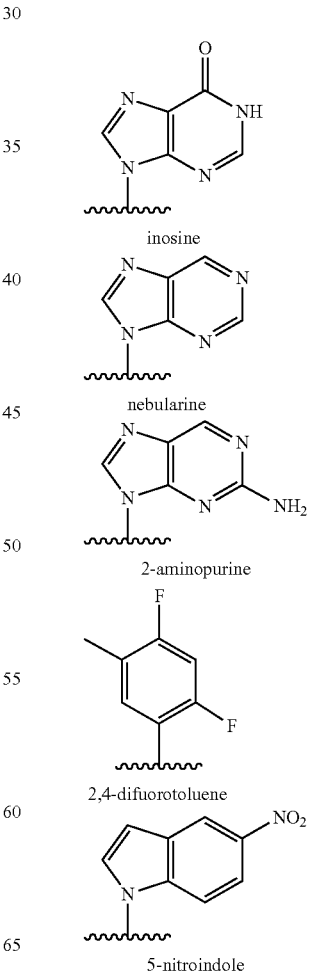

inosine nebularine 2-aminopurine 2,4-difluorotoluene 5-nitroindole

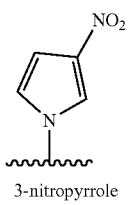

3-nitropyrrole

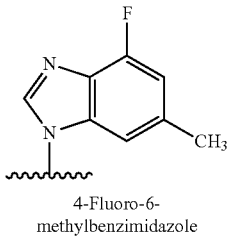

4-Fluoro-6-methylbenzimidazole

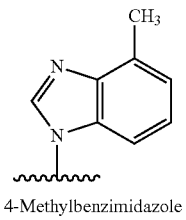

4-Methylbenzimidazole

In some embodiments, the thermally destabilizing modification of the duplex in the seed region of the antisense strand includes one or more α-nucleotide complementary to the base on the target mRNA, such as:

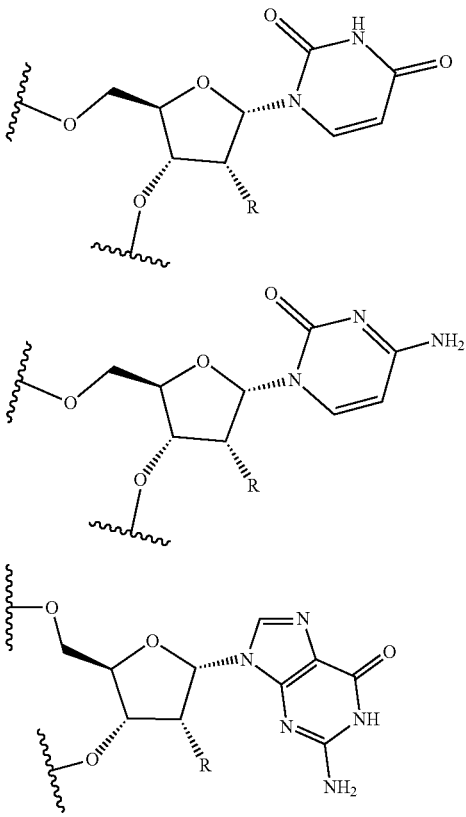

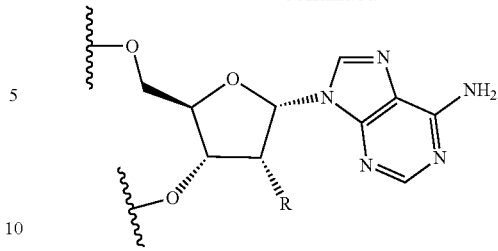

wherein R is H, OH, OCH$_3$, F, NH$_2$, NHMe, NMe$_2$ or O-alkyl.

Exemplary phosphate modifications known to decrease the thermal stability of dsRNA duplexes compared to natural phosphodiester linkages are:

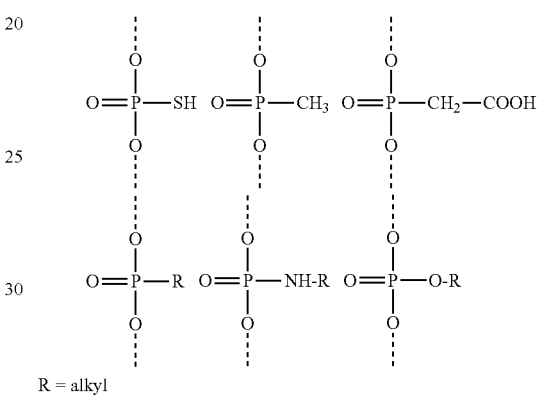

R = alkyl

The alkyl for the R group can be a C$_1$-C$_6$alkyl. Specific alkyls for the R group include, but are not limited to methyl, ethyl, propyl, isopropyl, butyl, pentyl and hexyl.

As the skilled artisan will recognize, in view of the functional role of nucleobases is defining specificity of a RNAi agent of the disclosure, while nucleobase modifications can be performed in the various manners as described herein, e.g., to introduce destabilizing modifications into a RNAi agent of the disclosure, e.g., for purpose of enhancing on-target effect relative to off-target effect, the range of modifications available and, in general, present upon RNAi agents of the disclosure tends to be much greater for non-nucleobase modifications, e.g., modifications to sugar groups or phosphate backbones of polyribonucleotides. Such modifications are described in greater detail in other sections of the instant disclosure and are expressly contemplated for RNAi agents of the disclosure, either possessing native nucleobases or modified nucleobases as described above or elsewhere herein.

In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14, and 16 from the 5'-end. In some other embodiments, the antisense comprises stabilizing modifications at positions 2, 6, 14, and 16 from the 5'-end. In still some other embodiments, the antisense comprises stabilizing modifications at positions 2, 14, and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions −1 and +1 from the position of the destabilizing modification.

In some embodiments, the antisense strand comprises at least two stabilizing modifications at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10, and 11 from the 5'-end. In some other embodiments, the sense strand comprises stabilizing modifications at positions 7, 9, 10, and 11 from the 5'-end. In some embodiments, the sense strand comprises stabilizing modifications at positions opposite or complimentary to positions 11, 12, and 15 of the antisense strand, counting from the 5'-end of the antisense strand. In some other embodiments, the sense strand comprises stabilizing modifications at positions opposite or complimentary to positions 11, 12, 13, and 15 of the antisense strand, counting from the 5'-end of the antisense strand. In some embodiments, the sense strand comprises a block of two, three, or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to, 2'-fluoro modifications. Other thermally stabilizing modifications include, but are not limited to, LNA.

In some embodiments, the dsRNA of the disclosure comprises at least four (e.g., four, five, six, seven, eight, nine, ten, or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten, or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14, and 16 from the 5'-end. In some other embodiments, the antisense comprises 2'-fluoro nucleotides at positions 2, 6, 14, and 16 from the 5'-end. In still some other embodiments, the antisense comprises 2'-fluoro nucleotides at positions 2, 14, and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position −1 or +1 from the position of the destabilizing modification. In some embodiments, the antisense strand comprises a 2'-fluoro nucleotide at each of the 5'-end and the 3'-end of the destabilizing modification, i.e., positions −1 and +1 from the position of the destabilizing modification.

In some embodiments, the antisense strand comprises at least two 2'-fluoro nucleotides at the 3'-end of the destabilizing modification, i.e., at positions +1 and +2 from the position of the destabilizing modification.

In some embodiments, the sense strand comprises at least two (e.g., two, three, four, five, six, seven, eight, nine, ten, or more) 2'-fluoro nucleotides. Without limitations, a 2'-fluoro modification in the sense strand can be present at any positions. In some embodiments, the antisense comprises 2'-fluoro nucleotides at positions 7, 10, and 11 from the 5'-end. In some other embodiments, the sense strand comprises 2'-fluoro nucleotides at positions 7, 9, 10, and 11 from the 5'-end. In some embodiments, the sense strand comprises 2'-fluoro nucleotides at positions opposite or complimentary to positions 11, 12, and 15 of the antisense strand, counting from the 5'-end of the antisense strand. In some other embodiments, the sense strand comprises 2'-fluoro nucleotides at positions opposite or complimentary to positions 11, 12, 13, and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

In some embodiments, the dsRNA molecule of the disclosure comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense.

In some embodiments, the dsRNA molecule of the disclosure comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand). For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA molecule of the disclosure comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; and (vi) the dsRNA comprises at least four 2'-fluoro modifications; and (vii) the dsRNA has a duplex region of 12-29 nucleotide pairs in length.

In some embodiments, every nucleotide in the sense strand and antisense strand of the dsRNA molecule may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases, the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro. It is to be understood that these modifications are in addition to the at least one thermally destabilizing modification of the duplex present in the antisense strand.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxy-2'-fluoro nucleotide, 2'-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide. Again, it is to be understood that these modifications are in addition to the at least one thermally destabilizing modification of the duplex present in the antisense strand.

In some embodiments, the dsRNA molecule of the disclosure comprises modifications of an alternating pattern. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNA molecule of the disclosure comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

In one particular example, the alternating motif in the sense strand is "ABABAB" s from 5'-3' of the strand, where each A is an unmodified ribonucleotide and each B is a 2'-Omethyl modified nucleotide.

In one particular example, the alternating motif in the sense strand is "ABABAB" s from 5'-3' of the strand, where each A is an 2'-deoxy-2'-fluoro modified nucleotide and each B is a 2'-Omethyl modified nucleotide.

In another particular example, the alternating motif in the antisense strand is "BABABA" from 3'-5' of the strand, where each A is a 2'-deoxy-2'-fluoro modified nucleotide and each B is a 2'-Omethyl modified nucleotide.

In one particular example, the alternating motif in the sense strand is "ABABAB" s from 5'-3' of the strand and the alternating motif in the antisense strand is "BABABA" from 3'-5' of the strand, where each A is an unmodified ribonucleotide and each B is a 2'-Omethyl modified nucleotide.

In one particular example, the alternating motif in the sense strand is "ABABAB" s from 5'-3' of the strand and the alternating motif in the antisense strand is "BABABA" from 3'-5' of the strand, where each A is a 2'-deoxy-2'-fluoro modified nucleotide and each B is a 2'-Omethyl modified nucleotide.

The dsRNA molecule of the disclosure may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA molecule comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA molecule comprises 1-10 blocks of two to ten phosphorothioate or methylphosphonate internucleotide linkages separated by 1, 2, 3, 4, 5, 6, 7, 8, 9, 10, 11, 12, 13, 14, 15, or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of three phosphorothioate or methylphosphonate internucleotide linkages separated by 1, 2, 3, 4, 5, 6, 7, 8, 9, 10, 11, 12, 13, 14, 15, or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of four phosphorothioate or methylphosphonate internucleotide linkages separated by 1, 2, 3, 4, 5, 6, 7, 8, 9, 10, 11, 12, 13, or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of five phosphorothioate or methylphosphonate internucleotide linkages separated by 1, 2, 3, 4, 5, 6, 7, 8, 9, 10, 11, or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of six phosphorothioate or methylphosphonate internucleotide linkages separated by 1, 2, 3, 4, 5, 6, 7, 8, 9, or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of seven phosphorothioate or methylphosphonate internucleotide linkages separated by 1, 2, 3, 4, 5, 6, 7, or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of eight phosphorothioate or methylphosphonate internucleotide linkages separated by 1, 2, 3, 4, 5, or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of nine phosphorothioate or methylphosphonate internucleotide linkages separated by 1, 2, 3, or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA molecule of the disclosure further comprises one or more phosphorothioate or methylphosphonate internucleotide linkage modification within 1-10 nucleotides of the termini position(s) of the sense or antisense strand. For example, at least 2, 3, 4, 5, 6, 7, 8, 9, or 10 nucleotides may be linked through phosphorothioate or methylphosphonate internucleotide linkage at one end or both ends of the sense or antisense strand.

In some embodiments, the dsRNA molecule of the disclosure further comprises one or more phosphorothioate or methylphosphonate internucleotide linkage modification within 1-10 of the internal region of the duplex of each of the sense or antisense strand. For example, at least nucleotides 2, 3, 4, 5, 6, 7, 8, 9, or 10 nucleotides may be linked through phosphorothioate methylphosphonate internucleotide linkage at position 8-16 of the duplex region counting from the 5'-end of the sense strand; the dsRNA molecule can optionally further comprise one or more phosphorothioate or methylphosphonate internucleotide linkage modification within 1-10 of the termini position(s).

In some embodiments, the dsRNA molecule of the disclosure further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA molecule of the disclosure further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 or 2 and two phosphorothioate or methylphosphonate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 or 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 or 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 or 2 and one phosphorothioate internucleotide linkage modification within positions 18-23 of the antisense strand (counting from the 5'-end).

In some embodiments, the dsRNA molecule of the disclosure further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the disclosure further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the disclosure further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the disclosure further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, compound of the disclosure comprises a pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than 7 internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, compound of the disclosure comprises a block that is a stereochemistry block. In some embodiments, a block is an Rp block in that each internucleotidic linkage of the block is Rp. In some embodiments, a 5'-block is an Rp block. In some embodiments, a 3'-block is an Rp block. In some embodiments, a block is an Sp block in that each internucleotidic linkage of the block is Sp. In some embodiments, a 5'-block is an Sp block. In some embodiments, a 3'-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage in a natural phosphate linkage.

In some embodiments, compound of the disclosure comprises a 5'-block that is an Sp block wherein each sugar moiety comprises a 2'-F modification. In some embodiments, a 5'-block is an Sp block wherein each of internucleotidic linkage is a modified internucleotidic linkage and each sugar moiety comprises a 2'-F modification. In some embodiments, a 5'-block is an Sp block wherein each of internucleotidic linkage is a phosphorothioate linkage and each sugar moiety comprises a 2'-F modification. In some embodiments, a 5'-block comprises 4 or more nucleoside units. In some embodiments, a 5'-block comprises 5 or more nucleoside units. In some embodiments, a 5'-block comprises 6 or more nucleoside units. In some embodiments, a 5'-block comprises 7 or more nucleoside units. In some embodiments, a 3'-block is an Sp block wherein each sugar moiety comprises a 2'-F modification. In some embodiments, a 3'-block is an Sp block wherein each of internucleotidic linkage is a modified internucleotidic linkage and each sugar moiety comprises a 2'-F modification. In some embodiments, a 3'-block is an Sp block wherein each of internucleotidic linkage is a phosphorothioate linkage and each sugar moiety comprises a 2'-F modification. In some embodiments, a 3'-block comprises 4 or more nucleoside units. In some embodiments, a 3'-block comprises 5 or more nucleoside units. In some embodiments, a 3'-block comprises 6 or more nucleoside units. In some embodiments, a 3'-block comprises 7 or more nucleoside units.

In some embodiments, compound of the disclosure comprises a type of nucleoside in a region or an oligonucleotide is followed by a specific type of internucleotidic linkage, e.g., natural phosphate linkage, modified internucleotidic linkage, Rp chiral internucleotidic linkage, Sp chiral internucleotidic linkage, etc. In some embodiments, A is followed by Sp. In some embodiments, A is followed by Rp. In some embodiments, A is followed by natural phosphate linkage (PO). In some embodiments, U is followed by Sp. In some embodiments, U is followed by Rp. In some embodiments, U is followed by natural phosphate linkage (PO). In some embodiments, C is followed by Sp. In some embodiments, C is followed by Rp. In some embodiments, C is followed by natural phosphate linkage (PO). In some embodiments, G is followed by Sp. In some embodiments, G is followed by Rp. In some embodiments, G is followed by natural phosphate linkage (PO). In some embodiments, C and U are followed by Sp. In some embodiments, C and U are followed by Rp. In some embodiments, C and U are followed by natural phosphate linkage (PO). In some embodiments, A and G are followed by Sp. In some embodiments, A and G are followed by Rp.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5, or 6 2'-fluoro modifications; (ii) the antisense comprises 3, 4, or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4, or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand. In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5, or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4, or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand.

In some embodiments, the dsRNA molecule of the disclosure comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA molecule of the disclosure comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

It was found that introducing 4'-modified or 5'-modified nucleotide to the 3'-end of a phosphodiester (PO), phosphorothioate (PS), or phosphorodithioate (PS2) linkage of a nucleotide at any position of single stranded or double stranded oligonucleotide can exert steric effect to the internucleotide linkage and, hence, protecting or stabilizing it against nucleases.

In some embodiments, 5'-modified nucleotide is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In some embodiments, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-O-alkyl of the ribose sugar can be racemic or chirally pure R or S isomer. An exemplary 4'-O-alkylated nucleoside is 4'-O-methyl nucleoside. The 4'-O-methyl can be either racemic or chirally pure R or S isomer.

In some embodiments, 5'-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In some embodiments, 4'-alkylated nucleoside is introduced at any position on the sense strand or antisense strand of a dsRNA, and such modification maintains or improves potency of the dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In some embodiments, 4'-O-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In some embodiments, the dsRNA molecule of the disclosure can comprise 2'-5' linkages (with 2'-H, 2'-OH and 2'-OMe and with P=O or P=S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA molecule of the disclosure can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

Various publications describe multimeric siRNA which can all be used with the dsRNA of the disclosure. Such publications include WO2007/091269, U.S. Pat. No. 7,858,769, WO2010/141511, WO2007/117686, WO2009/014887, and WO2011/031520 which are hereby incorporated by their entirely.

As described in more detail below, the RNAi agent that contains conjugations of one or more carbohydrate moieties to an RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the disclosure is an agent selected from the group of agents listed in any one of Tables 2-7, 12, 13, and 18-20. These agents may further comprise a ligand, such as one or more lipophilic moieties, one or more GalNAc derivatives, or both of one of more lipophilic moieties and one or more GalNAc derivatives.

IV. iRNAs Conjugated to Ligands

Another modification of the RNA of an iRNA of the invention involves chemically linking to the iRNA one or more ligands, moieties or conjugates that enhance the activity, cellular distribution or cellular uptake of the iRNA, e.g., into a cell. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylaminocarbonyloxycholesterol moiety (Crooke et al., *J. Pharmacol. Exp. Ther.,* 1996, 277:923-937).

In certain embodiments, a ligand alters the distribution, targeting or lifetime of an iRNA agent into which it is incorporated. In some embodiments, a ligand provides an enhanced affinity for a selected target, e.g., molecule, cell or cell type, compartment, e.g., a cellular or organ compartment, tissue, organ or region of the body, as, e.g., compared to a species absent such a ligand. Typical ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an a helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. In certain embodiments, the ligand is a multivalent galactose, e.g., an N-acetyl-galactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule can typically bind a serum protein, such as human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid-based ligand can be used to modulate, e.g., control (e.g., inhibit) the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid-based ligand binds HSA. For example, the ligand can bind HSA with a sufficient affinity such that distribution of the conjugate to a non-kidney tissue is enhanced. However, the affinity is typically not so strong that the HSA-ligand binding cannot be reversed.

In certain embodiments, the lipid-based ligand binds HSA weakly or not at all, such that distribution of the conjugate to the kidney is enhanced. Other moieties that target to kidney cells can also be used in place of or in addition to the lipid-based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

B. Cell Permeation Agents

In another aspect, the ligand is a cell-permeation agent, such as a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an α-helical agent and can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 31).

An RFGF analogue (e.g., amino acid sequence AALLPVL-LAAP (SEQ ID NO: 32)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 33)) and the *Drosophila* Antennapedia protein (RQIKIWFQNRRMKWKK (SEQ ID NO: 34)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Typically, the peptide or peptidomimetic tethered to a dsRNA agent via an incorporated monomer unit is a cell targeting peptide such as an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

An RGD peptide moiety can be used to target a particular cell type, e.g., a tumor cell, such as an endothelial tumor cell or a breast cancer tumor cell (Zitzmann et al., *Cancer Res.*, 62:5139-43, 2002). An RGD peptide can facilitate targeting of an dsRNA agent to tumors of a variety of other tissues, including the lung, kidney, spleen, or liver (Aoki et al., *Cancer Gene Therapy* 8:783-787, 2001). Typically, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., *Jour. Nucl. Med.*, 42:326-336, 2001).

A "cell permeation peptide" is capable of permeating a cell, e.g., a microbial cell, such as a bacterial or fungal cell, or a mammalian cell, such as a human cell. A microbial cell-permeating peptide can be, for example, an $\alpha$-helical linear peptide (e.g., LL-37 or Ceropin P1), a disulfide bond-containing peptide (e.g., $\alpha$-defensin, $\beta$-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

C. Carbohydrate Conjugates

In some embodiments of the compositions and methods of the invention, an iRNA further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and tri-saccharides include sugars having two or three monosaccharide units (e.g., C5, C6, C7, or C8).

In certain embodiments, a carbohydrate conjugate comprises a monosaccharide.

In certain embodiments, the monosaccharide is an N-acetylgalactosamine (GalNAc). GalNAc conjugates, which comprise one or more N-acetylgalactosamine (GalNAc) derivatives, are described, for example, in U.S. Pat. No. 8,106,022, the entire content of which is hereby incorporated herein by reference. In some embodiments, the GalNAc conjugate serves as a ligand that targets the iRNA to particular cells. In some embodiments, the GalNAc conjugate targets the iRNA to liver cells, e.g., by serving as a ligand for the asialoglycoprotein receptor of liver cells (e.g., hepatocytes).

In some embodiments, the carbohydrate conjugate comprises one or more GalNAc derivatives. The GalNAc derivatives may be attached via a linker, e.g., a bivalent or trivalent branched linker. In some embodiments the GalNAc conjugate is conjugated to the 3' end of the sense strand. In some embodiments, the GalNAc conjugate is conjugated to the iRNA agent (e.g., to the 3' end of the sense strand) via a linker, e.g., a linker as described herein. In some embodiments the GalNAc conjugate is conjugated to the 5' end of the sense strand. In some embodiments, the GalNAc conjugate is conjugated to the iRNA agent (e.g., to the 5' end of the sense strand) via a linker, e.g., a linker as described herein.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker. In other embodiments of the invention, the GalNAc or GalNAc derivative is attached to an iRNA agent of the invention via a tetravalent linker.

In certain embodiments, the double stranded RNAi agents of the invention comprise one GalNAc or GalNAc derivative attached to the iRNA agent. In certain embodiments, the double stranded RNAi agents of the invention comprise a plurality (e.g., 2, 3, 4, 5, or 6) of GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, the GalNAc conjugate is

Formula II

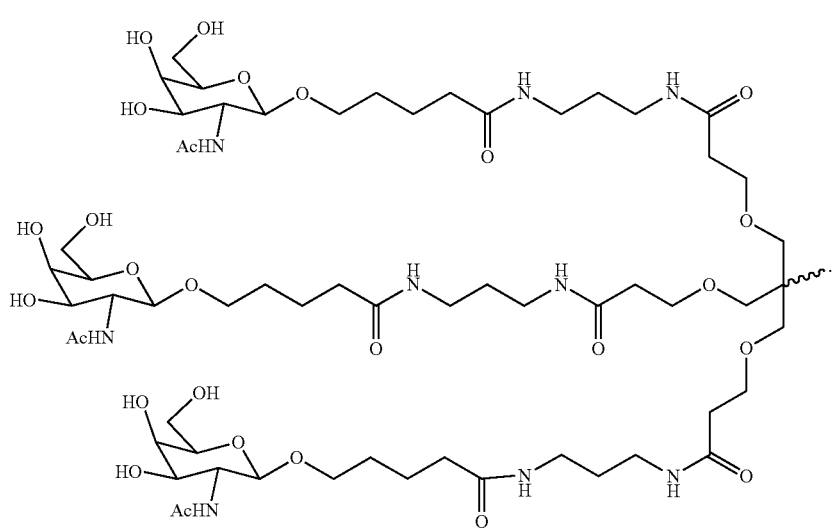

In some embodiments, the RNAi agent is attached to the carbohydrate conjugate via a linker as shown in the following schematic, wherein X is O or S

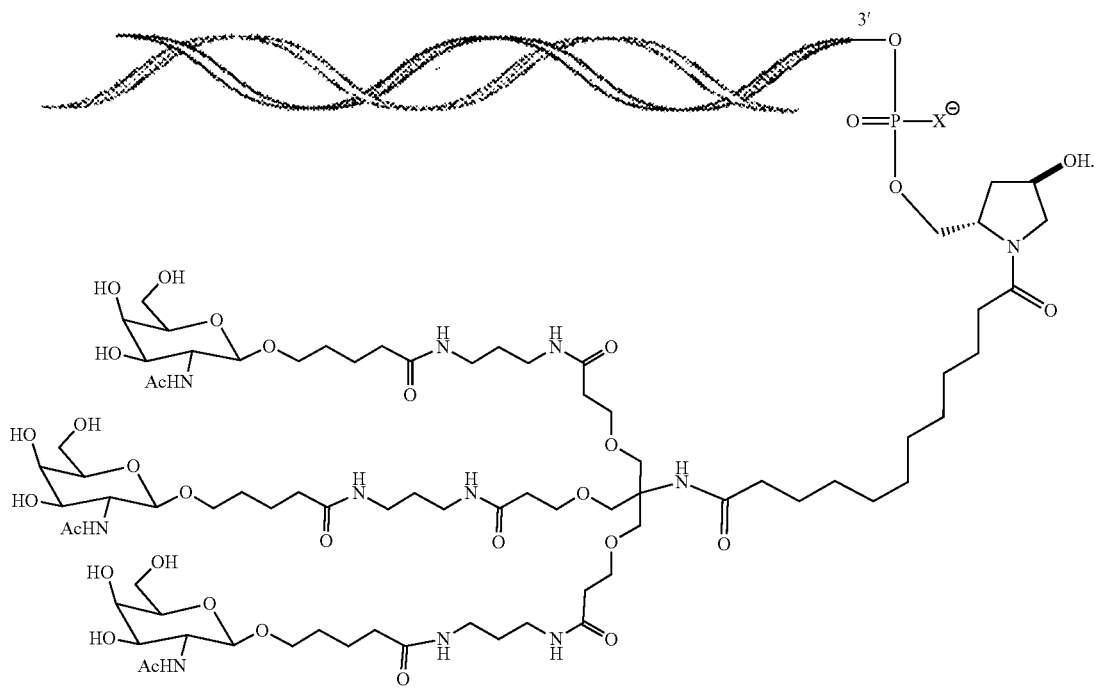

In some embodiments, the RNAi agent is conjugated to L96 as defined in Table 1 and shown below:
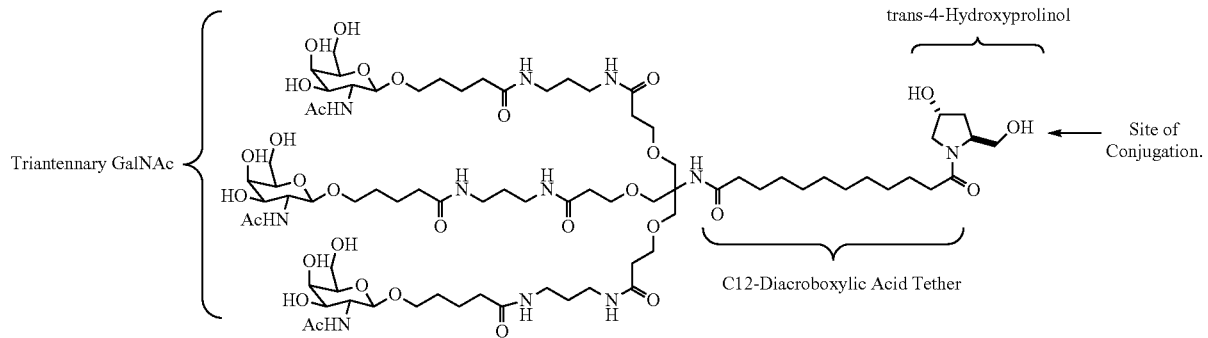
In certain embodiments, a carbohydrate conjugate for use in the compositions and methods of the invention is selected from the group consisting of:
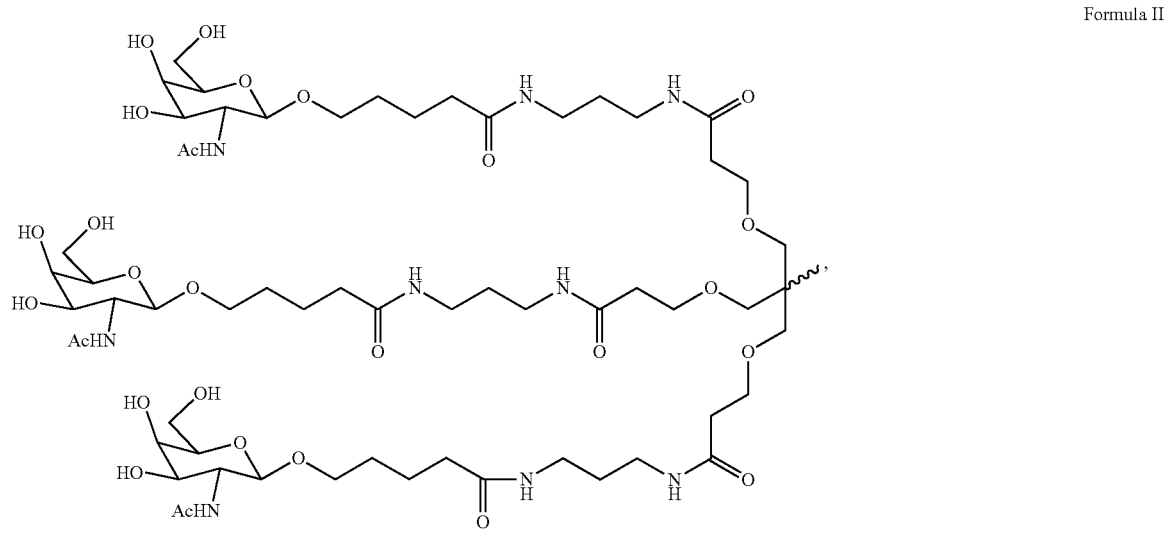
Formula II
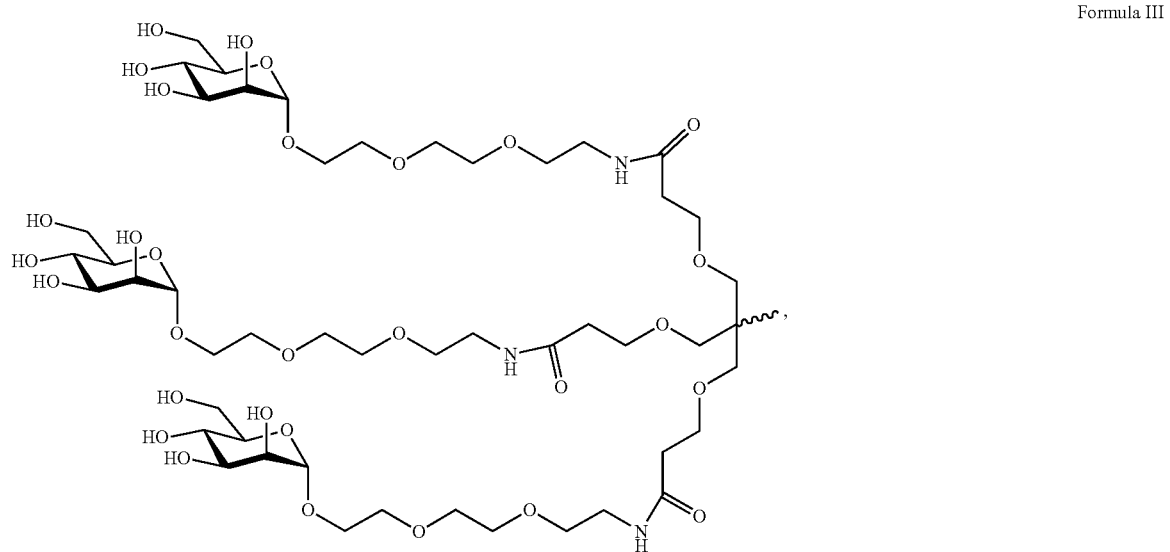
Formula III -continued
Formula IV
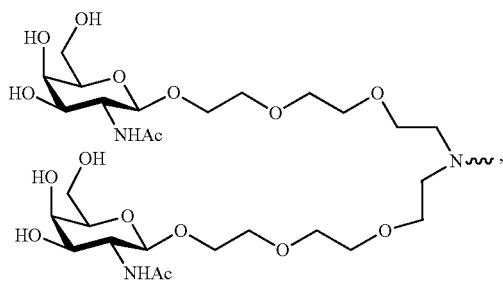
Formula V
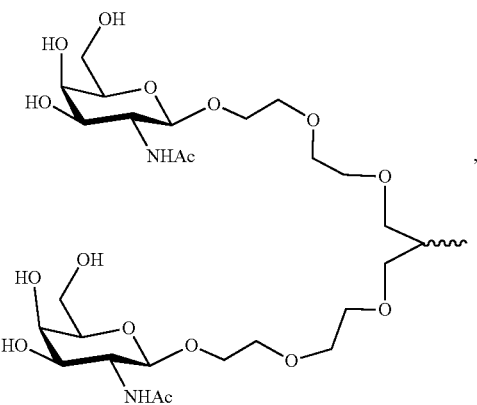
Formula VI
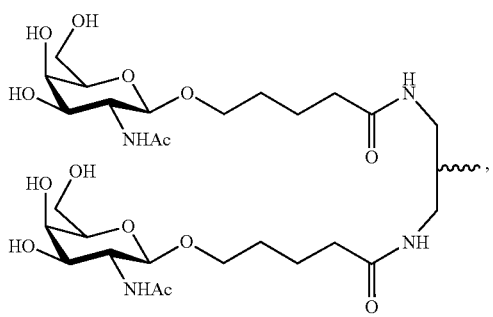
Formula VII
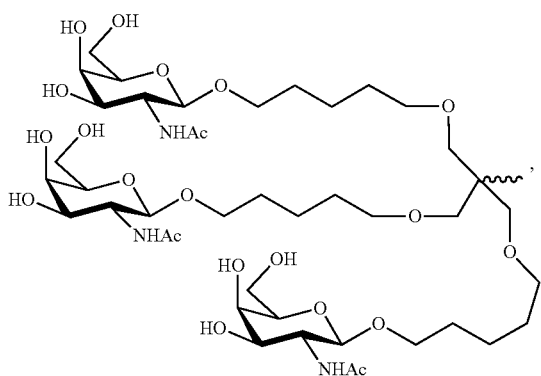
Formula VIII
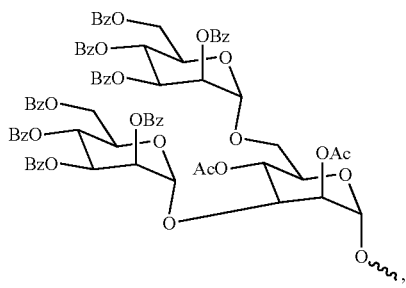
Formula IX
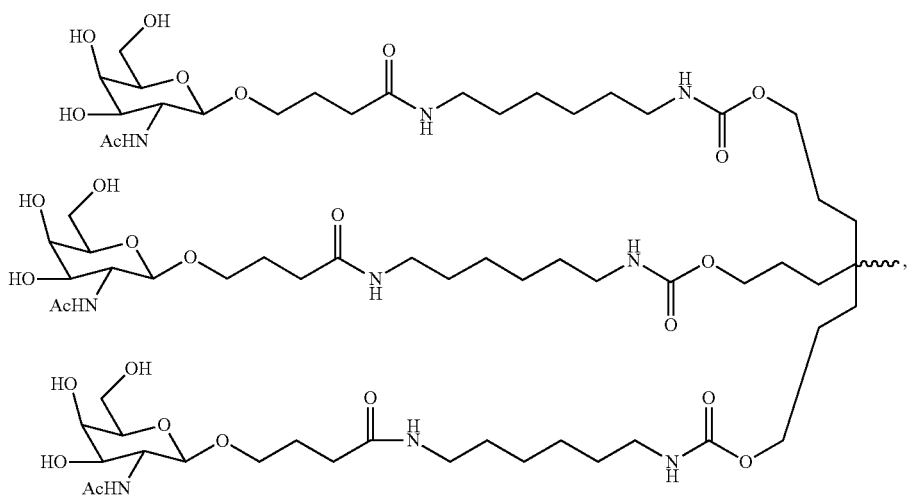

Formula X
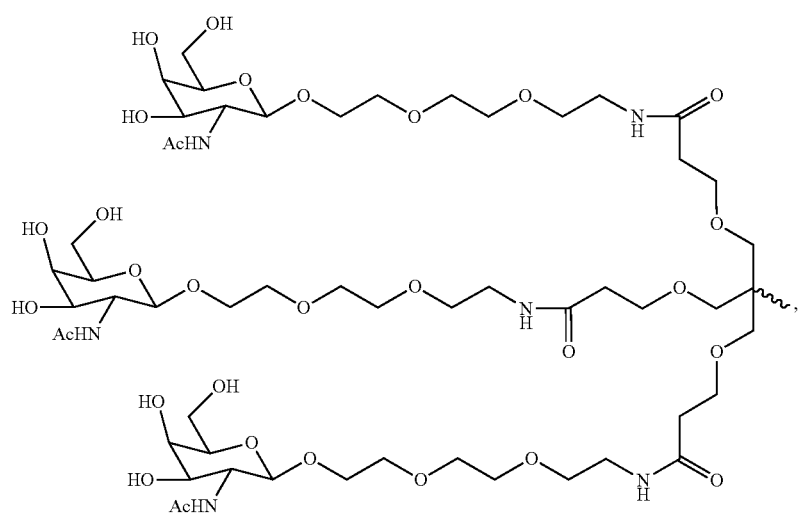
Formula XI
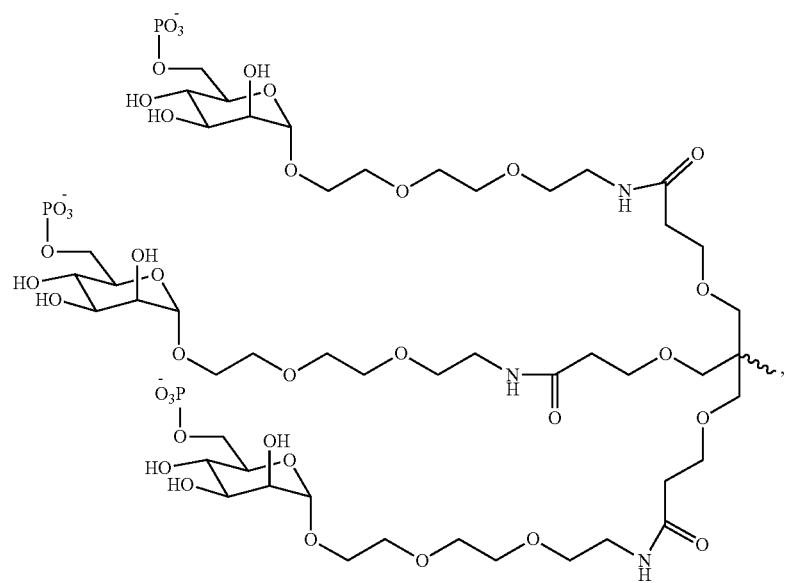

Formula XII
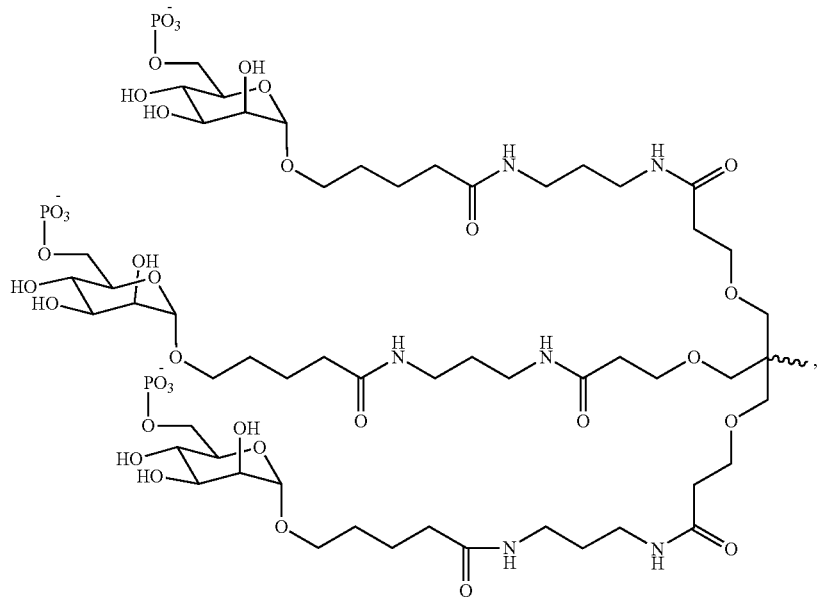
Formula XIII
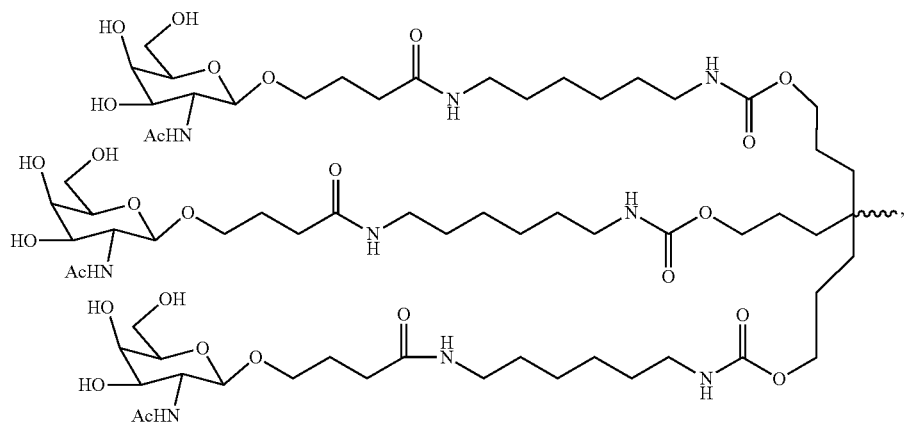
Formula XIV
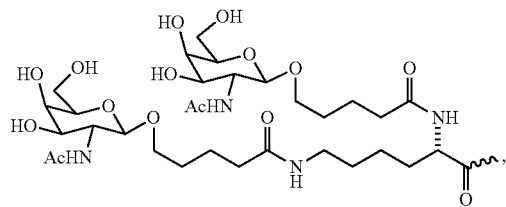
Formula XV
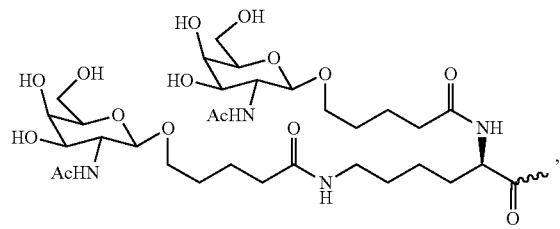
Formula XVI
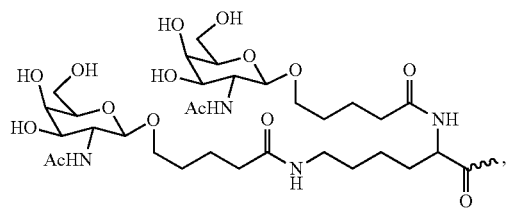
Formula XVII
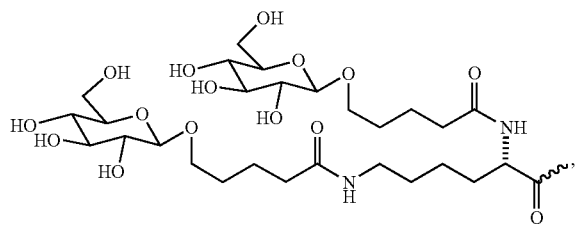

-continued
Formula XVIII
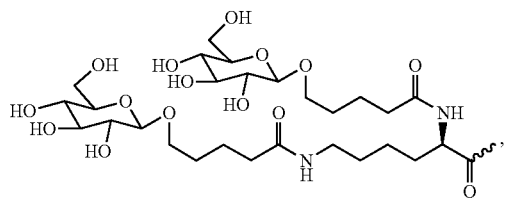
Formula XIX
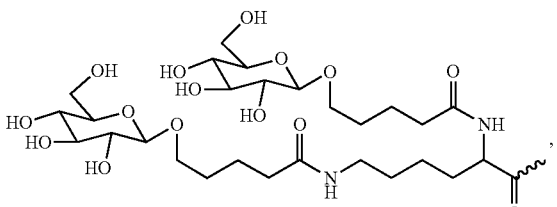
Formula XX
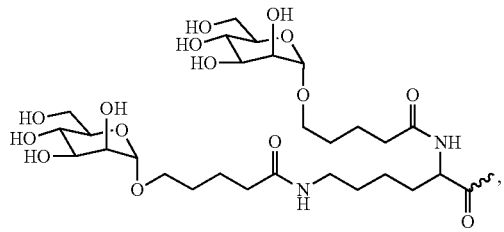
Formula XXI
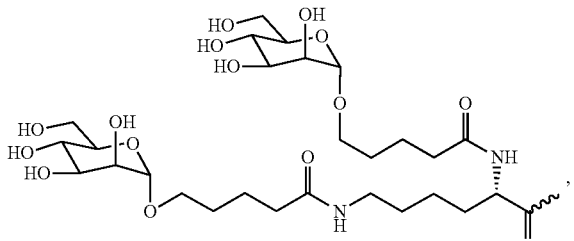
Formula XXII
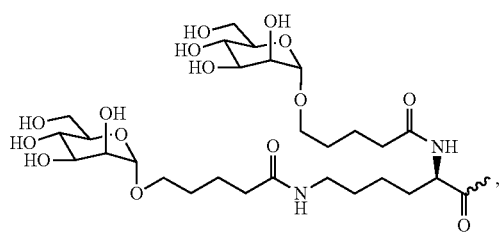
Formula XXIII
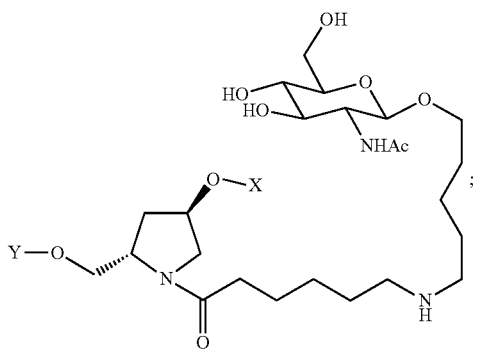
(Formula XXIV)
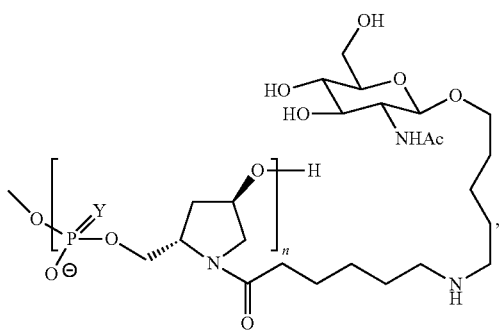
(Formula XXV)
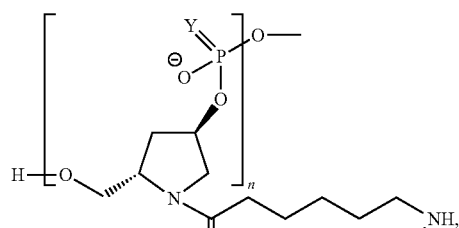
wherein Y is O or S and n is 3-6
wherein Y is O or S and n is 3-6
Formula XXVI
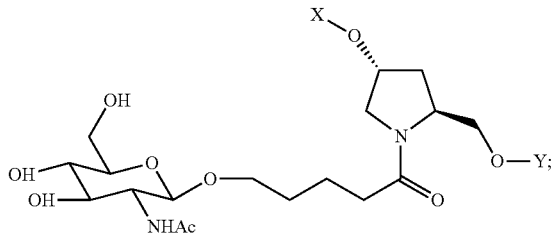

(Formula XXVII)
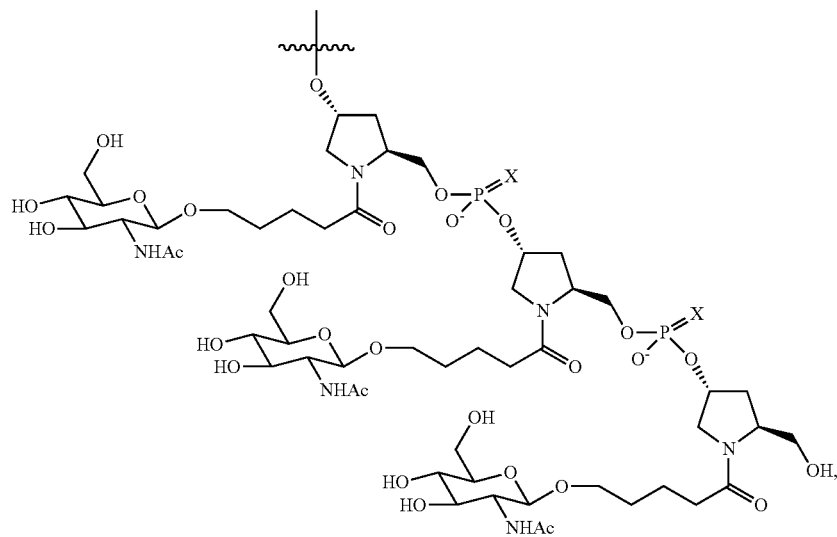
wherein X is O or S
Formula XXVII
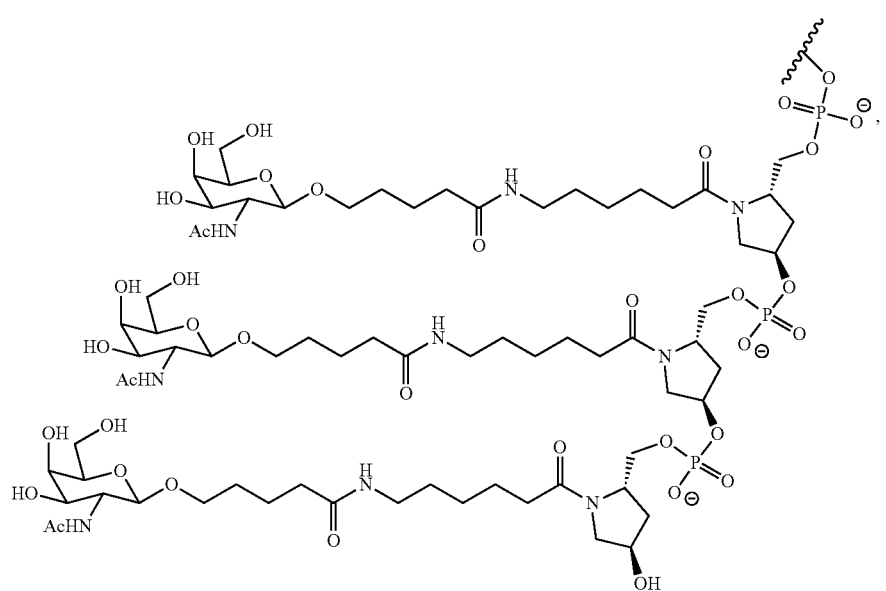

-continued
Formula XXIX
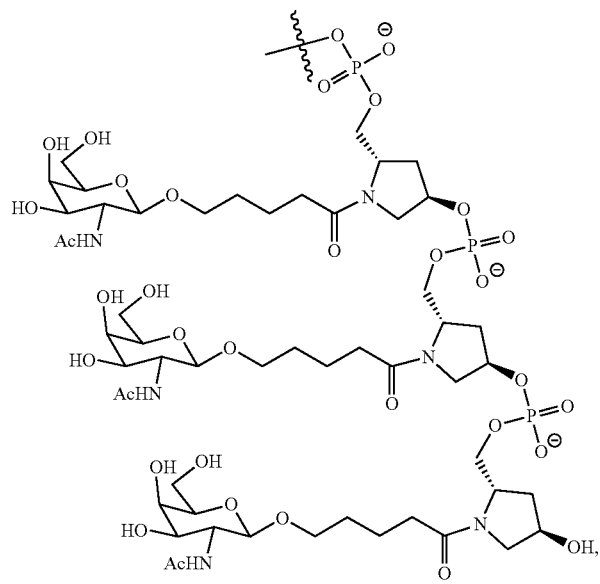
Formula XXX
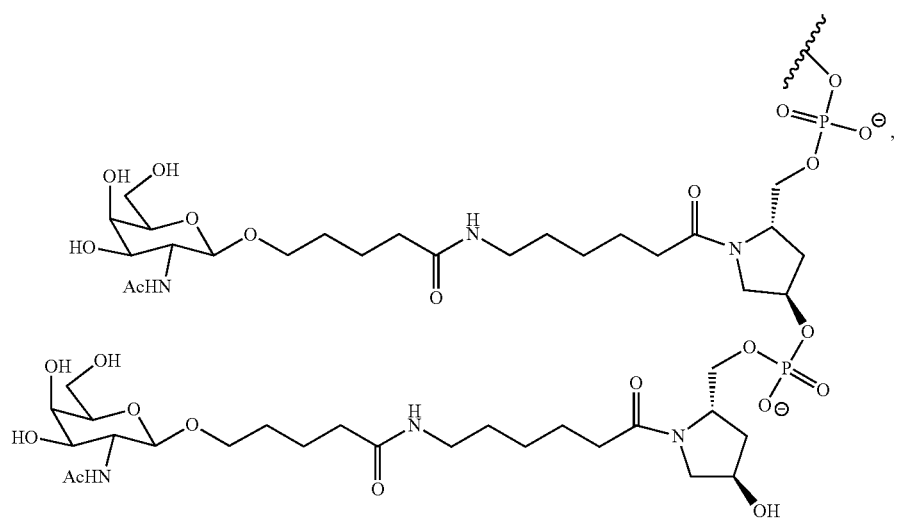
Formula XXXI
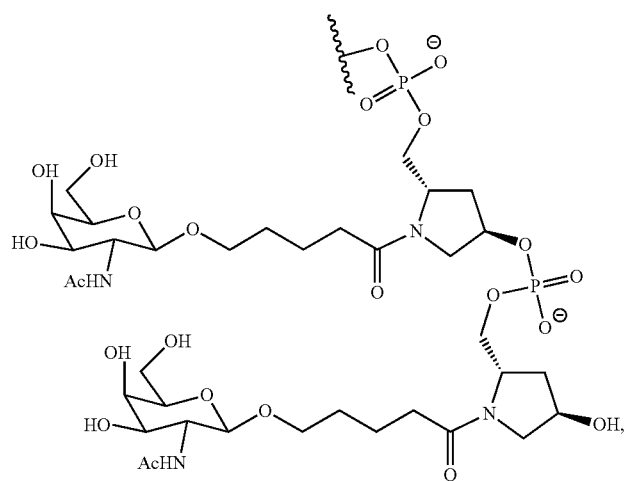

Formula XXXII
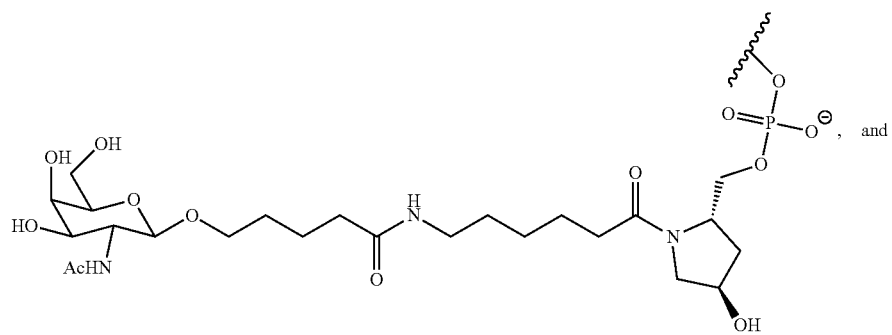
Formula XXXIII
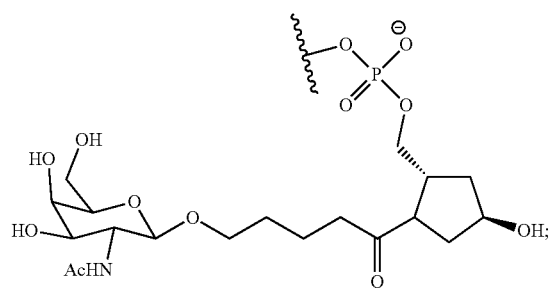
Formula XXXIV
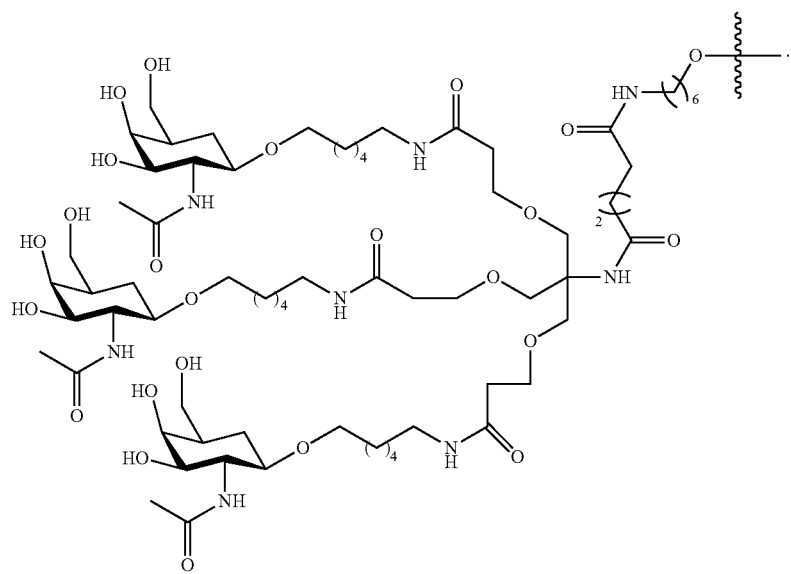

In certain embodiments, a carbohydrate conjugate for use in the compositions and methods of the invention is a monosaccharide. In certain embodiments, the monosaccharide is an N-acetylgalactosamine, such as
Formula II
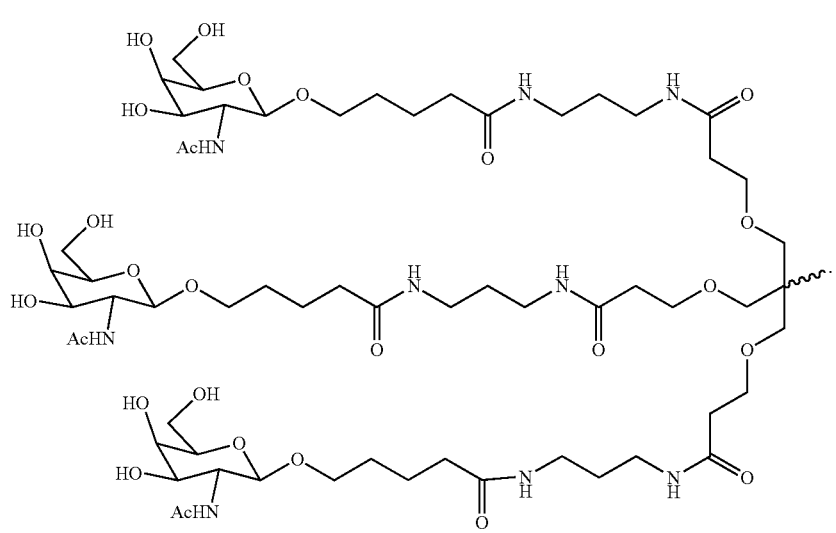
Another representative carbohydrate conjugate for use in the embodiments described herein includes, but is not limited to, (Formula XXXVI)
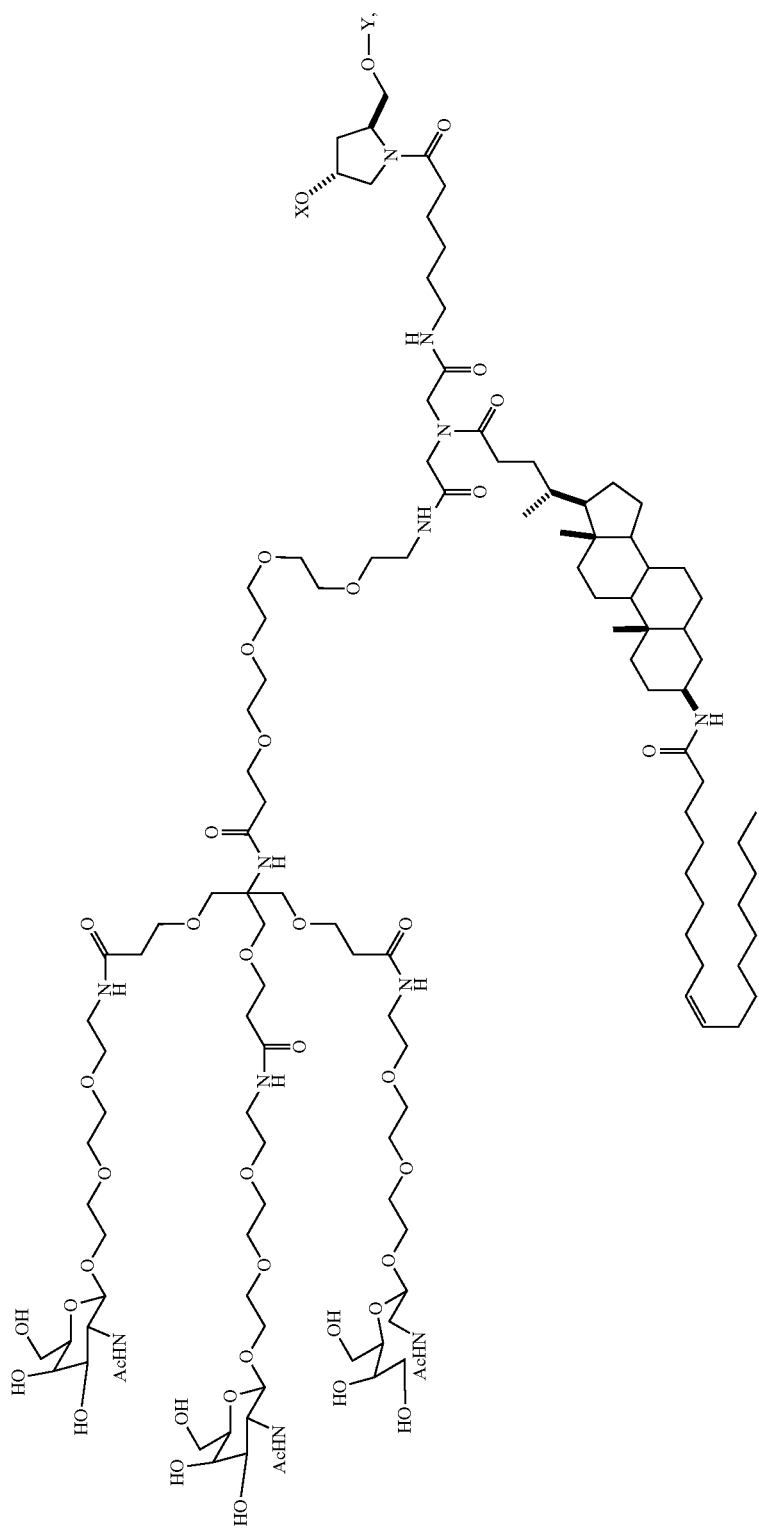

when one of X or Y is an oligonucleotide, the other is a hydrogen.

In some embodiments, a suitable ligand is a ligand disclosed in WO 2019/055633, the entire contents of which are incorporated herein by reference. In one embodiment the ligand comprises the structure below:

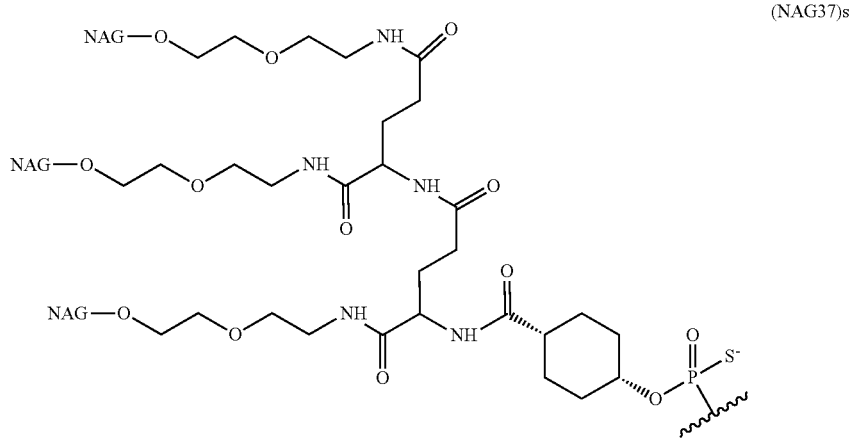

(NAG37)s

In certain embodiments, the RNAi agents of the disclosure may include GalNAc ligands, even if such GalNAc ligands are currently projected to be of limited value for the preferred intrathecal/intracerebroventricular/CNS delivery route(s) of the instant disclosure.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker. In other embodiments of the invention, the GalNAc or GalNAc derivative is attached to an iRNA agent of the invention via a tetravalent linker.

In certain embodiments, the double stranded RNAi agents of the invention comprise one GalNAc or GalNAc derivative attached to the iRNA agent, e.g., the 5' end of the sense strand of a dsRNA agent, or the 5' end of one or both sense strands of a dual targeting RNAi agent as described herein. In certain embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NRB, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In certain embodiments, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In certain embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—, wherein Rk at each occurrence can be, independently, C1-C20 alkyl, C1-C20 haloalkyl, C6-C10 aryl, or C7-C12 aralkyl. Exemplary embodiments include —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, and —O—P(S)(H)—S—. In certain embodiments a phosphate-based linking group is —O—P(O)(OH)—O—. These candidates can be evaluated using methods analogous to those described above.

iii. Acid Cleavable Linking Groups

In certain embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Cleavable Linking Groups

In certain embodiments, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleavable Linking Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O) NHCHR$^B$C(O)—, where R$^A$ and R$^B$ are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to,

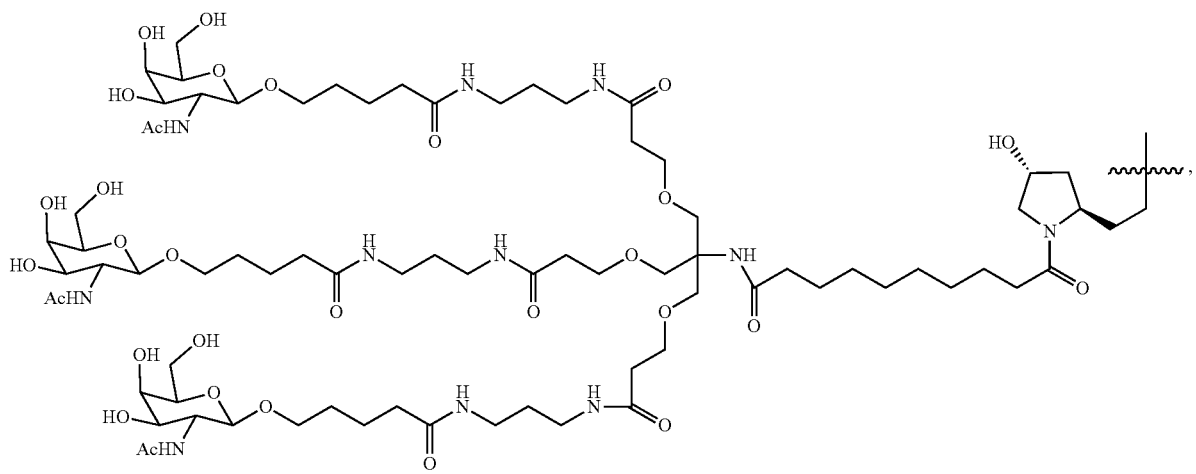

(Formula XXXVII)

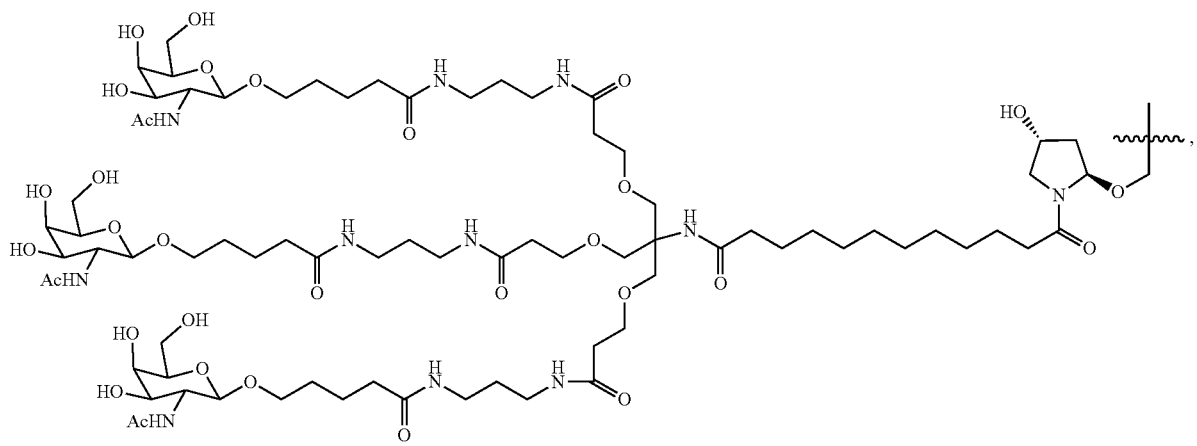

(Formula XXXVIII)

-continued
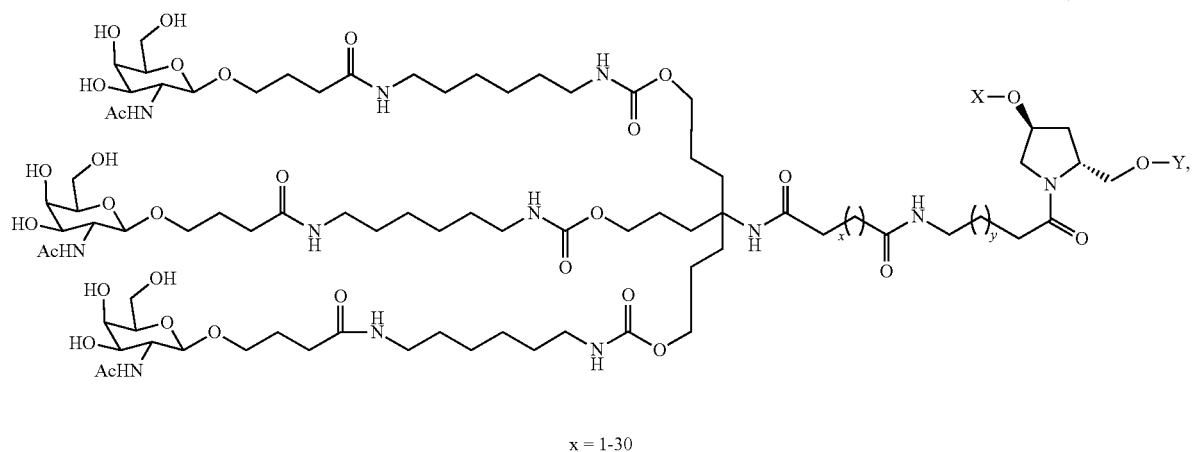
(Formula XXXIX)
x = 1-30
y = 1-15
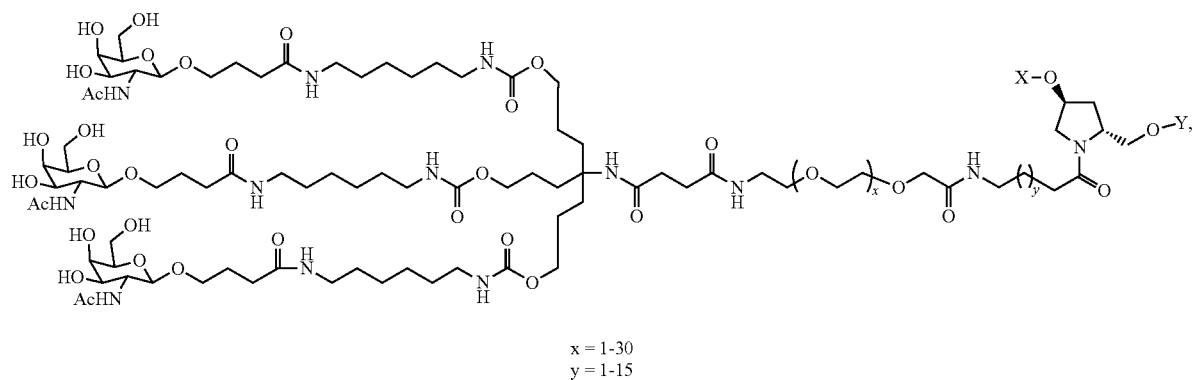
(Formula XL)
x = 1-30
y = 1-15
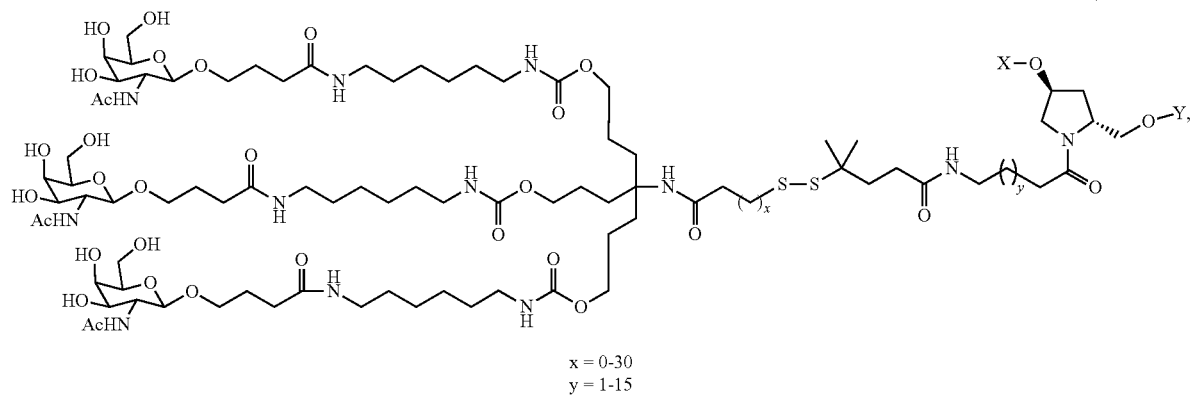
(Formula XLI)
x = 0-30
y = 1-15

(Formula XLII)

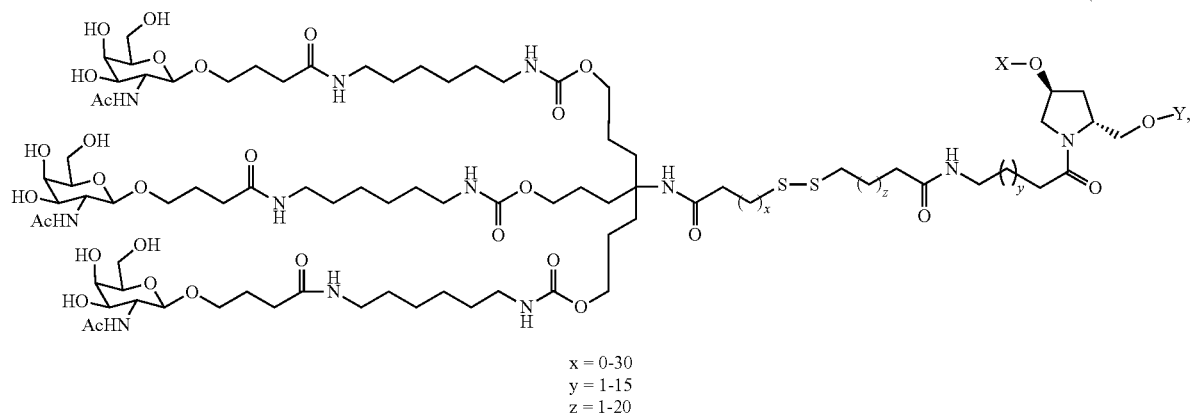

x = 0-30
y = 1-15
z = 1-20

(Formula XLIII)

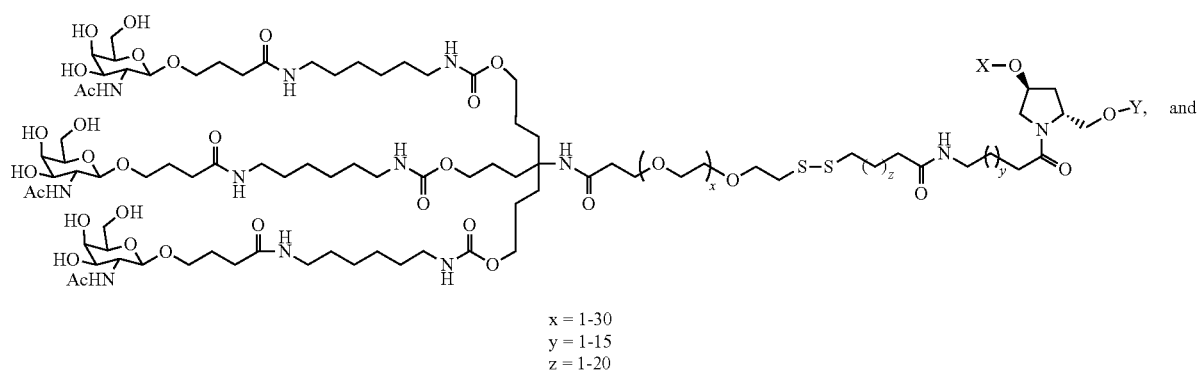

x = 1-30
y = 1-15
z = 1-20

(Formula XLIV)

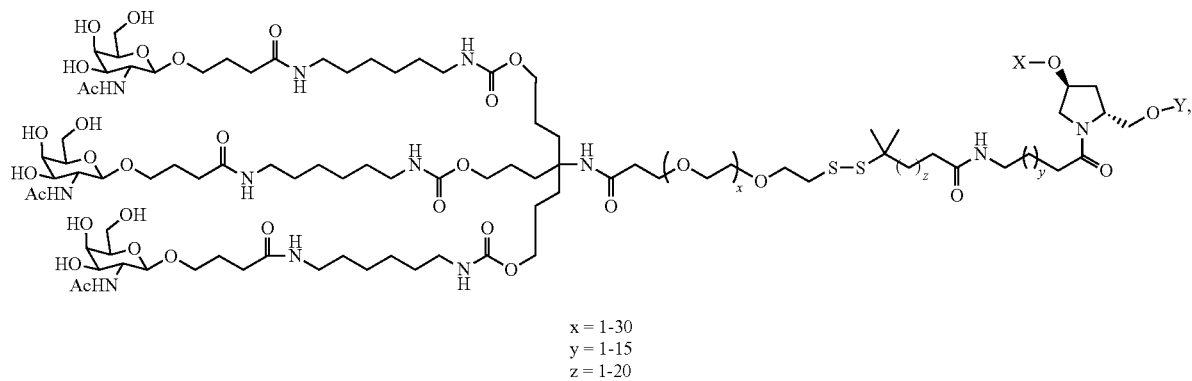

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In certain embodiments, a dsRNA of the invention is conjugated to a bivalent or trivalent branched linker selected from the group of structures shown in any of formula (XLV)-(XLVI):

Formula XXXXV

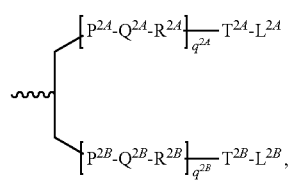

(IV)

Formula XLVI

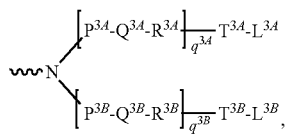

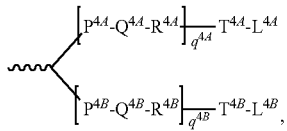

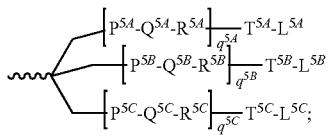

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$ $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), CM, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), CEC or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—O,

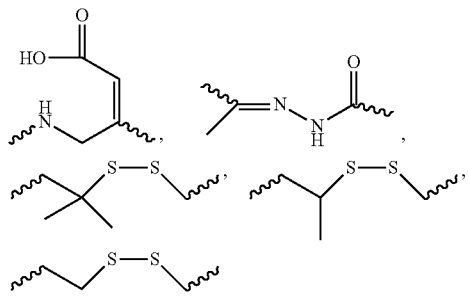

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

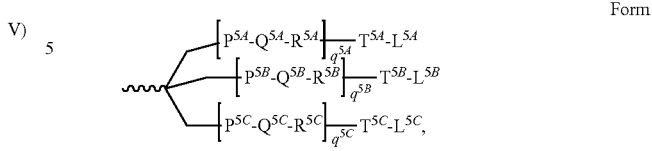

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. Patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNA agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T.

et al., *Biochem. Biophys. Res. Comm.,* 2007, 365(1):54-61; Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. In Vivo Testing of SOD1 Knockdown

Mouse models of SOD1-associated neurodegenerative disease have been generated and can further be used to demonstrate the in vivo efficacy of the RNAi agents provided herein.

Such models may express, e.g., overexpress, for example, human superoxide dismutase 1 (SOD1), in some instances comprising an ALS-related mutation (e.g., a G93A, G37R, G86R, G85R, L84V, G127X, H46R, D90A, L126Z, A4V, or A4V/SOD1WT mutation) (see, e.g., Mina M, et al. (2018) *J Transl Neurosci.* 3:9). Additionally, such models may contain constitutive or inducible expression, e.g., overexpression, of, for example, human amyloid precursor protein (APP), in some instances comprising a pathogenic mutation (e.g., a Swedish mutation (KM670/671NL)), constitutive or inducible expression, e.g., overexpression, of, human pre-senilin 1 (P51), in some instances comprising a pathogenic mutation (e.g., dE9 mutation) (see, e.g., Garcia-Alloza, M et al (2006) *Neurobiol Dis* 24(3): 516-24), and/or constituitive or inducible expression, e.g., overexpression, of 1N4R human tau protein, in some instances comprising a pathogenic mutation (e.g., a P301S mutation) (Wu, T et al (2019) *Cell Rep* 28(8): 2111-2123), superoxide dismutase 1 (SOD1) transgenic mice (see, e.g., Aziza (2018) *In Vivo* 32(983), mouse toxin models of Parkinson's disease (e.g., MPTP) and/or α-synuclein transgenic mice (Blesa and Przedborski (2014) *Front Neurosci* 8:155).

VI. Delivery of an RNAi Agent of the Disclosure

The delivery of a RNAi agent of the disclosure to a cell e.g., a cell within a subject, such as a human subject (e.g., a subject in need thereof, such as a subject having a SOD1-associated neurodegenerative disorder, e.g., Amyotrophic Lateral Sclerosis (ALS), Alzheimer's disease (AD), Parkinson's disease (PD), and Down's syndrome (DS) can be achieved in a number of different ways. For example, delivery may be performed by contacting a cell with an RNAi agent of the disclosure either in vitro or in vivo. In vivo delivery may also be performed directly by administering a composition comprising an RNAi agent, e.g., a dsRNA, to a subject. Alternatively, in vivo delivery may be performed indirectly by administering one or more vectors that encode and direct the expression of the RNAi agent. These alternatives are discussed further below.

In general, any method of delivering a nucleic acid molecule (in vitro or in vivo) can be adapted for use with a RNAi agent of the disclosure (see e.g., Akhtar S. and Julian R L., (1992) *Trends Cell. Biol.* 2(5):139-144 and WO94/02595, which are incorporated herein by reference in their entireties). For in vivo delivery, factors to consider in order to deliver an RNAi agent include, for example, biological stability of the delivered agent, prevention of non-specific effects, and accumulation of the delivered agent in the target tissue. The non-specific effects of an RNAi agent can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the RNAi agent to be administered. Several studies have shown successful knockdown of gene products when an RNAi agent is administered locally. For example, intraocular delivery of a VEGF dsRNA by intravitreal injection in cynomolgus monkeys (Tolentino, M J. et al., (2004) *Retina* 24:132-138) and subretinal injections in mice (Reich, S J. et al. (2003) *Mol. Vis.* 9:210-216) were both shown to prevent neovascularization in an experimental model of age-related macular degeneration. In addition, direct intratumoral injection of a dsRNA in mice reduces tumor volume (Pille, J. et al. (2005) *Mol. Ther.* 11:267-274) and can prolong survival of tumor-bearing mice (Kim, W J. et al., (2006) *Mol. Ther.* 14:343-350; Li, S. et al., (2007) *Mol. Ther.* 15:515-523). RNA interference has also shown success with local delivery to the CNS by direct injection (Dorn, G. et al., (2004) *Nucleic Acids* 32:e49; Tan, P H. et al. (2005) *Gene Ther.* 12:59-66; Makimura, H. et al. (2002) *BMC Neurosci.* 3:18; Shishkina, G T., et al. (2004) *Neuroscience* 129:521-528; Thakker, E R., et al. (2004) *Proc. Natl. Acad. Sci. U.S.A.* 101:17270-17275; Akaneya, Y., et al. (2005) *J. Neurophysiol.* 93:594-602) and to the lungs by intranasal administration (Howard, K A. et al., (2006) *Mol. Ther.* 14:476-484; Zhang, X. et al., (2004) *J. Biol. Chem.* 279:10677-10684; Bitko, V. et al., (2005) *Nat. Med.* 11:50-55). For administering a RNAi agent systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the RNAi agent to the target tissue and avoid undesirable off-target effects (e.g., without wishing to be bound by theory, use of GNAs as described herein has been identified to destabilize the seed region of a dsRNA, resulting in enhanced preference of such dsRNAs for on-target effectiveness, relative to off-target effects, as such off-target effects are significantly weakened by such seed region destabilization). RNAi agents can be modified by chemical conjugation to lipophilic groups such as cholesterol to enhance cellular uptake and prevent degradation. For example, a RNAi agent directed against ApoB conjugated to a lipophilic cholesterol moiety was injected systemically into mice and resulted in knockdown of apoB mRNA in both the liver and jejunum (Soutschek, J. et al., (2004) *Nature* 432:173-178). Conjugation of an RNAi agent to an aptamer has been shown to inhibit tumor growth and mediate tumor regression in a mouse model of prostate cancer (McNamara, J O. et al., (2006) *Nat. Biotechnol.* 24:1005-1015). In an alternative embodiment, the RNAi agent can be delivered using drug delivery systems such as a nanoparticle, a dendrimer, a polymer, liposomes, or a cationic delivery system. Positively charged cationic delivery systems facilitate binding of molecule RNAi agent (negatively charged) and also enhance interactions at the negatively charged cell membrane to permit efficient uptake of an RNAi agent by the cell. Cationic lipids, dendrimers, or polymers can either be bound to an RNAi agent, or induced to form a vesicle or micelle (see e.g., Kim S H. et al., (2008) *Journal of Controlled Release* 129(2):107-116) that encases an RNAi agent. The formation of vesicles or micelles further prevents degradation of the RNAi agent when administered systemically. Methods for making and administering cationic-RNAi agent complexes are well within the abilities of one skilled in the art (see e.g., Sorensen, D R., et al. (2003) *J. Mol. Biol* 327:761-766; Verma, U N. et al., (2003) *Clin. Cancer Res.* 9:1291-1300; Arnold, A S et al. (2007) J. Hypertens. 25:197-205, which are incorporated herein by reference in their entirety). Some non-limiting examples of drug delivery systems useful for systemic delivery of RNAi agents include DOTAP (Sorensen, D R., et al (2003), supra; Verma, U N. et al., (2003), supra), Oligofectamine, "solid nucleic acid lipid particles" (Zimmermann, T S. et al., (2006) *Nature* 441:111-114), cardiolipin (Chien, P Y. et al., (2005) *Cancer Gene Ther.* 12:321-328; Pal, A. et al., (2005) *Int J. Oncol.* 26:1087-1091), polyethyleneimine (Bonnet M E. et al., (2008) *Pharm. Res. August* 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A. et al., (2007) *Biochem. Soc. Trans.* 35:61-67; Yoo, H. et al., (1999) *Pharm. Res.* 16:1799-1804). In some embodiments, a RNAi agent forms a complex with cyclodextrin for systemic administration. Methods for administration and pharmaceutical compositions of RNAi agents and cyclodextrins can be found in U.S. Pat. No. 7,427,605, which is herein incorporated by reference in its entirety.

Certain aspects of the instant disclosure relate to a method of reducing the expression of a SOD1 target gene in a cell, comprising contacting said cell with the double-stranded RNAi agent of the disclosure. In one embodiment, the cell is a hepatic cell, optionally a hepatocyte. In one embodiment, the cell is an extrahepatic cell, optionally a CNS cell.

Another aspect of the disclosure relates to a method of reducing the expression of a SOD1 target gene in a subject, comprising administering to the subject the double-stranded RNAi agent of the disclosure.

Another aspect of the disclosure relates to a method of treating a subject having a SOD1-associated neurodegenerative disorder, comprising administering to the subject a therapeutically effective amount of the double-stranded RNAi agent of the disclosure, thereby treating the subject. Exemplary CNS disorders that can be treated by the method of the disclosure include Amyotrophic Lateral Sclerosis (ALS), Alzheimer's disease (AD), Parkinson's disease (PD), and Down's syndrome (DS).

In one embodiment, the double-stranded RNAi agent is administered subcutaneously.

In one embodiment, the double-stranded RNAi agent is administered by intraventricular administration.

In one embodiment, the double-stranded RNAi agent is administered intrathecally. In one embodiment, the double-stranded RNAi agent is administered intracerebroventricularly. By intrathecal or intracerebroventricular administration of the double-stranded RNAi agent, the method can reduce the expression of a SOD1 target gene in a brain (e.g., striatum) or spine tissue, for instance, cortex, cerebellum, cervical spine, lumbar spine, and thoracic spine.

For ease of exposition the formulations, compositions and methods in this section are discussed largely with regard to modified siRNA compounds. It may be understood, however, that these formulations, compositions and methods can be practiced with other siRNA compounds, e.g., unmodified siRNA compounds, and such practice is within the disclosure. A composition that includes a RNAi agent can be delivered to a subject by a variety of routes. Exemplary routes include intrathecal, subcutaneous, intravenous, intraventricular (also known as intracerebroventricular), intraperitoneal, intravitreal, topical, rectal, anal, vaginal, and ocular.

The RNAi agents of the disclosure can be incorporated into pharmaceutical compositions suitable for administration. Such compositions typically include one or more species of RNAi agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present disclosure may be administered in a number of ways depending upon whether local or systemic treatment is desired and upon the area to be treated. Administration may be topical (including ophthalmic, vaginal, rectal, transdermal), oral, or parenteral. Parenteral administration includes intravenous drip, subcutaneous, intraperitoneal, or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the RNAi agent in powder or aerosol form. The vascular endothelial cells could be targeted by coating a balloon catheter with the RNAi agent and mechanically introducing the RNA.

Formulations for topical administration may include transdermal patches, ointments, lotions, creams, gels, drops, suppositories, sprays, liquids, and powders. Conventional pharmaceutical carriers, aqueous, powder or oily bases, thickeners and the like may be necessary or desirable. Coated condoms, gloves, and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening or flavoring agents can be added.

Compositions for intrathecal or intraventricular administration may include sterile aqueous solutions which may also contain buffers, diluents, and other suitable additives.

Formulations for parenteral administration may include sterile aqueous solutions which may also contain buffers, diluents, and other suitable additives. Intraventricular injection may be facilitated by an intraventricular catheter, for example, attached to a reservoir. For intravenous use, the total concentration of solutes may be controlled to render the preparation isotonic.

In one embodiment, the administration of the siRNA compound, e.g., a double-stranded siRNA compound, or ssiRNA compound, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, urethral, or ocular. Administration can be provided by the subject or by another person, e.g., a health care provider. The medication can be provided in measured doses or in a dispenser which delivers a metered dose. Selected modes of delivery are discussed in more detail below.

Intrathecal Administration.

In one embodiment, the double-stranded RNAi agent is delivered by intrathecal injection (i.e., injection into the spinal fluid which bathes the brain and spinal cord tissue). Intrathecal injection of RNAi agents into the spinal fluid can be performed as a bolus injection or via minipumps which can be implanted beneath the skin, providing a regular and constant delivery of siRNA into the spinal fluid. The circulation of the spinal fluid from the choroid plexus, where it is produced, down around the spinal cord and dorsal root ganglia and subsequently up past the cerebellum and over the cortex to the arachnoid granulations, where the fluid can exit the CNS, that, depending upon size, stability, and solubility of the compounds injected, molecules delivered intrathecally could hit targets throughout the entire CNS.

In some embodiments, the intrathecal administration is via a pump. The pump may be a surgically implanted osmotic pump. In one embodiment, the osmotic pump is implanted into the subarachnoid space of the spinal canal to facilitate intrathecal administration.

In some embodiments, the intrathecal administration is via an intrathecal delivery system for a pharmaceutical including a reservoir containing a volume of the pharmaceutical agent, and a pump configured to deliver a portion of the pharmaceutical agent contained in the reservoir. More details about this intrathecal delivery system may be found in WO 2015/116658, which is incorporated by reference in its entirety.

The amount of intrathecally injected RNAi agents may vary from one target gene to another target gene and the appropriate amount that has to be applied may have to be determined individually for each target gene. Typically, this amount ranges from 10 µg to 2 mg, preferably 50 µg to 1500 µg, more preferably 100 µg to 1000 µg.

Vector Encoded RNAi Agents of the Disclosure

RNAi agents targeting the SOD1 gene can be expressed from transcription units inserted into DNA or RNA vectors (see, e.g., Couture, A, et al., *TIG.* (1996), 12:5-10; WO 00/22113, WO 00/22114, and U.S. Pat. No. 6,054,299). Expression is preferably sustained (months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., (1995) *Proc. Natl. Acad. Sci. USA* 92:1292).

The individual strand or strands of a RNAi agent can be transcribed from a promoter on an expression vector. Where two separate strands are to be expressed to generate, for example, a dsRNA, two separate expression vectors can be co-introduced (e.g., by transfection or infection) into a target cell. Alternatively, each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

RNAi agent expression vectors are generally DNA plasmids or viral vectors. Expression vectors compatible with eukaryotic cells, preferably those compatible with vertebrate cells, can be used to produce recombinant constructs for the expression of a RNAi agent as described herein. Delivery of RNAi agent expressing vectors can be systemic, such as by intravenous or intramuscular administration, by administration to target cells ex-planted from the patient followed by reintroduction into the patient, or by any other means that allows for introduction into a desired target cell.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of a RNAi agent will generally require regulatory elements, e.g., promoters, enhancers, etc., to ensure the expression of the RNAi agent in target cells. Other aspects to consider for vectors and constructs are known in the art.

VII. Pharmaceutical Compositions of the Invention

The present disclosure also includes pharmaceutical compositions and formulations which include the RNAi agents of the disclosure. In one embodiment, provided herein are pharmaceutical compositions containing an RNAi agent, as described herein, and a pharmaceutically acceptable carrier. The pharmaceutical compositions containing the RNAi agent are useful for treating a disease or disorder associated with the expression or activity of SOD1, e.g., a SOD1-associated neurodegenerative disease, such as Amyotrophic Lateral Sclerosis (ALS), Alzheimer's disease (AD), Parkinson's disease (PD), and Down's syndrome (DS).

Such pharmaceutical compositions are formulated based on the mode of delivery. One example is compositions that are formulated for systemic administration via parenteral delivery, e.g., by intravenous (IV), intramuscular (IM), or for subcutaneous (subQ) delivery. Another example is compositions that are formulated for direct delivery into the CNS, e.g., by intrathecal or intraventricular routes of injection, optionally by infusion into the brain (e.g., striatum), such as by continuous pump infusion.

In some embodiments, the pharmaceutical compositions of the invention are pyrogen free or non-pyrogenic.

The pharmaceutical compositions of the disclosure may be administered in dosages sufficient to inhibit expression of a SOD1 gene. In general, a suitable dose of an RNAi agent of the disclosure will be a flat dose in the range of about 0.001 to about 200.0 mgabout once per month to about once per year, typically about once per quarter (i.e., about once every three months) to about once per year, generally a flat dose in the range of about 1 to 50 mg about once per month to about once per year, typically about once per quarter to about once per year.

After an initial treatment regimen (e.g., loading dose), the treatments can be administered on a less frequent basis.

The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a composition can include a single treatment or a series of treatments.

Advances in mouse genetics have generated a number of mouse models for the study of various SOD1-associated neurodegenerative diseases that would benefit from reduction in the expression of SOD1. Such models can be used for in vivo testing of RNAi agents, as well as for determining a therapeutically effective dose. Suitable mouse models are known in the art and include, for example, the mouse models described elsewhere herein.

The pharmaceutical compositions of the present disclosure can be administered in a number of ways depending upon whether local or systemic treatment is desired and upon the area to be treated. Administration can be topical (e.g., by a transdermal patch), epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The RNAi agents can be delivered in a manner to target a particular tissue, such as the liver, the CNS (e.g., neuronal, glial or vascular tissue of the brain), or both the liver and CNS.

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the RNAi agents featured in the disclosure are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). RNAi agents featured in the disclosure can be encapsulated within liposomes or can form complexes thereto, in particular to cationic liposomes. Alternatively, RNAi agents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

A. RNAi Agent Formulations Comprising Membranous Molecular Assemblies

A RNAi agent for use in the compositions and methods of the disclosure can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the RNAi agent composition. The lipophilic material isolates the aqueous interior from an aqueous exterior, which typically does not include the RNAi agent composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the RNAi agent are delivered into the cell where the RNAi agent can specifically bind to a target RNA and can mediate RNAi. In some cases the liposomes are also specifically targeted, e.g., to direct the RNAi agent to particular cell types.

A liposome containing an RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., (1987) Proc. Natl. Acad. Sci. USA 8:7413-7417; U.S. Pat. Nos.

4,897,355; 5,171,678; Bangham et al., (1965) *M. Mol. Biol.* 23:238; Olson et al., (1979) *Biochim. Biophys. Acta* 557:9; Szoka et al., (1978) *Proc. Natl. Acad. Sci.* 75: 4194; Mayhew et al., (1984) *Biochim. Biophys. Acta* 775:169; Kim et al., (1983) *Biochim. Biophys. Acta* 728:339; and Fukunaga et al., (1984) *Endocrinol.* 115:757. Commonly used techniques for preparing lipid aggregates of appropriate size for use as delivery vehicles include sonication and freeze-thaw plus extrusion (see, e.g., Mayer et al., (1986) *Biochim. Biophys. Acta* 858:161. Microfluidization can be used when consistently small (50 to 200 nm) and relatively uniform aggregates are desired (Mayhew et al., (1984) *Biochim. Biophys. Acta* 775:169. These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) *Biochem. Biophys. Res. Commun.,* 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) *Journal of Controlled Release,* 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid or phosphatidylcholine or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, (1994) *J. Biol. Chem.* 269:2550; Nabel, (1993) *Proc. Natl. Acad. Sci.* 90:11307; Nabel, (1992) *Human Gene Ther.* 3:649; Gershon, (1993) Biochem. 32:7143; and Strauss, (1992) *EMBO J.* 11:417.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) *S.T.P. Pharma. Sci.,* 4(6):466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) *FEBS Letters,* 223:42; Wu et al., (1993) *Cancer Research,* 53:3765).

Various liposomes comprising one or more glycolipids are known in the art. Papahadjopoulos et al. (*Ann. N.Y. Acad. Sci.,* (1987), 507:64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* (1988), 85:6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., (1987) *Proc. Natl. Acad. Sci. USA* 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., (1991) *Biochim. Biophys. Res. Commun.* 179:280). Lipopolylysine, made by conjugating polylysine to DOPE, has been reported to be effective for transfection in the presence of serum (Zhou, X. et al., (1991) *Biochim. Biophys. Acta* 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., (1992) *Journal of Drug Targeting*, vol. 2, 405-410 and du Plessis et al., (1992) *Antiviral Research*, 18:259-265; Mannino, R. J. and Fould-Fogerite, S., (1998) *Biotechniques* 6:682-690; Itani, T. et al., (1987) *Gene* 56:267-276; Nicolau, C. et al. (1987) *Meth. Enzymol.* 149: 157-176; Straubinger, R. M. and Papahadjopoulos, D. (1983) *Meth. Enzymol.* 101:512-527; Wang, C. Y. and Huang, L., (1987) *Proc. Natl. Acad. Sci. USA* 84:7851-7855).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include RNAi agents can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present disclosure are described in PCT publication No. WO 2008/042973.

Transfersomes, yet another type of liposomes, are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as those described herein, particularlay in emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The RNAi agent for use in the methods of the disclosure can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to C22 alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol or m-cresol may be added to the mixed micellar composition to stabilize the formulation and protect against bacterial growth. Alternatively, phenol or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Lipid Particles

RNAi agents, e.g., dsRNAs of in the disclosure may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in WO 00/03683. The particles of the present disclosure typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present disclosure are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; United States Patent publication No. 2010/0324120 and WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the disclosure.

Certain specific LNP formulations for delivery of RNAi agents have been described in the art, including, e.g., "LNP01" formulations as described in, e.g., WO 2008/042973, which is hereby incorporated by reference.

Additional exemplary lipid-dsRNA formulations are identified in the table below.

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA~7:1 |

-continued

|  | Ionizable/Cationic Lipid | cationic lipid/non-cationic lipid/cholesterol/PEG-lipid conjugate Lipid:siRNA ratio |
|---|---|---|
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~6:1 |
| LNP06 | 2,2-Dilinoleyl-4-dimethylaminoethyl-[l,3]-dioxolane (XTC) | XTC/DSPC/Cholesterol/PEG-DMG 57.5/7.5/31.5/3.5 lipid:siRNA~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC-3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in WO 2009/127060, which is hereby incorporated by reference.
XTC comprising formulations are described in WO 2010/088537, the entire contents of which are hereby incorporated herein by reference.
MC3 comprising formulations are described, e.g., in United States Patent Publication No. 2010/0324120, the entire contents of which are hereby incorporated by reference.
ALNY-100 comprising formulations are described in WO 2010/054406, the entire contents of which are hereby incorporated herein by reference.
C12-200 comprising formulations are described in WO 2010/129709, the entire contents of which are hereby incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the disclosure are administered in conjunction with one or more penetration enhancer surfactants and chelators. Suitable surfactants include fatty acids or esters or salts thereof, bile acids or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the disclosure can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcyanoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, U.S. 2003/0027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the brain when treating SOD-1-associated diseases or disorders.

The pharmaceutical formulations of the present disclosure, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure can be formulated into any of many possible dosage forms such as, but not limited to, tablets, capsules, gel capsules, liquid syrups, soft gels, suppositories, and enemas. The compositions of the present disclosure can also be formulated as suspensions in aqueous, non-aqueous or mixed media. Aqueous suspensions can further contain substances which increase the viscosity of the suspension including, for example, sodium carboxymethylcellulose, sorbitol or dextran. The suspension can also contain stabilizers.

Additional Formulations i. Emulsions

The compositions of the present disclosure can be prepared and formulated as emulsions. Emulsions are typically heterogeneous systems of one liquid dispersed in another in the form of droplets usually exceeding 0.1 µm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise, a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present disclosure, the compositions of RNAi agents and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically, microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215).

Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used, and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143).

Often microemulsions can form spontaneously when their components are brought together at ambient temperature. This can be particularly advantageous when formulating thermolabile drugs, peptides or RNAi agents. Microemulsions have also been effective in the transdermal delivery of active components in both cosmetic and pharmaceutical applications. It is expected that the microemulsion compositions and formulations of the present disclosure will facilitate the increased systemic absorption of RNAi agents and nucleic acids from the gastrointestinal tract, as well as improve the local cellular uptake of RNAi agents and nucleic acids.

Microemulsions of the present disclosure can also contain additional components and additives such as sorbitan monostearate (Grill 3), Labrasol, and penetration enhancers to improve the properties of the formulation and to enhance the absorption of the RNAi agents and nucleic acids of the present disclosure. Penetration enhancers used in the microemulsions of the present disclosure can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles

An RNAi agent of the disclosure may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present disclosure employs various penetration enhancers to effect the efficient delivery of nucleic acids, particularly RNAi agents, to the skin of animals Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of RNAi agents through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present disclosure, can be defined as compounds that remove metallic ions from solution by forming complexes therewith, with the result that absorption of RNAi agents through the mucosa is enhanced. With regards to their use as penetration enhancers in the present disclosure, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rd., 1990, 14, 43-51).

As used herein, non-chelating non-surfactant penetration enhancing compounds can be defined as compounds that demonstrate insignificant activity as chelating agents or as surfactants but that nonetheless enhance absorption of RNAi agents through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of RNAi agents at the cellular level can also be added to the pharmaceutical and other compositions of the present disclosure. For example, cationic lipids, such as lipofectin (Junichi et al, U.S. Pat. No. 5,705,188), cationic glycerol derivatives, and polycationic molecules, such as polylysine (WO 97/30731), are also known to enhance the cellular uptake of dsRNAs.

Other agents can be utilized to enhance the penetration of the administered nucleic acids, including glycols such as ethylene glycol and propylene glycol, pyrrols such as 2-pyrrol, azones, and terpenes such as limonene and menthone.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present disclosure. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present disclosure can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings or aromatic substances and the like which do not deleteriously interact with the nucleic acid(s) of the formulation.

Aqueous suspensions can contain substances which increase the viscosity of the suspension including, for example, sodium carboxymethylcellulose, sorbitol or dextran. The suspension can also contain stabilizers.

In some embodiments, pharmaceutical compositions featured in the disclosure include (a) one or more RNAi agents and (b) one or more agents which function by a non-RNAi mechanism and which are useful in treating a SOD1-associated neurodegenerative disorder. Examples of such agents include, but are not limited to SSRIs, venlafaxine, bupropion, and atypical antipsychotics.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Compounds that exhibit high therapeutic indices are preferred.

The data obtained from cell culture assays and animal studies can be used in formulating a range of dosage for use in humans. The dosage of compositions featured herein in the disclosure lies generally within a range of circulating concentrations that include the $ED_{50}$ with little or no toxicity. The dosage can vary within this range depending upon the dosage form employed and the route of administration utilized. For any compound used in the methods featured in the disclosure, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the RNAi agents featured in the disclosure can be administered in combination with other known agents effective in treatment of pathological processes mediated by nucleotide repeat expression. In any event, the administering physician can adjust the amount and timing of RNAi agent administration on the basis of results observed using standard measures of efficacy known in the art or described herein.

VIII. Kits

In certain aspects, the instant disclosure provides kits that include a suitable container containing a pharmaceutical formulation of a siRNA compound, e.g., a double-stranded siRNA compound, or siRNA compound, (e.g., a precursor, e.g., a larger siRNA compound which can be processed into a siRNA compound, or a DNA which encodes an siRNA compound, e.g., a double-stranded siRNA compound, or siRNA compound, or precursor thereof). In certain embodiments the individual components of the pharmaceutical formulation may be provided in one container. Alternatively, it may be desirable to provide the components of the pharmaceutical formulation separately in two or more containers, e.g., one container for a siRNA compound preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

IX. Methods for Inhibiting SOD1 Expression

The present disclosure also provides methods of inhibiting expression of a SOD1 gene in a cell. The methods include contacting a cell with an RNAi agent, e.g., double stranded RNAi agent, in an amount effective to inhibit expression of SOD1 in the cell, thereby inhibiting expression of SOD1 in the cell. In certain embodiments of the disclosure, SOD1 is inhibited preferentially in CNS (e.g., brain) cells. In other embodiments of the disclosure, SOD1 is inhibited preferentially in the liver (e.g., hepatocytes). In certain embodiments of the disclosure, SOD1 is inhibited in CNS (e.g., brain) cells and in liver (e.g., hepatocytes) cells.

Contacting of a cell with a RNAi agent, e.g., a double stranded RNAi agent, may be done in vitro or in vivo. Contacting a cell in vivo with the RNAi agent includes contacting a cell or group of cells within a subject, e.g., a human subject, with the RNAi agent. Combinations of in vitro and in vivo methods of contacting a cell are also possible.

Contacting a cell may be direct or indirect, as discussed above. Furthermore, contacting a cell may be accomplished via a targeting ligand, including any ligand described herein or known in the art. In some embodiments, the targeting ligand is a carbohydrate moiety, e.g., a GalNAc ligand, or any other ligand that directs the RNAi agent to a site of interest.

The term "inhibiting," as used herein, is used interchangeably with "reducing," "silencing," "downregulating," "suppressing" and other similar terms, and includes any level of inhibition. In certain embodiments, a level of inhibition, e.g., for an RNAi agent of the instant disclosure, can be assessed in cell culture conditions, e.g., wherein cells in cell culture are transfected via Lipofectamine™-mediated transfection at a concentration in the vicinity of a cell of 10 nM or less, 1 nM or less, etc. Knockdown of a given RNAi agent can be determined via comparison of pre-treated levels in cell culture versus post-treated levels in cell culture, optionally also comparing against cells treated in parallel with a scrambled or other form of control RNAi agent. Knockdown in cell culture of, e.g., preferably 50% or more, can thereby be identified as indicative of "inhibiting" or "reducing", "downregulating" or "suppressing", etc. having occurred. It is expressly contemplated that assessment of targeted mRNA or encoded protein levels (and therefore an extent of "inhibiting", etc. caused by a RNAi agent of the disclosure) can also be assessed in in vivo systems for the RNAi agents of the instant disclosure, under properly controlled conditions as described in the art.

The phrase "inhibiting expression of a SOD1 gene" or "inhibiting expression of SOD1," as used herein, includes inhibition of expression of any SOD1 gene (such as, e.g., a mouse SOD1 gene, a rat SOD1 gene, a monkey SOD1 gene, or a human SOD1 gene) as well as variants or mutants of a SOD1 gene that encode a SOD1 protein. Thus, the SOD1 gene may be a wild-type SOD1 gene, a mutant SOD1 gene, or a transgenic SOD1 gene in the context of a genetically manipulated cell, group of cells, or organism.

"Inhibiting expression of a SOD1 gene" includes any level of inhibition of a SOD1 gene, e.g., at least partial suppression of the expression of a SOD1 gene, such as an inhibition by at least 20%. In certain embodiments, inhibition is by at least 30%, at least 40%, preferably at least 50%, at least about 60%, at least 70%, at least about 80%, at least 85%, at least 90%, at least 95%, at least 96%, at least 97%, at least 98%, or at least 99%; or to below the level of detection of the assay method. In a preferred method, inhibition is measured at a 10 nM concentration of the siRNA using the luciferase assay provided in Example 1.

The expression of a SOD1 gene may be assessed based on the level of any variable associated with SOD1 gene expression, e.g., SOD1 mRNA level or SOD1 protein level, or, for example, the level of neuroinflammation, e.g., microglial and astrocyte activation, and SOD1 deposition in areas of the brain associated with neuronal cell death.

Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the disclosure, expression of a SOD1 gene is inhibited by at least 20%, 30%, 40%, preferably at least 50%, 60%, 70%, 80%, 85%, 90%, or 95%, or to below the level of detection of the assay. In certain embodiments, the methods include a clinically relevant inhibition of expression of SOD1, e.g. as demonstrated by a clinically relevant outcome after treatment of a subject with an agent to reduce the expression of SOD1.

Inhibition of the expression of a SOD1 gene may be manifested by a reduction of the amount of mRNA expressed by a first cell or group of cells (such cells may be present, for example, in a sample derived from a subject) in which a SOD1 gene is transcribed and which has or have been treated (e.g., by contacting the cell or cells with a RNAi agent of the disclosure, or by administering a RNAi agent of the disclosure to a subject in which the cells are or were present) such that the expression of a SOD1 gene is inhibited, as compared to a second cell or group of cells substantially identical to the first cell or group of cells but which has not or have not been so treated (control cell(s) not treated with a RNAi agent or not treated with a RNAi agent targeted to the gene of interest). The degree of inhibition may be expressed in terms of:

$$\frac{(mRNA \text{ in control cells}) - (mRNA \text{ in treated cells})}{(mRNA \text{ in control cells})} \cdot 100\%$$

In other embodiments, inhibition of the expression of a SOD1 gene may be assessed in terms of a reduction of a parameter that is functionally linked to a SOD1 gene expression, e.g., SOD1 protein expression. SOD1 gene silencing may be determined in any cell expressing SOD1, either endogenous or heterologous from an expression construct, and by any assay known in the art.

Inhibition of the expression of a SOD1 protein may be manifested by a reduction in the level of the SOD1 protein that is expressed by a cell or group of cells (e.g., the level of protein expressed in a sample derived from a subject). As explained above, for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a SOD1 gene includes a cell or group of cells that has not yet been contacted with an RNAi agent of the disclosure. For example, the control cell or group of cells may be derived from an individual subject (e.g., a human or animal subject) prior to treatment of the subject with an RNAi agent.

The level of SOD1 mRNA that is expressed by a cell or group of cells may be determined using any method known in the art for assessing mRNA expression. In one embodiment, the level of expression of SOD1 in a sample is determined by detecting a transcribed polynucleotide, or portion thereof, e.g., mRNA of the SOD1 gene. RNA may be extracted from cells using RNA extraction techniques including, for example, using acid phenol/guanidine isothiocyanate extraction (RNAzol B; Biogenesis), RNeasy™ RNA preparation kits (Qiagen®) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Circulating SOD1 mRNA may be detected using methods the described in WO2012/177906, the entire contents of which are hereby incorporated herein by reference.

In some embodiments, the level of expression of SOD1 is determined using a nucleic acid probe. The term "probe", as used herein, refers to any molecule that is capable of selectively binding to a specific SOD1 nucleic acid or protein, or fragment thereof. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to SOD1 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of SOD1 mRNA.

An alternative method for determining the level of expression of SOD1 in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the disclosure, the level of expression of SOD1 is determined by quantitative fluorogenic RT-PCR (i.e., the TaqMan™ System), by a Dual-Glo® Luciferase assay, or by other art-recognized method for measurement of SOD1 expression or mRNA level.

The expression level of SOD1 mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of SOD1 expression level may also comprise using nucleic acid probes in solution.

In some embodiments, the level of mRNA expression is assessed using branched DNA (bDNA) assays or real time PCR (qPCR). The use of this PCR method is described and exemplified in the Examples presented herein. Such methods can also be used for the detection of SOD1 nucleic acids.

The level of SOD1 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like. Such assays can also be used for the detection of proteins indicative of the presence or replication of SOD1 proteins.

In some embodiments, the efficacy of the methods of the disclosure in the treatment of a SOD1-related disease is assessed by a decrease in SOD1 mRNA level (e.g, by assessment of a CSF sample for SOD1 level, by brain biopsy, or otherwise).

In some embodiments, the efficacy of the methods of the disclosure in the treatment of a SOD1-related disease is assessed by a decrease in SOD1 mRNA level (e.g, by assessment of a liver sample for SOD1 level, by biopsy, or otherwise).

In some embodiments of the methods of the disclosure, the RNAi agent is administered to a subject such that the RNAi agent is delivered to a specific site within the subject.

The inhibition of expression of SOD1 may be assessed using measurements of the level or change in the level of SOD1 mRNA or SOD1 protein in a sample derived from a specific site within the subject, e.g., CNS cells. In certain embodiments, the methods include a clinically relevant inhibition of expression of SOD1, e.g. as demonstrated by a clinically relevant outcome after treatment of a subject with an agent to reduce the expression of SOD1.

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

X. Methods of Treating or Preventing SOD1-Associated Neurodegenerative Diseases

The present disclosure also provides methods of using a RNAi agent of the disclosure or a composition containing a RNAi agent of the disclosure to reduce or inhibit SOD1 expression in a cell. The methods include contacting the cell with a dsRNA of the disclosure and maintaining the cell for a time sufficient to obtain degradation of the mRNA transcript of a SOD1 gene, thereby inhibiting expression of the SOD1 gene in the cell. Reduction in gene expression can be assessed by any methods known in the art. For example, a reduction in the expression of SOD1 may be determined by determining the mRNA expression level of SOD1 using methods routine to one of ordinary skill in the art, e.g., northern blotting, qRT-PCR; by determining the protein level of SOD1 using methods routine to one of ordinary skill in the art, such as western blotting, immunological techniques.

In the methods of the disclosure the cell may be contacted in vitro or in vivo, i.e., the cell may be within a subject.

A cell suitable for treatment using the methods of the disclosure may be any cell that expresses a SOD1 gene. A cell suitable for use in the methods of the disclosure may be a mammalian cell, e.g., a primate cell (such as a human cell or a non-human primate cell, e.g., a monkey cell or a chimpanzee cell), a non-primate cell (such as a rat cell, or a mouse cell. In one embodiment, the cell is a human cell, e.g., a human CNS cell. In one embodiment, the cell is a human cell, e.g., a human liver cell. In one embodiment, the cell is a human cell, e.g., a human CNS cell and a human liver cell.

SOD1 expression is inhibited in the cell by at least about 30, 40, 50, 55, 60, 65, 70, 75, 80, 85, 90, 95, 96, 97, 98, 99, or about 100%, i.e., to below the level of detection. In preferred embodiments, SOD1 expression is inhibited by at least 50%.

The in vivo methods of the disclosure may include administering to a subject a composition containing a RNAi agent, where the RNAi agent includes a nucleotide sequence that is complementary to at least a part of an RNA transcript of the SOD1 gene of the mammal to be treated. When the organism to be treated is a mammal such as a human, the composition can be administered by any means known in the art including, but not limited to oral, intraperitoneal, or parenteral routes, including intracranial (e.g., intraventricular (also referred to asintracerebroventricular), intraparenchymal, and intrathecal), intravenous, intramuscular, subcutaneous, transdermal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intrathecal injection. In certain embodiments, the compositions are administered by intracerebroventricular injection.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of SOD1, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intracranial, intravenous, subcutaneous, arterial, or epidural infusions. In preferred embodiments, the infusion pump is a subcutaneous infusion pump. In other embodiments, the pump is a surgically implanted pump that delivers the RNAi agent to the CNS.

The mode of administration may be chosen based upon whether local or systemic treatment is desired and based upon the area to be treated. The route and site of administration may be chosen to enhance targeting.

In one aspect, the present disclosure also provides methods for inhibiting the expression of a SOD1 gene in a mammal. The methods include administering to the mammal a composition comprising a dsRNA that targets a SOD1 gene in a cell of the mammal and maintaining the mammal for a time sufficient to obtain degradation of the mRNA transcript of the SOD1 gene, thereby inhibiting expression of the SOD1 gene in the cell. Reduction in gene expression can be assessed by any methods known it the art and by methods, e.g. qRT-PCR, described herein. Reduction in protein production can be assessed by any methods known it the art and by methods, e.g. ELISA, described herein. In one embodiment, a CNS biopsy sample or a cerebrospinal fluid (CSF) sample serves as the tissue material for monitoring the reduction in SOD1 gene or protein expression (or of a proxy therefore).

The present disclosure further provides methods of treatment of a subject in need thereof. The treatment methods of the disclosure include administering an RNAi agent of the disclosure to a subject, e.g., a subject that would benefit from inhibition of SOD1 expression, in a therapeutically effective amount of a RNAi agent targeting a SOD1 gene or a pharmaceutical composition comprising a RNAi agent targeting a SOD1 gene.

In addition, the present disclosure provides methods of preventing, treating or inhibiting the progression of a SOD1-associated neurodegenerative disease or disorder, such as Amyotrophic Lateral Sclerosis (ALS), Alzheimer's disease (AD), Parkinson's disease (PD), and Down's syndrome (DS).

The methods include administering to the subject a therapeutically effective amount of any of the RNAi agent, e.g., dsRNA agents, or the pharmaceutical composition provided herein, thereby preventing, treating, or inhibiting the progression of the SOD1-associated neurodegenerative disease or disorder in the subject.

An RNAi agent of the disclosure may be administered as a "free RNAi agent." A free RNAi agent is administered in the absence of a pharmaceutical composition. The naked RNAi agent may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the RNAi agent can be adjusted such that it is suitable for administering to a subject.

Alternatively, an RNAi agent of the disclosure may be administered as a pharmaceutical composition, such as a dsRNA liposomal formulation.

Subjects that would benefit from a reduction or inhibition of SOD1 gene expression are those having a SOD1-associated neurodegenerative disease.

The disclosure further provides methods for the use of a RNAi agent or a pharmaceutical composition thereof, e.g., for treating a subject that would benefit from reduction or inhibition of SOD1 expression, e.g., a subject having a SOD1-associated neurodegenerative disorder, in combination with other pharmaceuticals or other therapeutic methods, e.g., with known pharmaceuticals or known therapeutic methods, such as, for example, those which are currently employed for treating these disorders. For example, in certain embodiments, an RNAi agent targeting SOD1 is administered in combination with, e.g., an agent useful in treating a SOD1-associated neurodegenerative disorder as described elsewhere herein or as otherwise known in the art. For example, additional agents and treatments suitable for treating a subject that would benefit from reduction in SOD1 expression, e.g., a subject having a SOD1-associated neurodegenerative disorder, may include agents currently used to treat symptoms of SOD1. The RNAi agent and additional therapeutic agents may be administered at the same time or in the same combination, e.g., intrathecally, or the additional therapeutic agent can be administered as part of a separate composition or at separate times or by another method known in the art or described herein. The RNAi agent and additional therapeutic agents may be administered at the same time or in the same combination or the additional therapeutic agent can be administered as part of a separate composition or at separate times or by another method known in the art or described herein.

Exemplary additional therapeutics and treatments include, for example, sedatives, antidepressants, clonazepam, sodium valproate, opiates, antiepileptic drugs, cholinesterase inhibitors, memantine, benzodiazepines, levodopa, COMT inhibitors (e.g., tolcapone and entacapone), dopamine agonists (e.g., bromocriptine, pergolide, pramipexole, ropinirole, piribedil, cabergoline, apomorphine and lisuride), MAO-B inhibitors (e.g., safinamide, selegiline and rasagiline), amantadine, an anticholinergic, pimavanserin, doxepin, rasagline, an antipsychotic, an atypical antipsychotic (e.g., amisulpride, olanzapine, risperidone, and clozapine), riluzole, edaravone, deep brain stimulation, non-invasive ventilation (NIV), invasive ventilation physical therapy, occupational therapy, speech therapy, dietary changes and swallowing technique a feeding tube, a PEG tube, probiotics, and psychological therapy.

In one embodiment, the method includes administering a composition featured herein such that expression of the target SOD1 gene is decreased, for at least one month. In preferred embodiments, expression is decreased for at least 2 months, or 6 months.

Preferably, the RNAi agents useful for the methods and compositions featured herein specifically target RNAs (primary or processed) of the target SOD1 gene. Compositions and methods for inhibiting the expression of these genes using RNAi agents can be prepared and performed as described herein.

Administration of the dsRNA according to the methods of the disclosure may result in a reduction of the severity, signs, symptoms, or markers of such diseases or disorders in a patient with a SOD1-associated neurodegenerative disorder. By "reduction" in this context is meant a statistically significant or clinically significant decrease in such level. The reduction can be, for example, at least 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a SOD1-associated neurodegenerative disorder may be assessed, for example, by periodic monitoring of a subject's cognition, learning, or memory. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of a RNAi agent targeting SOD1 or pharmaceutical composition thereof, "effective against" a SOD1-associated neurodegenerative disorder indicates that administration in a clinically appropriate manner results in a beneficial effect for at least a statistically significant fraction of patients, such as an improvement of symptoms, a cure, a reduction in disease, extension of life, improvement in quality of life, or other effect generally recognized as positive by medical doctors familiar with treating SOD1-associated neurodegenerative disorders and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50%, or more can be indicative of effective treatment. Efficacy for a given RNAi agent drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale. Any positive change resulting in e.g., lessening of severity of disease measured using the appropriate scale, represents adequate treatment using a RNAi agent or RNAi agent formulation as described herein.

Subjects can be administered a therapeutic amount of dsRNA, such as about 0.01 mg/kg to about 200 mg/kg.

The RNAi agent can be administered intrathecally, intraventricularly, or by intravenous infusion over a period of time, on a regular basis. In certain embodiments, after an initial treatment regimen, the treatments can be administered on a less frequent basis. Administration of the RNAi agent can reduce SOD1 levels, e.g., in a cell, tissue, blood, CSF sample or other compartment of the patient by at least 20%, 30%, 40%, 50%, 55%, 60%, 65%, 70,% 75%, 80%, 85%, 90%, 95%, 96%, 97%, 98%, or at least about 99% or more. In a preferred embodiment, administration of the RNAi agent can reduce SOD1 levels, e.g., in a cell, tissue, blood, CSF sample or other compartment of the patient by at least 50%.

Before administration of a full dose of the RNAi agent, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Alternatively, the RNAi agent can be administered subcutaneously, i.e., by subcutaneous injection.

One or more injections may be used to deliver the desired, e.g., monthly dose of RNAi agent to a subject. The injections may be repeated over a period of time. The administration may be repeated on a regular basis. In certain embodiments, after an initial treatment regimen, the treatments can be administered on a less frequent basis. A repeat-dose regimine may include administration of a therapeutic amount of RNAi agent on a regular basis, such as monthly or extending to once a quarter, twice per year, once per year. In certain embodiments, the RNAi agent is administered about once per month to about once per quarter (i.e., about once every three months).

Unless otherwise defined, all technical and scientific terms used herein have the same meaning as commonly understood by one of ordinary skill in the art to which this invention belongs. Although methods and materials similar or equivalent to those described herein can be used in the practice or testing of the RNAi agents and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

An informal Sequence Listing is filed herewith and forms part of the specification as filed.

EXAMPLES

Example 1. RNAi Agent Design, Synthesis, Selection, and In Vitro Evaluation

This Example describes methods for the design, synthesis, selection, and in vitro evaluation of SOD1 RNAi agents.

Source of Reagents

Where the source of a reagent is not specifically given herein, such reagent can be obtained from any supplier of reagents for molecular biology at a quality/purity standard for application in molecular biology.

Bioinformatics siRNAs targeting the human superoxide dismutase 1 (SOD1) gene (human: NCBI refseqID NM_000454.4; NCBI GeneID: 6647), mouse SOD1 gene (refseqID NM_011434.1; NCBI GeneID: 20655), or *Macaca fascicularis* SOD1 gene (refseqID NM_001285406.1; NCBI GeneID: 102118687) were designed using custom R and Python scripts. The human NM_000454.4 REFSEQ mRNA has a length of 981 bases; the mouse NM_011434.1 REFSEQ mRNA has a length of 661 bases; and the *Macaca fascicularis* SOD1 NM_001285406.1 REFSEQ mRNA has a length of 465 bases.

Detailed lists of the unmodified SOD1 sense and antisense strand nucleotide sequences are shown in Tables 2, 4 and 6. Detailed lists of the modified SOD1 sense and antisense strand nucleotide sequences are shown in Tables 3, 5 and 7.

It is to be understood that, throughout the application, a duplex name without a decimal is equivalent to a duplex name with a decimal which merely references the batch number of the duplex. For example, AD-266859 is equivalent to AD-266859.1.

siRNA Synthesis

Briefly, siRNA sequences were synthesized on a 1 μmol scale using a Mermade 192 synthesizer (BioAutomation) with phosphoramidite chemistry on solid supports. The solid support was controlled pore glass (500-1000 Å) loaded with a custom GalNAc ligand (3'-GalNAc conjugates), universal solid support (AM Chemicals), or the first nucleotide of interest. Ancillary synthesis reagents and standard 2-cyanoethyl phosphoramidite monomers (2'-deoxy-2'-fluoro, 2'-O-methyl, RNA, DNA) were obtained from Thermo-Fisher (Milwaukee, Wis.), Hongene (China), or Chemgenes (Wilmington, Mass., USA). Additional phosphoramidite monomers were procured from commercial suppliers, prepared in-house, or procured using custom synthesis from various CMOs. Phosphoramidites were prepared at a concentration of 100 mM in either acetonitrile or 9:1 acetonitrile:DMF and were coupled using 5-Ethylthio-1H-tetrazole (ETT, 0.25 M in acetonitrile) with a reaction time of 400 s. Phosphorothioate linkages were generated using a 100 mM solution of 3-((Dimethylamino-methylidene) amino)-3H-1,2,4-dithiazole-3-thione (DDTT, obtained from Chemgenes (Wilmington, Mass., USA)) in anhydrous acetonitrile/pyridine (9:1 v/v). Oxidation time was 5 minutes. All sequences were synthesized with final removal of the DMT group ("DMT-Off").

Upon completion of the solid phase synthesis, solid-supported oligoribonucleotides were treated with 300 μL of Methylamine (40% aqueous) at room temperature in 96 well plates for approximately 2 hours to afford cleavage from the solid support and subsequent removal of all additional base-labile protecting groups. For sequences containing any natural ribonucleotide linkages (2'-OH) protected with a tert-butyl dimethyl silyl (TBDMS) group, a second deprotection step was performed using TEA.3HF (triethylamine trihydrofluoride). To each oligonucleotide solution in aqueous methylamine was added 200 μL of dimethyl sulfoxide (DMSO) and 300 μL TEA.3HF and the solution was incubated for approximately 30 mins at 60° C. After incubation, the plate was allowed to come to room temperature and crude oligonucleotides were precipitated by the addition of 1 mL of 9:1 acetontrile:ethanol or 1:1 ethanol:isopropanol. The plates were then centrifuged at 4° C. for 45 mins and the supernatant carefully decanted with the aid of a multichannel pipette. The oligonucleotide pellet was resuspended in 20 mM NaOAc and subsequently desalted using a HiTrap size exclusion column (5 mL, GE Healthcare) on an Agilent LC system equipped with an autosampler, UV detector, conductivity meter, and fraction collector. Desalted samples were collected in 96 well plates and then analyzed by LC-MS and UV spectrometry to confirm identity and quantify the amount of material, respectively.

Duplexing of single strands was performed on a Tecan liquid handling robot. Sense and antisense single strands were combined in an equimolar ratio to a final concentration of 10 μM in 1× PBS in 96 well plates, the plate sealed, incubated at 100° C. for 10 minutes, and subsequently allowed to return slowly to room temperature over a period of 2-3 hours. The concentration and identity of each duplex was confirmed and then subsequently utilized for in vitro screening assays.

Cell Culture and Transfections

Cells were transfected by adding 4.9 μL of Opti-MEM plus 0.1 μL of RNAiMAX per well (Invitrogen, Carlsbad Calif. cat #13778-150) to 5 μL of siRNA duplexes per well, with 4 replicates of each siRNA duplex, into a 384-well plate, and incubated at room temperature for 15 minutes. Forty μL of MEDIA containing ~5×10$^3$ cells were then added to the siRNA mixture. Cells were incubated for 24 hours prior to RNA purification. Experiments were performed at 10 nM and 0.1 nM in primary mouse hepatocytes (PMH) or primary cynomolgus hepatocytes (PCH).

Total RNA Isolation Using DYNABEADS mRNA Isolation Kit

RNA was isolated using an automated protocol on a BioTek-EL406 platform using DYNABEADs (Invitrogen, cat #61012). Briefly, 70 μL of Lysis/Binding Buffer and 10 μL of lysis buffer containing 3 μL of magnetic beads were added to the plate with cells. Plates were incubated on an electromagnetic shaker for 10 minutes at room temperature and then magnetic beads were captured and the supernatant was removed. Bead-bound RNA were then washed 2 times with 150 μL Wash Buffer A and once with Wash Buffer B. Beads are then washed with 150 μL Elution Buffer, re-captured and supernatant removed.

cDNA Synthesis Using ABI High Capacity cDNA Reverse Transcription Kit (Applied Biosystems, Foster City, Calif., Cat #4368813)

Ten μL of a master mix containing 1 μL 10× Buffer, 0.4 μL 25×dNTPs, 1 μL 10× Random primers, 0.5 μL Reverse Transcriptase, 0.5 μL RNase inhibitor and 6.6 μL of H$_2$O per reaction was added to RNA isolated above. Plates were sealed, mixed, and incubated on an electromagnetic shaker for 10 minutes at room temperature, followed by 2 hour incubation at 37° C.

Real Time PCR

Two μL of cDNA were added to a master mix containing 0.5 μL of human or mouse GAPDH TaqMan Probe (ThermoFisher cat 4352934E or 4351309) and 0.5 μL of appropriate SOD1 probe (commercially available, e.g., from Thermo Fisher) and 5 μL Lightcycler 480 probe master mix (Roche Cat #04887301001) per well in a 384 well plates (Roche cat #04887301001). Real time PCR was done in a LightCycler480 Real Time PCR system (Roche). Each duplex was tested with N=4 and data were normalized to cells transfected with a non-targeting control siRNA. To calculate relative fold change, real time data were analyzed using the ΔΔCt method and normalized to assays performed with cells transfected with a non-targeting control siRNA.

The results of single dose screens in primary Cynomolgus hepatocytes (PCH) of the duplexes in Tables 2 and 3 are provided in Table 8; the results of the single dose screens in primary mouse hepatocytes (PMH) of the duplexes in Tables 2 and 3 are provided in Table 9; the results of the single dose screens in primary Cynomolgus hepatocytes (PCH) of the duplexes in Tables 4 and 5 are provided in Table 10; and the results of the single dose screens in primary Cynomolgus hepatocytes (PCH) of the duplexes in Tables 6 and 7 are provided in Table 11.

TABLE 1

Abbreviations of nucleotide monomers used in nucleic acid sequence representation. It will be understood that these monomers, when present in an oligonucleotide, are mutually linked by 5'-3'-phosphodiester bonds; and it is understood that when the nucleotide contains a 2'-fluoro modification, then the fluoro replaces the hydroxy at that position in the parent nucleotide (i.e., it is a 2'-deoxy-2'-fluoronucleotide).

| Abbreviation | Nucleotide(s) |
|---|---|
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide, modified or unmodified |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol (Hyp-(GalNAc-alkyl)3) |
| | 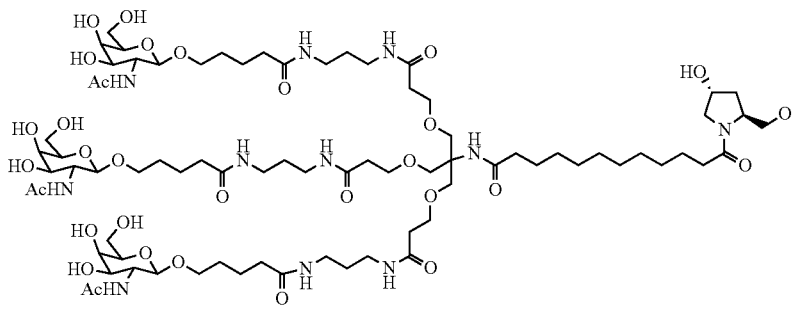 |
| Y34 | 2-hydroxymethyl-tetrahydrofurane-4-methoxy-3-phosphate (abasic 2'-OMe furanose) |
| |  |

TABLE 1-continued

Abbreviations of nucleotide monomers used in nucleic acid sequence representation. It will be understood that these monomers, when present in an oligonucleotide, are mutually linked by 5'-3'-phosphodiester bonds; and it is understood that when the nucleotide contains a 2'-fluoro modification, then the fluoro replaces the hydroxy at that position in the parent nucleotide (i.e., it is a 2'-deoxy-2'-fluoronucleotide).

| Abbreviation | Nucleotide(s) |
|---|---|
| Y44 | inverted abasic DNA (2-hydroxymethyl-tetrahydrofurane-5-phosphate) |
| L10 | N-(cholesterylcarboxamidocaproyl)-4-hydroxyprolinol (Hyp-C6-Chol) |
| (Agn) | Adenosine-glycol nucleic acid (GNA) S-Isomer |
| (Cgn) | Cytidine-glycol nucleic acid (GNA) S-Isomer |
| (Ggn) | Guanosine-glycol nucleic acid (GNA) S-Isomer |
| (Tgn) | Thymidine-glycol nucleic acid (GNA) S-Isomer |
| P | Phosphate |
| VP | Vinyl-phosphonate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |
| (C2p) | cytidine-2'-phosphate |
| (G2p) | guanosine-2'-phosphate |
| (U2p) | uridine-2'-phosphate |
| (A2p) | adenosine-2'-phosphate |
| (Ahd) | 2'-O-hexadecyl-adenosine-3'-phosphate |
| (Ahds) | 2'-O-hexadecyl-adenosine-3'-phosphorothioate |
| (Chd) | 2'-O-hexadecyl-cytidine-3'-phosphate |
| (Chds) | 2'-O-hexadecyl-cytidine-3'-phosphorothioate |
| (Ghd) | 2'-O-hexadecyl-guanosine-3'-phosphate |
| (Ghds) | 2'-O-hexadecyl-guanosine-3'-phosphorothioate |
| (Uhd) | 2'-O-hexadecyl-uridine-3'-phosphate |
| (Uhds) | 2'-O-hexadecyl-uridine-3'-phosphorothioate |
| s | phosphorothioate |

TABLE 2

Unmodified Sense and Antisense Strand Sequences of Superoxide Dismutase 1 dsRNA Agents

| Duplex Name | Sense Sequence 5' to 3' | SEQ ID NO: | Source Name | Range in Source, NM_001285406.1 | Antisense Sequence 5' to 3' | SEQ ID NO: | Source Name | Range in Source, NM_001285406.1 |
|---|---|---|---|---|---|---|---|---|
| AD-266859.1 | AUCAGUUUGGAGAUAAUACAU | 35 | NM_001285406.1_146-166_C21U_s | 146-166 | AUGUAUUAUCUCCAAACUGAUGA | 118 | NM_001285406.1_144-166_G1A_as | 144-166 |
| AD-266997.1 | UCUUUCGAAGAUUCUGUGAUU | 36 | NM_001285406.1_295-315_C21U_s | 295-315 | AAUCACAGAAUCUUCGAAAGACA | 119 | NM_001285406.1_293-315_G1A_as | 293-315 |
| AD-266992.1 | AGGUGUCUUUCGAAGAUUCUU | 37 | NM_001285406.1_290-310_C21U_s | 290-310 | AAGAAUCUUCGAAAGACACCUUG | 120 | NM_001285406.1_288-310_C1A_as | 288-310 |
| AD-266903.1 | CUUUAAUCCUCUAUCCAGACA | 38 | NM_001285406.1_192-212_s | 192-212 | UGUCUGGAUAGAGGAUUAAAGUG | 121 | NM_001285406.1_190-212_as | 190-212 |
| AD-266891.1 | UGCAGGUCCUCACUUUAAUCU | 39 | NM_001285406.1_180-200_C21U_s | 180-200 | AGAUUAAAGUGAGGACCUGCACU | 122 | NM_001285406.1_178-200_G1A_as | 178-200 |
| AD-266996.1 | GUCUUUCGAAGAUUCUGUGAU | 40 | NM_001285406.1_294-314_s | 294-314 | AUCACAGAAUCUUCGAAAGACAC | 123 | NM_001285406.1_292-314_as | 292-314 |
| AD-266893.1 | CAGGUCCUCACUUUAAUCCUU | 41 | NM_001285406.1_182-202_s | 182-202 | AAGGAUUAAAGUGAGGACCUGCA | 124 | NM_001285406.1_180-202_as | 180-202 |
| AD-266898.1 | CCUCACUUUAAUCCUCUAUCU | 42 | NM_001285406.1_187-207_C21U_s | 187-207 | AGAUAGAGGAUUAAAGUGAGGAC | 125 | NM_001285406.1_185-207_as | 185-207 |
| AD-266886.1 | ACCAGUGCAGGUCCUCACUUU | 43 | NM_001285406.1_175-195_s | 175-195 | AAAGUGAGGACCUGCACUGGUAC | 126 | NM_001285406.1_173-195_as | 173-195 |
| AD-267072.1 | AGCAGAUGACUUGGGCAAAGU | 44 | NM_001285406.1_369-389_G21U_s | 369-389 | ACUUUGCCCAAGUCAUCUGCUUU | 127 | NM_001285406.1_367-389_as | 367-389 |
| AD-267067.1 | GAAAAAGCAGAUGACUUGGGU | 45 | NM_001285406.1_364-384_C21U_s | 364-384 | ACCCAAGUCAUCUGCUUUUUCAU | 128 | NM_001285406.1_362-384_G1A_as | 362-384 |
| AD-266791.1 | UUCGAGCAGAAGAAAGUAAU | 46 | NM_001285406.1_61-81_s | 61-81 | AUUACUUUCCUUCUGCUCGAAAU | 129 | NM_001285406.1_59-81_as | 59-81 |
| AD-266789.1 | AUUUCGAGCAGAAGGAAAGUA | 47 | NM_001285406.1_59-79_s | 59-79 | UACUUUCCUUCUGCUCGAAAUUG | 130 | NM_001285406.1_57-79_as | 57-79 |
| AD-266861.1 | CAGUUUGGAGAUAAUACACAA | 48 | NM_001285406.1_148-168_s | 148-168 | UUGUGUAUUAUCUCCAAACUGAU | 131 | NM_001285406.1_146-168_as | 146-168 |
| AD-266856.1 | UUCAUCAGUUUGGAGAUAAUA | 49 | NM_001285406.1_143-163_s | 143-163 | UAUUAUCUCCAAACUGAUGAACA | 132 | NM_001285406.1_141-163_as | 141-163 |

TABLE 2-continued

Unmodified Sense and Antisense Strand Sequences of Superoxide Dismutase 1 dsRNA Agents

| Duplex Name | Sense Sequence 5' to 3' | SEQ ID NO: | Source Name | Range in Source, NM_001285406.1 | Antisense Sequence 5' to 3' | SEQ ID NO: | Source Name | Range in Source, NM_001285406.1 |
|---|---|---|---|---|---|---|---|---|
| AD-266899.1 | CUCACUUUAAUCCUCUAUCCA | 50 | NM_001285406.1_188-208_s | 188-208 | UGGAUAGAGGAUUAAAGUGAGGA | 133 | NM_001285406.1_186-208_as | 186-208 |
| AD-267000.1 | UUCGAAGAUUCUGUGAUCUCU | 51 | NM_001285406.1_298-318_G21U_s | 298-318 | AGAGAUCACAGAAUCUUCGAAAG | 134 | NM_001285406.1_296-318_C1A_as | 296-318 |
| AD-267071.1 | AAGCAGAUGACUGGGCAAAU | 52 | NM_001285406.1_368-388_G21U_s | 368-388 | AUUUGCCCAAGUCAUCUGCUUUU | 135 | NM_001285406.1_366-388_1A_as | 366-368 |
| AD-266895.1 | GGUCCUCACUUUAAUCCUCUA | 53 | NM_001285406.1_184-204_s | 184-204 | UAGAGGAUUAAAGUGAGGACCUG | 136 | NM_001285406.1_182-204_as | 182-204 |
| AD-266888.1 | CAGUGCAGGUCCUCACUUUAA | 54 | NM_001285406.1_177-197_s | 177-197 | UUAAAGUGAGGACCUGCACUGGU | 137 | NM_001285406.1_175-197_as | 175-197 |
| AD-266817.1 | CAUUACAGGAUUGACUGAAGU | 55 | NM_001285406.1_105-125_G21U_s | 105-125 | ACUUCAGUCAAUCCUGUAAUGCU | 138 | NM_001285406.1_103-125_C1A_as | 103-125 |
| AD-267083.1 | AAAGUAAAAGACAGGAAACU | 56 | NM_001285406.1_401-421_C21U_s | 401-421 | AGUUUCCUGUCUUUUUACUUUCU | 139 | NM_001285406.1_399-421_C1A_as | 399-421 |
| AD-266862.1 | AGUUUGGAGAUAUACACAAU | 57 | NM_001285406.1_149-169_G21U_s | 149-169 | AUUGUGUAUAUCUCCAAACUGA | 140 | NM_001285406.1_147-169_C1A_as | 147-169 |
| AD-267002.1 | CGAAGAUUCUGUGAUCUCGCU | 58 | NM_001285406.1_300-320_s | 300-320 | AGCGAGAUCACAGAAUCUUCGAA | 141 | NM_001285406.1_298-320_as | 298-320 |
| AD-266816.1 | GCAUUACAGGAUUGACUGAAU | 59 | NM_001285406.1_104-124_G21U_s | 104-124 | AUUCAGUCAAUCCUGUAAUGCUU | 142 | NM_001285406.1_102-124_C1A_as | 102-124 |
| AD-266857.1 | UCAUCAGUUUGGAGAUAUAUAU | 60 | NM_001285406.1_144-164_C21U_s | 144-164 | AUAUUAUCUCCAAACUGAUGAAC | 143 | NM_001285406.1_142-164_C1A_as | 142-164 |
| AD-266902.1 | ACUUUAAUCCUCUAUCCAGAU | 61 | NM_001285406.1_191-211_C21U_s | 191-211 | AUCUGGAUAGAGGAUUAAAGUGA | 144 | NM_001285406.1_189-211_C1A_as | 189-211 |
| AD-267086.1 | GUAAAAAGACAGGAAACGCUU | 62 | NM_001285406.1_404-424_G21U_s | 404-424 | AAGCGUUUCCUGUCUUUUUACUU | 145 | NM_001285406.1_402-424_C1A_as | 402-424 |
| AD-266785.1 | AUCAAUUUCGAGCAGAAGGAA | 63 | NM_001285406.1_55-75_s | 55-75 | UUCCUUCUCGAAAUUGAUGG | 146 | NM_001285406.1_53-75_as | 53-75 |
| AD-266897.1 | UCCUCACUUUAAUCCUCUAUU | 64 | NM_001285406.1_186-206_s | 186-206 | AAUAGAGGAUUAAAGUGAGGACC | 147 | NM_001285406.1_184-206_G1A_as | 184-206 |

TABLE 2-continued

Unmodified Sense and Antisense Strand Sequences of Superoxide Dismutase 1 dsRNA Agents

| Duplex Name | Sense Sequence 5' to 3' | SEQ ID NO: | Source Name | Range in Source, NM_001285406.1 | Antisense Sequence 5' to 3' | SEQ ID NO: | Source Name | Range in Source, NM_001285406.1 |
|---|---|---|---|---|---|---|---|---|
| AD-266896.1 | GUCCUCACUUUAAUCCUCUAU | 65 | NM_001285406.1_185-205_s | 185-205 | AUAGAGGAUUAAAGUGAGGACCU | 148 | NM_001285406.1_183-205_as | 183-205 |
| AD-266858.1 | CAUCAGUUUGGAGAUAAUACA | 66 | NM_001285406.1_145-165_s | 145-165 | UGUAUUAUCUCCAAACUGAUGAA | 149 | NM_001285406.1_143-165_as | 143-165 |
| AD-267084.1 | AAGUAAAAAGACAGGAAACGU | 67 | NM_001285406.1_402-422_C21U_s | 402-422 | ACGUUUCCUGUCUUUUUACUUUC | 150 | NM_001285406.1_400-422_C21U_as | 400-422 |
| AD-266815.1 | AGCAUUACAGGAUUGACUGAA | 68 | NM_001285406.1_103-123_s | 103-123 | UUCAGUCAAUCCUGUAAUGCUUC | 151 | NM_001285406.1_101-123_as | 101-123 |
| AD-267007.1 | AUUCUGUGAUCUCCUCUCAU | 69 | NM_001285406.1_305-325_G21U_s | 305-325 | AUGAGAGCGAGAUCACAGAAUCU | 152 | NM_001285406.1_303-325_C1A_as | 303-325 |
| AD-266855.1 | GUUCAUCAGUUUGGAGAUAAU | 70 | NM_001285406.1_142-162_s | 142-162 | AUUAUCUCCAAACUGAUGAACAU | 153 | NM_001285406.1_140-162_as | 140-162 |
| AD-266901.1 | CACUUUAAUCCUCUAUCCAGA | 71 | NM_001285406.1_190-210_s | 190-210 | UCUGGAUAGAGGAUUAAAGUGAG | 154 | NM_001285406.1_188-210_as | 188-210 |
| AD-266994.1 | GUGUCUUUCGAAGAAUCUGUU | 72 | NM_001285406.1_292-312_G21U_s | 292-312 | AACAGAAUCUUCGAAAGACACCU | 155 | NM_001285406.1_290-312_C1A_as | 290-312 |
| AD-266793.1 | CGAGCAGAAGGAAAGUAAUGU | 73 | NM_001285406.1_63-83_G21U_s | 63-83 | ACAUUACUUUCCUUCUGCUCGAA | 156 | NM_001285406.1_61-83_as | 61-83 |
| AD-266850.1 | UCCAUGUUCAUCAGUUUGGAU | 74 | NM_001285406.1_137-157_G21U_s | 137-157 | AUCCAAACUGAUGAACAUGGAAU | 157 | NM_001285406.1_135-157_C1A_as | 135-157 |
| AD-266887.1 | CCAGUGCAGGUCCUCACUUUA | 75 | NM_001285406.1_176-196_s | 176-196 | UAAAGUGAGGACCUGCACUGUA | 158 | NM_001285406.1_174-196_as | 174-196 |
| AD-266894.1 | AGGUCCUCACUUUAAUCCUCU | 76 | NM_001285406.1_183-203_s | 183-203 | AGAGGAUUAAAGUGAGGACCUGC | 159 | NM_001285406.1_181-203_as | 181-203 |
| AD-266988.1 | GCCAAGGUGUCUUUCGAAGAU | 77 | NM_001285406.1_286-306_s | 286-306 | AUCUUCGAAAGACACCUUGGCCA | 160 | NM_001285406.1_284-306_as | 284-306 |
| AD-267085.1 | AGUAAAAAGACAGGAAACGCU | 78 | NM_001285406.1_403-423_s | 403-423 | AGCGUUUCCUGUCUUUUUACUUU | 161 | NM_001285406.1_401-423_as | 401-423 |
| AD-266873.1 | AUACACAAGGCUGUACCAGUU | 79 | NM_001285406.1_161-181_s | 161-181 | AACUGGUACAGCCUUGUGUAUUA | 162 | NM_001285406.1_159-181_as | 159-181 |

TABLE 2-continued

Unmodified Sense and Antisense Strand Sequences of Superoxide Dismutase 1 dsRNA Agents

| Duplex Name | Sense Sequence 5' to 3' | SEQ ID NO: | Source Name | Range in Source, NM_001285406.1 | Antisense Sequence 5' to 3' | SEQ ID NO: | Source Name | Range in Source, NM_001285406.1 |
|---|---|---|---|---|---|---|---|---|
| AD-266907.1 | AAUCCUCUAUCCAGACAACAU | 80 | NM_001285406.1_196-216_C21U_s | 196-216 | AUGUUGUCUGGAUAGAGGAUUAA | 163 | NM_001285406.1_194-216_G1A_as | 194-216 |
| AD-266792.1 | UCGAGCAGAAGGAAAGUAAUU | 81 | NM_001285406.1_62-82_G21U_s | 62-82 | AAUUACUUUCCUUCUGCUCGAAA | 164 | NM_001285406.1_60-82_C1A_as | 60-82 |
| AD-266900.1 | UCACUUUAAUCCUCUAUCCAU | 82 | NM_001285406.1_189-209_G21U_s | 189-209 | AUGGAUAGAGGAUUAAAGUGAGG | 165 | NM_001285406.1_187-209_C1A_as | 187-209 |
| AD-266797.1 | CAGAAGGAAAGUAAUGGACCA | 83 | NM_001285406.1_67-87_s | 67-87 | UGGUCCAUUACUUUCCUUCUGCU | 166 | NM_001285406.1_65-87_as | 65-87 |
| AD-266787.1 | CAAUUUCGAGCAGAAGGAAAU | 84 | NM_001285406.1_57-77_G21U_s | 57-77 | AUUUCCUUCUGCUCGAAAUUGAU | 167 | NM_001285406.1_55-77_C1A_as | 55-77 |
| AD-266800.1 | AAGGAAAGUAAUGGACCAGUU | 85 | NM_001285406.1_70-90_G21Us | 70-90 | AACUGGUCCAUUACUUUCCUUCU | 168 | NM_001285406.1_68-90_C1A_as | 68-90 |
| AD-266889.1 | AGUGCAGGUCCCUCACUUUAAU | 86 | NM_001285406.1_178-198_s | 178-198 | AUUAAAGUGAGGGACCUGCACUGG | 169 | NM_001285406.1_176-198_as | 176-198 |
| AD-266847.1 | GAUUCCAUGUCAUCAGUUUG | 87 | NM_001285406.1_134-154_s | 134-154 | CAAACUGAUGAACAUGGAAUCCA | 170 | NM_001285406.1_132-154_as | 132-154 |
| AD-266998.1 | CUUUCGAAGAUUCUGUGAUCU | 88 | NM_001285406.1_296-316_s | 296-316 | AGAUCACAGAAUCUUCGAAAGAC | 171 | NM_001285406.1_294-316_as | 294-316 |
| AD-266790.1 | UUUCGAGCAGAAGGAAAGUAA | 89 | NM_001285406.1_60-80_s | 60-80 | UUACUUUCCUUCUGCUCGAAAUU | 172 | NM_001285406.1_58-80_as | 58-80 |
| AD-266906.1 | UAAUCCUCUAUCCAGACAACA | 90 | NM_001285406.1_195-215_s | 195-215 | UGUUGUCUGGAUAGAGGAUUAAA | 173 | NM_001285406.1_193-215_as | 193-215 |
| AD-266854.1 | UGUUCAUCAGUUUGGAGAUAA | 91 | NM_001285406.1_141-161_s | 141-161 | UUAUCUCCAAACUGAUGAACAUG | 174 | NM_001285406.1_139-161_as | 139-161 |
| AD-266890.1 | GUGCAGGUCCCUCACUUUAAU | 92 | NM_001285406.1_179-199_s | 179-199 | AAUUAAAGUGAGGGACCUGCACUG | 175 | NM_001285406.1_177-199_as | 177-199 |
| AD-266808.1 | UAAUGGACCAGUGAAGGUGU | 93 | NM_001285406.1_78-98_s | 78-98 | AACACCUUCACUGGUCCAUUACU | 176 | NM_001285406.1_76-98_G1A_as | 76-98 |
| AD-266905.1 | UUAAUCCUCUAUCCAGACAAU | 94 | NM_001285406.1_194-214_C21U_s | 194-214 | AUUGUCUGGAUAGAGGAUUAAAG | 177 | NM_001285406.1_192-214_G1A_as | 192-214 |

TABLE 2-continued

Unmodified Sense and Antisense Strand Sequences of Superoxide Dismutase 1 dsRNA Agents

| Duplex Name | Sense Sequence 5' to 3' | SEQ ID NO: | Source Name | Range in Source, NM_001285406.1 | SEQ ID NO: | Source Name | Antisense Sequence 5' to 3' | Range in Source, NM_001285406.1 |
|---|---|---|---|---|---|---|---|---|
| AD-267024.1 | UCAGGAGACCAUUCCAUCAUU | 95 | NM_001285406.1_322-342_s | 322-342 | 178 | NM_001285406.1_320-342_as | AAUGAUGGAAUGGUCUCCUGAGA | 320-342 |
| AD-266781.1 | CACCAUCAAUUUCGAGCAGAA | 96 | NM_001285406.1_51-71_s | 51-71 | 179 | NM_001285406.1_49-71_as | UUCUGCUCGAAAUUGAUGGUGCC | 49-71 |
| AD-266892.1 | GCAGGUCCUCACUUUAAUCCU | 97 | NM_001285406.1_181-201_s | 181-201 | 180 | NM_001285406.1_179-201_as | AGGAUUAAAGUGAGGACCUGCAC | 179-201 |
| AD-266999.1 | UUUCGAAGAUUCUGUGAUCUU | 98 | NM_001285406.1_297-317_C21U_s | 297-317 | 181 | NM_001285406.1_295-317_G1A_as | AAGAUCACAGAAUCUUCGAAAGA | 295-317 |
| AD-266841.1 | UGCAUGGAUUCCAUGUUCAUU | 99 | NM_001285406.1_128-148_C21U_s | 128-148 | 182 | NM_001285406.1_126-148_G1A_as | AAUGAACAUGGAAUCCAUGCAGG | 126-148 |
| AD-266908.1 | AUCUCUAUCCAGACAACACU | 100 | NM_001285406.1_197-217_G21U_s | 197-217 | 183 | NM_001285406.1_195-217_C1A_as | AGUGUUGUCUGGAUAGAGAUUA | 195-217 |
| AD-267005.1 | AGAUUCUGUGAUCUCGCUCUU | 101 | NM_001285406.1_303-323_C21U_s | 303-323 | 184 | NM_001285406.1_301-323_as | AAGAGCGAGAUCACAGAAUCUUC | 301-323 |
| AD-266942.1 | GAAGAGAGGCAUGUUGGAGAU | 102 | NM_001285406.1_232-252_C21U_s | 232-252 | 185 | NM_001285406.1_230-252_G1A_as | AUCUCCAACAUGCCUCUCUUCAU | 230-252 |
| AD-135967.3 | UUGGGCAAAGGUGGAAAUGAA | 103 | NM_011434.1_495-515_s | 495-515 | 186 | NM_011434.1_493-515_as | UUCAUUUCCACCUUUGCCCAAGU | 493-515 |
| AD-266786.1 | UCAAUUUCGAGCAGCAGAAGAAA | 104 | NM_001285406.1_56-76_s | 56-76 | 187 | NM_001285406.1_54-76_as | UUUCCUUCUGCUCGAAAUUGAUG | 54-76 |
| AD-267064.1 | CAUGAAAAAGCAGAUGACUUU | 105 | NM_001285406.1_361-381_G21U_s | 361-381 | 188 | NM_001285406.1_359-381_C1A_as | AAAGUCAUCUGCUUUUUCAUGGA | 359-381 |
| AD-266845.1 | UGGAUUCCAUGUUCAUCAGUU | 106 | NM_001285406.1_132-152_s | 132-152 | 189 | NM_001285406.1_130-152_as | AACUGAUGAACAUGGAAUCCAUG | 130-152 |
| AD-266944.1 | GAGAGGCAUGUUGGAGACCUU | 107 | NM_001285406.1_235-255_G21U_s | 235-255 | 190 | NM_001285406.1_233-255_C1A_as | AAGGUCUCCAACAUGCCUCUCUU | 233-255 |
| AD-267003.1 | GAAGAUUCUGUGAUCUCGCUU | 108 | NM_001285406.1_301-321_C21U_s | 301-321 | 191 | NM_001285406.1_299-321_G1A_as | AAGCGAGAUCACAGAAUCUUCGA | 299-321 |
| AD-266860.1 | UCAGUUUGGAGAUAAUACACA | 109 | NM_001285406.1_147-167_s | 147-167 | 192 | NM_001285406.1_145-167_as | UGUGUAUUAUCUCCAAACUGAUG | 145-167 |

TABLE 2-continued

Unmodified Sense and Antisense Strand Sequences of Superoxide Dismutase 1 dsRNA Agents

| Duplex Name | Sense Sequence 5' to 3' | SEQ ID NO: | Source Name | Range in Source, NM_001285406.1 | Antisense Sequence 5' to 3' | SEQ ID NO: | Source Name | Range in Source, NM_001285406.1 |
|---|---|---|---|---|---|---|---|---|
| AD-266990.1 | CAAGGUGUCUUUCGAAGAUUU | 110 | NM_001285406.1_288-308_C21U_s | 288-308 | AAAUCUUCGAAAGACACCUUGGC | 193 | NM_001285406.1_286-308_G1A_as | 286-308 |
| AD-266853.1 | AUGUUCAUCAGUUUGGAGAUA | 111 | NM_001285406.1_140-160_s | 140-160 | UAUCUCCAAACUGAUGAACAUGG | 194 | NM_001285406.1_138-160_as | 138-160 |
| AD-266782.1 | ACCAUCAAUUUCGAGCAGAAU | 112 | NM_001285406.1_52-72_G21U_s | 52-72 | AUUCCUGCUCGAAAUUGAUGGUGC | 195 | NM_001285406.1_50-72_C1A_as | 50-72 |
| AD-266962.1 | AUGUGACUGCUGGCAAAGAUU | 113 | NM_001285406.1_260-280_s | 260-280 | AAUCUUUGCCAGCAGUCACAUUG | 196 | NM_001285406.1_258-280_C1A_as | 258-280 |
| AD-267079.1 | GGUGGAAAUGAAGAAAGUAAA | 114 | NM_001285406.1_388-408_s | 388-408 | UUUACUUUCUUCAUUUCCACCUU | 197 | NM_001285406.1_386-408_as | 386-408 |
| AD-266846.1 | GGAUUCCAUGUCAUCACAGUUU | 115 | NM_001285406.1_133-153_s | 133-153 | AAACUGUGAACAUGGAAUCCAU | 198 | NM_001285406.1_131-153_as | 131-153 |
| AD-266961.1 | AAUGUGACUGCUGGCAAAGAU | 116 | NM_001285406.1_259-279_s | 259-279 | AUCUUUGCCAGCAGUCACAUUGC | 199 | NM_001285406.1_257-279_as | 257-279 |
| AD-267061.1 | GUCCAUGAAAAAGCAGAUGAU | 117 | NM_001285406.1_358-378_s | 358-378 | AUCAUCUGCUUUUUCAUGGACCA | 200 | NM_001285406.1_356-378_G1A_as | 356-378 |

TABLE 3

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: |
|---|---|---|---|---|
| AD-266859.1 | asuscaguUfuGfGfAfgauaauacauL96 | 201 | asUfsguaUfuAfUfcuccAfaAfcugausgsa | 284 |
| AD-266997.1 | uscsuuucGfaAfGfAfuucugugauuL96 | 202 | asAfsucaCfaGfAfaucuUfcGfaaagascsa | 285 |
| AD-266992.1 | asgsguguCfuUfUfCfgaagauucuuL96 | 203 | asAfsgaaUfcUfUfcgaaAfgAfcaccususg | 286 |
| AD-266903.1 | csusuuaaUfcCfUfCfuauccagacaL96 | 204 | usGfsucuGfgAfUfagagGfaUfuaaagsusg | 287 |
| AD-266891.1 | usgscaggUfcCfUfCfacuuuaaucuL96 | 205 | asGfsauuAfaAfGfugagGfaCfcugcascsu | 288 |
| AD-266996.1 | gsuscuuuCfgAfAfGfauucugugauL96 | 206 | asUfscacAfgAfAfucuuCfgAfaagacsasc | 289 |
| AD-266893.1 | csasgglucCfuCfAfCfuuuaauccuuL96 | 207 | asAfsggaUfuAfAfagugAfgGfaccugscsa | 290 |
| AD-266898.1 | cscsucacUfuUfAfAfuccucuaucuL96 | 208 | asGfsauaGfaGfGfauuaAfaGfugaggsasc | 291 |
| AD-266886.1 | ascscaguGfcAfGfGfuccucacuuuL96 | 209 | asAfsaguGfaGfGfaccuGfcAfcuggusasc | 292 |
| AD-267072.1 | asgscagaUfgAfCfUfugggcaaaguL96 | 210 | asCfsuuuGfcCfCfaaguCfaUfcugcsusu | 293 |
| AD-267067.1 | gsasaaaaGfcAfGfAfugacuuggguL96 | 211 | asCfsccaAfgUfCfaucuGfcUfuuuucsasu | 294 |
| AD-266791.1 | ususcgagCfaGfAfAfggaaaguaauL96 | 212 | asUfsuacUfuUfCfcuucUfgCfucgaasasu | 295 |
| AD-266789.1 | asusuucgAfgCfAfGfaaggaaaguaL96 | 213 | usAfscuuUfcCfUfucugCfuCfgaaausus | 296 |
| AD-266861.1 | csasguuuGfgAfGfAfuaauacacaaL96 | 214 | usUfsgugUfaUfUfaucuCfcAfaacugsasu | 297 |
| AD-266856.1 | ususcaucAfgUfUfUfggagauaauaL96 | 215 | usAfsuuaUfcUfCfcaaaCfuGfaugaascsa | 298 |
| AD-266899.1 | csuscacuUfuAfAfUfccucuauccaL96 | 216 | usGfsgauAfgAfGfgauuAfaAfgugagsgsa | 299 |
| AD-267000.1 | ususcgaaGfaUfUfCfugugaucucuL96 | 217 | asGfsagaUfcAfCfagaaUfcUfucgaasasg | 300 |
| AD-267071.1 | asasgcagAfuUfGfAfCfuugggcaaauL96 | 218 | asUfsuugCfcCfAfagucAfuCfugcuususu | 301 |
| AD-266895.1 | gsgsuccuCfaCfUfUfuaauccucuaL96 | 219 | usAfsgagGfaUfUfaaagUfgAfggaccsusg | 302 |
| AD-266888.1 | csasgugcAfgGfUfCfcucacuuuaaL96 | 220 | usUfsaaaGfuGfAfggacCfuGfcacugsgsu | 303 |
| AD-266817.1 | csasuuacAfgGfAfUfugacugaaguL96 | 221 | asCfsuucAfgUfCfaaucCfuGfuaaugscsu | 304 |
| AD-267083.1 | asasaguaAfaAfAfGfacaggaaacuL96 | 222 | asGfsuuuCfcUfGfucuuUfuUfacuuuscsu | 305 |
| AD-266862.1 | asgsuuugGfaGfAfUfaauacacaauL96 | 223 | asUfsuguGfuAfUfuaucUfcCfaaacusgsa | 306 |
| AD-267002.1 | csgsaagaUfcUfCfUfgugaucucguL96 | 224 | asGfscgaGfaUfCfacagAfaUfcuucgsasa | 307 |
| AD-266816.1 | gscsauuaCfaGfGfAfuugacugaauL96 | 225 | asUfsucaGfuCfAfauccUfgUfaaugscsu | 308 |
| AD-266857.1 | uscsaucaGfuUfUfGfgagauaauauL96 | 226 | asUfsauuAfuCfUfccaaAfcUfgaugasasc | 309 |
| AD-266902.1 | ascsuuuaAfuCfCfUfcuauccagauL96 | 227 | asUfscugGfaUfAfgaggAfuUfaaagusgsa | 310 |
| AD-267086.1 | gsusaaaaAfgAfCfAfggaaacgcuuL96 | 228 | asAfsgcgUfuUfCfcuguCfuUfuuuacsusu | 311 |
| AD-266785.1 | asuscaauUfuCfGfAfgcagaaggaaL96 | 229 | usUfsccuUfcUfGfcucgAfaAfuugasgsg | 312 |
| AD-266897.1 | uscscucaCfuUfUfAfauccucuauuL96 | 230 | asAfsuagAfgGfAfuuaaAfgUfgaggascsc | 313 |
| AD-266896.1 | gsuscccucAfcUfUfUfaauccucuauL96 | 231 | asUfsagaGfgAfUfuaaaGfuGfaggacscsu | 314 |
| AD-266858.1 | csasucagUfuUfGfGfagauaauacaL96 | 232 | usGfsuauUfaUfCfuccaAfaCfugaugsasa | 315 |
| AD-267084.1 | asasaguaaAfaAfGfAfcaggaaacguL96 | 233 | asCfsguuUfcCfUfgucuUfuUfacuususc | 316 |
| AD-266815.1 | asgscauuAfcAfGfGfauugacugaaL96 | 234 | usUfscagUfcAfAfuccuGfuAfaugcsusc | 317 |
| AD-267007.1 | asusucugUfgAfUfCfucgcucacauL96 | 235 | asUfsgagAfgCfGfagauCfaCfagaauscsu | 318 |
| AD-266855.1 | gsuscaucuCfaGfUfUfUfggagauaauaL96 | 236 | asUfsuauCfuCfCfaaacUfgAfugaacsasu | 319 |
| AD-266901.1 | csascuuuAfaUfCfCfucuauccagaL96 | 237 | usCfsuggAfuAfGfaggaUfuAfaagugsasg | 320 |

TABLE 3-continued

Modified Sense and Antisense Strand Sequences of Superoxide Dismutase 1 dsRNA Agents

| | | | | | |
|---|---|---|---|---|---|
| AD-266994.1 | gsusgucuUfuCfGfAfagauucuguuL96 | 238 | asAfscagAfaUfCfuucgAfaAfgacacscsu | 321 |
| AD-266793.1 | csgsagcaGfaAfGfGfaaaguaauguL96 | 239 | asCfsauuAfcUfUfuccuUfcUfgcucgsasa | 322 |
| AD-266850.1 | uscscaugUfuCfAfUfcaguuuggauL96 | 240 | asUfsccaAfaCfUfgaugAfaCfauggasasu | 323 |
| AD-266887.1 | cscsagugCfaGfGfUfccucacuuuaL96 | 241 | usAfsaagUfgAfGfgaccUfgCfacuggsusa | 324 |
| AD-266894.1 | asgsguccUfcAfCfUfuuaauccucuL96 | 242 | asGfsaggAfuUfAfaaguGfaGfgaccusgsc | 325 |
| AD-266988.1 | gscscaagGfuGfUfCfuuucgaagauL96 | 243 | asUfscuuCfgAfAfagacAfcCfuuggcscsa | 326 |
| AD-267085.1 | asgsuaaaAfaGfAfCfaggaaacgcuL96 | 244 | asGfscguUfuCfCfugucUfuUfuuacususu | 327 |
| AD-266873.1 | asusacacAfaGfGfCfuguaccaguuL96 | 245 | asAfscugGfuAfCfagccUfuGfuguaususa | 328 |
| AD-266907.1 | asasuccuCfuAfUfCfcagacaacauL96 | 246 | asUfsguuGfuCfUfggauAfgAfggauusasa | 329 |
| AD-266792.1 | uscsgagcAfgAfAfGfgaaaguaauuL96 | 247 | asAfsuuaCfuUfUfccuuCfuGfcucgasasa | 330 |
| AD-266900.1 | uscsacuuUfaAfUfCfcucuauccauL96 | 248 | asUfsggaUfaGfAfggauUfaAfagugasgsg | 331 |
| AD-266797.1 | csasgaagGfaAfAfGfuaauggaccaL96 | 249 | usGfsgucCfaUfUfacuuUfcCfuucugscsu | 332 |
| AD-266787.1 | csasauuuCfgAfGfCfagaaggaaauL96 | 250 | asUfsuucCfuUfCfugcuCfgAfaauugsasu | 333 |
| AD-266800.1 | asasggaaAfgUfAfAfuggaccaguuL96 | 251 | asAfscugGfuCfCfauuaCfuUfuccuuscsu | 334 |
| AD-266889.1 | asgsugcaGfgUfCfCfucacuuuaauL96 | 252 | asUfsuaaAfgUfGfaggaCfcUfgcacusgsg | 335 |
| AD-266847.1 | gsasuuccAfuGfUfUfcaucaguuugL96 | 253 | csAfsaacUfgAfUfgaacAfuGfgaaucscsa | 336 |
| AD-266998.1 | csusuucgAfaGfAfUfucugugaucuL96 | 254 | asGfsaucAfcAfGfaaucUfuCfgaaagsasc | 337 |
| AD-266790.1 | ususucgaGfcAfGfAfaggaaaguaaL96 | 255 | usUfsacuUfuCfCfuucuGfcUfcgaaasusu | 338 |
| AD-266906.1 | usasauccUfcUfAfUfccagacaacaL96 | 256 | usGfsuugUfcUfGfgauaGfaGfgauuasasa | 339 |
| AD-266854.1 | usgsuucaUfcAfGfUfuuggagauaaL96 | 257 | usUfsaucUfcCfAfaacuGfaUfgaacasusg | 340 |
| AD-266890.1 | gsusgcagGfuCfCfUfcacuuuaauuL96 | 258 | asAfsuuaAfaGfUfgaggAfcCfugcacsusg | 341 |
| AD-266808.1 | usasauggAfcCfAfGfugaagguguuL96 | 259 | asAfscacCfuUfCfacugGfuCfcauuascsu | 342 |
| AD-266905.1 | ususaaucCfuCfUfAfuccagacaauL96 | 260 | asUfsguCfuGfGfauaGfaGfgauuaasasg | 343 |
| AD-267024.1 | uscsaggaGfaCfCfAfuuccaucauuL96 | 261 | asAfsugaUfgGfAfauggUfcUfccugasgsa | 344 |
| AD-266781.1 | csasccauCfaAfUfUfucgagcagaaL96 | 262 | usUfscugCfuCfGfaaauUfgAfuggugscsc | 345 |
| AD-266892.1 | gscsagguCfcUfCfAfcuuuaauccuL96 | 263 | asGfsgauUfaAfAfguaGfaGfaccugcsasc | 346 |
| AD-266999.1 | ususucgaAfgAfUfUfcugugaucuuL96 | 264 | asAfsgauCfaCfAfgaauCfuUfcgaaasgsa | 347 |
| AD-266841.1 | usgscaugGfaUfUfCfcaguucauuL96 | 265 | asAfsugaAfcAfUfggaaUfcCfaugcasgsg | 348 |
| AD-266908.1 | asusccucUfaUfCfCfagacaacacuL96 | 266 | asGfsuguUfgUfCfuggaUfaGfaggaususa | 349 |
| AD-267005.1 | asgsauucUfgUfGfAfucucgcucuuL96 | 267 | asAfsgagCfgAfGfaucaCfaGfaaucususc | 350 |
| AD-266942.1 | gsasagagAfgGfCfAfuguuggagauL96 | 268 | asUfscucCfaAfCfaugcCfuCfucuucsasu | 351 |
| AD-135967.3 | ususgggcAfaAfGfGfuggaaaugaaL96 | 269 | usUfscauUfuCfCfaccuUfuGfcccaasgsu | 352 |
| AD-266786.1 | uscsaauuUfcGfAfGfcagaaggaaaL96 | 270 | usUfsuccUfuCfUfgcucGfaAfauugasusg | 353 |
| AD-267064.1 | csasugaaAfaAfGfCfagaugacuuuL96 | 271 | asAfsaguCfaUfCfugcuUfuUfucaugsgsa | 354 |
| AD-266845.1 | usgsgauuCfcAfUfGfuucaucaguuL96 | 272 | asAfscugAfuGfAfacauGfgAfauccasusg | 355 |
| AD-266944.1 | gsasagaggCfaUfGfUfUfuggagaccuuL96 | 273 | asAfsgguCfuCfCfaacaUfgCfcucucsusu | 356 |
| AD-267003.1 | gsasagauUfcUfGfUfgaucucgcuuL96 | 274 | asAfsgcgAfgAfUfcacaGfaAfucuucsgsa | 357 |
| AD-266860.1 | uscsaguuUfgGfAfGfauaauacacaL96 | 275 | usGfsuguAfuUfAfucucCfaAfacugasusg | 358 |
| AD-266990.1 | csasagguGfuCfUfUfucgaagauuuL96 | 276 | asAfsaucUfuCfGfaaagAfcAfccuugsgsc | 359 |

TABLE 3-continued

Modified Sense and Antisense Strand Sequences of Superoxide Dismutase 1 dsRNA Agents

| | | | | |
|---|---|---|---|---|
| AD-266853.1 | asusguucAfuCfAfAfGfuuuggagauaL96 | 277 | usAfsucuCfcAfAfacugAfuGfaacausgsg | 360 |
| AD-266782.1 | ascscaucAfaUfUfUfcgagcagaauL96 | 278 | asUfsucuGfcUfCfgaaaUfuGfauggusgsc | 361 |
| AD-266962.1 | asusgugaCfuGfCfUfggcaaagauuL96 | 279 | asAfsucuUfuGfCfcagcAfgUfcacausug | 362 |
| AD-267079.1 | gsgsuggaAfaUfGfAfagaaaguaaaL96 | 280 | usUfsuacUfuUfCfuucaUfuUfccaccsusu | 363 |
| AD-266846.1 | gsgsauucCfaUfGfUfucaucguuuL96 | 281 | asAfsacuGfaUfGfaacaUfgGfaauccsasu | 364 |
| AD-266961.1 | asasugugAfcUfGfCfuggcaaagauL96 | 282 | asUfscuuUfgCfCfagcaGfuCfacauusgsc | 365 |
| AD-267061.1 | gsusccauGfaAfAfAfagcagaugaL96 | 283 | asUfscauCfuGfCfuuuuUfcAfuggacscsa | 366 |

| Duplex Name | mRNA target sequence | SEQ ID NO: |
|---|---|---|
| 266859.1 | UCAUCAGUUUGGAGAUAAUACAC | 367 |
| 266997.1 | UGUCUUUCGAAGAUUCUGUGAUC | 368 |
| 266992.1 | CAAGGUGUCUUUCGAAGAUUCUG | 369 |
| 266903.1 | CACUUUAAUCCUCUAUCCAGACA | 370 |
| 266891.1 | AGUGCAGGUCCUCACUUUAAUCC | 371 |
| 266996.1 | GUGUCUUUCGAAGAUUCUGUGAU | 372 |
| 266893.1 | UGCAGGUCCUCACUUUAAUCCUC | 373 |
| 266898.1 | GUCCUCACUUUAAUCCUCUAUCC | 374 |
| 266886.1 | GUACCAGUGCAGGUCCUCACUUU | 375 |
| 267072.1 | AAAGCAGAUGACUUGGGCAAAGG | 376 |
| 267067.1 | AUGAAAAAGCAGAUGACUUGGGC | 377 |
| 266791.1 | AUUUCGAGCAGAAGGAAAGUAAU | 378 |
| 266789.1 | CAAUUUCGAGCAGAAGGAAAGUA | 379 |
| 266861.1 | AUCAGUUUGGAGAUAAUACACAA | 380 |
| 266856.1 | UGUUCAUCAGUUUGGAGAUAAUA | 381 |
| 266899.1 | UCCUCACUUUAAUCCUCUAUCCA | 382 |
| 267000.1 | CUUUCGAAGAUUCUGUGAUCUCG | 383 |
| 267071.1 | AAAAGCAGAUGACUUGGGCAAAG | 384 |
| 266895.1 | CAGGUCCUCACUUUAAUCCUCUA | 385 |
| 266888.1 | ACCAGUGCAGGUCCUCACUUUAA | 386 |
| 266817.1 | AGCAUUACAGGAUUGACUGAAGG | 387 |
| 267083.1 | AGAAAGUAAAAAGACAGGAAACG | 388 |
| 266862.1 | UCAGUUUGGAGAUAAUACACAAG | 389 |
| 267002.1 | UUCGAAGAUUCUGUGAUCUCGCU | 390 |
| 266816.1 | AAGCAUUACAGGAUUGACUGAAG | 391 |
| 266857.1 | GUUCAUCAGUUUGGAGAUAAUAC | 392 |
| 266902.1 | UCACUUUAAUCCUCUAUCCAGAC | 393 |
| 267086.1 | AAGUAAAAAGACAGGAAACGCUG | 394 |
| 266785.1 | CCAUCAAUUUCGAGCAGAAGGAA | 395 |
| 266897.1 | GGUCCUCACUUUAAUCCUCUAUC | 396 |
| 266896.1 | AGGUCCUCACUUUAAUCCUCUAU | 397 |

TABLE 3-continued

Modified Sense and Antisense Strand Sequences of Superoxide Dismutase 1 dsRNA Agents

| | | |
|---|---|---|
| 266858.1 | UUCAUCAGUUUGGAGAUAAUACA | 398 |
| 267084.1 | GAAAGUAAAAGACAGGAAACGC | 399 |
| 266815.1 | GAAGCAUUACAGGAUUGACUGAA | 400 |
| 267007.1 | AGAUUCUGUGAUCUCGCUCUCAG | 401 |
| 266855.1 | AUGUUCAUCAGUUUGGAGAUAAU | 402 |
| 266901.1 | CUCACUUUAAUCCUCUAUCCAGA | 403 |
| 266994.1 | AGGUGUCUUUCGAAGAUUCUGUG | 404 |
| 266793.1 | UUCGAGCAGAAGGAAAGUAAUGG | 405 |
| 266850.1 | AUUCCAUGUUCAUCAGUUUGGAG | 406 |
| 266887.1 | UACCAGUGCAGGUCCUCACUUUA | 407 |
| 266894.1 | GCAGGUCCUCACUUUAAUCCUCU | 408 |
| 266988.1 | UGGCCAAGGUGUCUUUCGAAGAU | 409 |
| 267085.1 | AAAGUAAAAGACAGGAAACGCU | 410 |
| 266873.1 | UAAUACACAAGGCUGUACCAGUG | 411 |
| 266907.1 | UUAAUCCUCUAUCCAGACAACAC | 412 |
| 266792.1 | UUUCGAGCAGAAGGAAAGUAAUG | 413 |
| 266900.1 | CCUCACUUUAAUCCUCUAUCCAG | 414 |
| 266797.1 | AGCAGAAGGAAAGUAAUGGACCA | 415 |
| 266787.1 | AUCAAUUUCGAGCAGAAGGAAAG | 416 |
| 266800.1 | AGAAGGAAAGUAAUGGACCAGUG | 417 |
| 266889.1 | CCAGUGCAGGUCCUCACUUUAAU | 418 |
| 266847.1 | UGGAUUCCAUGUUCAUCAGUUUG | 419 |
| 266998.1 | GUCUUUCGAAGAUUCUGUGAUCU | 420 |
| 266790.1 | AAUUUCGAGCAGAAGGAAAGUAA | 421 |
| 266906.1 | UUUAAUCCUCUAUCCAGACAACA | 422 |
| 266854.1 | CAUGUUCAUCAGUUUGGAGAUAA | 423 |
| 266890.1 | CAGUGCAGGUCCUCACUUUAAUC | 424 |
| 266808.1 | AGUAAUGGACCAGUGAAGGUGUG | 425 |
| 266905.1 | CUUUAAUCCUCUAUCCAGACAAC | 426 |
| 267024.1 | UCUCAGGAGACCAUUCCAUCAUU | 427 |
| 266781.1 | GGCACCAUCAAUUUCGAGCAGAA | 428 |
| 266892.1 | GUGCAGGUCCUCACUUUAAUCCU | 429 |
| 266999.1 | UCUUUCGAAGAUUCUGUGAUCUC | 430 |
| 266841.1 | CCUGCAUGGAUUCCAUGUUCAUC | 431 |
| 266908.1 | UAAUCCUCUAUCCAGACAACACG | 432 |
| 267005.1 | GAAGAUUCUGUGAUCUCGCUCUC | 433 |
| 266942.1 | AUGAAGAGAGGCAUGUUGGAGAC | 434 |
| 135967.3 | ACUUGGGCAAAGGUGGAAAUGAA | 435 |
| 266786.1 | CAUCAAUUUCGAGCAGAAGGAAA | 436 |

TABLE 3-continued

Modified Sense and Antisense Strand Sequences of Superoxide Dismutase 1 dsRNA Agents

| | | |
|---|---|---|
| 267064.1 | UCCAUGAAAAAGCAGAUGACUUG | 437 |
| 266845.1 | CAUGGAUUCCAUGUUCAUCAGUU | 438 |
| 266944.1 | AAGAGAGGCAUGUUGGAGACCUG | 439 |
| 267003.1 | UCGAAGAUUCUGUGAUCUCGCUC | 440 |
| 266860.1 | CAUCAGUUUGGAGAUAAUACACA | 441 |
| 266990.1 | GCCAAGGUGUCUUUCGAAGAUUC | 442 |
| 266853.1 | CCAUGUUCAUCAGUUUGGAGAUA | 443 |
| 266782.1 | GCACCAUCAAUUUCGAGCAGAAG | 444 |
| 266962.1 | CAAUGUGACUGCUGGCAAAGAUG | 445 |
| 267079.1 | AAGGUGGAAAUGAAGAAAGUAAA | 446 |
| 266846.1 | AUGGAUUCCAUGUUCAUCAGUUU | 447 |
| 266961.1 | GCAAUGUGACUGCUGGCAAAGAU | 448 |
| 267061.1 | UGGUCCAUGAAAAAGCAGAUGAC | 449 |

TABLE 4

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-135962.1 | AUGACUUGGGCAAAGGUGGAA | 450 | NM_011434.1_490-510_s | 490-510 | UUCCACCUUUGCCCAAGUCAUCU | 529 | NM_011434.1_488-510_as | 488-510 |
| AD-135963.1 | UGACUUGGGCAAAGGUGGAAA | 451 | NM_011434.1_491-511_s | 491-511 | UUUCCACCUUUGCCCAAGUCAUC | 530 | NM_011434.1_489-511_as | 489-511 |
| AD-135964.1 | GACUUGGGCAAAGGUGGAAAU | 452 | NM_011434.1_492-512_s | 492-512 | AUUUCCACCUUUGCCCAAGUCAU | 531 | NM_011434.1_490-512_as | 490-512 |
| AD-135967.5 | UUGGGCAAAGGUGGAAAUGA | 103 | NM_011434.1_495-515_s | 495-515 | UUCAUUUCCACCUUUGCCCAAGU | 186 | NM_011434.1_493-515_as | 493-515 |
| AD-135974.3 | AAGGUGGAAAUGAAGAAAGU | 453 | NM_011434.1_502-522_s | 502-522 | UACUUUCUUCAUUUCCACCUUG | 532 | NM_011434.1_500-522_as | 500-522 |
| AD-266788.1 | AAUUCGAGCAGAAGGAAAGU | 454 | NM_001285406.1_58-78_s | 58-78 | ACUUUCCUUCUGCUCGAAAUUGA | 533 | NM_001285406.1_56-78_as | 56-78 |
| AD-266789.2 | AUUUCGAGCAGAAGGAAAGU | 47 | NM_001285406.1_59-79_s | 59-79 | UACUUUCCUUCUGCUCGAAAUUG | 130 | NM_001285406.1_57-79_as | 57-79 |
| AD-266790.2 | UUUCGAGCAGAAGGAAAGUA | 89 | NM_001285406.1_60-80_s | 60-80 | UUACUUUCCUUCUGCUCGAAAUU | 172 | NM_001285406.1_58-80_as | 58-80 |
| AD-266791.3 | UUCGAGCAGAAGGAAAGUAA | 46 | NM_001285406.1_61-81_s | 61-81 | AUUACUUUCCUUCUGCUCGAAAU | 129 | NM_001285406.1_59-81_as | 59-81 |
| AD-266794.1 | GAGCAGAAGGAAAGUAAUGG | 455 | NM_001285406.1_64-84_s | 64-84 | UCCAUUACUUUCCUUCUGCUCGA | 534 | NM_001285406.1_62-84_as | 62-84 |
| AD-266798.1 | AGAAGGAAAGUAAUGGACCA | 456 | NM_001285406.1_68-88_G21U_s | 68-88 | AUGGUCCAUUACUUUCCUUCUGC | 535 | NM_001285406.1_66-88_C1A_as | 66-88 |
| AD-266799.1 | GAAGGAAAGUAAUGGACCAGU | 457 | NM_001285406.1_96-89_s | 69-89 | ACUGGUCCAUUACUUUCCUUCUG | 536 | NM_001285406.1_67-89_as | 67-89 |
| AD-266801.1 | AGGAAAGUAAUGGACCAGUG | 458 | NM_001285406.1_71-91_s | 71-91 | UCACUGGUCCAUUACUUUCCUUC | 537 | NM_001285406.1_69-91_as | 69-91 |
| AD-266802.1 | GGAAAGUAAUGGACCAGUGA | 459 | NM_001285406.1_72-92_s | 72-92 | UUCACUGGUCCAUUACUUUCCUU | 538 | NM_001285406.1_70-92_as | 70-92 |

TABLE 4-continued

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-266803.1 | GAAAGUAAUGGACCAGUGAAU | 460 | NM_001285406.1_73-93_G21U_s | 73-93 | AUUCACUGGUCCAUUACUUUCU | 539 | NM_001285406.1_71-93_C1A_as | 71-93 |
| AD-266804.1 | AAAGUAAUGGACCAGUGAAGU | 461 | NM_001285406.1_74-94_G21U_s | 74-94 | ACUUCACUGGUCCAUUACUUUCC | 540 | NM_001285406.1_72-94_C1A_as | 72-94 |
| AD-266805.1 | AAGUAAUGGACCAGUGAAGGU | 462 | NM_001285406.1_75-95_s | 75-95 | ACCUUCACUGGUCCAUUACUUUC | 541 | NM_001285406.1_73-95_as | 73-95 |
| AD-266806.1 | AGUAAUGGACCAGUGAAGGUU | 463 | NM_001285406.1_67-96_G21U_s | 76-96 | AACCUUCACUGGUCCAUUACUUU | 542 | NM_001285406.1_74-96_C1A_as | 74-96 |
| AD-266808.2 | UAAUGGACCAGUGAAGGUGUU | 93 | NM_001285406.1_78-98_G21U_s | 78-98 | AACACCUUCACUGGUCCAUUACU | 176 | NM_001285406.1_76-98_C1A_as | 76-98 |
| AD-266832.1 | UGAAGGCCUGCAUGGAUUCCA | 464 | NM_001285406.1_120-140_s | 120-140 | UGGAAUCCAUGCAGGCCUUCAGU | 543 | NM_001285406.1_118-140_as | 118-140 |
| AD-266834.1 | GAAGGCCUGCAUGGAUUCCAU | 465 | NM_001285406.1_121-141_s | 121-141 | AUGGAAUCCAUGCAGGCCUUCAG | 544 | NM_001285406.1_119-141_as | 119-141 |
| AD-266836.1 | AGGCCUGCAUGGAUUCCAUGU | 466 | NM_001285406.1_123-143_s | 123-143 | ACAUGGAAUCCAUGCAGGCCUUC | 545 | NM_001285406.1_121-143_as | 121-143 |
| AD-266837.1 | GGCCUGCAUGGAUUCCAUGUU | 467 | NM_001285406.1_124-144_s | 124-144 | AACAUGGAAUCCAUGCAGGCCUU | 546 | NM_001285406.1_122-144_as | 122-144 |
| AD-266838.1 | GCCUGCAUGGAUUCCAUGUUU | 468 | NM_001285406.1_125-145_C21U_s | 125-145 | AAACAUGGAAUCCAUGCAGGCCU | 547 | NM_001285406.1_123-145_G1A_as | 123-145 |
| AD-266839.1 | CCUGCAUGGAUUCCAUGUUCA | 469 | NM_001285406.1_126-146_s | 126-146 | UGAACAUGGAAUCCAUGCAGGCC | 548 | NM_001285406.1_124-146_as | 124-146 |
| AD-266840.1 | CUGCAUGGAUUCCAUGUUCAU | 470 | NM_001285406.1_127-147_s | 127-147 | AUGAACAUGGAAUCCAUGCAGGC | 549 | NM_001285406.1_125-147_as | 125-147 |
| AD-266841.3 | UGCAUGGAUUCCAUGUUCAUU | 99 | NM_001285406.1_128-148_C21U_s | 128-148 | AAUUGAACAUGGAAUCCAUGCAGG | 182 | NM_001285406.1_126-148_G1A_as | 126-148 |
| AD-266886.2 | ACCAGUGCAGGUCCUCACUUU | 43 | NM_001285406.1_175-195_s | 175-195 | AAAGUGAGGACCUGCACUGGUAC | 126 | NM_001285406.1_173-195_as | 173-195 |
| AD-266887.3 | CCAGUGCAGGUCCUCACUUUA | 75 | NM_001285406.1_176-196_s | 176-196 | UAAAGUGAGGACCUGCACUGGUA | 158 | NM_001285406.1_174-196_as | 174-196 |

TABLE 4-continued

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-266888.2 | CAGUGCAGGUCCUCACUUUAA | 54 | NM_001285406.1_177-197_s | 177-197 | UUAAAGUGAGGACCUGCACUGGU | 137 | NM_001285406.1_175-197_as | 175-197 |
| AD-266890.3 | GUGCAGGUCCUCACUUUAAUU | 92 | NM_001285406.1_179-199_C21U_s | 179-199 | AAUUAAAGUGAGGACCUGCACUG | 175 | NM_001285406.1_177-199_G1A_as | 177-199 |
| AD-266891.2 | UGCAGGUCCUCACUUUAAUCU | 39 | NM_001285406.1_180-200_C21U_s | 180-200 | AGAUUAAAGUGAGGACCUGCACU | 122 | NM_001285406.1_178-200_G1A_as | 178-200 |
| AD-266892.2 | GCAGGUCCUCACUUUAAUCCU | 97 | NM_001285406.1_181-201_s | 181-201 | AGGAUUAAAGUGAGGACCUGCAC | 180 | NM_001285406.1_179-201_as | 179-201 |
| AD-266899.2 | CUCACUUUAAUCCUCUCAUCCA | 50 | NM_001285406.1_188-208_s | 188-208 | UGGAUGAGAGGAUUAAAGUGAGA | 133 | NM_001285406.1_186-208_as | 186-208 |
| AD-266900.3 | UCACUUUAAUCCUCUCAUCCAU | 82 | NM_001285406.1_189-209_G21U_s | 189-209 | AUGGAUGAGAGGAUUAAAGUGAGG | 165 | NM_001285406.1_187-209_as | 187-209 |
| AD-266901.2 | CACUUUAAUCCUCUCAUCCAG | 71 | NM_001285406.1_190-210_s | 190-210 | UCUGGAUGAGAGGAUUAAAGUGAG | 154 | NM_001285406.1_188-210_as | 188-210 |
| AD-266928.1 | GGUGGGCCAAAGGAUGGAAGAU | 471 | NM_001285406.1_217-237_G21U_s | 217-237 | AUCUUCAUCCUUUGGCCCACCGU | 550 | NM_001285406.1_215-237_C1A_as | 215-237 |
| AD-266934.1 | GAUGAGAGAGGCAUGUUGGA | 472 | NM_011434.1_345-365_s | 345-365 | UCCAACAUGCCUCUCUCAUCCU | 551 | NM_011434.1 | 343-365 |
| AD-266936.1 | CAAAGGAUGAAGAGAGGCAUU | 473 | NM_001285406.1_224-244_G21U_s | 224-244 | AAUGCCUCUCUUCAUCCUUUGGC | 552 | NM_001285406.1_222-244_C1A_as | 222-244 |
| AD-266938.1 | AAGGAUGAAGAGAGGCAUGU | 474 | NM_001285406.1_226-246_s | 226-246 | AACAUGCCUCUCUUCAUCCUUG | 553 | NM_001285406.1_224-246_C1A_as | 224-246 |
| AD-266939.1 | AGGAUGAAGAGAGGCAUGUU | 475 | NM_001285406.1_227-247_G21U_s | 227-247 | AAACAUGCCUCUCUUCAUCCUU | 554 | NM_001285406.1_225-247_C1A_as | 225-247 |
| AD-266940.1 | GGAUGAAGAGAGGCAUGUUG | 476 | NM_001285406.1_228-248_G21U_s | 228-248 | ACAACAUGCCUCUCUUCAUCCUU | 555 | NM_001285406.1_226-248_C1A_as | 226-248 |
| AD-266941.1 | AUGAAGAGAGGCAUGUUGGA | 477 | NM_001285406.1_230-250_G21U_s | 230-250 | AUCCAACAUGCCUCUCUUCAUCC | 556 | NM_001285406.1_228-250_C1A_as | 228-250 |
| AD-266943.1 | AAGAGAGGCAUGUUGGAGAC | 478 | NM_001285406.1_233-253_C21U_s | 233-253 | AGUCUCCAACAUGCCUCUCUUCA | 557 | NM_001285406.1_231-253_G1A_as | 231-253 |

TABLE 4-continued

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-267035.1 | GAUGACUUGGGCAAAGGUGGA | 479 | NM_011434.1_489-509_s | 489-509 | UCCACCUUUGCCAAGUCAUCUG | 558 | NM_011434.1 | 487-509 |
| AD-267058.1 | GUGGUCCAUGAAAAAGCAGAU | 480 | NM_001285406.1_535-375_s | 355-375 | AUCUGCUUUUCAUGGACCACCA | 559 | NM_001285406.1_353-375_as | 353-375 |
| AD-267059.1 | UGGUCCAUGAAAAAGCAGAUU | 481 | NM_001285406.1_356-376_s | 356-376 | AAUCUGCUUUUCAUGGACCACC | 560 | NM_001285406.1_354-376_C1A_as | 354-376 |
| AD-267060.1 | GGUCCAUGAAAAAGCAGAUGA | 482 | NM_001285406.1_357-377_s | 357-377 | UCAUCUGCUUUUUCAUGGACCAC | 561 | NM_001285406.1_355-377_as | 355-377 |
| AD-267073.1 | GCAGAUGACUUGGGCAAAGGU | 483 | NM_001285406.1_370-390_s | 370-390 | ACCUUUGCCCAAGUCAUCUGCUU | 562 | NM_001285406.1_368-390_as | 368-390 |
| AD-267075.1 | AGAUGACUUGGGCAAAGGUGU | 484 | NM_001285406.1_372-392_G21U_s | 372-392 | ACACCUUUGCCCAAGUCAUCUGC | 563 | NM_001285406.1_370-392_C1A_as | 370-392 |
| AD-267076.1 | ACUUGGGCAAAGGUGGAAAUU | 485 | NM_001285406.1_377-397_G21U_s | 377-397 | AAUUUCCACCUUUGCCCAAGUCA | 564 | NM_001285406.1_375-397_C1A_as | 375-397 |
| AD-267118.1 | GCUUGUGUGUAAUUGGGGAU | 486 | NM_001285406.1_436-456_C21U_s | 436-456 | AAUCCCAAUUACACCACAAGC | 565 | NM_001285406.1_434-456_C1A_as | 434-456 |
| AD-267119.1 | CUUGUGUGUAAUUGGGAUC | 487 | NM_001285406.1_437-457_G21U_s | 437-457 | AGAUCCCAAUUACACCACAAGCC | 566 | NM_001285406.1_435-457_C1A_as | 435-457 |
| AD-267120.1 | UUGUGUGUAAUUGGGGAUCG | 488 | NM_001285406.1_438-458_C21U_s | 438-458 | ACCGAUCCCAAUUACACCACAAGC | 567 | NM_001285406.1_436-458_G1A_as | 436-458 |
| AD-267121.1 | UGUGUGUAAUUGGGAUCGC | 489 | NM_001285406.1_439-459_C21U_s | 439-459 | AGCGAUCCCAAUUACACCACAAG | 568 | NM_001285406.1_437-459_G1A_as | 437-459 |
| AD-267122.1 | GUGUGUAAUUGGGAUCGCC | 490 | NM_001285406.1_440-460_C21U_s | 440-460 | AGGCGAUCCCAAUUACACCACAA | 569 | NM_001285406.1_438-460_G1A_as | 438-460 |
| AD-295644.1 | UGCAGGGCAUCAUCAAUUUC | 491 | NM_000454.4_192-212_G21U_s | 192-212 | AGAAAUUGAUGAUGCCCUGCACU | 570 | NM_000454.4_190-212_C1A_as | 190-212 |
| AD-295645.1 | GCAGGGCAUCAUCAAUUUCG | 492 | NM_000454.4_193-213_s | 193-213 | UCGAAAUUGAUGAUGCCCUGCAC | 571 | NM_000454.4_191-213_as | 191-213 |
| AD-295646.1 | CAGGGCAUCAUCAAUUUCGA | 493 | NM_000454.4_194-214_G21U_s | 194-214 | AUCGAAAUUGAUGAUGCCCUGCA | 572 | NM_000454.4_192-214_C1A_as | 192-214 |

TABLE 4-continued

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-295647.1 | AGGGCAUCAUCAAUUCGAGU | 494 | NM_000454.4_195-215_C21U_s | 195-215 | ACUCGAAUUGAUGAUGCCCU GC | 573 | NM_000454.4_193-215_G1A_as | 193-215 |
| AD-295648.1 | GGGCAUCAUCAAUUCGAGCA | 495 | NM_000454.4_196-216_s | 196-216 | UGCUCGAAUUGAUGAUGCCC UG | 574 | NM_000454.4_194-216_as | 194-216 |
| AD-295649.1 | GGCAUCAUCAAUUCGAGCAU | 496 | NM_000454.4_197-217_G21U_s | 197-217 | AUGCUCGAAUUGAUGAUGCC CU | 575 | NM_000454.4_195-217_C1A_as | 195-217 |
| AD-295651.1 | CAUCAUCAAUUCGAGCAGA A | 497 | NM_000454.4_199_s | 199-219 | UUCUGCUCGAAUUGAUGAUG CC | 576 | NM_000454.4_197-219_as | 197-219 |
| AD-295652.1 | AUCAUCAAUUCGAGCAGAGAU | 498 | NM_000454.4_200-220_G21U_s | 200-220 | AUUCUGCUCGAAUUGAUGAU GC | 577 | NM_000454.4_198-220_as | 198-220 |
| AD-295653.1 | UCAUCAAUUCGAGCAGAAG U | 499 | NM_000454.4_201-221_G21U_s | 201-221 | ACUUCUGCUCGAAUUGAUGA UG | 578 | NM_000454.4_199-221_as | 199-221 |
| AD-295661.1 | AUUAAAGGACUGACUGAAGG U | 500 | NM_000454.4_254-274_C21U_s | 254-274 | ACCUUCAGUCAGUCCUUUAAU GC | 579 | NM_000454.4_252-274_G1A_as | 252-274 |
| AD-295685.1 | CAUGAUGAGUUUGGAGA | 501 | NM_000454.4_287-307_s | 287-307 | AUCUCCAAACUCAUGAUGCAUG GA | 580 | NM_000454.4_285-307_as | 285-307 |
| AD-295688.1 | GUUCAGAGUUUGGAGAUAA U | 502 | NM_000454.4_290-310_s | 290-310 | AUUAUCUCCAAACUCAUGAAC AU | 581 | NM_000454.4_288-310_as | 288-310 |
| AD-295689.1 | UUCAGAGUUUGGAGAUAAU A | 503 | NM_000454.4_291-311_s | 291-311 | UAUUAUCUCCAAACUCAUGAA CA | 582 | NM_000454.4_289-311_as | 289-311 |
| AD-295692.1 | AUGAGUUUGGAGAUAAUACA U | 504 | NM_000454.4_294-314_s | 294-314 | AUGUAUAUCUCCAAACUCAU GA | 583 | NM_000454.4_292-314_as | 292-314 |
| AD-295795.1 | UGUGUCUAUUGAAGAUUCUG U | 505 | NM_000454.4_439-459_s | 439-459 | ACAGAAUCUUCAAUAGACACA UC | 584 | NM_000454.4_437-459_as | 437-459 |
| AD-295796.1 | GUGUCUAUUGAAGAUUCUGU U | 506 | NM_000454.4_440-460_G21U_s | 440-460 | AACAGAAUCUUCAAUAGACAC AU | 585 | NM_000454.4_438-460_as | 438-460 |
| AD-295827.1 | UGGUGGUCCAUGAAAAAGCA U | 507 | NM_001285406.1_353-373_G21U_s | 353-373 | AUGCUUUUUCAUGGACCACCA GU | 586 | NM_001285406.1 | 351-373 |
| AD-295828.1 | GGUGGUCCAUGAAAAAGCAG A | 508 | NM_001285406.1_354-374_s | 354-374 | UCUGCUUUUUCAUGGACCACC AG | 587 | NM_001285406.1 | 352-374 |

TABLE 4-continued

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-295831.1 | GAGACCAUUGCAUCAUUGGCU | 509 | NM_000454.4_474-494_s | 474-494 | AGCCAAUGAUGCAAUGGUCUCU | 588 | NM_000454.4_472-494_G1A_as | 472-494 |
| AD-295856.1 | ACUGGUGGUCCAUGAAAAGU | 510 | NM_000454.4_499-519_s | 499-519 | ACUUUUCAUGGACCACCAGUGU | 589 | NM_000454.4_497-519_G1A_as | 497-519 |
| AD-295857.1 | CUGGUGGUCCAUGAAAAAGCU | 511 | NM_000454.4_500-520_s | 500-520 | UGCUUUUCAUGGACCACCAGUG | 590 | NM_000454.4_498-520_as | 498-520 |
| AD-295858.1 | AGGUGGAAAUGAAGAAAGUAU | 512 | NM_000454.4_535-555_C21U_s | 535-555 | AUACUUUCUUCAUUUCCACCUUU | 591 | NM_000454.4_533-555_G1A_as | 533-555 |
| AD-295867.1 | GAAAGUACAAAGACAGGAAAU | 513 | NM_000454.4_548-568_C21U_s | 548-568 | AUUUCCUGUCUUUGUACUUUCUU | 592 | NM_000454.4_546-568_G1A_as | 546-568 |
| AD-295868.1 | AAAGUACAAAGACAGGAAACU | 514 | NM_000454.4_549-569_G21U_s | 549-569 | AGUUUCCUGUCUUUGUACUUUCU | 593 | NM_000454.4_547-569_G1A_as | 547-569 |
| AD-295869.1 | AAGUACAAAGACAGGAAACGU | 515 | NM_000454.4_550-570_C21U_s | 550-570 | ACGUUUCCUGUCUUUGUACUUUC | 594 | NM_000454.4_548-570_G1A_as | 548-570 |
| AD-295870.1 | AGUACAAAGACAGGAAACGCU | 516 | NM_000454.4_551-571_s | 551-571 | AGCGUUUCCUGUCUUUGUACUUU | 595 | NM_000454.4_549-571_as | 549-571 |
| AD-295871.1 | GUACAAAGACAGGAAACGCUU | 517 | NM_000454.4_552-572_G21U_s | 552-572 | AAGCGUUUCCUGUCUUUGUACUU | 596 | NM_000454.4_550-572_C1A_as | 550-572 |
| AD-295872.1 | UACAAAGACAGGAAACGCUGU | 518 | NM_000454.4_553-573_G21U_s | 553-573 | ACAGCGUUUCCUGUCUUUGUACU | 597 | NM_000454.4_551-573_C1A_as | 551-573 |
| AD-295874.1 | CAAAGACAGGAAACGCUGGAA | 519 | NM_000454.4_555-575_s | 555-575 | UUCCAGCGUUUCCUGUCUUUGUA | 598 | NM_000454.4_553-575_as | 553-575 |
| AD-295879.1 | UGGCUUGUGGUGUAAUUGGG | 520 | NM_001285406.1_434-454_s | 434-454 | UCCCAAUUACACCACAAGCCAA | 599 | NM_001285406.1_432-454_as | 432-454 |
| AD-295880.1 | GGCUUGUGGUGUAAUUGGGAU | 521 | NM_001285406.1_435-455_s | 435-455 | AUCCCAAUUACACCACAAGCCAA | 600 | NM_001285406.1_433-455_as | 433-455 |
| AD-295897.1 | GUCGUUUGGCUUGUGGUGUAA | 522 | NM_000454.4_576-596_s | 576-596 | UUACACCACAAGCCAAACGACUU | 601 | NM_000454.4_574-596_as | 574-596 |
| AD-295898.1 | UCGUUUGGCUUGUGGUGUAAU | 523 | NM_000454.4_577-597_s | 577-597 | AUUACACCACAAGCCAAACGACU | 602 | NM_000454.4_575-597_as | 575-597 |

TABLE 4-continued

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-295899.1 | CGUUUGGCUUGUGGUGUAAU U | 524 | NM_000454.4_578-598_s | 578-598 | AAUUACACCACAAGCCAAACG AC | 603 | NM_000454.4_576-598_as | 576-598 |
| AD-295900.1 | GUUUGGCUUGUGGUGUAAUU U | 525 | NM_000454.4_579-599_G21U_s | 579-599 | AAAUUACACCACAAGCCAAAC GA | 604 | NM_000454.4_577-599_C1A_as | 577-599 |
| AD-295901.1 | UUUGGCUUGUGGUGUAAUUG U | 526 | NM_000454.4_580-600_G21U_s | 580-600 | ACAAUUACACCACAAGCCAAA CG | 605 | NM_000454.4_578-600_C1A_as | 578-600 |
| AD-295902.1 | UUGGCUUGUGGUGUAAUUGG U | 527 | NM_000454.4_581-601_G21U_s | 581-601 | ACCAAUUACACCACAAGCCAA AC | 606 | NM_000454.4_579-601_C1A_as | 579-601 |
| AD-295904.1 | GUAAUUGGGAUCGCCCAAUA A | 528 | NM_000454.4_593-613_s | 593-613 | UUAUUGGGCGAUCCCAAUUAC AC | 607 | NM_000454.4_591-613_as | 591-613 |

TABLE 5

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-135962.1 | asusgacuUfgGfCfCfaaaggugaaL96 | 608 | usUfsccaCfcUfUfugccCfaAfgucauscsu | 687 | AGAUGACUUGGGCCAAAGGUGGAA | 766 |
| AD-135963.1 | usgsacuuGfgCfCfAfaaggugaaaL96 | 609 | usUfsuccAfcCfUfuugcCfcAfagucasusc | 688 | GAUGACUUGGGCCAAAGGUGGAAA | 767 |
| AD-135964.1 | gsascuugGfgCfAfAfAfaggugaaauL96 | 610 | asUfsuucCfaCfCfuuugCfcCfaaguscasu | 689 | AUGACUUGGGCCAAAGGUGGAAAU | 768 |
| AD-135967.5 | ususgggcAfaAfGfGfUfuggaaaugaaL96 | 269 | usUfscauUfuCfCfaccuUfuGfcccaasgsu | 352 | ACUUGGGCCAAAGGUGGAAAUGAA | 435 |
| AD-135974.3 | asasggugCfaAfAfUfgaagaaaguaL96 | 611 | usAfscuuUfcUfUfcauuUfcCfaccususg | 690 | CAAAGGUGGAAAUGAAGAAAGUA | 769 |
| AD-135974.3 | asasuuucGfaGfCfAfgaagaaagulaL96 | 612 | asCfsuuuCfcUfUfcugcUfgCfaaaausgsa | 691 | UCAAUUUCGAGCAGAAGGAAAGU | 770 |
| AD-266788.1 | asasuucgAfgCfAfGfAfaggaaaguaaL96 | 213 | usAfscuuUfcCfUfucugCfucGfaaaususg | 296 | CAAUUUCGAGCAGAAGGAAAGUA | 379 |
| AD-266789.2 | ususucgaGfcAfGfAfagaaaguaaauL96 | 255 | usUfsacuUfuCfCfuucuGfcUfcgaaasusu | 338 | AAUUUCGAGCAGAAGGAAAGUAA | 421 |
| AD-266790.2 | ususcgagCfaGfAfAfgaaguaauggaL96 | 212 | asUfstuacUfuUfCfcuucUfuCfugucsgsa | 295 | AUUUCGAGCAGAAGGAAAGUAAU | 378 |
| AD-266791.3 | gsasgcagAfaGfAfGfuAfaaguaauggaL96 | 613 | usCfscauUfaCfUfuuccUfuCfugcucsgsa | 692 | UCGAGCAGAAGGAAAGUAAUGGA | 771 |
| AD-266794.1 | asgsaaggAfaAfGfuAfUfaauggaccauL96 | 614 | asUfsgguCfcAfUfuacuUfuCfcuucusgsc | 693 | GCAGAAGGAAAGUAAUGGACCAG | 772 |
| AD-266798.1 | gsasaggaAfaGfuAfUfAfauggaccaguL96 | 615 | asCfsugGfCfcAfuuacUfuUfccuucsusg | 694 | CAGAAGGAAAGUAAUGGACCAGU | 773 |
| AD-266799.1 | asgsgaaaGfuAfAfUfgGfaccagugaaL96 | 616 | usCfsacuGfgUfCfcauuAfcUfuuccusuc | 695 | GAAGGAAAGUAAUGGACCAGUGA | 774 |
| AD-266801.1 | gsgsaaaagUfaAfUfGfgaccagugaaL96 | 617 | usUfscacUfgGfUfccauUfaCfuuuccsusu | 696 | AAGGAAAGUAAUGGACCAGUGAA | 775 |
| AD-266802.1 | gsasaaguAfaUfGfGfaccagugaauL96 | 618 | asUfsucaCfuGfGfuccaUfuAfcuuucscsu | 697 | AGGAAAGUAAUGGACCAGUGAAG | 776 |
| AD-266803.1 | asasaguaAfuGfGfAfccagugaaguL96 | 619 | asCfsuucAfcUfGfGfguccAfuUfacuuuscsc | 698 | GGAAAGUAAUGGACCAGUGAAGG | 777 |
| AD-266804.1 | asasaguaaUfgGfAfCfcagugaaguuL96 | 620 | asCfstccuUfcAfCfUfggucCfaUfuacususc | 699 | GAAAGUAAUGGACCAGUGAAGGU | 778 |
| AD-266805.1 | asgsuaauGfgAfCfCfagugaagguuL96 | 621 | asCfsccuUfcAfCfuugguCfcAfuuacusus | 700 | AAAGUAAUGGACCAGUGAAGGUG | 779 |
| AD-266806.1 | usasauggGfaCfCfAfgugaagguguL96 | 259 | asAfscacCfuUfCfacugGfuCfcauuascsu | 342 | AGUAAUGGACCAGUGAAGGUGUG | 425 |
| AD-266808.2 | usgsaaggCfcUfGfCfaugaauccaL96 | 622 | usGfsgaaUfcCfAfaugcaGffCfcuucasgsu | 701 | ACUGAAGGCCUGCAUGGAUUCCA | 780 |
| AD-266832.1 | gsasaggcCfuGfCfAfUfggauuccauL96 | 623 | asUfsggaAfucCfCfaugcAfgGfccuucsasg | 702 | CUGAAGGCCUGCAUGGAUUCCAU | 781 |
| AD-266834.1 | asgsgccuGfcAfUfGfgauuccaugL96 | 624 | asCfsauGfgAfAfUfCfcauGfcAfggccususc | 703 | GAAGGCCUGCAUGGAUUCCAUGU | 782 |
| AD-266836.1 | gsgsccugCfaUfGfGfauuccaugulL96 | 625 | asAfscaugGfaAfuccaUfgfaggccsusu | 704 | AAGGCCUGCAUGGAUUCCAUGUU | 783 |

TABLE 5-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-266838.1 | gscscugcAfuGfGfAfuuccauguuuL96 | 626 | asAfsacaUfgGfAfauccAfuGfcaggcscsu | 705 | AGCCUGCAUGGAUCCAUGUUC | 784 |
| AD-266839.1 | cscsugcaUfgGfAfUfuccauguucaL96 | 627 | usGfsaacAfuGfGfaaucCfaUfgcaggscsc | 706 | GGCCUGCAUGGAUUCCAUGUUCA | 785 |
| AD-266840.1 | csusgcaUfgGfAfUfUfccauguucauL96 | 628 | asUfsgaaCfaUfGfgaauCfAfugcagsgsc | 707 | GCCUGCAUGGAUUCCAUGUUCAU | 786 |
| AD-266841.3 | usgscaugGfaUfUfCfcauguucauuL96 | 265 | asUfsugaAfcAfUfggaaUfCfaugcasgsg | 348 | CCUGCAUGGAUUCCAUGUUCAUC | 431 |
| AD-266886.2 | ascscaguGfcAfGfGfuccucacuuuL96 | 209 | asAfsaguGfaGfGfaccuGfAfcuggusasc | 292 | GUACCAGUGCAGGUCCUCACUUU | 375 |
| AD-266887.3 | cscsagugCfaGfGfUfccucacuuuaL96 | 241 | usAfsaagUfgAfGfgaccUfgCfacuggsusa | 324 | UACCAGUGCAGGUCCUCACUUUA | 407 |
| AD-266888.2 | csaasgugCfaGfGfUfCfcucacuuuaaL96 | 220 | usUfsaaaGfuGfAfggacCfuGfcacugsgsu | 303 | ACCAGUGCAGGUCCUCACUUUAA | 386 |
| AD-266890.3 | gsusgcagGfuCfCfUfcacuuuaauuL96 | 258 | asAfsuuaAfaGfUfgaggAfcCfugcacsusg | 341 | CAGUGCAGGUCCUCACUUUAAUC | 424 |
| AD-266891.2 | usgscaggUfcCfUfCfacuuuaaucuL96 | 205 | asGfsauuAfaAfAfGfugagGfaCfcugcasac | 288 | AGUGCAGGUCCUCACUUUAAUCC | 371 |
| AD-266892.2 | gscsaggUfCfCfUfCfAfcuuuaauccuL96 | 263 | asGfsgauUfaAfAfAfgugaGfgAfccugcsasc | 346 | GUGCAGGUCCUCACUUUAAUCCU | 429 |
| AD-266899.2 | csuscacuUfaAfAfUfccucuaucccaL96 | 216 | usGfsgauAfgGfAfgauuAfaAfgugasgsga | 299 | UCCUCACUUUAAUCCUCUAUCCA | 382 |
| AD-266900.3 | uscsacuuUfaAfUfCfcucuauccauL96 | 248 | usUfsggaAfuAfGfAfggauUfaAfaagusgsag | 331 | CCUCACUUUAAUCCUCUAUCCAG | 414 |
| AD-266901.2 | csasucuuUfaAfUfCfCfucuauccagaL96 | 237 | usCfsuggAfuAfGfAfggaaUfUfaaagusgsu | 320 | CUCACUUUAAUCCUCUAUCCAGA | 403 |
| AD-266928.1 | gsgsugggCfcAfAfAfgagaugaagauL96 | 629 | asUfscuuCfaUfCfccuuuGfgCfccaccsgsu | 708 | ACGGUGGCCAAAGGAUGAAGAG | 787 |
| AD-266934.1 | gsaasugaaGfaUfGfAfAfgagagaggcauL96 | 630 | usCfsatgCfcUfCfuCfuCfcuuugsgsc | 709 | AGGAUGAAGAGAGGCAUGUUGA | 788 |
| AD-266936.1 | csasaaggAfuGfAfAfgagaggcauuL96 | 631 | asAfsatgCfcUfCfUfcuucAfuCfcuuugsgsc | 710 | GCCAAAGGAUGAAGAGAGGCAUG | 789 |
| AD-266938.1 | asasaggauGfaUfGfAfAfgaggcauguuL96 | 632 | asAfscauGfcCfuCfucuuCfAfuccusususg | 711 | CAAAGGAUGAAGAGAGGCAUGUU | 790 |
| AD-266939.1 | asgsgaugAfaGfAfGfaggcaugugguL96 | 633 | asAfsacaAfuGfCfcucuCfuUfcauccsusu | 712 | AAAGGAUGAAGAGAGGCAUGUUG | 791 |
| AD-266940.1 | gsgsaugaAfgAfGfAfggcaugugugL96 | 634 | asCfsaacAfuGfCfCfucuCfuUfcauccsusu | 713 | AAGGAUGAAGAGAGGCAUGUUGG | 792 |
| AD-266941.1 | asusgaagAfgAfGfGfcaugugugacuL96 | 635 | asUfsccaAfcAfUfgccuCfuCfuuucasusc | 714 | GGAUGAAGAGAGGCAUGUUGGAG | 793 |
| AD-266943.1 | asasgagaGfgCfaUfGfUfugggagacuL96 | 636 | asGfsucuCfcAfAfcaugCfCfucucuusca | 715 | UGAAGAGAGGCAUGUUGGAGACC | 794 |
| AD-267035.1 | gsasugacUfuGfGfCfcaaaggugguaL96 | 637 | usCfscaccCfuUfUfgccAfAfgucaucsusg | 716 | CAGAUGACUUGGCCAAAGGUGA | 795 |
| AD-267058.1 | gsusggguCffuUfGfafaaagcagauL96 | 638 | asUfscugCfuUfUfucaAfGfaccaccsca | 717 | UGGUGGUCCAUGAAAAGCAGAU | 796 |
| AD-267059.1 | usgsguccAfuGfAfAfaaagcagauuL96 | 639 | asAfsucuGfcUfUfuucAfuGfgaccascsc | 718 | GGUGGUCCAUGAAAAGCAGAUG | 797 |

TABLE 5-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-267060.1 | gsgsuccaUfgAfAfAfaagcagaugaL96 | 640 | uscCfsaucUfgCfUfuuuuCfaUfggaccsasc | 719 | GUGGUCCAUGAAAAGCAGAUGA | 798 |
| AD-267073.1 | gscsagauGfaCfUfUfgggcaaaggUfL96 | 641 | acCfscuuUfgCfCfcaagUfcAfucugcsusu | 720 | AAGCAGAUGACUUGGGCAAAGGU | 799 |
| AD-267075.1 | asgsaugaCfuUfGfGfGfgcaaaggugUfL96 | 642 | asCfsaccUfuUfGfcccaAfgUfcaucusgsc | 721 | GCAGAUGACUUGGGCAAAGGUGG | 800 |
| AD-267076.1 | ascsuuggGfcAfAfAfggguugaaauuL96 | 643 | aaAfsuuuCfcAfCfcuuuGfcCfcaaguscsa | 722 | UGACUUGGGCAAAGGUGCAAAUG | 801 |
| AD-267118.1 | gscsuugGfgUfGfUfAfaauuggauuL96 | 644 | asAfsuccCfaAfUfuacaCfcAfcaagcscsa | 723 | UGGCUUGUGUGUAAUUGGGAUC | 802 |
| AD-267119.1 | csusugugGfuGfUfAfauugggaucuL96 | 645 | asGfsaucCfcAfAfuuacAfcCfacaagscsc | 724 | GGCUUGUGUGUAAUUGGGAUCG | 803 |
| AD-267120.1 | ususguggUfuAfAfUfuugggaucguUL96 | 646 | acCfsgauCfcCfAfauuaCfaCfacaasgsc | 725 | GCUUGUGUGUAAUUGGGAUCGC | 804 |
| AD-267121.1 | ususguggUfaAfAfUfugggaucgccL96 | 647 | asGfscgaUfcCfCfaauuAfcAfccacasasg | 726 | CUUGUGUGUAAUUGGGAUCGCC | 805 |
| AD-267122.1 | gsusgugUfaAfUfUfGfggaucgccuL96 | 648 | asGfsgcgAfuCfCfcaauUfaCffaccacasa | 727 | UUGUGUGUAAUUGGGAUCGCCC | 806 |
| AD-267644.1 | usgscaggGfcAfUfCfaucaauuucuL96 | 649 | asGfsaaaUfuGfAfugauGfcCfcugcascsu | 728 | AGUGCAGGGCAUCAUCAUUUCG | 807 |
| AD-267645.1 | gscsaggGfcAfUfCfAfucaauucgaL96 | 650 | usCfsgaaAfuUfGfaugaUfGfccugscsa | 729 | GUGCAGGGCAUCAUCAUUUCGA | 808 |
| AD-267646.1 | csasgggcAfUfCfAfUfcaauucgagL96 | 651 | asCfscgaAfuUfGfaugAfuGfccugsgsc | 730 | UGCAGGGCAUCAUCAUUUCGAG | 809 |
| AD-267647.1 | asgsggcaUfCfAfUfCfaauuucgagcL96 | 652 | usGfsucgAfaAfUfgauUfgAfugaugsc | 731 | GCAGGGCAUCAUCAUUUCGAGC | 810 |
| AD-267648.1 | gsgsgcauCfaUfCfAfuuucgagcauL96 | 653 | usGfscucGfaAfAfuugaUfgAfugcccsusg | 732 | CAGGGCAUCAUCAUUUCGAGCA | 811 |
| AD-267649.1 | gsgsgcauCfaUfCfAfUfuucgagcauL96 | 654 | asUfsgcuCfgAfAfauuAfgUfAfugccsscsu | 733 | AGGGCAUCAUCAUUUCGAGCAG | 812 |
| AD-267651.1 | csasucauCfaAfUfUfucgagcagaaL96 | 655 | usUfscugCfucCfGfaaauUfgAfugaugcsc | 734 | GGCAUCAAUUUCGAGCAGAA | 813 |
| AD-267652.1 | asusucauCfaAfUfUfUfcgagcagaaguL96 | 656 | asUfsucuGfcUfCfgaaaUfUfgAfugausgc | 735 | GCAUCAAUUUCGAGCAGAAG | 814 |
| AD-267653.1 | uscsaucaAfuUfUfCfgagcagaagcL96 | 657 | asCfsuucUfgCfUfcgaaAfUfugAfuausg | 736 | CAUCAAUUUCGAGCAGAAGC | 815 |
| AD-267661.1 | asusuaaAfgGfAfCfUfgacugaagguL96 | 658 | asCfscuuCfaGfUfcaguCfcuUfuauausg | 737 | GCAUUAAGGACUGACUGAAGGC | 816 |
| AD-267685.1 | csasuguuCfaUfGfAfguuuggagauL96 | 659 | asUfscauCfucUfcAfaaacUfgAfacaugsga | 738 | UCCAUGUUCAUGAGUUUGGAGAU | 817 |
| AD-267688.1 | gsusuucauGfaUfUfggagauauauL96 | 660 | asUfsuauCfucCfCfaaacUfcAfugaacsau | 739 | AUGUUCAUGAGUUUGGAGAUAU | 818 |
| AD-267689.1 | ususcaugAfgUfUfUfGfgagauauauacL96 | 661 | usAfsuauAfuCfUfCfcaaaCfucUfaugaascsa | 740 | UGUUCAUGAGUUUGGAGAUAUA | 819 |
| AD-267692.1 | asusgaguUfuGfGfAfgauauacauL96 | 662 | asUfsguaUfuAfUfUfcuccAfaAfcucausga | 741 | VCAUGAGUUUGGAGAUAUAUACAG | 820 |
| AD-267795.1 | usgsuguCfuAfUfUfgAfaagauucguL96 | 663 | asCfsagaAfuCfUfucaaUfaGfacacasusc | 742 | GAUGUGUCUAUUGAAGAUUCGU | 821 |

TABLE 5-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-295796.1 | gsusgucuAfuUfGfAfagauucuguuL96 | 664 | asGfscagAfaUfCfuucaAfuAfgacacsasu | 743 | AUGUGUCCUAUUGAAGAUUCUGUG | 822 |
| AD-295827.1 | usgsguggUfcCfAfUfgaaaaagcauL96 | 665 | asUfsgcuUfuUfUfucaugGfaCfcaccasgsu | 744 | ACUGGUGGUCCAUGAAAAAGCAU | 823 |
| AD-295828.1 | gsgsuggGfuCfcAfUfGfaaaaagcagaL96 | 666 | usCfsugcUfuGfUfUfucauGfgAfccaccsasg | 745 | CUGGUGGUCCAUGAAAAAGCAGA | 824 |
| AD-295831.1 | gsasgaccAfuUfGfCfcaucauuggcuL96 | 667 | gsCfscaaAfuGfGfucaAfugGfgucccscsu | 746 | AGGAGACCAUUGCCAUCAUUGGCC | 825 |
| AD-295856.1 | ascsugguGfgUfCfCfaugaaaaaguL96 | 668 | asCfsuuuUfuCfAfuggaCfcAfccagusgsu | 747 | ACACUGGUGGUCCAUGAAAAAGC | 826 |
| AD-295857.1 | csusggugGfuCfCfAfugaaaaagcaL96 | 669 | usGfscuuUfuUfCfauggAfcCfaccagsusg | 748 | CACUGGUGGUCCAUGAAAAAGCA | 827 |
| AD-295858.1 | asggguggAfaAfUfGfaagaaguauL96 | 670 | asUfsacuUfuCfUfucauUfucCfcaccususu | 749 | AAAGGUGAAAUGAAGAAGUAC | 828 |
| AD-295867.1 | gsasaaguAfcAfAfAfgacaggaaauL96 | 671 | asUfsuucCfuGfUfcuuuGfuAfcuuuscsu | 750 | AAGAAAGUACAAAGACAGGAAAC | 829 |
| AD-295868.1 | asasaguaCfaAfAfGfacaggaaacuL96 | 672 | asGfsuuuCfcUfGfucuuUfgUfacuusucsu | 751 | AGAAAGUACAAAGACAGGAAACG | 830 |
| AD-295869.1 | asasguacAfaAfGfAfcaggaaacgcuL96 | 673 | asCfsguuUfccCfUfGfucuUfuGfuacuusuc | 752 | GAAAGUACAAAGACAGGAAACGC | 831 |
| AD-295870.1 | asgsuacaAfaGfAfCfaggaaacgcuL96 | 674 | asGfscguUfuCfCfuguCfuUfguacususu | 753 | AAAGUACAAAGACAGGAAACGCU | 832 |
| AD-295871.1 | gsusacaaAfgAfCfAfGfggaaacgcuuL96 | 675 | asAfsgcgUfuUfCfcuguCfuUfuguacsusu | 754 | AAGUACAAAGACAGGAAACGCUG | 833 |
| AD-295872.1 | usascaaaGfaCfAfAfGfgaaacgcuguL96 | 676 | asCfsagcGfuUfUfccugUfcUfuuguascsu | 755 | AGUACAAAGACAGGAAACGCUGG | 834 |
| AD-295874.1 | csasaagaCfaGfGfAfAfaacgcuguaaL96 | 677 | usUfsccaGfcGfUfuuccUfgUfcuuugsusa | 756 | UACAAAGACAGGAAACCUGGAA | 835 |
| AD-295879.1 | usgsgcuuGfuGfUfGfuaauugggaL96 | 678 | usCfsccaAfuUfAfcaccAfaGfagccasasa | 757 | UUUGGCUUGUGUGUAAUUGGGA | 836 |
| AD-295880.1 | gsgscuugUfgGfUfGfuaauugggauL96 | 679 | asUfsccaAfuUfAfcacCfaCfaagccasa | 758 | UUGGCUUGUGUGUAAUUGGGAU | 837 |
| AD-295897.1 | gsuscguuUfgGfCfUfugugugaaL96 | 680 | usUfsacaCffaCfCfaagcCfaAfacacsu | 759 | AAGCGUUUGGCUUGUGUGUAA | 838 |
| AD-295898.1 | ascsguuuGfgCfUfUfgugugaaL96 | 681 | asUfsuaCfCfAfCfaagCfCfaAfaacgascu | 760 | AGUCGUUUGGCUUGUGUGUAAU | 839 |
| AD-295899.1 | csgsuuuGfgCfUfUfgugugaaauuL96 | 682 | asAfsuuaCfaCfCfacaaGfcCfaaacgsas | 761 | GUCGUUUGGCUUGUGUGUAAUU | 840 |
| AD-295900.1 | gsusuuggCfuUfgUfgUfguaauuuL96 | 683 | asAfsauuAfcAfCfcacaAfgCfcaaacsgsa | 762 | UCGUUUGGCUUGUGUGUAAUUG | 841 |
| AD-295901.1 | ususuggCfUfUfgUfgUfguaauuggL96 | 684 | asCfsaauUfaCfAfCfcacaAfgCfcaaacsg | 763 | CGUUUGGCUUGUGUGUAAUUGG | 842 |
| AD-295902.1 | ususuggcUfUfGfUfgfuguaauugguL96 | 685 | asCfscaaUfuAfCffaccaCfAfagccaasasc | 764 | GUUUGGCUUGUGUGUAAUUGGG | 843 |
| AD-295904.1 | gsusaauuGfgGfCfAfUfcgcccaauaaL96 | 686 | usUfsauuGfgGfCfgaucCffgaauuacsasc | 765 | GUGUAAUUGGGAUCGCCCAAUAA | 844 |

TABLE 6

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-301535.1 | UGCAGGGCAUCAUCAAUUUCU | 491 | NM_000454.4_192-212_G21U_s | 192-212 | AGAAAUTGAUGAUGCCCUGCACU | 846 | NM_000454.4_190-212_C1A_as | 190-212 |
| AD-301536.1 | GCAGGGCAUCAUCAAUUUCGA | 492 | NM_000454.4_193-213_s | 193-213 | UCGAAAUUGAUGAUGCCCUGCAC | 847 | NM_000454.4_191-213_as | 191-213 |
| AD-301537.1 | CAGGGCAUCAUCAAUUUCGAU | 493 | NM_000454.4_194-214_G21U_s | 194-214 | AUCGAAAUUGAUGAUGCCCUGCA | 572 | NM_000454.4_192-214_C1A_as | 192-214 |
| AD-301538.1 | AGGGCAUCAUCAAUUUCGAGU | 494 | NM_000454.4_195-215_C21U_s | 195-215 | ACUCGAAAUUGAUGAUGCCCUGC | 573 | NM_000454.4_193-215_G1A_as | 193-215 |
| AD-301539.1 | GGGCAUCAUCAAUUUCGAGCA | 495 | NM_000454.4_196-216_s | 196-216 | UGCUCGAAAUUGAUGAUGCCCUG | 574 | NM_000454.4_194-216_as | 194-216 |
| AD-301540.1 | GGCAUCAUCAAUUUCGAGCAU | 496 | NM_000454.4_197-217_G21U_s | 197-217 | AUGCUCGAAAUUGAUGAUGCCCU | 575 | NM_000454.4_195-217_C1A_as | 195-217 |
| AD-301542.1 | CAUCAUCAAUUUCGAGCAGAA | 497 | NM_000454.4_199-219_s | 199-219 | UUCUGCUCGAAAUGAUGAUGCC | 848 | NM_000454.4_197-219_as | 197-219 |
| AD-301543.1 | AUCAUCAAUUUCGAGCAGAAU | 498 | NM_000454.4_200-220_G21U_s | 200-220 | AUUCUGCUCGAAAUUGAUGAUGC | 577 | NM_000454.4_198-220_C1A_as | 198-220 |
| AD-301544.1 | UCAUCAAUUUCGAGCAGAAGU | 499 | NM_000454.4_201-221_G21U_s | 201-221 | ACUUCUGCUCGAAAUUGAUGAUG | 578 | NM_000454.4_199-221_C1A_as | 199-221 |
| AD-301549.1 | AAUUUCGAGCAGAAGGAAAGU | 454 | NM_001285406.1_58-78_s | 58-78 | ACUUUCCUUCUGCUCGAAAUUGA | 533 | NM_001285406.1 | 56-78 |
| AD-301550.1 | AUUUCGAGCAGAAGGAAAGUA | 47 | NM_001285406.1_59-79_s | 59-79 | UACUUUCCUUCUGCUCGAAAUUG | 130 | NM_001285406.1 | 57-79 |
| AD-301551.1 | UUUCGAGCAGAAGGAAAGUAA | 89 | NM_001285406.1_60-80_s | 60-80 | UUACUUUCCUUCUGCUCGAAAUU | 849 | NM_001285406.1 | 58-80 |
| AD-301552.1 | UUCGAGCAGAAGGAAAGUAAU | 46 | NM_001285406.1_61-81_s | 61-81 | AUUACUUUCCUUCUGCUCGAAAU | 850 | NM_001285406.1 | 59-81 |
| AD-301555.1 | GAGCAGAAGGAAAGUAAUGGA | 455 | NM_001285406.1_164-84_s | 64-84 | UCCAUUACUUUCCUUCUGCUCGA | 534 | NM_001285406.1 | 62-84 |

TABLE 6-continued

Unmodified Sense and Antisense Strand Sequences of Superoxide Dismutase 1 dsRNAAgents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-301559.1 | AGAAGGAAAGUAAUGGACCAU | 456 | NM_001285406.1_168-88_G21U_s | 68-88 | AUGGUCCAUUACUUUCCUUCUGC | 535 | NM_001285406.1 | 66-88 |
| AD-301560.1 | GAAGGAAAGUAAUGGACCAGU | 457 | NM_001285406.1_169-89_s | 69-89 | ACUGGUCCAUUACUUUCCUUCUG | 536 | NM_001285406.1 | 67-89 |
| AD-301562.1 | AGGAAAGUAAUGGACCAGUGA | 458 | NM_001285406.1_171-91_s | 71-91 | UCACUGGUCCAUUACUUUCCUUC | 537 | NM_001285406.1 | 69-91 |
| AD-301563.1 | GGAAAGUAAUGGACCAGUGAA | 459 | NM_001285406.1_172-92_s | 72-92 | UUCACUGGUCCAUUACUUUCCUU | 538 | NM_001285406.1 | 70-92 |
| AD-301564.1 | GAAAGUAAUGGACCAGUGAAU | 460 | NM_001285406.1_73-93_G21U_s | 73-93 | AUUCACUGGUCCAUUACUUUCCU | 851 | NM_001285406.1 | 71-93 |
| AD-301565.1 | AAAGUAAUGGACCAGUGAAGU | 461 | NM_001285406.1_74-94_G21U_s | 74-94 | ACUUCACUGGUCCAUUACUUUCC | 540 | NM_001285406.1 | 72-94 |
| AD-301566.1 | AAGUAAUGGACCAGUGAAGGU | 462 | NM_001285406.1_75-95_s | 75-95 | ACCUUCACUGGUCCAUUACUUUC | 541 | NM_001285406.1 | 73-95 |
| AD-301567.1 | AGUAAUGGACCAGUGAAGGUU | 463 | NM_001285406.1_76-96_G21U_s | 76-96 | AACCUUCACUGGUCCAUUACUUU | 542 | NM_001285406.1 | 74-96 |
| AD-301569.1 | UAAUGGACCAGUGAAGGUGUU | 93 | NM_001285406.1_78-98_G21U_s | 78-98 | AANACCUUCACUGGUCCAUUACU | 852 | NM_001285406.1 | 76-98 |
| AD-301579.1 | AUUAAAGGACUGAAGGUGAAGGU | 500 | NM_000454.4_254-274_C21U_s | 254-274 | ACCUUCAGUCAGUCCUUUAAUGC | 579 | NM_000454.4_252-274_G1A_as | 252-274 |
| AD-301593.1 | UGAAGGCCUGCAUGGAUUCCA | 464 | NM_001285406.1_120-140_s | 120-140 | UGGAAUCCAUGCAGGCCUUCAGU | 543 | NM_001285406.1 | 118-140 |
| AD-301594.1 | GAAGGCCUGCAUGGAUUCCAU | 465 | NM_001285406.1_121-141_s | 121-141 | AUGGAAUCCAUGCAGGCCUUCAG | 853 | NM_001285406.1 | 119-141 |
| AD-301596.1 | AGGCCUGCAUGGAUUCCAUGU | 466 | NM_001285406.1_123-143_s | 123-143 | ACAUGGAAUCCAUGCAGGCCUUC | 545 | NM_001285406.1 | 121-143 |
| AD-301597.1 | GGCCUGCAUGGAUUCCAUGUU | 467 | NM_001285406.1_124-144_s | 124-144 | AACAUGGAAUCCAUGCAGGCCUU | 546 | NM_001285406.1 | 122-144 |
| AD-301598.1 | GCCUGCAUGGAUUCCAUGUUU | 468 | NM_001285406.1_125-145_C21U_s | 125-145 | AAACAUGGAAUCCAUGCAGGCCU | 547 | NM_001285406.1 | 123-145 |

TABLE 6-continued

Unmodified Sense and Antisense Strand Sequences of Superoxide Dismutase 1 dsRNAAgents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-301599.1 | CCUGCAUGGAUUCCAUGUUCA | 469 | NM_001285406.1_126-146_s | 126-146 | UGAACAUGGAAUCCAUGCAGGCC | 854 | NM_001285406.1 | 124-146 |
| AD-301600.1 | CUGCAUGGAUUCCAUGUUCAU | 470 | NM_001285406.1_127-147_s | 127-147 | AUGAACAUGGAAUCCAUGCAGGC | 549 | NM_001285406.1 | 125-147 |
| AD-301601.1 | UGCAUGGAUUCCAUGUUCAUU | 99 | NM_001285406.1_128-148_C21U_s | 128-148 | AAUGAACAUGGAAUCCAUGCAGG | 182 | NM_001285406.1 | 126-148 |
| AD-301612.1 | CAUGUUCAUGAGUUUGGAGAU | 501 | NM_000454.4_287-307_s | 287-307 | AUCUCCAAACUCAUGAACAUGGA | 580 | NM_000454.4_285-307_as | 285-307 |
| AD-301615.1 | GUUCAUGAGUUUGGAGAUAAU | 502 | NM_000454.4_290-310_s | 290-310 | AUUAUCUCCAAACUCAUGAACAU | 855 | NM_000454.4_288-310_as | 288-310 |
| AD-301616.1 | UUCAUGAGUUUGGAGAUAAUA | 503 | NM_000454.4_291-311_s | 291-311 | UAUUAUCUCCAAACUCAUGAACA | 582 | NM_000454.4_289-311_as | 289-311 |
| AD-301619.1 | AUGAGUUUGGAGAUAAUACAU | 504 | NM_000454.4_294-314_G21U_s | 294-314 | AUGUAUUAUCUCCAAACUCAUGA | 856 | NM_000454.4_292-314_C1A_as | 292-314 |
| AD-301648.1 | ACCAGUGCAGGUCCUCACUUU | 43 | NM_001285406.1_175-195_s | 175-195 | AAAGUGAGGACCUGCACUGGUAC | 126 | NM_001285406.1 | 173-195 |
| AD-301649.1 | CCAGUGCAGGUCCUCACUUUA | 75 | NM_001285406.1_176-196_s | 176-196 | UAAAGUGAGGACCUGCACUGGUA | 158 | NM_001285406.1 | 174-196 |
| AD-301650.1 | CAGUGCAGGUCCUCACUUUAA | 54 | NM_001285406.1_177-197_s | 177-197 | UUAAAGUGAGGACCUGCACUGGU | 857 | NM_001285406.1 | 175-197 |
| AD-301652.1 | GUGCAGGUCCUCACUUUAAUU | 92 | NM_001285406.1_179-199_C21U_s | 179-199 | AAUUAAAGUGAGGACCUGCACUG | 175 | NM_001285406.1 | 177-199 |
| AD-301653.1 | UGCAGGUCCUCACUUUAAUCU | 39 | NM_001285406.1_180-200_C21U_s | 180-200 | AGAUUAAAGUGAGGACCUGCACU | 122 | NM_001285406.1 | 178-200 |
| AD-301654.1 | GCAGGUCCUCACUUUAAUCCU | 97 | NM_001285406.1_181-201_s | 181-201 | AGGAUUAAAGUGAGGACCUGCAC | 180 | NM_001285406.1 | 179-201 |
| AD-301661.1 | CUCACUUUAAUCCUCUAUCCA | 50 | NM_001285406.1_188-208_s | 188-208 | UGGAUAGAGGAUUAAAGUGAGGA | 133 | NM_001285406.1 | 186-208 |
| AD-301662.1 | UCACUUUAAUCCUCUAUCCAU | 82 | NM_001285406.1_189-209_G21U_s | 189-209 | AUGGAUAGAGGAUUAAAGUGAGG | 165 | NM_001285406.1 | 187-209 |

TABLE 6-continued

Unmodified Sense and Antisense Strand Sequences of Superoxide Dismutase 1 dsRNAAgents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-301663.1 | CACUUUAAUCUCUAUCCAGA | 71 | NM_001285406.1_190-210_s | 190-210 | UCUGGAUAGAGGAUUAAAGUGAG | 858 | NM_001285406.1 | 188-210 |
| AD-301688.1 | ACGUGGGCCAAAGGAUGAAU | 845 | NM_001285406.1_215-235_G21U_s | 215-235 | AUUCAUCCUUUGGCCCACCGUGU | 859 | NM_001285406.1 | 213-235 |
| AD-301690.1 | GGUGGGCCAAAGGAUGAAGAU | 471 | NM_001285406.1_217-237_G21U_s | 217-237 | AUCUUCAUCCUUUGGCCCACCGU | 550 | NM_001285406.1 | 215-237 |
| AD-301697.1 | CAAAGGAUGAAGAGAGGCAUU | 473 | NM_001285406.1_224-244_G21U_s | 224-244 | AAUGCCUCUCUUCAUCCUUUGGC | 860 | NM_001285406.1 | 222-244 |
| AD-301699.1 | AAGGAUGAAGAGAGGCAUGUU | 474 | NM_001285406.1_226-246_s | 226-246 | AACAUGCCUCUCUUCAUCCUUUG | 553 | NM_001285406.1 | 224-246 |
| AD-301700.1 | AGGAUGAAGAGAGGCAUGUUU | 475 | NM_001285406.1_227-247_G21U_s | 227-247 | AAACAUGCCUCUCUUCAUCCUUU | 554 | NM_001285406.1 | 225-247 |
| AD-301701.1 | GGAUGAAGAGAGGCAUGUUGU | 476 | NM_001285406.1_228-248_G21U_s | 228-248 | ACAACAUGCCUCUCUUCAUCCUU | 861 | NM_001285406.1 | 226-248 |
| AD-301702.1 | GAUGAAGAGAGGCAUGUUGGA | 472 | NM_011434.1_345-365_s | 345-365 | UCCAACAUGCCUCUCUUCAUCCU | 551 | NM_000454.4 | 304-326 |
| AD-301703.1 | AUGAAGAGAGGCAUGUUGGAU | 477 | NM_001285406.1-230-250_G21U_s | 230-250 | AUCCAACAUGCCUCUCUUCAUCC | 556 | NM_001285406.1 | 228-250 |
| AD-301706.1 | AAGAGAGGCAUGUUGGAGACU | 478 | NM_001285406.1_233-253_C21U_s | 233-253 | AGUCUCCAACAUGCCUCUCUUCA | 557 | NM_001285406.1 | 231-253 |
| AD-301764.1 | UGUGUCUAUUGAAGAUUCUGU | 505 | NM_000454.4_439-459s | 439-459 | ACAGAAUCUUCAAUAGACACAUC | 862 | NM_000454.4_437-459_as | 437-459 |
| AD-301765.1 | GUGUCUAUUGAAGAUUCUGUU | 506 | NM_000454.4_440-460_G21U_s | 440-460 | AACAGAAUCUUCAAUAGACACAU | 585 | NM_000454.4_438-460_C1A_as | 438-460 |
| AD-301799.1 | GAGACCAUUGCAUUGCU | 509 | NM_000454.4_474-494_C21U_s | 474-494 | AGCCAAUGAUGCAUGGUCUCCU | 863 | NM_000454.4_472-494_G1A_as | 472-494 |
| AD-301824.1 | ACUGUGGUCCAUGAAAAGU | 510 | NM_000454.4_499-519_C21U_s | 499-519 | ACUUUUUCAUGGACCACAGUGU | 864 | NM_000454.4_497-519_G1A_as | 497-519 |
| AD-301825.1 | CUGUGGUCCAUGAAAAGCA | 511 | NM_000454.4_500-520_s | 500-520 | UGCUUUUCAUGGACCACAGUG | 865 | NM_000454.4_498-520_as | 498-520 |

TABLE 6-continued

Unmodified Sense and Antisense Strand Sequences of Superoxide Dismutase 1 dsRNAiAgents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-301826.1 | UGGUGGUCCAUGAAAAAGCAU | 507 | NM_001285406.1_353-373_G21U_s | 353-373 | AUGCUUUUCAUGGACCACCAGU | 866 | NM_000454.4_499-521_C1A_as | 351-373 |
| AD-301827.1 | GGUGGUCCAUGAAAAAGCAGA | 508 | NM_001285406.1_354-374_s | 354-374 | UCUGCUUUUCAUGGACCACCAG | 867 | NM_000454.4_500-522_as | 352-374 |
| AD-301828.1 | GUGGUCCAUGAAAAAGCAGAU | 480 | NM_001285406.1_355-375_s | 355-375 | AUCUGCUUUUCAUGGACCACCA | 868 | NM_001285406.1 | 353-375 |
| AD-301829.1 | UGGUCCAUGAAAAAGCAGAUU | 481 | NM_001285406.1_356-376_G21U_s | 356-376 | AAUCUGCUUUUCAUGGACCACC | 560 | NM_001285406.1 | 354-376 |
| AD-301830.1 | GGUCCAUGAAAAAGCAGAUGA | 482 | NM_001285406.1_357-377_s | 357-377 | UCAUCUGCUUUUCAUGGACCAC | 561 | NM_001285406.1 | 355-377 |
| AD-301843.1 | GCAGAUGACUUGGGCAAAGGU | 483 | NM_001285406.1_370-390_s | 370-390 | ACCUUUGCCCAAGUCAUCUGCU | 562 | NM_001285406.1 | 368-390 |
| AD-301845.1 | AGAUGACUUGGGCAAAGGUGU | 484 | NM_001285406.1_372-392_G21U_s | 372-392 | ACACCUUUGCCCAAGUCAUCUGC | 869 | NM_001285406.1 | 370-392 |
| AD-301846.1 | GAUGACUUGGGCAAAGGUGGA | 479 | NM_011434.1_489-509_s | 489-509 | UCCACCUUUGCCCAAGUCAUCUG | 870 | NM_011434.1 | 486-509 |
| AD-301847.1 | AUGACUUGGGCAAAGGUGGAA | 450 | NM_011434.1_490-510_s | 490-510 | UUCCACCUUUGCCCAAGUCAUCU | 529 | NM_011434.1 | 488-510 |
| AD-301848.1 | UGACUUGGGCAAAGGUGGAAA | 451 | NM_011434.1_491-511_s | 491-511 | UUUCCACCUUUGCCCAAGUCAUC | 530 | NM_011434.1 | 489-511 |
| AD-301849.1 | GACUUGGGCAAAGGUGGAAAU | 452 | NM_011434.1_492-512_s | 492-512 | AUUUCCACCUUUGCCCAAGUCAU | 531 | NM_011434.1 | 490-512 |
| AD-301850.1 | ACUUGGGCAAAGGUGGAAAUU | 485 | NM_011434.1_377-397_G21U_s | 377-397 | AAUUUCCACCUUUGCCCAAGUCA | 564 | NM_001285406.1 | 375-397 |
| AD-301852.1 | UUGGGCAAAGGUGGAAAUGAA | 103 | NM_011434.1_495-515_s | 495-515 | UUCAUUUCCACCUUUGCCCAAGU | 871 | NM_011434.1 | 493-515 |
| AD-301859.1 | AAGGUGGAAAUGAAGAAAGUA | 453 | NM_011434.1_502-522_s | 502-522 | UACUUUCUUCAUUUCCACCUUUG | 532 | NM_011434.1 | 500-522 |
| AD-301860.1 | AGGUGGAAAUGAAGAAAGUAU | 512 | NM_000454.4_535-555_C21U_s | 535-555 | AUACUUUCUUCAUUUCCACCUUU | 872 | NM_000454.4_533-555_G1A_as | 533-555 |

TABLE 6-continued

Unmodified Sense and Antisense Strand Sequences of Superoxide Dismutase 1 dsRNA Agents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-301873.1 | GAAAGUACAAAGACAGGAAAU | 513 | NM_000454.4_548-568_C21U_s | 548-568 | AUUUCCUGUCUUUGUACUUUCUU | 873 | NM_000454.4_546-568_G1A_as | 546-568 |
| AD-301874.1 | AAAGUACAAAGACAGGAAACU | 514 | NM_000454.4_549-569_G21U_s | 549-569 | AGUUUCCUGUCUUUGUACUUUCU | 593 | NM_000454.4_547-569_C1A_as | 547-569 |
| AD-301875.1 | AAGUACAAAGACAGGAAACGU | 515 | NM_000454.4_550-570_C21U_s | 550-570 | ACGUUUCCUGUCUUUGUACUUUC | 594 | NM_000454.4_548-570_G1A_as | 548-570 |
| AD-301876.1 | AGUACAAAGACAGGAAACGCU | 516 | NM_000454.4_551-571_s | 551-571 | AGCGUUUCCUGUCUUUGUACUUU | 874 | NM_000454.4_549-571_as | 549-571 |
| AD-301877.1 | GUACAAAGACAGGAAACGCUU | 517 | NM_000454.4_552-572_G21U_s | 552-572 | AAGCGUUUCCUGUCUUUGUACUU | 875 | NM_000454.4_550-572_C1A_as | 550-572 |
| AD-301878.1 | UACAAAGACAGGAAACGCUGU | 518 | NM_000454.4_553-573_G21U_s | 553-573 | ACAGCGUUUCCUGUCUUUGUACU | 876 | NM_000454.4_155-573_C1A_as | 551-573 |
| AD-301880.1 | CAAAGACAGGAAACGCUGGAA | 519 | NM_000454.4_555-575_s | 555-575 | UUCCAGCGUUUCCUGUCUUUGUA | 598 | NM_000454.4_553-575_as | 553-575 |
| AD-301901.1 | GUCGUUUGGCUUGUGUGUGUAA | 522 | NM_000454.4_576-596_s | 576-596 | UUACACCACAAGCCAAACGACUU | 601 | NM_000454.4_457-596_as | 574-596 |
| AD-301902.1 | UCGUUUGGCUUGUGUGUGUAAU | 523 | NM_000454.4_577-597_s | 577-597 | AUUACACCACAAGCCAAACGACU | 602 | NM_000454.4_575-597_as | 575-597 |
| AD-301903.1 | CGUUUGGCUUGUGUGUGUAAUU | 524 | NM_000454.4_578-598_s | 578-598 | AAUUACACCACAAGCCAAACGAC | 603 | NM_000454.4_576-598_as | 576-598 |
| AD-301904.1 | GUUUGGCUUGUGUGUGUAAUUU | 525 | NM_000454.4_579-599_s | 579-599 | AAAUUACACCACAAGCCAAACGA | 604 | NM_000454.4_577-599_C1A_as | 577-599 |
| AD-301905.1 | UUUGGCUUGUGUGUGUAAUUGU | 526 | NM_000454.4_580-600_s | 580-600 | ACAAUUACACCACAAGCCAAACG | 605 | NM_000454.4_857-600_C1A_as | 578-600 |
| AD-301906.1 | UUGGCUUGUGUGUGUAAUUGGU | 527 | NM_000454.4_581-601_G21U_s | 581-601 | ACCAAUUACACCACAAGCCAAAC | 877 | NM_000454.4_579-601_C1A_as | 579-601 |
| AD-301907.1 | UGGCUUGUGUGUGUAAUUGGGA | 520 | NM_001285406.1_434-454_s | 434-454 | UCCCAAUUACACCACAAGCCAAA | 878 | NM_001285406.1 | 432-454 |
| AD-301908.1 | GGCUUGUGUGUGUAAUUGGGAU | 521 | NM_001285406.1_435-455_s | 435-455 | AUCCCAAUUACACCACAAGCCAA | 600 | NM_001285406.1 | 433-455 |

TABLE 6-continued

Unmodified Sense and Antisense Strand Sequences of Superoxide Dismutase 1 dsRNAAgents

| Duplex Name | Sense Sequence 5' to 3' | SEQ ID NO: | Source Name | Range in GenBank Acession No. in Source Name | Antisense Sequence 5' to 3' | SEQ ID NO: | Source Name | Range in GenBank Acession No. in Source Name |
|---|---|---|---|---|---|---|---|---|
| AD-301909.1 | GCUUGUGUAAUUGGGAUU | 486 | NM_001285406.1_436-456_C21U_s | 436-456 | AAUCCCAAUUACACCACAAGCCA | 565 | NM_001285406.1 | 434-456 |
| AD-301910.1 | CUUGUGUGUAAUUGGGAUCU | 487 | NM_001285406.1_437-457_G21U_s | 437-457 | AGAUCCCAAUUACACCACAAGCC | 566 | NM_001285406.1 | 435-457 |
| AD-301911.1 | UUGUGUGUAAUUGGGAUCGU | 488 | NM_001285406.1_438-458_C21U_s | 438-458 | ACGAUCCCAAUUACACCACAAGC | 567 | NM_001285406.1 | 436-458 |
| AD-301912.1 | UGUGUGUAAUUGGGAUCGCU | 489 | NM_001285406.1_439-459_C21U_s | 439-459 | AGCGAUCCCAAUUACACCACAAG | 568 | NM_001285406.1 | 437-459 |
| AD-301918.1 | GUAAUUGGGAUCGCCCAAUAA | 528 | NM_000454.4_593-613_s | 593-613 | UUAUUGGGCGAUCCCAAUUACAC | 607 | NM_000454.4_591-613_as | 591-613 |

TABLE 7

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-301535.1 | usgscaggGfCfAfUfCfaucaauuucuL96 | 649 | asGfsaaau(Tgn)gaugauGfcCfcugcascsu | 880 | AGUGCAGGGCAUCAUCAAUUUCG | 807 |
| AD-301536.1 | gscsagggCfaUfCfAfucaauuucgaL96 | 650 | usCfsgaaa(Tgn)ugaugaUfgCfccugcsasc | 881 | GUGCAGGGCAUCAUCAAUUUCGA | 808 |
| AD-301537.1 | csasgggCfaUfCfAfUfcaauuucgaL96 | 651 | asUfscgaa(Agn)uugaugAfuGfccougcsa | 882 | UGCAGGGCAUCAUCAAUUUCCAG | 809 |
| AD-301538.1 | asgsggcAfUfCfAfUfcaauuucgagcaL96 | 652 | asCfsucga(Agn)auugauUfgAfugcccusgc | 883 | GCAGGGCAUCAUCAAUUUCGAGC | 810 |
| AD-301539.1 | gsgsgcauCfaUfCfAfauuucgagcaL96 | 653 | usGfscucg(Agn)aauugaUfgAfugccsusg | 884 | CAGGGCAUCAUCAAUUUCGACCA | 811 |
| AD-301540.1 | gsgscaucAfuCfAfUfuuucgagcauL96 | 654 | asUfsgcuc(Ggn)aaauugAfugCfcscsu | 885 | AGGGCAUCAUCAAUUUCGAGCAG | 812 |
| AD-301542.1 | csasucauCfaAfUfUfucgagcagaaL96 | 655 | usUfscugc(Tgn)cgaaauUfgAfugaugsccsc | 886 | GGCAUCAUCAAUUUCGAGCAGAG | 813 |
| AD-301543.1 | asuscaucAfaUfUfUfcgagcagaauL96 | 656 | asUfsucug(Cgn)ucgaaaUfuGfaugausgc | 887 | GCAUCAUCAAUUUCGAGCAGAAG | 814 |
| AD-301544.1 | uscsaucaAfuUfUfUfCfgagcagaaguL96 | 657 | asCfsuucu(Ggn)cucgaaAfuUfgaugausg | 888 | CAUCAUCAAUUUCGAGCAGAAGG | 815 |
| AD-301549.1 | asasuuucGfaGfCfAfgaaggaaaguL96 | 612 | asCfsuuuc(Cgn)uucugcUfcGfaaauusga | 889 | UCAAUUUCGAGCAGAAGGAAAGU | 770 |
| AD-301550.1 | asusuucgAfgCfAfGfAfaaggaaaguaL96 | 213 | usAfscuuu(Cgn)cuucugCfuCfgaaausug | 890 | CAAUUUCGAGCAGAAGGAAAGUA | 379 |
| AD-301551.1 | ususucgaGfcAfGfAfAfaggaaaguaaL96 | 255 | usUfsacuu(Tgn)ccuucuGfcUfcgaaasusu | 891 | AAUUUCGAGCAGAAGGAAAGUAA | 421 |
| AD-301552.1 | uscsagcaGfaGfAfAfAfggaaaguaaUL96 | 212 | asUfsuacu(Tgn)uccuucUfgCfucgaasasu | 892 | AUUUCGAGCAGAAGGAAAGUAAU | 378 |
| AD-301555.1 | gsasgcagAfaGfGfAfAfaguaauggaL96 | 613 | usCfscauu(Agn)cuuuccUfuCfugcucsgsa | 893 | UCGAGCAGAAGGAAAGUAAUGGA | 771 |
| AD-301559.1 | asgsaaggAfaAfGfUfAfauggaccauL96 | 614 | asUfsgguc(Cgn)auuacuUfuCfcuucusgc | 894 | GCAGAAGGAAAGUAAUGGACCAG | 772 |
| AD-301560.1 | gsasaggaAfaAfGfUfAfauggaccagL96 | 615 | asCfsuggu(Cgn)cauuacUfuUfccuucsug | 895 | CAGAAGGAAAGUAAUGGACCAGU | 773 |
| AD-301562.1 | asgsgaaaGfuAfAfUfGfgaccagugaL96 | 616 | usCfsacug(Ggn)uccauuAfcUfuuccusga | 896 | GAAGGAAAGUAAUGGACCAGUGA | 774 |
| AD-301563.1 | gsgsaaaGfuAfAfUfGfgaccagugaaL96 | 617 | usUfscacu(Ggn)guccauUfaCfuuuccsusu | 897 | AAGGAAAGUAAUGGACCAGUGAA | 775 |
| AD-301564.1 | asasaguaAfuGfGfAfCfcagugaaguL96 | 618 | asUfsucac(Tgn)gguccaUfuAfcuuuscsc | 898 | AGGAAAGUAAUGGACCAGUGAAG | 776 |
| AD-301565.1 | asasaguaAfuGfGfAfCfcagugaaguL96 | 619 | asCfsuuca(Cgn)ugguccAfuUfacuuuscc | 899 | GGAAAGUAAUGGACCAGUGAAGG | 777 |
| AD-301566.1 | asasaguaaUfgGfGfAfCfcagugaagUL96 | 620 | asCfscuuc(Cgn)cuggucCfaUfuacuuusc | 900 | GAAAGUAAUGGACCAGUGAAGGU | 778 |
| AD-301567.1 | asgsuaauGfgAfCfCfagugaaggugL96 | 621 | asAfsccuu(Cgn)acugguCfcAfuuacusususu | 901 | AAAGUAAUGGACCAGUGAAGGUG | 779 |
| AD-301569.1 | usasauggAfcCfAfGfugaagguguuL96 | 259 | asAfscacc(Tgn)ucacugGfuCfcauuascsu | 902 | AGUAAUGGACCAGUGAAGGUGUG | 425 |

TABLE 7-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-301579.1 | asusuaaAgFcAfCfUFgacugaagguL96 | 658 | asCfscuuc(Agn)gucaguCfcUfuaaausgsc | 903 | GCAUUAAGGACUGACUGAAGGC | 816 |
| AD-301593.1 | usgsaaggCfcUfGfCfAfuggauuccauL96 | 622 | usGfsgaau(Cgn)caugcaGfgCfcuucsasgu | 904 | ACUGAAGGCCUGCAUGGAUUCCA | 780 |
| AD-301594.1 | gsasaggcCfuGfCfAfuggauuccauL96 | 623 | asUfsggaa(Tgn)ccaugcAfgGfccuucsasg | 905 | CUGAAGGCCUGCAUGGAUUCCAU | 781 |
| AD-301596.1 | asggcCfcuGfCfAfUfGfgauuccauguL96 | 624 | asCfsaugg(Agn)auccauGfcAfggcccsusuc | 906 | GAAGGCCUGCAUGGAUUCCAUGU | 782 |
| AD-301597.1 | gsgsccugCfaUfGfGfAfuuccauguuL96 | 625 | asAfscaug(Ggn)aauccaUfgCfaggccsusu | 907 | AAGGCCUGCAUGGAUUCCAUGUU | 783 |
| AD-301598.1 | gscsugcAfuGfGfAfAfuuccauguucL96 | 626 | asAfsacau(Ggn)gaauccAfuGfcaggcscsu | 908 | AGGCCUGCAUGGAUUCCAUGUUC | 784 |
| AD-301599.1 | cscsugcAfugGfAfAfUfuccauguucaL96 | 627 | usGfsaaca(Tgn)ggaaucCfaUfgcaggscsc | 909 | GGCCUGCAUGGAUUCCAUGUUCA | 785 |
| AD-301600.1 | csusgcAfugGfAfUfUfccauguucauL96 | 628 | asUfsgaac(Agn)uggaauCfcAfugcasgsc | 910 | GCCUGCAUGGAUUCCAUGUUCAU | 786 |
| AD-301601.1 | usgscaugGfaUfUfCfcauguucauuL96 | 265 | asAfsugaa(Cgn)auggaaUfcCfaugcasgsg | 911 | CCUGCAUGGAUUCCAUGUUCAUC | 431 |
| AD-301612.1 | csasguuCfaUfGfAfGfuuuggagauL96 | 659 | asUfscucc(Agn)aaucuaUfgAfacaugsgsa | 912 | UCCAUGUUCAUGAGUUUGGAGAU | 817 |
| AD-301615.1 | gsusucaugUfaGfUfUfUfggagauaauL96 | 660 | asUfsuauc(Tgn)ccaaacUfcAfugaascsau | 913 | AUGUUCAUGAGUUUGGAGAUAAU | 818 |
| AD-301616.1 | ususcaugAfugUfUfUfGfggagauaauaL96 | 661 | usAfsuuau(Cgn)uccaaaCfuCfaugaascsa | 914 | UGUUCAUGAGUUUGGAGAUAAUA | 819 |
| AD-301619.1 | asusgagUfuGfGfAfgagauaauaL96 | 662 | asUfsguau(Tgn)aucuccAfaAfcucausgsa | 915 | UCAUGAGUUUGGAGAUAAUACAG | 820 |
| AD-301648.1 | ascscaguGfcAfGfGfucccucacuuuL96 | 209 | asAfsagug(Agn)ggaccuGfcAfcuggusasc | 916 | GUACCAGUGCAGGUCCUCACUUU | 375 |
| AD-301649.1 | cscsaguGfcAfGfGfUfcccucacuuuaL96 | 241 | usAfsaagu(Ggn)aggaccUfgCfacugsusa | 917 | UACCAGUGCAGGUCCUCACUUUA | 407 |
| AD-301650.1 | csasguGfcAfGfGfUfcCfcucacuuuaaL96 | 220 | usUfsaaag(Tgn)gagaccUfcacugsgsu | 918 | ACCAGUGCAGGUCCUCACUUUAA | 386 |
| AD-301652.1 | gsusgcagGfuCfCfUfcacuuuaauL96 | 258 | asAfsuuaa(Agn)gugaggAfcCfugcasusg | 919 | CAGUGCAGGUCCUCACUUUAAUC | 424 |
| AD-301653.1 | usgscaggUfcCfUfCfacuuuaauccuL96 | 205 | asGfsauua(Agn)agugagGfaCfcugcascsu | 920 | AGUGCAGGUCCUCACUUUAAUCC | 371 |
| AD-301654.1 | gscsaggUfcCfUfCfAfcuuuaauccuL96 | 263 | asGfsgauu(Agn)aagugaGfgAfccugscsc | 921 | GUGCAGGUCCUCACUUUAAUCCU | 429 |
| AD-301661.1 | csuscacUfuAfAfUfCfcucuauccaL96 | 216 | usGfsgaua(Ggn)aggauuAfaAfagugsasg | 922 | UCCUCACUUUAAUCCUCUAUCCA | 382 |
| AD-301662.1 | uscsacuUfaAfUfCfCfucuauccauL96 | 248 | asGfsauua(Agn)auggauAfaAfagugasgsg | 923 | CCUCACUUUAAUCCUCUAUCCAG | 414 |
| AD-301663.1 | csascuuuAfaUfCfCfucuauccagaL96 | 237 | uscfsugga(Tgn)agaggaUfuAfaagugsasg | 924 | CUCACUUUAAUCCUCUAUCCAGA | 403 |
| AD-301688.1 | ascsggugCfaCfAfAfAfaggaugaauL96 | 879 | asUfsucau(Cgn)cuuuggCfcCfaccgusgsu | 925 | ACACGUGGGCCAAAGGAUGAAGA | 974 |
| AD-301690.1 | gsgsuggGfcCfAfAfAfggaugaagauL96 | 629 | asUfscuuc(Agn)uccuuuGfgCfcaccsgsu | 926 | ACGGUGGGCCAAAGGAUGAAGAG | 787 |

TABLE 7-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-301697.1 | csasaaggAfuGfAfAfgagaggcauuL96 | 631 | asAfsugcc(Tgn)cucuucAfucCfcuuugsgsc | 927 | GCCAAAGGAUGAAGAGAGGCAUG | 789 |
| AD-301699.1 | asasggauGfaAfGfAfgaggcauguuL96 | 632 | asAfscaug(Cgn)cucucuUfcAfuccucususg | 928 | CAAAGGAUGAAGAGAGGCAUGUU | 790 |
| AD-301700.1 | asgsgaugAfaGfAfGfaggcauguuuL96 | 633 | asAfsacau(Ggn)ccucucUfuCfauccucusu | 929 | AAAGGAUGAAGAGAGGCAUGUUG | 791 |
| AD-301701.1 | gsgsaugaAfgAfGfAfggcauguguL96 | 634 | ascCfsaaca(Tgn)gccucuUfcUfucaucscsu | 930 | AAGGAUGAAGAGAGGCAUGUUGG | 792 |
| AD-301702.1 | gsasugaaGfaGfAfGfgcauguuggaL96 | 630 | uscCfscaac(Agn)ugcucUfcUfucaucscsu | 931 | AGGAUGAAGAGAGGCAUGUUGGA | 788 |
| AD-301703.1 | asusgaagAfgAfGfGfcauguuggauL96 | 635 | asUfsccaa(Cgn)augccuTfcCfuucauscsc | 932 | GGAUGAAGAGAGGCAUGUUGGAG | 793 |
| AD-301706.1 | asasgagaGfcAfUfGfguuggagacuL96 | 636 | asGfsucuc(Cgn)aacaugCfcUfcucuusca | 933 | UGAAGAGAGGCAUGUUGGAGACC | 794 |
| AD-301764.1 | usgsugucUfaUfUfGfaagauucuguL96 | 663 | ascCfsagaa(Tgn)cuucaaUfaGfacacasusc | 934 | GAUGUGUCUAUUGAAGAUUCUGU | 821 |
| AD-301765.1 | gsusgucuAfuUfGfAfagauucuguuL96 | 664 | asAfscaga(Agn)ucuucaAfuAfgacacsasu | 935 | AUGUGUCUAUUGAAGAUUCUGUG | 822 |
| AD-301799.1 | gsasgaccAfuUfGfCfcaucauggccL96 | 667 | asGfsccaa(Tgn)gaugcaAfuGfgucucscsu | 936 | AGGAGACCAUUGCCAUCAUGGCC | 825 |
| AD-301824.1 | ascsuggugGfuCfCfCfaugaaaaagL96 | 668 | ascCfsuuuu(Tgn)cauggaCfcAfccagusgsu | 937 | ACACUGGUGUCCAUGAAAAAGC | 826 |
| AD-301825.1 | csusggugUfcCfCfAfugaaaaagcaL96 | 669 | usGfscuuu(Tgn)ucauggAfcCfaccagsu | 938 | CACUGGUGUCCAUGAAAAAGCA | 827 |
| AD-301826.1 | usgsgugUfcCfAfUfGfaaaaagcauL96 | 665 | asUfsgcuu(Tgn)uucaugGfaCfcaccagsu | 939 | ACUGGUGUCCAUGAAAAAGCAU | 823 |
| AD-301827.1 | gsgsugucCfcAfUfGfaaaaagcagaL96 | 666 | uscCfsugcu(Tgn)uuucaUfgGfaccaccsasg | 940 | CUGGUGUCCAUGAAAAAGCAGA | 824 |
| AD-301828.1 | gsusguccCfaUfGfAfaaaagcagauL96 | 638 | asUfscugc(Tgn)uuuucaUfgGfaccacscsa | 941 | UGGUGUCCAUGAAAAAGCAGAU | 796 |
| AD-301829.1 | usgsguccAfuGfAfAfaaagcagaugL96 | 639 | asAfsucug(Cgn)uuuucaUfuGfgaccacscsc | 942 | GGUGUCCAUGAAAAAGCAGAUG | 797 |
| AD-301830.1 | gsgsuccaUfgAfAfAfaAfaagcagaugaL96 | 640 | uscCfsaucu(Ggn)cuuuuCfaUfggaccsasc | 943 | GUGUCCAUGAAAAAGCAGAUGA | 798 |
| AD-301843.1 | gscsagauGfaCfuUfgggcaaaggguL96 | 641 | ascCfscuuu(Ggn)cccaagUfcAfucucsusu | 944 | AAGCAGAUGACUUGGGCAAGGU | 799 |
| AD-301845.1 | asgsaugaCfuUfGfGfgcaaaggugguL96 | 642 | ascCfsaccu(Tgn)ugcccaAfgUfcaucusgsc | 945 | GCAGAUGACUUGGGCAAAGGUGG | 800 |
| AD-301846.1 | gsasugacUfuGfGfGfcaaaggugaL96 | 637 | uscCfscacc(Tgn)uugcccAfaGfucaucsusg | 946 | CAGAUGACUUGGGCAAAGGUGA | 795 |
| AD-301847.1 | asusgacuUfgGfGfCfaaagguggaaL96 | 608 | usUfscuuu(Cgn)uugcccAfaGfucauscsu | 947 | AGAUGACUUGGGCAAAGGUGAA | 766 |
| AD-301848.1 | usgsacuuGfgGfCfAfaaaggugaaaL96 | 609 | usUfsucca(Cgn)cuuugcCfcAfagucasusc | 948 | GAUGACUUGGGCAAAGGUGAAA | 767 |
| AD-301849.1 | gsascuugGfgCfAfAfaggugaaauL96 | 610 | asUfsuucc(Agn)ccuuugCfcCfaagucsasu | 949 | AUGACUUGGGCAAAGGUGAAAU | 768 |
| AD-301850.1 | ascsuuggGfcAfAfAfAfaggugaaauuL96 | 643 | asAfsuuuc(Cgn)accuuugCfcCfcaaguscsa | 950 | UGACUUGGGCAAAGGUGAAAUG | 801 |

TABLE 7-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-301852.1 | ususgggcAfaAfGfGfuggaaaugaaL96 | 269 | usUfscauu(Tgn)ccaccuUfgFcccaasgsu | 951 | ACUUGGGCAAAGGUGGAAAUGAA | 435 |
| AD-301859.1 | asasggugGfaAfAfUfgaagaaaaguaL96 | 611 | usAfscuuu(Cgn)uucauuUfcCfaccuususg | 952 | CAAAGGUGAAAUGAAGAAAGUA | 769 |
| AD-301860.1 | asgsguggAfaAfAfUfGfaagaaaguaUL96 | 670 | asUfsacuu(Tgn)cuucacuUfcUfcaccususu | 953 | AAAGGUGGAAAUGAAGAAAGUAC | 828 |
| AD-301873.1 | gsasaaguaAfcAfAfAfgacaggaaaaUL96 | 671 | asGfsuucc(Tgn)gucuuuGfuAfcuuucsusu | 954 | AAGAAAGUACAAAGACAGGAAAC | 829 |
| AD-301874.1 | asasaguaCfaAfAfGfacaggaaacuL96 | 672 | asCfsuuuc(Cgn)uguccuUfgUfacuuuscsu | 955 | AGAAAGUACAAAGACAGGAAACG | 830 |
| AD-301875.1 | asasguacAfaAfGfAfcaggaaacgcuL96 | 673 | asCfsguuu(Cgn)cugucuUfuGfuacusususu | 956 | GAAAGUACAAAGACAGGAAACGC | 831 |
| AD-301876.1 | asgsuacaAfaGfAfCfaggaaacgcuL96 | 674 | asGfscguu(Tgn)ccugucUfuUfguacususu | 957 | AAAGUACAAAGACAGGAAACCUG | 832 |
| AD-301877.1 | gsusacaaAfgAfCfAfGfggaaacgcuuL96 | 675 | asAfsgcgu(Tgn)uccuguCfuUfuguacuscu | 958 | AAGUACAAAGACAGGAAACGCUG | 833 |
| AD-301878.1 | usascaaaGfacCfaFfAfGfGfaaacgcuguL96 | 676 | asCfsagcg(Tgn) uuccgcgUfcAfuuuguascsu | 959 | AGUACAAAGACAGGAAACGCUGG | 834 |
| AD-301880.1 | csasaagaCfaGfGfAfaacgcuguaaL96 | 677 | usUfsccag(Cgn)guuuccUfgUfcuuugsusa | 960 | UACAAAGACAGGAAACGCUGAA | 835 |
| AD-301901.1 | gsuscguuUfgGfCfUfuguguguaaL96 | 680 | usUfsacac(Cgn)acaagCfaAfacgacsusu | 961 | AAGUCGUUUGGCUUGUGUGUAA | 838 |
| AD-301902.1 | uscsguuuGfgCfUfUfgUfgUfguaauL96 | 681 | asUfsuaca(Cgn)caccaagCfcAfaacgascsu | 962 | AGUCGUUUGGCUUGUGUGUAAU | 839 |
| AD-301903.1 | csgsuuugGfcUfUfGfuGfuGfguaauuL96 | 682 | asAfsuuac(Agn)ccacaaGfcCfaaacgsasc | 963 | GUCGUUUGGCUUGUGUGUAAUU | 840 |
| AD-301904.1 | gsusuugGfcUfUfGfggUfguaauuuL96 | 683 | asAfsauua(Cgn)accacaAfgCfcaaacsgsa | 964 | UCGUUUGGCUUGUGUGUAAUUG | 841 |
| AD-301905.1 | ususuggCfuUfGfUfGfuGfuaauuguL96 | 684 | asCfsaauu(Agn)caccacAfgGfccaaascg | 965 | CGUUUGGCUUGUGUGUAAUUGG | 842 |
| AD-301906.1 | usuuggcCfuUfGfUfguguaauuggL96 | 685 | ascCfscaau(Tgn)acaccaCfaAfgccaasasc | 966 | GUUUGGCUUGUGUGUAAUUGGG | 843 |
| AD-301907.1 | usgsgcuuGfuGfUfgUfuaauugggaL96 | 678 | uscCfsccaa(Agn) uacaccAfcAfagccasasa | 967 | UUUGGCUUGUGUGUAAUUGGGA | 836 |
| AD-301908.1 | gsgscuugUfgUfGfUfaAfauugggauL96 | 679 | asUfscccca(Agn)uuacacCfaCfaagccsasa | 968 | UUGGCUUGUGUGUAAUUGGGAU | 837 |
| AD-301909.1 | gscsuugUfgUfGfUfaauugggauuuL96 | 644 | asAfsucc(Agn)auuacaCfcAfcaagcscsa | 969 | UGGCUUGUGUGUAAUUGGGAUC |802 |
| AD-301910.1 | csusuguGfuGfUfAfauugggaucuL96 | 645 | asGfsaucc(Cgn)aauuacAfcCfacaagscsc | 970 | GGCUUGUGUGUAAUUGGGAUCG | 803 |
| AD-301911.1 | ususuggUfgUfAfAfuugggaucugcL96 | 646 | asCfsgauc(Cgn)caauuaAfcCfacaasgsc | 971 | GCUUGUGUGUAAUUGGGAUCGC | 804 |
| AD-301912.1 | usgsuggUfuAfAfAfAfugggaucgcL96 | 647 | asGfscgau(Cgn)ccaauuAfcAfccacasasg | 972 | CUUGUGUGUAAUUGGGAUCCGCC | 805 |
| AD-301918.1 | gsusaauuGfgAfUfCfgccauauaaL96 | 686 | usUfsauug(Ggn)gcgaucCfaFfauuacsasc | 973 | GUGUAAUUGGGAUCGCCAUUAA | 844 |

TABLE 8

Superoxide Dismutase 1 In Vitro Single Dose Screens in Primary Cynomolgus Hepatocytes (PCH) cells

| Duplex | Dose - Unit 10 - nM Avg | SD | Dose - Unit 0.1 - nM Avg | SD |
|---|---|---|---|---|
| AD-266859.1 | 1.6 | 0.3 | 23.5 | 4.1 |
| AD-266997.1 | 1.2 | 0.4 | 15.3 | 4.3 |
| AD-266992.1 | 0.8 | 0.1 | 11.4 | 1.5 |
| AD-266903.1 | 6.5 | 0.8 | 81.9 | 8.0 |
| AD-266891.1 | 7.4 | 1.7 | 81.4 | 9.4 |
| AD-266996.1 | 10.8 | 7.1 | 78.4 | 6.0 |
| AD-266893.1 | 1.7 | 1.0 | 29.0 | 5.0 |
| AD-266898.1 | 3.5 | 2.1 | 60.5 | 7.6 |
| AD-266886.1 | 4.2 | 0.9 | 77.1 | 23.0 |
| AD-267072.1 | 7.9 | 2.0 | 104.4 | 22.5 |
| AD-267067.1 | 25.1 | 2.0 | 110.8 | 14.4 |
| AD-266791.1 | 1.3 | 0.3 | 11.8 | 2.0 |
| AD-266789.1 | 11.4 | 1.7 | 85.0 | 5.2 |
| AD-266861.1 | 1.9 | 0.3 | 33.6 | 1.9 |
| AD-266856.1 | 2.3 | 0.4 | 27.0 | 1.4 |
| AD-266899.1 | 7.8 | 0.9 | 65.6 | 4.9 |
| AD-267000.1 | 1.3 | 0.2 | 18.9 | 2.3 |
| AD-267071.1 | 1.9 | 0.5 | 26.1 | 4.9 |
| AD-266895.1 | 6.6 | 0.4 | 58.3 | 4.2 |
| AD-266888.1 | 3.8 | 0.7 | 51.4 | 16.5 |
| AD-266817.1 | 7.7 | 1.8 | 102.7 | 26.6 |
| AD-267083.1 | 5.1 | 2.0 | 77.8 | 17.5 |
| AD-266862.1 | 1.9 | 0.3 | 34.4 | 2.7 |
| AD-267002.1 | 2.1 | 0.3 | 33.3 | 2.9 |
| AD-266816.1 | 1.6 | 0.4 | 19.6 | 3.1 |
| AD-266857.1 | 1.6 | 0.2 | 21.8 | 1.6 |
| AD-266902.1 | 3.9 | 0.6 | 51.7 | 5.0 |
| AD-267086.1 | 2.8 | 0.1 | 39.0 | 4.4 |
| AD-266785.1 | 4.6 | 0.4 | 56.5 | 3.5 |
| AD-266897.1 | 2.7 | 0.4 | 34.1 | 4.4 |
| AD-266896.1 | 17.2 | 2.1 | 73.2 | 9.5 |
| AD-266858.1 | 2.8 | 0.6 | 49.9 | 12.5 |
| AD-267084.1 | 5.8 | 1.7 | 80.7 | 26.6 |
| AD-266815.1 | 9.6 | 1.2 | 76.0 | 4.2 |
| AD-267007.1 | 1.6 | 0.4 | 24.1 | 3.0 |
| AD-266855.1 | 1.2 | 0.3 | 14.0 | 1.5 |
| AD-266901.1 | 3.3 | 1.1 | 38.8 | 3.2 |
| AD-266994.1 | 1.9 | 0.4 | 25.0 | 1.9 |
| AD-266793.1 | 3.6 | 0.5 | 50.0 | 4.7 |
| AD-266850.1 | 2.9 | 0.2 | 42.0 | 4.9 |
| AD-266887.1 | 1.8 | 0.0 | 22.8 | 3.2 |
| AD-266894.1 | 4.3 | 0.4 | 50.6 | 5.4 |
| AD-266988.1 | 2.2 | 0.4 | 37.4 | 8.8 |
| AD-267085.1 | 6.6 | 1.4 | 78.5 | 20.6 |
| AD-266873.1 | 2.4 | 0.4 | 41.7 | 6.0 |
| AD-266907.1 | 8.3 | 0.9 | 60.5 | 5.7 |
| AD-266792.1 | 4.8 | 0.6 | 44.5 | 3.8 |
| AD-266900.1 | 3.0 | 0.6 | 33.8 | 1.4 |
| AD-266797.1 | 4.9 | 0.4 | 54.4 | 6.1 |
| AD-266787.1 | 2.5 | 0.6 | 32.0 | 1.8 |
| AD-266800.1 | 2.1 | 0.2 | 31.9 | 3.6 |
| AD-266889.1 | 1.9 | 0.2 | 18.1 | 2.2 |
| AD-266847.1 | 7.2 | 0.8 | 71.6 | 31.4 |
| AD-266998.1 | 3.8 | 0.5 | 65.0 | 26.6 |
| AD-266790.1 | 2.7 | 0.2 | 52.9 | 4.8 |
| AD-266906.1 | 57.9 | 5.2 | 81.0 | 4.8 |
| AD-266854.1 | 3.1 | 0.7 | 42.7 | 3.1 |
| AD-266890.1 | 2.4 | 0.2 | 25.6 | 2.1 |
| AD-266808.1 | 6.0 | 1.5 | 63.3 | 4.7 |
| AD-266905.1 | 1.7 | 0.4 | 19.7 | 1.6 |
| AD-267024.1 | 1.1 | 0.2 | 12.4 | 1.4 |
| AD-266781.1 | 2.3 | 0.3 | 26.2 | 4.1 |
| AD-266892.1 | 11.0 | 2.8 | 68.7 | 7.7 |
| AD-266999.1 | 7.5 | 2.9 | 88.9 | 7.0 |
| AD-266841.1 | 1.5 | 0.3 | 16.1 | 1.8 |
| AD-266908.1 | 2.7 | 0.1 | 42.2 | 6.2 |
| AD-267005.1 | 1.9 | 0.3 | 20.8 | 3.4 |
| AD-266942.1 | 9.4 | 1.9 | 70.3 | 5.6 |
| AD-135967.3 | 2.4 | 0.3 | 31.6 | 1.4 |
| AD-266786.1 | 11.2 | 0.9 | 74.2 | 26.2 |
| AD-267064.1 | 1.7 | 0.4 | 25.3 | 8.1 |
| AD-266845.1 | 2.7 | 0.4 | 48.8 | 12.7 |
| AD-266944.1 | 3.3 | 1.1 | 40.5 | 14.5 |
| AD-267003.1 | 5.9 | 1.3 | 100.7 | 5.4 |
| AD-266860.1 | 5.9 | 0.7 | 75.1 | 7.3 |
| AD-266990.1 | 1.4 | 0.0 | 13.7 | 1.5 |
| AD-266853.1 | 2.2 | 0.3 | 31.7 | 3.7 |
| AD-266782.1 | 1.8 | 0.3 | 44.6 | 7.5 |
| AD-266962.1 | 2.1 | 0.6 | 33.3 | 4.2 |
| AD-267079.1 | 1.7 | 0.1 | 29.1 | 6.6 |
| AD-266846.1 | 1.9 | 0.6 | 41.7 | 13.0 |
| AD-266961.1 | 5.1 | 2.8 | 72.8 | 19.3 |
| AD-267061.1 | 4.8 | 1.7 | 65.6 | 11.1 |

TABLE 9

Superoxide Dismutase 1 In Vitro Single Dose Screens in Primary Mouse Hepatocytes (PMH)

| Duplex | Dose - Unit 10 - nM Avg | SD | Dose - Unit 0.1 - nM Avg | SD |
|---|---|---|---|---|
| AD-266859.1 | 76.4 | 36.1 | 51.0 | 22.7 |
| AD-266997.1 | 60.0 | 20.9 | 51.8 | 4.2 |
| AD-266992.1 | 29.1 | 34.9 | 24.7 | 27.9 |
| AD-266903.1 | 48.1 | 13.8 | 47.6 | 16.2 |
| AD-266891.1 | 36.1 | 7.9 | 47.3 | 7.4 |
| AD-266996.1 | 67.0 | 28.3 | 67.5 | 25.6 |
| AD-266893.1 | 0.5 | 0.5 | 21.0 | 23.7 |
| AD-266898.1 | 58.6 | 17.9 | 89.5 | 56.8 |
| AD-266886.1 | 65.0 | 7.4 | 77.3 | 33.0 |
| AD-267072.1 | 4.8 | 9.2 | 104.7 | 66.4 |
| AD-267067.1 | 64.5 | 9.7 | 98.0 | 55.1 |
| AD-266791.1 | 2.2 | 2.8 | 52.1 | 7.0 |
| AD-266789.1 | 43.9 | 6.8 | 52.7 | 7.8 |
| AD-266861.1 | 60.5 | 23.4 | 50.9 | 7.5 |
| AD-266856.1 | 52.6 | 18.3 | 51.7 | 6.7 |
| AD-266899.1 | 72.0 | 12.2 | 58.1 | 14.2 |
| AD-267000.1 | 67.3 | 14.4 | 65.8 | 16.5 |
| AD-267071.1 | 0.3 | 0.1 | 27.9 | 7.2 |
| AD-266895.1 | 63.4 | 11.5 | 79.5 | 13.7 |
| AD-266888.1 | 2.1 | 0.6 | 75.6 | 27.2 |
| AD-266817.1 | 82.2 | 47.3 | 113.0 | 37.6 |
| AD-267083.1 | 89.1 | 42.8 | 122.5 | 36.2 |
| AD-266862.1 | 63.3 | 29.2 | 53.6 | 12.6 |
| AD-267002.1 | 46.8 | 9.0 | 64.5 | 9.9 |
| AD-266816.1 | 0.9 | 0.4 | 49.2 | 0.5 |
| AD-266857.1 | 58.6 | 14.7 | 64.5 | 6.3 |
| AD-266847.1 | 78.3 | 16.4 | 104.9 | 34.1 |
| AD-266998.1 | 79.2 | 23.4 | 114.2 | 52.0 |
| AD-266790.1 | 38.1 | 7.4 | 54.4 | 15.0 |
| AD-266906.1 | 44.1 | 8.5 | 49.5 | 4.1 |
| AD-266854.1 | 57.1 | 20.8 | 53.8 | 5.8 |
| AD-266890.1 | 4.8 | 3.7 | 48.7 | 3.0 |
| AD-266808.1 | 72.0 | 18.8 | 74.9 | 17.7 |
| AD-266905.1 | 72.0 | 12.3 | 71.2 | 3.1 |
| AD-267024.1 | 0.6 | 0.3 | 30.8 | 4.4 |
| AD-266781.1 | 73.5 | 13.8 | 88.8 | 14.6 |
| AD-266892.1 | 76.1 | 15.8 | 90.7 | 29.4 |
| AD-266999.1 | 96.0 | 59.3 | 114.2 | 44.5 |
| AD-266841.1 | 7.7 | 4.4 | 42.4 | 13.5 |
| AD-266908.1 | 44.5 | 4.9 | 50.5 | 16.1 |
| AD-267005.1 | 2.6 | 1.4 | 48.4 | 10.5 |
| AD-266942.1 | 1.2 | 0.6 | 47.2 | 11.7 |
| AD-266902.1 | 74.0 | 21.2 | 70.1 | 19.7 |
| AD-267086.1 | 67.0 | 17.7 | 84.8 | 17.6 |
| AD-266785.1 | 21.9 | 10.5 | 71.9 | 10.0 |
| AD-266897.1 | 62.2 | 15.8 | 80.2 | 22.7 |
| AD-266896.1 | 72.7 | 18.4 | 66.8 | 16.7 |

TABLE 9-continued

Superoxide Dismutase 1 In Vitro Single Dose
Screens in Primary Mouse Hepatocytes (PMH)

| Duplex | Dose - Unit 10 - nM Avg | SD | Dose - Unit 0.1 - nM Avg | SD |
|---|---|---|---|---|
| AD-266858.1 | 67.0 | 15.8 | 80.7 | 14.9 |
| AD-267084.1 | 79.2 | 28.4 | 110.7 | 45.7 |
| AD-266815.1 | 56.9 | 21.6 | 54.6 | 7.2 |
| AD-267007.1 | 0.4 | 0.1 | 31.6 | 7.3 |
| AD-266855.1 | 62.3 | 12.9 | 59.6 | 1.8 |
| AD-266901.1 | 64.5 | 13.2 | 61.6 | 13.7 |
| AD-266994.1 | 75.0 | 16.8 | 75.0 | 12.9 |
| AD-266793.1 | 68.3 | 9.5 | 84.9 | 15.4 |
| AD-266850.1 | 87.1 | 23.7 | 88.8 | 12.4 |
| AD-266887.1 | 5.6 | 3.0 | 96.5 | 10.9 |
| AD-266894.1 | 7.8 | 5.7 | 97.4 | 7.4 |
| AD-266988.1 | 71.6 | 14.6 | 86.0 | 11.7 |
| AD-267085.1 | 17.8 | 11.0 | 116.2 | 52.3 |
| AD-266873.1 | 0.1 | 0.0 | 21.6 | 5.2 |
| AD-266907.1 | 48.3 | 13.4 | 49.6 | 2.9 |
| AD-266792.1 | 55.4 | 16.5 | 65.4 | 16.5 |
| AD-266900.1 | 63.9 | 20.6 | 69.0 | 5.7 |
| AD-266797.1 | 64.6 | 20.7 | 72.8 | 11.8 |
| AD-266787.1 | 41.6 | 8.9 | 78.8 | 7.8 |
| AD-266800.1 | 83.6 | 21.8 | 86.3 | 11.2 |
| AD-266889.1 | 0.8 | 0.3 | 80.4 | 11.7 |
| AD-135967.3 | 0.2 | 0.1 | 38.8 | 27.3 |
| AD-266786.1 | 62.0 | 14.7 | 93.1 | 40.3 |
| AD-267064.1 | 71.8 | 15.9 | 70.7 | 11.3 |
| AD-266845.1 | 75.7 | 27.7 | 99.4 | 61.4 |
| AD-266944.1 | 0.6 | 0.2 | 72.2 | 38.7 |
| AD-267003.1 | 118.9 | 75.9 | 156.4 | 51.6 |
| AD-266860.1 | 39.3 | 8.1 | 24.6 | 16.1 |
| AD-266990.1 | 38.7 | 9.2 | 21.2 | 14.6 |
| AD-266853.1 | 37.8 | 37.7 | 15.2 | 17.2 |
| AD-266782.1 | 38.6 | 32.7 | 41.6 | 34.4 |
| AD-266962.1 | 0.4 | 0.2 | 28.8 | 19.9 |
| AD-267079.1 | 0.2 | 0.1 | 20.1 | 23.0 |
| AD-266846.1 | 62.8 | 8.1 | 85.3 | 66.2 |
| AD-266961.1 | 40.3 | 20.5 | 59.0 | 11.0 |
| AD-267061.1 | 87.4 | 31.4 | 110.3 | 49.9 |

TABLE 10

Superoxide Dismutase 1 In Vitro Single Dose Screens
in Primary Cynomolgus Hepatocytes (PCH) cells

| Duplex | Dose - Unit 10 - nM Avg | SD | Dose - Unit 0.1 - nM Avg | SD |
|---|---|---|---|---|
| AD-135962.1 | 83.19 | 8.92 | 101.60 | 7.55 |
| AD-135963.1 | 45.58 | 1.94 | 98.64 | 9.66 |
| AD-135964.1 | 5.28 | 0.63 | 49.17 | 5.26 |
| AD-135967.5 | 4.25 | 0.39 | 37.19 | 3.98 |
| AD-135974.3 | 5.42 | 1.40 | 45.31 | 3.47 |
| AD-266788.1 | 3.93 | 0.78 | 37.67 | 4.27 |
| AD-266789.2 | 26.33 | 3.94 | 96.69 | 5.67 |
| AD-266790.2 | 6.26 | 0.53 | 44.79 | 2.51 |
| AD-266791.3 | 2.20 | 0.29 | 24.12 | 3.18 |
| AD-266794.1 | 12.48 | 1.11 | 74.79 | 3.70 |
| AD-266798.1 | 11.78 | 1.66 | 66.55 | 9.45 |
| AD-266799.1 | 8.19 | 1.19 | 70.59 | 4.84 |
| AD-266801.1 | 13.29 | 1.01 | 87.14 | 4.40 |
| AD-266802.1 | 19.56 | 4.86 | 74.12 | 6.09 |
| AD-266803.1 | 4.12 | 0.71 | 54.10 | 12.04 |
| AD-266804.1 | 7.57 | 1.06 | 75.49 | 7.11 |
| AD-266805.1 | 79.23 | 3.60 | 91.30 | 7.81 |
| AD-266806.1 | 18.66 | 0.31 | 82.02 | 4.98 |
| AD-266808.2 | 9.95 | 1.04 | 81.05 | 4.63 |
| AD-266832.1 | 43.37 | 3.77 | 99.19 | 3.54 |
| AD-266834.1 | 4.39 | 1.02 | 36.56 | 8.26 |
| AD-266836.1 | 74.92 | 2.31 | 91.29 | 5.81 |

TABLE 10-continued

Superoxide Dismutase 1 In Vitro Single Dose Screens
in Primary Cynomolgus Hepatocytes (PCH) cells

| Duplex | Dose - Unit 10 - nM Avg | SD | Dose - Unit 0.1 - nM Avg | SD |
|---|---|---|---|---|
| AD-266837.1 | 28.04 | 3.97 | 101.92 | 7.61 |
| AD-266838.1 | 3.40 | 0.72 | 32.93 | 1.02 |
| AD-266839.1 | 7.64 | 1.23 | 61.20 | 5.51 |
| AD-266840.1 | 4.65 | 0.80 | 51.48 | 7.19 |
| AD-266841.3 | 2.35 | 0.51 | 20.69 | 3.24 |
| AD-266886.2 | 5.26 | 1.22 | 60.65 | 4.88 |
| AD-266887.3 | 2.21 | 0.16 | 36.90 | 7.14 |
| AD-266888.2 | 4.78 | 0.28 | 49.47 | 1.84 |
| AD-266890.3 | 6.38 | 1.33 | 34.83 | 4.96 |
| AD-266891.2 | 13.25 | 0.53 | 79.79 | 5.06 |
| AD-266892.2 | 20.45 | 3.03 | 82.90 | 5.65 |
| AD-266899.2 | 13.48 | 2.79 | 75.57 | 6.33 |
| AD-266900.3 | 5.86 | 1.58 | 40.45 | 2.63 |
| AD-266901.2 | 4.08 | 1.07 | 46.32 | 3.22 |
| AD-266928.1 | 87.89 | 3.19 | 104.83 | 10.57 |
| AD-266934.1 | 10.50 | 2.75 | 89.20 | 1.11 |
| AD-266936.1 | 5.20 | 1.59 | 57.85 | 12.38 |
| AD-266938.1 | 5.76 | 0.67 | 55.29 | 3.26 |
| AD-266939.1 | 3.47 | 0.62 | 37.20 | 7.60 |
| AD-266940.1 | 8.36 | 1.54 | 83.30 | 13.87 |
| AD-266941.1 | 9.85 | 1.24 | 81.42 | 3.29 |
| AD-266943.1 | 17.56 | 2.41 | 88.20 | 4.40 |
| AD-267035.1 | 21.32 | 1.33 | 87.91 | 4.72 |
| AD-267058.1 | 4.60 | 0.36 | 45.53 | 3.39 |
| AD-267059.1 | 5.06 | 0.87 | 45.02 | 6.93 |
| AD-267060.1 | 23.86 | 2.69 | 108.98 | 16.46 |
| AD-267073.1 | 11.04 | 1.93 | 83.91 | 9.60 |
| AD-267075.1 | 15.92 | 2.72 | 187.79 | 125.27 |
| AD-267076.1 | 63.80 | 5.42 | 87.64 | 8.46 |
| AD-267118.1 | 24.21 | 1.80 | 88.65 | 9.90 |
| AD-267119.1 | 54.00 | 4.01 | 97.77 | 3.05 |
| AD-267120.1 | 14.75 | 0.67 | 89.26 | 7.34 |
| AD-267121.1 | 8.76 | 1.55 | 77.47 | 8.50 |
| AD-267122.1 | 16.43 | 1.70 | 89.44 | 4.75 |
| AD-295644.1 | 50.36 | 7.62 | 96.21 | 5.50 |
| AD-295645.1 | 6.17 | 1.20 | 64.53 | 6.70 |
| AD-295646.1 | 11.96 | 1.00 | 73.74 | 2.20 |
| AD-295647.1 | 13.07 | 3.08 | 97.30 | 3.11 |
| AD-295648.1 | 15.63 | 0.98 | 88.39 | 8.08 |
| AD-295649.1 | 2.44 | 0.75 | 41.73 | 17.58 |
| AD-295651.1 | 2.73 | 1.12 | 34.65 | 3.73 |
| AD-295652.1 | 4.15 | 0.60 | 36.36 | 2.77 |
| AD-295653.1 | 19.69 | 2.24 | 76.48 | 3.43 |
| AD-295661.1 | 82.29 | 10.31 | 109.30 | 4.05 |
| AD-295685.1 | 96.98 | 6.95 | 107.38 | 2.09 |
| AD-295688.1 | 29.20 | 1.19 | 90.67 | 7.33 |
| AD-295689.1 | 83.92 | 12.63 | 96.81 | 3.43 |
| AD-295692.1 | 4.09 | 1.47 | 39.47 | 3.40 |
| AD-295795.1 | 90.87 | 13.20 | 91.02 | 8.08 |
| AD-295796.1 | 93.36 | 6.57 | 101.37 | 9.46 |
| AD-295827.1 | 36.07 | 4.64 | 84.17 | 4.85 |
| AD-295828.1 | 59.84 | 2.83 | 105.17 | 14.92 |
| AD-295831.1 | 89.14 | 4.03 | 109.23 | 12.98 |
| AD-295856.1 | 12.43 | 2.28 | 74.44 | 6.83 |
| AD-295857.1 | 14.73 | 1.83 | 73.35 | 5.77 |
| AD-295858.1 | 4.41 | 0.68 | 43.87 | 2.79 |
| AD-295867.1 | 72.40 | 3.25 | 105.71 | 1.62 |
| AD-295868.1 | 18.79 | 1.83 | 92.79 | 5.86 |
| AD-295869.1 | 16.91 | 2.13 | 86.65 | 12.21 |
| AD-295870.1 | 13.84 | 1.24 | 80.22 | 4.93 |
| AD-295871.1 | 8.36 | 1.51 | 84.76 | 7.34 |
| AD-295872.1 | 12.59 | 2.47 | 67.76 | 2.99 |
| AD-295874.1 | 9.68 | 1.33 | 86.08 | 14.84 |
| AD-295879.1 | 26.38 | 1.68 | 102.12 | 3.87 |
| AD-295880.1 | 56.67 | 5.40 | 92.87 | 7.90 |
| AD-295897.1 | 7.20 | 2.16 | 72.12 | 5.62 |
| AD-295898.1 | 7.50 | 1.96 | 66.17 | 3.69 |
| AD-295899.1 | 18.36 | 1.08 | 75.37 | 6.79 |
| AD-295900.1 | 34.17 | 4.15 | 82.75 | 4.97 |

TABLE 10-continued

Superoxide Dismutase 1 In Vitro Single Dose Screens in Primary Cynomolgus Hepatocytes (PCH) cells

| Duplex | Dose - Unit 10 - nM | | Dose - Unit 0.1 - nM | |
|---|---|---|---|---|
| | Avg | SD | Avg | SD |
| AD-295901.1 | 78.50 | 9.63 | 99.36 | 8.09 |
| AD-295902.1 | 39.46 | 0.94 | 85.36 | 8.06 |
| AD-295904.1 | 81.60 | 3.70 | 122.37 | 38.87 |

TABLE 11

Superoxide Dismutase 1 In Vitro Single Dose Screens in Primary Cynomolgus Hepatocytes (PCH) cells

| Duplex | Dose - Unit 10 - nM | | Dose - Unit 0.1 - nM | |
|---|---|---|---|---|
| | Avg | SD | Avg | SD |
| AD-301535.1 | 98.03 | 4.84 | 103.16 | 4.23 |
| AD-301536.1 | 13.08 | 3.95 | 91.41 | 4.56 |
| AD-301537.1 | 90.15 | 2.62 | 98.10 | 3.83 |
| AD-301538.1 | 78.20 | 1.84 | 99.10 | 2.94 |
| AD-301539.1 | 17.73 | 1.91 | 93.38 | 5.78 |
| AD-301540.1 | 4.00 | 1.11 | 18.66 | 3.72 |
| AD-301542.1 | 4.10 | 0.15 | 16.46 | 1.70 |
| AD-301543.1 | 19.93 | 2.34 | 42.34 | 2.20 |
| AD-301544.1 | 46.92 | 1.85 | 91.07 | 7.70 |
| AD-301549.1 | 7.47 | 2.11 | 36.82 | 2.61 |
| AD-301550.1 | 81.19 | 4.70 | 93.06 | 2.17 |
| AD-301551.1 | 12.82 | 2.60 | 59.20 | 4.04 |
| AD-301552.1 | 4.02 | 0.81 | 11.54 | 3.27 |
| AD-301555.1 | 16.41 | 2.27 | 79.37 | 2.67 |
| AD-301559.1 | 63.74 | 4.62 | 86.68 | 6.17 |
| AD-301560.1 | 26.30 | 2.05 | 81.69 | 5.23 |
| AD-301562.1 | 11.59 | 0.41 | 62.13 | 4.15 |
| AD-301563.1 | 13.26 | 3.63 | 82.33 | 8.84 |
| AD-301564.1 | 8.00 | 2.00 | 44.21 | 2.37 |
| AD-301565.1 | 93.58 | 18.36 | 91.71 | 5.14 |
| AD-301566.1 | 91.41 | 6.74 | 94.53 | 6.85 |
| AD-301567.1 | 81.95 | 2.20 | 92.89 | 1.58 |
| AD-301569.1 | 13.38 | 2.26 | 85.15 | 7.45 |
| AD-301579.1 | 98.66 | 3.16 | 93.09 | 6.57 |
| AD-301593.1 | 92.38 | 3.29 | 98.75 | 2.28 |
| AD-301594.1 | 7.28 | 0.98 | 64.65 | 3.75 |
| AD-301596.1 | 100.90 | 2.95 | 101.04 | 4.27 |
| AD-301597.1 | 9.98 | 1.83 | 67.09 | 2.22 |
| AD-301598.1 | 4.24 | 0.87 | 27.83 | 2.99 |
| AD-301599.1 | 9.11 | 0.46 | 66.87 | 2.62 |
| AD-301600.1 | 8.37 | 0.52 | 65.13 | 1.96 |
| AD-301601.1 | 27.44 | 1.54 | 74.81 | 1.51 |
| AD-301612.1 | 105.54 | 2.23 | 101.38 | 3.70 |
| AD-301615.1 | 86.32 | 2.18 | 93.33 | 4.73 |
| AD-301616.1 | 96.28 | 2.34 | 95.39 | 2.41 |
| AD-301619.1 | 56.80 | 2.91 | 76.46 | 3.60 |
| AD-301648.1 | 7.79 | 0.88 | 77.88 | 5.67 |
| AD-301649.1 | 12.76 | 1.77 | 70.13 | 3.81 |
| AD-301650.1 | 53.37 | 7.81 | 81.48 | 2.45 |
| AD-301652.1 | 22.62 | 0.96 | 63.95 | 3.43 |
| AD-301653.1 | 52.02 | 3.26 | 88.05 | 6.54 |
| AD-301654.1 | 47.36 | 2.57 | 95.09 | 4.89 |
| AD-301661.1 | 43.53 | 4.13 | 85.28 | 4.94 |
| AD-301662.1 | 47.23 | 5.69 | 88.54 | 3.58 |
| AD-301663.1 | 5.86 | 0.94 | 48.62 | 2.08 |
| AD-301688.1 | 91.87 | 1.85 | 98.28 | 4.04 |
| AD-301690.1 | 88.47 | 3.32 | 98.93 | 2.85 |
| AD-301697.1 | 4.24 | 0.46 | 34.14 | 5.74 |
| AD-301699.1 | 4.18 | 0.12 | 16.49 | 3.39 |
| AD-301700.1 | 10.31 | 1.39 | 53.80 | 6.12 |
| AD-301701.1 | 14.10 | 2.33 | 87.21 | 3.78 |
| AD-301702.1 | 37.88 | 3.57 | 99.22 | 6.26 |
| AD-301703.1 | 87.54 | 6.72 | 96.03 | 1.28 |
| AD-301706.1 | 75.02 | 2.08 | 94.98 | 5.30 |
| AD-301764.1 | 106.66 | 3.34 | 104.25 | 4.60 |

TABLE 11-continued

Superoxide Dismutase 1 In Vitro Single Dose Screens in Primary Cynomolgus Hepatocytes (PCH) cells

| Duplex | Dose - Unit 10 - nM | | Dose - Unit 0.1 - nM | |
|---|---|---|---|---|
| | Avg | SD | Avg | SD |
| AD-301765.1 | 92.11 | 4.56 | 97.95 | 4.52 |
| AD-301799.1 | 85.29 | 2.57 | 97.06 | 2.86 |
| AD-301824.1 | 51.16 | 1.47 | 92.79 | 4.17 |
| AD-301825.1 | 41.28 | 3.29 | 83.80 | 4.54 |
| AD-301826.1 | 78.25 | 14.04 | 88.09 | 3.75 |
| AD-301827.1 | 83.51 | 5.58 | 98.20 | 7.25 |
| AD-301828.1 | 5.26 | 0.41 | 39.91 | 3.31 |
| AD-301829.1 | 7.69 | 0.33 | 39.97 | 1.79 |
| AD-301830.1 | 21.72 | 1.98 | 91.45 | 6.31 |
| AD-301843.1 | 26.53 | 2.76 | 89.45 | 3.20 |
| AD-301845.1 | 19.80 | 4.82 | 93.62 | 7.53 |
| AD-301846.1 | 22.54 | 3.19 | 94.07 | 2.15 |
| AD-301847.1 | 89.51 | 1.30 | 99.77 | 2.02 |
| AD-301848.1 | 99.23 | 4.92 | 100.84 | 7.65 |
| AD-301849.1 | 5.32 | 0.70 | 30.99 | 3.27 |
| AD-301850.1 | 88.76 | 2.72 | 94.06 | 3.16 |
| AD-301852.1 | 4.61 | 0.15 | 20.03 | 3.42 |
| AD-301859.1 | 7.06 | 0.40 | 44.19 | 1.61 |
| AD-301860.1 | 5.80 | 1.55 | 33.00 | 5.38 |
| AD-301873.1 | 93.07 | 4.80 | 95.72 | 2.66 |
| AD-301874.1 | 94.25 | 5.82 | 99.41 | 6.79 |
| AD-301875.1 | 97.60 | 6.57 | 98.62 | 4.21 |
| AD-301876.1 | 38.17 | 1.34 | 90.73 | 3.16 |
| AD-301877.1 | 48.77 | 2.53 | 93.26 | 2.44 |
| AD-301878.1 | 51.91 | 2.81 | 89.98 | 4.17 |
| AD-301880.1 | 36.41 | 2.32 | 78.14 | 2.74 |
| AD-301901.1 | 98.04 | 5.09 | 98.26 | 3.62 |
| AD-301902.1 | 89.05 | 1.95 | 100.83 | 2.70 |
| AD-301903.1 | 95.54 | 5.42 | 102.78 | 3.31 |
| AD-301904.1 | 96.36 | 5.22 | 97.39 | 2.37 |
| AD-301905.1 | 90.02 | 3.46 | 97.35 | 2.27 |
| AD-301906.1 | 77.52 | 1.57 | 99.69 | 6.26 |
| AD-301907.1 | 82.84 | 3.43 | 91.36 | 4.32 |
| AD-301908.1 | 81.82 | 2.51 | 95.34 | 6.79 |
| AD-301909.1 | 61.89 | 1.32 | 89.93 | 3.70 |
| AD-301910.1 | 70.37 | 2.00 | 95.73 | 4.15 |
| AD-301911.1 | 12.59 | 1.24 | 84.00 | 5.08 |
| AD-301912.1 | 53.89 | 4.10 | 97.43 | 4.16 |
| AD-301918.1 | 69.96 | 8.26 | 91.14 | 5.80 |

Example 2. Design, Synthesis and In Vitro Screening of Additional dsRNA Duplexes Based on the results provided in Example 1, additional siRNAs targeting identified hot spots in SOD1 mRNA were designed, synthesized and prepared using methods known in the art and described above in Example 1.

Detailed lists of the additional unmodified SOD1 sense and antisense strand nucleotide sequences are shown in Table 12. Detailed lists of the modified SOD1 sense and antisense strand nucleotide sequences are shown in Table 13.

Single dose screens of the additional agents were performed by transfection. Experiments were performed at 50 mM, 10 nM, 1 nM and 0.1 nM in primary cynomolgus hepatocytes (PCH) or neuroblastoma Be(2)C cells.

Total RNA isolation was performed using DYNA-BEADS. Briefly, cells were lysed in 10 µl of Lysis/Binding Buffer containing 3 µL of beads per well and mixed for 10 minutes on an electrostatic shaker. The washing steps were automated on a Biotek EL406, using a magnetic plate support. Beads were washed (in 3 µL) once in Buffer A, once in Buffer B, and twice in Buffer E, with aspiration steps in between. Following a final aspiration, complete 12 µL RT mixture was added to each well, as described below.

For cDNA synthesis, a master mix of 1.5 μl 10× Buffer, 0.6 μl 10× dNTPs, 1.5 μl Random primers, 0.75 μl Reverse Transcriptase, 0.75 μl RNase inhibitor and 9.9 μl of $H_2O$ per reaction were added per well. Plates were sealed, agitated for 10 minutes on an electrostatic shaker, and then incubated at 37° C. for 2 hours. Following this, the plates were agitated at 80° C. for 8 minutes.

RT-qPCR was performed as described above and relative fold change was calculated as described above.

The results of the transfection assays in PCH cells are shown in Table 14 and the results of the transfection assays in BE(2)C cells are shown in Table 15, and illustrated as stacked bar graphs in FIGS. 12A-12H (as mapped to NM_00454.6).

TABLE 12

Unmodified Sense and Antisense Strand Sequences of Superoxide Dismutase 1 dsRNA Agents

| Duplex Name | Sense Sequence 5' to 3' | SEQ ID NO: | Range in GenBank Acession No. 001285406.1 | Range in GenBank NM 000454.4 | Antisense Sequence 5' to 3' | SEQ ID NO: | Range in GenBank Acession No. 001285406.1 | Range in GenBank NM 000454.5 |
|---|---|---|---|---|---|---|---|---|
| AD-1321202.1 | UCAUCAAUUUCGAGCAGAAGU | 499 | 53-73 | 201-221 | ACUUCUGCUCGAAAUUGAUGAUG | 578 | 51-73 | 199-221 |
| AD-1321203.1 | CAUCAAUUUCGAGCAGAAGGA | 975 | 54-74 | 202-222 | ACCUUCUGCUCGAAAUUGAUGAU | 1009 | 52-74 | 200-222 |
| AD-1321204.1 | AUCAAUUUCGAGCAGAAGGAA | 63 | 55-75 | 203-223 | UUCCUUCUGCUCGAAAUUGAUGA | 1010 | 53-75 | 201-223 |
| AD-1321205.1 | UCAAUUUCGAGCAGAAGGAAA | 104 | 56-76 | 204-224 | UUUCCUUCUGCUCGAAAUUGAUG | 1011 | 54-76 | 202-224 |
| AD-1321206.1 | CAAUUUCGAGCAGAAGGAAAU | 84 | 57-77 | 205-225 | AUUUCCUUCUGCUCGAAAUUGAU | 1012 | 55-77 | 203-225 |
| AD-1321207.1 | AAUUUCGAGCAGAAGGAAAGU | 454 | 58-78 | 206-226 | ACUUUCCUUCUGCUCGAAAUUGA | 1013 | 56-78 | 204-226 |
| AD-1321208.1 | AUUUCGAGCAGAAGGAAAGUA | 47 | 59-79 | 207-227 | UACUUUCCUUCUGCUCGAAAUUG | 1014 | 57-79 | 205-227 |
| AD-1321209.1 | UUUCGAGCAGAAGGAAAGUAA | 89 | 60-80 | 208-228 | UUACUUUCCUUCUGCUCGAAAUU | 1015 | 58-80 | 206-228 |
| AD-1321210.1 | UUCGAGCAGAAGGAAAGUAAU | 46 | 61-81 | 209-229 | AUUACUUUCCUUCUGCUCGAAAU | 850 | 59-81 | 207-229 |
| AD-1321211.1 | UCGAGCAGAAGGAAAGUAAUU | 81 | 62-82 | 210-230 | AAUUACUUUCCUUCUGCUCGAAA | 1016 | 60-82 | 208-230 |
| AD-1321212.1 | CGAGCAGAAGGAAAGUAAUGU | 73 | 63-83 | 211-231 | ACAUUACUUUCCUUCUGCUCGAA | 156 | 61-83 | 209-231 |
| AD-1321213.1 | GAGCAGAAGGAAAGUAAUGGA | 455 | 64-84 | 212-232 | UCCAUUACUUUCCUUCUGCUCGA | 1017 | 62-84 | 210-232 |
| AD-1321214.1 | AGCAGAAGGAAAGUAAUGGAU | 976 | 65-85 | 213-233 | AUCCAUUACUUUCCUUCUGCUCG | 1018 | 63-85 | 211-233 |
| AD-1321215.1 | GCAGAAGGAAAGUAAUGGACU | 977 | 66-86 | 214-234 | AGUCCAUUACUUUCCUUCUGCUC | 1019 | 64-86 | 212-234 |
| AD-1321216.1 | CAGAAGGAAAGUAAUGGACCA | 83 | 67-87 | 215-235 | UGGUCCAUUACUUUCCUUCUGCU | 166 | 65-87 | 213-235 |
| AD-1321217.1 | AGAAGGAAAGUAAUGGACCAU | 456 | 68-88 | 216-236 | AUGGUCCAUUACUUUCCUUCUGC | 1020 | 66-88 | 214-236 |
| AD-1321218.1 | GAAGGAAAGUAAUGGACCAGU | 457 | 69-89 | 217-237 | ACUGGUCCAUUACUUUCCUUCUG | 536 | 67-89 | 215-237 |
| AD-1321219.1 | AAGGAAAGUAAUGGACCAGUU | 85 | 70-90 | 218-238 | AACUGGUCCAUUACUUUCCUUCU | 1021 | 68-90 | 216-238 |
| AD-1321220.1 | AGGAAAGUAAUGGACCAGUGA | 458 | 71-91 | 219-239 | UCACUGGUCCAUUACUUUCCUUC | 1022 | 69-91 | 217-239 |
| AD-1321221.1 | GGAAAGUAAUGGACCAGUGAA | 459 | 72-92 | 220-240 | UUCACUGGUCCAUUACUUUCCUU | 538 | 70-92 | 218-240 |
| AD-1321222.1 | GAAAGUAAUGGACCAGUGAAU | 460 | 73-93 | 221-241 | AUUCACUGGUCCAUUACUUUCCU | 851 | 71-93 | 219-241 |
| AD-1321223.1 | AAAGUAAUGGACCAGUGAAGU | 461 | 74-94 | 222-242 | ACUUCACUGGUCCAUUACUUUCC | 540 | 72-94 | 220-242 |

TABLE 12-continued

Unmodified Sense and Antisense Strand Sequences of Superoxide Dismutase 1 dsRNA Agents

| Duplex Name | Sense Sequence 5' to 3' | SEQ ID NO: | Range in GenBank Acession No. 001285406.1 | Range in GenBank No. NM 000454.4 | Antisense Sequence 5' to 3' | SEQ ID NO: | Range in GenBank Acession No. 001285406.1 | Range in GenBank No. NM 000454.5 |
|---|---|---|---|---|---|---|---|---|
| AD-1321224.1 | AAGUAAUGGACCAGUGAAGGU | 462 | 75-95 | 223-243 | ACCUUCACUGGUCCAUUACUUC | 541 | 73-95 | 221-243 |
| AD-1321225.1 | AGUAAUGGACCAGUGAAGGUU | 463 | 76-96 | 224-244 | AACCUUCACUGGUCCAUUACUUU | 1023 | 74-96 | 222-244 |
| AD-1321226.1 | GUAAUGGACCAGUGAAGGUGU | 978 | 77-97 | 225-245 | ACACCUUCACUGGUCCAUUACUU | 1024 | 75-97 | 223-245 |
| AD-1321227.1 | UAAUGGACCAGUGAAGGUGUU | 93 | 78-98 | 226-246 | AACACCUUCACUGGUCCAUUACU | 1025 | 76-98 | 224-246 |
| AD-1321228.1 | AAUGGACCAGUGAAGGUGUGU | 979 | 79-99 | 227-247 | ACACACCUUCACUGGUCCAUUAC | 1026 | 77-99 | 225-247 |
| AD-1321229.1 | GUACCAGUGCAGGUCCCUCACU | 980 | 173-193 | 321-341 | AGUGAGGACCUGCACUGGUACAG | 1027 | 171-193 | 319-341 |
| AD-1321230.1 | UACCAGUGCAGGUCCCUCACUU | 981 | 174-194 | 322-342 | AAGUGAGGACCUGCACUGGUACA | 1028 | 172-194 | 320-342 |
| AD-1321231.1 | ACCAGUGCAGGUCCCUCACUUU | 43 | 175-195 | 323-343 | AAAGUGAGGACCUGCACUGGUAC | 158 | 173-195 | 321-343 |
| AD-1321232.1 | CCAGUGCAGGUCCCUCACUUUA | 75 | 176-196 | 324-344 | UAAAGUGAGGACCUGCACUGGUA | 857 | 174-196 | 322-344 |
| AD-1321233.1 | CAGUGCAGGUCCCUCACUUUAA | 54 | 177-197 | 325-345 | UUAAAGUGAGGACCUGCACUGGU | 169 | 175-197 | 323-345 |
| AD-1321234.1 | AGUGCAGGUCCCUCACUUUAAU | 86 | 178-198 | 326-346 | AUUAAAGUGAGGACCUGCACUGG | 175 | 176-198 | 324-346 |
| AD-1321235.1 | GUGCAGGUCCCUCACUUUAAUU | 92 | 179-199 | 327-347 | AAUUAAAGUGAGGACCUGCACUG | 122 | 177-199 | 325-347 |
| AD-1321236.1 | UGCAGGUCCCUCACUUUAAUCU | 39 | 180-200 | 328-348 | AGAUUAAAGUGAGGACCUGCACU | 180 | 178-200 | 326-348 |
| AD-1321237.1 | GCAGGUCCCUCACUUUAAUCCU | 97 | 181-201 | 329-349 | AGGAUUAAAGUGAGGACCUGCAC | 124 | 179-201 | 327-349 |
| AD-1321238.1 | CAGGUCCCUCACUUUAAUCCUU | 41 | 182-202 | 330-350 | AAGGAUUAAAGUGAGGACCUGCA | 159 | 180-202 | 328-350 |
| AD-1321239.1 | AGGUCCCUCACUUUAAUCCUCU | 76 | 183-203 | 331-351 | AGAGGAUUAAAGUGAGGACCUGC | 136 | 181-203 | 329-351 |
| AD-1321240.1 | GGUCCCUCACUUUAAUCCUCUA | 53 | 184-204 | 332-352 | UAGAGGAUUAAAGUGAGGACCUG | 148 | 182-204 | 330-352 |
| AD-1321241.1 | GUCCCUCACUUUAAUCCUCUAU | 65 | 185-205 | 333-353 | AUAGAGGAUUAAAGUGAGGACCU | 147 | 183-205 | 331-353 |
| AD-1321242.1 | UCCCUCACUUUAAUCCUCUAUU | 64 | 186-206 | 334-354 | AAUAGAGGAUUAAAGUGAGGACC | 125 | 184-206 | 332-354 |
| AD-1321243.1 | CCUCACUUUAAUCCUCUAUCU | 42 | 187-207 | 335-355 | AGAUAGAGGAUUAAAGUGAGGAC | 1029 | 185-207 | 333-355 |
| AD-1321244.1 | CUCACUUUAAUCCUCUAUCCA | 50 | 188-208 | 336-356 | AGGAUAGAGGAUUAAAGUGAGGA | 165 | 186-208 | 334-356 |
| AD-1321245.1 | UCACUUUAAUCCUCUAUCCAU | 82 | 189-209 | 337-357 | AUGGAUAGAGGAUUAAAGUGAGG | 1030 | 187-209 | 335-357 |
| AD-1321246.1 | CACUUUAAUCCUCUAUCCAGA | 71 | 190-210 | 338-358 | ACUGGAUAGAGGAUUAAAGUGAG | | 188-210 | 336-358 |

TABLE 12-continued

Unmodified Sense and Antisense Strand Sequences of Superoxide Dismutase 1 dsRNA Agents

| Duplex Name | Sense Sequence 5' to 3' | SEQ ID NO: | Range in GenBank Acession No. 001285406.1 | Range in GenBank NM 000454.4 | Antisense Sequence 5' to 3' | SEQ ID NO: | Range in GenBank Acession No. 001285406.1 | Range in GenBank NM 000454.5 |
|---|---|---|---|---|---|---|---|---|
| AD-1321247.1 | ACUUUAAUCCUCUAUCCAGAA | 982 | 191-211 | 339-359 | UUCUGGAUAGAGGAUUAAAGUGA | 1031 | 189-211 | 337-359 |
| AD-1321248.1 | GUGGGCCAAAGGAUGAAGAGA | 983 | 218-238 | 366-386 | UCUCUUCAUCCUUUGGCCCACCG | 1032 | 216-238 | 364-386 |
| AD-1321249.1 | UGGGCCAAAGGAUGAAGAGAU | 984 | 219-239 | 367-387 | AUCUCUUCAUCCUUUGGCCCACC | 1033 | 217-239 | 365-387 |
| AD-1321250.1 | GGGCCAAAGGAUGAAGAGAGU | 985 | 220-240 | 368-388 | ACUCUCUUCAUCCUUUGGCCCAC | 1034 | 218-240 | 366-388 |
| AD-1321251.1 | GGCCAAAGGAUGAAGAGAGGU | 986 | 221-241 | 369-389 | ACCUCUCUUCAUCCUUUGGCCCA | 1035 | 219-241 | 367-389 |
| AD-1321252.1 | GCCAAAGGAUGAAGAGAGGCA | 987 | 222-242 | 370-390 | UGCCUCUCUUCAUCCUUUGGCCC | 1036 | 220-242 | 368-390 |
| AD-1321253.1 | CCAAAGGAUGAAGAGAGGCAU | 988 | 223-243 | 371-391 | AUGCCUCUCUUCAUCCUUUGGCC | 1037 | 221-243 | 369-391 |
| AD-1321254.1 | CAAAGGAUGAAGAGAGGCAUU | 473 | 224-244 | 372-392 | AAUGCCUCUCUUCAUCCUUUGGC | 860 | 222-244 | 370-392 |
| AD-1321255.1 | AAAGGAUGAAGAGAGGCAUGU | 989 | 225-245 | 373-393 | ACAUGCCUCUCUUCAUCCUUUGG | 1038 | 223-245 | 371-393 |
| AD-1321256.1 | AAGGAUGAAGAGAGGCAUGUU | 474 | 226-246 | 374-394 | AACAUGCCUCUCUUCAUCCUUUG | 1039 | 224-246 | 372-394 |
| AD-1321257.1 | AGGAUGAAGAGAGGCAUGUUU | 475 | 227-247 | 375-395 | AAACAUGCCUCUCUUCAUCCUUU | 554 | 225-247 | 373-395 |
| AD-1321258.1 | GGAUGAAGAGAGGCAUGUUGU | 476 | 228-248 | 376-396 | ACAACAUGCCUCUCUUCAUCCUU | 555 | 226-248 | 374-396 |
| AD-1321259.1 | GAUGAAGAGAGGCAUGUUGGA | 472 | 229-249 | 377-397 | ACCAACAUGCCUCUCUUCAUCCU | 1040 | 227-249 | 375-397 |
| AD-1321260.1 | AUGAAGAGAGGCAUGUUGGAU | 477 | 230-250 | 378-398 | AUCCAACAUGCCUCUCUUCAUCC | 556 | 228-250 | 376-398 |
| AD-1321261.1 | UGAAGAGAGGCAUGUUGGAGA | 990 | 231-251 | 379-399 | ACUCCAACAUGCCUCUCUUCAUC | 1041 | 229-251 | 377-399 |
| AD-1321262.1 | GAAGAGAGGCAUGUUGGAGAU | 102 | 232-252 | 380-400 | AUCUCCAACAUGCCUCUCUUCAU | 185 | 230-252 | 378-400 |
| AD-1321263.1 | AAGAGAGGCAUGUUGGAGACU | 478 | 233-253 | 381-401 | AGUCUCCAACAUGCCUCUCUUCA | 1042 | 231-253 | 379-401 |
| AD-1321264.1 | AGAGAGGCAUGUUGGAGACUU | 991 | 234-254 | 382-402 | AAGUCUCCAACAUGCCUCUCUUC | 1043 | 232-254 | 380-402 |
| AD-1321265.1 | GAGAGGCAUGUUGGAGACUUU | 992 | 235-255 | 383-403 | AAAGUCUCCAACAUGCCUCUCUU | 1044 | 233-255 | 381-403 |
| AD-1321266.1 | AGAGGCAUGUUGGAGACUUUG | 993 | 236-256 | 384-404 | ACAAGUCUCCAACAUGCCUCUCU | 1045 | 234-256 | 382-404 |
| AD-1321267.1 | GCAGAUGACUUGGGCAAAGGU | 483 | 370-390 | 518-538 | ACCUUGCCCAAGUCAUCUGCUU | 1046 | 368-390 | 516-538 |
| AD-1321268.1 | CAGAUGACUUGGGCAAAGGUU | 994 | 371-391 | 519-539 | AACCUUUGCCCAAGUCAUCUGCU | 1047 | 369-391 | 517-539 |
| AD-1321269.1 | AGAUGACUUGGGCAAAGGUGU | 484 | 372-392 | 520-540 | ACACCUUUGCCCAAGUCAUCUGC | 563 | 370-392 | 518-540 |

TABLE 12-continued

Unmodified Sense and Antisense Strand Sequences of Superoxide Dismutase 1 dsRNA Agents

| Duplex Name | Sense Sequence 5' to 3' | SEQ ID NO: | Range in GenBank Acession No. 001285406.1 | Range in GenBank No. NM 000454.4 | Antisense Sequence 5' to 3' | SEQ ID NO: | Range in GenBank Acession No. 001285406.1 | Range in GenBank No. NM 000454.5 |
|---|---|---|---|---|---|---|---|---|
| AD-1321270.1 | GAUGACUUGGGCAAAGGUGGA | 479 | 373-393 | 521-541 | ACCACCUUUGCCCAAGUCAUCUG | 1048 | 371-393 | 519-541 |
| AD-1321271.1 | AUGACUUGGGCAAAGGUGGAA | 450 | 374-394 | 522-542 | UUCCACCUUUGCCCAAGUCAUCU | 529 | 372-394 | 520-542 |
| AD-1321272.1 | UGACUUGGGCAAAGGUGGAAA | 451 | 375-395 | 523-543 | UUUCCACCUUUGCCCAAGUCAUC | 530 | 373-395 | 521-543 |
| AD-1321273.1 | GACUUGGGCAAAGGUGGAAAU | 452 | 376-396 | 524-544 | AUUCCACCUUUGCCCAAGUCAU | 531 | 374-396 | 522-544 |
| AD-1321274.1 | ACUUGGGCAAAGGUGGAAAUU | 485 | 377-397 | 525-545 | AAUUCCACCUUUGCCCAAGUCA | 1049 | 375-397 | 523-545 |
| AD-1321275.1 | CUUGGGCAAAGGUGGAAAUGA | 995 | 378-398 | 526-546 | ACAUUCCACCUUUGCCCAAGUC | 1050 | 376-398 | 524-546 |
| AD-1321276.1 | UUGGGCAAAGGUGGAAAUGAA | 103 | 379-399 | 527-547 | UUCAUUCCACCUUUGCCCAAGU | 1051 | 377-399 | 525-547 |
| AD-1321277.1 | UGGGCAAAGGUGGAAAUGAAU | 996 | 380-400 | 528-548 | AUUCAUUCCACCUUUGCCCAAG | 1052 | 378-400 | 526-548 |
| AD-1321278.1 | GGGCAAAGGUGGAAAUGAAGA | 997 | 381-401 | 529-549 | ACUUCAUUUCCACCUUUGCCCAA | 1053 | 379-401 | 527-549 |
| AD-1321279.1 | GGCAAAGGUGGAAAUGAAGAA | 998 | 382-402 | 530-550 | UUCUUCAUUUCCACCUUUGCCCA | 1054 | 380-402 | 528-550 |
| AD-1321280.1 | GCAAAGGUGGAAAUGAAGAAA | 999 | 383-403 | 531-551 | UUUCUUCAUUUCCACCUUUGCCC | 1055 | 381-403 | 529-551 |
| AD-1321281.1 | CAAAGGUGGAAAUGAAGAAAU | 1000 | 384-404 | 532-552 | AUUUCUUCAUUUCCACCUUUGCC | 1056 | 382-404 | 530-552 |
| AD-1321282.1 | AAAGGUGGAAAUGAAGAAAGU | 1001 | 385-405 | 533-553 | ACUUUCUUCAUUUCCACCUUUGC | 1057 | 383-405 | 531-553 |
| AD-1321283.1 | AAGGUGGAAAUGAAGAAAGUA | 453 | 386-406 | 534-554 | UACUUUCUUCAUUUCCACCUUUG | 1058 | 384-406 | 532-554 |
| AD-1321284.1 | AGGUGGAAAUGAAGAAAGUAU | 512 | 387-407 | 535-555 | AUACUUUCUUCAUUUCCACCUUU | 1059 | 385-407 | 533-555 |
| AD-1321285.1 | GGUGGAAAUGAAGAAAGUACA | 1002 | 388-408 | 536-556 | AGUACUUUCUUCAUUUCCACCUU | 1060 | 386-408 | 534-556 |
| AD-1321286.1 | GUGGAAAUGAAGAAAGUACAA | 1003 | 389-409 | 537-557 | UUGUACUUUCUUCAUUUCCACCU | 1061 | 387-409 | 535-557 |
| AD-1321287.1 | UGGAAAUGAAGAAAGUACAAA | 1004 | 390-410 | 538-558 | UUUGUACUUUCUUCAUUUCCACC | 1062 | 388-410 | 536-558 |
| AD-1321288.1 | GGAAAUGAAGAAAGUACAAAU | 1005 | 391-411 | 539-559 | AUUUGUACUUUCUUCAUUUCCAC | 1063 | 389-411 | 537-559 |
| AD-1321289.1 | GAAAUGAAGAAAGUACAAAGA | 1006 | 392-412 | 540-560 | UCUUUGUACUUUCUUCAUUUCCA | 1064 | 390-412 | 538-560 |
| AD-1321290.1 | AAAUGAAGAAAGUACAAAGAU | 1007 | 393-413 | 541-561 | AUCUUUGUACUUUCUUCAUUUCC | 1065 | 391-413 | 539-561 |
| AD-1321291.1 | AAUGAAGAAAGUACAAAGACA | 1008 | 394-414 | 542-562 | UGUCUUUGUACUUUCUUCAUUUC | 1066 | 392-414 | 540-562 |

TABLE 13

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1321202.1 | uscsauc(Ahd)AfuUfCfgagcagaaguL96 | 1067 | asCfsuudCu(G2p)cucgaaAfuUfgaugasusg | 1157 | CACCAUCAAUUCGAGCAGAAGG | 1247 |
| AD-1321203.1 | csasuca(Ahd)UfuUfCfGfagcagaaggaL96 | 1068 | asCfscuuCfugcucgaAfaUfugaugsasu | 1158 | ACCAUCAAUUCGAGCAGAGAGGA | 1248 |
| AD-1321204.1 | asuscaa(Uhd)UfuCfCfAfgcagaaggaaL96 | 1069 | usUfsccdTu(C2p)ugcucgAfaAfuugausgsa | 1159 | CCAUCAAUUCGAGCAGAAGGAA | 395 |
| AD-1321205.1 | uscsaau(Uhd)UfcGfAfGfcagaaggaaaL96 | 1070 | usUfsucdCu(Tgn)cugcucgGfaAfauugasusg | 1160 | CAUCAAUUCGAGCAGAAGGAAA | 436 |
| AD-1321206.1 | csasauu(Uhd)CfgAfGfCfagaaggaaauL96 | 1071 | asUfsuudCc(Tgn)ucugcuCfgAfaauugsasu | 1161 | AUCAAUUCGAGCAGAAGGAAAG | 416 |
| AD-1321207.1 | asasuuu(Chd)GfaGfCfAfaggaaguL96 | 1072 | asCfsuudTc(C2p)uucugcUfcGfaaauusgsa | 1162 | UCAAUUCGAGCAGAAGGAAAGU | 770 |
| AD-1321208.1 | asusuuc(Ghd)AfgCfAfGfaaggaaaguaL96 | 1073 | usAfscudTu(C2p)cuucugCfuCfgaaausug | 1163 | CAAUUCGAGCAGAAGGAAAGUA | 379 |
| AD-1321209.1 | ususucg(Ahd)GfcAfGfAfaggaaaguaaL96 | 1074 | usUfsacdTu(Tgn)ccuucuGfcUfcgaasusu | 1164 | AAUUCGAGCAGAAGGAAAGUAA | 421 |
| AD-1321210.1 | ususcga(Ghd)CfaGfAfAfgaagaguauuL96 | 1075 | asUfsuadCu(Tgn)uccuucUfgCfucgaasasu | 1165 | AUUCGAGCAGAAGGAAAGUAAU | 378 |
| AD-1321211.1 | uscssgag(Chd)AfgAfAfGfgaaguaauuL96 | 1076 | asAfsuudAc(Tgn)uuccuuCfuGfcucgasasa | 1166 | UUUCGAGCAGAAGGAAAGUAAUG | 413 |
| AD-1321212.1 | csgsagc(Ahd)GfaAfGfGfaaaguaaugguL96 | 1077 | asCfsauuAfcuuuccuUfcUfgcucgsasa | 1167 | UUCGAGCAGAAGGAAAGUAAUGG | 405 |
| AD-1321213.1 | gsasgca(Ahd)AfaGfGfAfaaguaauuggaL96 | 1078 | asCfscauUfacuuuccUfuCfugcucsga | 1168 | UCGAGCAGAAGGAAAGUAAUGGA | 771 |
| AD-1321214.1 | asgscag(Ahd)AfgGfAfAfaguaauggauL96 | 1079 | asCfsccaUfuacuucCfiUfcugcuscsg | 1169 | CGAGCAGAAGGAAAGUAAUGGAC | 1249 |
| AD-1321215.1 | gscsaga(Ahd)GfgAfAfAfguaauggacuL96 | 1080 | asGfsucdCa(Tgn)uacuuuCfcUfucugcsusc | 1170 | GAGCAGAAGGAAAGUAAUGGACC | 1250 |
| AD-1321216.1 | csasgaa(Ghd)GfaAfAfAfguaauggaccaL96 | 1081 | usGfsgudCc(Agn)uuacuuUfcCfuucugscsu | 1171 | AGCAGAAGGAAAGUAAUGGACCA | 415 |

TABLE 13-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1321217.1 | asgsaag(Ghd)AfaAfGfUfaauggaccauL96 | 1082 | asUfsggdTc(C2p)auuacuUfcfuucusgsc | 1172 | GCAGAAGGAAAGUAAUGGACCAG | 772 |
| AD-1321218.1 | gsasagg(Ahd)AfaGfUfAfauggaccaguL96 | 1083 | asCfsugdGu(C2p)cauuacUfuUfccuucsusg | 1173 | CAGAGAAGGAAAGUAAUGGACCAGU | 773 |
| AD-1321219.1 | asasgga(Ahd)AfgUfAfAfAfuggaccaguuL96 | 1084 | asAfscudGg(Tgn)ccauuaCfuUfuccuuascsu | 1174 | AGAAGGAAAGUAAUGGACCAGUG | 417 |
| AD-1321220.1 | asgsgaa(Ahd)GfuAfAfUfggaccagugaL96 | 1085 | usCfsacdTg(G2p)uccauuAfcUfuuccususc | 1175 | GAAGGAAAGUAAUGGACCAGUGA | 774 |
| AD-1321221.1 | gsgsaaa(Ghd)UfaAfUfGfgaccagugaaL96 | 1086 | usUfscadCu(G2p)guccauUfaCfuuuccsusu | 1176 | AAGGAAAGUAAUGGACCAGUGAA | 775 |
| AD-1321222.1 | gsasaag(Ghd)AfaUfGfGfaccagugaauL96 | 1087 | asUfsucdAc(Tgn)gguccaUfuAfcuuucscsu | 1177 | AGGAAAGUAAUGGACCAGUGAAG | 776 |
| AD-1321223.1 | asasagu(Ahd)AfuGfGfAfccagugaaguL96 | 1088 | asCfsuucAfcugguccAfuUfacuuuscsc | 1178 | GGAAAGUAAUGGACCAGUGAAGG | 777 |
| AD-1321224.1 | asasgua(Ahd)UfgGfAfCfcagugaagguL96 | 1089 | asCfscuuCfacugguCfaUfuacuusususc | 1179 | GAAAGUAAUGGACCAGUGAAGGU | 778 |
| AD-1321225.1 | asgsguaa(Uhd)GfgAfCfCfagugaagguUL96 | 1090 | asAfsccdTu(C2p)acugguCfAfuuacususu | 1180 | AAAGUAAUGGACCAGUGAAGGUG | 779 |
| AD-1321226.1 | gsusuaau(Ghd)GfaCfCfAfgugaagguguL96 | 1091 | asCfsaccUfucacuggUfcCfauuacsusu | 1181 | AAGUAAUGGACCAGUGAAGGUGU | 1251 |
| AD-1321227.1 | usasaug(Ghd)AfcCfAfGfugaaggugUL96 | 1092 | asAfscacCfuucacugGfuCfcauuascsu | 1182 | AGUAAUGGACCAGUGAAGGUGUG | 425 |
| AD-1321228.1 | asasugg(Ahd)CfcAfGfUfgaaggugugL96 | 1093 | asCfsacaCfcuucacuGfgUfccauuasc | 1183 | GUAAUGGACCAGUGAAGGUGUGG | 1252 |
| AD-1321229.1 | gsusacc(Ahd)GfuGfAfAfggugugcacL96 | 1094 | asGfsugdAg(G2p)accugcAfcUfgguacsasg | 1184 | CUGUACCAGUCCAGGUCCUCACU | 1253 |
| AD-1321230.1 | usasccca(Ghd)GfuCfCfUfcacuuuL96 | 1095 | asAfsgudGa(G2p)gaccugCfaCfuggcascsa | 1185 | UGUACCAGUGCAGGUCCUCACUU | 1254 |
| AD-1321231.1 | ascscag(Uhd)GfcAfGfGfuccucacuuuL96 | 1096 | asAfsagdTg(Agn)ggaccuGfcAfcugguasc | 1186 | GUACCAGUGCAGGUCCUCACUUU | 375 |
| AD-1321232.1 | cscsagu(Ghd)CfaGfGfUfccucacuuuaL96 | 1097 | usAfsaadGu(G2p)aggaccUfgCfacuggsusa | 1187 | UACCAGUGCAGGUCCUCACUUUA | 407 |

TABLE 13-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1321233.1 | csasgug(Chd)AfgGfUfCfcucacuuuaaL96 | 1098 | usUfsaadAg(Tgn)gaggacCfuGfcacugsgsu | 1188 | ACCAGUGCAGGUCCUCACUUUAA | 386 |
| AD-1321234.1 | asgsugc(Ahd)GfgUfCfCfucacuuuaauL96 | 1099 | asUfsuadAa(G2p)ugaggaCfcUfgcacusgsg | 1189 | CCAGUGCAGGUCCUCACUUUAAU | 418 |
| AD-1321235.1 | gsusgca(Ghd)GfuCfCfUfcacuuuaauuL96 | 1100 | asAfsuuaAfaguaggAfcCfugcacusug | 1190 | CAGUGCAGGUCCUCACUUUAAUC | 424 |
| AD-1321236.1 | usgscag(Ghd)UfcCfUfCfacuuuaaucuL96 | 1101 | asGfsauuAfaagugagGfaCfcugcasccu | 1191 | AGUGCAGGUCCUCACUUUAAUCC | 371 |
| AD-1321237.1 | gscsagg(Uhd)CfcUfCfAfcuuuaauccuL96 | 1102 | asGfsgauUfaaagugaGfgAfccugcsaac | 1192 | GUGCAGGUCCUCACUUUAAUCCU | 429 |
| AD-1321238.1 | csasggu(Chd)CfucCfAfCfuuuaauccuuL96 | 1103 | asAfsggaUfuaaagugAfgGfaccugsca | 1193 | UGCAGGUCCUCACUUUAAUCCUC | 373 |
| AD-1321239.1 | asggguc(Chd)UfcAfCfUfuuaauccucuL96 | 1104 | asGfsaggAfuuaaaguGfaGfgaccusgc | 1194 | GCAGGUCCUCACUUUAAUCCUCU | 408 |
| AD-1321240.1 | gsgsucc(Uhd)CfacUfUfUfuaauccucuaL96 | 1105 | usAfsgadGg(Agn)uuaaaugUfgAfgaccusug | 1195 | CAGGUCCUCACUUUAAUCCUCUA | 385 |
| AD-1321241.1 | gsuscct(Chd)AfcUfUfUfaauccucuauL96 | 1106 | asUfsagdAg(G2p)auuaaaGfuGfaggacscsu | 1196 | AGGUCCUCACUUUAAUCCUCUAU | 397 |
| AD-1321242.1 | uscscuc(Ahd)CfuUfUfAfauccucuauuL96 | 1107 | asGfsuadGa(G2p)gauuaaAfgUfgaggasgsc | 1197 | GGUCCUCACUUUAAUCCUCUAUC | 396 |
| AD-1321243.1 | cscsuca(Chd)UfuUfAfAfuccucuauucL96 | 1108 | asGfsaudAg(Agn)ggauuaAfaCfugaggsasc | 1198 | GUCCUCACUUUAAUCCUCUAUCC | 374 |
| AD-1321244.1 | csuscac(Uhd)UfuAfAfUfccucuauccaL96 | 1109 | asGfsgauAfgaggauuAfaAfgugagsga | 1199 | UCCUCACUUUAAUCCUCUAUCCA | 382 |
| AD-1321245.1 | uscsact(Uhd)UfaAfUfCfcucuauccauL96 | 1110 | asUfsggaAfagaggauUfaAfagugasgg | 1200 | CCUCACUUUAAUCCUCUAUCCAG | 414 |
| AD-1321246.1 | csasuut(Chd)AfaUfCfCfucuauccagaL96 | 1111 | asCfsuggAfuagaggaUfuAfaagugsasg | 1201 | CUCACUUUAAUCCUCUAUCCAGA | 403 |
| AD-1321247.1 | ascsuuu(Ahd)AfuCfCfUfcuauccagaaL96 | 1112 | usUfscudGg(Agn)uagaggAfuUfaaagusga | 1202 | UCACUUUAAUCCUCUAUCCAGAC | 393 |
| AD-1321248.1 | gsusggg(Chd)CfaAfAfGfgaugaagagaL96 | 1113 | uscCfsucdTu(C2p)auccuuUfgCfccacscsg | 1203 | CGGUGGGCCAAAGGAUGAAGAGA | 1255 |

TABLE 13-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1321249.1 | usgsggc(Chd)AfaAfGfGfaugaagagauL96 | 1114 | asUfscudCu(Tgn)cauccuUfuGfgcccascsc | 1204 | GGUGGGCCAAAGGAUGAAGAGAG | 1256 |
| AD-1321250.1 | gggsgcc(Ahd)AfaGfGfAfugaagagaguL96 | 1115 | asCfsucdTc(Tgn)ucauccUfuUfggcccsasc | 1205 | GUGGGCCAAAGGAUGAAGAGAGG | 1257 |
| AD-1321251.1 | gggscca(Ahd)AfgGfAfUfgaagagagguL96 | 1116 | asCfscudCu(C2p)uucaucCfuUfuggccscsa | 1206 | UGGGCCAAAGGAUGAAGAGAGGC | 1258 |
| AD-1321252.1 | gscscaa(Ahd)GfgAfUfGfaagagaggcaL96 | 1117 | usGfsccdTc(Tgn)cuucacUfcUfuuggcscsc | 1207 | GGGCCAAAGGAUGAAGAGAGGCA | 1259 |
| AD-1321253.1 | cscsaaa(Ghd)GfaUfGfAfagagaggcauL96 | 1118 | asUfsgcdCu(C2p)ucuucaUfcCfuuuggscsc | 1208 | GGCCAAAGGAUGAAGAGAGGCAU | 1260 |
| AD-1321254.1 | csasaag(Ghd)AfuGfAfAfgagaggcauuL96 | 1119 | asAfsugdCc(Tgn)cucuucAfucCfcuuugsgsc | 1209 | GCCAAAGGAUGAAGAGAGGCAUG | 789 |
| AD-1321255.1 | asasagg(Ahd)UfgAfAfGfagaggcauguL96 | 1120 | asCfsaudGc(C2p)ucucuuCfaUfccuuusgsg | 1210 | CCAAAGGAUGAAGAGAGGCAUGU | 1261 |
| AD-1321256.1 | asasgga(Uhd)GfaAfGfAfgaggcauguuL96 | 1121 | asAfscadTg(C2p)cucucuuCfAfuccuususg | 1211 | CAAAGGAUGAAGAGAGGCAUGUU | 790 |
| AD-1321257.1 | aggsgau(Ahd)AfgAfGfAfggcaugauuL96 | 1122 | asAfsacdAu(G2p)ccucucUfuCfauccususu | 1212 | AAAGGAUGAAGAGAGGCAUGUUG | 791 |
| AD-1321258.1 | gggsaug(Ahd)AfgAfGfAfggcauguugaL96 | 1123 | asCfsaaaAfugcucucCfuUfcauccsusu | 1213 | AAGGAUGAAGAGAGGCAUGUUGG | 792 |
| AD-1321259.1 | gsasuga(Ahd)GfaGfAfGfgcauguggaL96 | 1124 | asCfscaaCfaugccucUfcUfucaucscsu | 1214 | AGGAUGAAGAGAGGCAUGUUGGA | 788 |
| AD-1321260.1 | asusgaa(Ahd)GfaGfAfGfgcauguggauL96 | 1125 | asCfsccaAfcaugccuCfiuCfuucauscsc | 1215 | GGAUGAAGAGAGGCAUGUUGGAG | 793 |
| AD-1321261.1 | usgsaag(Ahd)GfaGfCfCfauguuggagaL96 | 1126 | asCfsuccAfacaugccUfcUfcuucasusc | 1216 | GAUGAAGAGAGGCAUGUUGGAGA | 1262 |
| AD-1321262.1 | gsasaga(Ghd)AfgGfCfAfuguuggagacL96 | 1127 | asUfscucCfaacaugcCfuCfuucucsasu | 1217 | AUGAAGAGAGGCAUGUUGGAGAC | 434 |
| AD-1321263.1 | asasgag(Ghd)GfgCfAfUfguuggagacuL96 | 1128 | asGfsucdTc(C2p)aacaugCfcUfcucuuscsa | 1218 | UGAAGAGAGGCAUGUUGGAGACC | 794 |
| AD-1321264.1 | aggsaga(Ghd)GfcAfUfGfuuggagacuuL96 | 1129 | asAfsgudCu(C2p)caacaugCfcCfucucusuusc | 1219 | GAAGAGAGGCAUGUUGGAGACCU | 1263 |

TABLE 13-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1321265.1 | gsasgag(Ghd)CfaUfGfUfuggagacuuuL96 | 1130 | asAfsagdTc(Tgn)ccaacaUfgCfcucucsusu | 1220 | AAGAGAGGCAUGUUGGAGACCUG | 439 |
| AD-1321266.1 | aggsagg(Chd)AfuGfUfUfgagacuuguL96 | 1131 | asCfsaaadGu(C2p)uccaacAfuGfccucuscsu | 1221 | AGAGAGGCAUGUUGGAGACCUGG | 1264 |
| AD-1321267.1 | gscsaga(Uhd)GfaCfUfUfgggcaagguL96 | 1132 | asCfscudTu(G2p)cccaagUfcAfucugcsusu | 1222 | AAGCAGAUGACUUGGGCAAAGGU | 799 |
| AD-1321268.1 | csasgau(Ghd)AfcUfGfGfgcaaggguuL96 | 1133 | asAfsccuUfugcccaaGfuCfaucugscsu | 1223 | AGCAGAUGACUUGGGCAAAGGUG | 1265 |
| AD-1321269.1 | aggsaug(Ahd)CfuUfGfGfgcaaagugugL96 | 1134 | asCfsaccUfugcccaAfgUfcaucugsc | 1224 | GCAGAUGACUUGGGCAAAGGUGG | 800 |
| AD-1321270.1 | gsasuga(Chd)UfuGfGfGfcaaagguggaL96 | 1135 | asCfscaccUfuuugcccAfaGfucaucsug | 1225 | CAGAUGACUUGGGCAAAGGUGGA | 795 |
| AD-1321271.1 | asusugac(Uhd)UfgGfGfCfcaaagguggaaL96 | 1136 | usUfscccAc(C2p)uuugcccCfaAfgucaucsu | 1226 | AGAUGACUUGGGCAAAGGUGGAA | 766 |
| AD-1321272.1 | usgsacu(Uhd)GfgGfCfAfaaagguggaaaL96 | 1137 | usUfsucdCa(C2p)cuuugcCfcAfagucausuc | 1227 | GAUGACUUGGGCAAAGGUGGAAA | 767 |
| AD-1321273.1 | gsasucuu(Ghd)GfgCfAfAfaggugaaauL96 | 1138 | asUfsuudCc(Agn)ccuuugCfcCfaagucsasu | 1228 | AUGACUUGGGCAAAGGUGGAAAU | 768 |
| AD-1321274.1 | ascsuug(Ghd)GfcAfAfAfggugaaauuL96 | 1139 | asAfsuudTc(C2p)accuuuGfcCfcaagustcsa | 1229 | UGACUUGGGCAAAGGUGGAAAUG | 801 |
| AD-1321275.1 | csusugg(Ghd)CfaAfAfGfguggaaaugaL96 | 1140 | asCfsauuUfccaccuuUfgCfccaagsuc | 1230 | GACUUGGGCAAAGGUGGAAAUGA | 1266 |
| AD-1321276.1 | ususggg(Chd)AfaAfGfGfuggaaaugaaL96 | 1141 | usUfscadTu(Tgn)ccaccuUfuGfcccaagsu | 1231 | ACUUGGGCAAAGGUGGAAAUGAA | 435 |
| AD-1321277.1 | usgsggc(Ahd)AfaGfGfUfggaaaugaauL96 | 1142 | asUfsucdAu(Tgn)uccaccUfuUfgcccasag | 1232 | CUUGGGCAAAGGUGGAAAUGAAG | 1267 |
| AD-1321278.1 | gsgsgca(Ahd)AfgGfUfGfgaaaugaagaL96 | 1143 | asCfsuucAfuuuccacCfuUfugcccasa | 1233 | UUGGGCAAAGGUGGAAAUGAAGA | 1268 |
| AD-1321279.1 | gsgscaa(Ahd)GfgUfGfGfaaaugaagaaL96 | 1144 | usUfscudTc(Agn)uuuccaCfuUfugcccsa | 1234 | UGGGCAAAGGUGGAAAUGAAGAA | 1269 |
| AD-1321280.1 | gscsaaa(Ghd)GfuGfGfAfaaugaagaaaL96 | 1145 | usUfsucdTu(C2p)auuuccAfcCfuuuugcscsc | 1235 | GGGCAAAGGUGGAAAUGAAGAAA | 1270 |

TABLE 13-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1321281.1 | csasaaag(Ghd)UfgGfAfAfaugaagaaauL96 | 1146 | asUfsuudCu(Tgn)cauuucCfaCfcuuugscsc | 1236 | GGCAAAGGUGGAAAUGAAGAAAG | 1271 |
| AD-1321282.1 | asasagg(Uhd)GfGfAfAfugaagaaaguL96 | 1147 | asCfsuudTc(Tgn)ucauuuCfcAfccuuusgsc | 1237 | GCAAAGGUGGAAAUGAAGAAAGU | 1272 |
| AD-1321283.1 | asasggu(Ghd)GfaAfAfUfgaagaaaguaL96 | 1148 | usAfscudTu(C2p)uucauuUfcCfaccuususg | 1238 | CAAAGGUGGAAAUGAAGAAAGUA | 769 |
| AD-1321284.1 | asgsgug(Ghd)AfaAfUfGfaagaaaguauL96 | 1149 | asUfsacdTu(Tgn)cuucauUfuCfcaccususu | 1239 | AAAGGUGGAAAUGAAGAAAGUAA | 1273 |
| AD-1321285.1 | gsgsugg(Ahd)AfaUfGfAfagaaaguacaL96 | 1150 | asGfsuacUfuucucucaUfuUfccaccsusu | 1240 | AAGGUGGAAAUGAAGAAAGUAAA | 446 |
| AD-1321286.1 | gsusugga(Ahd)AfuGfAfAfgaaaguacaaL96 | 1151 | usUfsgudAc(Tgn)ucuucaAfuUfccacscsu | 1241 | AGGUGGAAAUGAAGAAAGUAAAA | 1274 |
| AD-1321287.1 | usgsgaa(Ahd)UfgAfAfGfaaaguacaaaL96 | 1152 | usUfsugdTa(C2p)uuucuuCfaUfuccascsc | 1242 | GGUGGAAAUGAAGAAAGUAAAAA | 1275 |
| AD-1321288.1 | gsgsaaa(Uhd)GfaAfAfGfaaguacaaaaL96 | 1153 | asUfsuudGu(Agn)cuuucuUfcAfuuuccsasc | 1243 | GUGGAAAUGAAGAAAGUAAAAAG | 1276 |
| AD-1321289.1 | gsasaau(Ghd)AfaAfGfAfaguacaaagaL96 | 1154 | usCfsuudTg(Tgn)acuuucUfuCfauuucscsa | 1244 | UGGAAAUGAAGAAAGUAAAAAGA | 1277 |
| AD-1321290.1 | asasaaug(Ahd)AfgAfAfAfguacaaagacL96 | 1155 | asUfscudTu(Tgn)uacuuuCfuUfcauuuscsc | 1245 | GGAAAUGAAGAAAGUAAAAAGAC | 1278 |
| AD-1321291.1 | asasauga(Ahd)GfaAfAfGfuacaaagacaL96 | 1156 | usGfsucdTu(Tgn)guacuuUfcUfuauuuusc | 1246 | GAAAUGAAGAAAGUAAAAAGACA | 1279 |

TABLE 14

Superoxide Dismutase 1 In Vitro Single Dose Screens in Primary Cynomolgus Hepatocytes (PCH) cells

| Duplex | 50 mM Avg | SD | 10 nM Avg | SD | 1 nM Avg | SD | 0.1 nM Avg | SD |
|---|---|---|---|---|---|---|---|---|
| AD-1321202.1 | 40.5 | 4.8 | 38.0 | 4.1 | 63.0 | 6.8 | 91.8 | 3.6 |
| AD-1321203.1 | 24.5 | 1.5 | 29.0 | 2.0 | 72.8 | 5.4 | 89.5 | 2.7 |
| AD-1321204.1 | 27.2 | 1.1 | 20.2 | 1.5 | 31.5 | 2.3 | 70.9 | 2.6 |
| AD-1321205.1 | 96.4 | 5.1 | 86.7 | 2.0 | 95.3 | 4.9 | 97.3 | 2.3 |
| AD-1321206.1 | 21.5 | 1.2 | 20.7 | 1.7 | 37.6 | 4.2 | 69.5 | 2.8 |
| AD-1321207.1 | 9.2 | 1.1 | 9.9 | 1.3 | 22.9 | 3.7 | 53.7 | 4.1 |
| AD-1321208.1 | 41.0 | 4.8 | 27.7 | 1.0 | 49.9 | 2.4 | 81.8 | 2.0 |
| AD-1321209.1 | 66.0 | 1.8 | 55.7 | 4.0 | 67.5 | 3.4 | 90.3 | 2.0 |
| AD-1321210.1 | 6.9 | 1.1 | 8.0 | 1.3 | 13.9 | 2.8 | 34.8 | 3.6 |
| AD-1321211.1 | 101.9 | 4.3 | 99.1 | 1.6 | 88.3 | 3.4 | 100.2 | 3.5 |
| AD-1321212.1 | 21.7 | 2.3 | 25.4 | 2.1 | 57.8 | 5.9 | 88.7 | 4.3 |
| AD-1321213.1 | 31.1 | 3.1 | 29.0 | 2.4 | 60.6 | 6.6 | 93.2 | 3.2 |
| AD-1321214.1 | 76.6 | 8.9 | 75.7 | 9.1 | 93.7 | 8.1 | 98.0 | 3.3 |
| AD-1321215.1 | 30.3 | 2.9 | 35.0 | 4.4 | 83.2 | 10.4 | 94.5 | 4.6 |
| AD-1321216.1 | 17.7 | 4.0 | 13.5 | 3.1 | 31.1 | 5.0 | 64.7 | 3.3 |
| AD-1321217.1 | 47.9 | 5.0 | 35.5 | 4.3 | 54.9 | 5.9 | 80.8 | 6.2 |
| AD-1321218.1 | 28.6 | 4.0 | 37.5 | 7.0 | 58.3 | 5.2 | 81.4 | 6.1 |
| AD-1321219.1 | 7.5 | 0.6 | 10.4 | 1.2 | 26.2 | 4.8 | 60.8 | 4.2 |
| AD-1321220.1 | 9.0 | 1.6 | 10.3 | 0.5 | 29.8 | 3.1 | 68.7 | 2.5 |
| AD-1321221.1 | 26.6 | 1.2 | 28.8 | 3.9 | 53.6 | 5.1 | 90.8 | 2.4 |
| AD-1321222.1 | 18.2 | 2.2 | 17.4 | 1.3 | 39.9 | 1.5 | 78.6 | 5.8 |
| AD-1321223.1 | 92.2 | 10.4 | 72.0 | 9.8 | 99.8 | 4.6 | 108.7 | 11.5 |
| AD-1321224.1 | 91.7 | 5.5 | 85.1 | 6.0 | 110.4 | 12.0 | 102.3 | 4.3 |
| AD-1321225.1 | 30.7 | 3.9 | 41.7 | 4.1 | 72.7 | 10.8 | 91.4 | 2.2 |
| AD-1321226.1 | 49.0 | 6.3 | 65.4 | 6.1 | 86.6 | 6.6 | 100.4 | 7.4 |
| AD-1321227.1 | 64.6 | 6.7 | 63.0 | 6.7 | 83.2 | 6.5 | 99.1 | 5.1 |
| AD-1321228.1 | 89.9 | 6.7 | 88.4 | 2.5 | 100.9 | 8.3 | 102.7 | 7.6 |
| AD-1321229.1 | 62.5 | 8.6 | 61.1 | 3.3 | 78.3 | 4.9 | 83.2 | 32.2 |
| AD-1321230.1 | 77.5 | 7.3 | 73.6 | 2.1 | 88.6 | 9.5 | 102.8 | 7.0 |
| AD-1321231.1 | 17.0 | 2.6 | 21.8 | 5.1 | 48.1 | 3.5 | 80.0 | 4.1 |
| AD-1321232.1 | 67.1 | 1.9 | 52.0 | 2.4 | 46.8 | 8.7 | 72.2 | 5.8 |
| AD-1321233.1 | 99.8 | 8.2 | 104.4 | 10.3 | 99.7 | 6.0 | 102.4 | 4.9 |
| AD-1321234.1 | 74.6 | 6.3 | 69.0 | 8.1 | 87.3 | 7.7 | 96.9 | 5.3 |
| AD-1321235.1 | 65.4 | 2.3 | 52.6 | 5.3 | 68.4 | 9.4 | 87.1 | 2.7 |
| AD-1321236.1 | 63.7 | 3.4 | 60.8 | 1.3 | 87.6 | 2.1 | 98.6 | 5.9 |
| AD-1321237.1 | 42.5 | 1.3 | 54.2 | 1.5 | 96.8 | 4.1 | 104.7 | 5.7 |
| AD-1321238.1 | 22.3 | 2.3 | 23.3 | 3.0 | 45.5 | 6.4 | 73.5 | 2.8 |
| AD-1321239.1 | 66.4 | 5.6 | 50.9 | 3.4 | 76.6 | 9.0 | 98.3 | 6.7 |
| AD-1321240.1 | 98.9 | 1.4 | 100.6 | 9.7 | 104.9 | 10.4 | 102.5 | 2.4 |
| AD-1321241.1 | 95.2 | 8.9 | 89.6 | 10.7 | 101.7 | 13.1 | 101.7 | 5.1 |
| AD-1321242.1 | 17.0 | 1.9 | 19.2 | 1.9 | 43.0 | 4.9 | 78.7 | 1.6 |
| AD-1321243.1 | 8.7 | 1.7 | 10.0 | 1.2 | 32.6 | 3.3 | 66.3 | 2.9 |
| AD-1321244.1 | 43.9 | 2.8 | 34.4 | 2.3 | 73.8 | 9.5 | 93.0 | 4.1 |
| AD-1321245.1 | 25.1 | 0.6 | 26.0 | 1.8 | 61.0 | 5.8 | 90.3 | 6.7 |
| AD-1321246.1 | 6.4 | 1.7 | 6.8 | 1.0 | 20.9 | 2.8 | 51.3 | 6.9 |
| AD-1321247.1 | 86.5 | 5.8 | 80.7 | 6.6 | 85.3 | 4.2 | 92.1 | 4.9 |
| AD-1321248.1 | 98.5 | 6.9 | 99.9 | 11.4 | 102.8 | 7.5 | 105.8 | 6.3 |
| AD-1321249.1 | 63.4 | 3.0 | 69.2 | 6.0 | 92.7 | 3.5 | 104.5 | 3.9 |
| AD-1321250.1 | 40.2 | 1.8 | 56.5 | 1.8 | 96.8 | 5.2 | 100.7 | 0.6 |
| AD-1321251.1 | 98.2 | 3.8 | 97.2 | 12.0 | 107.0 | 13.0 | 103.6 | 5.1 |
| AD-1321252.1 | 71.0 | 2.3 | 63.8 | 7.5 | 94.0 | 5.3 | 100.8 | 5.6 |
| AD-1321253.1 | 7.8 | 0.6 | 11.3 | 0.8 | 36.6 | 10.7 | 75.2 | 9.7 |
| AD-1321254.1 | 36.8 | 3.1 | 27.4 | 2.0 | 47.4 | 7.6 | 78.6 | 5.1 |
| AD-1321255.1 | 73.6 | 5.5 | 61.4 | 6.5 | 76.2 | 11.1 | 92.4 | 4.9 |
| AD-1321256.1 | 8.3 | 0.6 | 8.5 | 0.7 | 20.3 | 4.4 | 49.8 | 5.2 |
| AD-1321257.1 | 7.4 | 0.4 | 9.8 | 2.3 | 21.9 | 2.5 | 51.1 | 0.8 |
| AD-1321258.1 | 16.8 | 1.2 | 29.4 | 2.8 | 81.9 | 8.3 | 107.0 | 2.1 |
| AD-1321259.1 | 19.2 | 1.7 | 21.9 | 1.9 | 65.6 | 6.8 | 94.0 | 4.1 |
| AD-1321260.1 | 49.6 | 2.6 | 53.9 | 3.5 | 86.8 | 7.6 | 101.9 | 1.1 |
| AD-1321261.1 | 19.6 | 1.6 | 28.2 | 2.7 | 75.7 | 3.0 | 102.2 | 9.2 |
| AD-1321262.1 | 52.5 | 1.7 | 56.4 | 2.3 | 91.1 | 10.7 | 105.8 | 8.3 |
| AD-1321263.1 | 86.3 | 3.5 | 95.2 | 11.5 | 101.5 | 9.8 | 95.9 | 10.7 |
| AD-1321264.1 | 92.0 | 7.4 | 91.8 | 8.7 | 93.9 | 7.1 | 103.0 | 8.1 |
| AD-1321265.1 | 58.9 | 4.1 | 62.3 | 5.0 | 78.3 | 5.6 | 92.2 | 3.5 |
| AD-1321266.1 | 89.0 | 3.7 | 94.2 | 8.4 | 103.9 | 9.2 | 100.4 | 10.1 |
| AD-1321267.1 | 24.6 | 3.2 | 36.0 | 7.6 | 84.3 | 5.2 | 95.7 | 5.9 |
| AD-1321268.1 | 98.4 | 3.4 | 91.4 | 9.5 | 107.5 | 11.1 | 101.4 | 9.1 |
| AD-1321269.1 | 61.0 | 2.1 | 63.7 | 4.1 | 97.1 | 7.2 | 99.4 | 4.5 |
| AD-1321270.1 | 65.6 | 2.1 | 68.9 | 11.4 | 92.6 | 12.7 | 99.2 | 8.1 |
| AD-1321271.1 | 94.0 | 7.5 | 96.9 | 10.1 | 108.1 | 15.0 | 110.0 | 13.5 |
| AD-1321272.1 | 92.4 | 6.7 | 94.4 | 11.3 | 98.8 | 10.7 | 106.2 | 12.6 |
| AD-1321273.1 | 19.8 | 2.0 | 23.0 | 3.3 | 49.5 | 9.4 | 77.4 | 2.4 |
| AD-1321274.1 | 100.5 | 9.1 | 83.5 | 9.3 | 104.1 | 5.4 | 99.3 | 13.4 |
| AD-1321275.1 | 76.2 | 6.5 | 61.2 | 3.0 | 91.6 | 5.8 | 94.6 | 8.6 |
| AD-1321276.1 | 11.8 | 0.8 | 10.6 | 1.8 | 23.5 | 2.9 | 50.9 | 3.1 |
| AD-1321277.1 | 62.2 | 2.8 | 61.1 | 6.1 | 81.0 | 7.6 | 91.3 | 4.4 |
| AD-1321278.1 | 89.1 | 6.7 | 88.1 | 5.7 | 101.9 | 2.0 | 101.9 | 6.0 |
| AD-1321279.1 | 79.5 | 3.1 | 66.2 | 5.0 | 82.8 | 3.9 | 95.9 | 8.6 |
| AD-1321280.1 | 33.9 | 5.1 | 18.0 | 1.8 | 26.5 | 2.6 | 54.9 | 11.6 |
| AD-1321281.1 | 67.6 | 5.5 | 52.4 | 6.2 | 85.3 | 6.8 | 98.1 | 9.4 |
| AD-1321282.1 | 10.4 | 0.6 | 12.4 | 2.3 | 58.9 | 16.7 | 83.3 | 6.3 |
| AD-1321283.1 | 11.7 | 1.6 | 9.6 | 0.9 | 28.2 | 3.2 | 57.7 | 7.8 |
| AD-1321284.1 | 32.8 | 2.1 | 19.9 | 2.7 | 29.1 | 2.8 | 64.2 | 4.8 |
| AD-1321285.1 | 13.4 | 0.8 | 14.1 | 1.1 | 36.8 | 2.6 | 76.3 | 5.5 |
| AD-1321286.1 | 81.8 | 3.8 | 70.8 | 5.8 | 82.1 | 4.0 | 95.5 | 4.6 |
| AD-1321287.1 | 83.5 | 5.0 | 68.8 | 3.4 | 80.6 | 4.4 | 94.8 | 0.6 |
| AD-1321288.1 | 33.5 | 2.7 | 30.3 | 2.3 | 54.3 | 2.4 | 89.9 | 3.1 |
| AD-1321289.1 | 84.7 | 7.1 | 70.2 | 4.8 | 90.5 | 4.9 | 98.6 | 2.0 |
| AD-1321290.1 | 25.7 | 1.3 | 22.2 | 1.2 | 45.2 | 3.4 | 77.9 | 2.1 |
| AD-1321291.1 | 92.9 | 3.9 | 80.9 | 1.8 | 93.8 | 3.7 | 101.7 | 5.2 |

TABLE 15

Superoxide Dismutase 1 In Vitro Single Dose Screens in BE(2)C cells

| Duplex | 50 mM Avg | SD | 10 nM Avg | SD | 1 mM Avg | SD | 0.1 nM Avg | SD |
|---|---|---|---|---|---|---|---|---|
| AD-1321202.1 | 21.9 | 2.6 | 25.0 | 1.5 | 69.4 | 11.3 | 77.1 | 6.1 |
| AD-1321203.1 | 20.4 | 4.2 | 39.9 | 6.8 | 79.6 | 11.8 | 79.8 | 7.0 |
| AD-1321204.1 | 18.4 | 3.7 | 20.2 | 2.0 | 51.0 | 6.7 | 75.6 | 3.3 |
| AD-1321205.1 | 71.6 | 2.6 | 80.8 | 8.7 | 80.1 | 17.4 | 81.9 | 6.6 |
| AD-1321206.1 | 17.2 | 1.7 | 25.3 | 1.7 | 53.8 | 8.0 | 83.1 | 7.3 |
| AD-1321207.1 | 11.8 | 2.5 | 18.4 | 1.3 | 34.3 | 3.4 | 55.7 | 4.8 |
| AD-1321208.1 | 24.7 | 2.8 | 32.9 | 3.0 | 61.9 | 8.7 | 75.8 | 7.5 |
| AD-1321209.1 | 27.8 | 1.3 | 33.0 | 3.9 | 48.9 | 1.7 | 72.6 | 1.5 |
| AD-1321210.1 | 12.4 | 1.8 | 15.9 | 1.3 | 30.9 | 8.2 | 50.6 | 4.2 |
| AD-1321211.1 | 44.7 | 6.1 | 42.6 | 5.1 | 78.3 | 12.9 | 100.4 | 9.7 |
| AD-1321212.1 | 21.8 | 1.3 | 27.4 | 4.9 | 68.4 | 13.4 | 108.3 | 18.5 |
| AD-1321213.1 | 32.5 | 15.9 | 24.4 | 2.1 | 63.1 | 15.3 | 120.6 | 39.0 |
| AD-1321214.1 | 29.4 | 8.3 | 44.4 | 8.6 | 107.8 | 28.8 | 107.3 | 17.2 |
| AD-1321215.1 | 31.5 | 8.2 | 37.4 | 2.1 | 74.7 | 12.0 | 92.0 | 15.1 |
| AD-1321216.1 | 19.9 | 4.7 | 27.1 | 3.4 | 54.0 | 14.3 | 76.2 | 7.4 |
| AD-1321217.1 | 19.0 | 2.0 | 30.7 | 7.6 | 45.8 | 5.3 | 78.3 | 2.4 |
| AD-1321218.1 | 23.9 | 5.6 | 33.7 | 5.7 | 69.4 | 4.6 | 91.1 | 9.0 |
| AD-1321219.1 | 23.2 | 5.1 | 24.5 | 3.3 | 84.9 | 30.5 | 103.3 | 10.1 |
| AD-1321220.1 | 15.5 | 2.7 | 18.6 | 1.3 | 53.1 | 11.9 | 78.9 | 21.9 |
| AD-1321221.1 | 31.0 | 6.9 | 38.9 | 4.0 | 76.0 | 6.8 | 96.2 | 25.2 |
| AD-1321222.1 | 17.2 | 1.2 | 26.4 | 0.4 | 51.7 | 10.1 | 109.5 | 29.4 |
| AD-1321223.1 | 50.6 | 8.4 | 54.1 | 16.0 | 105.3 | 25.4 | 103.4 | 20.0 |
| AD-1321224.1 | 66.2 | 13.1 | 90.9 | 24.5 | 83.7 | 16.7 | 88.3 | 10.1 |
| AD-1321225.1 | 37.9 | 11.8 | 44.7 | 9.3 | 89.5 | 9.9 | 92.3 | 17.3 |
| AD-1321226.1 | 51.0 | 15.0 | 50.4 | 11.2 | 77.7 | 4.9 | 114.1 | 15.0 |
| AD-1321227.1 | 33.5 | 1.8 | 41.9 | 12.3 | 88.9 | 11.7 | 99.4 | 12.6 |
| AD-1321228.1 | 99.3 | 67.0 | 71.7 | 6.3 | 91.8 | 8.1 | 91.0 | 4.0 |
| AD-1321229.1 | 26.5 | 2.3 | 33.1 | 4.0 | 76.5 | 10.9 | 121.7 | 34.2 |
| AD-1321230.1 | 37.8 | 10.5 | 45.0 | 11.9 | 81.7 | 25.0 | 97.6 | 20.9 |
| AD-1321231.1 | 16.7 | 5.3 | 21.9 | 5.5 | 40.3 | 16.0 | 64.6 | 15.2 |
| AD-1321232.1 | 25.0 | 4.5 | 24.0 | 7.4 | 57.7 | 16.2 | 76.8 | 9.7 |
| AD-1321233.1 | 72.8 | 15.1 | 68.0 | 23.8 | 114.4 | 27.2 | 102.7 | 14.3 |
| AD-1321234.1 | 25.6 | 4.6 | 33.5 | 6.3 | 63.2 | 7.9 | 99.1 | 7.4 |
| AD-1321235.1 | 17.4 | 3.7 | 20.1 | 2.1 | 45.2 | 6.5 | 85.2 | 4.0 |
| AD-1321236.1 | 35.7 | 15.1 | 36.0 | 2.8 | 73.4 | 8.5 | 106.5 | 33.8 |
| AD-1321237.1 | 34.0 | 1.8 | 42.9 | 2.7 | 79.4 | 3.5 | 211.3 | 62.3 |
| AD-1321238.1 | 22.4 | 11.5 | 22.9 | 5.8 | 50.2 | 18.5 | 119.1 | 31.9 |
| AD-1321239.1 | 25.9 | 6.2 | 31.8 | 6.6 | 71.6 | 25.7 | 98.4 | 20.3 |
| AD-1321240.1 | 81.8 | 18.9 | 92.0 | 17.7 | 115.4 | 22.1 | 112.4 | 20.5 |
| AD-1321241.1 | 56.8 | 14.7 | 68.4 | 10.8 | 114.5 | 12.4 | 112.0 | 12.8 |
| AD-1321242.1 | 20.9 | 0.8 | 27.2 | 6.8 | 60.5 | 5.3 | 105.5 | 36.8 |
| AD-1321243.1 | 16.3 | 3.8 | 20.9 | 3.8 | 40.0 | 5.4 | 87.3 | 41.9 |
| AD-1321244.1 | 25.9 | 2.6 | 33.4 | 2.3 | 72.2 | 23.6 | 142.4 | 55.0 |

TABLE 15-continued

Superoxide Dismutase 1 In Vitro Single Dose Screens in BE(2)C cells

| Duplex | 50 mM Avg | SD | 10 nM Avg | SD | 1 mM Avg | SD | 0.1 nM Avg | SD |
|---|---|---|---|---|---|---|---|---|
| AD-1321245.1 | 19.6 | 3.2 | 26.5 | 3.3 | 53.4 | 3.3 | 87.5 | 25.1 |
| AD-1321246.1 | 13.2 | 1.1 | 18.8 | 2.8 | 51.6 | 16.9 | 72.2 | 17.2 |
| AD-1321247.1 | 51.2 | 6.7 | 58.7 | 18.8 | 106.1 | 24.6 | 110.8 | 29.0 |
| AD-1321248.1 | 72.4 | 26.1 | 68.2 | 16.5 | 127.1 | 27.3 | 104.4 | 4.6 |
| AD-1321249.1 | 50.0 | 2.6 | 63.0 | 7.4 | 104.3 | 6.6 | 120.2 | 26.5 |
| AD-1321250.1 | 42.9 | 7.2 | 85.7 | 22.3 | 99.3 | 14.1 | 147.4 | 32.8 |
| AD-1321251.1 | 73.8 | 17.4 | 95.7 | 12.4 | 102.3 | 4.7 | 122.5 | 17.5 |
| AD-1321252.1 | 67.0 | 12.9 | 74.3 | 11.8 | 107.9 | 18.3 | 98.8 | 10.7 |
| AD-1321253.1 | 19.7 | 3.5 | 29.9 | 13.6 | 92.2 | 20.1 | 119.7 | 30.0 |
| AD-1321254.1 | 17.5 | 3.7 | 31.6 | 12.1 | 68.1 | 28.4 | 82.7 | 5.0 |
| AD-1321255.1 | 28.9 | 8.6 | 34.5 | 7.8 | 99.4 | 31.3 | 101.2 | 10.5 |
| AD-1321256.1 | 22.5 | 4.9 | 21.2 | 3.1 | 63.6 | 18.1 | 80.1 | 8.2 |
| AD-1321257.1 | 16.5 | 1.8 | 23.7 | 3.8 | 41.4 | 15.2 | 78.4 | 9.8 |
| AD-1321258.1 | 24.0 | 3.1 | 37.7 | 7.4 | 84.8 | 14.6 | 106.0 | 15.1 |
| AD-1321259.1 | 23.1 | 1.8 | 30.6 | 3.1 | 73.6 | 5.5 | 132.6 | 38.2 |
| AD-1321260.1 | 34.0 | 7.0 | 44.6 | 19.7 | 79.6 | 10.4 | 102.5 | 23.9 |
| AD-1321261.1 | 20.1 | 3.0 | 34.9 | 12.3 | 78.3 | 18.5 | 109.5 | 28.6 |
| AD-1321262.1 | 40.8 | 4.8 | 63.8 | 14.1 | 101.9 | 37.9 | 97.4 | 15.7 |
| AD-1321263.1 | 46.9 | 6.2 | 54.8 | 7.4 | 88.2 | 17.4 | 112.6 | 32.6 |
| AD-1321264.1 | 34.3 | 2.4 | 43.1 | 11.3 | 101.2 | 31.5 | 125.3 | 29.6 |
| AD-1321265.1 | 19.1 | 2.5 | 21.7 | 4.5 | 53.6 | 1.0 | 78.5 | 5.8 |
| AD-1321266.1 | 37.1 | 3.4 | 51.1 | 15.7 | 85.1 | 11.7 | 106.4 | 13.8 |
| AD-1321267.1 | 30.9 | 7.9 | 45.6 | 10.0 | 80.9 | 7.5 | 88.7 | 9.2 |
| AD-1321268.1 | 91.7 | 22.7 | 110.6 | 34.2 | 93.5 | 24.1 | 92.9 | 12.1 |
| AD-1321269.1 | 40.8 | 2.0 | 63.9 | 16.8 | 87.6 | 25.6 | 108.8 | 40.7 |
| AD-1321270.1 | 29.1 | 1.6 | 38.0 | 5.0 | 87.4 | 19.0 | 114.4 | 43.7 |
| AD-1321271.1 | 73.6 | 4.5 | 95.7 | 35.7 | 118.4 | 16.7 | 106.0 | 18.9 |
| AD-1321272.1 | 65.8 | 3.9 | 70.6 | 20.3 | 134.7 | 50.9 | 159.4 | 62.2 |
| AD-1321273.1 | 18.8 | 2.7 | 32.7 | 8.3 | 58.3 | 4.5 | 143.3 | 40.1 |
| AD-1321274.1 | 43.4 | 1.9 | 72.3 | 13.9 | 104.3 | 31.6 | 154.1 | 37.6 |
| AD-1321275.1 | 35.0 | 4.0 | 69.5 | 6.7 | 104.2 | 28.2 | 142.6 | 53.5 |
| AD-1321276.1 | 13.4 | 1.4 | 24.2 | 10.8 | 38.0 | 11.4 | 65.8 | 8.5 |
| AD-1321277.1 | 23.7 | 4.5 | 31.7 | 2.5 | 67.8 | 9.1 | 78.3 | 3.6 |
| AD-1321278.1 | 44.1 | 3.9 | 64.6 | 12.3 | 90.8 | 7.4 | 112.7 | 16.7 |
| AD-1321279.1 | 33.5 | 3.8 | 50.9 | 12.8 | 100.6 | 45.8 | 104.9 | 22.6 |
| AD-1321280.1 | 15.7 | 2.2 | 29.2 | 9.7 | 47.9 | 10.5 | 106.6 | 17.4 |
| AD-1321281.1 | 31.0 | 3.0 | 67.9 | 14.8 | 101.8 | 20.2 | 143.5 | 22.6 |
| AD-1321282.1 | 20.1 | 3.6 | 40.9 | 12.3 | 74.5 | 18.4 | 163.2 | 37.1 |
| AD-1321283.1 | 16.7 | 1.1 | 36.6 | 5.5 | 46.5 | 8.9 | 85.1 | 3.7 |
| AD-1321284.1 | 19.0 | 1.4 | 26.0 | 9.1 | 37.1 | 4.3 | 67.3 | 12.0 |
| AD-1321285.1 | 12.6 | 1.2 | 16.6 | 3.4 | 47.6 | 2.0 | 75.9 | 8.5 |
| AD-1321286.1 | 13.5 | 1.3 | 15.8 | 4.1 | 33.8 | 6.5 | 70.6 | 13.0 |
| AD-1321287.1 | 12.9 | 0.9 | 16.9 | 1.1 | 29.8 | 4.5 | 62.9 | 10.2 |
| AD-1321288.1 | 13.7 | 2.1 | 17.1 | 2.7 | 31.6 | 3.5 | 65.2 | 4.8 |
| AD-1321289.1 | 21.7 | 3.6 | 29.3 | 11.3 | 74.4 | 19.5 | 81.0 | 10.9 |
| AD-1321290.1 | 15.8 | 2.2 | 24.1 | 8.2 | 50.3 | 12.3 | 111.6 | 32.3 |
| AD-1321291.1 | 17.1 | 3.1 | 29.3 | 9.6 | 57.8 | 17.7 | 95.2 | 20.9 |

Example 3. In Vivo Evaluation in Mice

Duplexes of interest, identified from the above studies, were further evaluated in vivo. In particular, at pre-dose day −14 wild-type mice (C57BL/6) were transduced by retro-orbital administration of $2 \times 10^{10}$ viral particles of an adeno-associated virus 8 (AAV8) vector encoding human SOD1.

At day 0, groups of three mice were subcutaneously administered a single 3 mg/kg dose of the agents of interest or PBS control. Table 16 provides the treatment groups and Table 18 provides the modified and unmodified nucleotide sequences of the sense and antisense strands of the duplexes of interest. At day 7 post-dose animals were sacrificed, retro-orbital bleeding were performed. Liver samples were collected at day 7 post-dose, and snap-frozen in liquid nitrogen. Tissue mRNA was extracted and analyzed by the RT-QPCR method.

Human SOD1 mRNA levels were compared to housekeeping gene GAPDH. The values were then normalized to the average of PBS vehicle control group. The data were expressed as percent of baseline value, and presented as mean plus standard deviation. The results, listed in Table 17 and shown in FIG. 1, demonstrate that the exemplary duplex agents tested effectively reduce the level of the human SOD1 messenger RNA in vivo.

TABLE 16

Treatment Groups

| Group # | Animal # | Treatment | Dose (mpk) | TD |
|---|---|---|---|---|
| 1 | 1 | PBS | n/a | d7 |
|  | 2 |  |  |  |
|  | 3 |  |  |  |
| 2 | 4 | AAV + Ctrl | 3 |  |
|  | 5 | (AD-64228.39) |  |  |
|  | 6 |  |  |  |
| 3 | 7 | AD-1321210.2 | 3 |  |
|  | 8 |  |  |  |
|  | 9 |  |  |  |
| 4 | 10 | AD-1321207.2 | 3 |  |
|  | 11 |  |  |  |
|  | 12 |  |  |  |
| 5 | 13 | AD-1321276.2 | 3 |  |
|  | 14 |  |  |  |
|  | 15 |  |  |  |
| 6 | 16 | AD-1321257.2 | 3 |  |
|  | 17 |  |  |  |
|  | 18 |  |  |  |
| 7 | 19 | AD-1321246.2 | 3 |  |
|  | 20 |  |  |  |
|  | 21 |  |  |  |
| 8 | 22 | AD-1321280.2 | 3 |  |
|  | 23 |  |  |  |
|  | 24 |  |  |  |
| 9 | 25 | AD-1321232.2 | 3 |  |
|  | 26 |  |  |  |
|  | 27 |  |  |  |
| 10 | 28 | AD-1321238.2 | 3 |  |
|  | 29 |  |  |  |
|  | 30 |  |  |  |
| 11 | 31 | AD-1321220.2 | 3 |  |
|  | 32 |  |  |  |
|  | 33 |  |  |  |
| 12 | 34 | AD-1321219.2 | 3 |  |
|  | 35 |  |  |  |
|  | 36 |  |  |  |
| 13 | 37 | AD-1321204.2 | 3 |  |
|  | 38 |  |  |  |
|  | 39 |  |  |  |
| 14 | 40 | AD-1321222.2 | 3 |  |
|  | 41 |  |  |  |
|  | 42 |  |  |  |
| 15 | 43 | AD-1321243.2 | 3 |  |
|  | 44 |  |  |  |
|  | 45 |  |  |  |
| 16 | 46 | AD-1321256.2 | 3 |  |
|  | 47 |  |  |  |
|  | 48 |  |  |  |
| 17 | 49 | AD-1321284.2 | 3 |  |
|  | 50 |  |  |  |
|  | 51 |  |  |  |
| 18 | 52 | Naïve | n/a |  |
|  | 53 | (AAV only) |  |  |
|  | 54 |  |  |  |
| 19 | 55 |  |  |  |
|  | 56 |  |  |  |
|  | 57 |  |  |  |
| 19 | 55 |  |  |  |
|  | 56 |  |  |  |
|  | 57 |  |  |  |

TABLE 17

| Duplex | % Message Remaining | SD | Sample |
|---|---|---|---|
| PBS | 101.2654922 | 19.63002982 | Liver |
| AAV + Ctrl (AD-64228.39) | 35.31638173 | 0.262604802 | Liver |
| AD-1321210.2 | 30.42438251 | 19.91605213 | Liver |
| AD-1321207.2 | 30.25915539 | 6.758286564 | Liver |
| AD-1321276.2 | 60.10435363 | 9.664373248 | Liver |
| AD-1321257.2 | 42.2278116 | 12.20020318 | Liver |
| AD-1321246.2 | 31.12908021 | 6.362946317 | Liver |
| AD-1321280.2 | 60.34803578 | 3.949191278 | Liver |
| AD-1321232.2 | 56.60772288 | 6.333661103 | Liver |
| AD-1321238.2 | 14.6775853 | 5.863189424 | Liver |
| AD-1321220.2 | 74.41995976 | 22.16007547 | Liver |
| AD-1321219.2 | 55.78880525 | 1.781783363 | Liver |
| AD-1321204.2 | 51.1507952 | 16.4638919 | Liver |
| AD-1321222.2 | 53.99310372 | 9.219313647 | Liver |
| AD-1321243.2 | 34.54117695 | 1.128855605 | Liver |
| AD-1321256.2 | 27.38377094 | 11.20122452 | Liver |
| AD-1321284.2 | 68.29130171 | 23.82285508 | Liver |
| Naïve (AAV only) | 75.69780392 | 23.65689142 | Liver |

Example 4. In Vivo Assessment of RNAi Agents Targeting SOD1 in G93A-SOD1 Transgenic Mice In order to demonstrate that a single intracerebroventricular injection (ICV) of a dsRNA agent similarly inhibits the expression of SOD1 in therapeutically relevant regions of the brain and spinal cord, male G93A-SOD1 transgenic mice received a single 25 µg, 50 µg, 100 µg, 150 µg, 200 µg, or 300 µg dose in a volume of 5 µl of AD-401824, or 5 µl of artificial CSF (aCSF) control (n=3 per group) by ICV injection using a Hamilton syringe and an angled 30 G needle at Day 0. G93A-SOD1 mice express human SOD1 with the G93A mutation under control of the cistronic human SOD1 promotor. Mutations in this gene have been linked to familial Amyotrophic Lateral Sclerosis (ALS or Lou Gehrig's disease). The SOD1-G93A mice show a phenotype similar to Amyotrophic Lateral Sclerosis in humans. They develop paralysis in one or more limbs within a few weeks of age (see, e.g., Henriques, et al. (2010) PLoS One 5(11): e15445).

At Day 14 post-dose, animals were sacrificed and brain samples (right hemisphere, left hemisphere, cerebellum and

TABLE 18

Unmodified and Modified Nucleotide Sequences of the Duplexes of Interest

| Duplex Name | Strand | Modified Sequence 5' to 3' | SEQ ID NO: | Unmodified Sequence 5' to 3' | SEQ ID NO: |
|---|---|---|---|---|---|
| AD-1321204.2 | sense | asuscaa(Uhd)UfuCfGfAfgcagaaggaaL96 | 1069 | AUCAAUUUCGAGCAGAAGGAA | 63 |
|  | antis | usUfsccdTu(C2p)ugcucgAfaAfuugausgsa | 1159 | UUCCUUCUGCUCGAAAUUGAUGA | 1010 |
| AD-1321207.2 | sense | asasuuu(Chd)GfaGfCfAfgaaggaaaguL96 | 1072 | AAUUUCGAGCAGAAGGAAAGU | 454 |
|  | antis | asCfsuudTc(C2p)uucugcUfcGfaaauusgsa | 1162 | ACUUUCCUUCUGCUCGAAAUUGA | 1013 |
| AD-1321210.2 | sense | ususcga(Ghd)CfaGfAfAfggaaaguaauL96 | 1075 | UUCGAGCAGAAGGAAAGUAAU | 46 |
|  | antis | asUfsuadCu(Tgn)uccuucUfgCfucgaasasu | 1165 | AUUACUUCCUUCUGCUCGAAAU | 850 |
| AD-1321219.2 | sense | asasgga(Ahd)AfgUfAfAfuggaccaguuL96 | 1084 | AAGGAAAGUAAUGGACCAGUU | 85 |
|  | antis | asAfscudGg(Tgn)ccauuaCfuUfuccuuscsu | 1174 | AACUGGUCCAUUACUUUCCUUCU | 1021 |
| AD-1321220.2 | sense | asgsgaa(Ahd)GfuAfAfUfggaccagugaL96 | 1085 | AGGAAAGUAAUGGACCAGUGA | 458 |
|  | antis | usCfsacdTg(G2p)uccauuAfcUfuuccususc | 1175 | UCACUGGUCCAUUACUUUCCUUC | 1022 |
| AD-1321222.2 | sense | gsasaag(Uhd)AfaUfGfGfaccagugaauL96 | 1087 | GAAAGUAAUGGACCAGUGAAU | 460 |
|  | antis | asUfsucdAc(Tgn)gguccaUfuAfcuuucscsu | 1177 | AUUCACUGGUCCAUUACUUUCCU | 851 |
| AD-1321232.2 | sense | cscsagu(Ghd)CfaGfGfUfccucacuuuaL96 | 1097 | CCAGUGCAGGUCCUCACUUUA | 75 |
|  | antis | usAfsaadGu(G2p)aggaccUfgCfacuggsusa | 1187 | UAAAGUGAGGACCUGCACUGGUA | 158 |
| AD-1321238.2 | sense | csasggu(Chd)CfuCfAfCfuuuaauccuuL96 | 1103 | CAGGUCCUCACUUUAAUCCUU | 41 |
|  | antis | asAfsggaUfuaaagugAfgGfaccugscsa | 1193 | AAGGAUUAAAGUGAGGACCUGCA | 124 |
| AD-1321243.2 | sense | cscsuca(Chd)UfuUfAfAfuccucuaucuL96 | 1108 | CCUCACUUUAAUCCUCUAUCU | 42 |
|  | antis | asGfsaudAg(Agn)ggauuaAfaGfugaggsasc | 1198 | AGAUAGAGGAUUAAAGUGAGGAC | 125 |
| AD-1321246.2 | sense | csascuu(Uhd)AfaUfCfCfucuauccagaL96 | 1111 | CACUUUAAUCCUCUAUCCAGA | 71 |
|  | antis | asCfsuggAfuagaggaUfuAfaagugsasg | 1201 | ACUGGAUAGAGGAUUAAAGUGAG | 1030 |
| AD-1321256.2 | sense | asasgga(Uhd)GfaAfGfAfgaggcauguuL96 | 1121 | AAGGAUGAAGAGAGGCAUGUU | 474 |
|  | antis | asAfscadTg(C2p)cucucuUfcAfuccuususg | 1211 | AACAUGCCUCUCUUCAUCCUUUG | 1039 |
| AD-1321257.2 | sense | asgsgau(Ghd)AfaGfAfGfaggcauguuuL96 | 1122 | AGGAUGAAGAGAGGCAUGUUU | 475 |
|  | antis | asAfsacdAu(G2p)ccucucUfuCfauccususu | 1212 | AAACAUGCCUCUCUUCAUCCUUU | 554 |
| AD-1321276.2 | sense | ususggg(Chd)AfaAfGfGfuggaaaugaaL96 | 1141 | UUGGGCAAAGGUGGAAAUGAA | 103 |
|  | antis | usUfscadTu(Tgn)ccaccuUfgUfcccaasgsu | 1231 | UUCAUAUCCACCUUUGCCCAAGU | 1051 |
| AD-1321280.2 | sense | gscsaaa(Ghd)GfuGfGfAfaaugaagaaaL96 | 1145 | GCAAAGGUGGAAAUGAAGAAA | 999 |
|  | antis | usUfsucdTu(C2p)auuuccAfcCfuuuugcscsc | 1235 | UUUCUUCAUUUCCACCUUUGCCC | 1055 |
| AD-1321284.2 | sense | asgsgug(Ghd)AfaAfUfGfaagaaaguauL96 | 1149 | AGGUGGAAAUGAAGAAAGUAU | 512 |
|  | antis | asUfsacdTu(Tgn)cuucauUfuCfcaccususu | 1239 | AUACUUUCUUCAUUUCCACCUUU | 1059 | brainstem) and spinal cord samples were collected and flash frozen in liquid nitrogen. mRNA was extracted from the tissue and analyzed by the RT-QPCR method.

Figure 2:
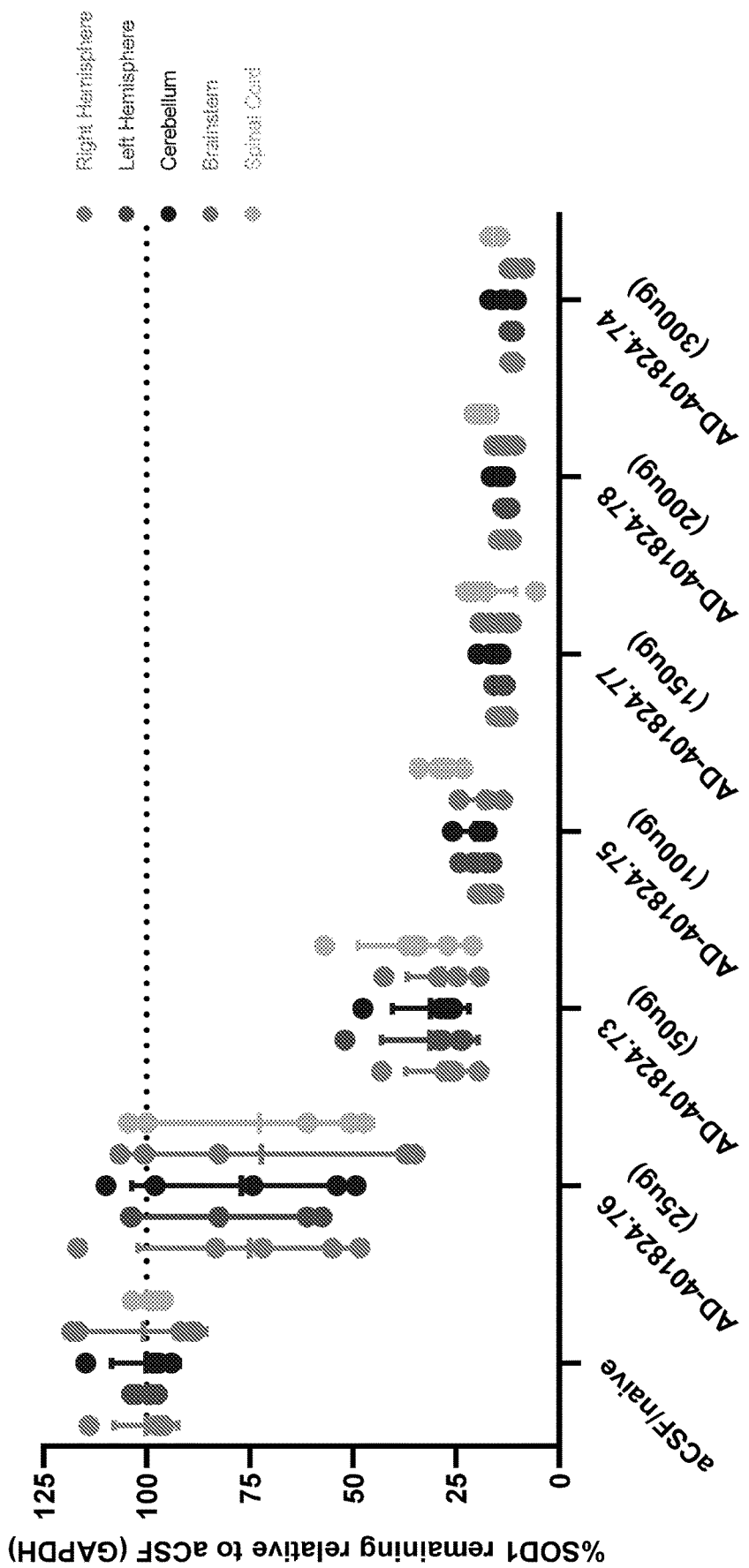
FIG. 2 is a graph depicting human SOD1 mRNA levels in the indicated areas of the brain and spinal cord of mice following intracerebroventricular injection (ICV) of a single 25 µg, 50 µg, 100 µg, 150 µg, 200 µg, or 300 µg dose of AD-401824, or artificial CSF (aCSF).

The results, depicted in FIG. 2, demonstrate that a single ICV injection of between 50-300 ug of dsRNA agent provides consistent and robust knockdown of SOD1 in the CNS in a dose dependent manner. The results also demonstrate that a single dose of dsRNA agent between 150-300 ug knocks down SOD1 mRNA to its lowest levels across all tissue types.

TABLE 19

Unmodified Sense and Antisense Strand Sequences of Superoxide Dismutase 1 dsRNA Agents

| Duplex Name | Sense Sequence 5' to 3' | SEQ ID NO: | Range in GenBank Accession No. 001285406.1 | Range in GenBank Accession No. NM 000454.4 | Antisense Sequence 5' to 3' | SEQ ID NO: | Range in GenBank Accession No. 001285406.1 | Range in GenBank Accession No. NM 000454.4 |
|---|---|---|---|---|---|---|---|---|
| AD-1321204.3 | AUCAAUUUCGAGCAGAAG GAA | 63 | 55-75 | 203-223 | UUCCUUCUGCUCGAAAUUGA UGA | 1010 | 53-75 | 201-223 |
| AD-1395718.1 | AUCAAUUUCGAGCAGAAG GAA | 63 | 55-75 | 203-223 | UUCCUUCUGCUCGAAAUUGA UGG | 1289 | 53-75 | 201-223 |
| AD-1395719.1 | AUCAAUUUCGAGCAGAAG GAA | 63 | 55-75 | 203-223 | UUCCUUCUGCUCGAAAUUGA UGG | 1289 | 53-75 | 201-223 |
| AD-1395720.1 | AUCAAUUUCGAGCAGAAG GAA | 63 | 55-75 | 203-223 | UUCCUUCUGCUCGAAAUUGA UGG | 1290 | 53-75 | 201-223 |
| AD-1395721.1 | AUCAAUUUCGAGCAGAAG GAA | 63 | 55-75 | 203-223 | UUCCUUCUGCUCGAAAUUGA UGG | 1290 | 53-75 | 201-223 |
| AD-1395722.1 | AUCAAUUUCGAGCAGAAG GAA | 63 | 55-75 | 203-223 | UUCCUUCUGCUCGAAAUUGA UGG | 1290 | 53-75 | 201-223 |
| AD-1395723.1 | AUCAAUUUCGAGCAGAAG GAA | 63 | 55-75 | 203-223 | UUCCUUCUGCUCGAAAUUGA UGG | 1290 | 53-75 | 201-223 |
| AD-1321207.3 | AAUUUCGAGCAGAAGGAA AGU | 454 | 58-78 | 206-226 | ACUUUCCUUCUGCUCGAAAU UGA | 1013 | 56-78 | 204-226 |
| AD-1395724.1 | AAUUUCGAGCAGAAGGAA AGA | 1280 | 58-78 | 206-226 | UCUUUCCUUCUGCUCGAAAU UGG | 1291 | 56-78 | 204-226 |
| AD-1395725.1 | AAUUUCGAGCAGAAGGAA AGA | 1280 | 58-78 | 206-226 | UCUUUCCUUCUGCUCGAAAU UGG | 1291 | 56-78 | 204-226 |
| AD-1395726.1 | AAUUUCGAGCAGAAGGAA AGA | 1280 | 58-78 | 206-226 | UCUUUCCUUCUGCUCGAAAU UGG | 1291 | 56-78 | 204-226 |
| AD-1395727.1 | AAUUUCGAGCAGAAGGAA AGA | 1280 | 58-78 | 206-226 | UCUUUCCUUCUGCUCGAAAU UGG | 1291 | 56-78 | 204-226 |
| AD-1395728.1 | AAUUUCGAGCAGAAGGAA AGA | 1280 | 58-78 | 206-226 | UCUUUCCUUCUGCUCGAAAU UGG | 1291 | 56-78 | 204-226 |
| AD-1395729.1 | AAUUUCGAGCAGAAGGAA AGA | 1280 | 58-78 | 206-226 | UCUUUCCUUCUGCUCGAAAU UGG | 1291 | 56-78 | 204-226 |
| AD-1321210.3 | UUCGAGCAGAAGGAAAGU AAU | 46 | 61-81 | 209-229 | AUUACUUCCUUCUGCUCGA AAU | 850 | 59-81 | 207-229 |

TABLE 19-continued

Unmodified Sense and Antisense Strand Sequences of Superoxide Dismutase 1 dsRNA Agents

| Duplex Name | Sense Sequence 5' to 3' | SEQ ID NO: | Range in GenBank Accession No. NM 001285406.1 | Range in GenBank Accession No. NM 000454.4 | Antisense Sequence 5' to 3' | SEQ ID NO: | Range in GenBank Accession No. NM 001285406.1 | Range in GenBank Accession No. NM 000454.4 |
|---|---|---|---|---|---|---|---|---|
| AD-1395730.1 | UUCGAGCAGAAGGAAAGUAAU | 46 | 61-81 | 209-229 | AUUACUUCCUUCUGCUCGAAAU | 850 | 59-81 | 207-229 |
| AD-1395731.1 | UUCGAGCAGAAGGAAAGUAAA | 1281 | 61-81 | 209-229 | UUUACUUCCUUCUGCUCGAAAU | 1292 | 59-81 | 207-229 |
| AD-1395732.1 | UUCGAGCAGAAGGAAAGUAAA | 1281 | 61-81 | 209-229 | UUUACUUCCUUCUGCUCGAAAU | 1292 | 59-81 | 207-229 |
| AD-1395733.1 | UUCGAGCAGAAGGAAAGUAAA | 1281 | 61-81 | 209-229 | UUUACUUCCUUCUGCUCGAAAU | 1292 | 59-81 | 207-229 |
| AD-1395734.1 | UUCGAGCAGAAGGAAAGUAAA | 1281 | 61-81 | 209-229 | UUACUCUUCCUUCUGCUCGAAAU | 1293 | 59-81 | 207-229 |
| AD-1395735.1 | UUCGAGCAGAAGGAAAGUAAA | 1281 | 61-81 | 209-229 | UUACUCUUCCUUCUGCUCGAAAU | 1293 | 59-81 | 207-229 |
| AD-1395736.1 | UUCGAGCAGAAGGAAAGUAAA | 1281 | 61-81 | 209-229 | UUACUCUUCCUUCUGCUCGAAAU | 1293 | 59-81 | 207-229 |
| AD-1321219.3 | AAGGAAAGUAAUGGACCAGUU | 85 | 70-90 | 218-238 | AACUGGUCCAUUACUUUCCUU | 1021 | 68-90 | 216-238 |
| AD-1395737.1 | AAGGAAAGUAAUGGACCAGUA | 1282 | 70-90 | 218-238 | UACUGGUCCAUUACUUUCCUU | 1294 | 68-90 | 216-238 |
| AD-1395738.1 | AAGGAAAGUAAUGGACCAGUA | 1282 | 70-90 | 218-238 | UACUGGUCCAUUACUUUCCUU | 1295 | 68-90 | 216-238 |
| AD-1395739.1 | AAGGAAAGUAAUGGACCAGUA | 1282 | 70-90 | 218-238 | UACUGGUCCAUUACUUUCCUU | 1296 | 68-90 | 216-238 |
| AD-1321220.3 | AGGAAAGUAAUGGACCAGUGA | 458 | 71-91 | 219-239 | UCACUGGUCCAUUACUUUCCUU | 1022 | 69-91 | 217-239 |
| AD-1395740.1 | AGGAAAGUAAUGGACCAGUGA | 458 | 71-91 | 219-239 | UCACUGGUCCAUUACUUUCCUU | 1022 | 69-91 | 217-239 |
| AD-1395741.1 | AGGAAAGUAAUGGACCAGUGA | 458 | 71-91 | 219-239 | UCACUGGUCCAUUACUUUCCUU | 1297 | 69-91 | 217-239 |
| AD-1395742.1 | AGGAAAGUAAUGGACCAGUGA | 458 | 71-91 | 219-239 | UCACUGGUCCAUUACUUUCCUU | 1298 | 69-91 | 217-239 |

TABLE 19-continued

Unmodified Sense and Antisense Strand Sequences of Superoxide Dismutase 1 dsRNA Agents

| Duplex Name | Sense Sequence 5' to 3' | SEQ ID NO: | Range in GenBank Accession No. NM 001285406.1 | Range in GenBank Accession No. NM 000454.4 | Antisense Sequence 5' to 3' | SEQ ID NO: | Range in GenBank Accession No. NM 001285406.1 | Range in GenBank Accession No. NM 000454.4 |
|---|---|---|---|---|---|---|---|---|
| AD-1321222.3 | GAAAGUAAUGGACCAGUGAAU | 460 | 73-93 | 221-241 | AUUCACTGGUCCAUUACUUUCCU | 851 | 71-93 | 219-241 |
| AD-1395743.1 | GAAAGUAAUGGACCAGUGAAA | 1283 | 73-93 | 221-241 | UUUCACTGGUCCAUUACUUUCCU | 1299 | 71-93 | 219-241 |
| AD-1395744.1 | GAAAGUAAUGGACCAGUGAAA | 1283 | 73-93 | 221-241 | UUUCACTGGUCCAUUACUUUCCU | 1299 | 71-93 | 219-241 |
| AD-1395745.1 | GAAAGUAAUGGACCAGUGAAA | 1283 | 73-93 | 221-241 | UUUCACTGGUCCAUUACUUUCCU | 1299 | 71-93 | 219-241 |
| AD-1395746.1 | GAAAGUAAUGGACCAGUGAAA | 1283 | 73-93 | 221-241 | UUCACTGGUCCAUUACUUUCCU | 1300 | 71-93 | 219-241 |
| AD-1395747.1 | GAAAGUAAUGGACCAGUGAAA | 1283 | 73-93 | 221-241 | UUCACTGGUCCAUUACUUUCCU | 1300 | 71-93 | 219-241 |
| AD-1395748.1 | GAAAGUAAUGGACCAGUGAAA | 1283 | 73-93 | 221-241 | UUCACTGGUCCAUUACUUUCCU | 1300 | 71-93 | 219-241 |
| AD-1321232.3 | CCAGUGCAGGUCCUCACUUUA | 75 | 176-196 | 324-344 | UAAAGUGAGGACCUGCACUGGUA | 158 | 174-196 | 322-344 |
| AD-1395749.1 | CCAGUGCAGGUCCUCACUUUA | 75 | 176-196 | 324-344 | UAAAGUGAGGACCUGCACUGGUA | 158 | 174-196 | 322-344 |
| AD-1395750.1 | CCAGUGCAGGUCCUCACUUUA | 75 | 176-196 | 324-344 | UAAAGUGAGGACCUGCACUGGUG | 1301 | 174-196 | 322-344 |
| AD-1395751.1 | CCAGUGCAGGUCCUCACUUUA | 75 | 176-196 | 324-344 | UAAAGUGAGGACCUGCACUGGUG | 1301 | 174-196 | 322-344 |
| AD-1395752.1 | CCAGUGCAGGUCCUCACUUUA | 75 | 176-196 | 324-344 | UAAAGUGAGGACCUGCACUGGUG | 1301 | 174-196 | 322-344 |
| AD-1395753.1 | CCAGUGCAGGUCCUCACUUUA | 75 | 176-196 | 324-344 | UAAAGUGAGGACCUGCACUGGUG | 1301 | 174-196 | 322-344 |
| AD-1395754.1 | CCAGUGCAGGUCCUCACUUUA | 75 | 176-196 | 324-344 | UAAAGUGAGGACCUGCACUGGUG | 1301 | 174-196 | 322-344 |
| AD-1395755.1 | CCAGUGCAGGUCCUCACUUUA | 75 | 176-196 | 324-344 | UAAAGUGAGGACCUGCACUGGUG | 1301 | 174-196 | 322-344 |

TABLE 19-continued

Unmodified Sense and Antisense Strand Sequences of Superoxide Dismutase 1 dsRNA Agents

| Duplex Name | Sense Sequence 5' to 3' | SEQ ID NO: | Range in GenBank Accession No. NM 001285406.1 | Range in GenBank Accession No. NM 000454.4 | Antisense Sequence 5' to 3' | SEQ ID NO: | Range in GenBank Accession No. 001285406.1 | Range in GenBank Accession No. NM 000454.4 |
|---|---|---|---|---|---|---|---|---|
| AD-1321238.3 | CAGGUCCUCACUUUAAUC CUU | 41 | 182-202 | 330-350 | AAGGAUUAAAGUGAGGACCU GCA | 124 | 180-202 | 328-350 |
| AD-1395756.1 | CAGGUCCUCACUUUAAUC CUA | 1284 | 182-202 | 330-350 | UAGGAUUAAAGUGAGGACCU GCG | 1302 | 180-202 | 328-350 |
| AD-1395757.1 | CAGGUCCUCACUUUAAUC CUA | 1284 | 182-202 | 330-350 | UAGGAUUAAAGTGAGGACCU GCG | 1302 | 180-202 | 328-350 |
| AD-1395758.1 | CAGGUCCUCACUUUAAUC CUA | 1284 | 182-202 | 330-350 | UAGGAUUAAAGTGAGGACCU GCG | 1302 | 180-202 | 328-350 |
| AD-1321243.3 | CCUCACUUUAAUCCUCUA UCU | 42 | 187-207 | 335-355 | AGAUAGAGGAUUAAAGUGA GGAC | 125 | 185-207 | 333-355 |
| AD-1395759.1 | CCUCACUUUAAUCCUCUA UCA | 1285 | 187-207 | 335-355 | UGAUAGAGGAUUAAAGUGA GGAC | 1303 | 185-207 | 333-355 |
| AD-1395760.1 | CCUCACUUUAAUCCUCUA UCA | 1285 | 187-207 | 335-355 | UGAUAGAGGAUUAAAGUGAG GAC | 1304 | 185-207 | 333-355 |
| AD-1395761.1 | CCUCACUUUAAUCCUCUA UCA | 1285 | 187-207 | 335-355 | UGAUAGAGGAUUAAAGUGAG GAC | 1304 | 185-207 | 333-355 |
| AD-1321246.3 | CACUUUAAUCCUCUAUCC AGA | 71 | 190-210 | 338-358 | ACUGGAUAGAGGAUUAAAG UGAG | 1030 | 188-210 | 336-358 |
| AD-1395762.1 | CACUUUAAUCCUCUAUCC AGA | 71 | 190-210 | 338-358 | UCUGGAUAGAGGAUUAAAGU GAG | 858 | 188-210 | 336-358 |
| AD-1395763.1 | CACUUUAAUCCUCUAUCC AGA | 71 | 190-210 | 338-358 | UCUGGAUAGAGGAUAUAAGU GAG | 1305 | 188-210 | 336-358 |
| AD-1321256.3 | AAGGAUGAAGAGAGGCAU GUU | 474 | 226-246 | 374-394 | AACAUGCCUCUCUUCAUCCU UUG | 1039 | 224-246 | 372-394 |
| AD-1395764.1 | AAGGAUGAAGAGAGGCAU GUA | 1286 | 226-246 | 374-394 | UACAUGCCUCUCUUCAUCCU UUG | 1306 | 224-246 | 372-394 |
| AD-1395765.1 | AAGGAUGAAGAGAGGCAU GUA | 1286 | 226-246 | 374-394 | UACAUGCCUCUCUUCAUCCU UUG | 1306 | 224-246 | 372-394 |
| AD-1395766.1 | AAGGAUGAAGAGAGGCAU GUA | 1286 | 226-246 | 374-394 | UACAUGCCUCUCUUCAUCCU UUG | 1306 | 224-246 | 372-394 |

TABLE 19-continued

Unmodified Sense and Antisense Strand Sequences of Superoxide Dismutase 1 dsRNA Agents

| Duplex Name | Sense Sequence 5' to 3' | SEQ ID NO: | Range in GenBank Accession No. 001285406.1 | Range in GenBank Accession No. NM 000454.4 | Antisense Sequence 5' to 3' | SEQ ID NO: | Range in GenBank Accession No. 001285406.1 | Range in GenBank Accession No. NM 000454.4 |
|---|---|---|---|---|---|---|---|---|
| AD-1395767.1 | AAGGAUGAAGAGAGGCAUGUA | 1286 | 226-246 | 374-394 | UACAUGCCUCUCUUCAUCCUUUG | 1306 | 224-246 | 372-394 |
| AD-1395768.1 | AAGGAUGAAGAGAGGCAUGUA | 1286 | 226-246 | 374-394 | UACAUGCCUCUCUUCAUCCUUUG | 1306 | 224-246 | 372-394 |
| AD-1395769.1 | AAGGAUGAAGAGAGGCAUGUA | 1286 | 226-246 | 374-394 | UACAUGCCUCUCUUCAUCCUUUG | 1306 | 224-246 | 372-394 |
| AD-1321257.3 | AGGAUGAAGAGAGGCAUGUUU | 475 | 227-247 | 375-395 | AAACAUGCCUCUCUUCAUCCUUU | 554 | 225-247 | 373-395 |
| AD-1395770.1 | AGGAUGAAGAGAGGCAUGUUU | 475 | 227-247 | 375-395 | AAACAUGCCUCUCUUCAUCCUUU | 554 | 225-247 | 373-395 |
| AD-1395771.1 | AGGAUGAAGAGAGGCAUGUUA | 1287 | 227-247 | 375-395 | UAACAUGCCUCUCUUCAUCCUUU | 1307 | 225-247 | 373-395 |
| AD-1395772.1 | AGGAUGAAGAGAGGCAUGUUA | 1287 | 227-247 | 375-395 | UAACAUGCCUCUCUUCAUCCUUU | 1307 | 225-247 | 373-395 |
| AD-1395773.1 | AGGAUGAAGAGAGGCAUGUUA | 1287 | 227-247 | 375-395 | UAACAUGCCCUCUCUUCAUCCUUU | 1308 | 225-247 | 373-395 |
| AD-1395774.1 | AGGAUGAAGAGAGGCAUGUUA | 1287 | 227-247 | 375-395 | UAACAUGCCCUCUCUUCAUCCUUU | 1308 | 225-247 | 373-395 |
| AD-1395775.1 | AGGAUGAAGAGAGGCAUGUUA | 1287 | 227-247 | 375-395 | UAACAUGCCUCUCUUCAUCCUUU | 1308 | 225-247 | 373-395 |
| AD-1321276.3 | UUGGGCAAAGGUGGAAAUGAA | 103 | 379-399 | 527-547 | UUCAUUUCCACCUUUGCCCAAGU | 1051 | 377-399 | 525-547 |
| AD-1395776.1 | UUGGGCAAAGGUGGAAAUGAA | 103 | 379-399 | 527-547 | UUCAUUUCCACCUUUGCCCAAGU | 1051 | 377-399 | 525-547 |
| AD-1395777.1 | UUGGGCAAAGGUGGAAAUGAA | 103 | 379-399 | 527-547 | UUCAUUUCCACCUUUGCCCAAGU | 1051 | 377-399 | 525-547 |
| AD-1395778.1 | UUGGGCAAAGGUGGAAAUGAA | 103 | 379-399 | 527-547 | UUCAUUUCCACCUUUGCCCAAGU | 1051 | 377-399 | 525-547 |
| AD-1395779.1 | UUGGGCAAAGGUGGAAAUGAA | 103 | 379-399 | 527-547 | UUCAUUUCCACCUUUGCCCAAGU | 1309 | 377-399 | 525-547 |

TABLE 19-continued

Unmodified Sense and Antisense Strand Sequences of Superoxide Dismutase 1 dsRNA Agents

| Duplex Name | Sense Sequence 5' to 3' | SEQ ID NO: | Range in GenBank Accession No. NM 001285406.1 | Range in GenBank Accession No. NM 000454.4 | Antisense Sequence 5' to 3' | SEQ ID NO: | Range in GenBank Accession No. 001285406.1 | Range in GenBank Accession No. NM 000454.4 |
|---|---|---|---|---|---|---|---|---|
| AD-1395780.1 | UUGGGCAAAGGUGGAAAU GAA | 103 | 379-399 | 527-547 | UUCAUUUCCACCUUUGCCCA AGU | 1309 | 377-399 | 525-547 |
| AD-1321280.3 | GCAAAGGUGGAAAUGAAG AAA | 999 | 383-403 | 531-551 | UUUCUUCAUUUCCACCUUUG CCC | 1055 | 381-403 | 529-551 |
| AD-1395781.1 | GCAAAGGUGGAAAUGAAG AAA | 999 | 383-403 | 531-551 | UUUCUUCAUUUCCACCUUUG CCC | 1055 | 381-403 | 529-551 |
| AD-1395782.1 | GCAAAGGUGGAAAUGAAG AAA | 999 | 383-403 | 531-551 | UUUCUUCAUUUCCACCUUUG CCC | 1055 | 381-403 | 529-551 |
| AD-1395783.1 | GCAAAGGUGGAAAUGAAG AAA | 999 | 383-403 | 531-551 | UUUCUUCAUUUCCACCUUUG CCC | 1055 | 381-403 | 529-551 |
| AD-1395784.1 | GCAAAGGUGGAAAUGAAG AAA | 999 | 383-403 | 531-551 | UUCUUCAUUUCCACCUUUG CCC | 1310 | 381-403 | 529-551 |
| AD-1395785.1 | GCAAAGGUGGAAAUGAAG AAA | 999 | 383-403 | 531-551 | UUCUUCAUUUCCACCUUUG CCC | 1310 | 381-403 | 529-551 |
| AD-1321284.3 | AGGUGGAAAUGAAGAAAG UAU | 512 | 387-407 | 535-555 | AUACUUUCUUCAUUUCCACC UUU | 1059 | 385-407 | 533-555 |
| AD-1395786.1 | AGGUGGAAAUGAAGAAAG UAU | 512 | 387-407 | 535-555 | AUACUUUCUUCAUUUCCACC UUU | 1059 | 385-407 | 533-555 |
| AD-1395787.1 | AGGUGGAAAUGAAGAAAG UAA | 1288 | 387-407 | 535-555 | UUACUUUCUUCAUUUCCACC UUU | 1311 | 385-407 | 533-555 |
| AD-1395788.1 | AGGUGGAAAUGAAGAAAG UAA | 1288 | 387-407 | 535-555 | UUACUUUCUUCAUUUCCACC UUU | 1311 | 385-407 | 533-555 |
| AD-1395789.1 | AGGUGGAAAUGAAGAAAG UAA | 1288 | 387-407 | 535-555 | UUACUUUCUUCAUUUCCACC UUU | 1311 | 385-407 | 533-555 |
| AD-1395790.1 | AGGUGGAAAUGAAGAAAG UAA | 1288 | 387-407 | 535-555 | UUACUUUCUUCAUUUCCACC UUU | 1312 | 385-407 | 533-555 |
| AD-1395791.1 | AGGUGGAAAUGAAGAAAG UAA | 1288 | 387-407 | 535-555 | UUACUUUCUUCAUUUCCACC UUU | 1312 | 385-407 | 533-555 |
| AD-1395792.1 | AGGUGGAAAUGAAGAAAG UAA | 1288 | 387-407 | 535-555 | UUACUUUCUUCAUUUCCACC UUU | 1312 | 385-407 | 533-555 |

TABLE 20

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1321204.3 | asuscaa(Uhd)UfuCfGfAfgcagaaggaaL96 | 1069 | usUfsccdTu(C2p)ugcucgAfaAfuugausgsa | 1159 | CCAUCAAUUUCGAGCAGAAGGAA | 395 |
| AD-1395718.1 | asuscaa(Uhd)uuCfGfAfgcagaaggsasa | 23 | VPusUfsccdTu(C2p)ugcucgAfaAfuugausgsg | 24 | CCAUCAAUUUCGAGCAGAAGGAA | 395 |
| AD-1395719.1 | asuscaa(Uhd)uuCfgAfgcgaaggsasa | 1313 | VPusUfsccdTu(C2p)ugcucgAfaAfuugausgsg | 1314 | CCAUCAAUUUCGAGCAGAGGAA | 395 |
| AD-1395720.1 | asuscaa(Uhd)uuCfgAfdGcagaaggsasa | 1314 | VPusUfsccdTu(C2p)ugcucgAfaAfuugausgsg | 1313 | CCAUCAAUUUCGAGCAGAAGGAA | 395 |
| AD-1395721.1 | asuscaa(Uhd)uuCfGfAfgcagaaggsasa | 23 | VPusdTsccdTu(C2p)ugcucgAfaauugaus gsg | 1313 | CCAUCAAUUUCGAGCAGAAGGAA | 395 |
| AD-1395722.1 | asuscaa(Uhd)uuCfgAfgcgaaggsasa | 1313 | VPusdTsccdTu(C2p)ugcucgAfaauugaus gsg | 1314 | CCAUCAAUUUCGAGCAGAGGAA | 395 |
| AD-1395723.1 | asuscaa(Uhd)uuCfgAfdGcagaaggsasa | 1314 | VPusdTsccdTu(C2p)ugcudCgAfaauugaus gsg | 1343 | CCAUCAAUUUCGAGCAGAAGGAA | 395 |
| AD-1321207.3 | asasuuu(Chd)GfaGfCfAfgaaggaaaguL96 | 1072 | asCfsuudTc(C2p)uucugcUfcGfaaausgsa | 1162 | UCAAUUUCGAGCAGAAGGAAAGU | 770 |
| AD-1395724.1 | asasuuu(Chd)gaGfCfAfgaaggaaasgsa | 29 | VPusCfsuudTc(C2p)uucugcUfcGfaaauusg sg | 30 | UCAAUUUCGAGCAGAAGGAAAGU | 770 |
| AD-1395725.1 | asasuuu(Chd)gagCfAfgaaggaaasgsa | 1315 | VPusCfsuudTc(C2p)uucugcUfcGfaaauusg sg | 30 | UCAAUUUCGAGCAGAAGGAAAGU | 770 |
| AD-1395726.1 | asasuuu(Chd)gadGcAfdGaaggaaasgs | 1316 | VPusCfsuudTc(C2p)uucugcUfcGfaaauusg sg | 1344 | UCAAUUUCGAGCAGAAGGAAAGU | 770 |
| AD-1395727.1 | asasuuu(Chd)gaGfCfAfgaaggaaasgsa | 29 | VPusCsuudTc(C2p)uucudGcUfcgaaauus gsg | 1344 | UCAAUUUCGAGCAGAAGGAAAGU | 770 |
| AD-1395728.1 | asasuuu(Chd)gagCfAfgaaggaaasgsa | 1315 | VPusCsuudTc(C2p)uucudGcUfcgaaauus gsg | 1344 | UCAAUUUCGAGCAGAAGGAAAGU | 770 |
| AD-1395729.1 | asasuuu(Chd)gadGcAfdGaaggaaasgs | 1316 | VPusCsuudTc(C2p)uucudGcUfcgaaauus gsg | 1344 | UCAAUUUCGAGCAGAAGGAAAGU | 770 |
| AD-1321210.3 | ususcga(Ghd)CfaGfAfAfggaaaguaauL96 | 1075 | asUfsuadCu(Tgn)uccuucUfgCfucgaasasu | 1165 | AUUUCGAGCAGAAGGAAAGUAAU | 378 |

TABLE 20-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1395730.1 | ususcgag(Chd)aGfAfAfggaaaguaauL96 | 1317 | asUfsuadCu(Tgn)uccuucUfgCfucgaasasu | 1165 | AUUUCGAGCAGAAGGAAAGUAAU | 378 |
| AD-1395731.1 | ususcgag(Chd)aGfAfAfggaaaguasasa | 15 | VPusUfsuadCu(Tgn)uccuucUfgCfucgaasa su | 16 | AUUUCGAGCAGAAGGAAAGUAAU | 378 |
| AD-1395732.1 | ususcgag(Chd)agAfAfggaaaguasasa | 1318 | VPusUfsuadCu(Tgn)uccuucUfgCfucgaasa su | 16 | AUUUCGAGCAGAAGGAAAGUAAU | 378 |
| AD-1395733.1 | ususcgag(Chd)adGaAfdGgaaaguasas a | 1319 | VPusUfsuadCu(Tgn)uccudTcUfgcucgaasa su | 1345 | AUUUCGAGCAGAAGGAAAGUAAU | 378 |
| AD-1395734.1 | ususcgag(Chd)aGfAfAfggaaaguasasa | 15 | VPusdTsuadCu(Tgn)uccudTcUfgcucgaasa su | 1345 | AUUUCGAGCAGAAGGAAAGUAAU | 378 |
| AD-1395735.1 | ususcgag(Chd)agAfAfggaaaguasasa | 1318 | VPusdTsuadCu(Tgn)uccudTcUfgcucgaasa su | 1345 | AUUUCGAGCAGAAGGAAAGUAAU | 378 |
| AD-1395736.1 | ususcgag(Chd)adGaAfdGgaaaguasasa | 1319 | VPusdTsuadCu(Tgn)uccudTcUfgcucgaasa su | 1345 | AUUUCGAGCAGAAGGAAAGUAAU | 378 |
| AD-1321219.3 | asasgga(Ahd)AfGfUfAfAfuggaccaguu L96 | 1084 | asAfscudGg(Tgn)ccauuaCfuFufuccuusc | 1174 | AGAAGGAAAGUAAUGGACCAGUG | 417 |
| AD-1395737.1 | asasgga(Ahd)agUfAfAfuggaccagsus a | 21 | VPusAfscudGg(Tgn)ccauuaCfuFufuccuus su | 1346 | AGAAGGAAAGUAAUGGACCAGUG | 417 |
| AD-1395738.1 | asasgga(Ahd)agUfAfAfuggaccagsus a | 21 | VPusdAscudGg(Tgn)ccaudTaCfuuuccuus csu | 22 | AGAAGGAAAGUAAUGGACCAGUG | 417 |
| AD-1395739.1 | asasgga(Ahd)agUfAfAfuggaccagsus a | 21 | VPusdAscudGg(Tgn)ccaudTadCudTuccuu scsu | 1347 | AGAAGGAAAGUAAUGGACCAGUG | 417 |
| AD-1321220.3 | asgsgaa(Ahd)GfUfAfAfUfgaccaguga L96 | 1085 | usCfsacdTg(G2p)uccauuaAfcUfuuccususc | 1175 | GAAGGAAAGUAAUGGACCAGUGA | 774 |
| AD-1395740.1 | asgsgaa(Ahd)guAfAfUfgaccagusus a | 1320 | VPusCfsacdTg(G2p)uccauuaAfcUfuuccusu sc | 1348 | GAAGGAAAGUAAUGGACCAGUGA | 774 |
| AD-1395741.1 | asgsgaa(Ahd)guAfAfUfgaccagusgs a | 1320 | VPusdCsacdTg(G2p)uccadTuAfcuuuccus usc | 1349 | GAAGGAAAGUAAUGGACCAGUGA | 774 |
| AD-1395742.1 | asgsgaa(Ahd)guAfAfUfgaccagusgs a | 1320 | VPusdCsacdTg(G2p)uccadTudAcdTuccuu susc | 1350 | GAAGGAAAGUAAUGGACCAGUGA | 774 |
| AD-1321222.3 | gsasaag(Uhd)AfaUfGfGfaccagugaau L96 | 1087 | asUfsucdAc(Tgn)gguccaUfuAfcuuucscsu | 1177 | AGGAAAGUAAUGGACCAGUGAAG | 776 |

TABLE 20-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1395743.1 | gsasaaag(Uhd)aaUfGfGfaccagugasasa | 17 | VPusUfsucdAc(Tgn)gguccaUfuAfcuuucsc su | 1321 | AGGAAAGUAAUGGACCAGUGAAG | 776 |
| AD-1395744.1 | gsasaaag(Uhd)aaUfgdGaccagugasasa | 1322 | VPusUfsucdAc(Tgn)gguccaUfuAfcuuucsc su | 1321 | AGGAAAGUAAUGGACCAGUGAAG | 776 |
| AD-1395745.1 | gsasaaag(Uhd)aaUfgdGAfcagugasasa a | 1322 | VPusUfsucdAc(Tgn)gguccaUfuAfcuuucsc su | 17 | AGGAAAGUAAUGGACCAGUGAAG | 776 |
| AD-1395746.1 | gsasaaag(Uhd)aaUfGfGfaccagugasasa | 17 | VPusUfsucdAc(Tgn)ggucdCaUfuacuuucs csu | 1351 | AGGAAAGUAAUGGACCAGUGAAG | 776 |
| AD-1395747.1 | gsasaaag(Uhd)aaUfgdGaccagugasasa | 1321 | VPusUfsucdAc(Tgn)ggucdCaUfuacuuucs csu | 1351 | AGGAAAGUAAUGGACCAGUGAAG | 776 |
| AD-1395748.1 | gsasaaag(Uhd)aaUfgdGAfcagugasasa a | 1322 | VPusdUfsucdAc(Tgn)ggucdCaUfuacuuucs csu | 1351 | AGGAAAGUAAUGGACCAGUGAAG | 776 |
| AD-1321232.3 | cscsagug(Ghd)CfaGfGfUfccucacuuua L96 | 1097 | usAfsaadGu(G2p)aggaccUfgCfacuggsusa | 1187 | UACCAGUGCAGGUCCUCACUUUA | 407 |
| AD-1395749.1 | cscsagug(Chd)aGfGfUfccucacuuuaL 96 | 1323 | usAfsaadGu(G2p)aggaccUfgCfacuggsusa | 1187 | UACCAGUGCAGGUCCUCACUUUA | 407 |
| AD-1395750.1 | cscsagug(Chd)aGfGfUfccucacuususa | 1324 | VPusAfsaadGu(G2p)aggaccUfgCfacuggsu sg | 1352 | UACCAGUGCAGGUCCUCACUUUA | 407 |
| AD-1395751.1 | cscsagug(Chd)adGgUfccucacuususa | 1325 | VPusAfsaadGu(G2p)aggaccUfgCfacuggsu sg | 1352 | UACCAGUGCAGGUCCUCACUUUA | 407 |
| AD-1395752.1 | cscsagug(Chd)adGgUfccucacuususa a | 1326 | VPusAfsaadGu(G2p)aggaccUfgCfacuggsu sg | 1352 | UACCAGUGCAGGUCCUCACUUUA | 407 |
| AD-1395753.1 | cscsagug(Chd)aGfGfUfccucacuususa | 1324 | VPusdAsaadGu(G2p)aggadCcUfgcacuggs usg | 1353 | UACCAGUGCAGGUCCUCACUUUA | 407 |
| AD-1395754.1 | cscsagug(Chd)adGgUfccucacuususa | 1325 | VPusdAsaadGu(G2p)aggadCcUfgcacuggs usg | 1353 | UACCAGUGCAGGUCCUCACUUUA | 407 |
| AD-1395755.1 | cscsagug(Chd)adGgUfccucacuususa a | 1326 | VPusdAsaadGu(G2p)aggadCcUfgcacuggs usg | 1353 | UACCAGUGCAGGUCCUCACUUUA | 407 |
| AD-1321238.3 | csasggu(Chd)cfuCfAfCfuuuaauccuu L96 | 1103 | asAfsggaUfuaaagugAfgGfaccugscsa | 1193 | UGCAGGUCCUCACUUUAAUCCUC | 373 |
| AD-1395756.1 | csasggu(Chd)cuCfAfCfuuuaauccusa | 13 | VPusdAsggdAudTaaagdTgAfgaccugscsg | 14 | UGCAGGUCCUCACUUUAAUCCUC | 373 |

TABLE 20-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1395757.1 | csasggu(Chd)cuCfaCfuuuaauccsusa | 13 | VPusdAsggdAudTaaagdTgdAgdGaccugsc sg | 1354 | UGCAGGUCCUCACUUUAAUCCUC | 373 |
| AD-1395758.1 | csasggu(Chd)cuCfaCfUfuuaauccsusa | 1327 | VPusdAsggdAudTaaagdTgdAgdGaccugsc sg | 1354 | UGCAGGUCCUCACUUUAAUCCUC | 373 |
| AD-1321243.3 | cscsuca(Chd)UfuUfAfAfuccucuaucu L96 | 1108 | asGfsaudAg(Agn)ggauuaAfaGfugaggsasc | 1198 | GUCCUCACUUUAAUCCUCUAUCC | 374 |
| AD-1395759.1 | cscsuca(Chd)uuUfAfAfuccucuauscsa | 25 | VPusGfsaudAg(Agn)ggauuaAfaGfugaggs asc | 1355 | GUCCUCACUUUAAUCCUCUAUCC | 374 |
| AD-1395760.1 | cscsuca(Chd)uuUfAfAfuccucuauscsa | 25 | VPusdAsgsaudAg(Agn)ggaudTaAfagugaggs asc | 26 | GUCCUCACUUUAAUCCUCUAUCC | 374 |
| AD-1395761.1 | cscsuca(Chd)uuUfAfAfuccucuauscsa | 25 | VPusdGsaudAg(Agn)ggaudTadAadGugag gsasc | 1356 | GUCCUCACUUUAAUCCUCUAUCC | 374 |
| AD-1321246.3 | csascuu(Uhd)AfaUfCfCfucuauccaga L96 | 1111 | asCfsuggAfuagaggaUfuAfaagugsasg | 1201 | CUCACUUUAAUCCUCUAUCCAGA | 403 |
| AD-1395762.1 | csascuu(Uhd)aaUfCfCfucuauccasgsa | 11 | VPusdCsugdGadTagagdGaUfuaaagugsasg | 12 | CUCACUUUAAUCCUCUAUCCAGA | 403 |
| AD-1395763.1 | csascuu(Uhd)aaUfCfCfucuauccasgsa | 11 | VPusdCsugdGadTagagdGadTudAaagugsa sg | 1357 | CUCACUUUAAUCCUCUAUCCAGA | 403 |
| AD-1321256.3 | asasgga(Uhd)GfaAfGfAfgaggcauguu L96 | 27 | asAfsfscadTg(C2p)cucucuUfcAfuccuususg | 1211 | CAAAGGAUGAAGAGAGGCAUGUU | 790 |
| AD-1395764.1 | asasgga(Uhd)gaAfGfAfgaggcaugsus a | 1328 | VPusAfscadTg(C2p)cucucuUfcAfuccuusu sg | 28 | CAAAGGAUGAAGAGAGGCAUGUU | 790 |
| AD-1395765.1 | asasgga(Uhd)gaAfGfAfgaggcaugsus a | 1328 | VPusAfscadTg(C2p)cucucuUfcAfuccuusu sg | 28 | CAAAGGAUGAAGAGAGGCAUGUU | 790 |
| AD-1395766.1 | asasgga(Uhd)gaAfGfAfgaggcaugsus a | 1329 | VPusAfscadTg(C2p)cucucuUfcAfuccuusu sg | 28 | CAAAGGAUGAAGAGAGGCAUGUU | 790 |
| AD-1395767.1 | asasgga(Uhd)gaAfGfAfgaggcaugsus a | 27 | VPusdAscadTg(C2p)cucudCfUfcauccuus usg | 1358 | CAAAGGAUGAAGAGAGGCAUGUU | 790 |
| AD-1395768.1 | asasgga(Uhd)gaAfgdGaggcaugsus a | 1328 | VPusdAscadTg(C2p)cucudCuUfcauccuus usg | 1358 | CAAAGGAUGAAGAGAGGCAUGUU | 790 |
| AD-1395769.1 | asasgga(Uhd)gadAgdAgaggcaugsusa | 1329 | VPusdAscadTg(C2p)cucudCuUfcauccuus usg | 1358 | CAAAGGAUGAAGAGAGGCAUGUU | 790 |

TABLE 20-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1321257.3 | asgsgau(Chd)AfaGfAfGfaggcauguuuL96 | 1122 | asAfsacdAu(G2p)ccucucUfuCfauccususu | 1212 | AAAGGAUGAAGAGAGGCAUGUUG | 791 |
| AD-1395770.1 | asgsga(Uhd)gAfaGfAfGfaggcauguuuL96 | 1330 | asAfsacdAu(G2p)ccucucUfuCfauccususu | 1212 | AAAGGAUGAAGAGAGGCAUGUUG | 791 |
| AD-1395771.1 | asgsga(Uhd)gaaGfAfGfaggcaugususa | 19 | VPusAfsacdAu(G2p)ccucucUfuCfauccusu su | 20 | AAAGGAUGAAGAGAGGCAUGUUG | 791 |
| AD-1395772.1 | asgsga(Uhd)gaadGaGaggcaugususa | 1331 | VPusAfsacdAu(G2p)ccucucUfuCfauccusu su | 20 | AAAGGAUGAAGAGAGGCAUGUUG | 791 |
| AD-1395773.1 | asgsga(Uhd)gaadGaDaGfggcaugusus a | 1332 | VPusAfsacdAu(G2p)ccucucUfuCfauccusu su | 1359 | AAAGGAUGAAGAGAGGCAUGUUG | 791 |
| AD-1395774.1 | asgsga(Uhd)gaadGaDAGfggcaugusus a | 1332 | VPusdAsacdAu(G2p)ccucdTcUfucauccus usu | 1359 | AAAGGAUGAAGAGAGGCAUGUUG | 791 |
| AD-1395775.1 | ususggg(Chd)AfaAfGfGfuggaaaugaa | 1141 | usUfscadTu(Tgn)ccaccuUfuGfcccaasgsu | 1231 | ACUUGGGCAAAGGUGGAAAUGAA | 435 |
| AD-1321276.3 | ususggg(Chd)aaAfGfGfuggaaaugsas a | 1333 | VPusUfscadTu(Tgn)ccaccuUfuGfcccaasgs u | 1360 | ACUUGGGCAAAGGUGGAAAUGAA | 435 |
| AD-1395776.1 | ususggg(Chd)aaAfgdGuggaaaugsasa | 1334 | VPusUfscadTu(Tgn)ccaccuUfuGfcccaasgs u | 1360 | ACUUGGGCAAAGGUGGAAAUGAA | 435 |
| AD-1395777.1 | ususggg(Chd)aaAfgdGuggaaaugsasa | 1334 | VPusUfscadTu(Tgn)ccacdCuUfugcccaasg su | 1361 | ACUUGGGCAAAGGUGGAAAUGAA | 435 |
| AD-1395778.1 | ususggg(Chd)aaAfgdGUfggaaaugsas a | 1335 | VPusUfscadTu(Tgn)ccacdCuUfugcccaasg su | 1361 | ACUUGGGCAAAGGUGGAAAUGAA | 435 |
| AD-1395779.1 | ususggg(Chd)aaAfgdGUfggaaaugsas a | 1335 | VPusdTscadTu(Tgn)ccacdCuUfugcccaasg su | 1361 | ACUUGGGCAAAGGUGGAAAUGAA | 435 |
| AD-1395780.1 | gscsaaag(Chd)GfuGfGfAfaaugagaaaL96 | 1145 | usUfsucdTu(C2p)auuuccAfcCfuuugcscsc | 1235 | GGGCAAAGGUGGAAAUGAGAAA | 1270 |
| AD-1321280.3 | gscsaaaggGfuGfGfAfaaug(Ahd)agaaa | 1336 | usUfsucdTu(C2p)auuuccAfcCfuuugcscsc | 1235 | GGGCAAAGGUGGAAAUGAGAAA | 1270 |
| AD-1395781.1 | gscsaaaggGfuGfGfAfaaug(Ahd)agasasa | 1337 | VPusUfsucdTu(C2p)auuucAfcCfuuugcscs sc | 1362 | GGGCAAAGGUGGAAAUGAGAAA | 1270 |

TABLE 20-continued

Modified Sense and Antisense Strand Sequences of Superoxide Dismutase 1 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1395783.1 | gscsaaaggudGgAfaaug(Ahd)agasasa | 1338 | VPusUfsucdTu(C2p)auuuccAfcCfuuugcsc | 1362 | GGGCAAAGGUGGAAAUGAAGAAA | 1270 |
| AD-1395784.1 | gscsaaaggugGfGfAfaaug(Ahd)agasasa | 1337 | VPusdTsucdTu(C2p)auuudCcAfccuuugcs | 1363 | GGGCAAAGGUGGAAAUGAAGAAA | 1270 |
| AD-1395785.1 | gscsaaaggudGgAfaaug(Ahd)agasasa | 1338 | VPusdTsucdTu(C2p)auuudCcAfccuuugcs | 1363 | GGGCAAAGGUGGAAAUGAAGAAA | 1270 |
| AD-1321284.3 | asgsgug(Ghd)AfaAfUfGfaagaaaguau L96 | 1149 | asUfsacdTu(Tgn)cuucauUfuCfcaccususu | 1239 | AAAGGUGGAAAUGAAGAAAGUAA | 1273 |
| AD-1395786.1 | asgsguggAfaAfUfGfaaga(Ahd)aguau L96 | 1339 | asUfsacdTu(Tgn)cuucauUfuCfcaccususu | 1239 | AAAGGUGGAAAUGAAGAAAGUAA | 1273 |
| AD-1395787.1 | asgsguggaaAfUfGfaaga(Ahd)agusasa | 1340 | VPusUfsacdTu(Tgn)cuucauUfuCfcaccusu su | 1364 | AAAGGUGGAAAUGAAGAAAGUAA | 1273 |
| AD-1395788.1 | asgsguggaaAfudGaaga(Ahd)agusasa | 1341 | VPusUfsacdTu(Tgn)cuucauUfuCfcaccusu su | 1364 | AAAGGUGGAAAUGAAGAAAGUAA | 1273 |
| AD-1395789.1 | asgsguggaaAfUfGfaaga(Ahd)agusasa | 1340 | VPusdTsacdTu(Tgn)cuucauUfuCfcaccusu su | 1365 | AAAGGUGGAAAUGAAGAAAGUAA | 1273 |
| AD-1395790.1 | asgsguggaaAfudGaaga(Ahd)agusasa | 1341 | VPusdTsacdTu(Tgn)cuucdAuUfuccaccusu su | 1365 | AAAGGUGGAAAUGAAGAAAGUAA | 1273 |
| AD-1395791.1 | asgsguggaaAfudGAfaga(Ahd)agusasa | 1342 | VPusdTsacdTu(Tgn)cuucdAuUfuccaccusu su | 1365 | AAAGGUGGAAAUGAAGAAAGUAA | 1273 |
| AD-1395792.1 | asgsguggaaAfudGAfaga(Ahd)agusasa | 1342 | VPusdTsacdTu(Tgn)cuucdAuUfuccaccusu su | 1365 | AAAGGUGGAAAUGAAGAAAGUAA | 1273 |

TABLE 21

Superoxide Dismutase 1 In Vitro Single Dose Screens in Primary Cynomolgus Hepatocytes (PCH) cells

| Duplex | 50 nM Avg | SD | 10 nM Avg | SD | 1 nM Avg | SD | 0.1 nM Avg | SD |
|---|---|---|---|---|---|---|---|---|
| AD-1321204.3 | 4.2 | 0.5 | 9.4 | 7.6 | 32.0 | 7.5 | 44.4 | 15.6 |
| AD-1395718.1 | 10.2 | 1.2 | 7.0 | 1.5 | 16.1 | 6.8 | 16.1 | 2.0 |
| AD-1395719.1 | 129.7 | 21.2 | 70.3 | 9.2 | 77.6 | 5.3 | 62.8 | 5.6 |
| AD-1395720.1 | 142.6 | 13.6 | 112.8 | 39.7 | 97.6 | 8.4 | 86.1 | 11.1 |
| AD-1395721.1 | 26.0 | 4.4 | 18.1 | 2.7 | 37.3 | 2.0 | 42.9 | 5.7 |
| AD-1395722.1 | 83.9 | 33.3 | 71.4 | 15.4 | 106.4 | 12.8 | 109.9 | 25.9 |
| AD-1395723.1 | 127.6 | 19.8 | 118.0 | 41.9 | 110.2 | 2.2 | 114.6 | 25.6 |
| AD-1321207.3 | 3.1 | 1.0 | 3.3 | 1.0 | 17.2 | 5.7 | 27.7 | 7.6 |
| AD-1395724.1 | 2.3 | 0.2 | 3.3 | 0.3 | 13.3 | 7.5 | 12.1 | 4.2 |
| AD-1395725.1 | 29.8 | 9.8 | 13.0 | 0.7 | 23.2 | 3.1 | 26.2 | 1.9 |
| AD-1395726.1 | 114.1 | 21.8 | 70.9 | 13.1 | 74.3 | 14.6 | 56.2 | 6.8 |
| AD-1395727.1 | 7.3 | 1.2 | 5.5 | 0.4 | 12.7 | 2.8 | 19.2 | 3.7 |
| AD-1395728.1 | 66.0 | 6.7 | 19.4 | 2.2 | 37.5 | 3.9 | 52.2 | 2.2 |
| AD-1395729.1 | 57.4 | 8.0 | 48.7 | 14.0 | 62.5 | 8.9 | 63.9 | 15.7 |
| AD-1321210.3 | 2.5 | 0.6 | 2.0 | 0.5 | 9.5 | 2.4 | 13.9 | 2.9 |
| AD-1395730.1 | 1.7 | 0.6 | 2.5 | 0.8 | 15.4 | 7.0 | 24.1 | 6.9 |
| AD-1395731.1 | 1.3 | 0.2 | 2.7 | 0.4 | 9.8 | 0.6 | 11.8 | 0.8 |
| AD-1395732.1 | 59.2 | 9.9 | 21.8 | 4.2 | 34.3 | 2.2 | 46.3 | 6.0 |
| AD-1395733.1 | 63.5 | 14.3 | 13.0 | 4.1 | 15.6 | 2.6 | 23.8 | 2.8 |
| AD-1395734.1 | 2.0 | 0.7 | 2.4 | 0.4 | 8.1 | 1.6 | 13.9 | 1.3 |
| AD-1395735.1 | 4.8 | 1.0 | 5.9 | 0.9 | 17.6 | 2.0 | 31.0 | 6.2 |
| AD-1395736.1 | 22.7 | 4.3 | 6.3 | 1.0 | 14.9 | 4.4 | 23.8 | 5.5 |
| AD-1321219.3 | 2.7 | 0.4 | 3.1 | 0.7 | 22.3 | 3.6 | 46.1 | 14.1 |
| AD-1395737.1 | 2.7 | 0.7 | 3.9 | 0.1 | 14.6 | 1.0 | 17.3 | 5.9 |
| AD-1395738.1 | 3.0 | 1.7 | 3.6 | 0.5 | 11.3 | 1.7 | 21.4 | 6.5 |
| AD-1395739.1 | 6.7 | 2.3 | 7.0 | 1.1 | 18.0 | 3.5 | 35.0 | 10.0 |
| AD-1321220.3 | 2.3 | 0.5 | 2.3 | 0.4 | 15.5 | 4.8 | 37.3 | 8.1 |
| AD-1395740.1 | 1.5 | 0.2 | 3.0 | 0.6 | 9.0 | 2.9 | 13.0 | 4.0 |
| AD-1395741.1 | 2.0 | 0.1 | 2.7 | 0.5 | 13.1 | 3.6 | 22.8 | 9.2 |
| AD-1395742.1 | 2.8 | 0.7 | 3.2 | 0.5 | 12.2 | 5.3 | 24.5 | 5.8 |
| AD-1321222.3 | 2.7 | 0.3 | 4.0 | 0.9 | 23.1 | 2.5 | 46.7 | 12.7 |
| AD-1395743.1 | 7.4 | 3.0 | 5.3 | 2.0 | 17.1 | 4.7 | 25.2 | 6.5 |
| AD-1395744.1 | 80.7 | 9.7 | 48.0 | 10.7 | 56.2 | 10.5 | 78.6 | 8.3 |
| AD-1395745.1 | 106.6 | 11.9 | 56.1 | 20.2 | 53.4 | 2.9 | 81.7 | 8.8 |
| AD-1395746.1 | 11.3 | 2.3 | 8.9 | 0.6 | 29.8 | 5.9 | 61.3 | 10.4 |
| AD-1395747.1 | 34.9 | 6.1 | 43.3 | 2.1 | 66.6 | 4.6 | 89.5 | 8.3 |
| AD-1395748.1 | 84.6 | 10.5 | 61.1 | 9.7 | 76.1 | 9.1 | 103.6 | 16.4 |
| AD-1321232.3 | 23.9 | 4.4 | 7.0 | 1.0 | 21.0 | 2.6 | 36.8 | 11.9 |
| AD-1395749.1 | 9.6 | 3.3 | 4.8 | 0.5 | 38.1 | 11.0 | 60.9 | 10.6 |
| AD-1395750.1 | 5.3 | 2.0 | 6.6 | 1.0 | 16.4 | 2.6 | 38.4 | 14.7 |
| AD-1395751.1 | 92.3 | 7.9 | 58.5 | 15.2 | 63.6 | 6.2 | 87.6 | 11.6 |
| AD-1395752.1 | 119.3 | 16.0 | 65.1 | 24.8 | 68.6 | 9.2 | 85.8 | 11.1 |
| AD-1395753.1 | 10.9 | 3.5 | 6.7 | 0.8 | 16.3 | 2.8 | 40.5 | 9.3 |
| AD-1395754.1 | 49.0 | 3.6 | 45.2 | 6.1 | 59.8 | 7.5 | 83.6 | 7.3 |
| AD-1395755.1 | 65.5 | 7.2 | 26.3 | 10.9 | 48.8 | 5.2 | 75.5 | 10.9 |
| AD-1321238.3 | 3.4 | 0.6 | 4.7 | 0.8 | 22.5 | 2.1 | 46.3 | 9.5 |
| AD-1395756.1 | 12.2 | 3.1 | 8.1 | 0.7 | 18.1 | 4.0 | 32.8 | 14.7 |
| AD-1395757.1 | 3.2 | 0.8 | 4.2 | 0.6 | 13.1 | 3.0 | 34.7 | 15.2 |
| AD-1395758.1 | 80.0 | 13.6 | 39.0 | 12.2 | 41.6 | 1.8 | 53.8 | 5.3 |
| AD-1321243.3 | 2.2 | 1.3 | 2.4 | 0.3 | 13.4 | 2.1 | 37.7 | 17.9 |
| AD-1395759.1 | 1.5 | 0.9 | 2.9 | 0.9 | 8.6 | 1.4 | 16.8 | 8.9 |
| AD-1395760.1 | 2.0 | 0.6 | 2.9 | 0.6 | 10.4 | 2.1 | 26.1 | 9.7 |
| AD-1395761.1 | 4.6 | 1.2 | 4.6 | 1.1 | 18.7 | 3.8 | 38.7 | 8.0 |
| AD-1321246.3 | 1.6 | 0.6 | 2.0 | 0.4 | 15.7 | 1.9 | 40.9 | 20.4 |
| AD-1395762.1 | 8.3 | 2.5 | 6.4 | 1.2 | 13.7 | 2.2 | 32.7 | 9.7 |
| AD-1395763.1 | 11.4 | 2.6 | 9.7 | 0.6 | 21.0 | 2.7 | 50.3 | 14.5 |
| AD-1321256.3 | 1.5 | 0.2 | 1.7 | 0.2 | 7.5 | 2.0 | 22.7 | 5.3 |
| AD-1395764.1 | 5.7 | 2.5 | 2.5 | 0.4 | 6.0 | 0.5 | 15.4 | 5.7 |
| AD-1395765.1 | 76.1 | 12.4 | 37.6 | 6.6 | 30.4 | 1.9 | 41.6 | 9.6 |
| AD-1395766.1 | 90.9 | 14.9 | 35.9 | 10.9 | 29.8 | 4.2 | 36.7 | 5.9 |
| AD-1395767.1 | 4.7 | 0.9 | 3.0 | 0.6 | 9.2 | 2.0 | 17.8 | 4.8 |
| AD-1395768.1 | 88.4 | 21.7 | 58.2 | 18.0 | 39.7 | 2.6 | 45.7 | 6.6 |
| AD-1395769.1 | 93.1 | 23.8 | 79.7 | 2.5 | 67.7 | 29.9 | 69.8 | 5.0 |
| AD-1321257.3 | 1.6 | 0.4 | 2.8 | 0.7 | 11.1 | 3.5 | 27.6 | 4.7 |
| AD-1395770.1 | 3.0 | 0.6 | 2.5 | 0.4 | 10.6 | 4.8 | 23.3 | 2.7 |
| AD-1395771.1 | 3.2 | 1.0 | 3.1 | 0.5 | 7.5 | 0.3 | 13.7 | 1.9 |
| AD-1395772.1 | 42.6 | 18.2 | 16.7 | 2.5 | 22.9 | 7.7 | 31.4 | 3.5 |
| AD-1395773.1 | 22.7 | 7.2 | 9.2 | 0.7 | 22.8 | 10.2 | 30.5 | 5.2 |
| AD-1395774.1 | 30.2 | 9.0 | 12.0 | 1.4 | 28.3 | 7.4 | 36.6 | 5.3 |
| AD-1395775.1 | 24.7 | 13.4 | 15.4 | 4.8 | 23.6 | 7.2 | 33.6 | 6.5 |
| AD-1321276.3 | 2.1 | 0.3 | 3.0 | 0.7 | 10.8 | 5.0 | 20.3 | 2.7 |
| AD-1395776.1 | 3.8 | 0.3 | 4.0 | 1.1 | 9.7 | 1.8 | 17.3 | 2.8 |
| AD-1395777.1 | 63.4 | 15.6 | 38.5 | 6.0 | 43.7 | 11.2 | 56.0 | 14.3 |
| AD-1395778.1 | 91.7 | 14.4 | 66.4 | 10.5 | 48.4 | 16.8 | 53.7 | 11.6 |
| AD-1395779.1 | 99.2 | 17.5 | 87.2 | 16.3 | 120.4 | 52.7 | 99.6 | 29.0 |
| AD-1395780.1 | 81.5 | 12.3 | 82.8 | 9.1 | 95.5 | 18.8 | 103.6 | 17.9 |
| AD-1321280.3 | 6.0 | 0.8 | 5.3 | 1.5 | 18.5 | 9.6 | 35.4 | 7.2 |
| AD-1395781.1 | 3.9 | 0.4 | 3.8 | 1.0 | 13.8 | 5.4 | 25.6 | 3.3 |
| AD-1395782.1 | 5.2 | 4.1 | 4.0 | 0.4 | 10.5 | 4.9 | 16.2 | 0.9 |
| AD-1395783.1 | 66.8 | 17.7 | 46.6 | 8.4 | 83.7 | 36.1 | 84.0 | 15.5 |
| AD-1395784.1 | 4.6 | 1.5 | 3.9 | 0.9 | 15.5 | 5.5 | 30.0 | 7.7 |
| AD-1395785.1 | 80.5 | 16.4 | 56.2 | 13.0 | 66.2 | 9.1 | 106.8 | 29.1 |
| AD-1321284.3 | 7.4 | 1.9 | 5.2 | 2.3 | 18.3 | 10.9 | 37.0 | 22.0 |
| AD-1395786.1 | 12.5 | 1.0 | 9.4 | 6.1 | 46.3 | 28.2 | 80.0 | 25.2 |
| AD-1395787.1 | 21.4 | 4.7 | 12.3 | 2.1 | 18.4 | 7.3 | 33.0 | 12.9 |
| AD-1395788.1 | 131.2 | 18.7 | 132.1 | 23.4 | 77.1 | 23.8 | 93.8 | 28.1 |
| AD-1395789.1 | 147.3 | 32.6 | 105.3 | 19.7 | 68.1 | 25.2 | 90.4 | 51.6 |
| AD-1395790.1 | 11.0 | 1.9 | 7.9 | 2.4 | 20.6 | 9.0 | 40.8 | 15.5 |
| AD-1395791.1 | 101.8 | 24.9 | 97.5 | 30.7 | 114.8 | 51.9 | 129.7 | 38.0 |
| AD-1395792.1 | 122.6 | 25.4 | 167.1 | 42.2 | 155.0 | 40.6 | 129.3 | 50.0 |

TABLE 22

Superoxide Dismutase 1 In Vitro Single Dose Screens in BE(2)C cells

| Duplex | 50 nM Avg | SD | 10 nM Avg | SD | 1 nM Avg | SD | 0.1 nM Avg | SD |
|---|---|---|---|---|---|---|---|---|
| AD-1321204.3 | 2.6 | 1.9 | 5.5 | 1.1 | 20.1 | 4.8 | 37.7 | 6.1 |
| AD-1395718.1 | 4.7 | 1.5 | 6.1 | 5.5 | 5.2 | 1.2 | 10.9 | 2.8 |
| AD-1395719.1 | 100.1 | 45.1 | 25.1 | 4.5 | 17.7 | 7.0 | 20.8 | 4.5 |
| AD-1395720.1 | 99.7 | 33.1 | 36.4 | 4.8 | 27.4 | 3.5 | 37.8 | 5.2 |
| AD-1395721.1 | 8.6 | 1.4 | 5.2 | 0.9 | 7.5 | 1.1 | 18.4 | 12.6 |
| AD-1395722.1 | 72.9 | 10.4 | 61.6 | 26.4 | 30.6 | 2.5 | 38.8 | 6.5 |
| AD-1395723.1 | 104.8 | 45.1 | 38.2 | 5.2 | 33.6 | 7.9 | 37.8 | 4.9 |
| AD-1321207.3 | 2.1 | 0.5 | 5.1 | 1.9 | 12.9 | 1.6 | 25.7 | 5.9 |
| AD-1395724.1 | 2.4 | 0.6 | 4.1 | 1.5 | 4.3 | 1.0 | 8.3 | 0.9 |
| AD-1395725.1 | 56.9 | 10.0 | 11.4 | 2.5 | 7.6 | 3.1 | 11.1 | 2.7 |
| AD-1395726.1 | 108.0 | 36.1 | 43.8 | 9.2 | 25.9 | 6.6 | 22.0 | 4.4 |
| AD-1395727.1 | 6.7 | 1.2 | 4.5 | 2.1 | 7.2 | 2.0 | 15.7 | 8.2 |
| AD-1395728.1 | 63.6 | 12.4 | 16.5 | 4.2 | 15.9 | 3.1 | 23.7 | 6.3 |
| AD-1395729.1 | 80.8 | 17.0 | 37.5 | 8.9 | 24.5 | 8.0 | 33.3 | 4.9 |
| AD-1321210.3 | 4.1 | 1.9 | 4.3 | 1.6 | 10.8 | 4.3 | 16.8 | 9.8 |
| AD-1395730.1 | 2.5 | 0.7 | 4.4 | 1.4 | 12.1 | 3.6 | 28.4 | 21.1 |
| AD-1395731.1 | 2.2 | 1.1 | 3.5 | 2.7 | 4.9 | 2.4 | 6.2 | 2.4 |
| AD-1395732.1 | 46.5 | 11.0 | 11.1 | 4.5 | 8.8 | 2.2 | 15.6 | 1.9 |
| AD-1395733.1 | 52.4 | 13.8 | 14.5 | 5.0 | 7.0 | 1.2 | 14.8 | 3.5 |
| AD-1395734.1 | 3.3 | 1.9 | 3.5 | 1.2 | 7.8 | 4.5 | 12.7 | 2.8 |
| AD-1395735.1 | 7.9 | 2.0 | 4.1 | 1.2 | 10.2 | 2.9 | 15.5 | 6.3 |
| AD-1395736.1 | 20.0 | 7.8 | 7.0 | 2.6 | 7.9 | 3.6 | 9.8 | 2.4 |
| AD-1321219.3 | 4.0 | 1.1 | 7.2 | 2.5 | 25.2 | 10.8 | 47.9 | 9.1 |
| AD-1395737.1 | 4.2 | 2.5 | 5.3 | 3.8 | 10.9 | 6.1 | 13.8 | 10.8 |
| AD-1395738.1 | 2.1 | 0.6 | 3.4 | 1.1 | 6.0 | 2.4 | 8.7 | 3.4 |
| AD-1395739.1 | 7.0 | 2.1 | 6.4 | 2.8 | 14.3 | 6.5 | 34.4 | 14.0 |
| AD-1321220.3 | 3.1 | 1.3 | 6.9 | 3.7 | 22.8 | 4.7 | 50.6 | 24.7 |
| AD-1395740.1 | 2.5 | 0.9 | 3.8 | 1.7 | 6.3 | 2.6 | 11.4 | 3.9 |
| AD-1395741.1 | 3.0 | 1.0 | 4.1 | 2.0 | 8.1 | 2.1 | 10.4 | 4.6 |
| AD-1395742.1 | 2.9 | 1.0 | 3.3 | 0.6 | 6.5 | 1.9 | 11.7 | 5.2 |
| AD-1321222.3 | 5.1 | 2.9 | 12.0 | 7.1 | 35.8 | 19.3 | 55.3 | 27.1 |
| AD-1395743.1 | 4.2 | 0.5 | 4.6 | 2.1 | 9.0 | 5.3 | 11.4 | 3.0 |
| AD-1395744.1 | 74.6 | 18.0 | 39.0 | 6.8 | 34.4 | 5.6 | 58.5 | 9.8 |
| AD-1395745.1 | 82.3 | 17.6 | 47.8 | 15.1 | 53.1 | 17.7 | 70.1 | 28.8 |
| AD-1395746.1 | 7.4 | 0.9 | 8.5 | 4.1 | 21.9 | 6.7 | 41.2 | 14.8 |
| AD-1395747.1 | 80.1 | 12.9 | 59.5 | 8.5 | 65.4 | 18.0 | 105.6 | 33.0 |
| AD-1395748.1 | 124.8 | 1.3 | 80.2 | 16.6 | 60.1 | 25.5 | 116.2 | 22.8 |
| AD-1321232.3 | 14.9 | 2.6 | 14.7 | 7.4 | 33.3 | 13.5 | 76.1 | 19.7 |
| AD-1395749.1 | 6.0 | 1.4 | 7.8 | 5.3 | 30.3 | 20.9 | 62.5 | 24.8 |
| AD-1395750.1 | 4.3 | 1.8 | 3.7 | 1.2 | 5.8 | 2.3 | 11.4 | 4.0 |
| AD-1395751.1 | 76.0 | 9.7 | 44.2 | 9.0 | 48.1 | 16.3 | 60.7 | 6.8 |
| AD-1395752.1 | 78.1 | 8.0 | 62.8 | 8.3 | 54.8 | 18.2 | 73.6 | 13.5 |
| AD-1395753.1 | 6.8 | 2.3 | 8.1 | 1.9 | 16.4 | 4.0 | 34.4 | 8.8 |

TABLE 22-continued

Superoxide Dismutase 1 In Vitro Single Dose Screens in BE(2)C cells

| Duplex | 50 nM Avg | 50 nM SD | 10 nM Avg | 10 nM SD | 1 nM Avg | 1 nM SD | 0.1 nM Avg | 0.1 nM SD |
|---|---|---|---|---|---|---|---|---|
| AD-1395754.1 | 68.1 | 21.5 | 27.7 | 7.1 | 65.5 | 14.9 | 79.4 | 27.9 |
| AD-1395755.1 | 98.0 | 24.7 | 37.0 | 16.2 | 67.5 | 18.0 | 83.0 | 20.7 |
| AD-1321238.3 | 3.5 | 1.5 | 6.8 | 3.6 | 16.5 | 13.3 | 22.6 | 4.2 |
| AD-1395756.1 | 5.6 | 1.1 | 3.3 | 1.2 | 4.7 | 1.9 | 5.6 | 2.0 |
| AD-1395757.1 | 2.9 | 1.2 | 2.7 | 1.8 | 8.0 | 3.0 | 35.2 | 15.8 |
| AD-1395758.1 | 36.1 | 7.6 | 15.0 | 3.6 | 16.8 | 3.3 | 29.6 | 11.3 |
| AD-1321243.3 | 3.5 | 2.0 | 7.0 | 2.5 | 17.1 | 2.9 | 24.0 | 2.4 |
| AD-1395759.1 | 3.8 | 1.8 | 3.2 | 1.5 | 5.8 | 1.8 | 9.0 | 4.6 |
| AD-1395760.1 | 3.2 | 2.3 | 3.5 | 1.3 | 6.4 | 4.9 | 9.1 | 2.8 |
| AD-1395761.1 | 5.3 | 1.1 | 5.9 | 1.5 | 10.7 | 1.9 | 19.4 | 8.8 |
| AD-1321246.3 | 3.4 | 3.7 | 3.3 | 0.9 | 10.3 | 3.3 | 23.1 | 13.1 |
| AD-1395762.1 | 1.6 | 1.3 | 2.1 | 0.6 | 2.9 | 0.8 | 5.6 | 2.6 |
| AD-1395763.1 | 3.6 | 0.7 | 3.4 | 0.6 | 6.6 | 1.8 | 14.1 | 5.7 |
| AD-1321256.3 | 3.1 | 2.2 | 6.3 | 5.1 | 10.9 | 3.3 | 20.3 | 1.1 |
| AD-1395764.1 | 2.3 | 1.0 | 2.5 | 0.3 | 6.1 | 1.4 | 11.3 | 3.0 |
| AD-1395765.1 | 86.7 | 33.4 | 31.8 | 8.0 | 19.0 | 7.6 | 23.7 | 4.1 |
| AD-1395766.1 | 67.2 | 29.3 | 19.8 | 10.2 | 13.0 | 4.3 | 16.7 | 3.3 |
| AD-1395767.1 | 5.0 | 1.1 | 7.0 | 3.0 | 10.5 | 4.4 | 16.4 | 5.2 |
| AD-1395768.1 | 100.0 | 28.9 | 56.1 | 31.8 | 7.8 | 1.0 | 11.6 | 2.0 |
| AD-1395769.1 | 49.7 | 34.7 | 28.2 | 6.5 | 11.2 | 2.4 | 16.9 | 3.9 |
| AD-1321257.3 | 3.0 | 0.7 | 4.0 | 2.5 | 11.9 | 3.9 | 24.8 | 4.9 |
| AD-1395770.1 | 3.5 | 2.1 | 4.5 | 1.3 | 12.7 | 1.8 | 24.3 | 8.1 |
| AD-1395771.1 | 2.7 | 1.1 | 1.9 | 0.8 | 5.6 | 2.0 | 8.1 | 2.2 |
| AD-1395772.1 | 55.4 | 13.2 | 17.8 | 9.3 | 12.5 | 4.2 | 11.3 | 8.5 |
| AD-1395773.1 | 43.6 | 15.7 | 8.6 | 2.1 | 13.6 | 5.4 | 16.4 | 1.4 |
| AD-1395774.1 | 26.4 | 6.7 | 6.8 | 2.3 | 24.8 | 32.6 | 13.0 | 3.5 |
| AD-1395775.1 | 13.4 | 6.7 | 4.9 | 1.0 | 10.3 | 10.2 | 9.3 | 1.6 |
| AD-1321276.3 | 2.5 | 0.9 | 3.9 | 2.0 | 29.3 | 28.0 | 19.6 | 3.2 |
| AD-1395776.1 | 2.4 | 0.8 | 12.8 | 14.4 | 26.7 | 26.0 | 12.7 | 4.4 |
| AD-1395777.1 | 86.1 | 34.8 | 16.8 | 4.3 | 15.9 | 4.6 | 17.5 | 3.2 |
| AD-1395778.1 | 80.3 | 37.1 | 33.8 | 11.2 | 20.9 | 14.3 | 17.6 | 3.6 |
| AD-1395779.1 | 57.8 | 19.2 | 25.0 | 6.9 | 19.6 | 4.5 | 30.8 | 5.3 |
| AD-1395780.1 | 62.9 | 18.7 | 21.0 | 6.3 | 15.0 | 7.1 | 26.4 | 5.5 |
| AD-1321280.3 | 4.1 | 1.8 | 4.5 | 0.9 | 20.5 | 5.0 | 34.4 | 10.0 |
| AD-1395781.1 | 5.2 | 2.0 | 5.2 | 1.3 | 16.3 | 9.8 | 34.4 | 24.1 |
| AD-1395782.1 | 3.8 | 1.3 | 2.5 | 1.0 | 5.1 | 0.6 | 10.2 | 2.6 |
| AD-1395783.1 | 50.6 | 15.8 | 15.3 | 4.1 | 18.6 | 3.7 | 42.6 | 10.3 |
| AD-1395784.1 | 5.1 | 1.2 | 3.0 | 0.7 | 7.7 | 2.8 | 13.7 | 2.1 |
| AD-1395785.1 | 63.8 | 28.5 | 20.2 | 10.0 | 22.9 | 6.5 | 46.9 | 13.7 |
| AD-1321284.3 | 9.9 | 2.5 | 7.5 | 2.6 | 26.3 | 3.9 | 37.9 | 10.9 |
| AD-1395786.1 | 24.7 | 21.5 | 13.7 | 3.1 | 91.2 | 59.0 | 94.0 | 39.7 |
| AD-1395787.1 | 17.3 | 6.1 | 9.8 | 4.4 | 7.8 | 1.0 | 25.0 | 7.8 |
| AD-1395788.1 | 69.3 | 16.3 | 70.6 | 28.2 | 56.4 | 40.4 | 36.8 | 12.4 |
| AD-1395789.1 | 70.7 | 24.9 | 31.2 | 5.2 | 30.6 | 19.8 | 43.0 | 24.7 |
| AD-1395790.1 | 9.4 | 3.2 | 8.4 | 6.3 | 9.6 | 3.7 | 21.0 | 6.2 |
| AD-1395791.1 | 75.9 | 22.1 | 34.4 | 12.2 | 27.8 | 6.5 | 46.6 | 12.1 |
| AD-1395792.1 | 74.7 | 29.5 | 27.8 | 4.7 | 19.2 | 1.6 | 51.3 | 19.8 |

Figures 3A, 3B:
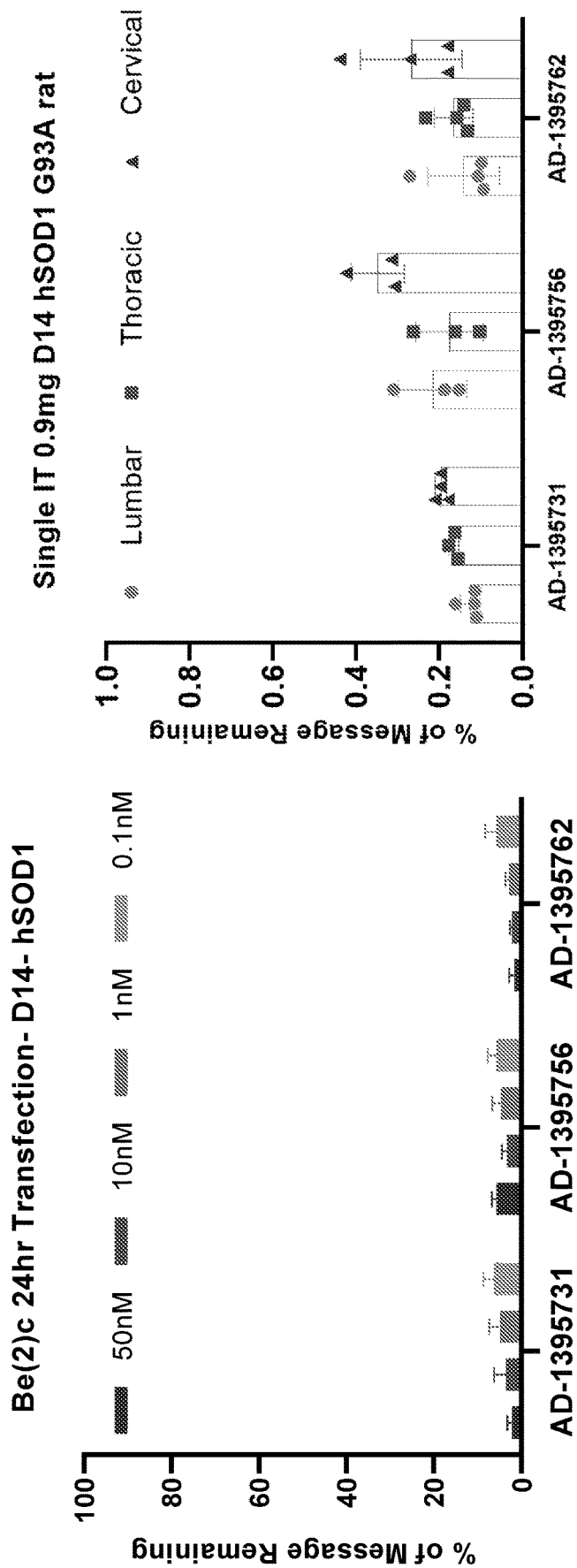
FIG. 3A is a graph depicting the effect of a single 50 nM, 10 nM, 1 nM, or 0.1 nM dose of the indicated duplexes on hSOD1 mRNA expression in BE(2)c cells on Day 14 post-dose.
FIG. 3B is a graph depicting the effect of a single 0.9 mg intrathecally administered dose of the indicated duplexes on hSOD1 mRNA expression in the lumbar, thoracic, and cervical spinal cord regions of G93A rats on Day 14 post-dose.

Example 5. In Vivo Assessment of RNAi Agents Targeting SOD1 in G93A-SOD1 Transgenic Rats Based on the in vitro and in vivo studies above, three duplexes, AD-1395762, AD-1395756, and AD-1395731 were selected for further analysis (see, e.g., Table 21). FIG. 3A summarizes the effects of these three duplexes observed in vitro, demonstrating that all three duplexes reduce human SOD1 (hSOD1) mRNA expression by greater than 90% in BE(2)c cells on Day 14 post-dose across all doses tested (50 nM, 10 nM, 1 nM, and 0.1 nM).

These three duplexes were further assessed for in vivo activity in G93A rats. This transgenic rat model, which over-expresses the mutant hSOD1G93A gene, reproduces the pathology and symptoms observed in ALS patients, e.g., paralysis in one or more limbs within a few weeks of age (see, e.g., Matsumoto A, et al. (2006) *J Neurosc Res* 83: 119-133).

Briefly, male G93A-SOD1 rats received a single 0.9 mg dose in a volume of 5 μl of AD-1395762, AD-1395756, or AD-1395731, or 5 μl of artificial CSF (aCSF) control (n=3 per group) by intrathecal injection using a Hamilton syringe and an angled 30 G needle at Day 0. At Day 14 post-dose, animals were sacrificed and tissue samples, including lumbar, thoracic and cervical spinal cord, were collected and flash frozen. mRNA was extracted from the tissue and analyzed by the RT-QPCR method.

The results, depicted in FIG. 3B, demonstrate that all three duplexes reduce target SOD1 (hSOD1) mRNA expression by greater than 90% in G93A rats on Day 14 post-dose in all three regions of the spinal cord (lumbar, thoracic, and cervical) following a single 0.9 mg intrathecally administered dose of the duplex.

Example 6. Preclinical Assessment of RNAi Agents Targeting SOD1

Metabolite Identification (MetID) was used to determine which metabolites and the amount of metabolites that were formed following administration of each of duplexes AD-1395762, AD-1395756, and AD-1395731, as well as the percent of parent duplex exposure (area under the curve (AUC)) in the brain and spine of treated wild-type rats.

Metabolite identification was performed on pooled rat cerebral cortex collected 4-1344 hr post-dose, and pooled lumbar spinal cord collected 4-1344 hr post-dose via LC-HRMS (see, e.g., methods in Liu et al., *Bioanalysis* (2019) 11(21), 1967-1981).

Figure 4A:
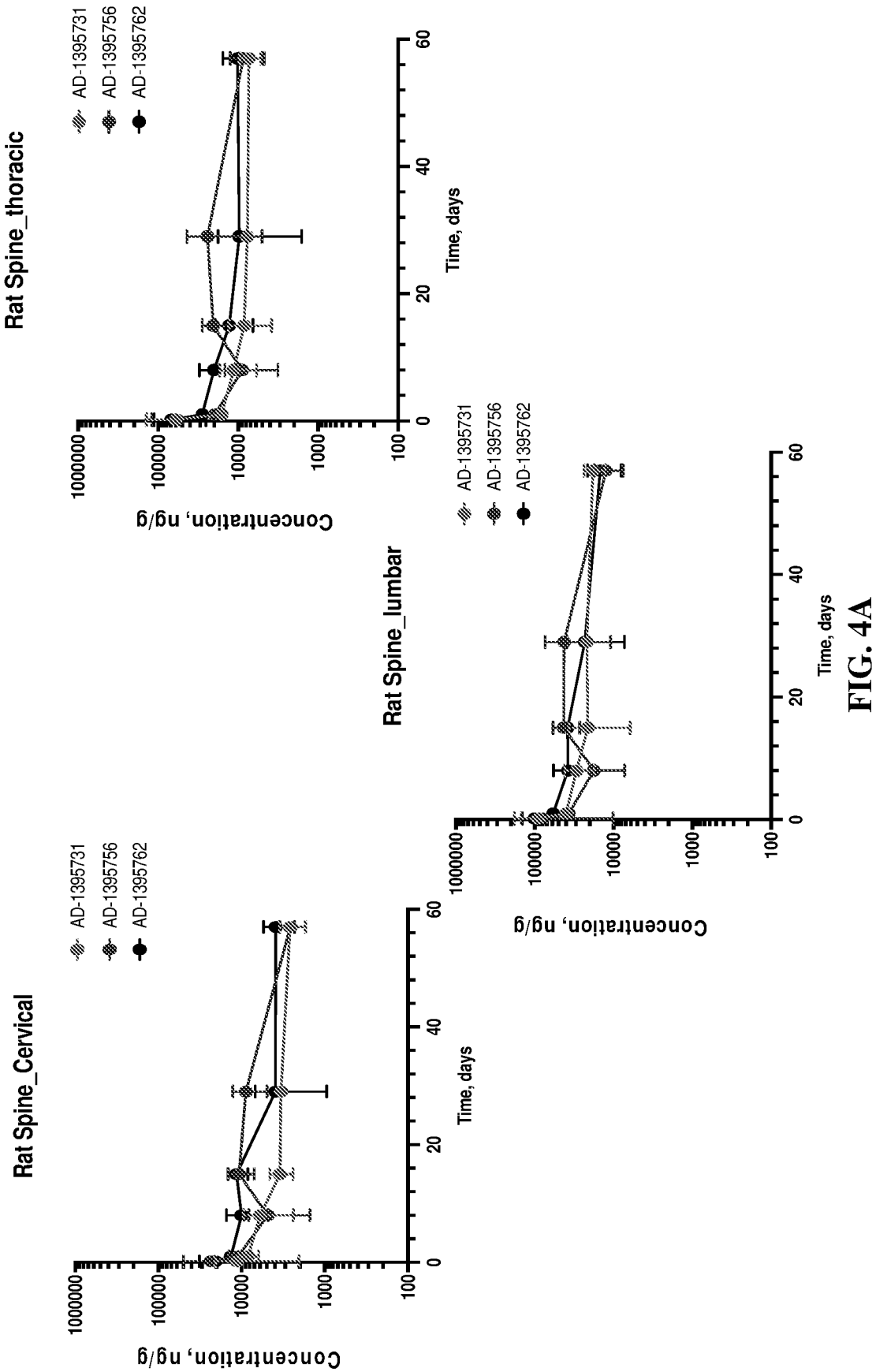
FIG. 4A are graphs depicting the concentration of the indicated duplexes in the cervical, thoracic or lumbar spinal cords of rats administered a single dose of the indicated duplexes.
Figures 4B, 4C:
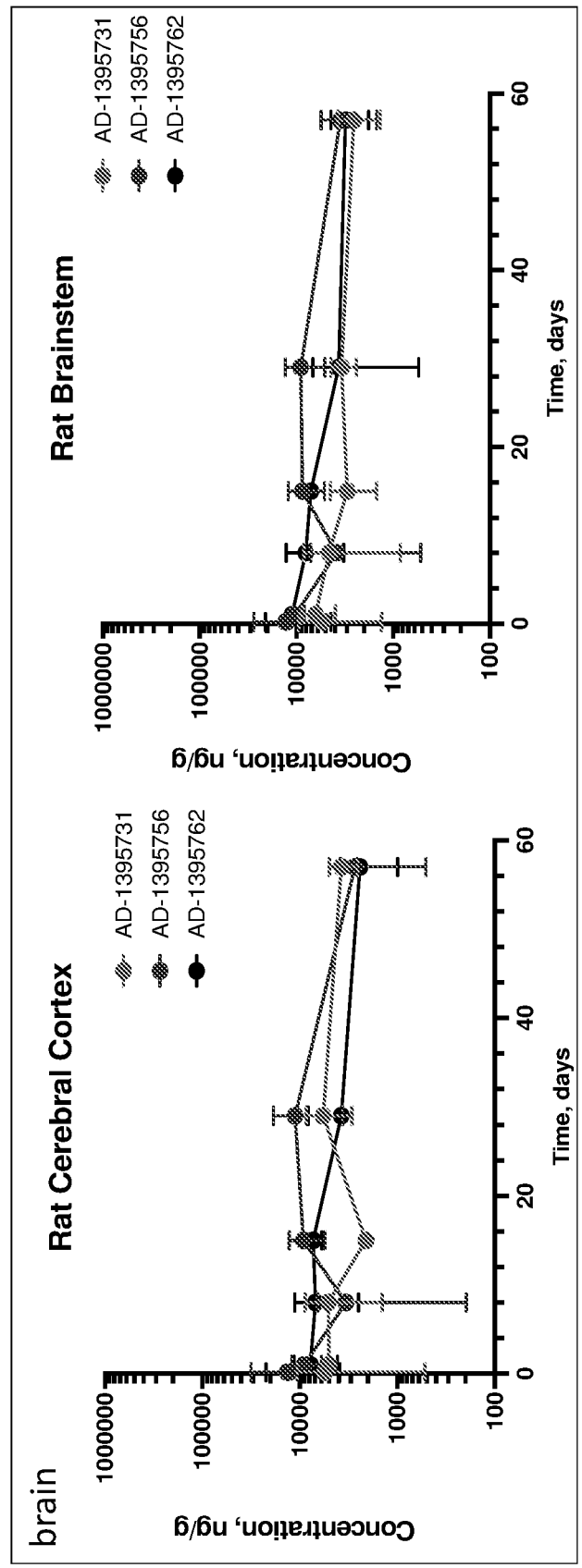
FIG. 4B are graphs depicting the concentration of the indicated duplexes in the cerebral cortices or brainstems of rats administered a single dose of the indicated duplexes.
FIG. 4C is a Table depicting the retention times of the indicated duplexes in the cervical spinal cords, thoracic spinal cords, lumbar spinal cords, cerebral cortices or brainstems of rats administered a single dose of the indicated duplexes.
Figure 5:
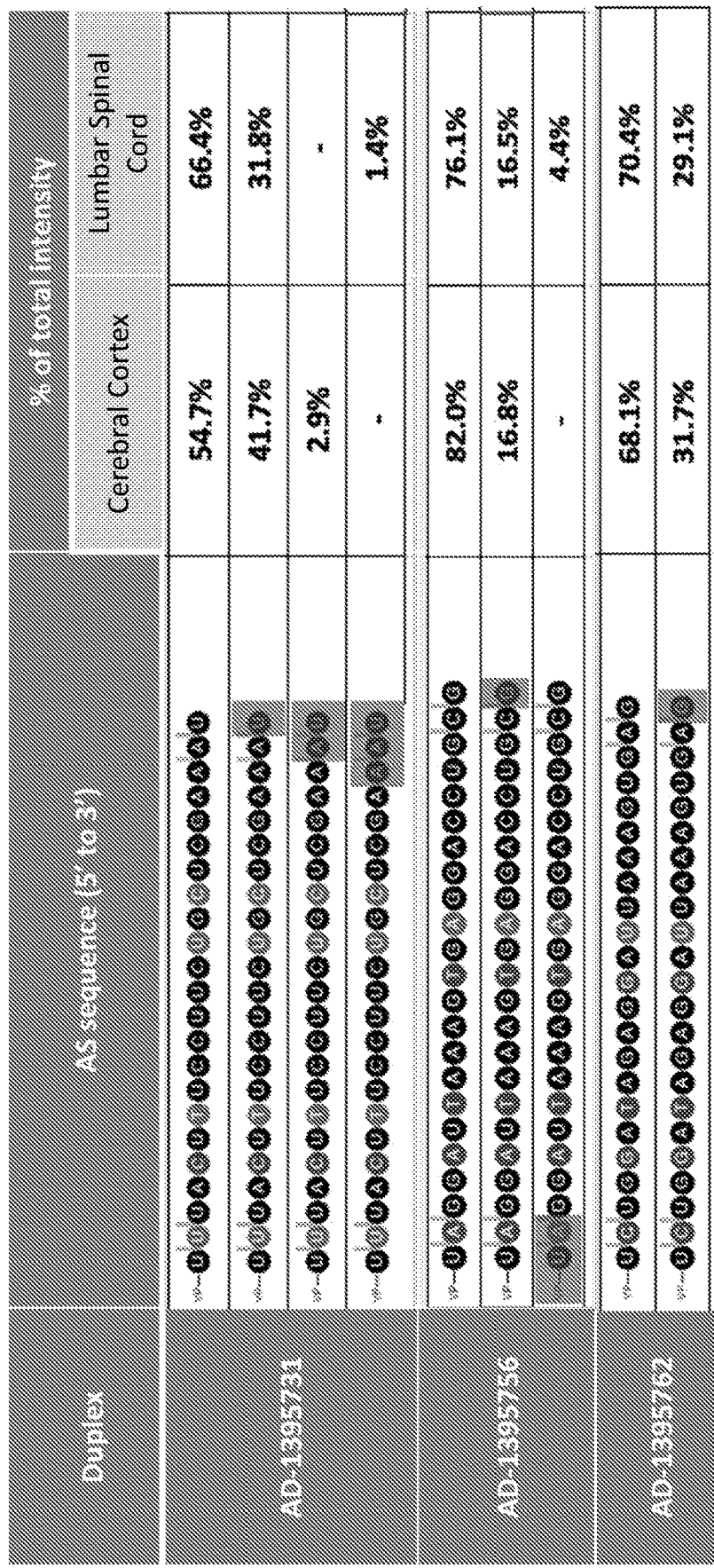
FIG. 5 is a Table depicting the metabolite profiles in the cerebral cortices and lumbar spinal cords of rats administered a single dose of the indicated duplexes.

The results of these studies are presented in FIGS. 4-5.

FIGS. 4A and 4B demonstrate that all three duplexes AD-1395762, AD-1395756, and AD-1395731, have similar exposure in rat spine (cervical, thoracic and lumbar; FIG. 4A) and brain (cerebral cortex and brainstem; FIG. 4B).

FIG. 4C demonstrates that all three duplexes AD-1395762, AD-1395756, and AD-1395731, have similar retention in rat spine (cervical, thoracic and lumbar; FIG. 4A) and brain (cerebral cortex and brainstem; FIG. 4B).

In addition, it was determined that the half-life ($t_{1/2}$) of each of these three duplexes is long (>20 days) and that the $t_{1/2}$ are comparable even when considering potential inter-animal dosing variability.

FIG. 5 demonstrates that all three duplexes AD-1395762, AD-1395756, and AD-1395731, have similar metabolite profiles in both brain and spine and that the antisense strand lacking the 3'-terminal nucleotide (3'N-1 AS) is the major active metabolite.

FIG. 6 is a Table summarizing the tissue exposure and metabolite profiling of duplexes AD-1395762, AD-1395756, and AD-1395731. Table 23 shows the nucleotide sequences for exemplary observed or predicted 3'N-1 AS metabolites for certain duplexes described herein.

TABLE 23

3'N-1 AS Metabolites.

| Duplex Name | Sense Sequence 5' to 3' | SEQ ID NO: | Antisense Sequence 5' to 3' | SEQ ID NO: | Antisense 3'N-1 Metabolite | SEQ ID NO: |
|---|---|---|---|---|---|---|
| AD-1395762 | csascuu(Uhd)aaUfCfCfucuauccasgsa | 11 | VPusdCsugdGadTagagdGaUfuaaagugsasg | 12 | VPusdCsugdGadTagagdGaUfuaaagugsa | 1369 |
| AD-1395756 | csasggu(Chd)cuCfAfCfuuuauccsusa | 13 | VPusdAsggdAudTaaagdTgAfggaccugscsg | 14 | VPusdAsggdAudTaaagdTgAfggaccugsc | 1370 |
| AD-1395731 | ususcgag(Chd)aGfAfAfggaaaguasasa | 15 | VPusUfsuadCu(Tgn)uccuucUfgCfucgaasasu | 16 | VPusUfsuadCu(Tgn)uccuucUfgCfucgaasa | 1371 |
| AD-1395743 | gsasaaag(Uhd)aaUfGfGfaccagugasacscsu | 17 | VPusUfsucdAc(Tgn)gguccaUfuAfcuuucscsu | 18 | VPusUfsucdAc(Tgn)gguccaUfuAfcuuucsc | 1372 |
| AD-1395771 | asgsgga(Ahd)gaaGfAfGfaggcaugsusa | 19 | VPusAfsacdAu(G2p)ccucucUfuCfaucccususu | 20 | VPusAfsacdAu(G2p)ccucucUfuCfaucccusu | 1373 |
| AD-1395738 | asasgga(Ahd)agUfAfAfuggaccagsusa | 21 | VPusdAscudGg(Tgn)ccaudTaCfuuuccuuscsu | 22 | VPusdAscudGg(Tgn)ccaudTaCfuuuccuusc | 1374 |
| AD-1395718 | asuscaa(Uhd)uuCfGfAfgcagaagsasa | 23 | VPusUfsccdTu(C2p)ugcucgAfaAfuugausgsg | 24 | VPusUfsccdTu(C2p)ugcucgAfaAfuugausg | 1375 |
| AD-1395760 | cscsuca(Chd)uuUfAfAfuccucusauscsa | 25 | VPusdGsaudAg(Agn)ggaudTaAfaguagsgsa | 26 | VPusdGsaudAg(Agn)ggaudTaAfaguaggsa | 1376 |
| AD-1395764 | asasgga(Uhd)gaAfGfAfgaggcaugsusa | 27 | VPusAfscadTg(C2p)cucucuUfcAfuccuususu | 28 | VPusAfscadTg(C2p)cucucuUfcAfuccuusu | 1377 |
| AD-1395724 | asasuuu(Chd)gaGfCfAfgaaggaaasgsa | 29 | VPusCfsuudTc(C2p)uucugcUfcGfaaaususg | 30 | VPusCfsuudTc(C2p)uucugcUfcGfaaauusg | 1378 |

Example 7. In Vivo Assessment of RNAi Agents in Non-Human Primates (NHP)

The effects of duplexes AD-1395762, AD-1395756, and AD-1395731 were also assessed in vivo in non-human primates (NHP).

As depicted in FIG. 7, on Day 0 non-human primates were intrathecally administered a single 70 mg dose of AD-1395762, AD-1395756, or AD-1395731 in a volume of 2 mL, or a single 120 mg dose of AD-1395731 in a volume of 2 mL, or 2 mL of artificial cerebrospinal fluid (aCSF) Animals were sacrificed at Day 31, Day 85, or Day 169 post-dose, tissue samples were collected and the level of SOD1 mRNA was quantified as described above.

Figure 8A:
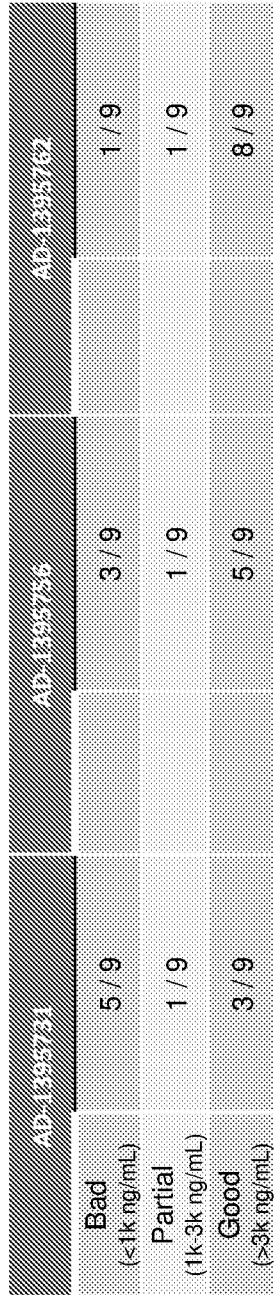
FIG. 8A is a Table depicting the numbers of non-human primates considered to have received "bad exposure" (duplex levels in a CSF sample <1,000 ng/mL at 24 hours), "good exposure" (duplex levels in a CSF sample >3,000 ng/mL at 24 hours), or "partial exposure" (duplex levels in a CSF sample 1,000-3,000 ng/mL at 24 hours) to a single 70 mg intrathecally administered dose of AD-1395762, AD-1395756, or AD-1395731.
Figure 8B:
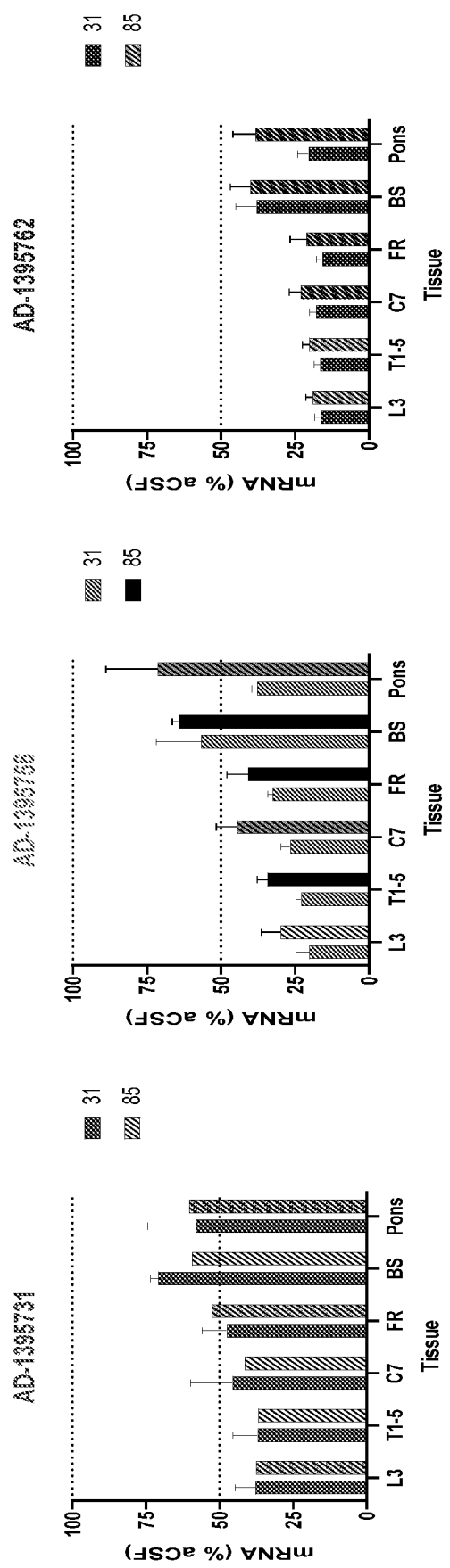
FIG. 8B are graphs depicting the level of SOD1 mRNA in lumbar spinal cord (L3), thoracic spinal cord (T1-T5), cervical spinal cord (C7), frontal cortex (FC), brainstem (BS), or pons samples in non-human primates following intrathecal administration of a single 70 mg dose of the indicated duplexes at Days 31 and 85 post-dose.
Figure 8C:
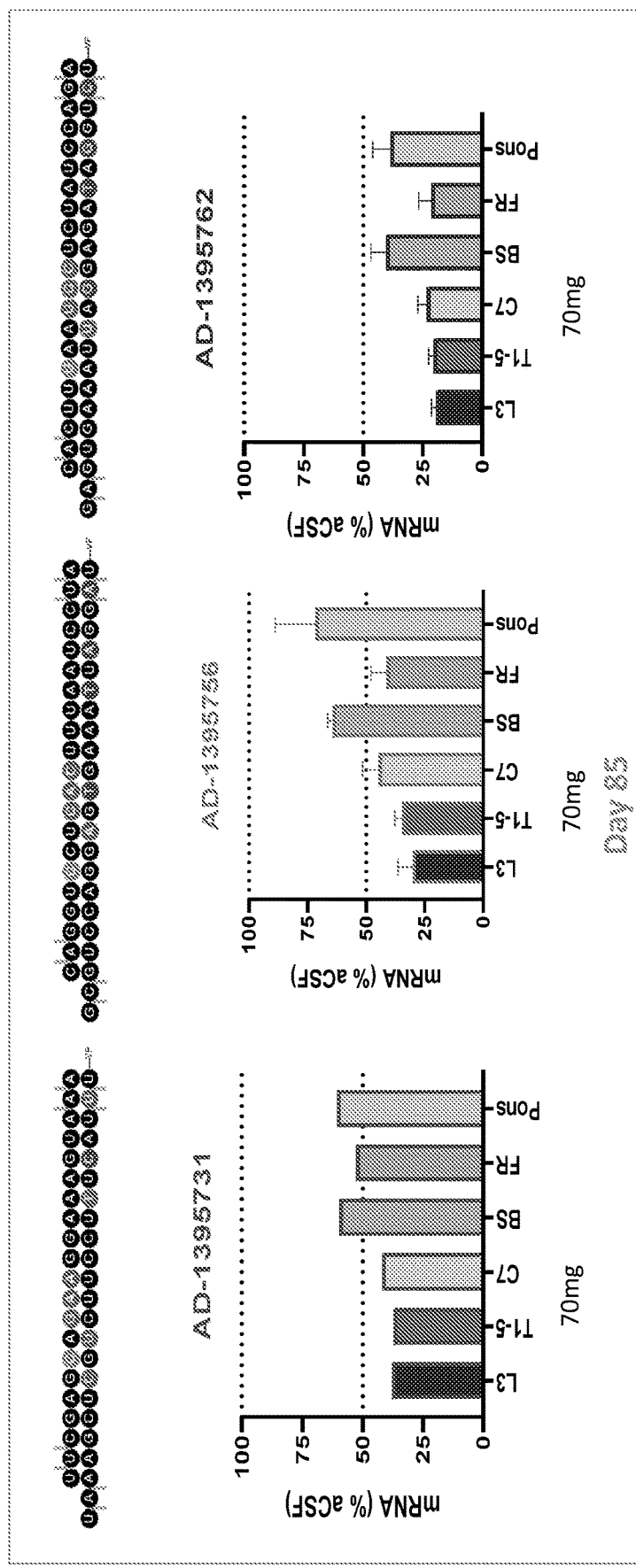
FIG. 8C are graphs depicting the level of SOD1 mRNA in lumbar spinal cord (L3), thoracic spinal cord (T1-T5), cervical spinal cord (C7), frontal cortex (FC), brainstem (BS), or pons samples in non-human primates following intrathecal administration of a single 70 mg dose of the indicated duplexes at Day 85 post-dose.

Due to differences in dosing of the animals (FIG. 8A), the relative potencies of each duplex was unclear. However, by removing samples having drug exposure levels at 24 hours in the CSF that were lower than 1500 ng/ml, which are considered suboptimal doses, the data demonstrate that a single intrathecally administered 70 mg dose of AD-1395762, AD-1395756, or AD-1395731 resulted in the reduction of SOD1 mRNA in various CNS tissues and that the reduction in SOD1 mRNA in various CNS tissues was durable and maintained out to Day 85 post-dose (FIG. 8B). Remarkably, as depicted in FIG. 8C, a single intrathecally administered 70 mg dose of AD-1395762, AD-1395756, or AD-1395731 reduced SOD1 mRNA by 75% in the cervical spinal cord at Day 85 post-dose and by 60% in the cortex by Day 85 post-dose (FIG. 8C).

Figure 9A:
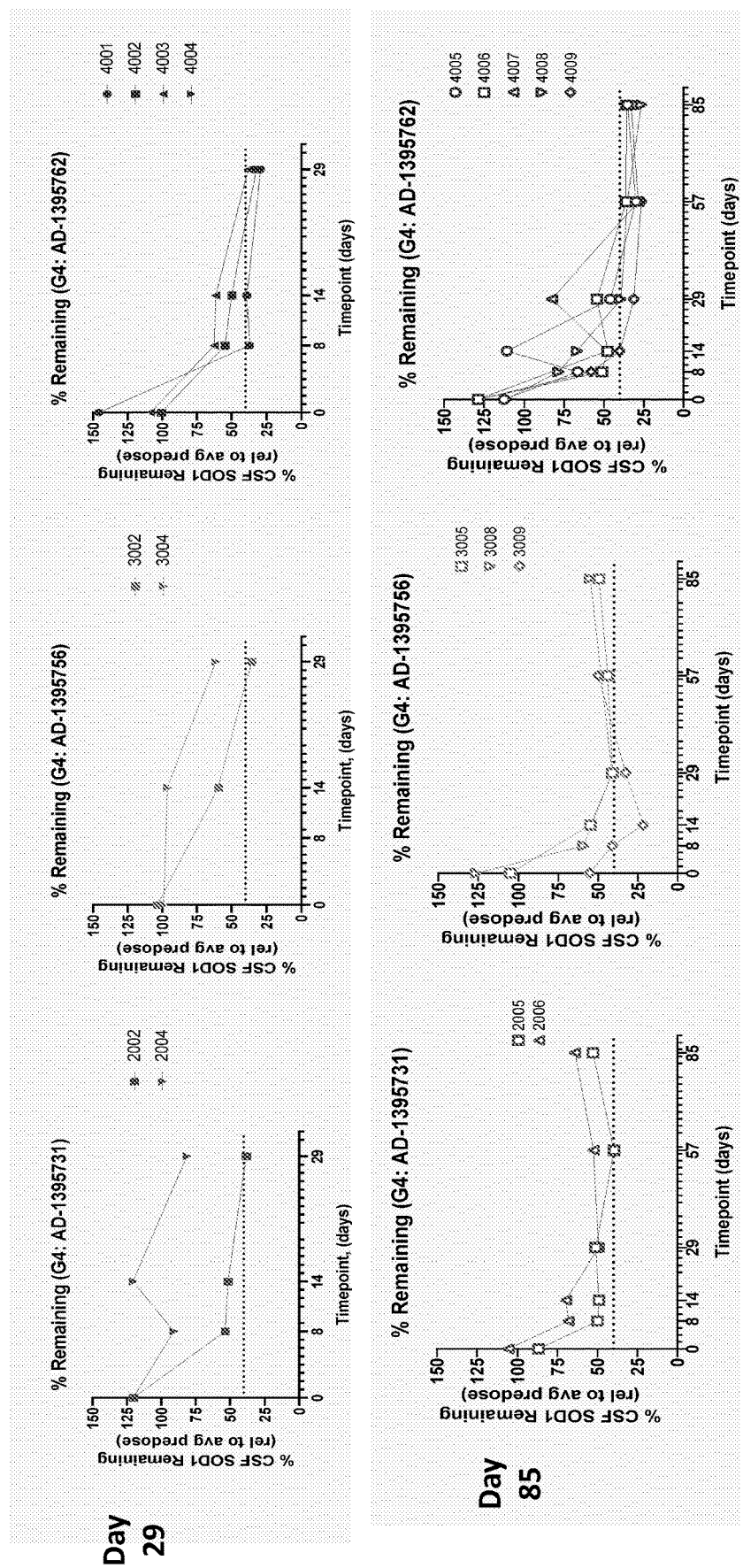
FIG. 9A are graphs depicting the level of SOD1 protein levels in CSF samples from individual non-human primates following intrathecal administration of a single 70 mg dose of the indicated duplexes at Days 0, 8, 14, 29, 57, and 85 post-dose.
Figure 9B:
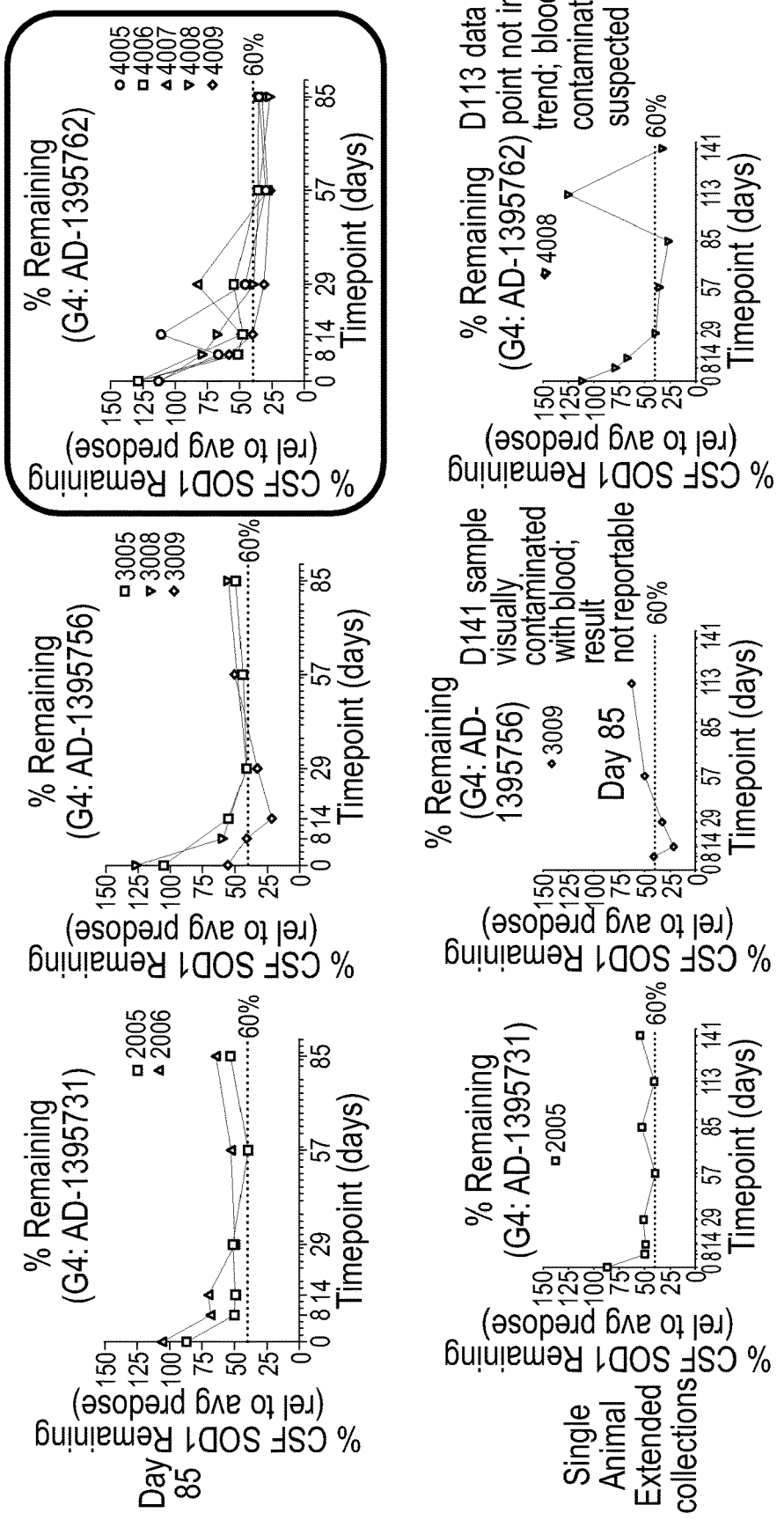
FIG. 9B are graphs depicting the level of SOD1 protein levels in CSF samples from individual non-human primates following intrathecal administration of a single 70 mg dose of the indicated duplexes out to Day 85 post-dose (top) and the level of SOD1 protein level in CSF samples from three individual non-human primates following intrathecal administration of a single 70 mg dose of the indicated duplexes in CSF samples from individual non-human primates following intrathecal administration of a single 70 mg dose of the indicated duplexes out to Day 85 post-dose extended out to Day 141 post-dose.
Figure 9C:
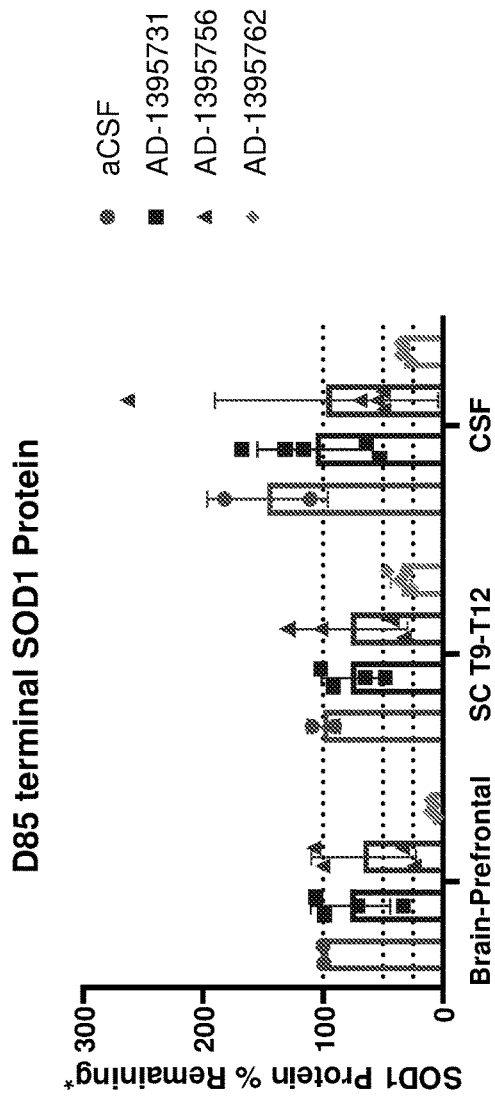
FIG. 9C is a graph depicting the level of SOD1 protein levels in prefrontal, thoracic spinal cord (T9-12) and CSF samples in non-human primates following intrathecal administration of a single 70 mg dose of the indicated duplexes at Day 85 post-dose.

In addition, as depicted in FIGS. 9A-9C, a single intrathecally administered 70 mg dose of AD-1395762, AD-1395756, or AD-1395731 resulted in the reduction of SOD1 protein in CSF samples by 60% out to Day 85 post-dose and, in three animals that were extended in the study, a single intrathecally administered 70 mg dose of AD-1395762, AD-1395756, or AD-1395731 resulted in the reduction of SOD1 protein in CSF samples by 60% out to Day 141 post-dose.

Figure 10:
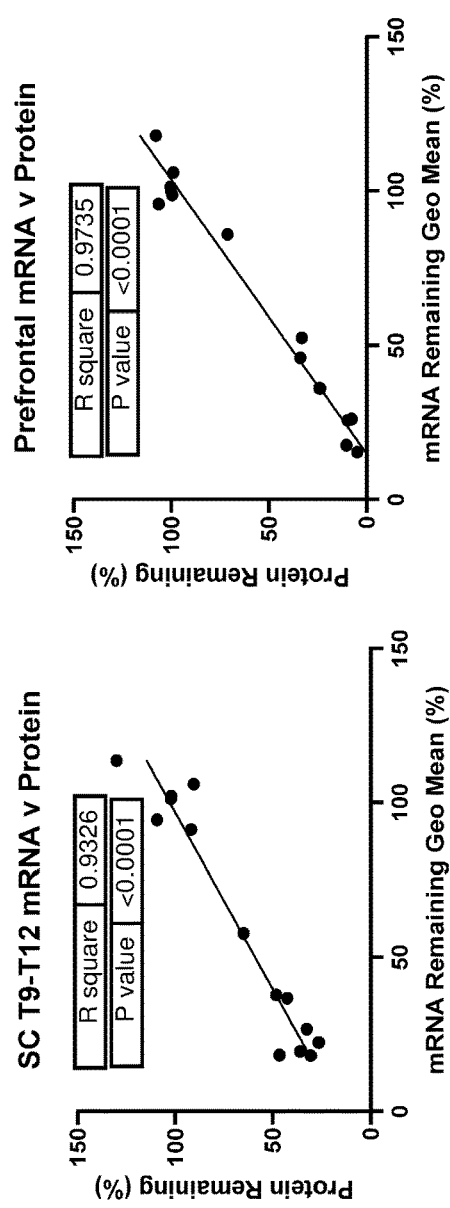
FIG. 10 are graphs depicting that the observed reductions in mRNA levels and protein levels in prefrontal cortex samples and thoracic spinal cord (T9-12) samples are highly and significantly correlated in NHP following intrathecal administration of a single 70 mg dose of the indicated duplexes.
Figure 13:
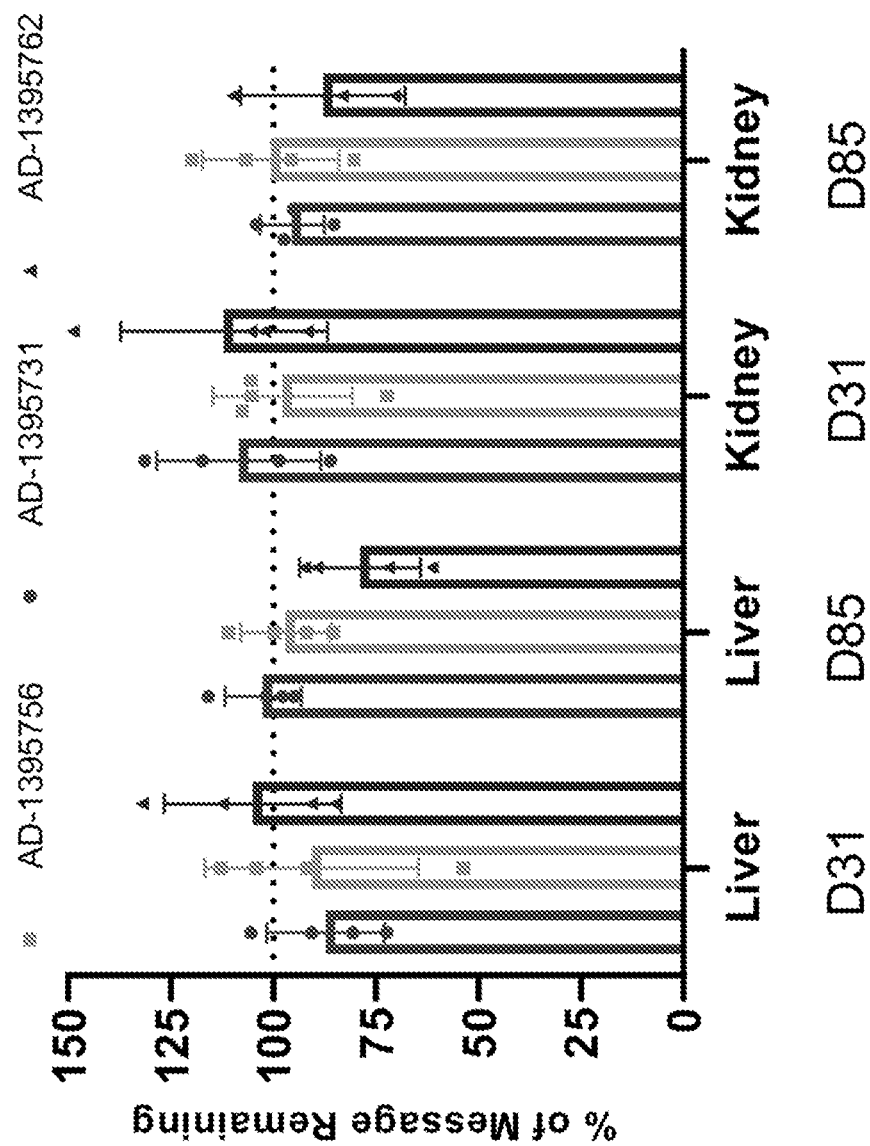
FIG. 13 is a graph showing a substantial absence of pharmacodynamic effect of the indicated dsRNA agents administered in the kidney and liver of NHP at Days 31 and 85 post-intrathecal administration.

As depicted in FIG. 10, the observed reductions in mRNA levels and protein levels in pre-frontal cortex samples and thoracic spinal cord samples are highly and significantly correlated in NHP. FIG. 13 shows that there was no substantial knockdown of SOD1 in kidney and liver at days 31 and 85 post-intrathecal administration of the three tested duplexes. Additionally, no significant differences were seen in the minimal effects at the kidney and liver among the duplexes.

Figure 11A:
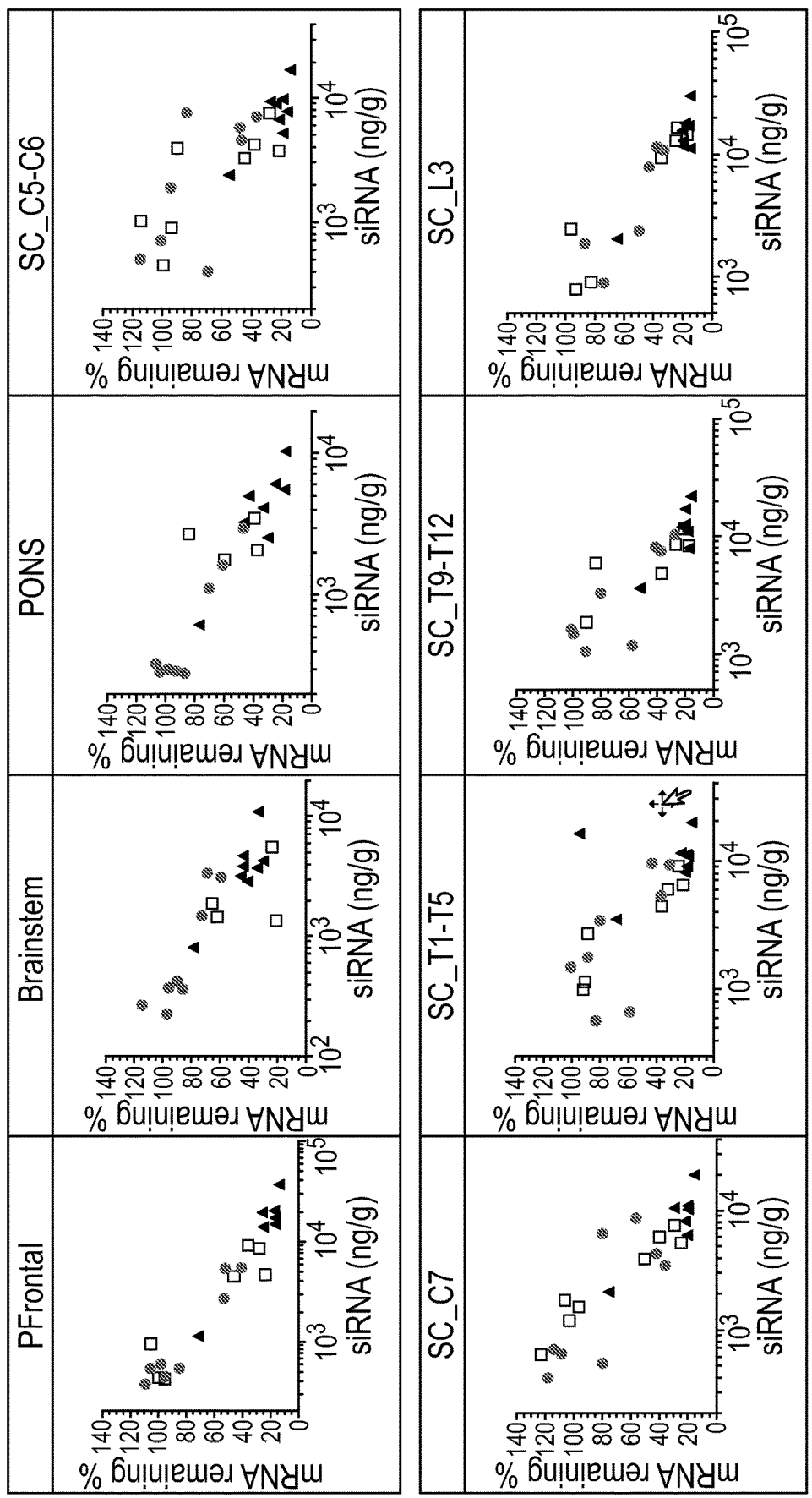
FIG. 11A are graphs depicting the mRNA remaining versus siRNA exposure in prefrontal, brainstem, pons, cervical spinal cord (SC_C5-C6), cervical spinal cord (SC_C7), thoracic spinal cord (SC_T1-T5), thoracic spinal cord (SC_T9-T12), and lumbar spinal cord (SC_L3) tissues following intrathecal administration of a single 70 mg dose of the indicated duplexes.
Figure 11B:
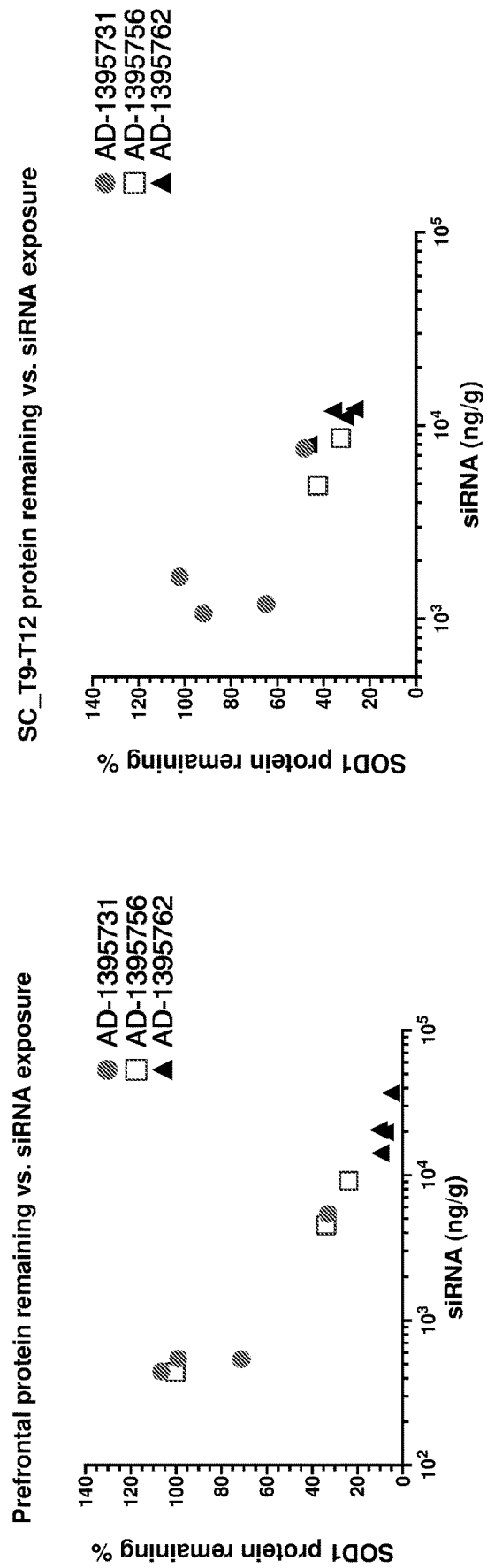
FIG. 11B are graphs depicting that there is a strong correlation between both mRNA and protein reduction to the amount of siRNA exposure in both prefrontal cortex and thoracic spinal cord (SC_T0-T12) samples following a single intrathecally administered 70 mg dose of the indicated duplexes.
Figures 12A, 12B:
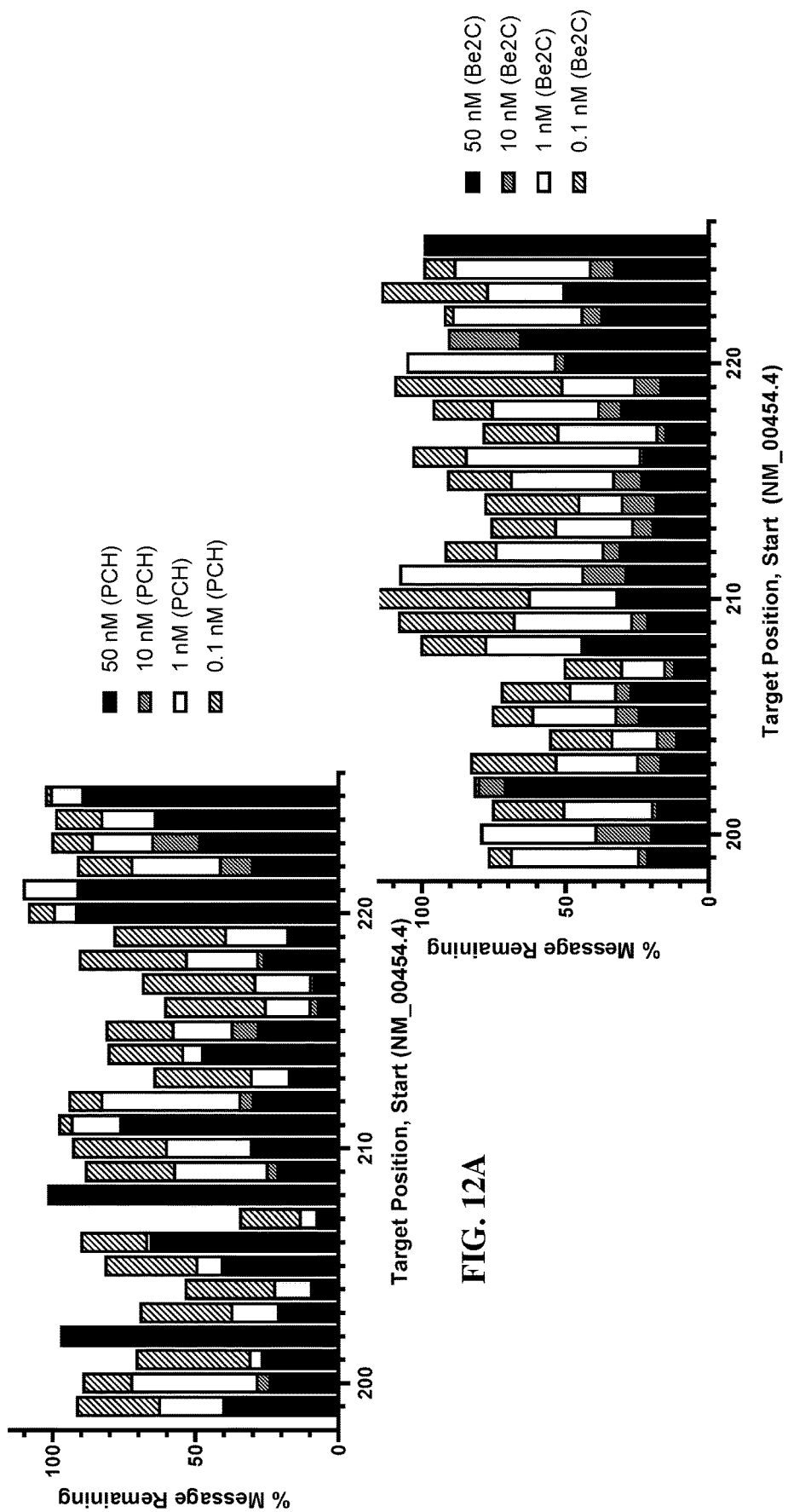
FIGS. 12A-12H are stacked bar graphs illustrating the in vitro SOD1 knockdown for each of the duplexes of Tables 14 and 15 in PCH or Be(2)C cells as mapped against NM_000454.4 for duplexes having target sequences starting at positions 199-225 (FIG. 12A, PCH.
Figures 12C, 12D:
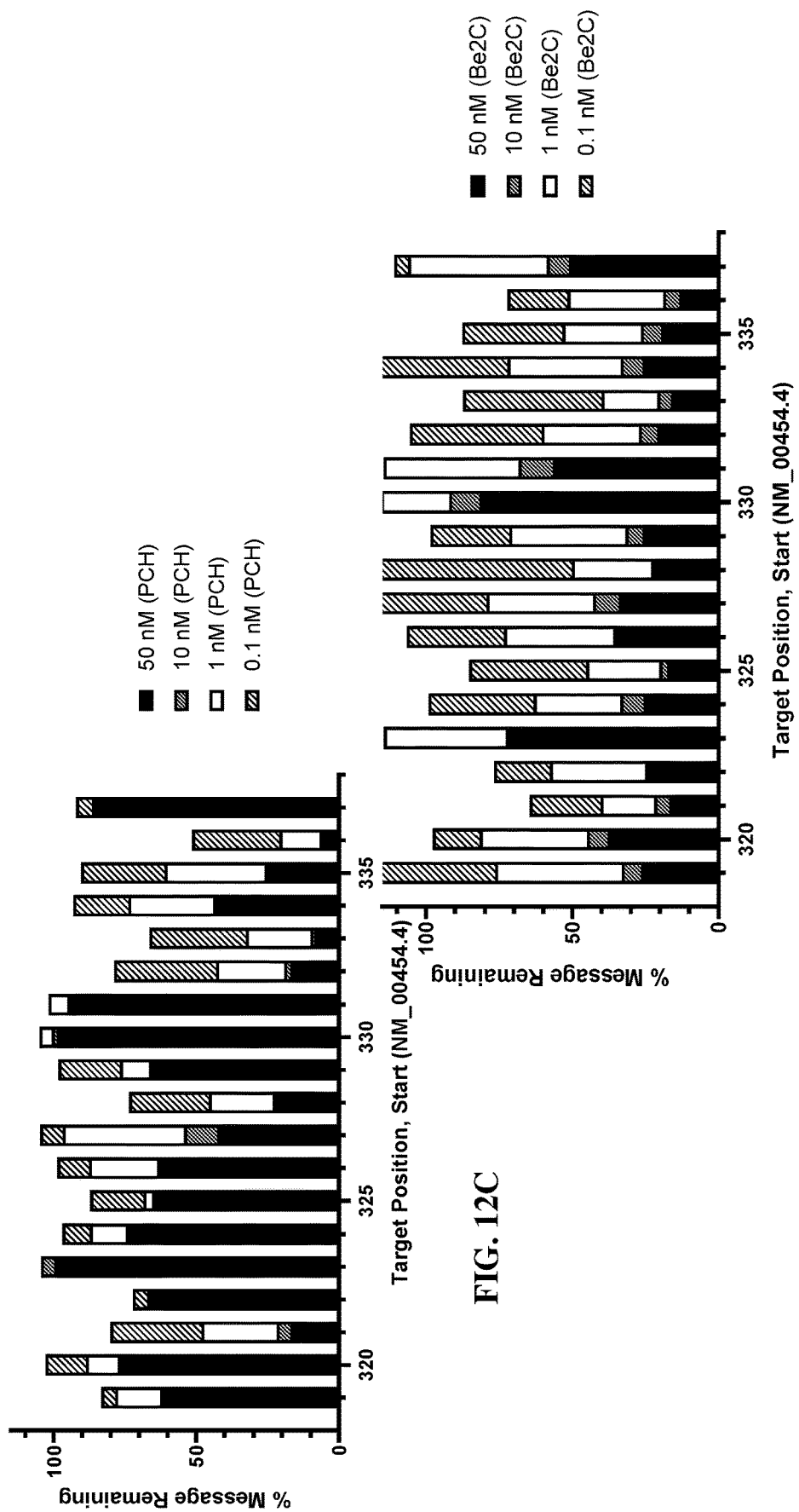
Figure 12E:
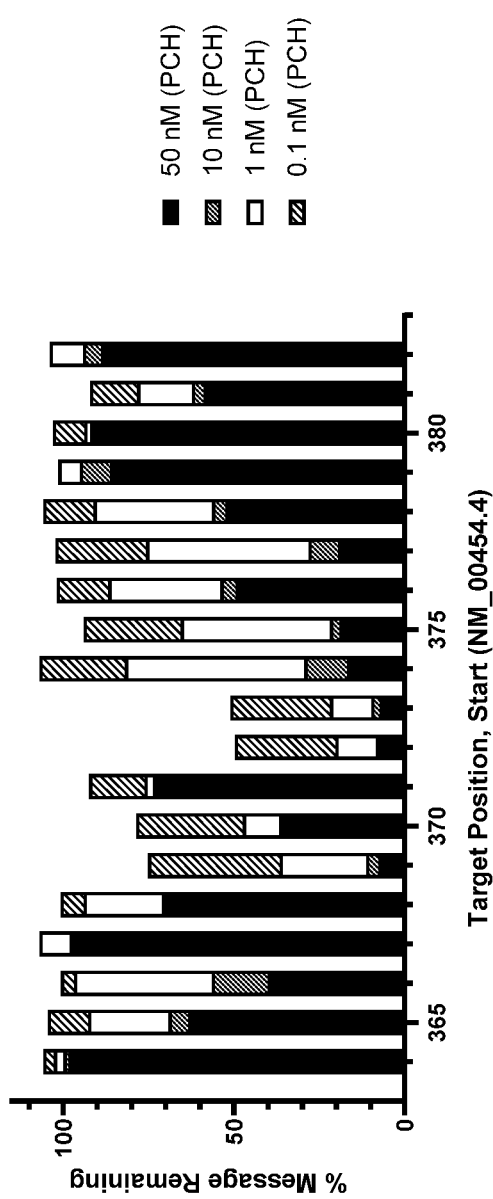
Figure 12F:
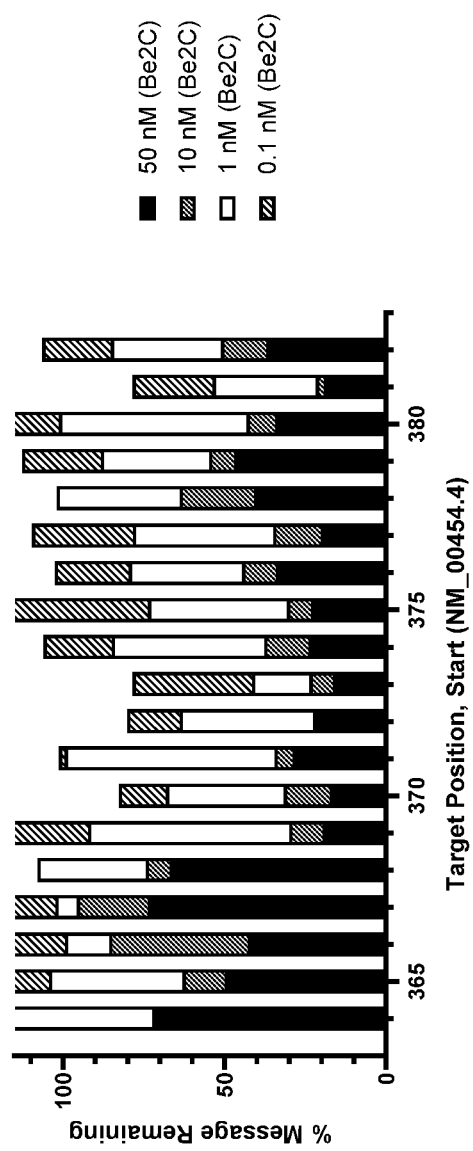
Figures 12G, 12H:
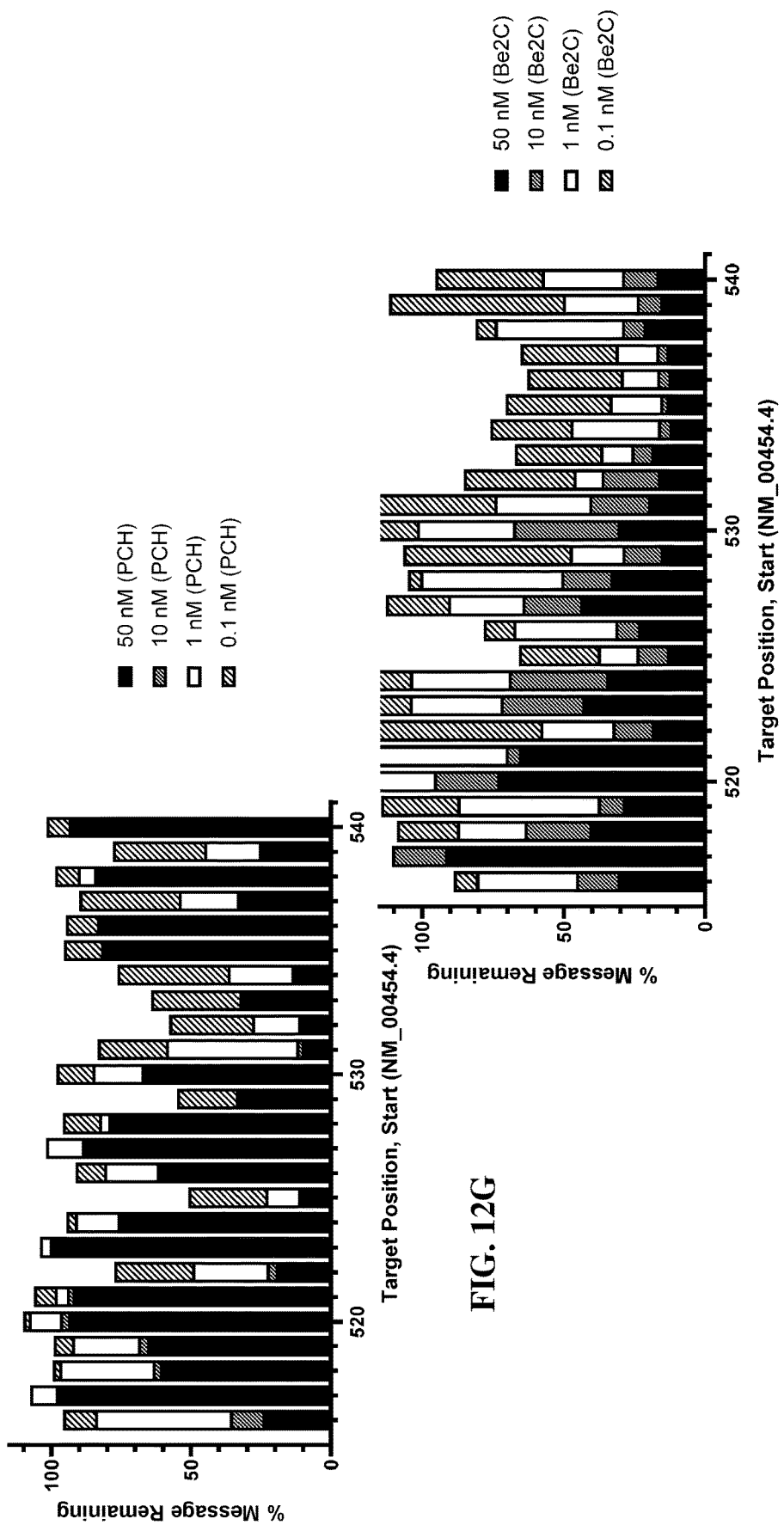

FIG. 11A depicts a set of graphs showing the mRNA remaining versus siRNA exposure in tissues that were examined following intrathecal administration of a single 70 mg dose of AD-1395762, AD-1395756, or AD-1395731. Analysis of the data demonstrated that there is a strong correlation between both mRNA and protein reduction to the amount of siRNA exposure in both prefrontal cortex and thoracic spinal cord samples following a single intrathecally administered 70 mg dose of AD-1395762, AD-1395756, or AD-1395731 (FIG. 11B).

We claim:

1. A double stranded ribonucleic acid (dsRNA) agent, or a pharmaceutically acceptable salt thereof, comprising a sense strand and an antisense strand forming a double stranded region, wherein the nucleotide sequence of the antisense strand differs by no more than three bases from the nucleotide sequence, (SEQ ID NO: 1369)
5'-VPusdCsugdGadTagagdGaUfuaaagugsa-3', wherein
VP is a 5'-vinyl phosphonate;
s is a phosphorothioate linkage;
a, g, and u are 2'-O-methyl (2'-OMe) A, G, and U;
dC, dG, and dT are 2'-deoxy C, G, and T; and
Uf is 2'-deoxy-2'-fluoro (2'-F) U.

2. The dsRNA agent, or pharmaceutically acceptable salt thereof, of claim 1, wherein the nucleotide sequence of the antisense strand differs by no more than two bases from the nucleotide sequence (SEQ ID NO: 1369)
5'-VPusdCsugdGadTagagdGaUfuaaagugsa-3'.

3. The dsRNA agent, or pharmaceutically acceptable salt thereof, of claim 1, wherein the nucleotide sequence of the antisense strand differs by no more than one base from the nucleotide sequence (SEQ ID NO: 1369)
5'-VPusdCsugdGadTagagdGaUfuaaagugsa-3'.

4. The dsRNA agent, or pharmaceutically acceptable salt thereof, of claim 1, wherein the nucleotide sequence of the antisense strand comprises the nucleotide sequence (SEQ ID NO: 1369)
5'-VPusdCsugdGadTagagdGaUfuaaagugsa-3'.

5. The dsRNA agent, or pharmaceutically acceptable salt thereof, of claim 1, wherein the antisense strand comprises the nucleotide sequence 5'-VPusdCsugdGadTagagdGaU-fuaaagugsasg-3' (SEQ ID NO:12).

6. The dsRNA agent, or pharmaceutically acceptable salt thereof, of claim 1, wherein the sense strand comprises the nucleotide sequence, (SEQ ID NO: 11)
5'-csascuu(Uhd)aaUfCfCfucuauccasgsa-3' wherein
(Uhd) is 2'-O-hexadecyl-uridine-3'-phosphate;
c is 2'-O-methyl (2'-OMe) C; and
Cf is 2'-deoxy-2'-fluoro (2'-F) C.

7. The dsRNA agent of claim 6, that is a sodium salt.

8. A double stranded ribonucleic acid (dsRNA) agent, or a pharmaceutically acceptable salt thereof, comprising a sense strand and an antisense strand forming a double stranded region, wherein the antisense strand comprises the nucleotide sequence, (SEQ ID NO: 12)
5'-VPusdCsugdGadTagagdGaUfuaaagugsasg-3'.

9. The dsRNA agent of claim 8, or a pharmaceutically acceptable salt thereof, wherein the sense strand comprises the nucleotide sequence, (SEQ ID NO: 11)
5'-csascuu(Uhd)aaUfCfCfucuauccasgsa-3' wherein
(Uhd) is 2'-O-hexadecyl-uridine-3'-phosphate;
c is 2'-O-methyl (2'-OMe) C; and
Cf is 2'-deoxy-2'-fluoro (2'-F) C.

10. The dsRNA agent of claim 9, that is a sodium salt.

11. A double stranded ribonucleic acid (dsRNA) agent, or a pharmaceutically acceptable salt thereof, comprising a sense strand and an antisense strand forming a double stranded region, wherein the sense strand consists of the nucleotide sequence, (SEQ ID NO: 11)
5'-csascuu(Uhd)aaUfCfCfucuauccasgsa-3' and the antisense strand consists of the nucleotide sequence, (SEQ ID NO: 12)
5'-VPusdCsugdGadTagagdGaUfuaaagugsasg-3', wherein
VP is a 5'-E-vinyl phosphonate;
s is a phosphorothioate linkage;
(Uhd) is 2'-O-hexadecyl-uridine-3'-phosphate;
a, c, g, and u are 2'-O-methyl (2'-OMe) A, C, G, and U;
dC, dG, and dT are 2'-deoxy C, G, and T; and
Cf and Uf are 2'-deoxy-2'-fluoro (2'-F) C and U.

12. The dsRNA agent of claim 11, that is a sodium salt.

13. A pharmaceutical composition comprising the dsRNA agent of claim 11 and a pharmaceutically acceptable diluent.

14. The pharmaceutical composition of claim 13, that is a sterile aqueous solution.

15. The pharmaceutical composition of claim 14, comprising a buffer.

16. The pharmaceutical composition of claim 14, wherein the diluent is saline or water.

17. A pharmaceutical composition comprising the dsRNA agent of claim 1 and a pharmaceutically acceptable diluent.

18. A pharmaceutical composition comprising the dsRNA agent of claim 8 and a pharmaceutically acceptable diluent.

19. A method of inhibiting expression of a SOD1 gene in a cell, the method comprising:
(a) contacting the cell with the dsRNA agent of claim 1; and
(b) maintaining the cell produced in step (a) for a time sufficient to obtain degradation of the mRNA transcript of the SOD1 gene, thereby inhibiting expression of the SOD1 gene in the cell.

20. A method of inhibiting expression of a SOD1 gene in a cell, the method comprising:
(a) contacting the cell with the dsRNA agent of claim 8; and
(b) maintaining the cell produced in step (a) for a time sufficient to obtain degradation of the mRNA transcript of the SOD1 gene, thereby inhibiting expression of the SOD1 gene in the cell.

21. A method of inhibiting expression of a SOD1 gene in a cell, the method comprising:
(a) contacting the cell with the dsRNA agent of claim 11; and
(b) maintaining the cell produced in step (a) for a time sufficient to obtain degradation of the mRNA transcript of the SOD1 gene, thereby inhibiting expression of the SOD1 gene in the cell.

22. A method for treating a SOD1-associated neurodegenerative disease, comprising administering to a patient in need thereof, a pharmaceutically effective amount of a dsRNA agent of claim 1.

23. The method of claim 22, wherein the SOD1-associated neurodegenerative disease is selected from the group consisting of Amyotrophic Lateral Sclerosis (ALS), Alzheimer's disease (AD), Parkinson's disease (PD), and Down's syndrome (DS).

24. The method of claim 23, wherein the SOD1-associated neurodegenerative disease is inherited familial amyotrophic lateral sclerosis (fALS).

25. A method for treating a SOD1-associated neurodegenerative disease, comprising administering to a patient in need thereof, a pharmaceutically effective amount of a dsRNA agent of claim 8.

26. The method of claim 25, wherein the SOD1-associated neurodegenerative disease is selected from the group consisting of Amyotrophic Lateral Sclerosis (ALS), Alzheimer's disease (AD), Parkinson's disease (PD), and Down's syndrome (DS).

27. The method of claim 26, wherein the SOD1-associated neurodegenerative disease is inherited familial amyotrophic lateral sclerosis (fALS).

28. A method for treating a SOD1-associated neurodegenerative disease, comprising administering to a patient in need thereof, a pharmaceutically effective amount of a dsRNA agent of claim 11.

29. The method of claim 28, wherein the SOD1-associated neurodegenerative disease is selected from the group consisting of Amyotrophic Lateral Sclerosis (ALS), Alzheimer's disease (AD), Parkinson's disease (PD), and Down's syndrome (DS).

30. The method of claim 29, wherein the SOD1-associated neurodegenerative disease is inherited familial amyotrophic lateral sclerosis (fALS).

\* \* \* \* \*

SEQUENCE LISTING

```
<160> NUMBER OF SEQ ID NOS: 1378

<210> SEQ ID NO 1
<211> LENGTH: 981
<212> TYPE: DNA
<213> ORGANISM: Homo sapiens

<400> SEQUENCE: 1
gtttggggcc agagtgggcg aggcgcggag gtctggccta taaagtagtc gcggagacgg      60
ggtgctggtt tgcgtcgtag tctcctgcag cgtctggggt ttccgttgca gtcctcggaa     120
ccaggacctc ggcgtggcct agcgagttat ggcgacgaag gccgtgtgcg tgctgaaggg     180
cgacggccca gtgcagggca tcatcaattt cgagcagaag gaaagtaatg gaccagtgaa     240
ggtgtgggga agcattaaag gactgactga aggcctgcat ggattccatg ttcatgagtt     300
tggagataat acagcaggct gtaccagtgc aggtcctcac tttaatcctc tatccagaaa     360
acacggtggg ccaaaggatg aagagaggca tgttggagac ttgggcaatg tgactgctga     420
caaagatggt gtggccgatg tgtctattga agattctgtg atctcactct caggagacca     480
ttgcatcatt ggccgcacac tggtggtcca tgaaaaagca gatgacttgg gcaaaggtgg     540
aaatgaagaa agtacaaaga caggaaacgc tggaagtcgt ttggcttgtg gtgtaattgg     600
gatcgcccaa taaacattcc cttggatgta gtctgaggcc ccttaactca tctgttatcc     660
tgctagctgt agaaatgtat cctgataaac attaaacact gtaatcttaa aagtgtaatt     720
gtgtgacttt ttcagagttg ctttaaagta cctgtagtga gaaactgatt tatgatcact     780
tggaagattt gtatagtttt ataaaactca gttaaaatgt ctgtttcaat gacctgtatt     840
ttgccagact taaatcacag atgggtatta aacttgtcag aatttctttg tcattcaagc     900
ctgtgaataa aaaccctgta tggcacttat tatgaggcta ttaaaagaat ccaaattcaa     960
```

```
actaaaaaaa aaaaaaaaaa a                                           981
```

<210> SEQ ID NO 2
<211> LENGTH: 981
<212> TYPE: DNA
<213> ORGANISM: Homo sapiens

<400> SEQUENCE: 2

```
tttttttttt tttttttag tttgaatttg gattctttta atagcctcat aataagtgcc    60
atacagggtt tttattcaca ggcttgaatg acaaagaaat tctgacaagt ttaataccca   120
tctgtgattt aagtctggca aaatacaggt cattgaaaca gacattttaa ctgagtttta   180
taaaactata caaatcttcc aagtgatcat aaatcagttt ctcactacag gtactttaaa   240
gcaactctga aaagtcaca caattacact tttaagatta cagtgtttaa tgtttatcag    300
gatacatttc tacagctagc aggataacag atgagttaag gggcctcaga ctacatccaa   360
gggaatgttt attgggcgat cccaattaca ccacaagcca aacgacttcc agcgtttcct   420
gtctttgtac tttcttcatt tccaccttg cccaagtcat ctgcttttc atggaccacc    480
agtgtgcggc caatgatgca atggtctcct gagagtgaga tcacagaatc ttcaatagac   540
acatcggcca caccatcttt gtcagcagtc acattgccca gtctccaac atgcctctct   600
tcatcctttg gcccaccgtg ttttctggat agaggattaa agtgaggacc tgcactggta   660
cagcctgctg tattatctcc aaactcatga acatggaatc catgcaggcc ttcagtcagt   720
cctttaatgc ttccccacac cttcactggt ccattacttt ccttctgctc gaaattgatg   780
atgccctgca ctgggccgtc gcccttcagc acgcacacgg ccttcgtcgc cataactcgc   840
taggccacgc cgaggtcctg gttccgagga ctgcaacgga accccagac gctgcaggag    900
actacgacgc aaaccagcac cccgtctccg cgactacttt ataggccaga cctccgcgcc   960
tcgcccactc tggccccaaa c                                           981
```

<210> SEQ ID NO 3
<211> LENGTH: 661
<212> TYPE: DNA
<213> ORGANISM: Mus musculus

<400> SEQUENCE: 3

```
gccagggcct cgttttttg cgcggtcctt tcctgcggcg ccttccgtcc gtcggcttct     60
cgtcttgctc tctctggtcc ctccggagga ggccgccgcg cgtctcccgg ggaagcatgg   120
cgatgaaagc ggtgtgcgtg ctgaagggcg acggtccggt gcagggaacc atccacttcg   180
agcagaaggc aagcggtgaa ccagttgtgt tgtcaggaca aattacagga ttaactgaag   240
gccagcatgg gttccacgtc catcagtatg gggacaatac acaaggctgt accagtgcag   300
gacctcattt taatcctcac tctaagaaac atggtggccc ggcggatgaa gagaggcatg   360
ttggagacct gggcaatgtg actgctggaa aggacggtgt ggccaatgtg tccattgaag   420
atcgtgtgat ctcactctca ggagagcatt ccatcattgg ccgtacaatg gtggtccatg   480
agaaacaaga tgacttgggc aaaggtggaa atgaagaaag tacaaagact ggaaatgctg   540
ggagccgctt ggcctgtgga gtgattggga ttgcgcagta acattccct gtgtggtctg    600
agtctcagac tcatctgcta ccctcaaacc attaaactgt aatctgaaaa aaaaaaaaa    660
a                                                                 661
```

<210> SEQ ID NO 4
<211> LENGTH: 661

```
<212> TYPE: DNA
<213> ORGANISM: Mus musculus

<400> SEQUENCE: 4
tttttttttt tttttcagat tacagtttaa tggtttgagg gtagcagatg agtctgagac    60
tcagaccaca cagggaatgt ttactgcgca atcccaatca ctccacaggc caagcggctc   120
ccagcatttc cagtctttgt actttcttca tttccacctt tgcccaagtc atcttgtttc   180
tcatggacca ccattgtacg gccaatgatg gaatgctctc ctgagagtga gatcacacga   240
tcttcaatgg acacattggc cacaccgtcc tttccagcag tcacattgcc caggtctcca   300
acatgcctct cttcatccgc cgggccacca tgtttcttag agtgaggatt aaaatgaggt   360
cctgcactgg tacagccttg tgtattgtcc ccatactgat ggacgtggaa cccatgctgg   420
ccttcagtta atcctgtaat ttgtcctgac aacacaactg gttcaccgct tgccttctgc   480
tcgaagtgga tggttccctg caccggaccg tcgcccttca gcacgcacac cgctttcatc   540
gccatgcttc cccgggagac gcgcggcggc ctcctccgga gggaccagag agagcaagac   600
gagaagccga cggacggaag gcgccgcagg aaaggaccgc gcaaaaaaac gaggccctgg   660
c                                                                  661

<210> SEQ ID NO 5
<211> LENGTH: 465
<212> TYPE: DNA
<213> ORGANISM: Macaca fascicularis

<400> SEQUENCE: 5
atggcgatga aggccgtgtg cgtgttgaag ggcgacagcc cagtgcaggg caccatcaat    60
ttcgagcaga aggaaagtaa tggaccagtg aaggtgtggg gaagcattac aggattgact   120
gaaggcctgc atggattcca tgttcatcag tttggagata atacacaagg ctgtaccagt   180
gcaggtcctc actttaatcc tctatccaga caacacggtg ggccaaagga tgaagagagg   240
catgttggag acctgggcaa tgtgactgct ggcaaagatg gtgtggccaa ggtgtctttc   300
gaagattctg tgatctcgct ctcaggagac cattccatca ttggccgcac attggtggtc   360
catgaaaaag cagatgactt gggcaaaggt ggaaatgaag aaagtaaaaa gacaggaaac   420
gctggaggtc gtctggcttg tggtgtaatt gggatcgccc aataa                   465

<210> SEQ ID NO 6
<211> LENGTH: 465
<212> TYPE: DNA
<213> ORGANISM: Macaca fascicularis

<400> SEQUENCE: 6
ttattgggcg atcccaatta caccacaagc cagacgacct ccagcgtttc ctgtcttttt    60
actttcttca tttccacctt tgcccaagtc atctgctttt tcatggacca ccaatgtgcg   120
gccaatgatg gaatggtctc ctgagagcga gatcacagaa tcttcgaaag acaccttggc   180
cacaccatct ttgccagcag tcacattgcc caggtctcca acatgcctct cttcatcctt   240
tggcccaccg tgttgtctgg atagaggatt aaagtgagga cctgcactgg tacagccttg   300
tgtattatct ccaaactgat gaacatggaa tccatgcagg ccttcagtca atcctgtaat   360
gcttccccac accttcactg gtccattact ttccttctgc tcgaaattga tggtgccctg   420
cactgggctg tcgcccttca acacgcacac ggccttcatc gccat                   465

<210> SEQ ID NO 7
```

```
<211> LENGTH: 474
<212> TYPE: DNA
<213> ORGANISM: Canis lupus familiaris
<220> FEATURE:
<221> NAME/KEY: modified_base
<222> LOCATION: (165)..(165)
<223> OTHER INFORMATION: a, c, t, g, unknown or other

<400> SEQUENCE: 7
cgagtcatgg agatgaaggc cgtgtgcgtg ttgaagggcc agggcccggt ggagggcacc      60
atccacttcg tgcagaaggg aagtgggcct gttgtggtat caggaaccat tacagggctg    120
actgaaggcg agcatggatt ccacgtccat cagtttgaag ataanacaca aggctgtact    180
agtgcaggtc ctcactttaa tcctctgtcc aaaaaacatg gtgggccaaa agatcaagag    240
aggcatgttg gagacctggg caatgtgact gctggcaagg atggcgtggc cattgtgtcc    300
atagaagatt ctctgattgc actctcagga gactattcca tcattggccg caccatggtg    360
gtccacgaga aacgagatga cttgggcaaa ggtgacaatg aagaaagtac acagacagga    420
aacgccggga gtcgtttggc ttgtggtgtc attgggatcg cccaataaac attc           474

<210> SEQ ID NO 8
<211> LENGTH: 474
<212> TYPE: DNA
<213> ORGANISM: Canis lupus familiaris
<220> FEATURE:
<221> NAME/KEY: modified_base
<222> LOCATION: (310)..(310)
<223> OTHER INFORMATION: a, c, t, g, unknown or other

<400> SEQUENCE: 8
gaatgtttat tgggcgatcc caatgacacc acaagccaaa cgactcccgg cgtttcctgt      60
ctgtgtactt tcttcattgt caccttcgcc caagtcatct cgtttctcgt ggaccaccat    120
ggtgcggcca atgatggaat agtctcctga gagtgcaatc agagaatctt ctatggacac    180
aatggccacg ccatccttgc cagcagtcac attgcccagg tctccaacat gcctctcttg    240
atcttttggc ccaccatgtt ttttggacag aggattaaag tgaggacctg cactagtaca    300
gccttgtgtn ttatcttcaa actgatggac gtggaatcca tgctcgcctt cagtcagccc    360
tgtaatggtt cctgatacca caacaggccc acttcccttc tgcacgaagt ggatggtgcc    420
ctccaccggg ccctggccct tcaacacgca cacggccttc atctccatga ctcg           474

<210> SEQ ID NO 9
<211> LENGTH: 650
<212> TYPE: DNA
<213> ORGANISM: Rattus norvegicus

<400> SEQUENCE: 9
gttttgcacc ttcgtttcct gcggcggctt ctgtcgtctc cttgcttttt gctctcccag      60
gttccgaggc cgccgcgcgt ctcccgggga agcatggcga tgaaggccgt gtgcgtgctg    120
aagggcgacg gtccggtgca gggcgtcatt cacttcgagc agaaggcaag cggtgaacca    180
gttgtggtgt caggacagat tacaggatta actgaaggcg agcatggggtt ccatgtccat    240
caatatgggg acaatacaca aggctgtacc actgcaggac ctcattttaa tcctcactct    300
aagaaacatg gcggtccagc ggatgaagag aggcatgttg gagacctggg caatgtggct    360
gctgaaaagg acggtgtggc caatgtgtcc attgaagatc gtgtgatctc actctcagga    420
gagcattcca tcattggccg tactatggtg gtccacgaga acaagatga cttgggcaaa    480
ggtggaaatg aagaaagtac aaagactgga aatgctggaa gccgcttggc ttgtggtgtg    540
```

```
attgggattg cccaataaac attccctatg tggtctgagt ctcagactca tctgctgtcc    600
tgctaaactg tagaaaaaaa ccaaaccatt aaactgtaat cttaacagtt              650
```

<210> SEQ ID NO 10
<211> LENGTH: 650
<212> TYPE: DNA
<213> ORGANISM: Rattus norvegicus

<400> SEQUENCE: 10

```
aactgttaag attacagttt aatggtttgg ttttttttcta cagtttagca ggacagcaga    60
tgagtctgag actcagacca catagggaat gtttattggg caatcccaat cacaccacaa   120
gccaagcggc ttccagcatt tccagtcttt gtactttctt catttccacc tttgcccaag   180
tcatcttgtt tctcgtggac caccatagta cggccaatga tggaatgctc tcctgagagt   240
gagatcacac gatcttcaat ggacacattg gccacaccgt cctttccagc agccacattg   300
cccaggtctc caacatgcct ctcttcatcc gctggaccgc catgtttctt agagtgagga   360
ttaaaatgag gtcctgcagt ggtacagcct tgtgtattgt ccccatattg atggacatgg   420
aacccatgct cgccttcagt taatcctgta atctgtcctg acaccacaac tggttcaccg   480
cttgccttct gctcgaagtg aatgacgccc tgcaccggac cgtcgccctt cagcacgcac   540
acggccttca tcgccatgct tccccgggag acgcgcggcg gcctcggaac ctgggagagc   600
aaaaagcaag gagacgacag aagccgccgc aggaaacgaa ggtgcaaaac              650
```

<210> SEQ ID NO 11
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11

```
cacuuuaauc cucuauccag a                                              21
```

<210> SEQ ID NO 12
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12

```
ucuggataga ggauuaaagu gag                                            23
```

<210> SEQ ID NO 13
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
cagguccuca cuuuaauccu a								21

<210> SEQ ID NO 14
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
uaggautaaa gtgaggaccu gcg							23

<210> SEQ ID NO 15
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
uucgagcaga aggaaaguaa a								21

<210> SEQ ID NO 16
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
uuuacutucc uucugcucga aau							23

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
gaaaguaaug gaccagugaa a								21

<210> SEQ ID NO 18
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 18
uuucactggu ccauuacuuu ccu                                          23

<210> SEQ ID NO 19
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
aggaugaaga gaggcauguu a                                            21

<210> SEQ ID NO 20
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
uaacaugccu cucuucaucc uuu                                          23

<210> SEQ ID NO 21
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
aaggaaagua auggaccagu a                                            21

<210> SEQ ID NO 22
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 22
uacuggtcca utacuuuccu ucu                                          23

<210> SEQ ID NO 23
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
aucaauuucg agcagaagga a                                            21
```

```
<210> SEQ ID NO 24
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 24 uuccucugc ucgaaauuga ugg                                             23

<210> SEQ ID NO 25
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
ccucacuuua auccucuauc a                                              21

<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 26
ugauagagga utaaagugag gac                                            23

<210> SEQ ID NO 27
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
aaggaugaag agaggcaugu a                                              21

<210> SEQ ID NO 28
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 28
```
uacaugccuc ucuucauccu uug                                          23

<210> SEQ ID NO 29
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
aauuucgagc agaaggaaag a                                            21

<210> SEQ ID NO 30
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 30
ucuuuccuuc ugcucgaaau ugg                                          23

<210> SEQ ID NO 31
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      RFGF peptide sequence"

<400> SEQUENCE: 31

Ala Ala Val Ala Leu Leu Pro Ala Val Leu Leu Ala Leu Leu Ala Pro
1               5                   10                  15

<210> SEQ ID NO 32
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue peptide sequence"

<400> SEQUENCE: 32

Ala Ala Leu Leu Pro Val Leu Leu Ala Ala Pro
1               5                   10

<210> SEQ ID NO 33
<211> LENGTH: 13
<212> TYPE: PRT
<213> ORGANISM: Human immunodeficiency virus 1

<400> SEQUENCE: 33

Gly Arg Lys Lys Arg Arg Gln Arg Arg Pro Pro Gln
1               5                   10

<210> SEQ ID NO 34
<211> LENGTH: 16

```
<212> TYPE: PRT
<213> ORGANISM: Drosophila sp.

<400> SEQUENCE: 34

Arg Gln Ile Lys Ile Trp Phe Gln Asn Arg Arg Met Lys Trp Lys Lys
1               5                   10                  15

<210> SEQ ID NO 35
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
aucaguuugg agauaauaca u                                           21

<210> SEQ ID NO 36
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
ucuuucgaag auucugugau u                                           21

<210> SEQ ID NO 37
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
aggugucuuu cgaagauucu u                                           21

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
cuuuaauccu cuauccagac a                                           21

<210> SEQ ID NO 39
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
ugcagguccu cacuuuaauc u                                           21
```

```
<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gucuuucgaa gauucuguga u                                            21

<210> SEQ ID NO 41
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
cagguccuca cuuuaauccu u                                            21

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ccucacuuua auccucuauc u                                            21

<210> SEQ ID NO 43
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
accagugcag guccucacuu u                                            21

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
agcagaugac uugggcaaag u                                            21

<210> SEQ ID NO 45
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 45
gaaaaagcag augacuuggg u                                              21

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
uucgagcaga aggaaaguaa u                                              21

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
auuucgagca gaaggaaagu a                                              21

<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
caguuuggag auaauacaca a                                              21

<210> SEQ ID NO 49
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
uucaucaguu uggagauaau a                                              21

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
cucacuuuaa uccucuaucc a                                              21

<210> SEQ ID NO 51
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 51
uucgaagauu cugugaucuc u                                              21

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
aagcagauga cuugggcaaa u                                              21

<210> SEQ ID NO 53
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
gguccucacu uuaauccucu a                                              21

<210> SEQ ID NO 54
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
cagugcaggu ccucacuuua a                                              21

<210> SEQ ID NO 55
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
cauuacagga uugacugaag u                                              21

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
aaaguaaaaa gacaggaaac u                                              21
```

```
<210> SEQ ID NO 57
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
aguuuggaga uaauacacaa u                                              21

<210> SEQ ID NO 58
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
cgaagauucu gugaucucgc u                                              21

<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
gcauuacagg auugacugaa u                                              21

<210> SEQ ID NO 60
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ucaucaguuu ggagauaaua u                                              21

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
acuuuaaucc ucuauccaga u                                              21

<210> SEQ ID NO 62
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 62
guaaaaagac aggaaacgcu u                                              21

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
aucaauuucg agcagaagga a                                              21

<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
uccucacuuu aauccucuau u                                              21

<210> SEQ ID NO 65
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
guccucacuu uaauccucua u                                              21

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
caucaguuug gagauaauac a                                              21

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
aaguaaaaag acaggaaacg u                                              21

<210> SEQ ID NO 68
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
agcauuacag gauugacuga a                                              21

<210> SEQ ID NO 69
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
auucugugau cucgcucuca u                                              21

<210> SEQ ID NO 70
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
guucaucagu uuggagauaa u                                              21

<210> SEQ ID NO 71
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
cacuuuaauc cucuauccag a                                              21

<210> SEQ ID NO 72
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
gugucuuucg aagauucugu u                                              21

<210> SEQ ID NO 73
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
cgagcagaag gaaaguaaug u                                              21
```

```
<210> SEQ ID NO 74
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
uccauguuca ucaguuugga u                                               21

<210> SEQ ID NO 75
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
ccagugcagg uccucacuuu a                                               21

<210> SEQ ID NO 76
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
agguccucac uuuaauccuc u                                               21

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
gccaaggugu cuuucgaaga u                                               21

<210> SEQ ID NO 78
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
aguaaaaaga caggaaacgc u                                               21

<210> SEQ ID NO 79
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"

<400> SEQUENCE: 79
auacacaagg cguaccagu u                                       21

<210> SEQ ID NO 80
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
aauccucuau ccagacaaca u                                      21

<210> SEQ ID NO 81
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
ucgagcagaa ggaaaguaau u                                      21

<210> SEQ ID NO 82
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
ucacuuuaau ccucuaucca u                                      21

<210> SEQ ID NO 83
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
cagaaggaaa guaauggacc a                                      21

<210> SEQ ID NO 84
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
caauuucgag cagaaggaaa u                                      21

<210> SEQ ID NO 85
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
aaggaaagua auggaccagu u                                              21

<210> SEQ ID NO 86
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
agugcagguc cucacuuuaa u                                              21

<210> SEQ ID NO 87
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
gauuccaugu ucaucaguuu g                                              21

<210> SEQ ID NO 88
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
cuuucgaaga uucugugauc u                                              21

<210> SEQ ID NO 89
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
uuucgagcag aaggaaagua a                                              21

<210> SEQ ID NO 90
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
```
uaauccucua uccagacaac a                                              21

<210> SEQ ID NO 91
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
uguucaucag uuuggagaua a                                              21

<210> SEQ ID NO 92
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
gugcaggucc ucacuuuaau u                                              21

<210> SEQ ID NO 93
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
uaauggacca gugaaggugu u                                              21

<210> SEQ ID NO 94
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
uuaauccucu auccagacaa u                                              21

<210> SEQ ID NO 95
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
ucaggagacc auccaucau u                                               21

<210> SEQ ID NO 96
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
caccaucaau uucgagcaga a                                              21

<210> SEQ ID NO 97
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gcagguccuc acuuuaaucc u                                              21

<210> SEQ ID NO 98
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
uuucgaagau ucugugaucu u                                              21

<210> SEQ ID NO 99
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
ugcauggauu ccauguucau u                                              21

<210> SEQ ID NO 100
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
auccucuauc cagacaacac u                                              21

<210> SEQ ID NO 101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
agauucugug aucucgcucu u                                              21

<210> SEQ ID NO 102

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
gaagagaggc auguuggaga u                                          21

<210> SEQ ID NO 103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
uugggcaaag guggaaauga a                                          21

<210> SEQ ID NO 104
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
ucaauuucga gcagaaggaa a                                          21

<210> SEQ ID NO 105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
caugaaaaag cagaugacuu u                                          21

<210> SEQ ID NO 106
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
uggauuccau guucaucagu u                                          21

<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
```
gagaggcaug uuggagaccu u                                              21

<210> SEQ ID NO 108
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
gaagauucug ugaucucgcu u                                              21

<210> SEQ ID NO 109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
ucaguuugga gauaauacac a                                              21

<210> SEQ ID NO 110
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
caaggugucu uucgaagauu u                                              21

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
auguucauca guuuggagau a                                              21

<210> SEQ ID NO 112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
accaucaauu ucgagcagaa u                                              21

<210> SEQ ID NO 113
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 113
augugacugc uggcaaagau u                                             21

<210> SEQ ID NO 114
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gguggaaaug aagaaaguaa a                                             21

<210> SEQ ID NO 115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
ggauuccaug uucaucaguu u                                             21

<210> SEQ ID NO 116
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
aaugugacug cuggcaaaga u                                             21

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
guccaugaaa aagcagauga u                                             21

<210> SEQ ID NO 118
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
auguauuauc uccaaacuga uga                                           23
```

```
<210> SEQ ID NO 119
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
aaucacagaa ucuucgaaag aca                                              23

<210> SEQ ID NO 120
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
aagaaucuuc gaaagacacc uug                                              23

<210> SEQ ID NO 121
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
ugucuggaua gaggauuaaa gug                                              23

<210> SEQ ID NO 122
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
agauuaaagu gaggaccugc acu                                              23

<210> SEQ ID NO 123
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
aucacagaau cuucgaaaga cac                                              23

<210> SEQ ID NO 124
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 124
aaggauuaaa gugaggaccu gca                                          23

<210> SEQ ID NO 125
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
agauagagga uuaaagugag gac                                          23

<210> SEQ ID NO 126
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
aaagugagga ccugcacugg uac                                          23

<210> SEQ ID NO 127
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
acuuugccca agucaucugc uuu                                          23

<210> SEQ ID NO 128
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
acccaaguca ucugcuuuuu cau                                          23

<210> SEQ ID NO 129
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
auuacuuucc uucugcucga aau                                          23

<210> SEQ ID NO 130
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 130
uacuuuccuu cugcucgaaa uug                                           23

<210> SEQ ID NO 131
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
uuguguauua ucuccaaacu gau                                           23

<210> SEQ ID NO 132
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
uauuaucucc aaacugauga aca                                           23

<210> SEQ ID NO 133
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
uggauagagg auuaaaguga gga                                           23

<210> SEQ ID NO 134
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
agagaucaca gaaucuucga aag                                           23

<210> SEQ ID NO 135
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
auuugcccaa gucaucugcu uuu                                           23
```

```
<210> SEQ ID NO 136
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
uagaggauua aagugaggac cug                                              23

<210> SEQ ID NO 137
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
uuaaagugag gaccugcacu ggu                                              23

<210> SEQ ID NO 138
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
acuucaguca auccuguaau gcu                                              23

<210> SEQ ID NO 139
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139 aguuccugu cuuuuacuu ucu                                                23

<210> SEQ ID NO 140
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
auuguguauu aucuccaaac uga                                              23

<210> SEQ ID NO 141
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 141
agcgagauca cagaaucuuc gaa                                       23

<210> SEQ ID NO 142
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
auucagucaa uccuguaaug cuu                                       23

<210> SEQ ID NO 143
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
auauuaucuc caaacugaug aac                                       23

<210> SEQ ID NO 144
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
aucuggauag aggauuaaag uga                                       23

<210> SEQ ID NO 145
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
aagcguuucc ugucuuuuua cuu                                       23

<210> SEQ ID NO 146
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
uuccuucugc ucgaaauuga ugg                                       23

<210> SEQ ID NO 147
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
aauagaggau uaaagugagg acc                                            23

<210> SEQ ID NO 148
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
auagaggauu aaagugagga ccu                                            23

<210> SEQ ID NO 149
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
uguauuaucu ccaaacugau gaa                                            23

<210> SEQ ID NO 150
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150 acguuccug ucuuuuacu uuc                                              23

<210> SEQ ID NO 151
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
uucagucaau ccuguaaugc uuc                                            23

<210> SEQ ID NO 152
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
augagagcga gaucacagaa ucu                                            23
```

<210> SEQ ID NO 153
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
auuaucucca aacugaugaa cau                                            23

<210> SEQ ID NO 154
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
ucuggauaga ggauuaaagu gag                                            23

<210> SEQ ID NO 155
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
aacagaaucu ucgaaagaca ccu                                            23

<210> SEQ ID NO 156
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
acauuacuuu ccuucugcuc gaa                                            23

<210> SEQ ID NO 157
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
auccaaacug augaacaugg aau                                            23

<210> SEQ ID NO 158
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 158
uaaagugagg accugcacug gua　　　　　　　　　　　　　　　　23

<210> SEQ ID NO 159
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
agaggauuaa agugaggacc ugc　　　　　　　　　　　　　　　　23

<210> SEQ ID NO 160
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
aucuucgaaa gacaccuugg cca　　　　　　　　　　　　　　　　23

<210> SEQ ID NO 161
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
agcguuuccu gucuuuuuac uuu　　　　　　　　　　　　　　　　23

<210> SEQ ID NO 162
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
aacugguaca gccuugugua uua　　　　　　　　　　　　　　　　23

<210> SEQ ID NO 163
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
auguugucug gauagaggau uaa　　　　　　　　　　　　　　　　23

<210> SEQ ID NO 164
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
aauuacuuuc cuucugcucg aaa                                            23

<210> SEQ ID NO 165
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
auggauagag gauuaaagug agg                                            23

<210> SEQ ID NO 166
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
ugguccauua cuuccuucu gcu                                             23

<210> SEQ ID NO 167
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167 auuccuucu gcucgaaauu gau                                             23

<210> SEQ ID NO 168
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
aacuggucca uuacuuuccu ucu                                            23

<210> SEQ ID NO 169
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
```

```
auuaaaguga ggaccugcac ugg                                           23

<210> SEQ ID NO 170
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
caaacugaug aacauggaau cca                                           23

<210> SEQ ID NO 171
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
agaucacaga aucuucgaaa gac                                           23

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
uuacuuuccu ucugcucgaa auu                                           23

<210> SEQ ID NO 173
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
uguugucugg auagaggauu aaa                                           23

<210> SEQ ID NO 174
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
uuaucuccaa acugaugaac aug                                           23

<210> SEQ ID NO 175
<211> LENGTH: 23
<212> TYPE: RNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"

<400> SEQUENCE: 175
aauuaaagug aggaccugca cug                                          23

<210> SEQ ID NO 176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
aacaccuuca cugguccauu acu                                          23

<210> SEQ ID NO 177
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
auugucugga uagaggauua aag                                          23

<210> SEQ ID NO 178
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
aaugauggaa uggucuccug aga                                          23

<210> SEQ ID NO 179
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
uucugcucga aaugauggu gcc                                           23

<210> SEQ ID NO 180
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
aggauuaaag ugaggaccug cac                                          23

<210> SEQ ID NO 181
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
aagaucacag aaucuucgaa aga                                            23

<210> SEQ ID NO 182
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
aaugaacaug gaauccaugc agg                                            23

<210> SEQ ID NO 183
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
aguguugucu ggauagagga uua                                            23

<210> SEQ ID NO 184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
aagagcgaga ucacagaauc uuc                                            23

<210> SEQ ID NO 185
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
aucuccaaca ugccucucuu cau                                            23

<210> SEQ ID NO 186
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
```

```
uucauuucca ccuuugccca agu                                        23

<210> SEQ ID NO 187
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187 uuccuucug cucgaaauug aug                                         23

<210> SEQ ID NO 188
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
aaagucaucu gcuuuucau gga                                         23

<210> SEQ ID NO 189
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
aacugaugaa cauggaaucc aug                                        23

<210> SEQ ID NO 190
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
aaggucucca acaugccucu cuu                                        23

<210> SEQ ID NO 191
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
aagcgagauc acagaaucuu cga                                        23

<210> SEQ ID NO 192
<211> LENGTH: 23
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 192
uguguauuau cuccaaacug aug                                              23

<210> SEQ ID NO 193
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
aaaucuucga aagacaccuu ggc                                              23

<210> SEQ ID NO 194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
uaucuccaaa cugaugaaca ugg                                              23

<210> SEQ ID NO 195
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
auucugcucg aaauugaugg ugc                                              23

<210> SEQ ID NO 196
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
aaucuuugcc agcagucaca uug                                              23

<210> SEQ ID NO 197
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
uuuacuuucu ucauuccac cuu                                               23
```

```
<210> SEQ ID NO 198
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
aaacugauga acauggaauc cau                                           23

<210> SEQ ID NO 199
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
aucuuugcca gcagucacau ugc                                           23

<210> SEQ ID NO 200
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
aucaucugcu uuucaugga cca                                            23

<210> SEQ ID NO 201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
aucaguuugg agauaauaca u                                             21

<210> SEQ ID NO 202
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
ucuuucgaag auucugugau u                                             21

<210> SEQ ID NO 203
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 203
aggugucuuu cgaagauucu u                                              21

<210> SEQ ID NO 204
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
cuuuaauccu cuauccagac a                                              21

<210> SEQ ID NO 205
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
ugcagguccu cacuuuaauc u                                              21

<210> SEQ ID NO 206
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
gucuuucgaa gauucuguga u                                              21

<210> SEQ ID NO 207
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
cagguccuca cuuuaauccu u                                              21

<210> SEQ ID NO 208
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
ccucacuuua auccucuauc u                                              21

<210> SEQ ID NO 209
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 209
accagugcag guccucacuu u                                               21

<210> SEQ ID NO 210
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
agcagaugac uugggcaaag u                                               21

<210> SEQ ID NO 211
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
gaaaaagcag augacuuggg u                                               21

<210> SEQ ID NO 212
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
uucgagcaga aggaaaguaa u                                               21

<210> SEQ ID NO 213
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
auuucgagca gaaggaaagu a                                               21

<210> SEQ ID NO 214
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
caguuuggag auaauacaca a                                               21
```

<210> SEQ ID NO 215
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 215
uucaucaguu uggagauaau a                                              21

<210> SEQ ID NO 216
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 216
cucacuuuaa uccucuaucc a                                              21

<210> SEQ ID NO 217
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 217
uucgaagauu cugugaucuc u                                              21

<210> SEQ ID NO 218
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 218
aagcagauga cuugggcaaa u                                              21

<210> SEQ ID NO 219
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 219
gguccucacu uuaauccucu a                                              21

<210> SEQ ID NO 220
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 220
cagugcaggu ccucacuuua a                                              21

<210> SEQ ID NO 221
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
cauuacagga uugacugaag u                                              21

<210> SEQ ID NO 222
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
aaaguaaaaa gacaggaaac u                                              21

<210> SEQ ID NO 223
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
aguuuggaga uaauacacaa u                                              21

<210> SEQ ID NO 224
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
cgaagauucu gugaucucgc u                                              21

<210> SEQ ID NO 225
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
gcauuacagg auugacugaa u                                              21

<210> SEQ ID NO 226
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
ucaucaguuu ggagauaaua u                                              21

<210> SEQ ID NO 227
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
acuuuaaucc ucuauccaga u                                              21

<210> SEQ ID NO 228
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
guaaaaagac aggaaacgcu u                                              21

<210> SEQ ID NO 229
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
aucaauuucg agcagaagga a                                              21

<210> SEQ ID NO 230
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
uccucacuuu aauccucuau u                                              21

<210> SEQ ID NO 231
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
guccucacuu uaauccucua u                                              21
```

<210> SEQ ID NO 232
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
caucaguuug gagauaauac a                                           21

<210> SEQ ID NO 233
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
aaguaaaaag acaggaaacg u                                           21

<210> SEQ ID NO 234
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
agcauuacag gauugacuga a                                           21

<210> SEQ ID NO 235
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
auucugugau cucgcucuca u                                           21

<210> SEQ ID NO 236
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
guucaucagu uuggagauaa u                                           21

<210> SEQ ID NO 237
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 237
cacuuuaauc cucuauccag a					21

<210> SEQ ID NO 238
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
gugucuuucg aagauucugu u					21

<210> SEQ ID NO 239
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
cgagcagaag gaaaguaaug u					21

<210> SEQ ID NO 240
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
uccauguuca ucaguuugga u					21

<210> SEQ ID NO 241
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
ccagugcagg uccucacuuu a					21

<210> SEQ ID NO 242
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
agguccucac uuuaauccuc u					21

<210> SEQ ID NO 243
<211> LENGTH: 21

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
gccaaggugu cuuucgaaga u                                              21

<210> SEQ ID NO 244
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
aguaaaaaga caggaaacgc u                                              21

<210> SEQ ID NO 245
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
auacacaagg cuguaccagu u                                              21

<210> SEQ ID NO 246
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
aauccucuau ccagacaaca u                                              21

<210> SEQ ID NO 247
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ucgagcagaa ggaaaguaau u                                              21

<210> SEQ ID NO 248
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
```

-continued ucacuuuaau ccucuaucca u						21

<210> SEQ ID NO 249
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
cagaaggaaa guaauggacc a						21

<210> SEQ ID NO 250
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
caauuucgag cagaaggaaa u						21

<210> SEQ ID NO 251
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
aaggaaagua auggaccagu u						21

<210> SEQ ID NO 252
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
agugcagguc cucacuuuaa u						21

<210> SEQ ID NO 253
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
gauuccaugu ucaucaguuu g						21

<210> SEQ ID NO 254
<211> LENGTH: 21
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 254
cuuucgaaga uucugugauc u                                         21

<210> SEQ ID NO 255
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
uuucgagcag aaggaaagua a                                         21

<210> SEQ ID NO 256
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
uaauccucua uccagacaac a                                         21

<210> SEQ ID NO 257
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
uguucaucag uuuggagaua a                                         21

<210> SEQ ID NO 258
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
gugcaggucc ucacuuuaau u                                         21

<210> SEQ ID NO 259
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
uaauggacca gugaaggugu u                                         21

<210> SEQ ID NO 260

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
uuaauccucu auccagacaa u                                             21

<210> SEQ ID NO 261
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
ucaggagacc auuccaucau u                                             21

<210> SEQ ID NO 262
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
caccaucaau uucgagcaga a                                             21

<210> SEQ ID NO 263
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
gcagguccuc acuuuaaucc u                                             21

<210> SEQ ID NO 264
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
uuucgaagau ucugugaucu u                                             21

<210> SEQ ID NO 265
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
```
ugcauggauu ccauguucau u                                              21

<210> SEQ ID NO 266
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
auccucuauc cagacaacac u                                              21

<210> SEQ ID NO 267
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
agauucugug aucucgcucu u                                              21

<210> SEQ ID NO 268
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
gaagagaggc auguuggaga u                                              21

<210> SEQ ID NO 269
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
uugggcaaag guggaaauga a                                              21

<210> SEQ ID NO 270
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
ucaauuucga gcagaaggaa a                                              21

<210> SEQ ID NO 271
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 271
caugaaaaag cagaugacuu u                                              21

<210> SEQ ID NO 272
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
uggauuccau guucaucagu u                                              21

<210> SEQ ID NO 273
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
gagaggcaug uuggagaccu u                                              21

<210> SEQ ID NO 274
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
gaagauucug ugaucucgcu u                                              21

<210> SEQ ID NO 275
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
ucaguuugga gauaauacac a                                              21

<210> SEQ ID NO 276
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
caaggugucu uucgaagauu u                                              21

```
<210> SEQ ID NO 277
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
auguucauca guuuggagau a                                              21

<210> SEQ ID NO 278
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
accaucaauu ucgagcagaa u                                              21

<210> SEQ ID NO 279
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
augugacugc uggcaaagau u                                              21

<210> SEQ ID NO 280
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
gguggaaaug aagaaaguaa a                                              21

<210> SEQ ID NO 281
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281 ggauccaug uucaucaguu u                                               21

<210> SEQ ID NO 282
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 282
aaugugacug cuggcaaaga u                                              21

<210> SEQ ID NO 283
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
guccaugaaa aagcagauga u                                              21

<210> SEQ ID NO 284
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
auguauuauc uccaaacuga uga                                            23

<210> SEQ ID NO 285
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
aaucacagaa ucuucgaaag aca                                            23

<210> SEQ ID NO 286
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
aagaaucuuc gaaagacacc uug                                            23

<210> SEQ ID NO 287
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
ugucuggaua gaggauuaaa gug                                            23

<210> SEQ ID NO 288
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 288
agauuaaagu gaggaccugc acu                                          23

<210> SEQ ID NO 289
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
aucacagaau cuucgaaaga cac                                          23

<210> SEQ ID NO 290
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
aaggauuaaa gugaggaccu gca                                          23

<210> SEQ ID NO 291
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
agauagagga uuaaagugag gac                                          23

<210> SEQ ID NO 292
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
aaagugagga ccugcacugg uac                                          23

<210> SEQ ID NO 293
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
acuuugccca agucaucugc uuu                                          23
```

```
<210> SEQ ID NO 294
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
acccaaguca ucugcuuuuu cau                                              23

<210> SEQ ID NO 295
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
auuacuuucc uucugcucga aau                                              23

<210> SEQ ID NO 296
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
uacuuuccuu cugcucgaaa uug                                              23

<210> SEQ ID NO 297
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
uuguguauua ucuccaaacu gau                                              23

<210> SEQ ID NO 298
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
uauuaucucc aaacugauga aca                                              23

<210> SEQ ID NO 299
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 299
uggauagagg auuaaaguga gga                                          23

<210> SEQ ID NO 300
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
agagaucaca gaaucuucga aag                                          23

<210> SEQ ID NO 301
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
auuugcccaa gucaucugcu uuu                                          23

<210> SEQ ID NO 302
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
uagaggauua aagugaggac cug                                          23

<210> SEQ ID NO 303
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
uuaaagugag gaccugcacu ggu                                          23

<210> SEQ ID NO 304
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
acuucaguca auccuguaau gcu                                          23

<210> SEQ ID NO 305
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
aguuuccugu cuuuuacuu ucu                                            23

<210> SEQ ID NO 306
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
auuguguauu aucuccaaac uga                                           23

<210> SEQ ID NO 307
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
agcgagauca cagaaucuuc gaa                                           23

<210> SEQ ID NO 308
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
auucagucaa uccuguaaug cuu                                           23

<210> SEQ ID NO 309
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
auauuaucuc caaacugaug aac                                           23

<210> SEQ ID NO 310
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
aucuggauag aggauuaaag uga                                           23
```

<210> SEQ ID NO 311
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
aagcguuucc ugucuuuuua cuu                                           23

<210> SEQ ID NO 312
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
uuccuucugc ucgaaauuga ugg                                           23

<210> SEQ ID NO 313
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
aauagaggau uaaagugagg acc                                           23

<210> SEQ ID NO 314
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
auagaggauu aaagugagga ccu                                           23

<210> SEQ ID NO 315
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
uguauuaucu ccaaacugau gaa                                           23

<210> SEQ ID NO 316
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
      Synthetic oligonucleotide"

<400> SEQUENCE: 316 acguuccug ucuuuuacu uuc                                              23

<210> SEQ ID NO 317
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
uucagucaau ccuguaaugc uuc                                            23

<210> SEQ ID NO 318
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
augagagcga gaucacagaa ucu                                            23

<210> SEQ ID NO 319
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
auuaucucca aacugaugaa cau                                            23

<210> SEQ ID NO 320
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
ucuggauaga ggauuaaagu gag                                            23

<210> SEQ ID NO 321
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
aacagaaucu ucgaaagaca ccu                                            23

<210> SEQ ID NO 322
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
acauuacuuu ccuucugcuc gaa                                              23

<210> SEQ ID NO 323
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
auccaaacug augaacaugg aau                                              23

<210> SEQ ID NO 324
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
uaaagugagg accugcacug gua                                              23

<210> SEQ ID NO 325
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
agaggauuaa agugaggacc ugc                                              23

<210> SEQ ID NO 326
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
aucuucgaaa gacaccuugg cca                                              23

<210> SEQ ID NO 327
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
```
agcguuuccu gucuuuuuac uuu                                         23

<210> SEQ ID NO 328
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
aacugguaca gccuugugua uua                                         23

<210> SEQ ID NO 329
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
auguugucug gauagaggau uaa                                         23

<210> SEQ ID NO 330
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
aauuacuuuc cuucugcucg aaa                                         23

<210> SEQ ID NO 331
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
auggauagag gauuaaagug agg                                         23

<210> SEQ ID NO 332
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
ugguccauua cuuccuucu gcu                                          23

<210> SEQ ID NO 333
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 333 auuccuucu gcucgaaauu gau                                             23

<210> SEQ ID NO 334
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
aacuggucca uuacuuuccu ucu                                            23

<210> SEQ ID NO 335
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
auuaaaguga ggaccugcac ugg                                            23

<210> SEQ ID NO 336
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
caaacugaug aacauggaau cca                                            23

<210> SEQ ID NO 337
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
agaucacaga aucuucgaaa gac                                            23

<210> SEQ ID NO 338
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
uuacuuuccu ucugcucgaa auu                                            23

<210> SEQ ID NO 339
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
uguugucugg auagaggauu aaa                                               23

<210> SEQ ID NO 340
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
uuaucuccaa acugaugaac aug                                               23

<210> SEQ ID NO 341
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
aauuaaagug aggaccugca cug                                               23

<210> SEQ ID NO 342
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
aacaccuuca cugguccauu acu                                               23

<210> SEQ ID NO 343
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
auugucugga uagaggauua aag                                               23

<210> SEQ ID NO 344
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
```
aaugauggaa uggucuccug aga         23

<210> SEQ ID NO 345
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
uucugcucga aaugauggu gcc         23

<210> SEQ ID NO 346
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
aggauuaaag ugaggaccug cac         23

<210> SEQ ID NO 347
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
aagaucacag aaucuucgaa aga         23

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
aaugaacaug gaauccaugc agg         23

<210> SEQ ID NO 349
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
aguguugucu ggauagagga uua         23

<210> SEQ ID NO 350
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 350
aagagcgaga ucacagaauc uuc                                              23

<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
aucuccaaca ugccucucuu cau                                              23

<210> SEQ ID NO 352
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
uucauuucca ccuuugccca agu                                              23

<210> SEQ ID NO 353
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
uuuccuucug cucgaaauug aug                                              23

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
aaagucaucu gcuuuuucau gga                                              23

<210> SEQ ID NO 355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
aacugaugaa cauggaaucc aug                                              23

```
<210> SEQ ID NO 356
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
aaggucucca acaugccucu cuu                                              23

<210> SEQ ID NO 357
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
aagcgagauc acagaaucuu cga                                              23

<210> SEQ ID NO 358
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358 uuguauuau cuccaaacug aug                                               23

<210> SEQ ID NO 359
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
aaaucuucga aagacaccuu ggc                                              23

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
uaucuccaaa cugaugaaca ugg                                              23

<210> SEQ ID NO 361
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 361
auucugcucg aaauugaugg ugc                                              23

<210> SEQ ID NO 362
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
aaucuuugcc agcagucaca uug                                              23

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
uuuacuuucu ucauuccac cuu                                               23

<210> SEQ ID NO 364
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
aaacugauga acauggaauc cau                                              23

<210> SEQ ID NO 365
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
aucuuugcca gcagucacau ugc                                              23

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
aucaucugcu uuucaugga cca                                               23

<210> SEQ ID NO 367
<211> LENGTH: 23
<212> TYPE: RNA
<213> ORGANISM: Homo sapiens
```

```
<400> SEQUENCE: 367
ucaucaguuu ggagauaaua cac                                          23

<210> SEQ ID NO 368
<211> LENGTH: 23
<212> TYPE: RNA
<213> ORGANISM: Homo sapiens

<400> SEQUENCE: 368
ugucuuucga agauucugug auc                                          23

<210> SEQ ID NO 369
<211> LENGTH: 23
<212> TYPE: RNA
<213> ORGANISM: Homo sapiens

<400> SEQUENCE: 369
caaggugucu uucgaagauu cug                                          23

<210> SEQ ID NO 370
<211> LENGTH: 23
<212> TYPE: RNA
<213> ORGANISM: Homo sapiens

<400> SEQUENCE: 370
cacuuuaauc cucuauccag aca                                          23

<210> SEQ ID NO 371
<211> LENGTH: 23
<212> TYPE: RNA
<213> ORGANISM: Homo sapiens

<400> SEQUENCE: 371
agugcagguc cucacuuuaa ucc                                          23

<210> SEQ ID NO 372
<211> LENGTH: 23
<212> TYPE: RNA
<213> ORGANISM: Homo sapiens

<400> SEQUENCE: 372
gugucuuucg aagauucugu gau                                          23

<210> SEQ ID NO 373
<211> LENGTH: 23
<212> TYPE: RNA
<213> ORGANISM: Homo sapiens

<400> SEQUENCE: 373
ugcagguccu cacuuuaauc cuc                                          23

<210> SEQ ID NO 374
<211> LENGTH: 23
<212> TYPE: RNA
<213> ORGANISM: Homo sapiens

<400> SEQUENCE: 374
guccucacuu uaauccucua ucc                                          23

<210> SEQ ID NO 375
<211> LENGTH: 23
<212> TYPE: RNA
```

```
<213> ORGANISM: Homo sapiens

<400> SEQUENCE: 375
guaccagugc agguccucac uuu                                              23

<210> SEQ ID NO 376
<211> LENGTH: 23
<212> TYPE: RNA
<213> ORGANISM: Homo sapiens

<400> SEQUENCE: 376
aaagcagaug acuugggcaa agg                                              23

<210> SEQ ID NO 377
<211> LENGTH: 23
<212> TYPE: RNA
<213> ORGANISM: Homo sapiens

<400> SEQUENCE: 377 augaaaagc agaugacuug ggc                                               23

<210> SEQ ID NO 378
<211> LENGTH: 23
<212> TYPE: RNA
<213> ORGANISM: Homo sapiens

<400> SEQUENCE: 378
auuucgagca gaaggaaagu aau                                              23

<210> SEQ ID NO 379
<211> LENGTH: 23
<212> TYPE: RNA
<213> ORGANISM: Homo sapiens

<400> SEQUENCE: 379
caauuucgag cagaaggaaa gua                                              23

<210> SEQ ID NO 380
<211> LENGTH: 23
<212> TYPE: RNA
<213> ORGANISM: Homo sapiens

<400> SEQUENCE: 380
aucaguuugg agauaauaca caa                                              23

<210> SEQ ID NO 381
<211> LENGTH: 23
<212> TYPE: RNA
<213> ORGANISM: Homo sapiens

<400> SEQUENCE: 381
uguucaucag uuuggagaua aua                                              23

<210> SEQ ID NO 382
<211> LENGTH: 23
<212> TYPE: RNA
<213> ORGANISM: Homo sapiens

<400> SEQUENCE: 382
uccucacuuu aauccucuau cca                                              23

<210> SEQ ID NO 383
<211> LENGTH: 23
```

```
<212> TYPE: RNA
<213> ORGANISM: Homo sapiens

<400> SEQUENCE: 383
cuuucgaaga uucgugauc ucg                                              23

<210> SEQ ID NO 384
<211> LENGTH: 23
<212> TYPE: RNA
<213> ORGANISM: Homo sapiens

<400> SEQUENCE: 384
aaaagcagau gacuugggca aag                                             23

<210> SEQ ID NO 385
<211> LENGTH: 23
<212> TYPE: RNA
<213> ORGANISM: Homo sapiens

<400> SEQUENCE: 385
cagguccuca cuuuaauccu cua                                             23

<210> SEQ ID NO 386
<211> LENGTH: 23
<212> TYPE: RNA
<213> ORGANISM: Homo sapiens

<400> SEQUENCE: 386
accagugcag guccucacuu uaa                                             23

<210> SEQ ID NO 387
<211> LENGTH: 23
<212> TYPE: RNA
<213> ORGANISM: Homo sapiens

<400> SEQUENCE: 387
agcauuacag gauugacuga agg                                             23

<210> SEQ ID NO 388
<211> LENGTH: 23
<212> TYPE: RNA
<213> ORGANISM: Homo sapiens

<400> SEQUENCE: 388
agaaaguaaa aagacaggaa acg                                             23

<210> SEQ ID NO 389
<211> LENGTH: 23
<212> TYPE: RNA
<213> ORGANISM: Homo sapiens

<400> SEQUENCE: 389
ucaguuugga gauaauacac aag                                             23

<210> SEQ ID NO 390
<211> LENGTH: 23
<212> TYPE: RNA
<213> ORGANISM: Homo sapiens

<400> SEQUENCE: 390
uucgaagauu cugugaucuc gcu                                             23

<210> SEQ ID NO 391
```

```
<211> LENGTH: 23
<212> TYPE: RNA
<213> ORGANISM: Homo sapiens

<400> SEQUENCE: 391
aagcauuaca ggauugacug aag                                            23

<210> SEQ ID NO 392
<211> LENGTH: 23
<212> TYPE: RNA
<213> ORGANISM: Homo sapiens

<400> SEQUENCE: 392
guucaucagu uuggagauaa uac                                            23

<210> SEQ ID NO 393
<211> LENGTH: 23
<212> TYPE: RNA
<213> ORGANISM: Homo sapiens

<400> SEQUENCE: 393
ucacuuuaau ccucuaucca gac                                            23

<210> SEQ ID NO 394
<211> LENGTH: 23
<212> TYPE: RNA
<213> ORGANISM: Homo sapiens

<400> SEQUENCE: 394
aaguaaaaag acaggaaacg cug                                            23

<210> SEQ ID NO 395
<211> LENGTH: 23
<212> TYPE: RNA
<213> ORGANISM: Homo sapiens

<400> SEQUENCE: 395
ccaucaauuu cgagcagaag gaa                                            23

<210> SEQ ID NO 396
<211> LENGTH: 23
<212> TYPE: RNA
<213> ORGANISM: Homo sapiens

<400> SEQUENCE: 396
gguccucacu uuaauccucu auc                                            23

<210> SEQ ID NO 397
<211> LENGTH: 23
<212> TYPE: RNA
<213> ORGANISM: Homo sapiens

<400> SEQUENCE: 397
agguccucac uuuaauccuc uau                                            23

<210> SEQ ID NO 398
<211> LENGTH: 23
<212> TYPE: RNA
<213> ORGANISM: Homo sapiens

<400> SEQUENCE: 398
uucaucaguu uggagauaau aca                                            23
```

```
<210> SEQ ID NO 399
<211> LENGTH: 23
<212> TYPE: RNA
<213> ORGANISM: Homo sapiens

<400> SEQUENCE: 399
gaaaguaaaa agacaggaaa cgc                                              23

<210> SEQ ID NO 400
<211> LENGTH: 23
<212> TYPE: RNA
<213> ORGANISM: Homo sapiens

<400> SEQUENCE: 400
gaagcauuac aggauugacu gaa                                              23

<210> SEQ ID NO 401
<211> LENGTH: 23
<212> TYPE: RNA
<213> ORGANISM: Homo sapiens

<400> SEQUENCE: 401
agauucugug aucucgcucu cag                                              23

<210> SEQ ID NO 402
<211> LENGTH: 23
<212> TYPE: RNA
<213> ORGANISM: Homo sapiens

<400> SEQUENCE: 402
auguucauca guuuggagau aau                                              23

<210> SEQ ID NO 403
<211> LENGTH: 23
<212> TYPE: RNA
<213> ORGANISM: Homo sapiens

<400> SEQUENCE: 403
cucacuuuaa uccucuaucc aga                                              23

<210> SEQ ID NO 404
<211> LENGTH: 23
<212> TYPE: RNA
<213> ORGANISM: Homo sapiens

<400> SEQUENCE: 404
aggugucuuu cgaagauucu gug                                              23

<210> SEQ ID NO 405
<211> LENGTH: 23
<212> TYPE: RNA
<213> ORGANISM: Homo sapiens

<400> SEQUENCE: 405
uucgagcaga aggaaaguaa ugg                                              23

<210> SEQ ID NO 406
<211> LENGTH: 23
<212> TYPE: RNA
<213> ORGANISM: Homo sapiens

<400> SEQUENCE: 406
auuccauguu caucaguuug gag                                              23
```

-continued

```
<210> SEQ ID NO 407
<211> LENGTH: 23
<212> TYPE: RNA
<213> ORGANISM: Homo sapiens

<400> SEQUENCE: 407
uaccagugca gguccucacu uua                                              23

<210> SEQ ID NO 408
<211> LENGTH: 23
<212> TYPE: RNA
<213> ORGANISM: Homo sapiens

<400> SEQUENCE: 408
gcagguccuc acuuuaaucc ucu                                              23

<210> SEQ ID NO 409
<211> LENGTH: 23
<212> TYPE: RNA
<213> ORGANISM: Homo sapiens

<400> SEQUENCE: 409
uggccaaggu gucuuucgaa gau                                              23

<210> SEQ ID NO 410
<211> LENGTH: 23
<212> TYPE: RNA
<213> ORGANISM: Homo sapiens

<400> SEQUENCE: 410
aaaguaaaaa gacaggaaac gcu                                              23

<210> SEQ ID NO 411
<211> LENGTH: 23
<212> TYPE: RNA
<213> ORGANISM: Homo sapiens

<400> SEQUENCE: 411
uaauacacaa ggcuguacca gug                                              23

<210> SEQ ID NO 412
<211> LENGTH: 23
<212> TYPE: RNA
<213> ORGANISM: Homo sapiens

<400> SEQUENCE: 412
uuaauccucu auccagacaa cac                                              23

<210> SEQ ID NO 413
<211> LENGTH: 23
<212> TYPE: RNA
<213> ORGANISM: Homo sapiens

<400> SEQUENCE: 413
uuucgagcag aaggaaagua aug                                              23

<210> SEQ ID NO 414
<211> LENGTH: 23
<212> TYPE: RNA
<213> ORGANISM: Homo sapiens

<400> SEQUENCE: 414
ccucacuuua auccucuauc cag                                              23
```

```
<210> SEQ ID NO 415
<211> LENGTH: 23
<212> TYPE: RNA
<213> ORGANISM: Homo sapiens

<400> SEQUENCE: 415
agcagaagga aaguaaugga cca                                              23

<210> SEQ ID NO 416
<211> LENGTH: 23
<212> TYPE: RNA
<213> ORGANISM: Homo sapiens

<400> SEQUENCE: 416
aucaauuucg agcagaagga aag                                              23

<210> SEQ ID NO 417
<211> LENGTH: 23
<212> TYPE: RNA
<213> ORGANISM: Homo sapiens

<400> SEQUENCE: 417
agaaggaaag uaauggacca gug                                              23

<210> SEQ ID NO 418
<211> LENGTH: 23
<212> TYPE: RNA
<213> ORGANISM: Homo sapiens

<400> SEQUENCE: 418
ccagugcagg uccucacuuu aau                                              23

<210> SEQ ID NO 419
<211> LENGTH: 23
<212> TYPE: RNA
<213> ORGANISM: Homo sapiens

<400> SEQUENCE: 419
uggauuccau guucaucagu uug                                              23

<210> SEQ ID NO 420
<211> LENGTH: 23
<212> TYPE: RNA
<213> ORGANISM: Homo sapiens

<400> SEQUENCE: 420
gucuuucgaa gauucuguga ucu                                              23

<210> SEQ ID NO 421
<211> LENGTH: 23
<212> TYPE: RNA
<213> ORGANISM: Homo sapiens

<400> SEQUENCE: 421
aauuucgagc agaaggaaag uaa                                              23

<210> SEQ ID NO 422
<211> LENGTH: 23
<212> TYPE: RNA
<213> ORGANISM: Homo sapiens

<400> SEQUENCE: 422
```
uuuaauccuc uauccagaca aca 23

<210> SEQ ID NO 423
<211> LENGTH: 23
<212> TYPE: RNA
<213> ORGANISM: Homo sapiens

<400> SEQUENCE: 423
cauguucauc aguuuggaga uaa 23

<210> SEQ ID NO 424
<211> LENGTH: 23
<212> TYPE: RNA
<213> ORGANISM: Homo sapiens

<400> SEQUENCE: 424
cagugcaggu ccucacuuua auc 23

<210> SEQ ID NO 425
<211> LENGTH: 23
<212> TYPE: RNA
<213> ORGANISM: Homo sapiens

<400> SEQUENCE: 425
aguaauggac cagugaaggu gug 23

<210> SEQ ID NO 426
<211> LENGTH: 23
<212> TYPE: RNA
<213> ORGANISM: Homo sapiens

<400> SEQUENCE: 426
cuuuaauccu cuauccagac aac 23

<210> SEQ ID NO 427
<211> LENGTH: 23
<212> TYPE: RNA
<213> ORGANISM: Homo sapiens

<400> SEQUENCE: 427
ucucaggaga ccauuccauc auu 23

<210> SEQ ID NO 428
<211> LENGTH: 23
<212> TYPE: RNA
<213> ORGANISM: Homo sapiens

<400> SEQUENCE: 428
ggcaccauca auuucgagca gaa 23

<210> SEQ ID NO 429
<211> LENGTH: 23
<212> TYPE: RNA
<213> ORGANISM: Homo sapiens

<400> SEQUENCE: 429
gugcaggucc ucacuuuaau ccu 23

<210> SEQ ID NO 430
<211> LENGTH: 23
<212> TYPE: RNA
<213> ORGANISM: Homo sapiens

<400> SEQUENCE: 430
ucuuucgaag auucugugau cuc                                          23

<210> SEQ ID NO 431
<211> LENGTH: 23
<212> TYPE: RNA
<213> ORGANISM: Homo sapiens

<400> SEQUENCE: 431
ccugcaugga uuccauguuc auc                                          23

<210> SEQ ID NO 432
<211> LENGTH: 23
<212> TYPE: RNA
<213> ORGANISM: Homo sapiens

<400> SEQUENCE: 432
uaauccucua uccagacaac acg                                          23

<210> SEQ ID NO 433
<211> LENGTH: 23
<212> TYPE: RNA
<213> ORGANISM: Homo sapiens

<400> SEQUENCE: 433
gaagauucug ugaucucgcu cuc                                          23

<210> SEQ ID NO 434
<211> LENGTH: 23
<212> TYPE: RNA
<213> ORGANISM: Homo sapiens

<400> SEQUENCE: 434
augaagagag gcauguugga gac                                          23

<210> SEQ ID NO 435
<211> LENGTH: 23
<212> TYPE: RNA
<213> ORGANISM: Homo sapiens

<400> SEQUENCE: 435
acuugggcaa agguggaaau gaa                                          23

<210> SEQ ID NO 436
<211> LENGTH: 23
<212> TYPE: RNA
<213> ORGANISM: Homo sapiens

<400> SEQUENCE: 436
caucaauuuc gagcagaagg aaa                                          23

<210> SEQ ID NO 437
<211> LENGTH: 23
<212> TYPE: RNA
<213> ORGANISM: Homo sapiens

<400> SEQUENCE: 437
uccaugaaaa agcagaugac uug                                          23

<210> SEQ ID NO 438
<211> LENGTH: 23
<212> TYPE: RNA
<213> ORGANISM: Homo sapiens

```
<400> SEQUENCE: 438
cauggauucc auguucauca guu                                             23

<210> SEQ ID NO 439
<211> LENGTH: 23
<212> TYPE: RNA
<213> ORGANISM: Homo sapiens

<400> SEQUENCE: 439
aagagaggca uguuggagac cug                                             23

<210> SEQ ID NO 440
<211> LENGTH: 23
<212> TYPE: RNA
<213> ORGANISM: Homo sapiens

<400> SEQUENCE: 440
ucgaagauuc ugugaucucg cuc                                             23

<210> SEQ ID NO 441
<211> LENGTH: 23
<212> TYPE: RNA
<213> ORGANISM: Homo sapiens

<400> SEQUENCE: 441
caucaguuug gagauaauac aca                                             23

<210> SEQ ID NO 442
<211> LENGTH: 23
<212> TYPE: RNA
<213> ORGANISM: Homo sapiens

<400> SEQUENCE: 442
gccaaggugu cuuucgaaga uuc                                             23

<210> SEQ ID NO 443
<211> LENGTH: 23
<212> TYPE: RNA
<213> ORGANISM: Homo sapiens

<400> SEQUENCE: 443
ccauguucau caguuggag aua                                              23

<210> SEQ ID NO 444
<211> LENGTH: 23
<212> TYPE: RNA
<213> ORGANISM: Homo sapiens

<400> SEQUENCE: 444
gcaccaucaa uuucgagcag aag                                             23

<210> SEQ ID NO 445
<211> LENGTH: 23
<212> TYPE: RNA
<213> ORGANISM: Homo sapiens

<400> SEQUENCE: 445
caaugugacu gcuggcaaag aug                                             23

<210> SEQ ID NO 446
<211> LENGTH: 23
<212> TYPE: RNA
<213> ORGANISM: Homo sapiens
```

```
<400> SEQUENCE: 446
aagguggaaa ugaagaaagu aaa                                          23

<210> SEQ ID NO 447
<211> LENGTH: 23
<212> TYPE: RNA
<213> ORGANISM: Homo sapiens

<400> SEQUENCE: 447
auggauucca uguucaucag uuu                                          23

<210> SEQ ID NO 448
<211> LENGTH: 23
<212> TYPE: RNA
<213> ORGANISM: Homo sapiens

<400> SEQUENCE: 448
gcaaugugac ugcuggcaaa gau                                          23

<210> SEQ ID NO 449
<211> LENGTH: 23
<212> TYPE: RNA
<213> ORGANISM: Homo sapiens

<400> SEQUENCE: 449
ugguccauga aaaagcagau gac                                          23

<210> SEQ ID NO 450
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
augacuuggg caaaggugga a                                            21

<210> SEQ ID NO 451
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
ugacuugggc aaagguggaa a                                            21

<210> SEQ ID NO 452
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452 gacuuggca aagguggaaa u                                             21

<210> SEQ ID NO 453
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
aagguggaaa ugaagaaagu a                                              21

<210> SEQ ID NO 454
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
aauuucgagc agaaggaaag u                                              21

<210> SEQ ID NO 455
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
gagcagaagg aaaguaaugg a                                              21

<210> SEQ ID NO 456
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
agaaggaaag uaauggacca u                                              21

<210> SEQ ID NO 457
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
gaaggaaagu aauggaccag u                                              21

<210> SEQ ID NO 458
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
```
aggaaaguaa uggaccagug a                                              21

<210> SEQ ID NO 459
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
ggaaaguaau ggaccaguga a                                              21

<210> SEQ ID NO 460
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
gaaaguaaug gaccagugaa u                                              21

<210> SEQ ID NO 461
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
aaaguaaugg accagugaag u                                              21

<210> SEQ ID NO 462
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
aaguaaugga ccagugaagg u                                              21

<210> SEQ ID NO 463
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
aguaauggac cagugaaggu u                                              21

<210> SEQ ID NO 464
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 464
ugaaggccug cauggauucc a                                            21

<210> SEQ ID NO 465
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
gaaggccugc auggauucca u                                            21

<210> SEQ ID NO 466
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
aggccugcau ggauuccaug u                                            21

<210> SEQ ID NO 467
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
ggccugcaug gauuccaugu u                                            21

<210> SEQ ID NO 468
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
gccugcaugg auuccauguu u                                            21

<210> SEQ ID NO 469
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
ccugcaugga uuccauguuc a                                            21

```
<210> SEQ ID NO 470
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
cugcauggau uccauguuca u                                              21

<210> SEQ ID NO 471
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
ggugggccaa aggaugaaga u                                              21

<210> SEQ ID NO 472
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
gaugaagaga ggcauguugg a                                              21

<210> SEQ ID NO 473
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
caaaggauga agagaggcau u                                              21

<210> SEQ ID NO 474
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
aaggaugaag agaggcaugu u                                              21

<210> SEQ ID NO 475
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 475
aggaugaaga gaggcauguu u					21

<210> SEQ ID NO 476
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
ggaugaagag aggcauguug u					21

<210> SEQ ID NO 477
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
augaagagag gcauguugga u					21

<210> SEQ ID NO 478
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
aagagaggca uguuggagac u					21

<210> SEQ ID NO 479
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
gaugacuugg gcaaaggugg a					21

<210> SEQ ID NO 480
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
gugguccaug aaaaagcaga u					21

<210> SEQ ID NO 481
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 481
ugguccauga aaaagcagau u                                               21

<210> SEQ ID NO 482
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
gguccaugaa aaagcagaug a                                               21

<210> SEQ ID NO 483
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
gcagaugacu ugggcaaagg u                                               21

<210> SEQ ID NO 484
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
agaugacuug ggcaaaggug u                                               21

<210> SEQ ID NO 485
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
acuugggcaa agguggaaau u                                               21

<210> SEQ ID NO 486
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486 gcuugguggug uaauugggau u                                              21
```

<210> SEQ ID NO 487
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
cuuguggugu aauugggauc u                                              21

<210> SEQ ID NO 488
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488 uugguguguaa auugggaucg u                                             21

<210> SEQ ID NO 489
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
ugugguguaa uugggaucgc u                                              21

<210> SEQ ID NO 490
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
gugguguaau ugggaucgcc u                                              21

<210> SEQ ID NO 491
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
ugcagggcau caucaauuuc u                                              21

<210> SEQ ID NO 492
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 492
gcagggcauc aucaauuucg a                                              21

<210> SEQ ID NO 493
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
cagggcauca ucaauuucga u                                              21

<210> SEQ ID NO 494
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
agggcaucau caauuucgag u                                              21

<210> SEQ ID NO 495
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
gggcaucauc aauuucgagc a                                              21

<210> SEQ ID NO 496
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
ggcaucauca auuucgagca u                                              21

<210> SEQ ID NO 497
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
caucaucaau uucgagcaga a                                              21

<210> SEQ ID NO 498
<211> LENGTH: 21
<212> TYPE: RNA

-continued

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
aucaucaauu ucgagcagaa u                                              21

<210> SEQ ID NO 499
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
ucaucaauuu cgagcagaag u                                              21

<210> SEQ ID NO 500
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
auuaaaggac ugacugaagg u                                              21

<210> SEQ ID NO 501
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
cauguucaug aguuuggaga u                                              21

<210> SEQ ID NO 502
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
guucaugagu uuggagauaa u                                              21

<210> SEQ ID NO 503
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
uucaugaguu uggagauaau a                                              21

```
<210> SEQ ID NO 504
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
augaguuugg agauaauaca u                                              21

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505 ugugcuauu gaagauucug u                                               21

<210> SEQ ID NO 506
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
gugucuauug aagauucugu u                                              21

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
ugguggucca ugaaaaagca u                                              21

<210> SEQ ID NO 508
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
ggugguccau gaaaaagcag a                                              21

<210> SEQ ID NO 509
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 509
gagaccauug caucauuggc u					21

<210> SEQ ID NO 510
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
acuggugguc caugaaaaag u					21

<210> SEQ ID NO 511
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
cugguggucc augaaaaagc a					21

<210> SEQ ID NO 512
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
agguggaaau gaagaaagua u					21

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
gaaaguacaa agacaggaaa u					21

<210> SEQ ID NO 514
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
aaaguacaaa gacaggaaac u					21

<210> SEQ ID NO 515
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
aaguacaaag acaggaaacg u                                              21

<210> SEQ ID NO 516
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
aguacaaaga caggaaacgc u                                              21

<210> SEQ ID NO 517
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
guacaaagac aggaaacgcu u                                              21

<210> SEQ ID NO 518
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
uacaaagaca ggaaacgcug u                                              21

<210> SEQ ID NO 519
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
caaagacagg aaacgcugga a                                              21

<210> SEQ ID NO 520
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
```
uggcuugugg uguaauuggg a                    21

<210> SEQ ID NO 521
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
ggcuuguggu guaauuggga u                    21

<210> SEQ ID NO 522
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522 gucguuggc uugggugua a                      21

<210> SEQ ID NO 523
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
ucguuuggcu ugugguguaa u                    21

<210> SEQ ID NO 524
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524 cguuggcuu gugguguaau u                     21

<210> SEQ ID NO 525
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
guuuggcuug ugguguaauu u                    21

<210> SEQ ID NO 526
<211> LENGTH: 21
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 526
uuuggcuugu gguguaauug u                                              21

<210> SEQ ID NO 527
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
uuggcuugug guguaauugg u                                              21

<210> SEQ ID NO 528
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
guaauuggga ucgcccaaua a                                              21

<210> SEQ ID NO 529
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
uuccaccuuu gcccaaguca ucu                                            23

<210> SEQ ID NO 530
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
uuuccaccuu ugcccaaguc auc                                            23

<210> SEQ ID NO 531
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
auuuccaccu uugcccaagu cau                                            23

<210> SEQ ID NO 532
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
uacuuucuuc auuuccaccu uug                                                23

<210> SEQ ID NO 533
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533 acuuccuuc ugcucgaaau uga                                                 23

<210> SEQ ID NO 534
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
uccauuacuu uccuucugcu cga                                                23

<210> SEQ ID NO 535
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
augguccauu acuuccuuc ugc                                                 23

<210> SEQ ID NO 536
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
acugguccau uacuuuccuu cug                                                23

<210> SEQ ID NO 537
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
```
ucacuggucc auuacuuucc uuc                                              23

<210> SEQ ID NO 538
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
uucacugguc cauuacuuuc cuu                                              23

<210> SEQ ID NO 539
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
auucacuggu ccauuacuuu ccu                                              23

<210> SEQ ID NO 540
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
acuucacugg uccauuacuu ucc                                              23

<210> SEQ ID NO 541
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
accuucacug guccauuacu uuc                                              23

<210> SEQ ID NO 542
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
aaccuucacu gguccauuac uuu                                              23

<210> SEQ ID NO 543
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 543
uggaauccau gcaggccuuc agu                                              23

<210> SEQ ID NO 544
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
auggaaucca ugcaggccuu cag                                              23

<210> SEQ ID NO 545
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
acauggaauc caugcaggcc uuc                                              23

<210> SEQ ID NO 546
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
aacauggaau ccaugcaggc cuu                                              23

<210> SEQ ID NO 547
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
aaacauggaa uccaugcagg ccu                                              23

<210> SEQ ID NO 548
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
ugaacaugga auccaugcag gcc                                              23
```

```
<210> SEQ ID NO 549
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
augaacaugg aauccaugca ggc                                           23

<210> SEQ ID NO 550
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
aucuucaucc uuuggcccac cgu                                           23

<210> SEQ ID NO 551
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
uccaacaugc cucucuucau ccu                                           23

<210> SEQ ID NO 552
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
aaugccucuc uucauccuuu ggc                                           23

<210> SEQ ID NO 553
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
aacaugccuc ucuucauccu uug                                           23

<210> SEQ ID NO 554
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 554
aaacaugccu cucuucaucc uuu                                              23

<210> SEQ ID NO 555
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
acaacaugcc ucucuucauc cuu                                              23

<210> SEQ ID NO 556
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
auccaacaug ccucucuuca ucc                                              23

<210> SEQ ID NO 557
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557 agucccaac augccucucu uca                                               23

<210> SEQ ID NO 558
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
uccaccuuug cccaagucau cug                                              23

<210> SEQ ID NO 559
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
aucugcuuuu ucauggacca cca                                              23

<210> SEQ ID NO 560
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 560
aaucugcuuu uucauggacc acc                                           23

<210> SEQ ID NO 561
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
ucaucugcuu uuucauggac cac                                           23

<210> SEQ ID NO 562
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
accuuugccc aagucaucug cuu                                           23

<210> SEQ ID NO 563
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
acaccuuugc ccaagucauc ugc                                           23

<210> SEQ ID NO 564
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
aauuuccacc uuugcccaag uca                                           23

<210> SEQ ID NO 565
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
aaucccaauu acaccacaag cca                                           23
```

<210> SEQ ID NO 566
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 566
agaucccaau uacaccacaa gcc                                          23

<210> SEQ ID NO 567
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 567
acgaucccaa uuacaccaca agc                                          23

<210> SEQ ID NO 568
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 568
agcgauccca auuacaccac aag                                          23

<210> SEQ ID NO 569
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 569
aggcgauccc aauuacacca caa                                          23

<210> SEQ ID NO 570
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 570
agaaauugau gaugcccugc acu                                          23

<210> SEQ ID NO 571
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 571
ucgaaauuga ugaugcccug cac                                              23

<210> SEQ ID NO 572
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
aucgaaauug augaugcccu gca                                              23

<210> SEQ ID NO 573
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
acucgaaauu gaugaugccc ugc                                              23

<210> SEQ ID NO 574
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
ugcucgaaau ugaugaugcc cug                                              23

<210> SEQ ID NO 575
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
augcucgaaa uugaugaugc ccu                                              23

<210> SEQ ID NO 576
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
uucugcucga aauugaugau gcc                                              23

<210> SEQ ID NO 577
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
auucugcucg aaauugauga ugc                                               23

<210> SEQ ID NO 578
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
acuucugcuc gaaauugaug aug                                               23

<210> SEQ ID NO 579
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
accuucaguc aguccuuuaa ugc                                               23

<210> SEQ ID NO 580
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
aucuccaaac ucaugaacau gga                                               23

<210> SEQ ID NO 581
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
auuaucucca aacucaugaa cau                                               23

<210> SEQ ID NO 582
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
uauuaucucc aaacucauga aca                                               23
```

-continued

<210> SEQ ID NO 583
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
auguauuauc uccaaacuca uga                                              23

<210> SEQ ID NO 584
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
acagaaucuu caauagacac auc                                              23

<210> SEQ ID NO 585
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
aacagaaucu ucaauagaca cau                                              23

<210> SEQ ID NO 586
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
augcuuuuuc auggaccacc agu                                              23

<210> SEQ ID NO 587
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
ucugcuuuuu cauggaccac cag                                              23

<210> SEQ ID NO 588
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 588
agccaaugau gcaauggucu ccu                                    23

<210> SEQ ID NO 589
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589 acuuuucau ggaccaccag ugu                                     23

<210> SEQ ID NO 590
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590 ugcuuuuca uggaccacca gug                                     23

<210> SEQ ID NO 591
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
auacuuucuu cauuccacc uuu                                     23

<210> SEQ ID NO 592
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592 auuccuguc uuuguacuuu cuu                                     23

<210> SEQ ID NO 593
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593 aguuccugu cuuuguacuu ucu                                     23

<210> SEQ ID NO 594
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594 acguuccug ucuuguacu uuc                                           23

<210> SEQ ID NO 595
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595 agcguuccu gucuuguac uuu                                           23

<210> SEQ ID NO 596
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
aagcguuucc ugucuuugua cuu                                         23

<210> SEQ ID NO 597
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
acagcguuuc cugucuuugu acu                                         23

<210> SEQ ID NO 598
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
uuccagcguu uccugucuuu gua                                         23

<210> SEQ ID NO 599
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
```
ucccaauuac accacaagcc aaa						23

<210> SEQ ID NO 600
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
aucccaauua caccacaagc caa						23

<210> SEQ ID NO 601
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
uuacaccaca agccaaacga cuu						23

<210> SEQ ID NO 602
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
auuacaccac aagccaaacg acu						23

<210> SEQ ID NO 603
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
aauuacacca caagccaaac gac						23

<210> SEQ ID NO 604
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
aaauuacacc acaagccaaa cga						23

<210> SEQ ID NO 605
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 605
acaauuacac cacaagccaa acg                                            23

<210> SEQ ID NO 606
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
accaauuaca ccacaagcca aac                                            23

<210> SEQ ID NO 607
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
uuauugggcg aucccaauua cac                                            23

<210> SEQ ID NO 608
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
augacuuggg caaaggugga a                                              21

<210> SEQ ID NO 609
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
ugacuugggc aaagguggaa a                                              21

<210> SEQ ID NO 610
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
gacuugggca aagguggaaa u                                              21

<210> SEQ ID NO 611
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
aagguggaaa ugaagaaagu a                                                  21

<210> SEQ ID NO 612
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
aauuucgagc agaaggaaag u                                                  21

<210> SEQ ID NO 613
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
gagcagaagg aaaguaaugg a                                                  21

<210> SEQ ID NO 614
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
agaaggaaag uaauggacca u                                                  21

<210> SEQ ID NO 615
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
gaaggaaagu aauggaccag u                                                  21

<210> SEQ ID NO 616
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
```
aggaaaguaa uggaccagug a                                              21

<210> SEQ ID NO 617
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
ggaaaguaau ggaccaguga a                                              21

<210> SEQ ID NO 618
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
gaaaguaaug gaccagugaa u                                              21

<210> SEQ ID NO 619
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
aaaguaaugg accagugaag u                                              21

<210> SEQ ID NO 620
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
aaguaaugga ccagugaagg u                                              21

<210> SEQ ID NO 621
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
aguaauggac cagugaaggu u                                              21

<210> SEQ ID NO 622
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 622
ugaaggccug cauggauucc a         21

<210> SEQ ID NO 623
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
gaaggccugc auggauucca u         21

<210> SEQ ID NO 624
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
aggccugcau ggauuccaug u         21

<210> SEQ ID NO 625
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
ggccugcaug gauuccaugu u         21

<210> SEQ ID NO 626
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
gccugcaugg auuccauguu u         21

<210> SEQ ID NO 627
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
ccugcaugga uuccauguuc a         21

```
<210> SEQ ID NO 628
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
cugcauggau uccauguuca u                                              21

<210> SEQ ID NO 629
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
ggugggccaa aggaugaaga u                                              21

<210> SEQ ID NO 630
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
gaugaagaga ggcauguugg a                                              21

<210> SEQ ID NO 631
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
caaaggauga agagaggcau u                                              21

<210> SEQ ID NO 632
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
aaggaugaag agaggcaugu u                                              21

<210> SEQ ID NO 633
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 633
aggaugaaga gaggcauguu u                                              21

<210> SEQ ID NO 634
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
ggaugaagag aggcauguug u                                              21

<210> SEQ ID NO 635
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
augaagagag gcauguugga u                                              21

<210> SEQ ID NO 636
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
aagagaggca uguuggagac u                                              21

<210> SEQ ID NO 637
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
gaugacuugg gcaaaggugg a                                              21

<210> SEQ ID NO 638
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
gugguccaug aaaaagcaga u                                              21

<210> SEQ ID NO 639
<211> LENGTH: 21
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 639
ugguccauga aaaagcagau u                                              21

<210> SEQ ID NO 640
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
gguccaugaa aaagcagaug a                                              21

<210> SEQ ID NO 641
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
gcagaugacu ugggcaaagg u                                              21

<210> SEQ ID NO 642
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
agaugacuug ggcaaaggug u                                              21

<210> SEQ ID NO 643
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
acuugggcaa aggugaaau u                                               21

<210> SEQ ID NO 644
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644 gcuugguggug uaauugggau u                                             21
```

<210> SEQ ID NO 645
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 645
cuuguggugu aauuggauc u                                              21

<210> SEQ ID NO 646
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 646 uugguguua auugggaucg u                                              21

<210> SEQ ID NO 647
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 647
ugugguguaa uugggaucgc u                                             21

<210> SEQ ID NO 648
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 648
gugguguaau ugggaucgcc u                                             21

<210> SEQ ID NO 649
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 649
ugcagggcau caucaauuuc u                                             21

<210> SEQ ID NO 650
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 650
gcagggcauc aucaauuucg a					21

<210> SEQ ID NO 651
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
cagggcauca ucaauuucga u					21

<210> SEQ ID NO 652
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
agggcaucau caauuucgag u					21

<210> SEQ ID NO 653
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
gggcaucauc aauuucgagc a					21

<210> SEQ ID NO 654
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
ggcaucauca auuucgagca u					21

<210> SEQ ID NO 655
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
caucaucaau uucgagcaga a					21

<210> SEQ ID NO 656
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
aucaucaauu ucgagcagaa u                                        21

<210> SEQ ID NO 657
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
ucaucaauuu cgagcagaag u                                        21

<210> SEQ ID NO 658
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
auuaaaggac ugacugaagg u                                        21

<210> SEQ ID NO 659
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
cauguucaug aguuuggaga u                                        21

<210> SEQ ID NO 660
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
guucaugagu uuggagauaa u                                        21

<210> SEQ ID NO 661
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
uucaugaguu uggagauaau a                                        21
```

```
<210> SEQ ID NO 662
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
augaguuugg agauaauaca u                                              21

<210> SEQ ID NO 663
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
ugugucuauu gaagauucug u                                              21

<210> SEQ ID NO 664
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
gugucuauug aagauucugu u                                              21

<210> SEQ ID NO 665
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
ugguggucca ugaaaaagca u                                              21

<210> SEQ ID NO 666
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
ggugguccau gaaaaagcag a                                              21

<210> SEQ ID NO 667
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 667
gagaccauug caucauuggc u           21

<210> SEQ ID NO 668
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
acuggugguc caugaaaaag u           21

<210> SEQ ID NO 669
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
cugguggucc augaaaaagc a           21

<210> SEQ ID NO 670
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
agguggaaau gaagaaagua u           21

<210> SEQ ID NO 671
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
gaaaguacaa agacaggaaa u           21

<210> SEQ ID NO 672
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
aaaguacaaa gacaggaaac u           21

<210> SEQ ID NO 673
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
aaguacaaag acaggaaacg u                                              21

<210> SEQ ID NO 674
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
aguacaaaga caggaaacgc u                                              21

<210> SEQ ID NO 675
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
guacaaagac aggaaacgcu u                                              21

<210> SEQ ID NO 676
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
uacaaagaca ggaaacgcug u                                              21

<210> SEQ ID NO 677
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
caaagacagg aaacgcugga a                                              21

<210> SEQ ID NO 678
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
```

-continued uggcuugugg uguaauuggg a                                            21

<210> SEQ ID NO 679
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
ggcuuguggu guaauuggga u                                            21

<210> SEQ ID NO 680
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680 gucguuggc uugguggugua a                                            21

<210> SEQ ID NO 681
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
ucguuuggcu ugugguguaa u                                            21

<210> SEQ ID NO 682
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
cguuuggcuu gugguguaau u                                            21

<210> SEQ ID NO 683
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
guuuggcuug gugguaauu u                                             21

<210> SEQ ID NO 684
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 684
uuuggcuugu gguguaauug u                                              21

<210> SEQ ID NO 685
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
uuggcuugug guguaauugg u                                              21

<210> SEQ ID NO 686
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
guaauuggga ucgcccaaua a                                              21

<210> SEQ ID NO 687
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
uuccaccuuu gcccaaguca ucu                                            23

<210> SEQ ID NO 688
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
uuuccaccuu ugcccaaguc auc                                            23

<210> SEQ ID NO 689
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
auuuccaccu uugcccaagu cau                                            23

<210> SEQ ID NO 690
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
uacuuucuuc auuuccaccu uug                                               23

<210> SEQ ID NO 691
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691 acuuccuuc ugcucgaaau uga                                                23

<210> SEQ ID NO 692
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
uccauuacuu uccuucugcu cga                                               23

<210> SEQ ID NO 693
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
augguccauu acuuuccuuc ugc                                               23

<210> SEQ ID NO 694
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
acugguccau uacuuuccuu cug                                               23

<210> SEQ ID NO 695
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
```
ucacuggucc auuacuuucc uuc                                        23

<210> SEQ ID NO 696
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
uucacugguc cauuacuuuc cuu                                        23

<210> SEQ ID NO 697
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
auucacuggu ccauuacuuu ccu                                        23

<210> SEQ ID NO 698
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
acuucacugg uccauuacuu ucc                                        23

<210> SEQ ID NO 699
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
accuucacug guccauuacu uuc                                        23

<210> SEQ ID NO 700
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
aaccuucacu gguccauuac uuu                                        23

<210> SEQ ID NO 701
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 701
uggaauccau gcaggccuuc agu                                              23

<210> SEQ ID NO 702
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
auggaaucca ugcaggccuu cag                                              23

<210> SEQ ID NO 703
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
acauggaauc caugcaggcc uuc                                              23

<210> SEQ ID NO 704
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
aacauggaau ccaugcaggc cuu                                              23

<210> SEQ ID NO 705
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
aaacauggaa uccaugcagg ccu                                              23

<210> SEQ ID NO 706
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
ugaacaugga auccaugcag gcc                                              23

```
<210> SEQ ID NO 707
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
augaacaugg aauccaugca ggc                                              23

<210> SEQ ID NO 708
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
aucuucaucc uuuggcccac cgu                                              23

<210> SEQ ID NO 709
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
uccaacaugc cucucuucau ccu                                              23

<210> SEQ ID NO 710
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
aaugccucuc uucauccuuu ggc                                              23

<210> SEQ ID NO 711
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
aacaugccuc ucuucauccu uug                                              23

<210> SEQ ID NO 712
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 712
aaacaugccu cucuucaucc uuu                                              23

<210> SEQ ID NO 713
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
acaacaugcc ucucuucauc cuu                                              23

<210> SEQ ID NO 714
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714
auccaacaug ccucucuuca ucc                                              23

<210> SEQ ID NO 715
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715 agucccaac augccucucu uca                                               23

<210> SEQ ID NO 716
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
uccaccuuug cccaagucau cug                                              23

<210> SEQ ID NO 717
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
aucugcuuuu ucauggacca cca                                              23

<210> SEQ ID NO 718
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 718
aaucugcuuu uucauggacc acc                                          23

<210> SEQ ID NO 719
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
ucaucugcuu uuucauggac cac                                          23

<210> SEQ ID NO 720
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
accuuugccc aagucaucug cuu                                          23

<210> SEQ ID NO 721
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
acaccuuugc ccaagucauc ugc                                          23

<210> SEQ ID NO 722
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
aauuuccacc uuugcccaag uca                                          23

<210> SEQ ID NO 723
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
aaucccaauu acaccacaag cca                                          23
```

<210> SEQ ID NO 724
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
agaucccaau uacaccacaa gcc                                              23

<210> SEQ ID NO 725
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
acgaucccaa uuacaccaca agc                                              23

<210> SEQ ID NO 726
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
agcgauccca auuacaccac aag                                              23

<210> SEQ ID NO 727
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
aggcgauccc aauuacacca caa                                              23

<210> SEQ ID NO 728
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
agaaauugau gaugcccugc acu                                              23

<210> SEQ ID NO 729
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
ucgaaauuga ugaugcccug cac                                          23

<210> SEQ ID NO 730
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
aucgaaauug augaugcccu gca                                          23

<210> SEQ ID NO 731
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 731
acucgaaauu gaugaugccc ugc                                          23

<210> SEQ ID NO 732
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
ugcucgaaau ugaugaugcc cug                                          23

<210> SEQ ID NO 733
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
augcucgaaa uugaugaugc ccu                                          23

<210> SEQ ID NO 734
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
uucugcucga aauugaugau gcc                                          23

<210> SEQ ID NO 735
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735
auucugcucg aaauugauga ugc                                              23

<210> SEQ ID NO 736
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 736
acuucugcuc gaaauugaug aug                                              23

<210> SEQ ID NO 737
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
accuucaguc aguccuuuaa ugc                                              23

<210> SEQ ID NO 738
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
aucuccaaac ucaugaacau gga                                              23

<210> SEQ ID NO 739
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
auuaucucca aacucaugaa cau                                              23

<210> SEQ ID NO 740
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740
uauuaucucc aaacucauga aca                                              23
```

<210> SEQ ID NO 741
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
auguauuauc uccaaacuca uga                                           23

<210> SEQ ID NO 742
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742
acagaaucuu caauagacac auc                                           23

<210> SEQ ID NO 743
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
aacagaaucu ucaauagaca cau                                           23

<210> SEQ ID NO 744
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
augcuuuuuc auggaccacc agu                                           23

<210> SEQ ID NO 745
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
ucugcuuuuu cauggaccac cag                                           23

<210> SEQ ID NO 746
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 746
agccaaugau gcaauggucu ccu                                              23

<210> SEQ ID NO 747
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
acuuuuucau ggaccaccag ugu                                              23

<210> SEQ ID NO 748
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
ugcuuuuuca uggaccacca gug                                              23

<210> SEQ ID NO 749
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
auacuuucuu cauuccacc uuu                                               23

<210> SEQ ID NO 750
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750 auuccuguc uuuguacuuu cuu                                               23

<210> SEQ ID NO 751
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751 aguuccugu cuuuguacuu ucu                                               23

<210> SEQ ID NO 752
<211> LENGTH: 23

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752 acguuccug ucuuuguacu uuc                                              23

<210> SEQ ID NO 753
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753 agcguuccu gucuuuguac uuu                                              23

<210> SEQ ID NO 754
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 754
aagcguuucc ugucuuugua cuu                                             23

<210> SEQ ID NO 755
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
acagcguuuc cugucuuugu acu                                             23

<210> SEQ ID NO 756
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
uuccagcguu uccugucuuu gua                                             23

<210> SEQ ID NO 757
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
```
ucccaauuac accacaagcc aaa                                               23

<210> SEQ ID NO 758
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
aucccaauua caccacaagc caa                                               23

<210> SEQ ID NO 759
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
uuacaccaca agccaaacga cuu                                               23

<210> SEQ ID NO 760
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
auuacaccac aagccaaacg acu                                               23

<210> SEQ ID NO 761
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
aauuacacca caagccaaac gac                                               23

<210> SEQ ID NO 762
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
aaauuacacc acaagccaaa cga                                               23

<210> SEQ ID NO 763
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 763
acaauuacac cacaagccaa acg                                              23

<210> SEQ ID NO 764
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
accaauuaca ccacaagcca aac                                              23

<210> SEQ ID NO 765
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
uuauugggcg aucccaauua cac                                              23

<210> SEQ ID NO 766
<211> LENGTH: 23
<212> TYPE: RNA
<213> ORGANISM: Homo sapiens

<400> SEQUENCE: 766
agaugacuug ggcaaaggug gaa                                              23

<210> SEQ ID NO 767
<211> LENGTH: 23
<212> TYPE: RNA
<213> ORGANISM: Homo sapiens

<400> SEQUENCE: 767
gaugacuugg gcaaaggugg aaa                                              23

<210> SEQ ID NO 768
<211> LENGTH: 23
<212> TYPE: RNA
<213> ORGANISM: Homo sapiens

<400> SEQUENCE: 768
augacuuggg caaaggugga aau                                              23

<210> SEQ ID NO 769
<211> LENGTH: 23
<212> TYPE: RNA
<213> ORGANISM: Homo sapiens

<400> SEQUENCE: 769
caaaggugga aaugaagaaa gua                                              23

<210> SEQ ID NO 770
<211> LENGTH: 23
<212> TYPE: RNA
```

```
<213> ORGANISM: Homo sapiens

<400> SEQUENCE: 770
ucaauuucga gcagaaggaa agu                                           23

<210> SEQ ID NO 771
<211> LENGTH: 23
<212> TYPE: RNA
<213> ORGANISM: Homo sapiens

<400> SEQUENCE: 771
ucgagcagaa ggaaaguaau gga                                           23

<210> SEQ ID NO 772
<211> LENGTH: 23
<212> TYPE: RNA
<213> ORGANISM: Homo sapiens

<400> SEQUENCE: 772
gcagaaggaa aguaauggac cag                                           23

<210> SEQ ID NO 773
<211> LENGTH: 23
<212> TYPE: RNA
<213> ORGANISM: Homo sapiens

<400> SEQUENCE: 773
cagaaggaaa guaauggacc agu                                           23

<210> SEQ ID NO 774
<211> LENGTH: 23
<212> TYPE: RNA
<213> ORGANISM: Homo sapiens

<400> SEQUENCE: 774
gaaggaaagu aauggaccag uga                                           23

<210> SEQ ID NO 775
<211> LENGTH: 23
<212> TYPE: RNA
<213> ORGANISM: Homo sapiens

<400> SEQUENCE: 775
aaggaaagua auggaccagu gaa                                           23

<210> SEQ ID NO 776
<211> LENGTH: 23
<212> TYPE: RNA
<213> ORGANISM: Homo sapiens

<400> SEQUENCE: 776
aggaaaguaa uggaccagug aag                                           23

<210> SEQ ID NO 777
<211> LENGTH: 23
<212> TYPE: RNA
<213> ORGANISM: Homo sapiens

<400> SEQUENCE: 777
ggaaaguaau ggaccaguga agg                                           23

<210> SEQ ID NO 778
<211> LENGTH: 23
```

-continued

<212> TYPE: RNA
<213> ORGANISM: Homo sapiens

<400> SEQUENCE: 778
gaaaguaaug gaccagugaa ggu                                    23

<210> SEQ ID NO 779
<211> LENGTH: 23
<212> TYPE: RNA
<213> ORGANISM: Homo sapiens

<400> SEQUENCE: 779
aaaguaaugg accagugaag gug                                    23

<210> SEQ ID NO 780
<211> LENGTH: 23
<212> TYPE: RNA
<213> ORGANISM: Homo sapiens

<400> SEQUENCE: 780
acugaaggcc ugcauggauu cca                                    23

<210> SEQ ID NO 781
<211> LENGTH: 23
<212> TYPE: RNA
<213> ORGANISM: Homo sapiens

<400> SEQUENCE: 781
cugaaggccu gcauggauuc cau                                    23

<210> SEQ ID NO 782
<211> LENGTH: 23
<212> TYPE: RNA
<213> ORGANISM: Homo sapiens

<400> SEQUENCE: 782
gaaggccugc auggauucca ugu                                    23

<210> SEQ ID NO 783
<211> LENGTH: 23
<212> TYPE: RNA
<213> ORGANISM: Homo sapiens

<400> SEQUENCE: 783
aaggccugca uggauuccau guu                                    23

<210> SEQ ID NO 784
<211> LENGTH: 23
<212> TYPE: RNA
<213> ORGANISM: Homo sapiens

<400> SEQUENCE: 784
aggccugcau ggauuccaug uuc                                    23

<210> SEQ ID NO 785
<211> LENGTH: 23
<212> TYPE: RNA
<213> ORGANISM: Homo sapiens

<400> SEQUENCE: 785
ggccugcaug gauuccaugu uca                                    23

<210> SEQ ID NO 786

```
<211> LENGTH: 23
<212> TYPE: RNA
<213> ORGANISM: Homo sapiens

<400> SEQUENCE: 786
gccugcaugg auuccauguu cau                                              23

<210> SEQ ID NO 787
<211> LENGTH: 23
<212> TYPE: RNA
<213> ORGANISM: Homo sapiens

<400> SEQUENCE: 787
acggugggcc aaaggaugaa gag                                              23

<210> SEQ ID NO 788
<211> LENGTH: 23
<212> TYPE: RNA
<213> ORGANISM: Homo sapiens

<400> SEQUENCE: 788
aggaugaaga gaggcauguu gga                                              23

<210> SEQ ID NO 789
<211> LENGTH: 23
<212> TYPE: RNA
<213> ORGANISM: Homo sapiens

<400> SEQUENCE: 789
gccaaaggau gaagagaggc aug                                              23

<210> SEQ ID NO 790
<211> LENGTH: 23
<212> TYPE: RNA
<213> ORGANISM: Homo sapiens

<400> SEQUENCE: 790
caaaggauga agagaggcau guu                                              23

<210> SEQ ID NO 791
<211> LENGTH: 23
<212> TYPE: RNA
<213> ORGANISM: Homo sapiens

<400> SEQUENCE: 791
aaaggaugaa gagaggcaug uug                                              23

<210> SEQ ID NO 792
<211> LENGTH: 23
<212> TYPE: RNA
<213> ORGANISM: Homo sapiens

<400> SEQUENCE: 792
aaggaugaag agaggcaugu ugg                                              23

<210> SEQ ID NO 793
<211> LENGTH: 23
<212> TYPE: RNA
<213> ORGANISM: Homo sapiens

<400> SEQUENCE: 793
ggaugaagag aggcauguug gag                                              23
```

```
<210> SEQ ID NO 794
<211> LENGTH: 23
<212> TYPE: RNA
<213> ORGANISM: Homo sapiens

<400> SEQUENCE: 794
ugaagagagg cauguuggag acc                                              23

<210> SEQ ID NO 795
<211> LENGTH: 23
<212> TYPE: RNA
<213> ORGANISM: Homo sapiens

<400> SEQUENCE: 795
cagaugacuu gggcaaaggu gga                                              23

<210> SEQ ID NO 796
<211> LENGTH: 23
<212> TYPE: RNA
<213> ORGANISM: Homo sapiens

<400> SEQUENCE: 796
ugguggucca ugaaaagca gau                                               23

<210> SEQ ID NO 797
<211> LENGTH: 23
<212> TYPE: RNA
<213> ORGANISM: Homo sapiens

<400> SEQUENCE: 797
ggugguccau gaaaaagcag aug                                              23

<210> SEQ ID NO 798
<211> LENGTH: 23
<212> TYPE: RNA
<213> ORGANISM: Homo sapiens

<400> SEQUENCE: 798
gugguccaug aaaaagcaga uga                                              23

<210> SEQ ID NO 799
<211> LENGTH: 23
<212> TYPE: RNA
<213> ORGANISM: Homo sapiens

<400> SEQUENCE: 799
aagcagauga cuugggcaaa ggu                                              23

<210> SEQ ID NO 800
<211> LENGTH: 23
<212> TYPE: RNA
<213> ORGANISM: Homo sapiens

<400> SEQUENCE: 800
gcagaugacu ugggcaaagg ugg                                              23

<210> SEQ ID NO 801
<211> LENGTH: 23
<212> TYPE: RNA
<213> ORGANISM: Homo sapiens

<400> SEQUENCE: 801
ugacuugggc aaaggugga aug                                               23
```

```
<210> SEQ ID NO 802
<211> LENGTH: 23
<212> TYPE: RNA
<213> ORGANISM: Homo sapiens

<400> SEQUENCE: 802
uggcuugugg uguaauuggg auc                                              23

<210> SEQ ID NO 803
<211> LENGTH: 23
<212> TYPE: RNA
<213> ORGANISM: Homo sapiens

<400> SEQUENCE: 803
ggcuuguggu guaauuggga ucg                                              23

<210> SEQ ID NO 804
<211> LENGTH: 23
<212> TYPE: RNA
<213> ORGANISM: Homo sapiens

<400> SEQUENCE: 804
gcuuguggug uaauugggau cgc                                              23

<210> SEQ ID NO 805
<211> LENGTH: 23
<212> TYPE: RNA
<213> ORGANISM: Homo sapiens

<400> SEQUENCE: 805 cuugguguqu aauugggauc gcc                                              23

<210> SEQ ID NO 806
<211> LENGTH: 23
<212> TYPE: RNA
<213> ORGANISM: Homo sapiens

<400> SEQUENCE: 806 uugguguqua auugggaucg ccc                                              23

<210> SEQ ID NO 807
<211> LENGTH: 23
<212> TYPE: RNA
<213> ORGANISM: Homo sapiens

<400> SEQUENCE: 807
agugcagggc aucaucaauu ucg                                              23

<210> SEQ ID NO 808
<211> LENGTH: 23
<212> TYPE: RNA
<213> ORGANISM: Homo sapiens

<400> SEQUENCE: 808
gugcagggca ucaucaauuu cga                                              23

<210> SEQ ID NO 809
<211> LENGTH: 23
<212> TYPE: RNA
<213> ORGANISM: Homo sapiens

<400> SEQUENCE: 809
ugcagggcau caucaauuuc gag                                              23
```

```
<210> SEQ ID NO 810
<211> LENGTH: 23
<212> TYPE: RNA
<213> ORGANISM: Homo sapiens

<400> SEQUENCE: 810
gcagggcauc aucaauuucg agc                                              23

<210> SEQ ID NO 811
<211> LENGTH: 23
<212> TYPE: RNA
<213> ORGANISM: Homo sapiens

<400> SEQUENCE: 811
cagggcauca ucaauuucga gca                                              23

<210> SEQ ID NO 812
<211> LENGTH: 23
<212> TYPE: RNA
<213> ORGANISM: Homo sapiens

<400> SEQUENCE: 812
agggcaucau caauuucgag cag                                              23

<210> SEQ ID NO 813
<211> LENGTH: 23
<212> TYPE: RNA
<213> ORGANISM: Homo sapiens

<400> SEQUENCE: 813
ggcaucauca auuucgagca gaa                                              23

<210> SEQ ID NO 814
<211> LENGTH: 23
<212> TYPE: RNA
<213> ORGANISM: Homo sapiens

<400> SEQUENCE: 814
gcaucaucaa uuucgagcag aag                                              23

<210> SEQ ID NO 815
<211> LENGTH: 23
<212> TYPE: RNA
<213> ORGANISM: Homo sapiens

<400> SEQUENCE: 815
caucaucaau uucgagcaga agg                                              23

<210> SEQ ID NO 816
<211> LENGTH: 23
<212> TYPE: RNA
<213> ORGANISM: Homo sapiens

<400> SEQUENCE: 816
gcauuaaagg acugacugaa ggc                                              23

<210> SEQ ID NO 817
<211> LENGTH: 23
<212> TYPE: RNA
<213> ORGANISM: Homo sapiens

<400> SEQUENCE: 817
```
uccauguuca ugaguuugga gau        23

<210> SEQ ID NO 818
<211> LENGTH: 23
<212> TYPE: RNA
<213> ORGANISM: Homo sapiens

<400> SEQUENCE: 818
auguucauga guuuggagau aau        23

<210> SEQ ID NO 819
<211> LENGTH: 23
<212> TYPE: RNA
<213> ORGANISM: Homo sapiens

<400> SEQUENCE: 819
uguucaugag uuuggagaua aua        23

<210> SEQ ID NO 820
<211> LENGTH: 23
<212> TYPE: RNA
<213> ORGANISM: Homo sapiens

<400> SEQUENCE: 820
ucaugaguuu ggagauaaua cag        23

<210> SEQ ID NO 821
<211> LENGTH: 23
<212> TYPE: RNA
<213> ORGANISM: Homo sapiens

<400> SEQUENCE: 821
gaugugucua uugaagauuc ugu        23

<210> SEQ ID NO 822
<211> LENGTH: 23
<212> TYPE: RNA
<213> ORGANISM: Homo sapiens

<400> SEQUENCE: 822
augugucuau ugaagauucu gug        23

<210> SEQ ID NO 823
<211> LENGTH: 23
<212> TYPE: RNA
<213> ORGANISM: Homo sapiens

<400> SEQUENCE: 823
acuggugguc caugaaaaag cau        23

<210> SEQ ID NO 824
<211> LENGTH: 23
<212> TYPE: RNA
<213> ORGANISM: Homo sapiens

<400> SEQUENCE: 824
cugguggucc augaaaaagc aga        23

<210> SEQ ID NO 825
<211> LENGTH: 23
<212> TYPE: RNA
<213> ORGANISM: Homo sapiens

<400> SEQUENCE: 825
aggagaccau ugcaucauug gcc                      23

<210> SEQ ID NO 826
<211> LENGTH: 23
<212> TYPE: RNA
<213> ORGANISM: Homo sapiens

<400> SEQUENCE: 826
acacuggugg uccaugaaaa agc                      23

<210> SEQ ID NO 827
<211> LENGTH: 23
<212> TYPE: RNA
<213> ORGANISM: Homo sapiens

<400> SEQUENCE: 827
cacugguggu ccaugaaaaa gca                      23

<210> SEQ ID NO 828
<211> LENGTH: 23
<212> TYPE: RNA
<213> ORGANISM: Homo sapiens

<400> SEQUENCE: 828
aaagguggaa augaagaaag uac                      23

<210> SEQ ID NO 829
<211> LENGTH: 23
<212> TYPE: RNA
<213> ORGANISM: Homo sapiens

<400> SEQUENCE: 829
aagaaaguac aaagacagga aac                      23

<210> SEQ ID NO 830
<211> LENGTH: 23
<212> TYPE: RNA
<213> ORGANISM: Homo sapiens

<400> SEQUENCE: 830
agaaaguaca aagacaggaa acg                      23

<210> SEQ ID NO 831
<211> LENGTH: 23
<212> TYPE: RNA
<213> ORGANISM: Homo sapiens

<400> SEQUENCE: 831
gaaaguacaa agacaggaaa cgc                      23

<210> SEQ ID NO 832
<211> LENGTH: 23
<212> TYPE: RNA
<213> ORGANISM: Homo sapiens

<400> SEQUENCE: 832
aaaguacaaa gacaggaaac gcu                      23

<210> SEQ ID NO 833
<211> LENGTH: 23
<212> TYPE: RNA
<213> ORGANISM: Homo sapiens

```
<400> SEQUENCE: 833
aaguacaaag acaggaaacg cug                                          23

<210> SEQ ID NO 834
<211> LENGTH: 23
<212> TYPE: RNA
<213> ORGANISM: Homo sapiens

<400> SEQUENCE: 834
aguacaaaga caggaaacgc ugg                                          23

<210> SEQ ID NO 835
<211> LENGTH: 23
<212> TYPE: RNA
<213> ORGANISM: Homo sapiens

<400> SEQUENCE: 835
uacaaagaca ggaaacgcug gaa                                          23

<210> SEQ ID NO 836
<211> LENGTH: 23
<212> TYPE: RNA
<213> ORGANISM: Homo sapiens

<400> SEQUENCE: 836
uuuggcuugu gguguaauug gga                                          23

<210> SEQ ID NO 837
<211> LENGTH: 23
<212> TYPE: RNA
<213> ORGANISM: Homo sapiens

<400> SEQUENCE: 837
uuggcuugug guguaauugg gau                                          23

<210> SEQ ID NO 838
<211> LENGTH: 23
<212> TYPE: RNA
<213> ORGANISM: Homo sapiens

<400> SEQUENCE: 838
aagucguuug gcuugguggug uaa                                         23

<210> SEQ ID NO 839
<211> LENGTH: 23
<212> TYPE: RNA
<213> ORGANISM: Homo sapiens

<400> SEQUENCE: 839
agucguuugg cuuguggugu aau                                          23

<210> SEQ ID NO 840
<211> LENGTH: 23
<212> TYPE: RNA
<213> ORGANISM: Homo sapiens

<400> SEQUENCE: 840
gucguuuggc uugugguguaa auu                                         23

<210> SEQ ID NO 841
<211> LENGTH: 23
<212> TYPE: RNA
<213> ORGANISM: Homo sapiens
```

```
<400> SEQUENCE: 841
ucguuuggcu uggguguaa uug                                          23

<210> SEQ ID NO 842
<211> LENGTH: 23
<212> TYPE: RNA
<213> ORGANISM: Homo sapiens

<400> SEQUENCE: 842
cguuuggcuu gugguguaau ugg                                         23

<210> SEQ ID NO 843
<211> LENGTH: 23
<212> TYPE: RNA
<213> ORGANISM: Homo sapiens

<400> SEQUENCE: 843
guuuggcuug ugguguaauu ggg                                         23

<210> SEQ ID NO 844
<211> LENGTH: 23
<212> TYPE: RNA
<213> ORGANISM: Homo sapiens

<400> SEQUENCE: 844
guguaauugg gaucgcccaa uaa                                         23

<210> SEQ ID NO 845
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
acggugggcc aaaggaugaa u                                           21

<210> SEQ ID NO 846
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 846
agaaautgau gaugcccugc acu                                         23

<210> SEQ ID NO 847
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

```
                                          -continued
      Molecule: Synthetic oligonucleotide"

<400> SEQUENCE: 847
ucgaaatuga ugaugcccug cac                                              23

<210> SEQ ID NO 848
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 848
uucugctcga aauugaugau gcc                                              23

<210> SEQ ID NO 849
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 849
uuacuutccu ucugcucgaa auu                                              23

<210> SEQ ID NO 850
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 850
auuacutucc uucugcucga aau                                              23

<210> SEQ ID NO 851
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 851
auucactggu ccauuacuuu ccu                                              23
```

```
<210> SEQ ID NO 852
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 852
aacacctuca cugguccauu acu                                              23

<210> SEQ ID NO 853
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 853
auggaatcca ugcaggccuu cag                                              23

<210> SEQ ID NO 854
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 854
ugaacatgga auccaugcag gcc                                              23

<210> SEQ ID NO 855
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 855
auuauctcca aacucaugaa cau                                              23

<210> SEQ ID NO 856
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

```
                          Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 856
auguautauc uccaaacuca uga                                              23

<210> SEQ ID NO 857
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 857
uuaaagtgag gaccugcacu ggu                                              23

<210> SEQ ID NO 858
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 858
ucuggataga ggauuaaagu gag                                              23

<210> SEQ ID NO 859
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
auucauccuu uggcccaccg ugu                                              23

<210> SEQ ID NO 860
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 860
aaugcctcuc uucauccuuu ggc                                              23
```

```
<210> SEQ ID NO 861
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 861
acaacatgcc ucucuucauc cuu                                             23

<210> SEQ ID NO 862
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 862
acagaatcuu caauagacac auc                                             23

<210> SEQ ID NO 863
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 863
agccaatgau gcaauggucu ccu                                             23

<210> SEQ ID NO 864
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 864
acuuuutcau ggaccaccag ugu                                             23

<210> SEQ ID NO 865
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 865
ugcuuutuca uggaccacca gug                                              23

<210> SEQ ID NO 866
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 866
augcuutuuc auggaccacc agu                                              23

<210> SEQ ID NO 867
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 867
ucugcutuuu cauggaccac cag                                              23

<210> SEQ ID NO 868
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 868
aucugctuuu ucauggacca cca                                              23

<210> SEQ ID NO 869
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 869
acaccutugc ccaagucauc ugc                      23

<210> SEQ ID NO 870
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 870
uccaccuuug cccaagucau cug                      23

<210> SEQ ID NO 871
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 871
uucauutcca ccuuugccca agu                      23

<210> SEQ ID NO 872
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 872
auacuutcuu cauuuccacc uuu                      23

<210> SEQ ID NO 873
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 873
auuucctguc uuuguacuuu cuu                      23

<210> SEQ ID NO 874
<211> LENGTH: 23
<212> TYPE: DNA

-continued

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 874
agcguutccu gucuuuguac uuu                                                  23

<210> SEQ ID NO 875
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 875
aagcgutucc ugucuuugua cuu                                                  23

<210> SEQ ID NO 876
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 876
acagcgtuuc cugucuuugu acu                                                  23

<210> SEQ ID NO 877
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 877
accaautaca ccacaagcca aac                                                  23

<210> SEQ ID NO 878
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source

```
<223> OTHER INFORMATION: /note="Description of Combined DNA/RNA
      Molecule: Synthetic oligonucleotide"

<400> SEQUENCE: 878
ucccaatuac accacaagcc aaa                                          23

<210> SEQ ID NO 879
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879 acgguggggcc aaaggaugaa u                                            21

<210> SEQ ID NO 880
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 880
agaaautgau gaugcccugc acu                                          23

<210> SEQ ID NO 881
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 881
ucgaaatuga ugaugcccug cac                                          23

<210> SEQ ID NO 882
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
aucgaaauug augaugcccu gca                                          23

<210> SEQ ID NO 883
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 883
acucgaaauu gaugaugccc ugc                                              23

<210> SEQ ID NO 884
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
ugcucgaaau ugaugaugcc cug                                              23

<210> SEQ ID NO 885
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
augcucgaaa uugaugaugc ccu                                              23

<210> SEQ ID NO 886
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 886
uucugctcga aauugaugau gcc                                              23

<210> SEQ ID NO 887
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
auucugcucg aaauugauga ugc                                              23

<210> SEQ ID NO 888
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
acuucugcuc gaaauugaug aug                                              23

```
<210> SEQ ID NO 889
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889 acuuccuuc ugcucgaaau uga                                              23

<210> SEQ ID NO 890
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 890 uacuuccuu cugcucgaaa uug                                              23

<210> SEQ ID NO 891
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 891
uuacuutccu ucugcucgaa auu                                             23

<210> SEQ ID NO 892
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 892
auuacutucc uucugcucga aau                                             23

<210> SEQ ID NO 893
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
uccauuacuu uccuucugcu cga                                             23
```

```
<210> SEQ ID NO 894
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
augguccauu acuuccuuc ugc                                             23

<210> SEQ ID NO 895
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 895
acugguccau uacuuccuu cug                                             23

<210> SEQ ID NO 896
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
ucacuggucc auuacuuucc uuc                                            23

<210> SEQ ID NO 897
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
uucacugguc cauuacuuuc cuu                                            23

<210> SEQ ID NO 898
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 898
auucactggu ccauuacuuu ccu                                            23

<210> SEQ ID NO 899
<211> LENGTH: 23
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 899
acuucacugg uccauuacuu ucc                                             23

<210> SEQ ID NO 900
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 900
accuucacug guccauuacu uuc                                             23

<210> SEQ ID NO 901
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
aaccuucacu gguccauuac uuu                                             23

<210> SEQ ID NO 902
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 902
aacacctuca cugguccauu acu                                             23

<210> SEQ ID NO 903
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
accuucaguc aguccuuuaa ugc                                             23

<210> SEQ ID NO 904
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 904
uggaauccau gcaggccuuc agu                                          23

<210> SEQ ID NO 905
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 905
auggaatcca ugcaggccuu cag                                          23

<210> SEQ ID NO 906
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
acauggaauc caugcaggcc uuc                                          23

<210> SEQ ID NO 907
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
aacauggaau ccaugcaggc cuu                                          23

<210> SEQ ID NO 908
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
aaacauggaa uccaugcagg ccu                                          23

<210> SEQ ID NO 909
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 909
```
ugaacatgga auccaugcag gcc          23

<210> SEQ ID NO 910
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
augaacaugg aauccaugca ggc          23

<210> SEQ ID NO 911
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
aaugaacaug gaauccaugc agg          23

<210> SEQ ID NO 912
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 912
aucuccaaac ucaugaacau gga          23

<210> SEQ ID NO 913
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 913
auuauctcca aacucaugaa cau          23

<210> SEQ ID NO 914
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
uauuaucucc aaacucauga aca          23

<210> SEQ ID NO 915

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 915
auguautauc uccaaacuca uga                                              23

<210> SEQ ID NO 916
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916
aaagugagga ccugcacugg uac                                              23

<210> SEQ ID NO 917
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 917
uaaagugagg accugcacug gua                                              23

<210> SEQ ID NO 918
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 918
uuaaagtgag gaccugcacu ggu                                              23

<210> SEQ ID NO 919
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
aauuaaagug aggaccugca cug                                              23

<210> SEQ ID NO 920
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
agauuaaagu gaggaccugc acu                                              23

<210> SEQ ID NO 921
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
aggauuaaag ugaggaccug cac                                              23

<210> SEQ ID NO 922
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
uggauagagg auuaaaguga gga                                              23

<210> SEQ ID NO 923
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923
auggauagag gauuaaagug agg                                              23

<210> SEQ ID NO 924
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 924
ucuggataga ggauuaaagu gag                                              23

<210> SEQ ID NO 925
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

```
<210> SEQ ID NO 926
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
auucauccuu uggcccaccg ugu                                              23

<210> SEQ ID NO 926
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
aucuucaucc uuuggcccac cgu                                              23

<210> SEQ ID NO 927
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 927
aaugcctcuc uucauccuuu ggc                                              23

<210> SEQ ID NO 928
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
aacaugccuc ucuucauccu uug                                              23

<210> SEQ ID NO 929
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 929
aaacaugccu cucuucaucc uuu                                              23

<210> SEQ ID NO 930
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 930
acaacaugcc ucucuucauc cuu                                          23

<210> SEQ ID NO 931
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
uccaacaugc cucucuucau ccu                                          23

<210> SEQ ID NO 932
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
auccaacaug ccucucuuca ucc                                          23

<210> SEQ ID NO 933
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
agucuccaac augccucucu uca                                          23

<210> SEQ ID NO 934
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 934
acagaatcuu caauagacac auc                                          23

<210> SEQ ID NO 935
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
aacagaaucu ucaauagaca cau                                          23
```

<210> SEQ ID NO 936
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 936
agccaatgau gcaauggucu ccu                                           23

<210> SEQ ID NO 937
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 937
acuuuutcau ggaccaccag ugu                                           23

<210> SEQ ID NO 938
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 938
ugcuuutuca uggaccacca gug                                           23

<210> SEQ ID NO 939
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 939
augcuutuuc auggaccacc agu                                           23

<210> SEQ ID NO 940
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 940
ucugcutuuu cauggaccac cag                                              23

<210> SEQ ID NO 941
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 941
aucugctuuu ucauggacca cca                                              23

<210> SEQ ID NO 942
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
aaucugcuuu uucauggacc acc                                              23

<210> SEQ ID NO 943
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
ucaucugcuu uuucauggac cac                                              23

<210> SEQ ID NO 944
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
accuuugccc aagucaucug cuu                                              23

<210> SEQ ID NO 945
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 945
acaccutugc ccaagucauc ugc                                              23

<210> SEQ ID NO 946
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 946
uccacctuug cccaagucau cug                                              23

<210> SEQ ID NO 947
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947
uuccaccuuu gcccaaguca ucu                                              23

<210> SEQ ID NO 948
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948
uuuccaccuu ugcccaaguc auc                                              23

<210> SEQ ID NO 949
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 949 auuccaccu uugcccaagu cau                                               23

<210> SEQ ID NO 950
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 950
aauuuccacc uuugcccaag uca                                              23

<210> SEQ ID NO 951
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 951
uucauutcca ccuuugccca agu                                              23

<210> SEQ ID NO 952
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 952
uacuuucuuc auuuccaccu uug                                              23

<210> SEQ ID NO 953
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 953
auacuutcuu cauuuccacc uuu                                              23

<210> SEQ ID NO 954
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 954
auuucctguc uuuguacuuu cuu                                              23

<210> SEQ ID NO 955
<211> LENGTH: 23
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 955
aguuuccugu cuuguacuu ucu                                                 23

<210> SEQ ID NO 956
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956 acguuccug ucuuuguacu uuc                                                 23

<210> SEQ ID NO 957
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 957
agcguutccu gucuuuguac uuu                                                23

<210> SEQ ID NO 958
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 958
aagcgutucc ugucuuugua cuu                                                23

<210> SEQ ID NO 959
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 959
acagcgtuuc cugucuuugu acu                                                23

<210> SEQ ID NO 960
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960
uuccagcguu uccugucuuu gua                                              23

<210> SEQ ID NO 961
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 961
uuacaccaca agccaaacga cuu                                              23

<210> SEQ ID NO 962
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 962
auuacaccac aagccaaacg acu                                              23

<210> SEQ ID NO 963
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 963
aauuacacca caagccaaac gac                                              23

<210> SEQ ID NO 964
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 964
aaauuacacc acaagccaaa cga                                              23

<210> SEQ ID NO 965
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
```
acaauuacac cacaagccaa acg                                          23

<210> SEQ ID NO 966
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 966
accaautaca ccacaagcca aac                                          23

<210> SEQ ID NO 967
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 967
ucccaatuac accacaagcc aaa                                          23

<210> SEQ ID NO 968
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 968
aucccaauua caccacaagc caa                                          23

<210> SEQ ID NO 969
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 969
aaucccaauu acaccacaag cca                                          23

<210> SEQ ID NO 970
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 970
agaucccaau uacaccacaa gcc                                          23

<210> SEQ ID NO 971
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971
acgaucccaa uuacaccaca agc                                           23

<210> SEQ ID NO 972
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972
agcgauccca auuacaccac aag                                           23

<210> SEQ ID NO 973
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 973 uuaugggcg aucccaauua cac                                            23

<210> SEQ ID NO 974
<211> LENGTH: 23
<212> TYPE: RNA
<213> ORGANISM: Homo sapiens

<400> SEQUENCE: 974
acacgguggg ccaaaggaug aag                                           23

<210> SEQ ID NO 975
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 975
caucaauuuc gagcagaagg a                                             21

<210> SEQ ID NO 976
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 976
agcagaagga aaguaaugga u 21

<210> SEQ ID NO 977
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 977
gcagaaggaa aguaauggac u 21

<210> SEQ ID NO 978
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 978
guaauggacc agugaaggug u 21

<210> SEQ ID NO 979
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 979
aauggaccag ugaaggugug u 21

<210> SEQ ID NO 980
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 980
guaccagugc agguccucac u 21

<210> SEQ ID NO 981
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 981
uaccagugca gguccucacu u 21

<210> SEQ ID NO 982
<211> LENGTH: 21
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 982
acuuuaaucc ucuauccaga a                                              21

<210> SEQ ID NO 983
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 983
gugggccaaa ggaugaagag a                                              21

<210> SEQ ID NO 984
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
ugggccaaag gaugaagaga u                                              21

<210> SEQ ID NO 985
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 985
gggccaaagg augaagagag u                                              21

<210> SEQ ID NO 986
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
ggccaaagga ugaagagagg u                                              21

<210> SEQ ID NO 987
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 987
gccaaaggau gaagagaggc a                                              21

<210> SEQ ID NO 988

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
ccaaaggaug aagagaggca u                                              21

<210> SEQ ID NO 989
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 989
aaaggaugaa gagaggcaug u                                              21

<210> SEQ ID NO 990
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 990
ugaagagagg cauguuggag a                                              21

<210> SEQ ID NO 991
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 991
agagaggcau guuggagacu u                                              21

<210> SEQ ID NO 992
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 992
gagaggcaug uuggagacuu u                                              21

<210> SEQ ID NO 993
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
```
agaggcaugu uggagacuug u                                            21

<210> SEQ ID NO 994
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 994
cagaugacuu gggcaaaggu u                                            21

<210> SEQ ID NO 995
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 995
cuugggcaaa gguggaaaug a                                            21

<210> SEQ ID NO 996
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 996
ugggcaaagg uggaaaugaa u                                            21

<210> SEQ ID NO 997
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 997
gggcaaaggu ggaaaugaag a                                            21

<210> SEQ ID NO 998
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 998
ggcaaaggug gaaaugaaga a                                            21

<210> SEQ ID NO 999
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 999
gcaaaggugg aaaugaagaa a                                              21

<210> SEQ ID NO 1000
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1000
caaaggugga aaugaagaaa u                                              21

<210> SEQ ID NO 1001
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
aaagguggaa augaagaaag u                                              21

<210> SEQ ID NO 1002
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1002
gguggaaaug aagaaaguac a                                              21

<210> SEQ ID NO 1003
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
guggaaauga agaaaguaca a                                              21

<210> SEQ ID NO 1004
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1004
uggaaaugaa gaaaguacaa a                                              21
```

-continued

```
<210> SEQ ID NO 1005
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1005
ggaaaugaag aaaguacaaa u                                                    21

<210> SEQ ID NO 1006
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1006
gaaaugaaga aaguacaaag a                                                    21

<210> SEQ ID NO 1007
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1007
aaaugaagaa aguacaaaga u                                                    21

<210> SEQ ID NO 1008
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1008
aaugaagaaa guacaaagac a                                                    21

<210> SEQ ID NO 1009
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1009
accuucugcu cgaaauugau gau                                                  23

<210> SEQ ID NO 1010
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 1010 uuccucucugc ucgaaauuga uga                                              23

<210> SEQ ID NO 1011
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1011 uuccutcug cucgaaauug aug                                                23

<210> SEQ ID NO 1012
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1012 auuccutcu gcucgaaauu gau                                                23

<210> SEQ ID NO 1013
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1013
acuutccuuc ugcucgaaau uga                                               23

<210> SEQ ID NO 1014
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1014
uacutuccuu cugcucgaaa uug                                               23
```

<210> SEQ ID NO 1015
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1015
uuactutccu ucugcucgaa auu                                              23

<210> SEQ ID NO 1016
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1016 aauuacuuc cuucugcucg aaa                                               23

<210> SEQ ID NO 1017
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1017
accauuacuu uccuucugcu cga                                              23

<210> SEQ ID NO 1018
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1018
auccauuacu uuccuucugc ucg                                              23

<210> SEQ ID NO 1019
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

<400> SEQUENCE: 1019
aguccatuac uuuccuucug cuc                                        23

<210> SEQ ID NO 1020
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1020
auggtccauu acuuccuuc ugc                                         23

<210> SEQ ID NO 1021
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1021
aacuggtcca uuacuuuccu ucu                                        23

<210> SEQ ID NO 1022
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1022
ucactggucc auuacuuucc uuc                                        23

<210> SEQ ID NO 1023
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1023
aacctucacu gguccauuac uuu                                        23

<210> SEQ ID NO 1024
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1024
acaccuucac ugguccauua cuu                                          23

<210> SEQ ID NO 1025
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1025
acacaccuuc acugguccau uac                                          23

<210> SEQ ID NO 1026
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1026
agugaggacc ugcacuggua cag                                          23

<210> SEQ ID NO 1027
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1027
aagugaggac cugcacuggu aca                                          23

<210> SEQ ID NO 1028
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1028
aaagtgagga ccugcacugg uac                                          23

<210> SEQ ID NO 1029
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1029
aggauagagg auuaaaguga gga                                          23

<210> SEQ ID NO 1030
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1030
acuggauaga ggauuaaagu gag                                          23

<210> SEQ ID NO 1031
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1031
uucuggauag aggauuaaag uga                                          23

<210> SEQ ID NO 1032
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1032
ucuctucauc cuuuggccca ccg                                          23

<210> SEQ ID NO 1033
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1033
aucucutcau ccuuuggccc acc                                          23

<210> SEQ ID NO 1034
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 1034
acuctctuca uccuuuggcc cac                                               23

<210> SEQ ID NO 1035
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1035
accucucuuc auccuuuggc cca                                               23

<210> SEQ ID NO 1036
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1036
ugcctctcuu cauccuuugg ccc                                               23

<210> SEQ ID NO 1037
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1037
augccucucu ucauccuuug gcc                                               23

<210> SEQ ID NO 1038
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1038
acaugccucu cuucauccuu ugg                                               23

<210> SEQ ID NO 1039
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 1039
aacatgccuc ucuucauccu uug                                           23

<210> SEQ ID NO 1040
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1040
accaacaugc cucucuucau ccu                                           23

<210> SEQ ID NO 1041
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1041
acuccaacau gccucucuuc auc                                           23

<210> SEQ ID NO 1042
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1042
aguctccaac augccucucu uca                                           23

<210> SEQ ID NO 1043
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1043
aagucuccaa caugccucuc uuc                                           23

<210> SEQ ID NO 1044
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 1044
aaagtctcca acaugccucu cuu                                               23

<210> SEQ ID NO 1045
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1045
acaagucucc aacaugccuc ucu                                               23

<210> SEQ ID NO 1046
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1046
accutugccc aagucaucug cuu                                               23

<210> SEQ ID NO 1047
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1047
aaccuuugcc caagucaucu gcu                                               23

<210> SEQ ID NO 1048
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1048
accaccuuug cccaagucau cug                                               23

<210> SEQ ID NO 1049
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

```
      Molecule: Synthetic oligonucleotide"

<400> SEQUENCE: 1049
aauutccacc uuugcccaag uca                                              23

<210> SEQ ID NO 1050
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1050 acauuccac cuuugcccaa guc                                               23

<210> SEQ ID NO 1051
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1051
uucatutcca ccuuugccca agu                                              23

<210> SEQ ID NO 1052
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1052
auucautucc accuuugccc aag                                              23

<210> SEQ ID NO 1053
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1053
acuucauuuc caccuuugcc caa                                              23

<210> SEQ ID NO 1054
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 1054
uucutcauuu ccaccuuugc cca                                         23

<210> SEQ ID NO 1055
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1055 uuucucauu uccaccuuug ccc                                          23

<210> SEQ ID NO 1056
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1056
auuucutcau uuccaccuuu gcc                                         23

<210> SEQ ID NO 1057
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1057
acuutctuca uuuccaccuu ugc                                         23

<210> SEQ ID NO 1058
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1058
```
uacutucuuc auuuccaccu uug                                              23

<210> SEQ ID NO 1059
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1059
auactutcuu cauuuccacc uuu                                              23

<210> SEQ ID NO 1060
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1060
aguacuuucu ucauuccac cuu                                               23

<210> SEQ ID NO 1061
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1061 uuguacuuc uucauuucca ccu                                               23

<210> SEQ ID NO 1062
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1062
uuugtacuuu cuucauuucc acc                                              23

<210> SEQ ID NO 1063
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 1063
auuuguacuu ucuucauuuc cac                                          23

<210> SEQ ID NO 1064
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1064
ucuutgtacu uucuucauuu cca                                          23

<210> SEQ ID NO 1065
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1065
aucutuguac uuucuucauu ucc                                          23

<210> SEQ ID NO 1066
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1066
uguctutgua cuuucuucau uuc                                          23

<210> SEQ ID NO 1067
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1067
ucaucaauuu cgagcagaag u                                            21

<210> SEQ ID NO 1068
<211> LENGTH: 21
<212> TYPE: RNA
<213> ORGANISM: Artificial Sequence
<220> FEATURE:
```

-continued

```
<221> NAME/KEY: source
<223> OTHER INFORMATION: /note="Description of Artificial Sequence:
      Synthetic oligonucleotide"

<400> SEQUENCE: 1068
caucaauuuc gagcagaagg a                                              21

<210> SEQ ID NO 1069
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1069
aucaauuucg agcagaagga a                                              21

<210> SEQ ID NO 1070
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1070
ucaauuucga gcagaaggaa a                                              21

<210> SEQ ID NO 1071
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1071
caauuucgag cagaaggaaa u                                              21

<210> SEQ ID NO 1072
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1072
aauuucgagc agaaggaaag u                                              21

<210> SEQ ID NO 1073
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1073
auuucgagca gaaggaaagu a                                              21
```

-continued

```
<210> SEQ ID NO 1074
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1074
uuucgagcag aaggaaagua a                                             21

<210> SEQ ID NO 1075
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1075
uucgagcaga aggaaaguaa u                                             21

<210> SEQ ID NO 1076
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1076
ucgagcagaa ggaaaguaau u                                             21

<210> SEQ ID NO 1077
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1077
cgagcagaag gaaaguaaug u                                             21

<210> SEQ ID NO 1078
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1078
gagcagaagg aaaguaaugg a                                             21

<210> SEQ ID NO 1079
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1079
agcagaagga aaguaaugga u                                              21

<210> SEQ ID NO 1080
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1080
gcagaaggaa aguaauggac u                                              21

<210> SEQ ID NO 1081
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1081
cagaaggaaa guaauggacc a                                              21

<210> SEQ ID NO 1082
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1082
agaaggaaag uaauggacca u                                              21

<210> SEQ ID NO 1083
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1083
gaaggaaagu aauggaccag u                                              21

<210> SEQ ID NO 1084
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1084
aaggaaagua auggaccagu u                                              21

<210> SEQ ID NO 1085
<211> LENGTH: 21
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 1085
aggaaaguaa uggaccagug a                                             21

<210> SEQ ID NO 1086
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1086
ggaaaguaau ggaccaguga a                                             21

<210> SEQ ID NO 1087
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1087
gaaaguaaug gaccagugaa u                                             21

<210> SEQ ID NO 1088
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1088
aaaguaaugg accagugaag u                                             21

<210> SEQ ID NO 1089
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1089
aaguaaugga ccagugaagg u                                             21

<210> SEQ ID NO 1090
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1090 aguauggac cagugaaggu u                                              21
```

```
<210> SEQ ID NO 1091
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1091
guaauggacc agugaaggug u                                              21

<210> SEQ ID NO 1092
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1092
uaauggacca gugaaggugu u                                              21

<210> SEQ ID NO 1093
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1093
aauggaccag ugaaggugug u                                              21

<210> SEQ ID NO 1094
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1094
guaccagugc agguccucac u                                              21

<210> SEQ ID NO 1095
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1095
uaccagugca gguccucacu u                                              21

<210> SEQ ID NO 1096
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 1096
accagugcag guccucacuu u                                              21

<210> SEQ ID NO 1097
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1097
ccagugcagg uccucacuuu a                                              21

<210> SEQ ID NO 1098
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1098
cagugcaggu ccucacuuua a                                              21

<210> SEQ ID NO 1099
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1099
agugcagguc cucacuuuaa u                                              21

<210> SEQ ID NO 1100
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1100
gugcaggucc ucacuuuaau u                                              21

<210> SEQ ID NO 1101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1101
ugcagguccu cacuuuaauc u                                              21

<210> SEQ ID NO 1102
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1102
gcagguccuc acuuuaaucc u                                              21

<210> SEQ ID NO 1103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1103
cagguccuca cuuuaauccu u                                              21

<210> SEQ ID NO 1104
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1104
agguccucac uuuaauccuc u                                              21

<210> SEQ ID NO 1105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1105
gguccucacu uuaauccucu a                                              21

<210> SEQ ID NO 1106
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1106
guccucacuu uaauccucua u                                              21

<210> SEQ ID NO 1107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1107
uccucacuuu aauccucuau u                                              21
```

<210> SEQ ID NO 1108
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1108
ccucacuuua auccucuauc u                                              21

<210> SEQ ID NO 1109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1109
cucacuuuaa uccucuaucc a                                              21

<210> SEQ ID NO 1110
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1110
ucacuuuaau ccucuaucca u                                              21

<210> SEQ ID NO 1111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1111
cacuuuaauc cucuauccag a                                              21

<210> SEQ ID NO 1112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1112
acuuuaaucc ucuauccaga a                                              21

<210> SEQ ID NO 1113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 1113
gugggccaaa ggaugaagag a                21

<210> SEQ ID NO 1114
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1114
ugggccaaag gaugaagaga u                21

<210> SEQ ID NO 1115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1115
gggccaaagg augaagagag u                21

<210> SEQ ID NO 1116
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1116
ggccaaagga ugaagagagg u                21

<210> SEQ ID NO 1117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1117
gccaaaggau gaagagaggc a                21

<210> SEQ ID NO 1118
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1118
ccaaaggaug aagagaggca u                21

<210> SEQ ID NO 1119
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1119
caaaggauga agagaggcau u                                              21

<210> SEQ ID NO 1120
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1120
aaaggaugaa gagaggcaug u                                              21

<210> SEQ ID NO 1121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1121
aaggaugaag agaggcaugu u                                              21

<210> SEQ ID NO 1122
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1122
aggaugaaga gaggcauguu u                                              21

<210> SEQ ID NO 1123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1123
ggaugaagag aggcauguug u                                              21

<210> SEQ ID NO 1124
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1124
```
gaugaagaga ggcauguugg a                                        21

<210> SEQ ID NO 1125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1125
augaagagag gcauguugga u                                        21

<210> SEQ ID NO 1126
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1126
ugaagagagg cauguuggag a                                        21

<210> SEQ ID NO 1127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1127
gaagagaggc auguuggaga u                                        21

<210> SEQ ID NO 1128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1128
aagagaggca uguuggagac u                                        21

<210> SEQ ID NO 1129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1129
agagaggcau guuggagacu u                                        21

<210> SEQ ID NO 1130
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1130
gagaggcaug uuggagacuu u                                              21

<210> SEQ ID NO 1131
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1131
agaggcaugu uggagacuug u                                              21

<210> SEQ ID NO 1132
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1132
gcagaugacu ugggcaaagg u                                              21

<210> SEQ ID NO 1133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1133
cagaugacuu gggcaaaggu u                                              21

<210> SEQ ID NO 1134
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1134
agaugacuug ggcaaaggug u                                              21

<210> SEQ ID NO 1135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1135
gaugacuugg gcaaaggugg a                                              21

<210> SEQ ID NO 1136

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1136
augacuuggg caaaggugga a                                              21

<210> SEQ ID NO 1137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1137
ugacuugggc aaagguggaa a                                              21

<210> SEQ ID NO 1138
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1138 gacuuggggca aagguggaaa u                                             21

<210> SEQ ID NO 1139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1139
acuugggcaa agguggaaau u                                              21

<210> SEQ ID NO 1140
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1140
cuugggcaaa gguggaaaug a                                              21

<210> SEQ ID NO 1141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1141
```

-continued uugggcaaag guggaaauga a                                            21

<210> SEQ ID NO 1142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1142
ugggcaaagg uggaaaugaa u                                            21

<210> SEQ ID NO 1143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1143
gggcaaaggu ggaaaugaag a                                            21

<210> SEQ ID NO 1144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1144
ggcaaaggug gaaaugaaga a                                            21

<210> SEQ ID NO 1145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1145
gcaaaggugg aaaugaagaa a                                            21

<210> SEQ ID NO 1146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1146
caaaggugga aaugaagaaa u                                            21

<210> SEQ ID NO 1147
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1147
aaagguggaa augaagaaag u                                              21

<210> SEQ ID NO 1148
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1148
aagguggaaa ugaagaaagu a                                              21

<210> SEQ ID NO 1149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1149
agguggaaau gaagaaagua u                                              21

<210> SEQ ID NO 1150
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1150
gguggaaaug aagaaaguac a                                              21

<210> SEQ ID NO 1151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1151
guggaaauga agaaaguaca a                                              21

<210> SEQ ID NO 1152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1152
uggaaaugaa gaaaguacaa a                                              21
```

-continued

<210> SEQ ID NO 1153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1153
ggaaaugaag aaaguacaaa u                                               21

<210> SEQ ID NO 1154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1154
gaaaugaaga aaguacaaag a                                               21

<210> SEQ ID NO 1155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1155
aaaugaagaa aguacaaaga u                                               21

<210> SEQ ID NO 1156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1156
aaugaagaaa guacaaagac a                                               21

<210> SEQ ID NO 1157
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1157
acuucugcuc gaaauugaug aug                                             23

<210> SEQ ID NO 1158
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1158
accuucugcu cgaaauugau gau                           23

<210> SEQ ID NO 1159
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1159 uuccucugc ucgaaauuga uga                            23

<210> SEQ ID NO 1160
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1160
uuuccutcug cucgaaauug aug                           23

<210> SEQ ID NO 1161
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1161 auuccucu gcucgaaauu gau                             23

<210> SEQ ID NO 1162
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1162
acuutccuuc ugcucgaaau uga                           23

<210> SEQ ID NO 1163
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1163
uacutuccuu cugcucgaaa uug                                              23

<210> SEQ ID NO 1164
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1164
uuactutccu ucugcucgaa auu                                              23

<210> SEQ ID NO 1165
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1165
auuacutucc uucugcucga aau                                              23

<210> SEQ ID NO 1166
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1166
aauuactuuc cuucugcucg aaa                                              23

<210> SEQ ID NO 1167
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1167
acauuacuuu ccuucugcuc gaa                                              23

<210> SEQ ID NO 1168
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1168
accauuacuu uccuucugcu cga                                              23

<210> SEQ ID NO 1169
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1169
auccauuacu uuccuucugc ucg                                              23

<210> SEQ ID NO 1170
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1170
aguccatuac uuuccuucug cuc                                              23

<210> SEQ ID NO 1171
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1171
ugguccauua cuuuccuucu gcu                                              23

<210> SEQ ID NO 1172
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1172
```
auggtccauu acuuccuuc ugc    23

<210> SEQ ID NO 1173
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1173
acugguccau uacuuccuu cug    23

<210> SEQ ID NO 1174
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1174
aacuggtcca uuacuuccu ucu    23

<210> SEQ ID NO 1175
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1175
ucactggucc auuacuuucc uuc    23

<210> SEQ ID NO 1176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1176
uucacugguc cauuacuuuc cuu    23

<210> SEQ ID NO 1177
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1177
auucacuggu ccauuacuuu ccu                                              23

<210> SEQ ID NO 1178
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1178
acuucacugg uccauuacuu ucc                                              23

<210> SEQ ID NO 1179
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1179
accuucacug guccauuacu uuc                                              23

<210> SEQ ID NO 1180
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1180
aacctucacu gguccauuac uuu                                              23

<210> SEQ ID NO 1181
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1181
acaccuucac ugguccauua cuu                                              23

<210> SEQ ID NO 1182
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1182
aacaccuuca cugguccauu acu                                              23

-continued

<210> SEQ ID NO 1183
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1183
acacaccuuc acugguccau uac                                              23

<210> SEQ ID NO 1184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1184
agugaggacc ugcacuggua cag                                              23

<210> SEQ ID NO 1185
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1185
aagugaggac cugcacuggu aca                                              23

<210> SEQ ID NO 1186
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1186
aaagtgagga ccugcacugg uac                                              23

<210> SEQ ID NO 1187
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1187
uaaagugagg accugcacug gua                                              23

<210> SEQ ID NO 1188
<211> LENGTH: 23
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1188
uuaaagtgag gaccugcacu ggu                                                23

<210> SEQ ID NO 1189
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1189
auuaaaguga ggaccugcac ugg                                                23

<210> SEQ ID NO 1190
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1190
aauuaaagug aggaccugca cug                                                23

<210> SEQ ID NO 1191
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1191
agauuaaagu gaggaccugc acu                                                23

<210> SEQ ID NO 1192
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1192
aggauuaaag ugaggaccug cac                                                23

<210> SEQ ID NO 1193
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1193
aaggauuaaa gugaggaccu gca                                     23

<210> SEQ ID NO 1194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1194
agaggauuaa agugaggacc ugc                                     23

<210> SEQ ID NO 1195
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1195
uagaggauua aagugaggac cug                                     23

<210> SEQ ID NO 1196
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1196
auagaggauu aaagugagga ccu                                     23

<210> SEQ ID NO 1197
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1197
aauagaggau uaaagugagg acc                                     23

<210> SEQ ID NO 1198
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1198
agauagagga uuaaagugag gac                                     23

<210> SEQ ID NO 1199
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1199
aggauagagg auuaaaguga gga                                           23

<210> SEQ ID NO 1200
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1200
auggauagag gauuaaagug agg                                           23

<210> SEQ ID NO 1201
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1201
acuggauaga ggauuaaagu gag                                           23

<210> SEQ ID NO 1202
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1202
uucuggauag aggauuaaag uga                                           23

<210> SEQ ID NO 1203
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1203
ucucucuauc cuuuggccca ccg                                           23

<210> SEQ ID NO 1204
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 1204
aucucutcau ccuuuggccc acc                                              23

<210> SEQ ID NO 1205
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1205
acuctctuca uccuuuggcc cac                                              23

<210> SEQ ID NO 1206
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1206
accucucuuc auccuuuggc cca                                              23

<210> SEQ ID NO 1207
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1207
ugcctctcuu cauccuuugg ccc                                              23

<210> SEQ ID NO 1208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1208
augccucucu ucauccuuug gcc                                              23

<210> SEQ ID NO 1209
<211> LENGTH: 23
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1209
aaugcctcuc uucauccuuu ggc                                              23

<210> SEQ ID NO 1210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1210
acaugccucu cuucauccuu ugg                                              23

<210> SEQ ID NO 1211
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1211
aacatgccuc ucuucauccu uug                                              23

<210> SEQ ID NO 1212
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1212
aaacaugccu cucuucaucc uuu                                              23

<210> SEQ ID NO 1213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1213
acaacaugcc ucucuucauc cuu                                              23

<210> SEQ ID NO 1214
<211> LENGTH: 23
<212> TYPE: RNA
<213> ORGANISM: Artificial Sequence
<220> FEATURE:
<221> NAME/KEY: source
```

-continued

<223> OTHER INFORMATION: /note="Description of Artificial Sequence:
      Synthetic oligonucleotide"

<400> SEQUENCE: 1214
accaacaugc cucucuucau ccu                                              23

<210> SEQ ID NO 1215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1215
auccaacaug ccucucuuca ucc                                              23

<210> SEQ ID NO 1216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1216
acuccaacau gccucucuuc auc                                              23

<210> SEQ ID NO 1217
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1217
aucuccaaca ugccucucuu cau                                              23

<210> SEQ ID NO 1218
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1218
aguctccaac augccucucu uca                                              23

<210> SEQ ID NO 1219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1219
aagucuccaa caugccucuc uuc                                              23

<210> SEQ ID NO 1220
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1220
aaagtctcca acaugccucu cuu                                              23

<210> SEQ ID NO 1221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1221
acaagucucc aacaugccuc ucu                                              23

<210> SEQ ID NO 1222
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1222
accutugccc aagucaucug cuu                                              23

<210> SEQ ID NO 1223
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1223
aaccuuugcc caagucaucu gcu                                              23

<210> SEQ ID NO 1224
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1224
acaccuuugc ccaagucauc ugc                                              23

```
<210> SEQ ID NO 1225
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1225
accaccuuug cccaagucau cug                                              23

<210> SEQ ID NO 1226
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1226
uuccaccuuu gcccaaguca ucu                                              23

<210> SEQ ID NO 1227
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1227
uuuccaccuu ugcccaaguc auc                                              23

<210> SEQ ID NO 1228
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1228
auuuccaccu uugcccaagu cau                                              23

<210> SEQ ID NO 1229
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1229
aauutccacc uuugcccaag uca                                              23

<210> SEQ ID NO 1230
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1230
acauuuccac cuuugcccaa guc                                            23

<210> SEQ ID NO 1231
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1231
uucatutcca ccuuugccca agu                                            23

<210> SEQ ID NO 1232
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1232
auucautucc accuuugccc aag                                            23

<210> SEQ ID NO 1233
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1233
acuucauuuc caccuuugcc caa                                            23

<210> SEQ ID NO 1234
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1234
uucutcauuu ccaccuuugc cca                                            23
```

```
<210> SEQ ID NO 1235
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1235 uuucucauu uccaccuuug ccc                                              23

<210> SEQ ID NO 1236
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1236
auuucutcau uuccaccuuu gcc                                             23

<210> SEQ ID NO 1237
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1237
acuutctuca uuuccaccuu ugc                                             23

<210> SEQ ID NO 1238
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1238
uacutucuuc auuuccaccu uug                                             23

<210> SEQ ID NO 1239
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1239
auactutcuu cauuccacc uuu                                                 23

<210> SEQ ID NO 1240
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1240
aguacuuucu ucauuccac cuu                                                 23

<210> SEQ ID NO 1241
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1241
uuguacuuuc uucauuucca ccu                                                23

<210> SEQ ID NO 1242
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1242
uuugtacuuu cuucauuucc acc                                                23

<210> SEQ ID NO 1243
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1243
auuuguacuu ucuucauuuc cac                                                23

<210> SEQ ID NO 1244
<211> LENGTH: 23
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1244
ucuutgtacu uucuucauuu cca                                         23

<210> SEQ ID NO 1245
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1245
aucutuguac uuucuucauu ucc                                         23

<210> SEQ ID NO 1246
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1246
uguctutgua cuuucuucau uuc                                         23

<210> SEQ ID NO 1247
<211> LENGTH: 23
<212> TYPE: RNA
<213> ORGANISM: Homo sapiens

<400> SEQUENCE: 1247
caccaucaau uucgagcaga agg                                         23

<210> SEQ ID NO 1248
<211> LENGTH: 23
<212> TYPE: RNA
<213> ORGANISM: Homo sapiens

<400> SEQUENCE: 1248
accaucaauu ucgagcagaa gga                                         23

<210> SEQ ID NO 1249
<211> LENGTH: 23
<212> TYPE: RNA
<213> ORGANISM: Homo sapiens

<400> SEQUENCE: 1249
cgagcagaag gaaaguaaug gac                                         23
```

```
<210> SEQ ID NO 1250
<211> LENGTH: 23
<212> TYPE: RNA
<213> ORGANISM: Homo sapiens

<400> SEQUENCE: 1250
gagcagaagg aaaguaaugg acc                                              23

<210> SEQ ID NO 1251
<211> LENGTH: 23
<212> TYPE: RNA
<213> ORGANISM: Homo sapiens

<400> SEQUENCE: 1251
aaguaaugga ccagugaagg ugu                                              23

<210> SEQ ID NO 1252
<211> LENGTH: 23
<212> TYPE: RNA
<213> ORGANISM: Homo sapiens

<400> SEQUENCE: 1252
guaauggacc agugaaggug ugg                                              23

<210> SEQ ID NO 1253
<211> LENGTH: 23
<212> TYPE: RNA
<213> ORGANISM: Homo sapiens

<400> SEQUENCE: 1253
cuguaccagu gcagguccuc acu                                              23

<210> SEQ ID NO 1254
<211> LENGTH: 23
<212> TYPE: RNA
<213> ORGANISM: Homo sapiens

<400> SEQUENCE: 1254
uguaccagug cagguccuca cuu                                              23

<210> SEQ ID NO 1255
<211> LENGTH: 23
<212> TYPE: RNA
<213> ORGANISM: Homo sapiens

<400> SEQUENCE: 1255
cggugggcca aaggaugaag aga                                              23

<210> SEQ ID NO 1256
<211> LENGTH: 23
<212> TYPE: RNA
<213> ORGANISM: Homo sapiens

<400> SEQUENCE: 1256
ggugggccaa aggaugaaga gag                                              23

<210> SEQ ID NO 1257
<211> LENGTH: 23
<212> TYPE: RNA
<213> ORGANISM: Homo sapiens

<400> SEQUENCE: 1257
gugggccaaa ggaugaagag agg                                              23
```

```
<210> SEQ ID NO 1258
<211> LENGTH: 23
<212> TYPE: RNA
<213> ORGANISM: Homo sapiens

<400> SEQUENCE: 1258
ugggccaaag gaugaagaga ggc                                              23

<210> SEQ ID NO 1259
<211> LENGTH: 23
<212> TYPE: RNA
<213> ORGANISM: Homo sapiens

<400> SEQUENCE: 1259
gggccaaagg augaagagag gca                                              23

<210> SEQ ID NO 1260
<211> LENGTH: 23
<212> TYPE: RNA
<213> ORGANISM: Homo sapiens

<400> SEQUENCE: 1260
ggccaaagga ugaagagagg cau                                              23

<210> SEQ ID NO 1261
<211> LENGTH: 23
<212> TYPE: RNA
<213> ORGANISM: Homo sapiens

<400> SEQUENCE: 1261
ccaaaggaug aagagaggca ugu                                              23

<210> SEQ ID NO 1262
<211> LENGTH: 23
<212> TYPE: RNA
<213> ORGANISM: Homo sapiens

<400> SEQUENCE: 1262
gaugaagaga ggcauguugg aga                                              23

<210> SEQ ID NO 1263
<211> LENGTH: 23
<212> TYPE: RNA
<213> ORGANISM: Homo sapiens

<400> SEQUENCE: 1263
gaagagaggc auguuggaga ccu                                              23

<210> SEQ ID NO 1264
<211> LENGTH: 23
<212> TYPE: RNA
<213> ORGANISM: Homo sapiens

<400> SEQUENCE: 1264
agagaggcau guuggagacc ugg                                              23

<210> SEQ ID NO 1265
<211> LENGTH: 23
<212> TYPE: RNA
<213> ORGANISM: Homo sapiens

<400> SEQUENCE: 1265
```

```
agcagaugac uugggcaaag gug                                              23

<210> SEQ ID NO 1266
<211> LENGTH: 23
<212> TYPE: RNA
<213> ORGANISM: Homo sapiens

<400> SEQUENCE: 1266 gacuuggca aagguggaaa uga                                               23

<210> SEQ ID NO 1267
<211> LENGTH: 23
<212> TYPE: RNA
<213> ORGANISM: Homo sapiens

<400> SEQUENCE: 1267
cuugggcaaa gguggaaaug aag                                              23

<210> SEQ ID NO 1268
<211> LENGTH: 23
<212> TYPE: RNA
<213> ORGANISM: Homo sapiens

<400> SEQUENCE: 1268
uugggcaaag guggaaauga aga                                              23

<210> SEQ ID NO 1269
<211> LENGTH: 23
<212> TYPE: RNA
<213> ORGANISM: Homo sapiens

<400> SEQUENCE: 1269
ugggcaaagg uggaaaugaa gaa                                              23

<210> SEQ ID NO 1270
<211> LENGTH: 23
<212> TYPE: RNA
<213> ORGANISM: Homo sapiens

<400> SEQUENCE: 1270
gggcaaaggu ggaaaugaag aaa                                              23

<210> SEQ ID NO 1271
<211> LENGTH: 23
<212> TYPE: RNA
<213> ORGANISM: Homo sapiens

<400> SEQUENCE: 1271
ggcaaaggug gaaaugaaga aag                                              23

<210> SEQ ID NO 1272
<211> LENGTH: 23
<212> TYPE: RNA
<213> ORGANISM: Homo sapiens

<400> SEQUENCE: 1272
gcaaaggugg aaaugaagaa agu                                              23

<210> SEQ ID NO 1273
<211> LENGTH: 23
<212> TYPE: RNA
<213> ORGANISM: Homo sapiens

<400> SEQUENCE: 1273
```
aaagguggaa augaagaaag uaa                                              23

<210> SEQ ID NO 1274
<211> LENGTH: 23
<212> TYPE: RNA
<213> ORGANISM: Homo sapiens

<400> SEQUENCE: 1274
agguggaaau gaagaaagua aaa                                              23

<210> SEQ ID NO 1275
<211> LENGTH: 23
<212> TYPE: RNA
<213> ORGANISM: Homo sapiens

<400> SEQUENCE: 1275
gguggaaaug aagaaaguaa aaa                                              23

<210> SEQ ID NO 1276
<211> LENGTH: 23
<212> TYPE: RNA
<213> ORGANISM: Homo sapiens

<400> SEQUENCE: 1276
guggaaauga agaaaguaaa aag                                              23

<210> SEQ ID NO 1277
<211> LENGTH: 23
<212> TYPE: RNA
<213> ORGANISM: Homo sapiens

<400> SEQUENCE: 1277
uggaaaugaa gaaaguaaaa aga                                              23

<210> SEQ ID NO 1278
<211> LENGTH: 23
<212> TYPE: RNA
<213> ORGANISM: Homo sapiens

<400> SEQUENCE: 1278
ggaaaugaag aaaguaaaaa gac                                              23

<210> SEQ ID NO 1279
<211> LENGTH: 23
<212> TYPE: RNA
<213> ORGANISM: Homo sapiens

<400> SEQUENCE: 1279
gaaaugaaga aguaaaaag aca                                               23

<210> SEQ ID NO 1280
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1280
aauuucgagc agaaggaaag a                                                21

<210> SEQ ID NO 1281

-continued

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1281
uucgagcaga aggaaaguaa a                                              21

<210> SEQ ID NO 1282
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1282
aaggaaagua auggaccagu a                                              21

<210> SEQ ID NO 1283
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1283
gaaaguaaug gaccagugaa a                                              21

<210> SEQ ID NO 1284
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1284
cagguccuca cuuuaauccu a                                              21

<210> SEQ ID NO 1285
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1285
ccucacuuua auccucuauc a                                              21

<210> SEQ ID NO 1286
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1286
aaggaugaag agaggcaugu a                                    21

<210> SEQ ID NO 1287
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1287
aggaugaaga gaggcauguu a                                    21

<210> SEQ ID NO 1288
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1288
agguggaaau gaagaaagua a                                    21

<210> SEQ ID NO 1289
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1289
uucctucugc ucgaaauuga ugg                                  23

<210> SEQ ID NO 1290
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1290
utcctucugc ucgaaauuga ugg                                  23

<210> SEQ ID NO 1291
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 1291
ucuutccuuc ugcucgaaau ugg                                              23

<210> SEQ ID NO 1292
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1292
uuuacutucc uucugcucga aau                                              23

<210> SEQ ID NO 1293
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1293
utuacutucc utcugcucga aau                                              23

<210> SEQ ID NO 1294
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1294
uacuggtcca uuacuuuccu ucu                                              23

<210> SEQ ID NO 1295
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1295
uacuggtcca utacuuuccu ucu                                              23

```
<210> SEQ ID NO 1296
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1296
uacuggtcca utacutuccu ucu                                              23

<210> SEQ ID NO 1297
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1297
ucactggucc atuacuuucc uuc                                              23

<210> SEQ ID NO 1298
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1298
ucactggucc atuacuuucc uuc                                              23

<210> SEQ ID NO 1299
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1299
uuucactggu ccauuacuuu ccu                                              23

<210> SEQ ID NO 1300
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1300
utucactggu ccauuacuuu ccu                                             23

<210> SEQ ID NO 1301
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1301
uaaagugagg accugcacug gug                                             23

<210> SEQ ID NO 1302
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1302
uaggautaaa gtgaggaccu gcg                                             23

<210> SEQ ID NO 1303
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1303
ugauagagga uuaaagugag gac                                             23

<210> SEQ ID NO 1304
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1304
ugauagagga utaaagugag gac                                             23

<210> SEQ ID NO 1305
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1305
ucuggataga ggatuaaagu gag                                        23

<210> SEQ ID NO 1306
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1306
uacatgccuc ucuucauccu uug                                        23

<210> SEQ ID NO 1307
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1307
uaacaugccu cucuucaucc uuu                                        23

<210> SEQ ID NO 1308
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1308
uaacaugccu ctcuucaucc uuu                                        23

<210> SEQ ID NO 1309
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1309
```
utcatutcca ccuuugccca agu                                           23

<210> SEQ ID NO 1310
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1310
utuctucauu uccaccuuug ccc                                           23

<210> SEQ ID NO 1311
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1311
uuactutcuu cauuccacc uuu                                            23

<210> SEQ ID NO 1312
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1312
utactutcuu cauuccacc uuu                                            23

<210> SEQ ID NO 1313
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1313
aucaauuucg agcagaagga a                                             21

<210> SEQ ID NO 1314
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 1314
aucaauuucg agcagaagga a                                              21

<210> SEQ ID NO 1315
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1315
aauuucgagc agaaggaaag a                                              21

<210> SEQ ID NO 1316
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1316
aauuucgagc agaaggaaag a                                              21

<210> SEQ ID NO 1317
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1317
uucgagcaga aggaaaguaa u                                              21

<210> SEQ ID NO 1318
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1318
uucgagcaga aggaaaguaa a                                              21

<210> SEQ ID NO 1319
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1319
uucgagcaga aggaaaguaa a                                              21

<210> SEQ ID NO 1320
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1320
aggaaaguaa uggaccagug a                                              21

<210> SEQ ID NO 1321
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1321
gaaaguaaug gaccagugaa a                                              21

<210> SEQ ID NO 1322
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1322
gaaaguaaug gaccagugaa a                                              21

<210> SEQ ID NO 1323
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1323
ccagugcagg uccucacuuu a                                              21

<210> SEQ ID NO 1324
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1324
ccagugcagg uccucacuuu a                                              21

<210> SEQ ID NO 1325
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1325
ccagugcagg uccucacuuu a                                              21
```

```
<210> SEQ ID NO 1326
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1326
ccagugcagg uccucacuuu a                                              21

<210> SEQ ID NO 1327
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1327
cagguccuca cuuuaauccu a                                              21

<210> SEQ ID NO 1328
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1328
aaggaugaag agaggcaugu a                                              21

<210> SEQ ID NO 1329
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1329
aaggaugaag agaggcaugu a                                              21

<210> SEQ ID NO 1330
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1330
aggaugaaga gaggcauguu u                                              21

<210> SEQ ID NO 1331
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"

<400> SEQUENCE: 1331
aggaugaaga gaggcauguu a                                          21

<210> SEQ ID NO 1332
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1332
aggaugaaga gaggcauguu a                                          21

<210> SEQ ID NO 1333
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1333
uugggcaaag guggaaauga a                                          21

<210> SEQ ID NO 1334
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1334
uugggcaaag guggaaauga a                                          21

<210> SEQ ID NO 1335
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1335
uugggcaaag guggaaauga a                                          21

<210> SEQ ID NO 1336
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1336
gcaaaggugg aaaugaagaa a                                          21

<210> SEQ ID NO 1337
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1337
gcaaaggugg aaaugaagaa a                                          21

<210> SEQ ID NO 1338
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1338
gcaaaggugg aaaugaagaa a                                          21

<210> SEQ ID NO 1339
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1339
agguggaaau gaagaaagua u                                          21

<210> SEQ ID NO 1340
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1340
agguggaaau gaagaaagua a                                          21

<210> SEQ ID NO 1341
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1341
agguggaaau gaagaaagua a                                          21

<210> SEQ ID NO 1342
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1342
```
agguggaaau gaagaaagua a                          21

<210> SEQ ID NO 1343
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1343
utcctucugc ucgaaauuga ugg                        23

<210> SEQ ID NO 1344
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1344
ucuutccuuc ugcucgaaau ugg                        23

<210> SEQ ID NO 1345
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1345
utuacutucc utcugcucga aau                        23

<210> SEQ ID NO 1346
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1346
uacuggtcca uuacuuuccu ucu                        23

<210> SEQ ID NO 1347
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1347
uacuggtcca utacutuccu ucu                                            23

<210> SEQ ID NO 1348
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1348
ucactggucc auuacuuucc uuc                                            23

<210> SEQ ID NO 1349
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1349
ucactggucc atuacuuucc uuc                                            23

<210> SEQ ID NO 1350
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1350
ucactggucc atuactuucc uuc                                            23

<210> SEQ ID NO 1351
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 1351
utucactggu ccauuacuuu ccu                                              23

<210> SEQ ID NO 1352
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1352
uaaagugagg accugcacug gug                                              23

<210> SEQ ID NO 1353
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1353
uaaagugagg accugcacug gug                                              23

<210> SEQ ID NO 1354
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1354
uaggautaaa gtgaggaccu gcg                                              23

<210> SEQ ID NO 1355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1355
ugauagagga uuaaagugag gac                                              23

<210> SEQ ID NO 1356
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1356
ugauagagga utaaagugag gac                                              23

<210> SEQ ID NO 1357
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1357
ucuggataga ggatuaaagu gag                                              23

<210> SEQ ID NO 1358
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1358
uacatgccuc ucuucauccu uug                                              23

<210> SEQ ID NO 1359
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1359
uaacaugccu ctcuucaucc uuu                                              23

<210> SEQ ID NO 1360
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1360
uucatutcca ccuuugccca agu                                              23

<210> SEQ ID NO 1361

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1361
utcatutcca ccuuugccca agu                                            23

<210> SEQ ID NO 1362
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1362
uuuctucauu uccaccuuug ccc                                            23

<210> SEQ ID NO 1363
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1363
utuctucauu uccaccuuug ccc                                            23

<210> SEQ ID NO 1364
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1364
uuactutcuu cauuuccacc uuu                                            23

<210> SEQ ID NO 1365
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<220> FEATURE:
<221> NAME/KEY: source
<223> OTHER INFORMATION: /note="Description of Combined DNA/RNA
      Molecule: Synthetic oligonucleotide"

<400> SEQUENCE: 1365
utactutcuu cauuuccacc uuu                                              23

<210> SEQ ID NO 1366
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1366
uuuacutucc uucugcucga aau                                              23

<210> SEQ ID NO 1367
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1367
uaggautaaa gtgaggaccu gcg                                              23

<210> SEQ ID NO 1368
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1368
ucuggataga ggauuaaagu gag                                              23

<210> SEQ ID NO 1369
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1369
```
ucuggataga ggauuaaagu ga						22

<210> SEQ ID NO 1370
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1370
uaggautaaa gtgaggaccu gc						22

<210> SEQ ID NO 1371
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1371
uuuacutucc uucugcucga aa						22

<210> SEQ ID NO 1372
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1372
uuucactggu ccauuacuuu cc						22

<210> SEQ ID NO 1373
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1373
uaacaugccu cucuucaucc uu						22

<210> SEQ ID NO 1374
<211> LENGTH: 22
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1374
uacuggtcca utacuuuccu uc                                              22

<210> SEQ ID NO 1375
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1375 uuccucugc ucgaaauuga ug                                               22

<210> SEQ ID NO 1376
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1376
ugauagagga uaaagugag ga                                               22

<210> SEQ ID NO 1377
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1377
uacatgccuc ucuucauccu uu                                              22

<210> SEQ ID NO 1378
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

```
       Molecule: Synthetic oligonucleotide"

<400> SEQUENCE: 1378
ucuutccuuc ugcucgaaau ug                                              22
```